US012624023B2

(12) United States Patent
Bock et al.

(10) Patent No.: US 12,624,023 B2
(45) Date of Patent: May 12, 2026

(54) SULFONYLUREA DERIVATIVES AND USES THEREOF

(71) Applicant: NodThera Limited, Essex (GB)

(72) Inventors: Mark G. Bock, Lexington, MA (US); David Harrison, Essex (GB); Jane E. Scanlon, Essex (GB)

(73) Assignee: NodThera Limited, Little Chesterford (GB)

( * ) Notice: Subject to any disclaimer, the term of this patent is extended or adjusted under 35 U.S.C. 154(b) by 1164 days.

(21) Appl. No.: 17/618,188

(22) PCT Filed: Jun. 11, 2020

(86) PCT No.: PCT/EP2020/066185
§ 371 (c)(1),
(2) Date: Dec. 10, 2021

(87) PCT Pub. No.: WO2020/249664
PCT Pub. Date: Dec. 17, 2020

(65) Prior Publication Data
US 2023/0083495 A1 Mar. 16, 2023

Related U.S. Application Data

(60) Provisional application No. 62/860,664, filed on Jun. 12, 2019.

(51) Int. Cl.
*C07D 409/14* (2006.01)
*C07D 405/14* (2006.01)
*C07D 417/14* (2006.01)

(52) U.S. Cl.
CPC ......... *C07D 409/14* (2013.01); *C07D 405/14* (2013.01); *C07D 417/14* (2013.01)

(58) Field of Classification Search
CPC ... C07D 417/14; C07D 405/14; C07D 409/14
See application file for complete search history.

(56) References Cited

U.S. PATENT DOCUMENTS 4,515,620 A 5/1985 Bohner
5,288,757 A 2/1994 Picard et al.
5,422,335 A 6/1995 Hagen et al.
5,424,450 A 6/1995 Boswell et al.
5,512,681 A 4/1996 Boswell et al.
5,604,178 A 2/1997 Kanda et al.
5,610,121 A 3/1997 Riebel et al.
5,612,287 A 3/1997 Kanda et al.
5,683,964 A 11/1997 Kanda et al.
6,028,201 A 2/2000 Dinsmore et al.
6,303,541 B1 10/2001 Gesing et al.
6,329,323 B1 12/2001 Bettarini et al.
6,593,356 B2 7/2003 Nugiel et al.
6,887,831 B1 5/2005 Gesing et al.
7,144,911 B2 12/2006 Flynn et al.
7,202,257 B2 4/2007 Flynn et al.
7,279,576 B2 10/2007 Flynn et al.
7,342,037 B2 3/2008 Flynn et al.
7,531,566 B2 5/2009 Flynn et al.
7,666,895 B2 2/2010 Flynn et al.
7,737,283 B2 6/2010 Flynn et al.
8,642,660 B2 2/2014 Goldfarb
9,271,969 B2 3/2016 Kim et al.
9,410,217 B2 8/2016 Lipiecki et al.
11,518,757 B2 12/2022 Harrison et al.
12,012,397 B2 6/2024 Harrison et al.
12,054,461 B2 8/2024 Bock et al.
2003/0134898 A1 7/2003 Homan
2007/0191336 A1 8/2007 Flynn et al.
2008/0187978 A1 8/2008 Flynn et al.
2009/0069310 A1 3/2009 Flynn et al.
(Continued)

FOREIGN PATENT DOCUMENTS

CN 103288750 A 9/2013
CN 107428696 A 12/2017
(Continued)

OTHER PUBLICATIONS

Clarivate English Translation of JP60214785 (Year: 1985).*
Keane (Front. Neurol. 2018. 9:135. 1-9) (Year: 2018).*
Zitvogel (Nat Immunol 13, 343-351 (2012).) (Year: 2012).*
Aggarwal, B.B. et al. (2009) "Targeting inflammatory pathways for prevention and therapy of cancer: short-term friend, long-term foe" Clinical Cancer Research, 15(2):425-430.
Ahmad, I. et al. (Jul. 2013) "Thymoquinone suppresses metastasis of melanoma cells by inhibition of NLRPB inflammasome" Toxicology and Applied Pharmacology, 270(1):70-76.
Amieva, M. and R.M. Peek (Jan. 2016) "Pathobiology of Helicobacter pylori-Induced Gastric Cancer" Gastroenterology, 150(1):64-78.
Apte, R.N. et al. (Sep. 2006) "The involvement of IL-1 in tumorigenesis, tumor invasiveness, metastasis and tumor-host interactions" Cancer and Metastasis Reviews, 25(3):387-408.
(Continued)

*Primary Examiner* — Kortney L. Klinkel
*Assistant Examiner* — Richard Grant Peckham
(74) *Attorney, Agent, or Firm* — Fenwick & West LLP; Heidi A. Erlacher; Christine McCain

(57) ABSTRACT

The present disclosure relates to compounds of Formula (I)

(I)

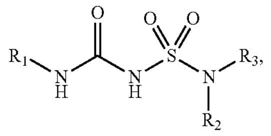

and to their prodrugs, pharmaceutically acceptable salts, pharmaceutical compositions, methods of use, and methods for their preparation. The compounds disclosed herein are useful for inhibiting the maturation of cytokines of the IL-1 family by inhibiting inflammasomes and may be used in the treatment of disorders in which inflammasome activity is implicated, such as inflammatory, autoinflammatory and autoimmune diseases and cancers.

14 Claims, No Drawings

(56) References Cited

U.S. PATENT DOCUMENTS

| | | | |
|---|---|---|---|
| 2009/0105230 A1 | 4/2009 | Flynn et al. | |
| 2009/0137021 A1 | 5/2009 | Flynn et al. | |
| 2009/0312349 A1 | 12/2009 | Flynn et al. | |
| 2017/0304270 A1 | 10/2017 | Or et al. | |
| 2017/0304271 A1 | 10/2017 | Or et al. | |
| 2017/0304272 A1 | 10/2017 | Or et al. | |
| 2017/0333399 A1 | 11/2017 | Or et al. | |
| 2017/0334893 A1 | 11/2017 | Or et al. | |
| 2017/0334894 A1 | 11/2017 | Or et al. | |
| 2020/0299284 A1 | 9/2020 | O'Neill et al. | |
| 2021/0002261 A1 | 1/2021 | Harrison et al. | |
| 2022/0194923 A1* | 6/2022 | Cooper | C07D 401/14 |
| 2022/0227715 A1 | 7/2022 | Bock et al. | |
| 2022/0267300 A1 | 8/2022 | Bock et al. | |
| 2023/0145050 A1 | 5/2023 | Harrison et al. | |
| 2024/0043410 A1 | 2/2024 | Bock et al. | |
| 2024/0368129 A1 | 11/2024 | Harrison et al. | |

FOREIGN PATENT DOCUMENTS

| | | | |
|---|---|---|---|
| EP | 696589 A1 * | 2/1996 | A01N 47/36 |
| EP | 0569193 B1 | 2/1997 | |
| EP | 3272739 A1 | 1/2018 | |
| EP | 3259253 B1 | 1/2020 | |
| GB | 2110689 A | 6/1983 | |
| JP | S60214785 A | 10/1985 | |
| JP | H09132574 A | 5/1997 | |
| JP | H1029990 A | 2/1998 | |
| JP | 2001026574 A | 1/2001 | |
| JP | 4112127 B2 | 7/2008 | |
| WO | WO-9208694 A1 | 5/1992 | |
| WO | WO-9304045 A1 | 3/1993 | |
| WO | WO-9304046 A1 | 3/1993 | |
| WO | WO-9324482 A1 | 12/1993 | |
| WO | WO-9418176 A1 | 8/1994 | |
| WO | WO-9418177 A1 | 8/1994 | |
| WO | WO-9800408 A1 | 1/1998 | |
| WO | WO-9832733 A1 | 7/1998 | |
| WO | WO-0064866 A1 | 11/2000 | |
| WO | WO-0123349 A1 | 4/2001 | |
| WO | WO-03029226 A1 | 4/2003 | |
| WO | WO-2016131098 A1 | 8/2016 | |
| WO | WO-2017140778 A1 | 8/2017 | |
| WO | WO-2018015445 A1 | 1/2018 | |
| WO | WO-2019023147 A1 | 1/2019 | |
| WO | WO-2019034686 A1 | 2/2019 | |
| WO | WO-2019034688 A1 | 2/2019 | |
| WO | WO-2019034690 A1 | 2/2019 | |
| WO | WO-2019034692 A1 | 2/2019 | |
| WO | WO-2019034693 A1 | 2/2019 | |
| WO | WO-2019034696 A1 | 2/2019 | |
| WO | WO-2019034697 A1 | 2/2019 | |
| WO | WO-2019121691 A1 | 6/2019 | |
| WO | WO-2020035464 A1 | 2/2020 | |
| WO | WO-2020035466 A1 | 2/2020 | |
| WO | WO-2020249664 A1 | 12/2020 | |
| WO | WO-2020249667 A1 | 12/2020 | |
| WO | WO-2020249669 A1 | 12/2020 | |
| WO | WO-2022051582 A1 | 3/2022 | |

OTHER PUBLICATIONS

Basso, D. et al. (1996) "Helicobacter pylori infection enhances mucosal interleukin-1beta, interleukin-6, and the soluble receptor of interleukin-2" Int J Clin Lab Res, 26:207-210.

Bernstein, C.N. et al. (Feb. 2001) "Cancer risk in patients with inflammatory bowel disease: a population-based study" Cancer, 91(4):854-862.

Bruchard, M. et al. (Jan. 2013) "Chemotherapy-triggered cathepsin B release in myeloid-derived suppressor cells activates the Nlrp3 inflammasome and promotes tumour growth" Nature Medicine, 19(1):57-64; including "Online Methods", 2 pages.

Carrascal, M.T. et al. (2003) "Interleukin-18 binding protein reduces B16 melanoma hepatic metastasis by neutralizing adhesiveness and growth factors of sinusoidal endothelium" Cancer Research, 63(2):491-497.

Chae, J.J. et al. (May 2, 20117) "Gain-of-Function Pyrin Mutations Induce NLRP3 Protein-Independent Interleukin-1 beta Activation and Severe Autoinflammation in Mice" Immunity, 34:755-768.

Coll R.C., et al., "A Small-Molecule Inhibitor of the NLRP3 Inflammasome for the Treatment of Inflammatory Diseases," Nature Medicine, vol. 21(3), pp. 248-255, including "Online Methods", 2 pages, doi: 10.1038/nm.3806 (Feb. 2015).

Dinarello, C.A. (Mar. 2004) "Unraveling the NALP-3/IL-1beta inflammasome: a big lesson from a small mutation" Immunity, 20(3):243-244.

Dinarello, C.A. et al. (Aug. 2010) "Role of IL-1beta in type 2 diabetes" Curr Opin Endocrinol Diabetes Obes, 17(4):314-321.

Elaraj, D.M. et al. (Feb. 2006) "The role of interleukin 1 in growth and metastasis of human cancer xenografts" Clinical Cancer Research, 12(4):1088-1096.

Gabay, C. and I.B. Mcinnes (2009) "The biological and clinical importance of the 'new generation' cytokines in rheumatic diseases" Arthritis Research & Therapy, 11(3):230, 14 pages.

Gasse, P. et al. (May 2009) "Uric acid is a danger signal activating NALP3 inflammasome in lung injury inflammation and fibrosis" Am J Respir Crit Care Med, 179(10):903-913.

Grivennikov, S.I. et al. (Mar. 2010) "Immunity, inflammation, and cancer" Cell, 140(6):883-899.

Halle, A. et al. (Aug. 2008) "The NALP3 inflammasome is involved in the innate immune response to amyloid-beta" Nat Immunol, 9(8):857-865.

Heneka, M.T. et al. (Jan. 31, 2013) "NLRP3 is activated in Alzheimer's disease and contributes to pathology in APP/PS1 mice" Nature, 493:674-678.

Hoffman, H.M. et al. (Nov. 2001) "Mutation of a new gene encoding a putative pyrin-like protein causes familial cold autoinflammatory syndrome and Muckle-Wells syndrome" Nat Genet, 29(3):301-305.

Hoffman, H.M. et al., "Periodic Fever Disorders" Reumatología, 21(3):96-100 (2005).

Holen, I et al. (Nov. 2016) "IL-1 drives breast cancer growth and bone metastasis in vivo" Oncotarget, 7(46):75571-75584.

Jee, C.D. et al. (2005) "Loss of caspase-1 gene expression in human gastric carcinomas and cell lines" Int J Oncol, 26:1265-1271.

Kagan, J. and Horng, T. (Aug. 2013) "NLRP3 inflammasome activation: CD36 serves double duty" Nature Immunology, 14(8):772-774.

Kim, J.M. (Dec. 2011) "Inflammatory Bowel Diseases and Inflammasome" Korean J Gastroenterol, vol. 58 No. 6, pp. 300-310 (Korean, English Abstract on p. 300).

Latz, E. et al. (Jun. 2013) "Activation and regulation of the inflammasomes" Nat Rev Immunol, 13(6):397-411.

Lazar-Molnar, E. et al. (2000) "Autocrine and paracrine regulation by cytokines and growth factors in melanoma" Cytokine, 12(6):547-554.

Lewis, A.M. et al. (Nov. 2006) "Interleukin-1 and cancer progression: the emerging role of interleukin-1 receptor antagonist as a novel therapeutic agent in cancer treatment" Journal of Translational Medicine, 4:48; 12 pages.

Li, L. and Liu, Y. (Dec. 2014) "Aging-related gene signature regulated by NlrpB predicts glioma progression" American Journal of Cancer Research, 5(1):442-449.

Luo, J. et al., "Principles of Cancer Therapy: Oncogene and Non-oncogene Addiction" Cell, 136, pp. 823-837 (Mar. 2009).

Martinon, F. et al. (2009) "The inflammasomes: guardians of the body" Annu Rev Immunol, 27:229-265.

Masters, S.L. et al. (2009) "Horror Autoinflammaticus: The Molecular Pathophysiology of Autoinflammatory Disease" Annu Rev Immunol, 27:621-668.

Mortaz, E. et al. (2011) "Identification of Novel Therapeutic Targets in COPD" Tanaffos, 10(2):9-14.

Mucke, L., "Alzheimer's disease," Nature, vol. 461, pp. 895-897 (Oct. 2009).

Nath, A. et al. (Oct. 2015) "Elevated free fatty acid uptake via CD36 promotes epithelial-mesenchymal transition in hepatocellular carcinoma" Scientific Reports, 5:14752; 19 pages.

(56) References Cited

OTHER PUBLICATIONS

NIH National Institute on Aging, "Preventing Alzheimer's Disease: What Do We Know?" Obtained from https://www.nia.nih.gov/health/preventing-alzheimers-disease-what-do-we-know on Dec. 30, 2020 (Sep. 2018) (8 total pages).
Ozaki et al., Targeting the NLRP3 inflammasome in chronic inflammatory diseases: current perspectives. J Inflamm Res. Jan. 16, 2015;8:15-27. doi: 10.2147/JIR.S51250.
Pascual, G. et al. (Jan. 2017) "Targeting metastasis-initiating cells through the fatty acid receptor CD36" Nature, 541(7635):41-45; including Supplementary Information, 25 pages.
Perregaux, D.G. et al. (Oct. 2001) "Identification and characterization of a novel class of interleukin-1 post-translational processing inhibitors" J Pharmacol Exp Ther, 299(1):187-197.
Saresella, M. et al. (Mar. 2016) "The NLRP3 and NLRP1 inflammasomes are activated in Alzheimer's disease" Mol Neurodegener, 11:23; 14 pages.
Schett, G. et al. (Jan. 2016) "Interleukin-1 function and role in rheumatic disease" Nat Rev Rheumatol, 12(1):14-24.
Sims, J. and Smith, D.E. (Feb. 2010) "The IL-1 family: regulators of immunity" Nature Reviews Immunology, 10:89-102.
Voronov, E. et al. (Mar. 2003) "IL-1 is required for tumor invasiveness and angiogenesis" Proceedings of the National Academy of Sciences USA, 100(5):2645-2650.
Wang, P. et al. (2006) "Association of interleukin-1 gene polymorphisms with gastric cancer: a meta-analysis" Int J Cancer, 120:552-562.
WebMD, Crohn's Disease Health Center, Crohn's Disease—Prevention, obtained from www.webmd.com/ibd-crohns-disease/crohns-disease/tc/crohns-disease-prevention, on Apr. 5, 2015 (May 2013) (2 total pages).
WebMD "Diabetes Health Center, Prevention", obtained from www.webmd.com/diabetes/guide/type-1-diabetes-prevention, on Apr. 5, 2015 (Jan. 2014) (3 total pages).
Xu, Y. et al. (Nov. 2013) "Mycoplasma hyorhinis Activates the NLRP3 Inflammasome and Promotes Migration and Invasion of Gastric Cancer Cells" PLoS ONE, 8(11):e77955, 14 pages.
Zahid, A. et al., "Pharmacological Inhibitors of the NLRP3 Inflammasome" Frontiers in Immunology, 10:2538, 10 pages (Oct. 2019).
Zhang, B. et al. (2004) "IL-18 increases invasiveness of HL-60 myeloid leukemia cells: up-regulation of matrix metalloproteinases-9 (MMP-9) expression" Leukemia Research, 28(1):91-95.
Chen et al. "Blockage of the NLRP3 inflammasome by MCC950 improves anti-tumor immune responses in head and neck squamous cell carcinoma", Cellular and Molecular Life Sciences, (2018); 75:2045-2058.
Cuisset et al. "Genetic linkage of the Muckle-Wells syndrome to chromosome 1q44", The American Journal of Human Genetics, (1999); 65(4):1054-1059.
Feldman et al. "Chronic infantile neurological cutaneous and articular syndrome is caused by mutations in CIAS1, a gene highly expressed in polymorphonuclear cells and chondrocytes", The American Journal of Human Genetics, (2002); 71(1):198-203.
Fusco, R., et al.; "Focus on the Role of NLRP3 Inflammasome in Diseases," Int J Mol Sci., (2020); 21(12):4223, 26 pages.
Hoffman, H.M. et al. "Familial cold autoinflammatory syndrome: phenotype and genotype of an autosomal dominant periodic fever", Journal of Allergy and Clinical Immunology, (2001); 108(4):615-620.
Ising et al. "NLRP3 inflammasome activation drives tau pathology", Nature, (2019); 575:669-673 (24 pages).
Mangan, M.S.J., et al.; "Targeting the NLRP3 inflammasome in inflammatory diseases," Nat Rev Drug Discov., (2018); 17(8):588-606.
Matthews, C. P. et al., "Dominant-Negative Activator Protein 1 (TAM67) Targets Cyclooxygenase-2 and Osteopontin under Conditions in Which it Specifically Inhibits Tumorigenesis," Cancer Res., 2007, vol. 67. No. 6, pp. 2430-2438.
Moossavi, M., et al.; "Role of the NLRP3 inflammasome in cancer," Mol. Cancer (2018); 17(1):158, 13 pages.
Rheinheimer, J., et al.; "Current role of the NLRP3 inflammasome on obesity and insulin resistance: A systematic review," Metabolism (2017); 74, pp. 1-9.
Shahbaz, S.K., et al.; "Inflammasomes and Colorectal Cancer," Cells (2021); 10(9):2172, 22 pages.
Shen et al. "NLRP3: A promising therapeutic target for autoimmune diseases", Autoimmunity Reviews, (2018); 17(7):694-702.
Stancu et al. "Aggregated Tau activates NLRP3—ASC inflammasome exacerbating exogenously seeded and non-exogenously seeded Tau pathology in vivo", Acta Neuropathologica, (2019); 137:599-617.
Thi et al. "Inflammasome as a therapeutic target for cancer prevention and treatment", Journal of Cancer Prevention, (2017); 22(2):62-73.
Wang, H., et al.; "NLRP3 promotes tumor growth and metastasis in human oral squamous cell carcinoma," BMC Cancer (2018); 18(1):500, 10 pages.
Yu, L., et al.; "The NLRP3 Inflammasome in Non-Alcoholic Fatty Liver Disease and Steatohepatitis: Therapeutic Targets and Treatment," Front Pharmacol., (2022); 13:780496, 19 pages.
Zhang, W-J., et al.; "Inflammasomes and Fibrosis," Front Immunol., (2021); 12:643149, 13 pages.
Zhen, Y., et al., "NLRP3 Inflammasome and Inflammatory Bowel Disease, " Front Immunol., (2019); 10:276, 10 pages.
Database Registry RN 147000-89-3 STN Registry Apr. 15, 1993, 1 page.
Graf, R., "Umsetzungen mit N-Carbonyl-sulfamidsäure-chlorid, II. Alkohole und Phenole," Chemische Berichte, (Jan. 1963); 96(1):56-67. With English Abstract. https://doi.org/10.1002/cber.19630960106.
Pinto et al. "Thermoanalytical studies of carbamazepine: hydration/dehydration, thermal decomposition, and solid phase transitions" Brazilian Journal of Pharmaceutical Sciences (2014); 50(4):877-884.

* cited by examiner

SULFONYLUREA DERIVATIVES AND USES THEREOF

RELATED APPLICATION

This application is a U.S. National Phase Application, filed under 35 U.S.C. § 371, of International Application No. PCT/EP2020/066185, filed on Jun. 11, 2020, which claims priority to, and the benefit of, U.S. provisional application No. 62/860,664, filed Jun. 12, 2019, the contents of which are hereby incorporated by reference in their entireties.

FIELD OF THE DISCLOSURE

The present disclosure relates to sulfonylurea derivatives, prodrugs, and pharmaceutically acceptable salts thereof, which may possess inflammasome inhibitory activity and are accordingly useful in methods of treatment of the human or animal body. The present disclosure also relates to processes for the preparation of these compounds, to pharmaceutical compositions comprising them and to their use in the treatment of disorders in which inflammasome activity is implicated, such as inflammatory, autoinflammatory, autoimmune and oncological diseases.

BACKGROUND

Autoimmune diseases are associated with the overproduction of proinflammatory factors. One of them is interleukin-1 (IL-1), produced by activated macrophages, monocytes, fibroblasts, and other components of the innate immune system like dendritic cells. IL-1 is involved in a variety of cellular activities, including cell proliferation, differentiation and apoptosis (Seth L. al. Rev. Immunol. 2009. 27:621-68).

In humans, 22 NLR proteins are divided into four NLR subfamilies according to their N-terminal domains. NLRA contains a CARD-AT domain, NLRB (NAIP) contains a BIR domain, NLRC (including NOD1 and NOD2) contains a CARD domain, and NLRP contains a pyrin domain. Multiple NLR family members are associated with inflammasome formation.

Although inflammasome activation appears to have evolved as an important component of host immunity to pathogens, the NLRP3 inflammasome is unique in its ability activate in response to endogenous sterile danger signals. Many such sterile signals have been elucidated, and their formation is associated with specific disease states. For example, uric acid crystals found in gout patients are effective triggers of NLRP3 activation. Similarly, cholesterol crystals found in atherosclerotic patients can also promote NLRP3 activation. Recognition of the role of sterile danger signals as NLRP3 activators led to IL-1 and IL-18 being implicated in a diverse range of pathophysiological indications including metabolic, physiologic, inflammatory, hematologic and immunologic disorders.

The disclosure arises from a need to provide further compounds for the specific modulation of NLRP3-dependent cellular processes. In particular, compounds with improved physicochemical, pharmacological and pharmaceutical properties to existing compounds are desirable.

SUMMARY

In some aspects, the present disclosure provides, inter alia, a compound of Formula (I):

(I)

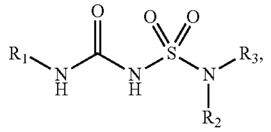

or a prodrug, solvate, or pharmaceutically acceptable salt thereof, wherein:

$R_1$ is 5- to 12-membered heterocycloalkyl or 5- to 12-membered heteroaryl optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), —($C_1$-$C_6$ alkyl)-O($C_1$-$C_6$ alkyl), cyano, halo, $C_3$-$C_8$ cycloalkyl, $C_3$-$C_8$ aryl, 3- to 8-membered heterocycloalkyl, or 3- to 8-membered heteroaryl;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH ($C_1$-$C_6$ alkyl), —N($C_1$-$C_6$ alkyl)$_2$, or oxo; and $R_3$ is 5- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some aspects, the present disclosure provides a compound obtainable by, or obtained by, a method for preparing a compound as described herein (e.g., a method comprising one or more steps described in Schemes 1-6).

In some aspects, the present disclosure provides a pharmaceutical composition comprising a compound of the present disclosure, or a pharmaceutically acceptable salt thereof, and a pharmaceutically acceptable diluent or carrier.

In some aspects, the present disclosure provides an intermediate as described herein, being suitable for use in a method for preparing a compound as described herein (e.g., the intermediate is selected from the intermediates described in Examples 1-17).

In some aspects, the present disclosure provides a method of inhibiting inflammasome (e.g., the NLRP3 inflammasome) activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in inhibiting inflammasome (e.g., the NLRP3 inflammasome) activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides use of a compound of the present disclosure or a pharmaceutically acceptable salt thereof in the manufacture of a medicament for inhibiting inflammasome (e.g., the NLRP3 inflammasome) activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

Autoimmune diseases are associated with the overproduction of proinflammatory factors. One of them is interleukin-1 (IL-1), produced by activated macrophages, monocytes, fibroblasts, and other components of the innate immune system like dendritic cells, involved in a variety of cellular activities, including cell proliferation, differentiation and apoptosis (Seth L. al. Rev. Immunol. 2009. 27:621-68).

Autoimmune diseases are associated with the overproduction of proinflammatory factors. One of them is interleukin-1 (IL-1), produced by activated macrophages, monocytes, fibroblasts, and other components of the innate immune system like dendritic cells, involved in a variety of cellular activities, including cell proliferation, differentiation and apoptosis (Seth L. al. Rev. Immunol. 2009. 27:621-68).

Cytokines from the IL-1 family are highly active and, as important mediators of inflammation, primarily associated with acute and chronic inflammation (Sims J. et al. Nature Reviews Immunology 10, 89-102 (February 2010)). The overproduction of IL-1 is considered to be a mediator of some autoimmune and autoinflammatory diseases. Autoinflammatory diseases are characterised by recurrent and unprovoked inflammation in the absence of autoantibodies, infection, or antigen-specific T lymphocytes.

Proinflammatory cytokines of the IL-1 superfamily include IL-1α, IL-1β, IL-18, and IL-36α, β, λ and are produced in response to pathogens and other cellular stressors as part of a host innate immune response. Unlike many other secreted cytokines, which are processed and released via the standard cellular secretory apparatus consisting of the endoplasmic reticulum and Golgi apparatus, IL-1 family members lack leader sequences required for endoplasmic reticulum entry and thus are retained intracellularly following translation. In addition, IL-1β, IL-18, and IL-36α, β, λ are synthesised as procytokines that require proteolytic activation to become optimal ligands for binding to their cognate receptors on target cells.

In the case of IL-1α, IL-1β and IL-18, it is now appreciated that a multimeric protein complex known as an inflammasome is responsible for activating the proforms of IL-1β and IL-18 and for release of these cytokines extracellularly. An inflammasome complex typically consists of a sensor molecule, such as an NLR (Nucleotide-Oligerimisation Domain (NOD)-like receptor), an adaptor molecule ASC (Apoptosis-associated speck-like protein containing a CARD (Caspase Recruitment Domain)) and procaspase-1. In response to a variety of "danger signals", including pathogen-associated molecule patterns (PAMPs) and danger associated molecular patterns (DAMPs), subunits of an inflammasome oligomerise to form a supramolecular structure within the cell. PAMPs include molecules such as peptidoglycan, viral DNA or RNA and bacterial DNA or RNA. DAMPs, on the other hand, consist of a wide range of endogenous or exogenous sterile triggers including monosodium urate crystals, silica, alum, asbestos, fatty acids, ceramides, cholesterol crystals and aggregates of beta-amyloid peptide. Assembly of an inflammasome platform facilitates autocatalysis of procaspase-1 yielding a highly active cysteine protease responsible for activation and release of pro-IL-1β and pro-IL-18. Thus, release of these highly inflammatory cytokines is achieved only in response to inflammasome sensors detecting and responding to specific molecular danger signals.

In humans, 22 NLR proteins are divided into four NLR subfamilies according to their N-terminal domains. NLRA contains a CARD-AT domain, NLRB (NAIP) contains a BIR domain, NLRC (including NOD1 and NOD2) contains a CARD domain, and NLRP contains a pyrin domain. Multiple NLR family members are associated with inflammasome formation including NLRP1, NLRP3, NLRP6, NLRP7, NLRP12 and NLRC4 (IPAF).

Two other structurally distinct inflammasome structures containing a PYHIN domain (pyrin and HIN domain containing protein) namely Absent in Melanoma 2 (AIM2) and IFNλ-inducible protein 16 (IFI16) (Latz et al., Nat Rev Immunol 2013 13(6) 397-311) serve as intracellular DNA sensors. Pyrin (encoded by the MEFV gene) represents another type of inflammasome platform associated with proIL-1β activation (Chae et al., Immunity 34, 755-768, 2011).

Requiring assembly of an inflammasome platform to achieve activation and release of IL-1β and IL-18 from monocytes and macrophages ensures their production is carefully orchestrated via a 2-step process. First, the cell must encounter a priming ligand (such as the TLR4 receptor ligand LPS, or an inflammatory cytokine such as TNFα) which leads to NFkB dependent transcription of NLRP3, pro-IL-1β and pro-IL-18. The newly translated procytokines remain intracellular and inactive unless producing cells encounter a second signal leading to activation of an inflammasome scaffold and maturation of procaspase-1.

In addition to proteolytic activation of pro-IL-1β and pro-IL-18, active caspase-1 also triggers a form of inflammatory cell death known as pyroptosis through cleavage of gasdermin-D. Pyroptosis allows the mature forms of IL-1β and IL-18 to be externalised along with release of alarmin molecules (compounds that promote inflammation and activate innate and adaptive immunity) such as high mobility group box 1 protein (HMGB1), IL-33, and IL-1α.

Although inflammasome activation appears to have evolved as an important component of host immunity to pathogens, the NLRP3 inflammasome is unique in its ability activate in response to endogenous and exogenous sterile danger signals. Many such sterile signals have been elucidated, and their formation is associated with specific disease states. For example, uric acid crystals found in gout patients are effective triggers of NLRP3 activation. Similarly, cholesterol crystals found in atherosclerotic patients can also promote NLRP3 activation. Recognition of the role of sterile danger signals as NLRP3 activators led to IL-1β and IL-18 being implicated in a diverse range of pathophysiological indications including metabolic, physiologic, inflammatory, hematologic and immunologic disorders.

A link to human disease is best exemplified by discovery that mutations in the NLRP3 gene which lead to gain-of-function confer a range of autoinflammatory conditions collectively known as cryopyrin-associated periodic syndromes (CAPS) including familial cold autoinflammatory syndrome (FCAS), Muckle-Wells syndrome (MWS) and Neonatal onset multisystem inflammatory disease (NOMID) (Hoffman et al., Nat Genet. 29(3) (2001) 301-305). Likewise, sterile mediator-induced activation of NLRP3 has been implicated in a wide range of disorders including joint degeneration (gout, rheumatoid arthritis, osteoarthritis), cardiometabolic (type 2 diabetes, atherosclerosis, hypertension), Central Nervous System (Alzheimer's Disease, Parkinson's disease, multiple sclerosis), gastrointestinal (Crohn's disease, ulcerative colitis), lung (chronic obstructive pulmonary disease (COPD), asthma, idiopathic pulmonary fibrosis) and liver (fibrosis, non-alcoholic fatty liver disease, non-alcoholic steatohepatitis (NASH)). It is further believed that NLRP3 activation promotes kidney inflammation and thus contributes to chronic kidney disease (CKD).

Current treatment options for diseases where IL-1 is implicated as a contributor to pathogenesis include the IL-1 receptor antagonist anakinra, an Fc-containing fusion construct of the extracellular domains of the IL-1 receptor and IL-1 receptor accessory protein (rilonacept) and the anti-IL-1β monoclonal antibody canakinumab. For example, canakinumab is licensed for CAPS, Tumor Necrosis Factor Receptor Associated Periodic Syndrome (TRAPS), Hyperimmunoglobulin D Syndrome (HIDS)/Mevalonate Kinase Deficiency (MKD), Familial Mediterranean Fever (FMF) and gout.

Some small molecules have been reported to inhibit function of the NLRP3 inflammasome. Glyburide, for example, is a specific inhibitor of NLRP3 activation, albeit at micromolar concentrations which are unlikely attainable in vivo. Non-specific agents such as parthenolide, Bay 11-7082, and 3,4-methylenedioxy-β-nitrostyrene are reported to impair NLRP3 activation but are expected to possess limited therapeutic utility due to their sharing of a common structural feature consisting of an olefin activated by substitution with an electron withdrawing group; this can lead to undesirable formation of covalent adducts with protein-bearing thiol groups. A number of natural products, for example β-hydroxybutyrate, sulforaphane, quercetin, and salvianolic acid, also are reported to suppress NLRP3 activation. Likewise, numerous effectors/modulators of other molecular targets have been reported to impair NLRP3 activation including agonists of the G-protein coupled receptor TGR5, an inhibitor of sodium-glucose co-transport epigliflozin, the dopamine receptor antagonist A-68930, the serotonin reuptake inhibitor fluoxetine, fenamate non-steroidal anti-inflammatory drugs, and the β-adrenergic receptor blocker nebivolol. Utility of these molecules as therapeutics for the chronic treatment of NLRP3-dependent inflammatory disorders remains to be established. A series of sulfonylurea-containing molecules was previously identified as potent and selective inhibitors of post-translational processing of pro-IL-1β (Perregaux et al., J Pharmacol. Exp. Ther. 299, 187-197, 2001). The exemplar molecule CP-456,773 from this work was recently characterised as a specific inhibitor of NLRP3 activation (Coll et al., Nat Med 21.3 (2015): 248-255.).

The disclosure relates to compounds useful for the specific modulation of NLRP3-dependent cellular processes. In particular, compounds with improved physicochemical, pharmacological and pharmaceutical properties to existing NLRP3-modulating compounds are desired.

Definitions

Unless otherwise stated, the following terms used in the specification and claims have the following meanings set out below.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intends to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl). In some embodiments, the heterocycloalkyl is 5,6-dihydro-4H-cyclopenta[b]thiophenyl (e.g., 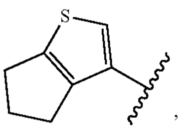, 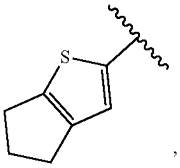, or 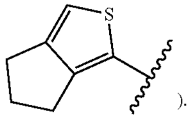).

In some embodiments, the heterocycloalkyl is 4,5,6,7-tetrahydrobenzofuranyl (e.g., 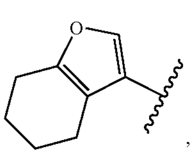, 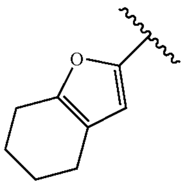, or 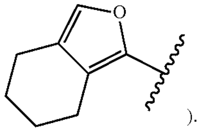).

In some embodiments, the heterocycloalkyl is 4,5,6,7-tetrahydrobenzo[b]thiophenyl (e.g., 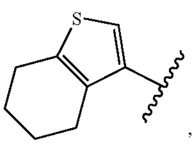, 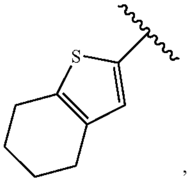, or 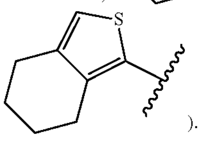).

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like. Conveniently, an aryl is phenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidised (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, isothiazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl). In some embodiments, the heteroaryl is thiophenyl or benzothiophenyl. In some embodiments, the heteroaryl is thiophenyl. In some embodiments, the heteroaryl benzothiophenyl.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a RM, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O$^-$.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5$^{th}$ edition, John Wiley & Sons: New York, 2001; Greene, T. W., Wuts, P. G. M., *Protective Groups in Organic Synthesis,* 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognised reference textbooks of organic synthesis known to those in the art One of ordinary skill in the art will note that, during the reaction sequences and synthetic schemes described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* 3$^{rd}$ edition, John Wiley & Sons: New York, 1999.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. It is to be further understood, unless otherwise stated, any description of a method of treatment includes use of the compounds to prepare a medicament to treat such condition. The treatment includes treatment of human or non-human animals including rodents and other disease models As used herein, the term "subject" is interchangeable with the term "subject in need thereof", both of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

As used herein, the term "therapeutically effective amount", refers to an amount of a pharmaceutical agent to treat or ameliorate an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilisation. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebuliser.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. Improvement in survival and growth indicates regression. As used herein, the term "dosage effective manner" refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

The dosage regimen utilising the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in *Remington: the Science and Practice of Pharmacy,* 19$^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Compounds of the Present Disclosure

In some aspects, the present disclosure provides, inter alia, a compound of Formula (I):

(I)

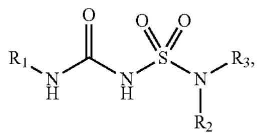

or a prodrug, solvate, or pharmaceutically acceptable salt thereof, wherein:

$R_1$ is 5- to 12-membered heterocycloalkyl or 5- to 12-membered heteroaryl optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), —($C_1$-$C_6$ alkyl)-O($C_1$-$C_6$ alkyl), cyano, halo, $C_3$-$C_8$ cycloalkyl, $C_3$-$C_8$ aryl, 3- to 8-membered heterocycloalkyl, or 3- to 8-membered heteroaryl;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 5- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some aspects, the present disclosure provides, inter alia, a compound of Formula (I):

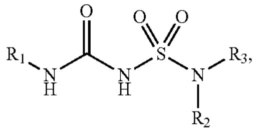

(I)

or a prodrug, solvate, or pharmaceutically acceptable salt thereof, wherein:

$R_1$ is 5- to 12-membered heterocycloalkyl or 5- to 12-membered heteroaryl optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), —($C_1$-$C_6$ alkyl)-O($C_1$-$C_6$ alkyl), cyano, halo, $C_3$-$C_8$ cycloalkyl, $C_3$-$C_8$ aryl, 3- to 8-membered heterocycloalkyl, or 3- to 8-membered heteroaryl;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some aspects, the compound is of Formula (I), or a prodrug, solvate, or pharmaceutically acceptable salt thereof, wherein:

$R_1$ is 5- to 12-membered heterocycloalkyl or 5- to 12-membered heteroaryl, wherein at least one heteroatom in the 5- to 12-membered heterocycloalkyl or 5- to 12-membered heteroaryl is O or S, and wherein the 5- to 12-membered heterocycloalkyl or 5- to 12-membered heteroaryl is optionally substituted with one or more $R_{1S}$;

each $R_{1S}$ is independently $C_1$-$C_6$ alkyl, $C_1$-$C_6$ haloalkyl, —O($C_1$-$C_6$ alkyl), cyano, halo, $C_3$-$C_8$ cycloalkyl, or $C_3$-$C_8$ aryl;

$R_2$ is —$(CH_2)_n$—$R_{2S}$, wherein n is 0, 1, or 2;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, halo, —OH, —O($C_1$-$C_6$ alkyl), —$NH_2$, —NH($C_1$-$C_6$ alkyl), or —N($C_1$-$C_6$ alkyl)$_2$; and $R_3$ is 5- to 6-membered heterocycloalkyl or 5- or 6-membered heteroaryl, wherein the 5- to 12-membered heterocycloalkyl or 5- or 6-membered heteroaryl is optionally substituted with one or more $C_1$-$C_6$ alkyl, $C_3$-$C_8$ cycloalkyl, or halo.

In some aspects, the compound is of Formula (I), or a prodrug, solvate, or pharmaceutically acceptable salt thereof, wherein:

$R_1$ is 5- to 12-membered heterocycloalkyl or 5- to 12-membered heteroaryl, wherein at least one heteroatom in the 5- to 12-membered heterocycloalkyl or 5- to 12-membered heteroaryl is O or S, and wherein the 5- to 12-membered heterocycloalkyl or 5- to 12-membered heteroaryl is optionally substituted with one or more $R_{1S}$;

each $R_{1S}$ is independently $C_1$-$C_6$ alkyl, $C_1$-$C_6$ haloalkyl, —O($C_1$-$C_6$ alkyl), cyano, halo, $C_3$-$C_8$ cycloalkyl, or $C_3$-$C_8$ aryl;

$R_2$ is —$(CH_2)_n$—$R_{2S}$, wherein n is 0, 1, or 2;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, halo, —OH, —O($C_1$-$C_6$ alkyl), —$NH_2$, —NH($C_1$-$C_6$ alkyl), or —N($C_1$-$C_6$ alkyl)$_2$; and $R_3$ is 5- or 6-membered heteroaryl optionally substituted with one or more $C_1$-$C_6$ alkyl, $C_3$-$C_8$ cycloalkyl, or halo.

In some embodiments, the compound is of Formula (I), or a prodrug, solvate, or pharmaceutically acceptable salt thereof, wherein:

$R_1$ is 5- to 12-membered heteroaryl optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, the compound is of Formula (I), or a prodrug, solvate, or pharmaceutically acceptable salt thereof, wherein:

$R_1$ is 5- to 12-membered heteroaryl optionally substituted with one or more $R_{1S}$, wherein at least one heteroatom in the 5- to 12-membered heteroaryl is S;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, the compound is of Formula (I), or a prodrug, solvate, or pharmaceutically acceptable salt thereof, wherein:

$R_1$ is 5- to 12-membered heteroaryl optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, the compound is of Formula (I), or a prodrug, solvate, or pharmaceutically acceptable salt thereof, wherein:

$R_1$ is 5- to 12-membered heteroaryl optionally substituted with one or more $R_{1S}$, wherein at least one heteroatom in the 5- to 12-membered heteroaryl is S;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, the compound is of Formula (I) or a prodrug, solvate, or pharmaceutically acceptable salt thereof, wherein:

$R_1$ is 5- to 12-membered heteroaryl optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is $R_{2S}$;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, the compound is of Formula (I) or a prodrug, solvate, or pharmaceutically acceptable salt thereof, wherein:

$R_1$ is thiophenyl or benzothiophenyl, wherein the thiophenyl or benzothiophenyl is optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is $R_{2S}$;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, the compound is of Formula (I) or a prodrug, solvate, or pharmaceutically acceptable salt thereof, wherein:

$R_1$ is thiophenyl or benzothiophenyl, wherein the thiophenyl or benzothiophenyl is optionally substituted with one or more $R_{1S}$;

each $R_{1S}$ is $C_1$-$C_6$ alkyl or halo;

$R_2$ is $R_{2S}$;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

It is understood that, for a compound of Formula (I), $R_1$, $R_{1S}$, $R_2$, $R_{2S}$, $R_3$, $R_{3S}$, and $X_2$ can each be, where applicable, selected from the groups described herein, and any group described herein for any of $R_1$, $R_{1S}$, $R_2$, $R_{2S}$, $R_3$, $R_{3S}$, and $X_2$ can be combined, where applicable, with any group described herein for one or more of the remainder of $R_1$, $R_{1S}$, $R_2$, $R_{2S}$, $R_3$, $R_{3S}$, and $X_2$.

In some embodiments, the compound of Formula I is not N-(4,6-dimethoxy-1,3,5-triazin-2-yl)-N'-[[(4,6-dimethyl-2-pyrimidinyl)methylamino]sulfonyl]-urea, N-[[(4,6-dimethyl-2-pyrimidinyl)methylamino]sulfonyl]-N'-(4-methoxy-6-methyl-1,3,5-triazin-2-yl)-urea, N-(4,6-dimethoxy-2-pyrimidinyl)-N'-[(methyl-1H-pyrrol-1-ylamino)sulfonyl]-urea, or N-(4,6-dimethoxy-2-pyrimidinyl)-N'-[[(4,6-dimethyl-2-pyrimidinyl) methylamino]sulfonyl]-urea.

In some embodiments, the compound of Formula I is not N-(4,6-dimethoxy-1,3,5-triazin-2-yl)-N'-[[(4,6-dimethyl-2-pyrimidinyl)methylamino]sulfonyl]-urea, N-[[(4,6-dimethyl-2-pyrimidinyl)methylamino]sulfonyl]-N'-(4-methoxy-6-methyl-1,3,5-triazin-2-yl)-urea, N-(4,6-dimethoxy-2-pyrimidinyl)-N'-[(methyl-1H-pyrrol-1-ylamino)sulfonyl]-urea, N-(4,6-dimethoxy-2-pyrimidinyl)-N'-[[(4,6-dimethyl-2-pyrimidinyl)methylamino]sulfonyl]-urea, or a prodrug, solvate, or pharmaceutically acceptable salt thereof.

In some embodiments, $R_1$ is 5- to 12-membered heterocycloalkyl or 5- to 12-membered heteroaryl, wherein at least one heteroatom in the 5- to 12-membered heterocycloalkyl or 5- to 12-membered heteroaryl is O or S, and wherein the 5- to 12-membered heterocycloalkyl or 5- to 12-membered heteroaryl is optionally substituted with one or more $R_{1S}$.

In some embodiments, $R_1$ is 5- to 12-membered heterocycloalkyl or 5- to 12-membered heteroaryl, wherein the 5- to 12-membered heterocycloalkyl or 5- to 12-membered heteroaryl is optionally substituted with one or more $R_{1S}$, and wherein $R_1$ is attached to the rest of Formula (I) via a carbon atom in $R_1$.

In some embodiments, $R_1$ is 5- to 12-membered heterocycloalkyl or 5- to 12-membered heteroaryl, wherein at least one heteroatom in the 5- to 12-membered heterocycloalkyl or 5- to 12-membered heteroaryl is O or S; wherein the 5- to 12-membered heterocycloalkyl or 5- to 12-membered heteroaryl is optionally substituted with one or more $R_{1S}$; and wherein $R_1$ is attached to the rest of Formula (I) via a carbon atom in $R_1$.

In some embodiments, $R_1$ is attached to the rest of Formula (I) via a carbon atom in $R_1$.

In some embodiments, $R_1$ is 5- to 12-membered heterocycloalkyl optionally substituted with one or more $R_{1S}$.

In some embodiments, $R_1$ is 5- to 12-membered heterocycloalkyl optionally substituted with one or more $R_{1S}$, wherein $R_1$ is attached to the rest of Formula (I) via a carbon atom in the $C_5$-$C_{12}$ heterocycloalkyl.

In some embodiments, $R_1$ is 5- to 12-membered heterocycloalkyl optionally substituted with one or more $C_1$-$C_6$ alkyl or halo.

In some embodiments, $R_1$ is 5- to 12-membered heterocycloalkyl optionally substituted with one or more $C_1$-$C_6$ alkyl (e.g., methyl, ethyl, or propyl).

In some embodiments, $R_1$ is 5- to 12-membered heterocycloalkyl optionally substituted with one or more halo (e.g., Cl).

In some embodiments, $R_1$ is 5- to 12-membered heterocycloalkyl.

In some embodiments, $R_1$ is 5- to 12-membered heterocycloalkyl substituted with one or more $R_{1S}$.

In some embodiments, $R_1$ is 5- to 12-membered heterocycloalkyl substituted with one or more $C_1$-$C_6$ alkyl or halo.

In some embodiments, $R_1$ is 5- to 12-membered heterocycloalkyl substituted with one or more $C_1$-$C_6$ alkyl (e.g., methyl, ethyl, or propyl).

In some embodiments, $R_1$ is 5- to 12-membered heterocycloalkyl substituted with one or more halo (e.g., Cl).

In some embodiments, $R_1$ is 5- to 12-membered heterocycloalkyl optionally substituted with one or more $R_{1S}$, wherein at least one heteroatom in the 5- to 12-membered heterocycloalkyl is N, O, or S.

In some embodiments, $R_1$ is 5- to 12-membered heterocycloalkyl optionally substituted with one or more $R_{1S}$, wherein at least one heteroatom in the 5- to 12-membered heterocycloalkyl is S.

In some embodiments, $R_1$ is 5- to 12-membered heterocycloalkyl optionally substituted with one or more $R_{1S}$, wherein the 5- to 12-membered heterocycloalkyl comprises one heteroatom.

In some embodiments, $R_1$ is 5- to 9-membered monocyclic heterocycloalkyl optionally substituted with one or more $R_{1S}$.

In some embodiments, $R_1$ is 5- to 6-membered monocyclic heterocycloalkyl optionally substituted with one or more $R_{1S}$.

In some embodiments, $R_1$ is 8- to 12-membered bicyclic heterocycloalkyl optionally substituted with one or more $R_{1S}$.

In some embodiments, $R_1$ is 8- to 10-membered bicyclic heterocycloalkyl optionally substituted with one or more $R_{1S}$.

In some embodiments, $R_1$ is 8- to 9-membered bicyclic heterocycloalkyl optionally substituted with one or more $R_{1S}$.

In some embodiments, $R_1$ is 8- to 9-membered bicyclic heterocycloalkyl optionally substituted with one or more $R_{1S}$, wherein at least one heteroatom in the 8- to 9-membered bicyclic heterocycloalkyl is O or S.

In some embodiments, $R_1$ is 8- to 9-membered bicyclic heterocycloalkyl optionally substituted with one or more $R_{1S}$, wherein at least one heteroatom in the 8- to 9-membered bicyclic heterocycloalkyl is O.

In some embodiments, $R_1$ is 8- to 9-membered bicyclic heterocycloalkyl optionally substituted with one or more $R_{1S}$, wherein at least one heteroatom in the 8- to 9-membered bicyclic heterocycloalkyl is S.

In some embodiments, $R_1$ is 8-membered bicyclic heterocycloalkyl optionally substituted with one or more $R_{1S}$.

In some embodiments, $R_1$ is 8-membered bicyclic heterocycloalkyl optionally substituted with one or more $R_{1S}$, wherein at least one heteroatom in the 8-membered bicyclic heterocycloalkyl is O or S.

In some embodiments, $R_1$ is 8-membered bicyclic heterocycloalkyl optionally substituted with one or more $R_{1S}$, wherein at least one heteroatom in the 8-membered bicyclic heterocycloalkyl is O.

In some embodiments, $R_1$ is 8-membered bicyclic heterocycloalkyl optionally substituted with one or more $R_{1S}$, wherein at least one heteroatom in the 8-membered bicyclic heterocycloalkyl is S.

In some embodiments, $R_1$ is 5,6-dihydro-4H-cyclopenta[b]thiophenyl optionally substituted with one or more $R_{1S}$.

In some embodiments, $R_1$ is 5,6-dihydro-4H-cyclopenta[b]thiophenyl optionally substituted with one or more $R_{1S}$, wherein $R_1$ is attached to the rest of Formula (I) via a carbon atom in the 5,6-dihydro-4H-cyclopenta[b]thiophenyl.

In some embodiments, $R_1$ is 5,6-dihydro-4H-cyclopenta[b]thiophenyl.

In some embodiments, $R_1$ is

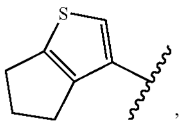,
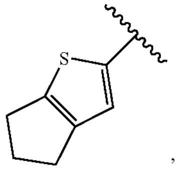, or
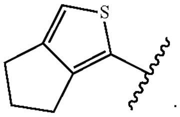.

In some embodiments, $R_1$ is 5,6-dihydro-4H-cyclopenta[b]thiophenyl substituted with one or more $R_{1S}$.

In some embodiments, $R_1$ is

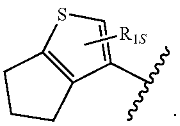.

In some embodiments, $R_1$ is

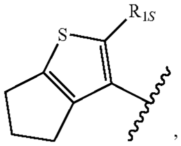,
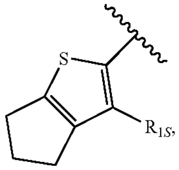 or
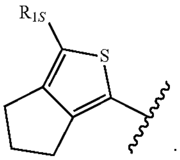.

In some embodiments, $R_1$ is 5,6-dihydro-4H-cyclopenta[b]thiophenyl substituted with one or more $C_1$-$C_6$ alkyl, $C_1$-$C_6$ haloalkyl, —O($C_1$-$C_6$ alkyl), or halo.

In some embodiments, $R_1$ is 5,6-dihydro-4H-cyclopenta[b]thiophenyl substituted with one or more $C_1$-$C_6$ alkyl, $C_1$-$C_6$ haloalkyl, or —O($C_1$-$C_6$ alkyl).

In some embodiments, $R_1$ is 5,6-dihydro-4H-cyclopenta[b]thiophenyl substituted with one or more $C_1$-$C_6$ alkyl (e.g., methyl, ethyl, propyl, or butyl).

In some embodiments, $R_1$ is 5,6-dihydro-4H-cyclopenta[b]thiophenyl substituted with one or more $C_1$-$C_6$ haloalkyl (e.g., —$CF_3$).

In some embodiments, $R_1$ is 5,6-dihydro-4H-cyclopenta[b]thiophenyl substituted with one or more —O($C_1$-$C_6$ alkyl) (e.g., —$OCH_3$).

In some embodiments, $R_1$ is 5,6-dihydro-4H-cyclopenta[b]thiophenyl substituted with one or more halo (e.g., Cl).

In some embodiments, $R_1$ is

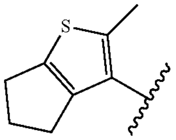,
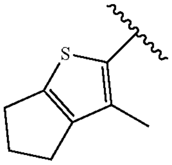,
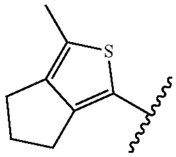,
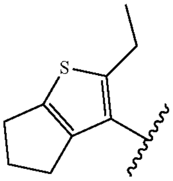,
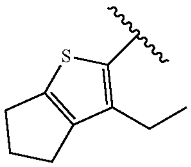,
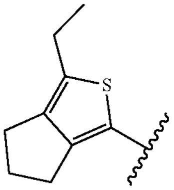,
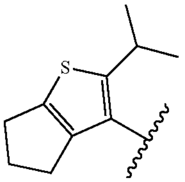,
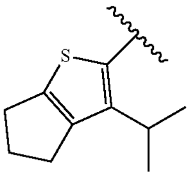,
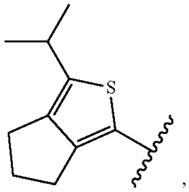,
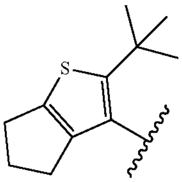,
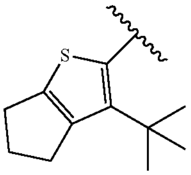,
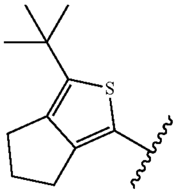,
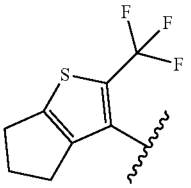,
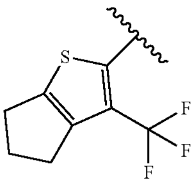,
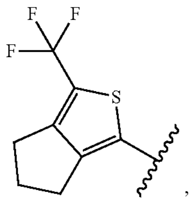,
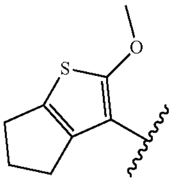, -continued

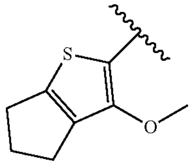
, or
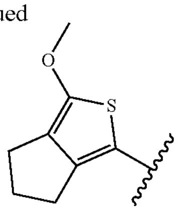
.

In some embodiments, $R_1$ is

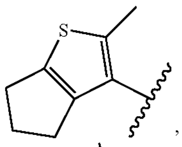
,
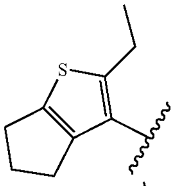
,
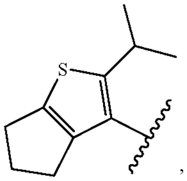
, or
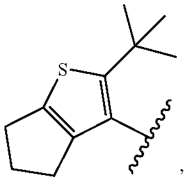
,
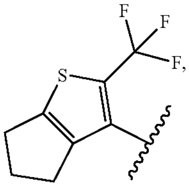
or
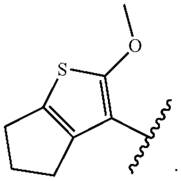
.

In some embodiments, $R_1$ is 9-membered bicyclic heterocycloalkyl optionally substituted with one or more $R_{1S}$.

In some embodiments, $R_1$ is 9-membered bicyclic heterocycloalkyl optionally substituted with one or more $R_{1S}$, wherein at least one heteroatom in the 8-membered bicyclic heterocycloalkyl is O or S.

In some embodiments, $R_1$ is 9-membered bicyclic heterocycloalkyl optionally substituted with one or more $R_{1S}$, wherein at least one heteroatom in the 8-membered bicyclic heterocycloalkyl is O.

In some embodiments, $R_1$ is 4,5,6,7-tetrahydrobenzofuranyl optionally substituted with one or more $R_{1S}$.

In some embodiments, $R_1$ is 4,5,6,7-tetrahydrobenzofuranyl optionally substituted with one or more $R_{1S}$, wherein $R_1$ is attached to the rest of Formula (I) via a carbon atom in the 54,5,6,7-tetrahydrobenzofuranyl.

In some embodiments, $R_1$ is 4,5,6,7-tetrahydrobenzofuranyl.

In some embodiments, $R_1$ is

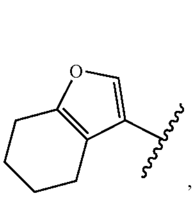
,
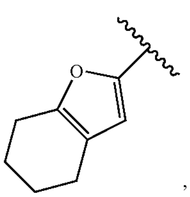
, or

-continued

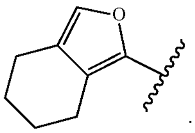
.

In some embodiments, $R_1$ is 4,5,6,7-tetrahydrobenzofuranyl substituted with one or more $R_{1S}$.

In some embodiments, $R_1$ is

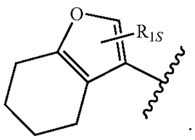
.

In some embodiments, $R_1$ is

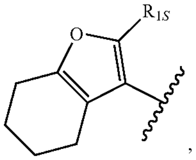
,
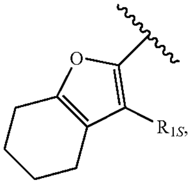
or
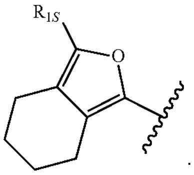
.

In some embodiments, $R_1$ is 44,5,6,7-tetrahydrobenzofuranyl substituted with one or more $C_1$-$C_6$ alkyl.

In some embodiments, $R_1$ is

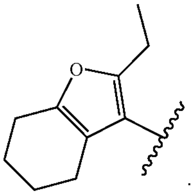 [SMILES: *c1c(CC)oc2c1CCCC2]
.

In some embodiments, $R_1$ is 9-membered bicyclic heterocycloalkyl optionally substituted with one or more $R_{1S}$, wherein at least one heteroatom in the 8-membered bicyclic heterocycloalkyl is S.

In some embodiments, $R_1$ is 4,5,6,7-tetrahydrobenzo[b]thiophenyl optionally substituted with one or more $R_{1S}$.

In some embodiments, $R_1$ is 4,5,6,7-tetrahydrobenzo[b]thiophenyl optionally substituted with one or more $R_{1S}$, wherein $R_1$ is attached to the rest of Formula (I) via a carbon atom in the 4,5,6,7-tetrahydrobenzo[b]thiophenyl.

In some embodiments, $R_1$ is 4,5,6,7-tetrahydrobenzo[b]thiophenyl.

In some embodiments, $R_1$ is

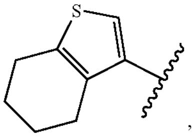

,

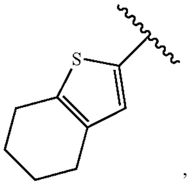

, or

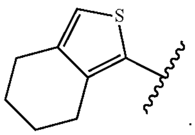

.

In some embodiments, $R_1$ is 4,5,6,7-tetrahydrobenzo[b]thiophenyl substituted with one or more $R_{1S}$.

In some embodiments, $R_1$ is

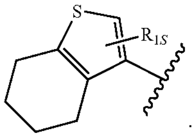

.

In some embodiments, $R_1$ is

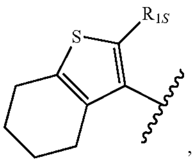

,

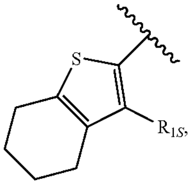

or

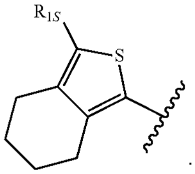

.

In some embodiments, $R_1$ is 4,5,6,7-tetrahydrobenzo[b]thiophenyl substituted with one or more $C_1$-$C_6$ alkyl.

In some embodiments, $R_1$ is

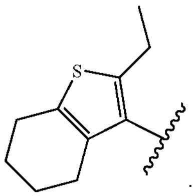 [SMILES: *c1c(CC)sc2c1CCCC2]

.

In some embodiments, $R_1$ is

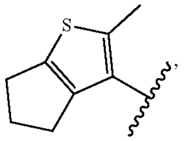

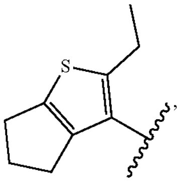

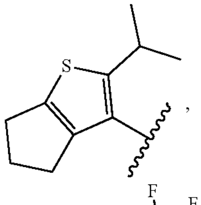

, or

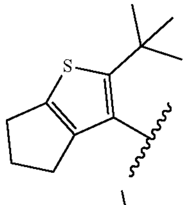

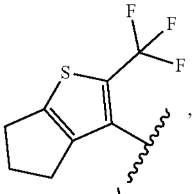

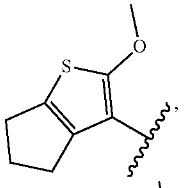

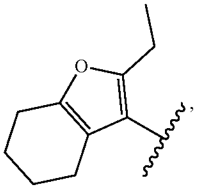

or

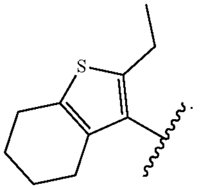

In some embodiments, $R_1$ is 5- to 12-membered heteroaryl optionally substituted with one or more $R_{1S}$.

In some embodiments, $R_1$ is 5- to 12-membered heteroaryl optionally substituted with one or more $R_{1S}$, wherein $R_1$ is attached to the rest of Formula (I) via a carbon atom in the $C_5$-$C_{12}$ heteroaryl.

In some embodiments, $R_1$ is 5- to 12-membered heteroaryl optionally substituted with one or more $C_1$-$C_6$ alkyl or halo.

In some embodiments, $R_1$ is 5- to 12-membered heteroaryl optionally substituted with one or more $C_1$-$C_6$ alkyl (e.g., methyl, ethyl, or propyl).

In some embodiments, $R_1$ is 5- to 12-membered heteroaryl optionally substituted with one or more halo (e.g., Cl).

In some embodiments, $R_1$ is 5- to 12-membered heteroaryl.

In some embodiments, $R_1$ is 5- to 12-membered heteroaryl substituted with one or more $R_{1S}$.

In some embodiments, $R_1$ is 5- to 12-membered heteroaryl substituted with one or more $C_1$-$C_6$ alkyl or halo.

In some embodiments, $R_1$ is 5- to 12-membered heteroaryl substituted with one or more $C_1$-$C_6$ alkyl (e.g., methyl, ethyl, or propyl).

In some embodiments, $R_1$ is 5- to 12-membered heteroaryl substituted with one or more halo (e.g., Cl).

In some embodiments, $R_1$ is 5- to 12-membered heteroaryl optionally substituted with one or more $R_{1S}$, wherein at least one heteroatom in the 5- to 12-membered heteroaryl is N, O, or S.

In some embodiments, $R_1$ is 5- to 12-membered heteroaryl optionally substituted with one or more $R_{1S}$, wherein at least one heteroatom in the 5- to 12-membered heteroaryl is S.

In some embodiments, $R_1$ is 5- to 12-membered heteroaryl optionally substituted with one or more $R_{1S}$, wherein the 5- to 12-membered heteroaryl comprises one heteroatom.

In some embodiments, $R_1$ is 5- to 9-membered monocyclic heteroaryl optionally substituted with one or more $R_{1S}$.

In some embodiments, $R_1$ is 5- to 6-membered monocyclic heteroaryl optionally substituted with one or more $R_{1S}$.

In some embodiments, $R_1$ is 5-membered monocyclic heteroaryl optionally substituted with one or more $R_{1S}$.

In some embodiments, $R_1$ is 5-membered monocyclic heteroaryl optionally substituted with one or more $R_{1S}$, wherein at least one heteroatom in the $C_5$ monocyclic heteroaryl is O.

In some embodiments, $R_1$ is 5-membered monocyclic heteroaryl optionally substituted with one or more $R_{1S}$, wherein at least one heteroatom in the $C_5$ monocyclic heteroaryl is S.

In some embodiments, $R_1$ is 5-membered monocyclic heteroaryl optionally substituted with one or more $R_{1S}$, wherein at least one heteroatom in the $C_5$ monocyclic heteroaryl is S, and wherein at least one heteroatom in the $C_5$ monocyclic heteroaryl is N.

In some embodiments, $R_1$ is 5-membered monocyclic heteroaryl optionally substituted with one or more $R_{1S}$, wherein the $C_5$ monocyclic heteroaryl comprises one heteroatom.

In some embodiments, $R_1$ is 5-membered monocyclic heteroaryl optionally substituted with one or more $R_{1S}$, wherein the $C_5$ monocyclic heteroaryl comprises one heteroatom being O.

In some embodiments, $R_1$ is furanyl optionally substituted with one or more $R_{1S}$.

In some embodiments, $R_1$ is furanyl optionally substituted with one or more $R_{1S}$, wherein $R_1$ is attached to the rest of Formula (I) via a carbon atom in the furanyl.

In some embodiments, $R_1$ is furanyl.

In some embodiments, $R_1$ is or

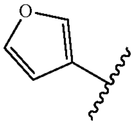 or 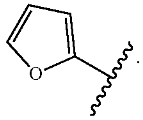.

In some embodiments, $R_1$ is furanyl substituted with one or more $R_{1S}$.

In some embodiments, $R_1$ is

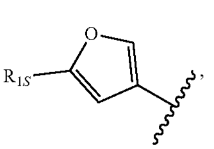, 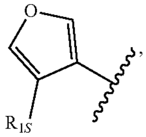, 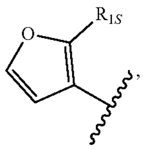, 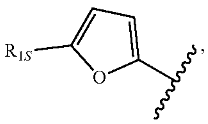, 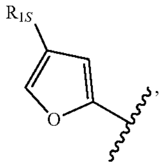, or

-continued

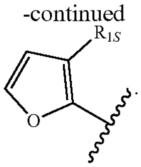.

In some embodiments, $R_1$ is

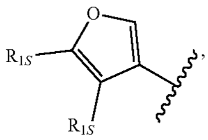, 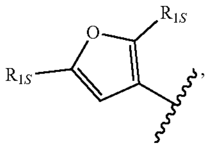, 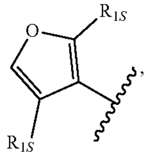, 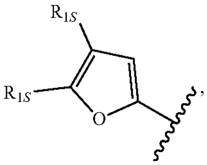, 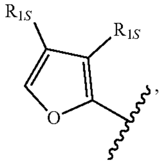, or 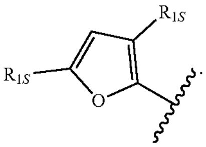.

In some embodiments, $R_1$ is

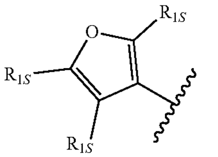 or 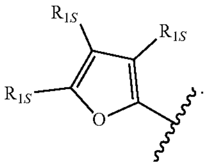.

In some embodiments, $R_1$ is furanyl substituted with one or more $C_1$-$C_6$ alkyl or halo.

In some embodiments, $R_1$ is furanyl substituted with one or more $C_1$-$C_6$ alkyl (e.g., methyl, ethyl, or propyl).

In some embodiments, $R_1$ is furanyl substituted with one or more halo (e.g. Cl).

In some embodiments, $R_1$ is

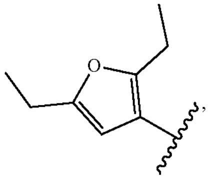, 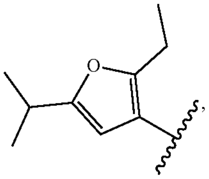, 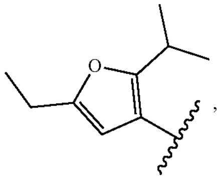, 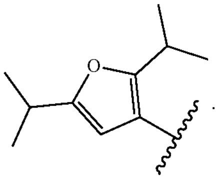.

In some embodiments, $R_1$ is 5-membered monocyclic heteroaryl optionally substituted with one or more $R_{1S}$, wherein the $C_5$ monocyclic heteroaryl comprises one heteroatom being S.

In some embodiments, $R_1$ is thiophenyl optionally substituted with one or more $R_{1S}$.

In some embodiments, $R_1$ is thiophenyl optionally substituted with one or more $R_{1S}$, wherein $R_1$ is attached to the rest of Formula (I) via a carbon atom in the thiophenyl.

In some embodiments, $R_1$ is thiophenyl.

In some embodiments, $R_1$ is

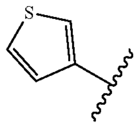 or 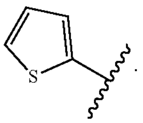.

In some embodiments, $R_1$ is thiophenyl substituted with one or more $R_{1S}$.

In some embodiments, $R_1$ is

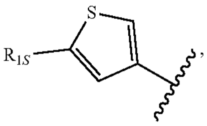, 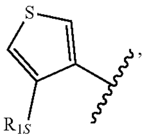, 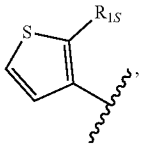,

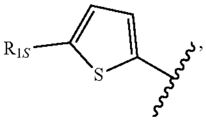, 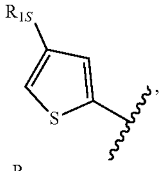, or

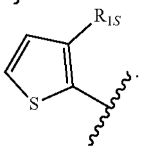.

In some embodiments, $R_1$ is

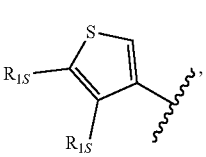, 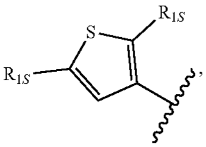,

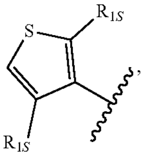, 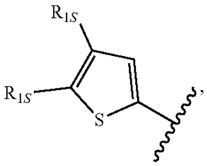,

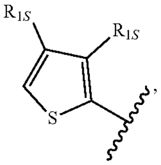 or 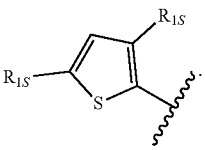.

In some embodiments, $R_1$ is

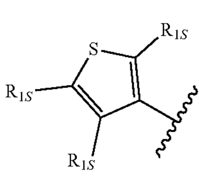 or 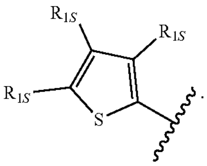.

In some embodiments, $R_1$ is thiophenyl substituted with one or more $C_1$-$C_6$ alkyl or halo.

In some embodiments, $R_1$ is thiophenyl substituted with one or more $C_1$-$C_6$ alkyl (e.g., methyl, ethyl, or propyl).

In some embodiments, $R_1$ is thiophenyl substituted with one or more halo (e.g., Cl).

In some embodiments $R_1$ is

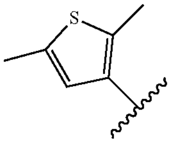, 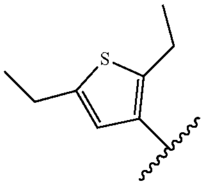,

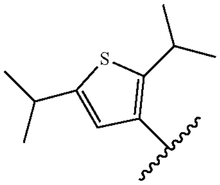, 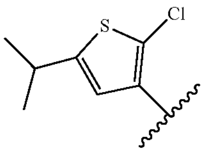,

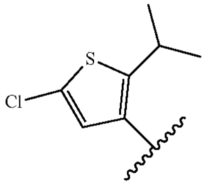, 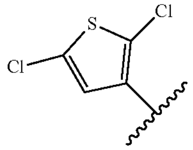,

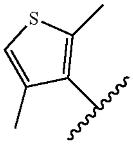, 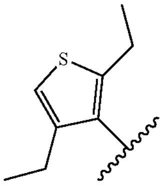, 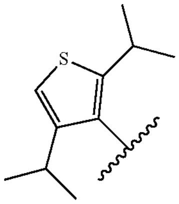,

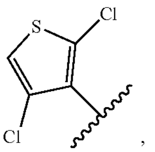, 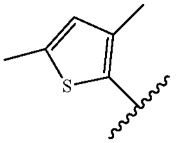,

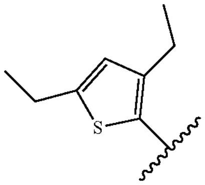, 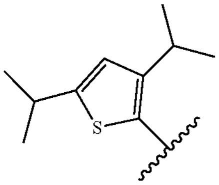,

-continued
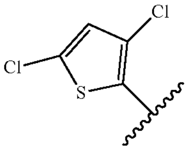,
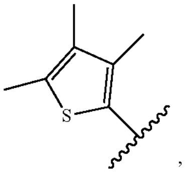,
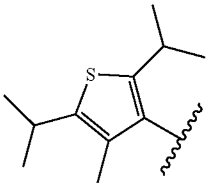,
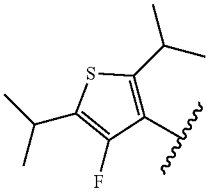,
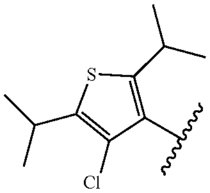, or
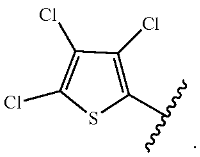.
In some embodiments, $R_1$ is
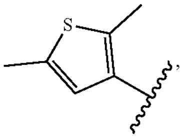,
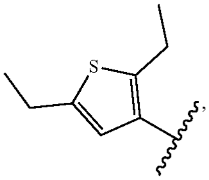,
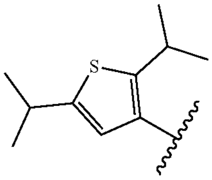,
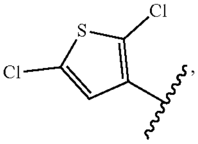,
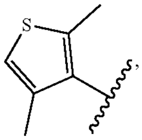,
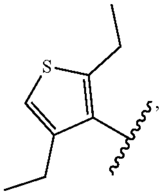,
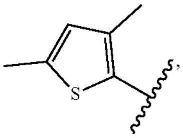 or
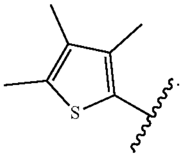.
In some embodiments, $R_1$ is
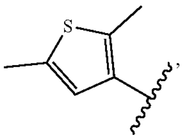,
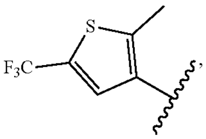,
-continued
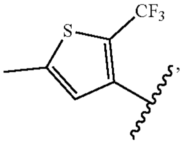,
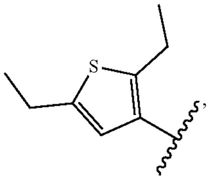,
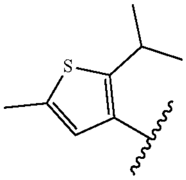,
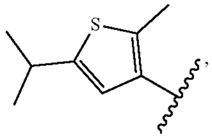,
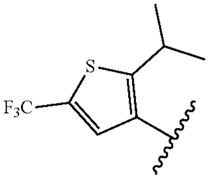,
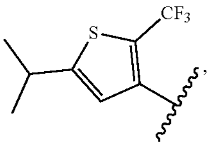,
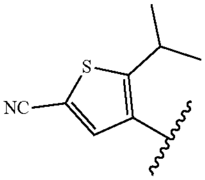,
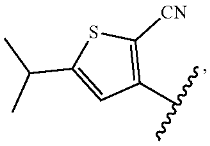,
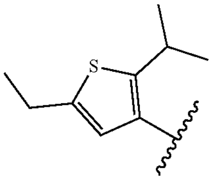,
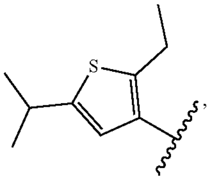,
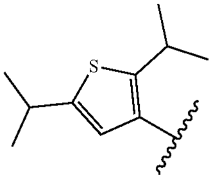,
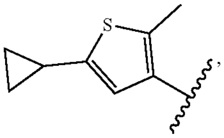,
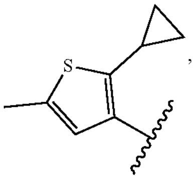,
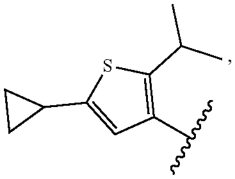,
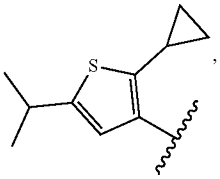,
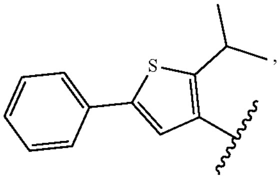,
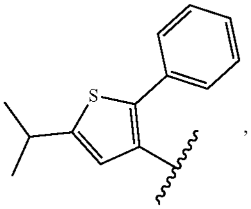,
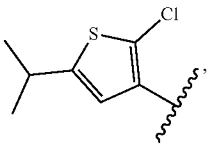, -continued

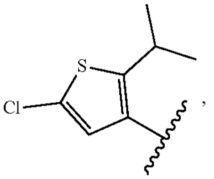 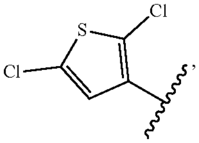

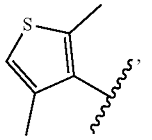 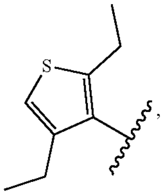 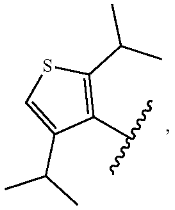

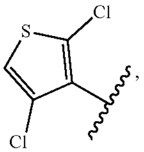 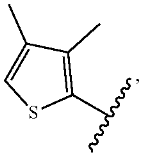 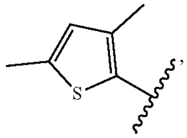

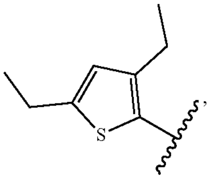 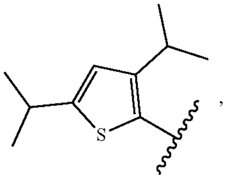

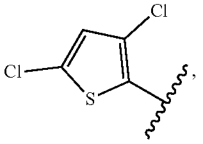 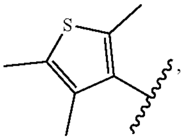

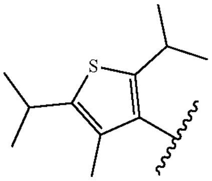 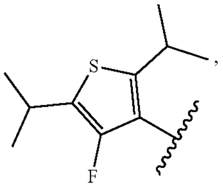

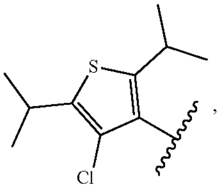 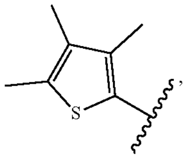 or

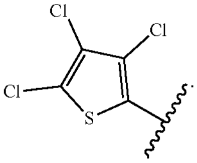

In some embodiments, $R_1$ is 5-membered monocyclic heteroaryl optionally substituted with one or more $R_{1S}$, wherein the $C_5$ monocyclic heteroaryl comprises two heteroatoms.

In some embodiments, $R_1$ is 5-membered monocyclic heteroaryl optionally substituted with one or more $R_{1S}$, wherein the $C_5$ monocyclic heteroaryl comprises two heteroatoms, wherein one heteroatom is S and the other heteroatom is N.

In some embodiments, $R_1$ is thiazolyl optionally substituted with one or more $R_{1S}$.

In some embodiments, $R_1$ is thiazolyl optionally substituted with one or more $R_{1S}$, wherein $R_1$ is attached to the rest of Formula (I) via a carbon atom in the thiazolyl.

In some embodiments, $R_1$ is thiazolyl.

In some embodiments, $R_1$ is

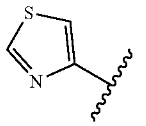 or 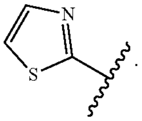

In some embodiments, $R_1$ is thiazolyl substituted with one or more $R_{1S}$.

In some embodiments, $R_1$ is

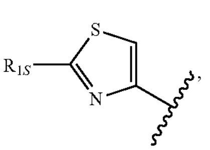 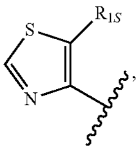

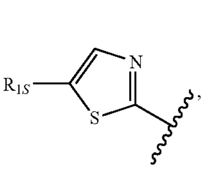 or 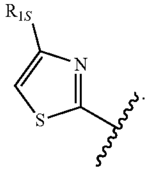

In some embodiments, $R_1$ is

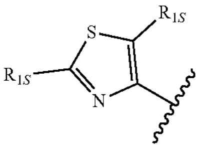 or 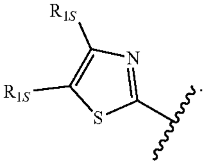

In some embodiments, $R_1$ is thiazolyl substituted with one or more $C_1$-$C_6$ alkyl or halo.

In some embodiments, $R_1$ is thiazolyl substituted with one or more $C_1$-$C_6$ alkyl (e.g., methyl, ethyl, or propyl).

In some embodiments, $R_1$ is thiazolyl substituted with one or more halo (e.g., Cl).

In some embodiments, $R_1$ is

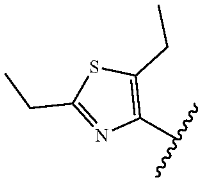 or 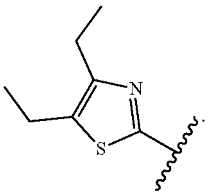

In some embodiments, $R_1$ is isothiazolyl optionally substituted with one or more $R_{1S}$.

In some embodiments, $R_1$ is isothiazolyl optionally substituted with one or more $R_{1S}$, wherein $R_1$ is attached to the rest of Formula (I) via a carbon atom in the isothiazolyl.

In some embodiments, $R_1$ is isothiazolyl.

In some embodiments, $R_1$ is

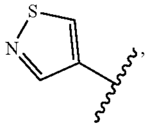, 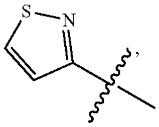, or 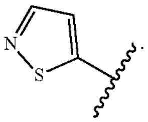.

In some embodiments, $R_1$ is isothiazolyl substituted with one or more $R_{1S}$.

In some embodiments, $R_1$ is

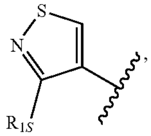, 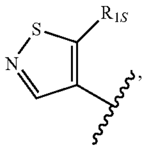, 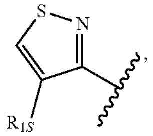,

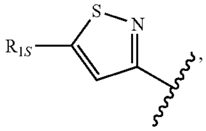, 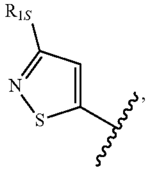, or 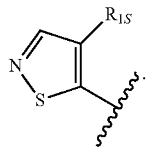.

In some embodiments, $R_1$ is

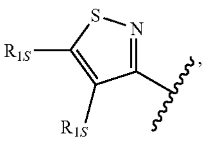, 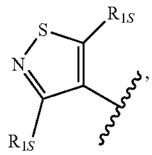, or 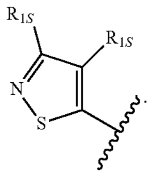.

In some embodiments, $R_1$ is isothiazolyl substituted with one or more $C_1$-$C_6$ alkyl or halo.

In some embodiments, $R_1$ is isothiazolyl substituted with one or more $C_1$-$C_6$ alkyl (e.g., methyl, ethyl, or propyl).

In some embodiments, $R_1$ is isothiazolyl substituted with one or more halo (e.g., Cl).

In some embodiments, $R_1$ is

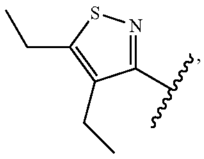, 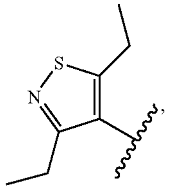, 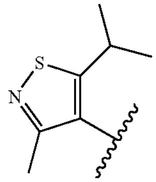, or

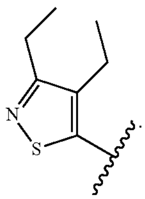.

In some embodiments, $R_1$ is 9- to 12-membered bicyclic heteroaryl optionally substituted with one or more $R_{1S}$.

In some embodiments, $R_1$ is 9- to 10-membered bicyclic heteroaryl optionally substituted with one or more $R_{1S}$.

In some embodiments, $R_1$ is 9-membered bicyclic heteroaryl optionally substituted with one or more $R_{1S}$.

In some embodiments, $R_1$ is 9-membered bicyclic heteroaryl optionally substituted with one or more $R_{1S}$, wherein at least one heteroatom in the 9-membered bicyclic heteroaryl is S.

In some embodiments, $R_1$ is benzothiophenyl optionally substituted with one or more $R_{1S}$.

In some embodiments, $R_1$ is benzothiophenyl optionally substituted with one or more $R_{1S}$, wherein $R_1$ is attached to the rest of Formula (I) via a carbon atom in the benzothiophenyl.

In some embodiments, $R_1$ is benzothiophenyl.

In some embodiments, $R_1$ is

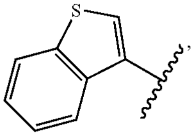, 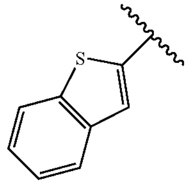, or

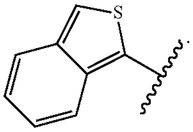.

In some embodiments, $R_1$ is benzothiophenyl substituted with one or more $R_{1S}$.

In some embodiments, $R_1$ is

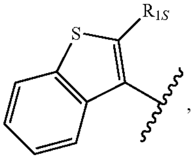, 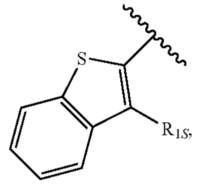, or

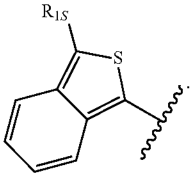.

In some embodiments, $R_1$ is benzothiophenyl substituted with one or more $C_1$-$C_6$ alkyl or halo.

In some embodiments, $R_1$ is benzothiophenyl substituted with one or more $C_1$-$C_6$ alkyl (e.g., methyl, ethyl, or propyl).

In some embodiments, $R_1$ is benzothiophenyl substituted with one or more halo (e.g., Cl).

In some embodiments, $R_1$ is

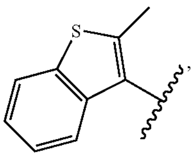, 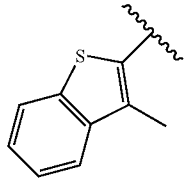, or

-continued
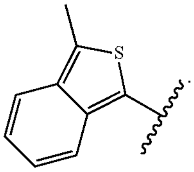
.
In some embodiments, $R_1$ is
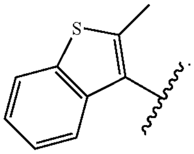 [SMILES: *c1c(C)sc2ccccc12]
.
In some embodiments, $R_1$ is
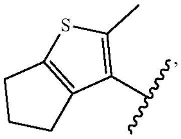
,
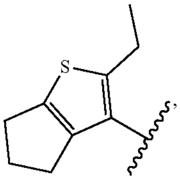
,
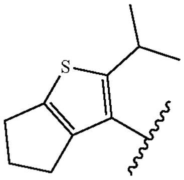
,
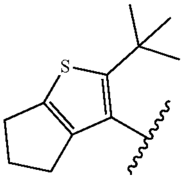
,
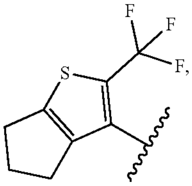
,
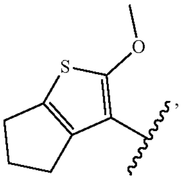
,
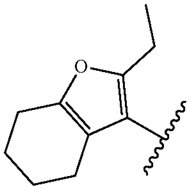
,
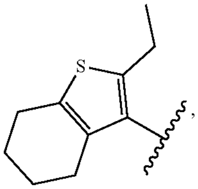
,
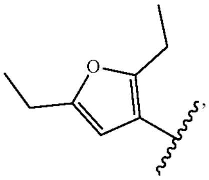
,
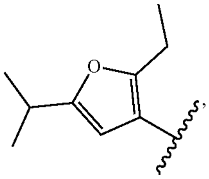
,
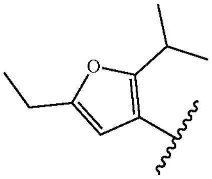
,
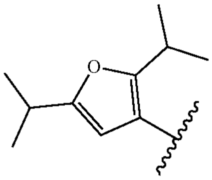
,
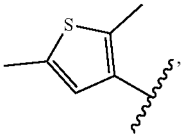
,
-continued
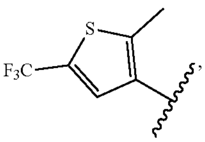
,
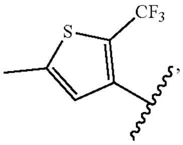
,
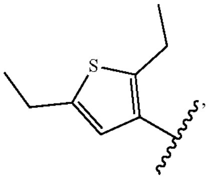
,
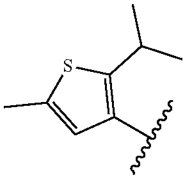
,
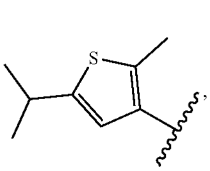
,
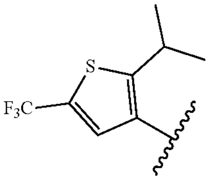
,
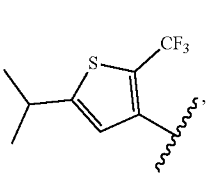
,
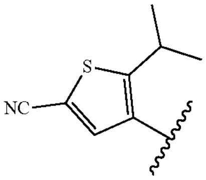
,
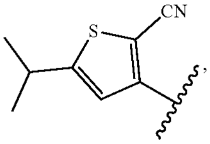
,
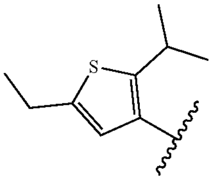
,
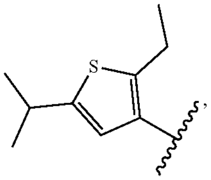
,
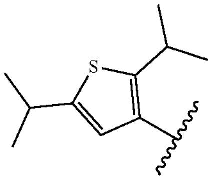
,
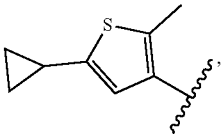
,
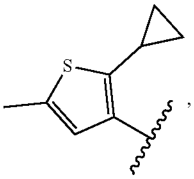
,
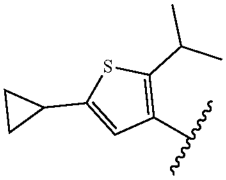
,
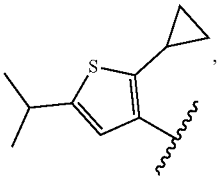
,
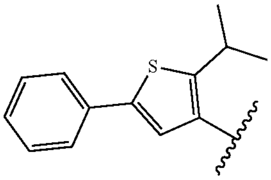
, -continued

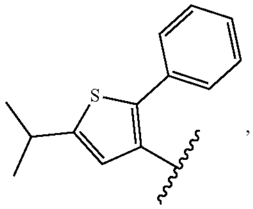,
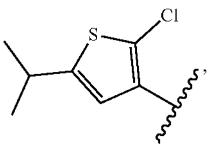,
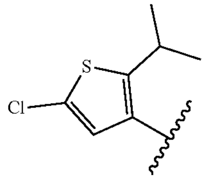,
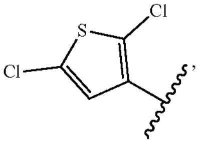,
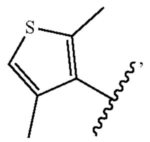,
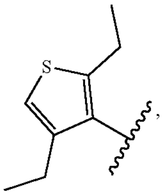,
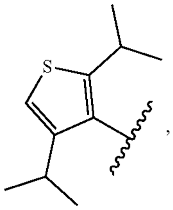,
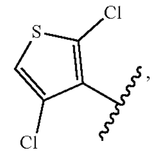,
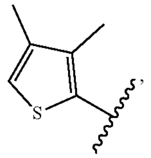,
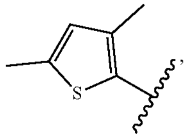,
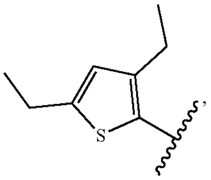,
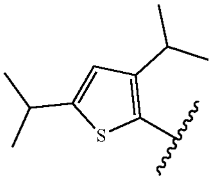,
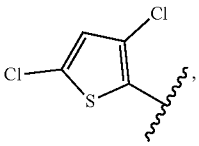,
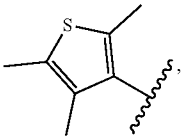,
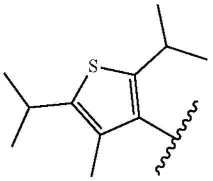,
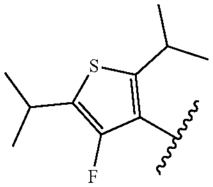,
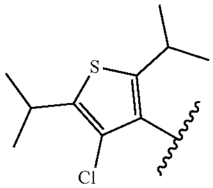,
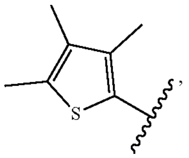,
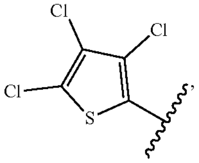,
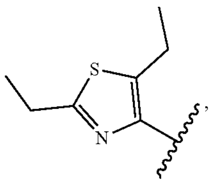, -continued

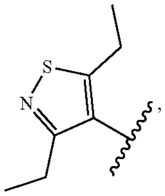,
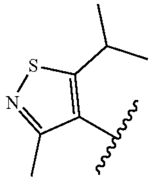, or
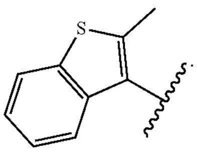.

In some embodiments, at least one $R_{1S}$ is $C_1$-$C_6$ alkyl, $C_1$-$C_6$ haloalkyl, —O($C_1$-$C_6$ alkyl), —O($C_1$-$C_6$ haloalkyl), —($C_1$-$C_6$ alkyl)-O($C_1$-$C_6$ alkyl), cyano, or halo.

In some embodiments, at least one $R_{1S}$ is $C_1$-$C_6$ alkyl, $C_1$-$C_6$ haloalkyl, —O($C_1$-$C_6$ alkyl), —O($C_1$-$C_6$ haloalkyl), —($C_1$-$C_6$ alkyl)-O($C_1$-$C_6$ alkyl), or halo.

In some embodiments, at least one $R_{1S}$ is $C_1$-$C_6$ alkyl, $C_1$-$C_6$ haloalkyl, —O($C_1$-$C_6$ alkyl), —O($C_1$-$C_6$ haloalkyl), or —($C_1$-$C_6$ alkyl)-O($C_1$-$C_6$ alkyl).

In some embodiments, at least one $R_{1S}$ is $C_1$-$C_6$ alkyl, $C_1$-$C_6$ haloalkyl, —O($C_1$-$C_6$ alkyl), —O($C_1$-$C_6$ haloalkyl), or halo.

In some embodiments, at least one $R_{1S}$ is $C_1$-$C_6$ alkyl, $C_1$-$C_6$ haloalkyl, —O($C_1$-$C_6$ alkyl), or halo.

In some embodiments, at least one $R_{1S}$ is $C_1$-$C_6$ alkyl, $C_1$-$C_6$ haloalkyl, or halo.

In some embodiments, at least one $R_{1S}$ is $C_1$-$C_6$ alkyl (e.g., methyl, ethyl, or propyl or halo (e.g., Cl).

In some embodiments, at least one $R_{1S}$ is methyl, ethyl, propyl, or Cl.

In some embodiments, at least one $R_{1S}$ is $C_1$-$C_6$ alkyl or $C_1$-$C_6$ haloalkyl.

In some embodiments, at least one $R_{1S}$ is $C_1$-$C_6$ alkyl (e.g. linear or branched).

In some embodiments, at least one $R_{1S}$ is methyl, ethyl, or propyl.

In some embodiments, at least one $R_{1S}$ is methyl. In some embodiments, at least one $R_{1S}$ is ethyl. In some embodiments, at least one $R_{1S}$ is propyl. In some embodiments, at least one $R_{1S}$ is butyl. In some embodiments, at least one $R_{1S}$ is pentyl. In some embodiments, at least one $R_{1S}$ is hexyl. In some embodiments, at least one $R_{1S}$ is isopropyl. In some embodiments, at least one $R_{1S}$ is isobutyl. In some embodiments, at least one $R_{1S}$ is isopentyl. In some embodiments, at least one $R_{1S}$ is isohexyl. In some embodiments, at least one $R_{1S}$ is secbutyl. In some embodiments, at least one $R_{1S}$ is secpentyl. In some embodiments, at least one $R_{1S}$ is sechexyl.

In some embodiments, at least one $R_{1S}$ is $C_1$-$C_6$ haloalkyl (e.g. methyl, ethyl, propyl, butyl, pentyl, or hexyl substituted with one or more halogen).

In some embodiments, at least one $R_{1S}$ is —$CH_2F$, —$CHF_2$, —$CF_3$.

In some embodiments, at least one $R_{1S}$ is —$CH_2F$. In some embodiments, at least one $R_{1S}$ is —$CHF_2$. In some embodiments, at least one $R_{1S}$ is —$CF_3$.

In some embodiments, at least one $R_{1S}$ is —O($C_1$-$C_6$ alkyl) or —O($C_1$-$C_6$ haloalkyl).

In some embodiments, at least one $R_{1S}$ is —O($C_1$-$C_6$ alkyl).

In some embodiments, at least one $R_{1S}$ is methoxy. In some embodiments, at least one $R_{1S}$ is ethoxy. In some embodiments, at least one $R_{1S}$ is propoxy. In some embodiments, at least one $R_{1S}$ is butoxy. In some embodiments, at least one $R_{1S}$ is pentoxy. In some embodiments, at least one $R_{1S}$ is hexoxy.

In some embodiments, at least one $R_{1S}$ is —O($C_1$-$C_6$ haloalkyl) (e.g. methoxy, ethoxy, propoxy, butoxy, pentoxy, or hexoxy substituted with one or more halogen).

In some embodiments, at least one $R_{1S}$ is halomethoxy. In some embodiments, at least one $R_{1S}$ is haloethoxy. In some embodiments, at least one $R_{1S}$ is halopropoxy. In some embodiments, at least one $R_{1S}$ is halobutoxy. In some embodiments, at least one $R_{1S}$ is halopentoxy. In some embodiments, at least one $R_{1S}$ is halohexoxy.

In some embodiments, at least one $R_{1S}$ is —$OCF_3$.

In some embodiments, at least one $R_{1S}$ is —$OCH_2CF_3$.

In some embodiments, at least one $R_{1S}$ is —($C_1$-$C_6$ alkyl)-O($C_1$-$C_6$ alkyl).

In some embodiments, at least one $R_{1S}$ is cyano or halo.

In some embodiments, at least one $R_{1S}$ is cyano.

In some embodiments, at least one $R_{1S}$ is halo.

In some embodiments, at least one $R_{1S}$ is F, Cl, Br, or I.

In some embodiments, at least one $R_{1S}$ is F or Cl.

In some embodiments, at least one $R_{1S}$ is F.

In some embodiments, at least one $R_{1S}$ is Cl.

In some embodiments, at least one $R_{1S}$ is methyl, ethyl, isopropyl, isobutyl, secbutyl, methoxy, ethoxy, —$CF_3$, —$OCF_3$, —$OCH_2CF_3$, F, or Cl.

In some embodiments, at least one $R_{1S}$ is $C_3$-$C_8$ cycloalkyl, $C_3$-$C_8$ aryl, 3- to 8-membered heterocycloalkyl, or 3- to 8-membered heteroaryl.

In some embodiments, at least one $R_{1S}$ is $C_3$-$C_8$ cycloalkyl.

In some embodiments, at least one $R_{1S}$ is $C_3$-$C_8$ aryl.

In some embodiments, at least one $R_{1S}$ is $C_5$-$C_6$ aryl.

In some embodiments, at least one $R_{1S}$ is phenyl.

In some embodiments, at least one $R_{1S}$ is 3- to 8-membered heterocycloalkyl.

In some embodiments, at least one $R_{1S}$ is 3- to 8-membered heteroaryl.

In some embodiments, $R_2$ is $R_{2S}$.

In some embodiments, $R_2$ is —$(CX_2X_2)_n$—$R_{2S}$, wherein n is 1 or 2.

In some embodiments, $R_2$ is —$(CX_2X_2)$—$R_{2S}$.

In some embodiments, $R_2$ is —$(CX_2X_2)_2$—$R_{2S}$.

In some embodiments, $R_2$ is —$(CH_2)_n$—$R_{2S}$, wherein n is 1. In some embodiments, $R_2$ is —$(CH_2)_n$—$R_{2S}$, wherein n is 2.

In some embodiments, at least one $X_2$ is H.

In some embodiments, each $X_2$ is H.

In some embodiments, at least one $X_2$ is $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $X_2$ is $C_1$-$C_6$ alkyl or $C_2$-$C_6$ alkenyl, wherein the $C_1$-$C_6$ alkyl or $C_2$-$C_6$ alkenyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $X_2$ is $C_1$-$C_6$ alkyl (e.g., methyl, ethyl, propyl, butyl, pentyl, or hexyl) optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $X_2$ is $C_1$-$C_6$ alkyl (e.g., methyl, ethyl, propyl, butyl, pentyl, or hexyl).

In some embodiments, at least one $X_2$ is $C_2$-$C_6$ alkenyl (e.g., ethenyl, propenyl, butenyl, pentenyl, or hexenyl) optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $X_2$ is $C_2$-$C_6$ alkenyl (e.g., ethenyl, propenyl, butenyl, pentenyl, or hexenyl).

In some embodiments, at least one $X_2$ is $C_2$-$C_6$ alkynyl (e.g., ethynyl, propynyl, butynyl, pentynyl, or hexynyl) optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $X_2$ is $C_2$-$C_6$ alkynyl (e.g., ethynyl, propynyl, butynyl, pentynyl, or hexynyl) optionally substituted with one or more halo, —CN, —O($C_1$-$C_6$ alkyl), —$NH_2$, —NH($C_1$-$C_6$ alkyl), or —N($C_1$-$C_6$ alkyl)$_2$.

In some embodiments, at least one $X_2$ is $C_2$-$C_6$ alkynyl (e.g., ethynyl, propynyl, butynyl, pentynyl, or hexynyl) optionally substituted with one halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $X_2$ is $C_2$-$C_6$ alkynyl (e.g., ethynyl, propynyl, butynyl, pentynyl, or hexynyl) optionally substituted with one halo, —CN, —O($C_1$-$C_6$ alkyl), —$NH_2$, —NH($C_1$-$C_6$ alkyl), or —N($C_1$-$C_6$ alkyl)$_2$.

In some embodiments, at least one $X_2$ is $C_2$-$C_6$ alkynyl (e.g., ethynyl, propynyl, butynyl, pentynyl, or hexynyl).

In some embodiments, n is 0.

In some embodiments, n is 1 or 2.

In some embodiments, n is 1.

In some embodiments, n is 2.

In some embodiments, $R_{2S}$ is $C_1$-$C_6$ alkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is $C_1$-$C_6$ alkyl optionally substituted with one or more $C_2$-$C_6$ alkenyl, $C_2$-$C_6$ alkynyl, or $C_1$-$C_6$ haloalkyl.

In some embodiments, $R_{2S}$ is $C_1$-$C_6$ alkyl optionally substituted with one or more $C_1$-$C_6$ haloalkyl.

In some embodiments, $R_{2S}$ is $C_1$-$C_6$ alkyl optionally substituted with one or more halo, —CN, or —OH.

In some embodiments, $R_{2S}$ is $C_1$-$C_6$ alkyl optionally substituted with one or more halo. In some embodiments, $R_{2S}$ is $C_1$-$C_6$ alkyl optionally substituted with one or more F, Cl, Br, or I. In some embodiments, $R_{2S}$ is $C_1$-$C_6$ alkyl optionally substituted with one or more F or Cl. In some embodiments, $R_{2S}$ is $C_1$-$C_6$ alkyl optionally substituted with one or more F. In some embodiments, $R_{2S}$ is $C_1$-$C_6$ alkyl optionally substituted with one or more Cl.

In some embodiments, $R_{2S}$ is $C_1$-$C_6$ alkyl optionally substituted with one or more —CN.

In some embodiments, $R_{2S}$ is $C_1$-$C_6$ alkyl optionally substituted with one or more —OH.

In some embodiments, $R_{2S}$ is $C_1$-$C_6$ alkyl optionally substituted with one or more —O($C_1$-$C_6$ alkyl), —$NH_2$, —NH($C_1$-$C_6$ alkyl), or —N($C_1$-$C_6$ alkyl)$_2$.

In some embodiments, $R_{2S}$ is $C_1$-$C_6$ alkyl optionally substituted with one or more —O($C_1$-$C_6$ alkyl).

In some embodiments, $R_{2S}$ is $C_1$-$C_6$ alkyl optionally substituted with one or more —$NH_2$, —NH($C_1$-$C_6$ alkyl), or —N($C_1$-$C_6$ alkyl)$_2$.

In some embodiments, $R_{2S}$ is $C_1$-$C_6$ alkyl optionally substituted with one or more —$NH_2$.

In some embodiments, $R_{2S}$ is $C_1$-$C_6$ alkyl optionally substituted with one or more —NH($C_1$-$C_6$ alkyl).

In some embodiments, $R_{2S}$ is $C_1$-$C_6$ alkyl optionally substituted with one or more —NH(methyl).

In some embodiments, $R_{2S}$ is $C_1$-$C_6$ alkyl optionally substituted with one or more —N($C_1$-$C_6$ alkyl)$_2$.

In some embodiments, $R_{2S}$ is $C_1$-$C_6$ alkyl optionally substituted with one or more —N(methyl)$_2$.

In some embodiments, $R_{2S}$ is $C_1$-$C_6$ alkyl optionally substituted with one or more oxo.

In some embodiments, $R_{2S}$ is $C_1$-$C_6$ alkyl (e.g., methyl, ethyl, propyl, butyl, pentyl, or hexyl).

In some embodiments, $R_{2S}$ is $C_3$-$C_{16}$ cycloalkyl or 4- to 8-membered heterocycloalkyl, wherein the $C_3$-$C_{16}$ cycloalkyl or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is $C_3$-$C_{16}$ cycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is $C_3$-$C_{16}$ cycloalkyl optionally substituted with one or more $C_1$-$C_6$ alkyl, $C_2$-$C_6$ alkenyl, $C_2$-$C_6$ alkynyl, or $C_1$-$C_6$ haloalkyl.

In some embodiments, $R_{2S}$ is $C_3$-$C_{16}$ cycloalkyl optionally substituted with one or more $C_1$-$C_6$ alkyl, $C_2$-$C_6$ alkenyl, or $C_2$-$C_6$ alkynyl.

In some embodiments, $R_{2S}$ is $C_3$-$C_{16}$ cycloalkyl optionally substituted with one or more $C_1$-$C_6$ alkyl. In some embodiments, $R_{2S}$ is $C_3$-$C_{16}$ cycloalkyl optionally substituted with one or more $C_2$-$C_6$ alkenyl. In some embodiments, $R_{2S}$ is $C_3$-$C_{16}$ cycloalkyl optionally substituted with one or more $C_2$-$C_6$ alkynyl.

In some embodiments, $R_{2S}$ is $C_3$-$C_{16}$ cycloalkyl optionally substituted with one or more $C_1$-$C_6$ haloalkyl.

In some embodiments, $R_{2S}$ is $C_3$-$C_{16}$ cycloalkyl optionally substituted with one or more halo, —CN, or —OH.

In some embodiments, $R_{2S}$ is $C_3$-$C_{16}$ cycloalkyl optionally substituted with one or more halo. In some embodiments, $R_{2S}$ is $C_3$-$C_{16}$ cycloalkyl optionally substituted with one or more F, Cl, Br, or I. In some embodiments, $R_{2S}$ is $C_3$-$C_{16}$ cycloalkyl optionally substituted with one or more F or Cl. In some embodiments, $R_{2S}$ is $C_3$-$C_{16}$ cycloalkyl optionally substituted with one or more F. In some embodiments, $R_{2S}$ is $C_3$-$C_{16}$ cycloalkyl optionally substituted with one or more Cl.

In some embodiments, $R_{2S}$ is $C_3$-$C_{16}$ cycloalkyl optionally substituted with one or more —CN. In some embodiments, $R_{2S}$ is $C_3$-$C_{16}$ cycloalkyl optionally substituted with one or more —OH.

In some embodiments, $R_{2S}$ is $C_3$-$C_{16}$ cycloalkyl optionally substituted with one or more —O($C_1$-$C_6$ alkyl), —$NH_2$, —NH($C_1$-$C_6$ alkyl), or —N($C_1$-$C_6$ alkyl)$_2$.

In some embodiments, $R_{2S}$ is $C_3$-$C_{16}$ cycloalkyl optionally substituted with one or more —O($C_1$-$C_6$ alkyl).

In some embodiments, $R_{2S}$ is $C_3$-$C_{16}$ cycloalkyl optionally substituted with one or more —$NH_2$, —NH($C_1$-$C_6$ alkyl), or —N($C_1$-$C_6$ alkyl)$_2$.

In some embodiments, $R_{2S}$ is $C_3$-$C_{16}$ cycloalkyl optionally substituted with one or more —$NH_2$.

In some embodiments, $R_{2S}$ is $C_3$-$C_{16}$ cycloalkyl optionally substituted with one or more —NH($C_1$-$C_6$ alkyl).

In some embodiments, $R_{2S}$ is $C_3$-$C_{16}$ cycloalkyl optionally substituted with one or more —NH(methyl).

In some embodiments, $R_{2S}$ is $C_3$-$C_{16}$ cycloalkyl optionally substituted with one or more —N($C_1$-$C_6$ alkyl)$_2$.

In some embodiments, $R_{2S}$ is $C_3$-$C_{16}$ cycloalkyl optionally substituted with one or more —N(methyl)$_2$.

In some embodiments, $R_{2S}$ is $C_3$-$C_{16}$ cycloalkyl optionally substituted with one or more oxo.

In some embodiments, $R_{2S}$ is $C_3$-$C_{16}$ cycloalkyl.

In some embodiments, at least one $R_{2S}$ is $C_3$-$C_8$ cycloalkyl.

In some embodiments, at least one $R_{2S}$ is $C_3$-$C_8$ cycloalkyl optionally substituted with —O($C_1$-$C_6$ alkyl), —N($C_1$-$C_6$ alkyl)$_2$, halo, or —CN.

In some embodiments, at least one $R_{2S}$ is $C_3$-$C_7$ cycloalkyl. In some embodiments, at least one $R_{2S}$ is $C_3$-$C_6$ cycloalkyl. In some embodiments, at least one $R_{2S}$ is $C_3$-$C_5$ cycloalkyl. In some embodiments, at least one $R_{2S}$ is $C_3$-$C_4$ cycloalkyl.

In some embodiments, at least one $R_{2S}$ is cyclopropyl.

In some embodiments, at least one $R_{2S}$ is cyclobutyl.

In some embodiments, at least one $R_{2S}$ is cyclobutyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $R_{2S}$ is cyclopentyl.

In some embodiments, at least one $R_{2S}$ is cyclopentyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, at least one $R_{2S}$ is cyclopentyl optionally substituted with one or more —O($C_1$-$C_6$ alkyl).

In some embodiments, $R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —$NH_2$, or oxo.

In some embodiments, $R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, or oxo.

In some embodiments, $R_{2S}$ is 4- to 8-membered heterocycloalkyl optionally substituted with one or more $C_1$-$C_6$ alkyl, $C_1$-$C_6$ haloalkyl, or oxo.

In some embodiments, $R_{2S}$ is 4- to 8-membered heterocycloalkyl.

In some embodiments, $R_{2S}$ is 5- to 8-membered heterocycloalkyl.

In some embodiments, $R_{2S}$ is 5- to 7-membered heterocycloalkyl.

In some embodiments, $R_{2S}$ is 5- to 6-membered heterocycloalkyl.

In some embodiments, $R_{2S}$ is 5- or 6-membered heterocycloalkyl having one or more heteroatoms selected from N and O.

In some embodiments, $R_{2S}$ is 5- or 6-membered heterocycloalkyl having one heteroatom selected from N and O.

In some embodiments, $R_{2S}$ is 5- or 6-membered heterocycloalkyl having two heteroatoms selected from N or O.

In some embodiments, $R_{2S}$ is 6-membered heterocycloalkyl.

In some embodiments, $R_{2S}$ is 6-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is 6-membered heterocycloalkyl optionally substituted with one or more $C_1$-$C_6$ alkyl, $C_1$-$C_6$ haloalkyl, or oxo.

In some embodiments, $R_{2S}$ is 6-membered heterocycloalkyl optionally substituted with one or more $C_1$-$C_6$ alkyl or oxo.

In some embodiments, $R_{2S}$ is 6-membered heterocycloalkyl optionally substituted with one or more $C_1$-$C_6$ alkyl or $C_1$-$C_6$ haloalkyl.

In some embodiments, $R_{2S}$ is 6-membered heterocycloalkyl optionally substituted with one or more $C_1$-$C_6$ alkyl.

In some embodiments, $R_{2S}$ is tetrahydropyranyl optionally substituted with one or more $C_1$-$C_6$ alkyl, $C_1$-$C_6$ haloalkyl, or oxo.

In some embodiments, $R_{2S}$ is tetrahydropyranyl optionally substituted with one or more $C_1$-$C_6$ alkyl or oxo.

In some embodiments, $R_{2S}$ is tetrahydropyranyl optionally substituted with one or more $C_1$-$C_6$ alkyl or $C_1$-$C_6$ haloalkyl.

In some embodiments, $R_{2S}$ is tetrahydropyranyl optionally substituted with one or more $C_1$-$C_6$ alkyl.

In some embodiments, $R_{2S}$ is tetrahydropyranyl optionally substituted with one or more methyl. In some embodiments, $R_{2S}$ is tetrahydropyranyl optionally substituted with one or more ethyl. In some embodiments, $R_{2S}$ is tetrahydropyranyl optionally substituted with one or more propyl. In some embodiments, $R_{2S}$ is tetrahydropyranyl optionally substituted with one or more butyl. In some embodiments, $R_{2S}$ is tetrahydropyranyl optionally substituted with one or more pentyl. In some embodiments, $R_{2S}$ is tetrahydropyranyl optionally substituted with one or more hexyl.

In some embodiments, $R_{2S}$ is tetrahydropyranyl optionally substituted with one or more oxo.

In some embodiments, $R_{2S}$ is tetrahydropyranyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

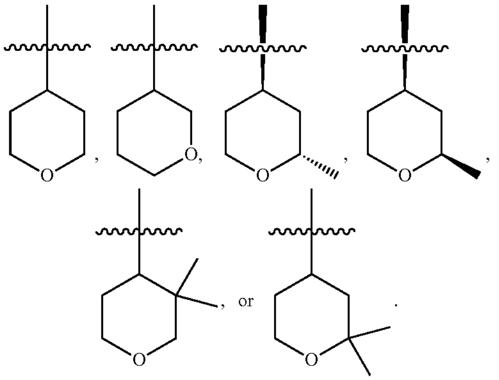

In some embodiments, $R_{2S}$ is

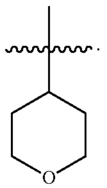

In some embodiments, $R_{2S}$ is piperidinyl optionally substituted with one or more $C_1$-$C_6$ alkyl, $C_1$-$C_6$ haloalkyl, or oxo.

In some embodiments, $R_{2S}$ piperidinyl optionally substituted with one or more $C_1$-$C_6$ alkyl or oxo.

In some embodiments, $R_{2S}$ is piperidinyl optionally substituted with one or more $C_1$-$C_6$ alkyl or $C_1$-$C_6$ haloalkyl.

In some embodiments, $R_{2S}$ is piperidinyl optionally substituted with one or more $C_1$-$C_6$ alkyl.

In some embodiments, $R_{2S}$ is piperidinyl optionally substituted with one or more methyl. In some embodiments, $R_{2S}$ is piperidinyl optionally substituted with one or more ethyl. In some embodiments, $R_{2S}$ is piperidinyl optionally substituted with one or more propyl. In some embodiments, $R_{2S}$ is piperidinyl optionally substituted with one or more butyl. In some embodiments, $R_{2S}$ is piperidinyl optionally substituted with one or more pentyl. In some embodiments, $R_{2S}$ is piperidinyl optionally substituted with one or more hexyl.

In some embodiments, $R_{2S}$ is piperidinyl optionally substituted with one or more oxo.

In some embodiments, $R_{2S}$ is piperidinyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is piperidinyl optionally substituted with one or more $—CH_2F$, $—CHF_2$, $—CF_3$, $—(CH)_2CH_2F$, $—(CH)_2CHF_2$, or $—(CH)_2CF_3$.

In some embodiments, $R_{2S}$ is

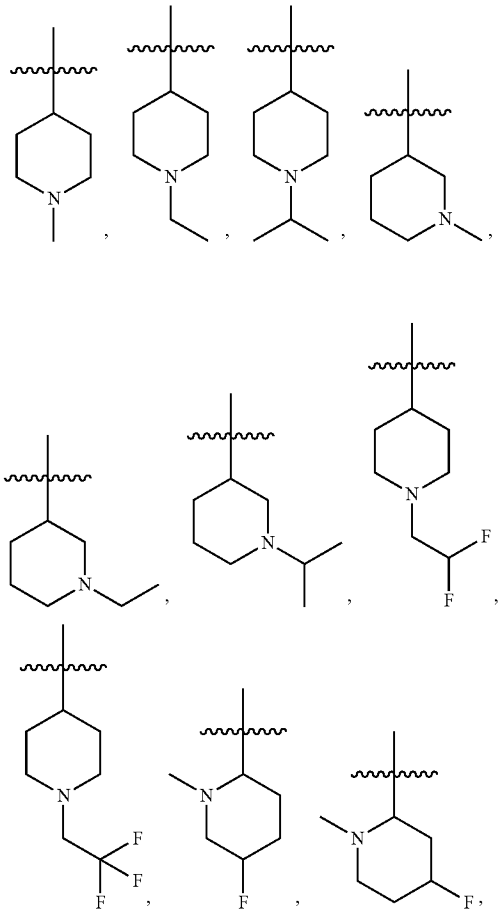

-continued

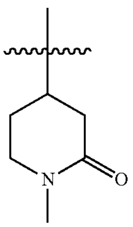
,
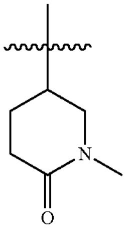
, or
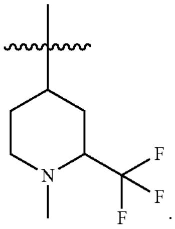
.

In some embodiments, $R_{2S}$ is

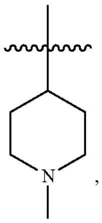
,
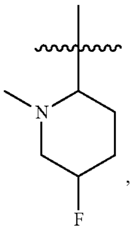
,
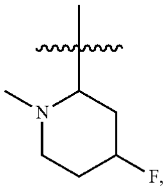
or

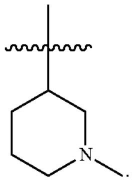
.

In some embodiments, $R_{2S}$ is morpholinyl.

In some embodiments, $R_{2S}$ is morpholinyl optionally substituted with one or more $C_1$-$C_6$ alkyl, $C_1$-$C_6$ haloalkyl, or oxo.

In some embodiments, $R_{2S}$ morpholinyl optionally substituted with one or more $C_1$-$C_6$ alkyl or oxo.

In some embodiments, $R_{2S}$ is morpholinyl optionally substituted with one or more $C_1$-$C_6$ alkyl or $C_1$-$C_6$ haloalkyl.

In some embodiments, $R_{2S}$ is morpholinyl optionally substituted with one or more $C_1$-$C_6$ alkyl.

In some embodiments, $R_{2S}$ is morpholinyl optionally substituted with one or more methyl. In some embodiments, $R_{2S}$ is morpholinyl optionally substituted with one or more ethyl. In some embodiments, $R_{2S}$ is morpholinyl optionally substituted with one or more propyl. In some embodiments, $R_{2S}$ is morpholinyl optionally substituted with one or more butyl. In some embodiments, $R_{2S}$ is morpholinyl optionally substituted with one or more pentyl. In some embodiments, $R_{2S}$ is morpholinyl optionally substituted with one or more hexyl.

In some embodiments, $R_{2S}$ is morpholinyl optionally substituted with one or more oxo.

In some embodiments, $R_{2S}$ is morpholinyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

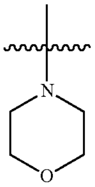
or
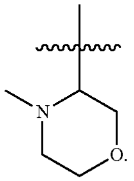

In some embodiments, $R_2$ is $—(CH_2)_n—R_{2S}$, wherein n is 0 and $R_{2S}$ is 6-membered heterocycloalkyl.

In some embodiments, $R_2$ is $—(CH_2)_n—R_{2S}$, wherein n is 0 and $R_{2S}$ is 6-membered heterocycloalkyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 0 and $R_{2S}$ is tetrahydropyranyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 0 and $R_{2S}$ is piperidinyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 0 and $R_{2S}$ is morpholinyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 1 and $R_{2S}$ is 6-membered heterocycloalkyl.

In some embodiments, $R_2$ is $—(CH_2)_n—R_{2S}$, wherein n is 1 and $R_{2S}$ is 6-membered heterocycloalkyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 1 and $R_{2S}$ is tetrahydropyranyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 1 and $R_{2S}$ is piperidinyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 1 and $R_{2S}$ is morpholinyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 2 and $R_{2S}$ is 6-membered heterocycloalkyl.

In some embodiments, $R_2$ is $—(CH_2)_n—R_{2S}$, wherein n is 2 and $R_{2S}$ is 6-membered heterocycloalkyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 2 and $R_{2S}$ is tetrahydropyranyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 2 and $R_{2S}$ is piperidinyl optionally substituted with one or more $C_1$-$C_6$ alkyl, $C_1$-$C_6$ haloalkyl, or oxo.

In some embodiments, $R_2$ is $—(CH_2)_n—R_{2S}$, wherein n is 2 and $R_{2S}$ is morpholinyl optionally substituted with one or more $C_1$-$C_6$ alkyl, $C_1$-$C_6$ haloalkyl, or oxo.

In some embodiments, $R_{2S}$ is 5-membered heterocycloalkyl.

In some embodiments, $R_{2S}$ is 5-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, $—O(C_1$-$C_6$ alkyl), $—NH_2$, $—NH(C_1$-$C_6$ alkyl), $—N(C_1$-$C_6$ $alkyl)_2$, or oxo.

In some embodiments, $R_{2S}$ is 5-membered heterocycloalkyl optionally substituted with one or more $C_1$-$C_6$ alkyl, $C_1$-$C_6$ haloalkyl, or oxo.

In some embodiments, $R_{2S}$ is 5-membered heterocycloalkyl optionally substituted with one or more $C_1$-$C_6$ alkyl or oxo.

In some embodiments, $R_{2S}$ is 5-membered heterocycloalkyl optionally substituted with one or more $C_1$-$C_6$ alkyl or $C_1$-$C_6$ haloalkyl.

In some embodiments, $R_{2S}$ is 5-membered heterocycloalkyl optionally substituted with one or more $C_1$-$C_6$ alkyl.

In some embodiments, $R_{2S}$ is tetrahydrofuranyl optionally substituted with one or more $C_1$-$C_6$ alkyl, $C_1$-$C_6$ haloalkyl, or oxo.

In some embodiments, $R_{2S}$ is tetrahydrofuranyl optionally substituted with one or more $C_1$-$C_6$ alkyl or oxo.

In some embodiments, $R_{2S}$ is tetrahydrofuranyl optionally substituted with one or more $C_1$-$C_6$ alkyl or $C_1$-$C_6$ haloalkyl.

In some embodiments, $R_{2S}$ is tetrahydrofuranyl optionally substituted with one or more $C_1$-$C_6$ alkyl.

In some embodiments, $R_{2S}$ is tetrahydrofuranyl optionally substituted with one or more methyl. In some embodiments, $R_{2S}$ is tetrahydrofuranyl optionally substituted with one or more ethyl. In some embodiments, $R_{2S}$ is tetrahydrofuranyl optionally substituted with one or more propyl. In some embodiments, $R_{2S}$ is tetrahydrofuranyl optionally substituted with one or more butyl. In some embodiments, $R_{2S}$ is tetrahydrofuranyl optionally substituted with one or more pentyl. In some embodiments, $R_{2S}$ is tetrahydrofuranyl optionally substituted with one or more hexyl.

In some embodiments, $R_{2S}$ is tetrahydrofuranyl optionally substituted with one or more oxo.

In some embodiments, $R_{2S}$ is tetrahydrofuranyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

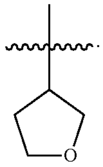 [SMILES: *C1CCOC1]

In some embodiments, $R_{2S}$ is pyrrolidinyl optionally substituted with one or more $C_1$-$C_6$ alkyl, $C_1$-$C_6$ haloalkyl, or oxo.

In some embodiments, $R_{2S}$ is pyrrolidinyl optionally substituted with one or more $C_1$-$C_6$ alkyl or oxo.

In some embodiments, $R_{2S}$ is pyrrolidinyl optionally substituted with one or more $C_1$-$C_6$ alkyl or $C_1$-$C_6$ haloalkyl.

In some embodiments, $R_{2S}$ is pyrrolidinyl optionally substituted with one or more $C_1$-$C_6$ alkyl.

In some embodiments, $R_{2S}$ is pyrrolidinyl optionally substituted with one or more methyl. In some embodiments, $R_{2S}$ is pyrrolidinyl optionally substituted with one or more ethyl. In some embodiments, $R_{2S}$ is pyrrolidinyl optionally substituted with one or more propyl. In some embodiments, $R_{2S}$ is pyrrolidinyl optionally substituted with one or more butyl. In some embodiments, $R_{2S}$ is pyrrolidinyl optionally substituted with one or more pentyl. In some embodiments, $R_{2S}$ is pyrrolidinyl optionally substituted with one or more hexyl.

In some embodiments, $R_{2S}$ is pyrrolidinyl optionally substituted with one or more oxo.

In some embodiments, $R_{2S}$ is pyrrolidinyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

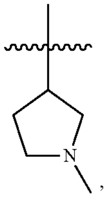 , 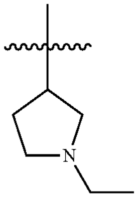 , 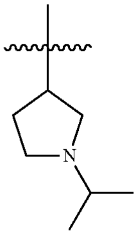 ,

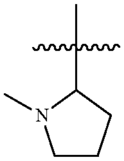 , 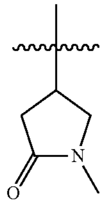 , 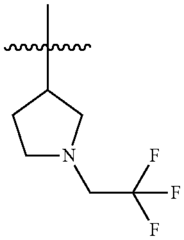 ,

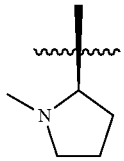 , 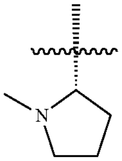 , 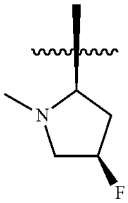 ,

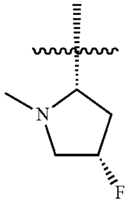 , 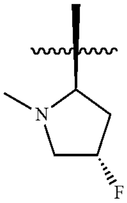 , 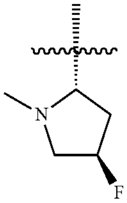 ,

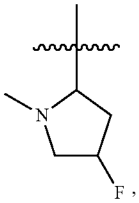 , 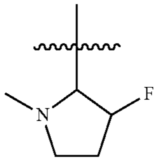 ,

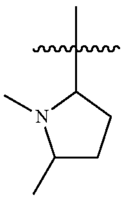 , or 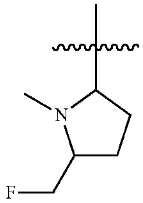 .

In some embodiments, $R_2$ is $-(CH_2)_n-R_{2S}$, wherein n is 0 and $R_{2S}$ is 5-membered heterocycloalkyl.

In some embodiments, $R_2$ is $-(CH_2)_n-R_{2S}$, wherein n is 0 and $R_{2S}$ is 5-membered heterocycloalkyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 0 and $R_{2S}$ is tetrahydrofuranyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 0 and $R_{2S}$ is pyrrolidinyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 1 and $R_{2S}$ is 5-membered heterocycloalkyl.

In some embodiments, $R_2$ is $-(CH_2)_n-R_{2S}$, wherein n is 1 and $R_{2S}$ is 5-membered heterocycloalkyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 1 and $R_{2S}$ is tetrahydrofuranyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 1 and $R_{2S}$ is pyrrolidinyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 2 and $R_{2S}$ is 5-membered heterocycloalkyl.

In some embodiments, $R_2$ is $-(CH_2)_n-R_{2S}$, wherein n is 2 and $R_{2S}$ is 5-membered heterocycloalkyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 2 and $R_{2S}$ is tetrahydrofuranyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 2 and $R_{2S}$ is pyrrolidinyl optionally substituted with one or more $C_1$-$C_6$ alkyl, $C_1$-$C_6$ haloalkyl, or oxo.

In some embodiments, $R_{2S}$ is 4-membered heterocycloalkyl.

In some embodiments, $R_{2S}$ is 4-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, $-CN$, $-OH$, $-O(C_1$-$C_6$ alkyl), $-NH_2$, $-NH(C_1$-$C_6$ alkyl), $-N(C_1$-$C_6$ alkyl$)_2$, or oxo.

In some embodiments, $R_{2S}$ is 4-membered heterocycloalkyl optionally substituted with one or more $C_1$-$C_6$ alkyl, $C_1$-$C_6$ haloalkyl, or oxo.

In some embodiments, $R_{2S}$ is 4-membered heterocycloalkyl optionally substituted with one or more $C_1$-$C_6$ alkyl or oxo.

In some embodiments, $R_{2S}$ is 4-membered heterocycloalkyl optionally substituted with one or more $C_1$-$C_6$ alkyl or $C_1$-$C_6$ haloalkyl.

In some embodiments, $R_{2S}$ is 4-membered heterocycloalkyl optionally substituted with one or more $C_1$-$C_6$ alkyl.

In some embodiments, $R_{2S}$ is oxetanyl optionally substituted with one or more $C_1$-$C_6$ alkyl, $C_1$-$C_6$ haloalkyl, or oxo.

In some embodiments, $R_{2S}$ is oxetanyl optionally substituted with one or more $C_1$-$C_6$ alkyl or oxo.

In some embodiments, $R_{2S}$ is oxetanyl optionally substituted with one or more $C_1$-$C_6$ alkyl or $C_1$-$C_6$ haloalkyl.

In some embodiments, $R_{2S}$ is oxetanyl optionally substituted with one or more $C_1$-$C_6$ alkyl.

In some embodiments, $R_{2S}$ is oxetanyl optionally substituted with one or more methyl. In some embodiments, $R_{2S}$ is oxetanyl optionally substituted with one or more ethyl. In some embodiments, $R_{2S}$ is oxetanyl optionally substituted with one or more propyl. In some embodiments, $R_{2S}$ is oxetanyl optionally substituted with one or more butyl. In some embodiments, $R_{2S}$ is oxetanyl optionally substituted with one or more pentyl. In some embodiments, $R_{2S}$ is oxetanyl optionally substituted with one or more hexyl.

In some embodiments, $R_{2S}$ is oxetanyl optionally substituted with one or more oxo.

In some embodiments, $R_{2S}$ is oxetanyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

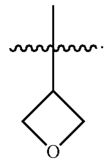 [SMILES: *C1COC1]

In some embodiments, $R_{2S}$ is azetidinyl optionally substituted with one or more $C_1$-$C_6$ alkyl, $C_1$-$C_6$ haloalkyl, or oxo.

In some embodiments, $R_{2S}$ is azetidinyl optionally substituted with one or more $C_1$-$C_6$ alkyl or oxo.

In some embodiments, $R_{2S}$ is azetidinyl optionally substituted with one or more $C_1$-$C_6$ alkyl or $C_1$-$C_6$ haloalkyl.

In some embodiments, $R_{2S}$ is azetidinyl optionally substituted with one or more $C_1$-$C_6$ alkyl.

In some embodiments, $R_{2S}$ is azetidinyl optionally substituted with one or more methyl. In some embodiments, $R_{2S}$ is azetidinyl optionally substituted with one or more ethyl. In some embodiments, $R_{2S}$ is azetidinyl optionally substituted with one or more propyl. In some embodiments, $R_{2S}$ is azetidinyl optionally substituted with one or more butyl. In some embodiments, $R_{2S}$ is azetidinyl optionally substituted with one or more pentyl. In some embodiments, $R_{2S}$ is azetidinyl optionally substituted with one or more hexyl.

In some embodiments, $R_{2S}$ is azetidinyl optionally substituted with one or more oxo.

In some embodiments, $R_{2S}$ is azetidinyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

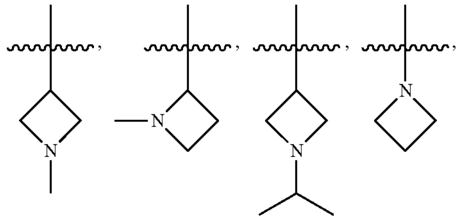

or

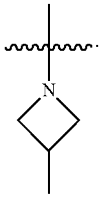

In some embodiments, $R_2$ is $-(CH_2)_n-R_{2S}$, wherein n is 0 and $R_{2S}$ is 4-membered heterocycloalkyl.

In some embodiments, $R_2$ is $-(CH_2)_n-R_{2S}$, wherein n is 0 and $R_{2S}$ is 4-membered heterocycloalkyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 0 and $R_{2S}$ is oxetanyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 0 and $R_{2S}$ is azetidinyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 1 and $R_{2S}$ is 4-membered heterocycloalkyl.

In some embodiments, $R_2$ is $-(CH_2)_n-R_{2S}$, wherein n is 1 and $R_{2S}$ is 4-membered heterocycloalkyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 1 and $R_{2S}$ is oxetanyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 1 and $R_{2S}$ is azetidinyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 2 and $R_{2S}$ is 4-membered heterocycloalkyl.

In some embodiments, $R_2$ is $-(CH_2)_n-R_{2S}$, wherein n is 2 and $R_{2S}$ is 4-membered heterocycloalkyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 2 and $R_{2S}$ is oxetanyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 2 and $R_{2S}$ is azetidinyl optionally substituted with one or more $C_1$-$C_6$ alkyl, $C_1$-$C_6$ haloalkyl, or oxo.

In some embodiments, $R_{2S}$ is 7-membered heterocycloalkyl.

In some embodiments, $R_{2S}$ is 7-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is 7-membered heterocycloalkyl optionally substituted with one or more $C_1$-$C_6$ alkyl, $C_1$-$C_6$ haloalkyl, or oxo.

In some embodiments, $R_{2S}$ is 7-membered heterocycloalkyl optionally substituted with one or more $C_1$-$C_6$ alkyl or oxo.

In some embodiments, $R_{2S}$ is 7-membered heterocycloalkyl optionally substituted with one or more $C_1$-$C_6$ alkyl or $C_1$-$C_6$ haloalkyl.

In some embodiments, $R_{2S}$ is 7-membered heterocycloalkyl optionally substituted with one or more $C_1$-$C_6$ alkyl.

In some embodiments, $R_{2S}$ is oxepanyl optionally substituted with one or more $C_1$-$C_6$ alkyl, $C_1$-$C_6$ haloalkyl, or oxo.

In some embodiments, $R_{2S}$ is oxepanyl optionally substituted with one or more $C_1$-$C_6$ alkyl or oxo.

In some embodiments, $R_{2S}$ is oxepanyl optionally substituted with one or more $C_1$-$C_6$ alkyl or $C_1$-$C_6$ haloalkyl.

In some embodiments, $R_{2S}$ is oxepanyl optionally substituted with one or more $C_1$-$C_6$ alkyl.

In some embodiments, $R_{2S}$ is oxepanyl optionally substituted with one or more methyl. In some embodiments, $R_{2S}$ is oxepanyl optionally substituted with one or more ethyl. In some embodiments, $R_{2S}$ is oxepanyl optionally substituted with one or more propyl. In some embodiments, $R_{2S}$ is oxepanyl optionally substituted with one or more butyl. In some embodiments, $R_{2S}$ is oxepanyl optionally substituted with one or more pentyl. In some embodiments, $R_{2S}$ is oxepanyl optionally substituted with one or more hexyl.

In some embodiments, $R_{2S}$ is oxepanyl optionally substituted with one or more oxo.

In some embodiments, $R_{2S}$ is oxepanyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is azepanyl optionally substituted with one or more $C_1$-$C_6$ alkyl, $C_1$-$C_6$ haloalkyl, or oxo.

In some embodiments, $R_{2S}$ is azepanyl optionally substituted with one or more $C_1$-$C_6$ alkyl or oxo.

In some embodiments, $R_{2S}$ is azepanyl optionally substituted with one or more $C_1$-$C_6$ alkyl or $C_1$-$C_6$ haloalkyl.

In some embodiments, $R_{2S}$ is azepanyl optionally substituted with one or more $C_1$-$C_6$ alkyl.

In some embodiments, $R_{2S}$ is azepanyl optionally substituted with one or more methyl. In some embodiments, $R_{2S}$ is azepanyl optionally substituted with one or more ethyl. In some embodiments, $R_{2S}$ is azepanyl optionally substituted with one or more propyl. In some embodiments, $R_{2S}$ is azepanyl optionally substituted with one or more butyl. In some embodiments, $R_{2S}$ is azepanyl optionally substituted with one or more pentyl. In some embodiments, $R_{2S}$ is azepanyl optionally substituted with one or more hexyl.

In some embodiments, $R_{2S}$ is azepanyl optionally substituted with one or more oxo.

In some embodiments, $R_{2S}$ is azepanyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is

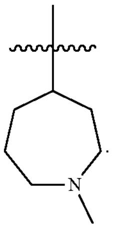

In some embodiments, $R_2$ is $-(CH_2)_n-R_{2S}$, wherein n is 0 and $R_{2S}$ is 7-membered heterocycloalkyl.

In some embodiments, $R_2$ is $-(CH_2)_n-R_{2S}$, wherein n is 0 and $R_{2S}$ is 7-membered heterocycloalkyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 0 and $R_{2S}$ is oxepanyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 0 and $R_{2S}$ is azepanyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 1 and $R_{2S}$ is 7-membered heterocycloalkyl.

In some embodiments, $R_2$ is $-(CH_2)_n-R_{2S}$, wherein n is 1 and $R_{2S}$ is 7-membered heterocycloalkyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 1 and $R_{2S}$ is oxepanyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 1 and $R_{2S}$ is azepanyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 2 and $R_{2S}$ is 7-membered heterocycloalkyl.

In some embodiments, $R_2$ is $-(CH_2)_n-R_{2S}$, wherein n is 2 and $R_{2S}$ is 7-membered heterocycloalkyl optionally substituted with one or more $C_1$-$C_6$ alkyl, $C_1$-$C_6$ haloalkyl, or oxo.

In some embodiments, $R_2$ is $-(CH_2)_n-R_{2S}$, wherein n is 2 and $R_{2S}$ is oxepanyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is azepanyl optionally substituted with one or more $C_1$-$C_6$ alkyl, $C_1$-$C_6$ haloalkyl, or oxo.

In some embodiments, $R_{2S}$ is 8-membered heterocycloalkyl.

In some embodiments, $R_{2S}$ is 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is 8-membered heterocycloalkyl optionally substituted with one or more $C_1$-$C_6$ alkyl, $C_1$-$C_6$ haloalkyl, or oxo.

In some embodiments, $R_{2S}$ is 8-membered heterocycloalkyl optionally substituted with one or more $C_1$-$C_6$ alkyl or oxo.

In some embodiments, $R_{2S}$ is 8-membered heterocycloalkyl optionally substituted with one or more $C_1$-$C_6$ alkyl or $C_1$-$C_6$ haloalkyl.

In some embodiments, $R_{2S}$ is 8-membered heterocycloalkyl optionally substituted with one or more $C_1$-$C_6$ alkyl.

In some embodiments, $R_{2S}$ is oxocanyl optionally substituted with one or more $C_1$-$C_6$ alkyl, $C_1$-$C_6$ haloalkyl, or oxo.

In some embodiments, $R_{2S}$ is oxocanyl optionally substituted with one or more $C_1$-$C_6$ alkyl or oxo.

In some embodiments, $R_{2S}$ is oxocanyl optionally substituted with one or more $C_1$-$C_6$ alkyl or $C_1$-$C_6$ haloalkyl.

In some embodiments, $R_{2S}$ is oxocanyl optionally substituted with one or more $C_1$-$C_6$ alkyl.

In some embodiments, $R_{2S}$ is oxocanyl optionally substituted with one or more methyl. In some embodiments, $R_{2S}$ is oxocanyl optionally substituted with one or more ethyl. In some embodiments, $R_{2S}$ is oxocanyl optionally substituted with one or more propyl. In some embodiments, $R_{2S}$ is oxocanyl optionally substituted with one or more butyl. In some embodiments, $R_{2S}$ is oxocanyl optionally substituted with one or more pentyl. In some embodiments, $R_{2S}$ is oxocanyl optionally substituted with one or more hexyl.

In some embodiments, $R_{2S}$ is oxocanyl optionally substituted with one or more oxo.

In some embodiments, $R_{2S}$ is oxocanyl optionally substituted with one or more $C_1$-$C_6$ haloalkyl (e.g. methyl, ethyl, propyl, butyl, pentyl, or hexyl optionally substituted with one or more halo).

In some embodiments, $R_{2S}$ is azocanyl optionally substituted with one or more $C_1$-$C_6$ alkyl, $C_1$-$C_6$ haloalkyl, or oxo.

In some embodiments, $R_{2S}$ is azocanyl optionally substituted with one or more $C_1$-$C_6$ alkyl or oxo.

In some embodiments, $R_{2S}$ is azocanyl optionally substituted with one or more $C_1$-$C_6$ alkyl or $C_1$-$C_6$ haloalkyl.

In some embodiments, $R_{2S}$ is azocanyl optionally substituted with one or more $C_1$-$C_6$ alkyl.

In some embodiments, $R_{2S}$ is azocanyl optionally substituted with one or more methyl. In some embodiments, $R_{2S}$ is azocanyl optionally substituted with one or more ethyl. In some embodiments, $R_{2S}$ is azocanyl optionally substituted with one or more propyl. In some embodiments, $R_{2S}$ is azocanyl optionally substituted with one or more butyl. In some embodiments, $R_{2S}$ is azocanyl optionally substituted with one or more pentyl. In some embodiments, $R_{2S}$ is azocanyl optionally substituted with one or more hexyl.

In some embodiments, $R_{2S}$ is azocanyl optionally substituted with one or more oxo.

In some embodiments, $R_{2S}$ is azocanyl optionally substituted with one or more $C_1$-$C_6$ haloalkyl (e.g. methyl, ethyl, propyl, butyl, pentyl, or hexyl optionally substituted with one or more halo).

In some embodiments, $R_2$ is —$(CH_2)_n$—$R_{2S}$, wherein n is 0 and $R_{2S}$ is 8-membered heterocycloalkyl.

In some embodiments, $R_2$ is —$(CH_2)_n$—$R_{2S}$, wherein n is 0 and $R_{2S}$ is 8-membered heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 0 and $R_{2S}$ is oxocanyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 0 and $R_{2S}$ is azocanyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is 8-membered heterocycloalkyl.

In some embodiments, $R_2$ is —$(CH_2)_n$—$R_{2S}$, wherein n is 1 and $R_{2S}$ is 8-membered heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is oxocanyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is azocanyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is 8-membered heterocycloalkyl.

In some embodiments, $R_2$ is —$(CH_2)_n$—$R_{2S}$, wherein n is 2 and $R_{2S}$ is 8-membered heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is oxocanyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is azocanyl optionally substituted with one or more $C_1$-$C_6$ alkyl, $C_1$-$C_6$ haloalkyl, or oxo.

In some embodiments, $R_{2S}$ is spiro heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S}$ is spiro heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 0 and $R_{2S}$ is spiro heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 1 and $R_{2S}$ is spiro heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S}$, wherein n is 2 and $R_{2S}$ is spiro heterocycloalkyl optionally substituted with one or more $C_1$-$C_6$ alkyl, $C_1$-$C_6$ haloalkyl, or oxo.

In some embodiments, $R_{2S}$ is spiro 7-membered heterocycloalkyl optionally substituted with one or more $C_1$-$C_6$ alkyl, $C_1$-$C_6$ haloalkyl, or oxo.

In some embodiments, $R_{2S}$ is spiro 7-membered heterocycloalkyl optionally substituted with one or more $C_1$-$C_6$ alkyl.

In some embodiments, $R_{2S}$ is spiro 7-membered heterocycloalkyl optionally substituted with one or more $C_1$-$C_6$ haloalkyl.

In some embodiments, $R_{2S}$ is 2-azaspiro[3.3]heptane optionally substituted with one or more $C_1$-$C_6$ alkyl, $C_1$-$C_6$ haloalkyl, or oxo. In some embodiments, $R_{2S}$ is 2-oxaspiro[3.3]heptane optionally substituted with one or more $C_1$-$C_6$ alkyl, $C_1$-$C_6$ haloalkyl, or oxo.

In some embodiments, $R_{2S'}$ is

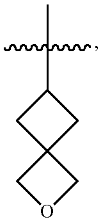, 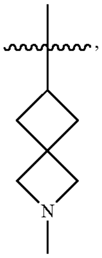, or 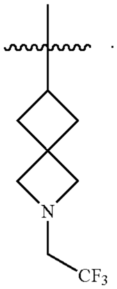.

In some embodiments, $R_{2S'}$ is bridged heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo.

In some embodiments, $R_{2S'}$ is bridged heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S'}$, wherein n is 0 and $R_{2S'}$ is bridged heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S'}$, wherein n is 1 and $R_{2S'}$ is bridged heterocycloalkyl optionally substituted with one or more $C_1$-$C_6$ alkyl, $C_1$-$C_6$ haloalkyl, or oxo.

In some embodiments, $R_2$ is —$(CH_2)_n$—$R_{2S'}$, wherein n is 2 and $R_{2S'}$ is bridged heterocycloalkyl optionally substituted with one or more $C_1$-$C_6$ alkyl, $C_1$-$C_6$ haloalkyl, or oxo.

In some embodiments, $R_{2S'}$ is bridged 8-membered heterocycloalkyl optionally substituted with one or more $C_1$-$C_6$ alkyl, $C_1$-$C_6$ haloalkyl, or oxo.

In some embodiments, $R_{2S'}$ is bridged quinuclidinyl optionally substituted with one or more $C_1$-$C_6$ alkyl, $C_1$-$C_6$ haloalkyl, or oxo.

In some embodiments, $R_{2S'}$ is

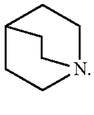.

In some embodiments, $R_2$ is

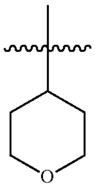, 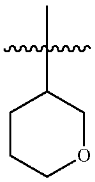, 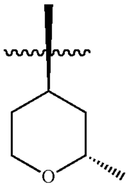, 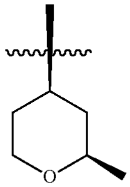, 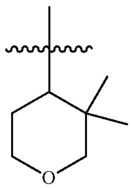, 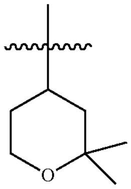, 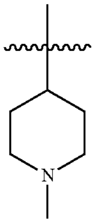, 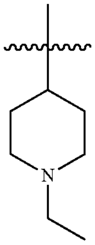, -continued

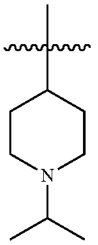, 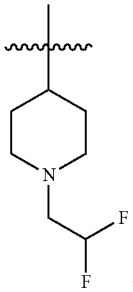, 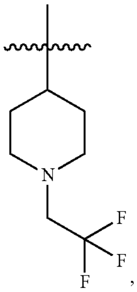, 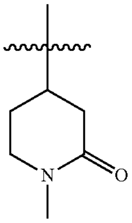,

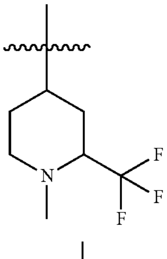, 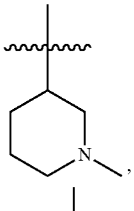, 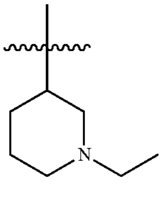,

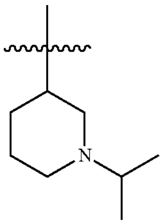, 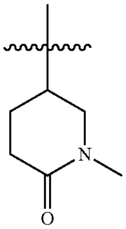, 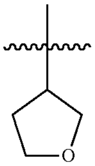,

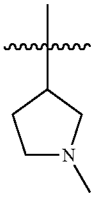, 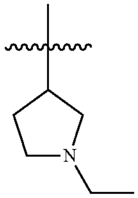, 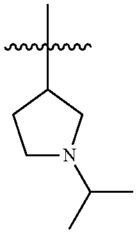,

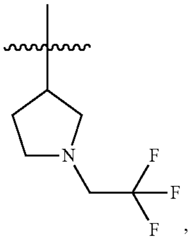, 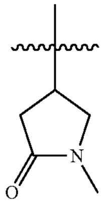, 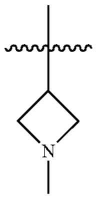, 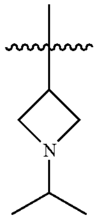,

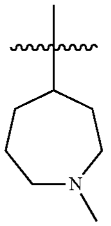, 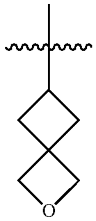, 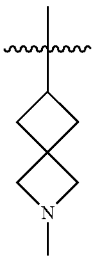, 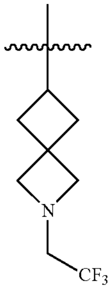,

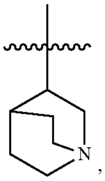, 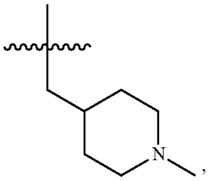, 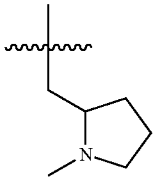,

-continued
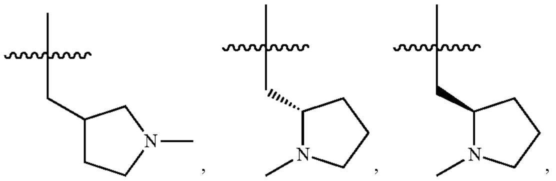
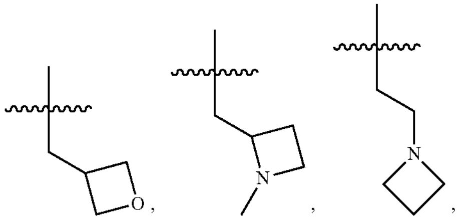
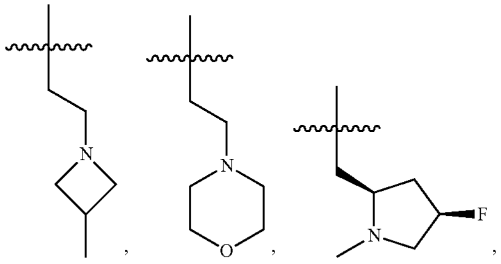
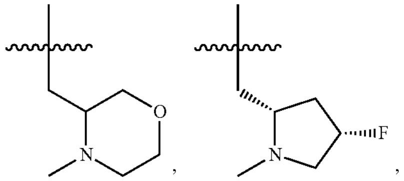
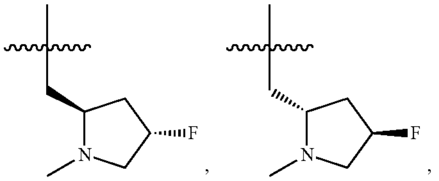
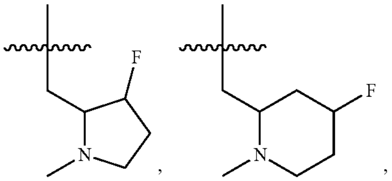
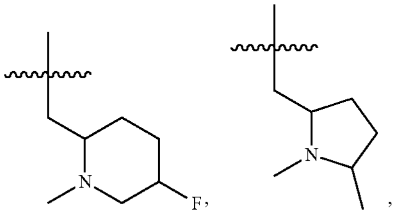
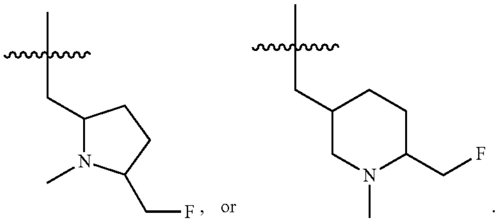
or
In some embodiments, $R_2$ is
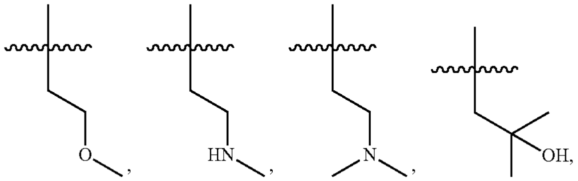
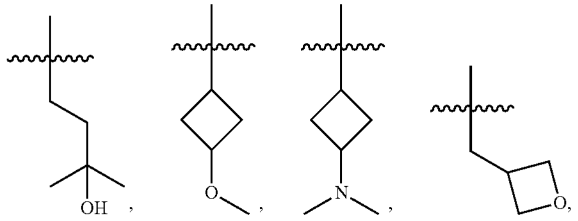
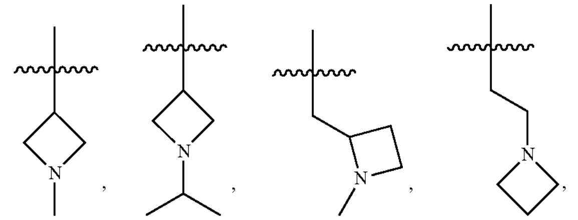
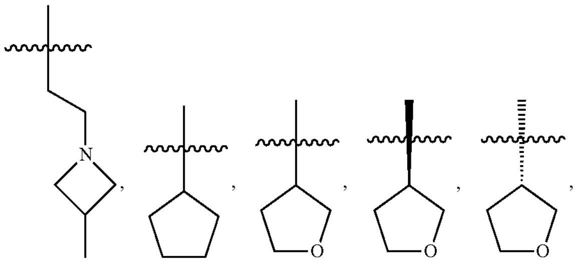
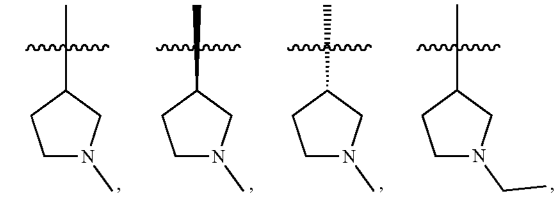
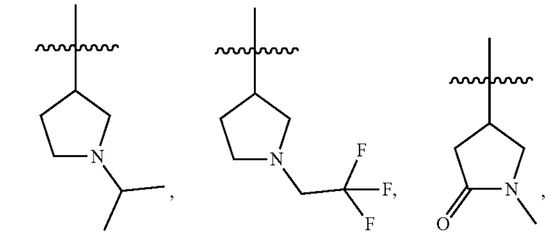
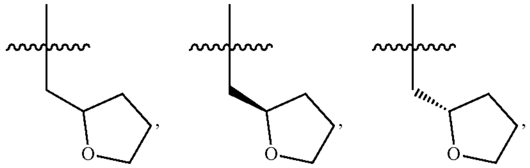
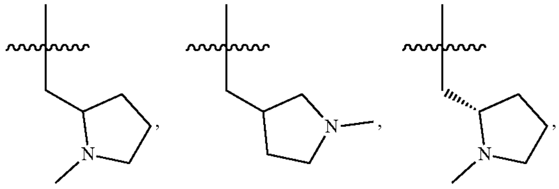

-continued
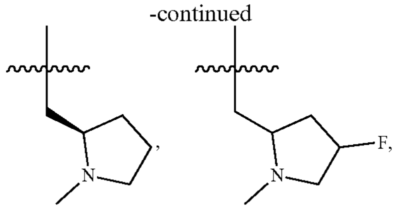
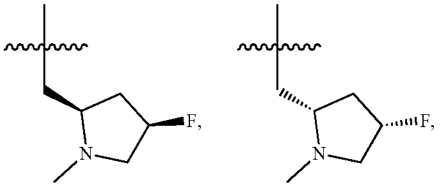
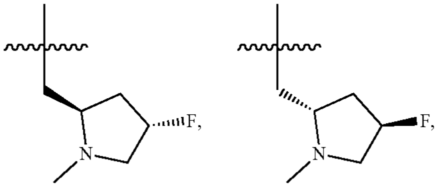
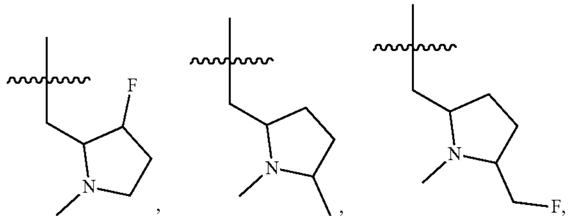
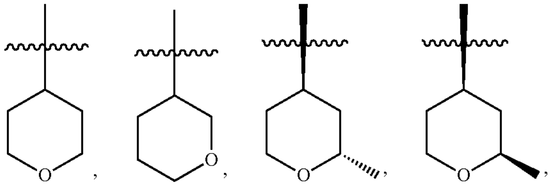
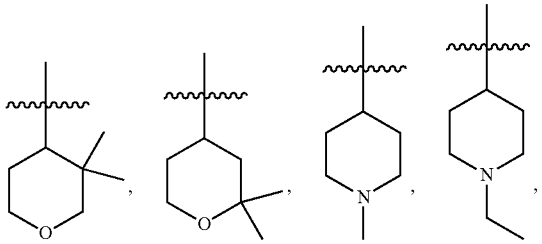
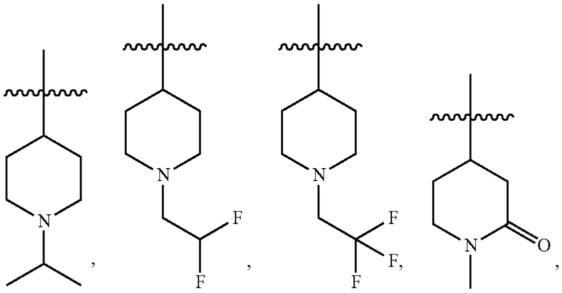
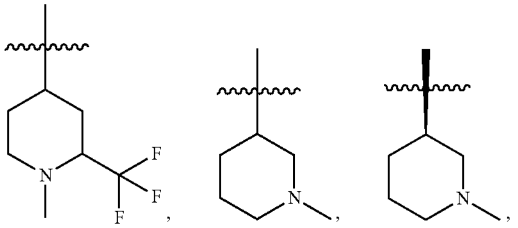
-continued
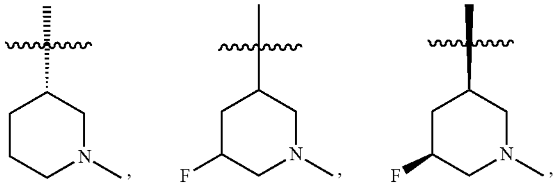
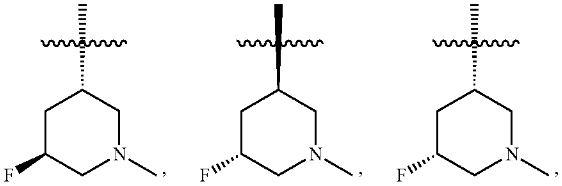
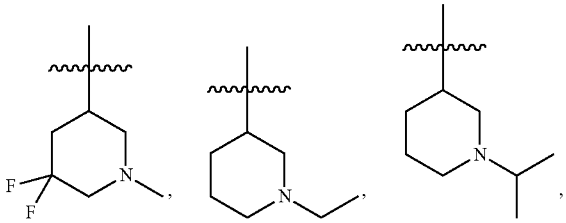
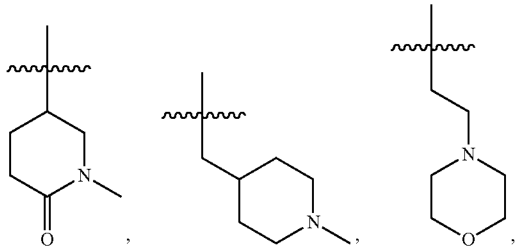
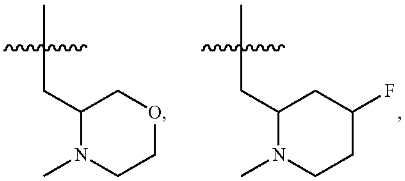
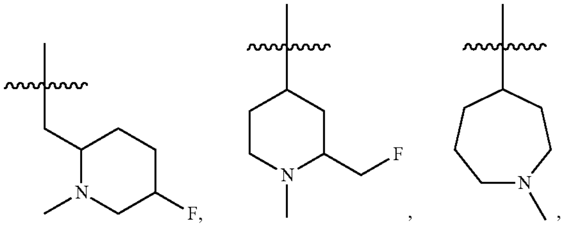
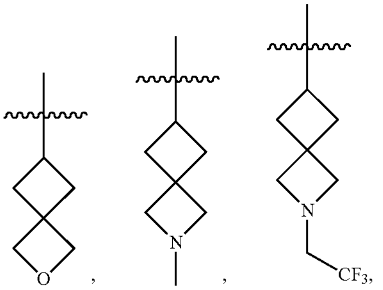
or
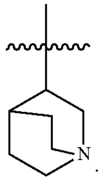

In some embodiments, $R_2$ is

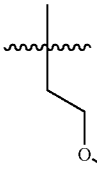, 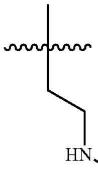, 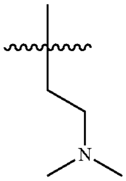, 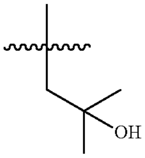, 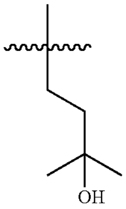, 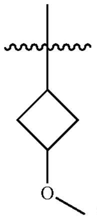, 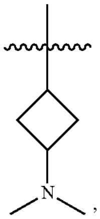, 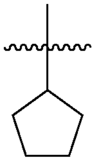, 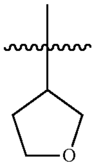, 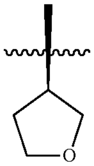, 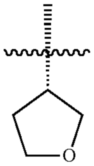, 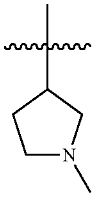, 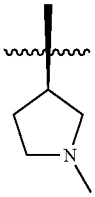, 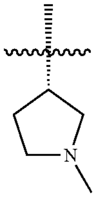, 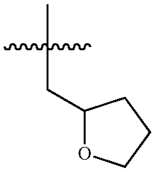, 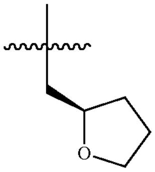, 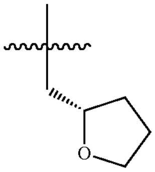, 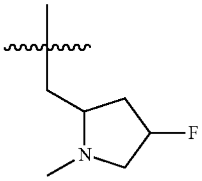, 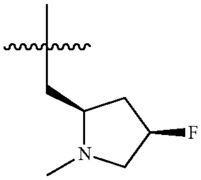, 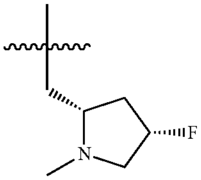, 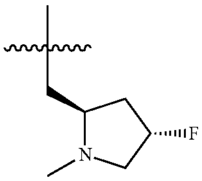, 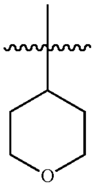, 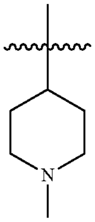, 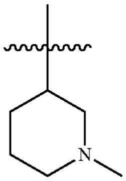, 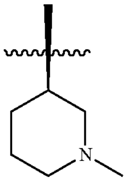, 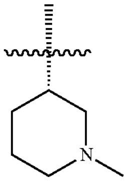, 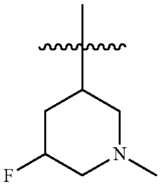, 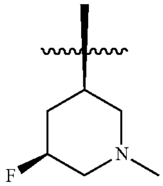, -continued

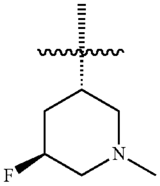, 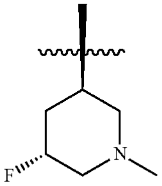, 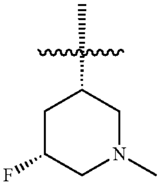, or 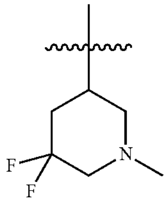.

In some embodiments, $R_2$ is

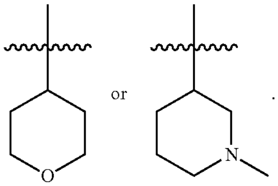 or .

In some embodiments, $R_3$ is 5- to 6-membered heterocycloalkyl optionally substituted with one or more $R_{3S}$.

In some embodiments, $R_3$ is

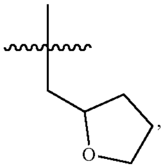, 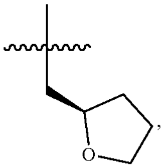, 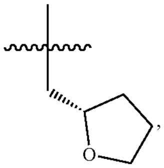, 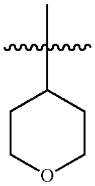, 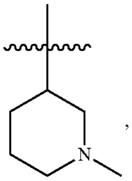, 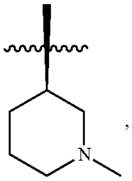, or 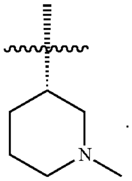.

In some embodiments, $R_3$ is 7- to 12-membered heterocycloalkyl optionally substituted with one or more $R_{3S}$.

In some embodiments, $R_3$ is 7- to 12-membered heterocycloalkyl.

In some embodiments, $R_3$ is 8- to 11-membered heterocycloalkyl optionally substituted with one or more $R_{3S}$.

In some embodiments, $R_3$ is 8- to 11-membered heterocycloalkyl.

In some embodiments, $R_3$ is 9- or 10-membered heterocycloalkyl optionally substituted with one or more $R_{3S}$.

In some embodiments, $R_3$ is 9- or 10-membered heterocycloalkyl.

In some embodiments, $R_3$ is 9-membered heterocycloalkyl optionally substituted with one or more $R_{3S}$.

In some embodiments, $R_3$ is 9-membered heterocycloalkyl.

In some embodiments, $R_3$ is

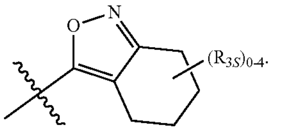

In some embodiments, $R_3$ is

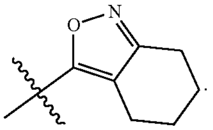 [SMILES: *c1onc2c1CCCC2]

In some embodiments, $R_3$ is 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, or —CN.

In some embodiments, $R_3$ is 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein $C_1$-$C_6$ alkyl is optionally substituted with —O($C_1$-$C_6$ alkyl), —N($C_1$-$C_6$ alkyl)$_2$, halo, or —CN.

In some embodiments, $R_3$ is 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein $C_1$-$C_6$ alkyl is optionally substituted with —O($C_1$-$C_6$ alkyl) or —N($C_1$-$C_6$ alkyl)$_2$.

In some embodiments, $R_3$ is 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl.

In some embodiments, $R_3$ is 5- or 6-membered heteroaryl optionally substituted with one or more $R_{3S}$, wherein each $R_{3S}$ is independently $C_1$-$C_6$ alkyl or $C_1$-$C_6$ haloalkyl.

In some embodiments, $R_3$ is 5- or 6-membered heteroaryl having one, two, or three heteroatoms.

In some embodiments, $R_3$ is 5- or 6-membered heteroaryl having one, two, or three heteroatoms selected from N and O.

In some embodiments, $R_3$ is 5- or 6-membered heteroaryl having one heteroatom selected from N and O.

In some embodiments, $R_3$ is 5- or 6-membered heteroaryl having two heteroatoms selected from N and O.

In some embodiments, $R_3$ is 5-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, $R_3$ is 5-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein $C_1$-$C_6$ alkyl is optionally substituted with —O($C_1$-$C_6$ alkyl), —N($C_1$-$C_6$ alkyl)$_2$, halo, or —CN.

In some embodiments, $R_3$ is 5-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein $C_1$-$C_6$ alkyl is optionally substituted with —O($C_1$-$C_6$ alkyl) or —N($C_1$-$C_6$ alkyl)$_2$.

In some embodiments, $R_3$ is 5-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl.

In some embodiments, $R_3$ is 5-membered heteroaryl optionally substituted with one or more $R_{3S}$, wherein each $R_{3S}$ is independently $C_1$-$C_6$ alkyl, $C_1$-$C_6$ haloalkyl, or $C_3$-$C_8$ cycloalkyl.

In some embodiments, $R_3$ is 5-membered heteroaryl optionally substituted with one or more $R_{3S}$, wherein each $R_{3S}$ is independently $C_1$-$C_6$ alkyl or $C_1$-$C_6$ haloalkyl.

In some embodiments, $R_3$ is 5-membered heteroaryl optionally substituted with one or more $R_{3S}$, wherein each $R_{3S}$ is independently $C_1$-$C_6$ alkyl.

In some embodiments, $R_3$ is 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, $R_3$ is 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl.

In some embodiments, $R_3$ is 6-membered heteroaryl optionally substituted with one or more $R_{3S}$, wherein each $R_{3S}$ is independently $C_1$-$C_6$ alkyl.

In some embodiments, $R_3$ is 5- or 6-membered heteroaryl optionally substituted with one or more $R_{3S}$.

In some embodiments, $R_3$ is 5-membered heteroaryl optionally substituted with one or more $R_{3S}$.

In some embodiments, $R_3$ is pyrrolyl optionally substituted with one or more $R_{3S}$.

In some embodiments, $R_3$ is

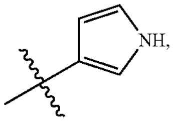 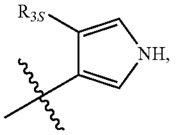 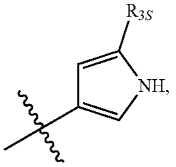

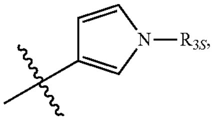 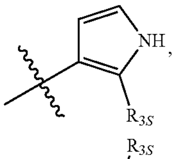 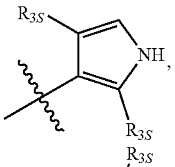

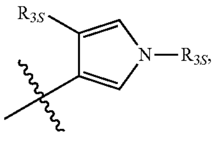 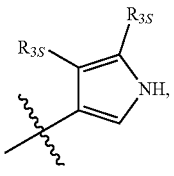 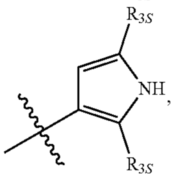

-continued
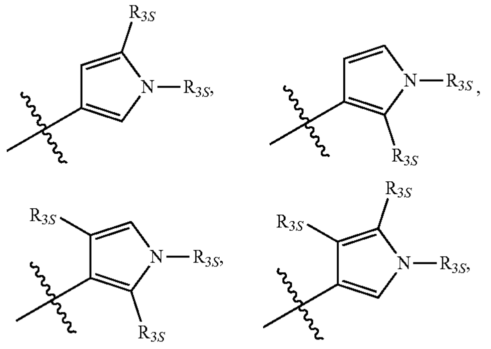
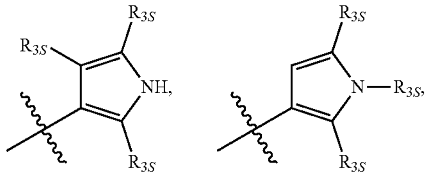
or
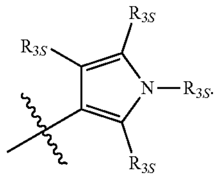
In some embodiments, $R_3$ is
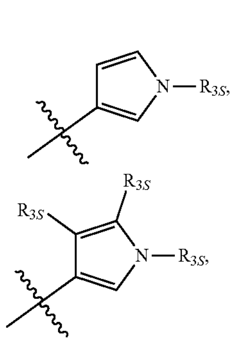
or
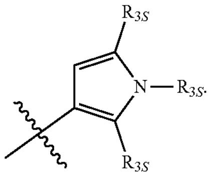
In some embodiments, $R_3$ is
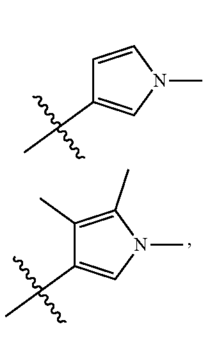
or
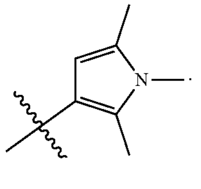
In some embodiments, $R_3$ is pyrazolyl optionally substituted with one or more $R_{3S}$.
In some embodiments, $R_3$ is
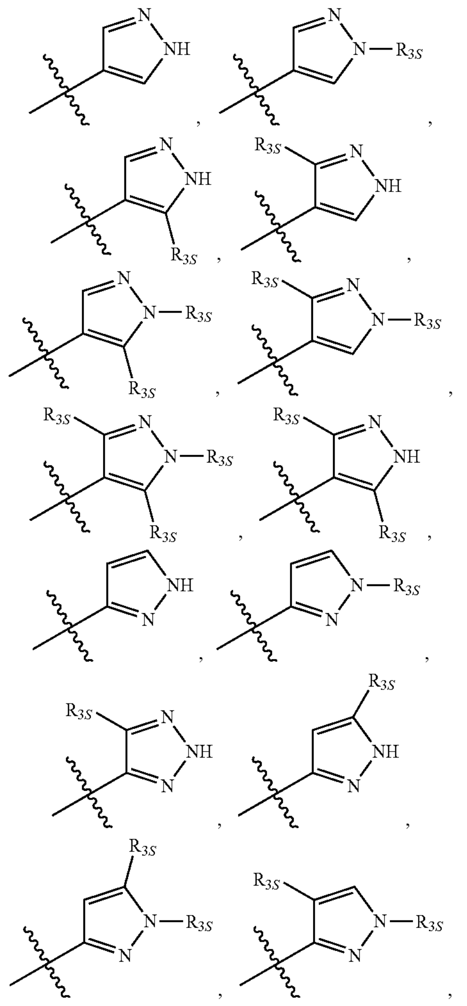
or
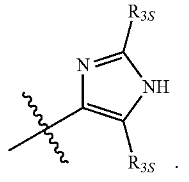
In some embodiments, $R_3$ is
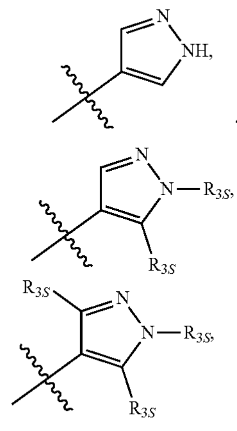
or
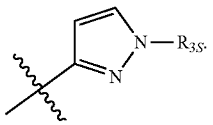

In some embodiments, $R_3$ is
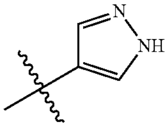, 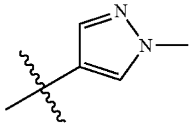, 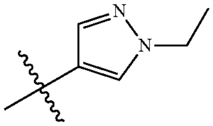, 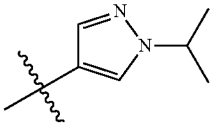, 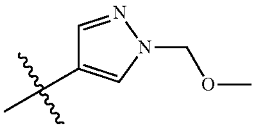, 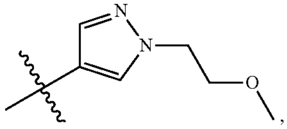, 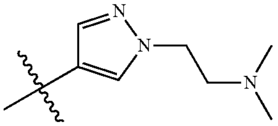, 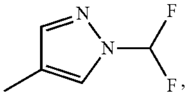 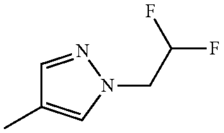, 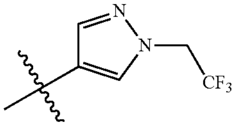, 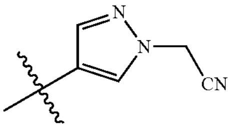, 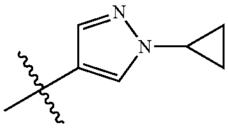, 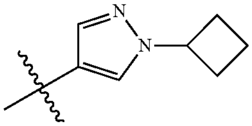, 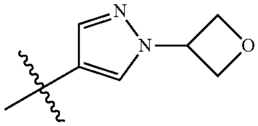, 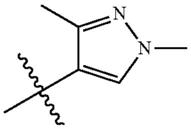, 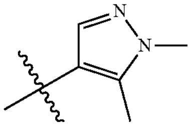, 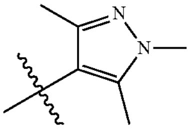, or 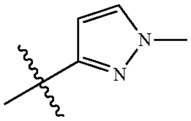.
In some embodiments, $R_3$ is
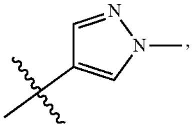 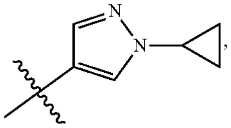 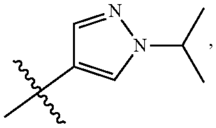, 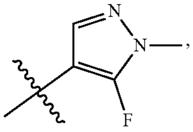
-continued
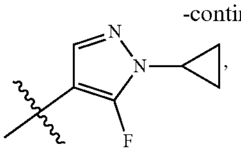 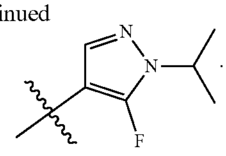
In some embodiments, $R_3$ is
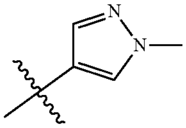 or 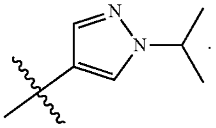
In some embodiments, $R_3$ is
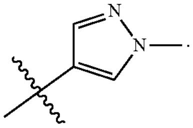 [SMILES: *c1cnn(C)c1]
In some embodiments, $R_3$ is imidazolyl optionally substituted with one or more $R_{3S}$.
In some embodiments, $R_3$ is
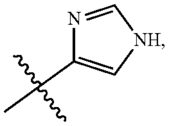 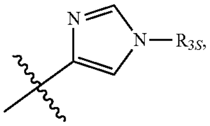 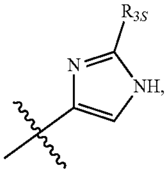 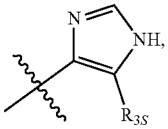 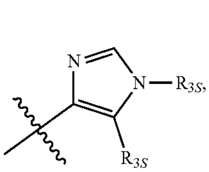 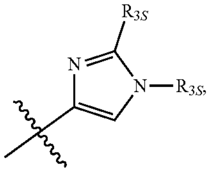 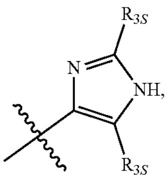 or 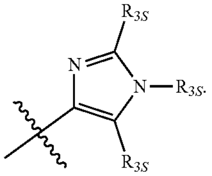
In some embodiments, $R_3$ is
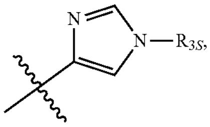

In some embodiments, $R_3$ is

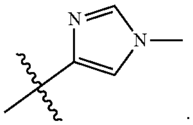 [SMILES: *c1cn(C)cn1]

.

In some embodiments, $R_3$ is triazolyl optionally substituted with one or more $R_{3S}$.

In some embodiments, $R_{3S}$ is

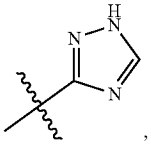

,

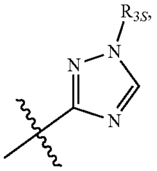

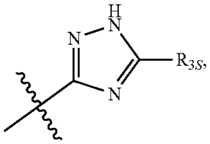

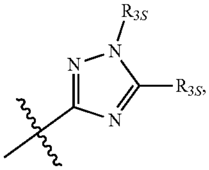

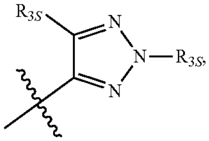

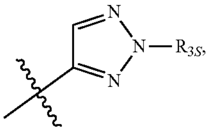

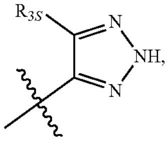

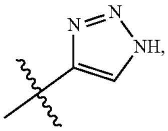

or

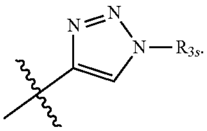

In some embodiments, $R_3$ is

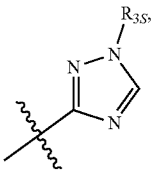

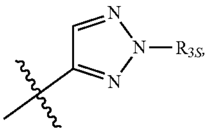

or

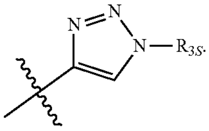

In some embodiments, $R_3$ is

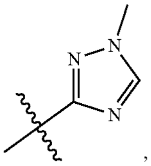

,

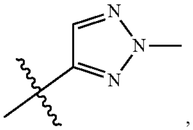

, or

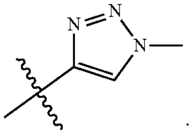

.

In some embodiments, $R_3$ is tetrazolyl optionally substituted with one or more $R_{3S}$.

In some embodiments, $R_3$ is

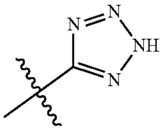

or

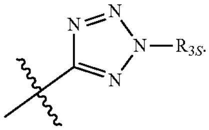

In some embodiments, $R_3$ is

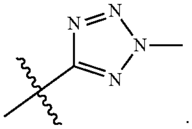 [SMILES: *c1nnn(C)n1]

.

In some embodiments, $R_3$ is isoxazolyl optionally substituted with one or more $R_{3S}$.

In some embodiments, $R_3$ is

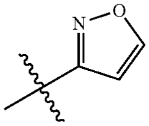

,

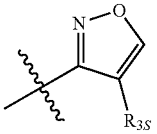

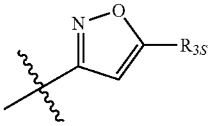

,

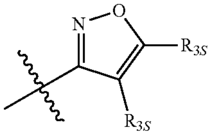

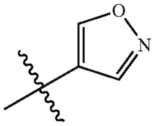

,

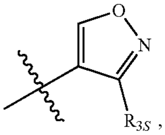

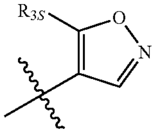

,

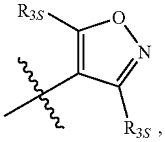

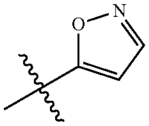

,

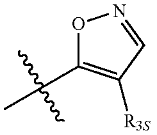

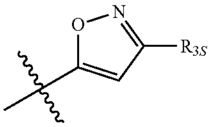

, or

-continued
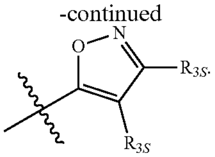
In some embodiments, $R_3$ is
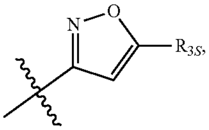
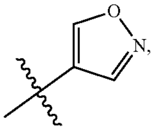
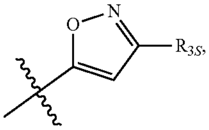
or
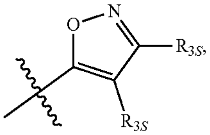
In some embodiments, $R_3$ is
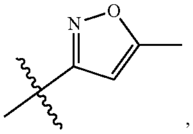
,
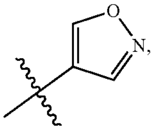
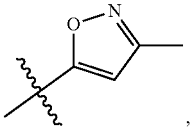
,
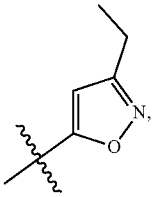
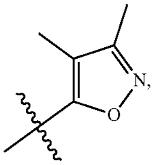
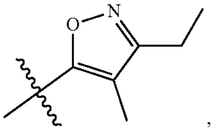
,
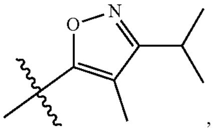
,
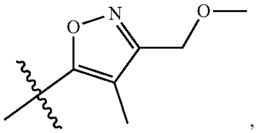
, or
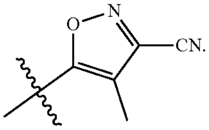
In some embodiments, $R_3$ is furanyl optionally substituted with one or more $R_{3S}$.
In some embodiments, $R_3$ is
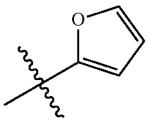
,
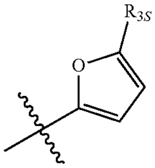
,
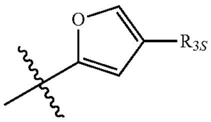
,
-continued
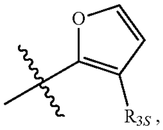
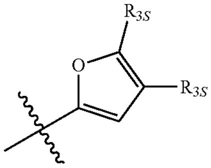
,
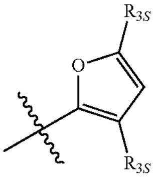
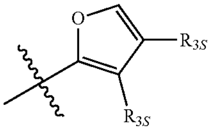
,
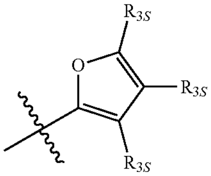
,
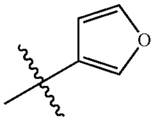
,
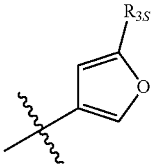
,
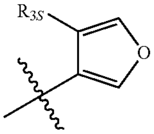
,
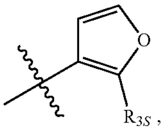
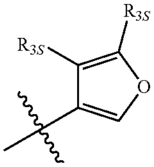
,
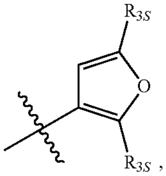
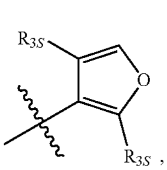
, or
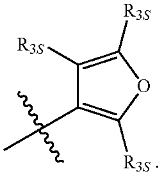
In some embodiments, $R_3$ is
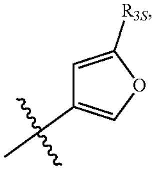
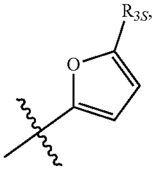
or
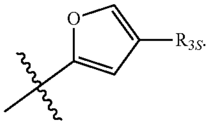

In some embodiments, $R_3$ is

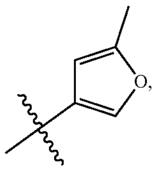

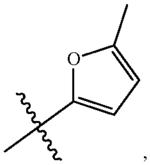
,
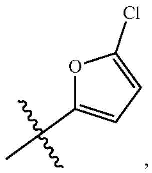
,

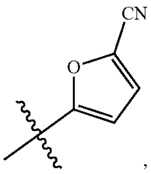
, or
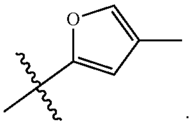
.

In some embodiments, $R_3$ is oxazolyl optionally substituted with one or more $R_{3S}$.

In some embodiments, $R_3$ is

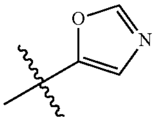
,
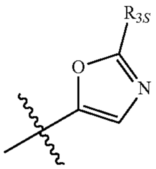
,
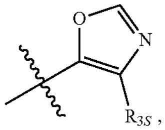
,
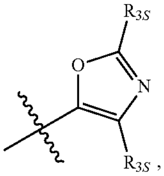
,
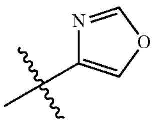
,
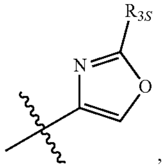
,
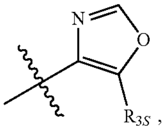
,
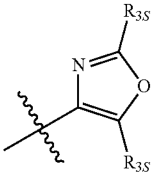
,
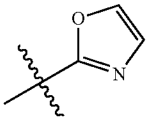
,
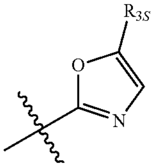
,
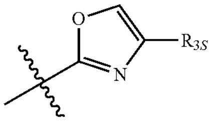
, or
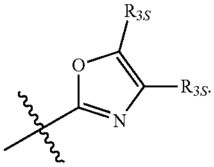

In some embodiments, $R_3$ is

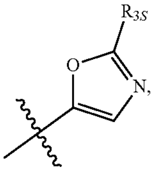

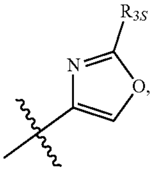

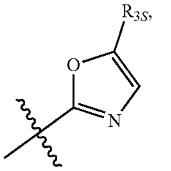
or
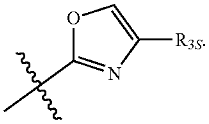

In some embodiments, $R_3$ is

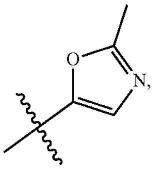

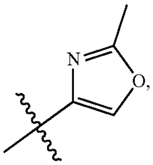

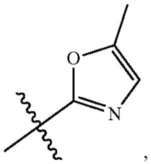
, or
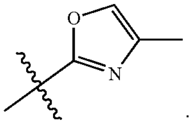
.

In some embodiments, $R_3$ is 4,5,6,7-tetrahydrobenzo[c]isoxazole optionally substituted with one or more $R_{3S}$.

In some embodiments, $R_3$ is

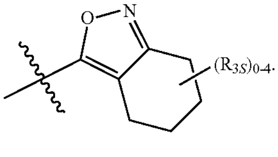

In some embodiments, $R_3$ is

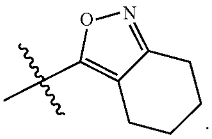 [SMILES: *c1onc2c1CCCC2]
.

In some embodiments, $R_3$ is isothiazolyl optionally substituted with one or more $R_{3S}$.

In some embodiments, $R_3$ is

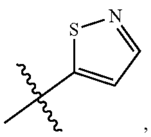
,
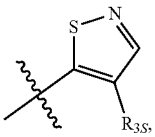

-continued

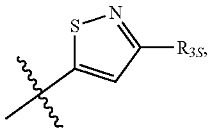 or 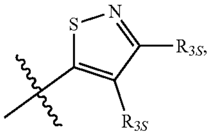

In some embodiments, $R_3$ is

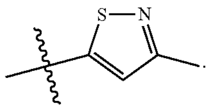 [SMILES: *c1cc(C)ns1]

In some embodiments, $R_3$ is thiazolyl optionally substituted with one or more $R_{3S}$.

In some embodiments, $R_3$ is

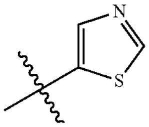, 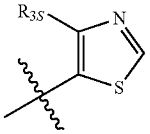, 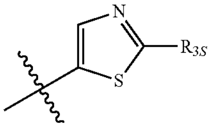,

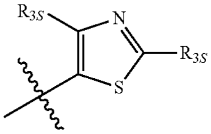, 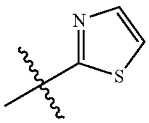,

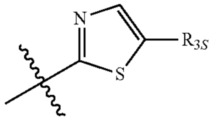, 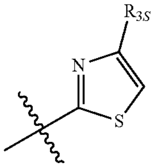,

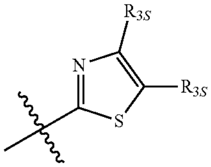, 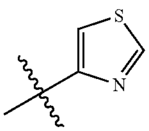,

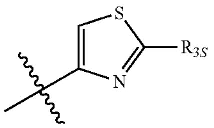, 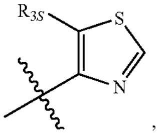, or

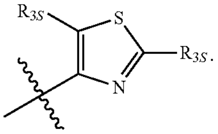

In some embodiments, $R_3$ is

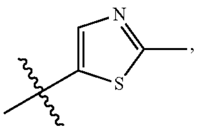, 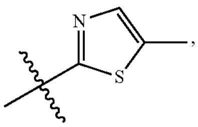, or

-continued

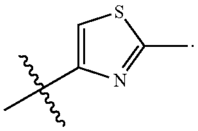

In some embodiments, $R_3$ is thiadiazolyl optionally substituted with one $R_{3S}$.

In some embodiments, $R_3$ is

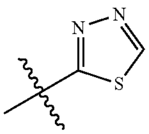 or 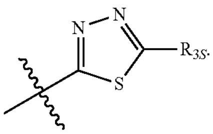

In some embodiments, $R_3$ is

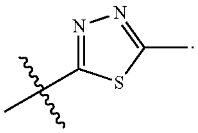 [SMILES: *c1nnc(C)s1]

In some embodiments, $R_3$ is 6-membered heteroaryl optionally substituted with one or more $R_{3S}$.

In some embodiments, $R_3$ is pyridinyl optionally substituted with one or more $R_{3S}$. In some embodiments, $R_3$ is diazinyl optionally substituted with one or more $R_{3S}$. In some embodiments, $R_3$ is pyridazinyl optionally substituted with one or more $R_{3S}$. In some embodiments, $R_3$ is pyrimidinyl optionally substituted with one or more $R_{3S}$. In some embodiments, $R_3$ is pyrazinyl optionally substituted with one or more $R_{3S}$. In some embodiments, $R_3$ is triazinyl optionally substituted with one or more $R_{3S}$. In some embodiments, $R_3$ is tetrazinyl optionally substituted with one $R_{3S}$. In some embodiments, $R_3$ is pentazinyl.

In some embodiments, $R_3$ is

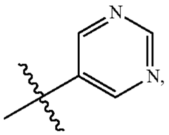 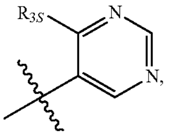 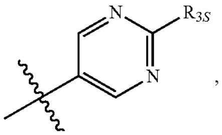,

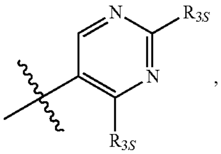, 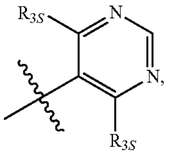 or

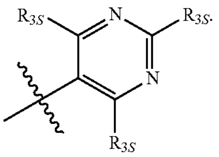

In some embodiments, $R_3$ is

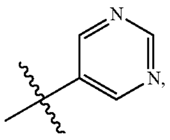
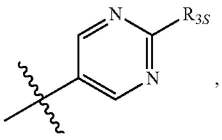
, or
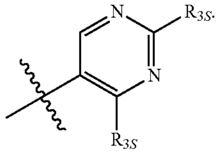

In some embodiments, $R_3$ is

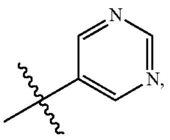
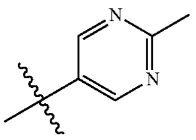
,
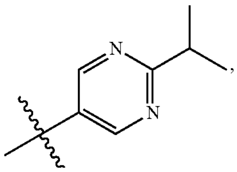
, or
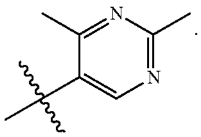
.

In some embodiments, $R_3$ is

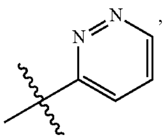
,
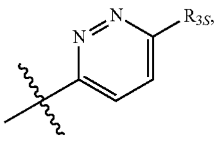
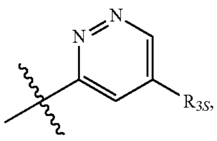
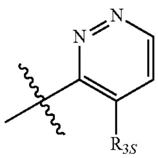
,
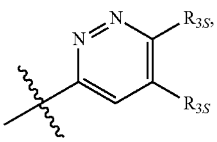
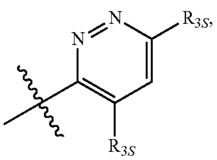
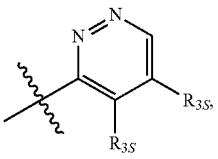
or
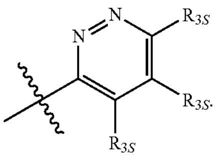

In some embodiments, $R_3$ is

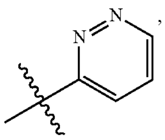
,
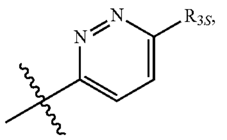
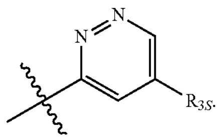

In some embodiments, $R_3$ is

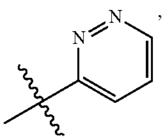
,
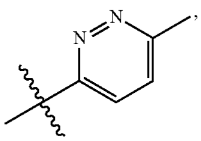
, or
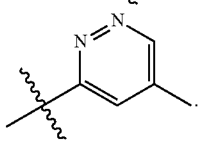
.

In some embodiments, at least one $R_{3S}$ is $C_1$-$C_6$ alkyl, $C_1$-$C_6$ haloalkyl, $C_3$-$C_8$ cycloalkyl, halo, or $C_3$-$C_8$ heterocycloalkyl.

In some embodiments, at least one $R_{3S}$ is $C_1$-$C_6$ alkyl, $C_1$-$C_6$ haloalkyl, or $C_3$-$C_8$ cycloalkyl.

In some embodiments, at least one $R_{3S}$ is $C_1$-$C_6$ alkyl or $C_1$-$C_6$ haloalkyl.

In some embodiments, at least one $R_{3S}$ is $C_1$-$C_6$ alkyl (e.g. linear or branched).

In some embodiments, at least one $R_{3S}$ is methyl. In some embodiments, at least one $R_{3S}$ is ethyl. In some embodiments, at least one $R_{3S}$ is propyl. In some embodiments, at least one $R_{3S}$ is butyl. In some embodiments, at least one $R_{3S}$ is pentyl. In some embodiments, at least one $R_{3S}$ is hexyl. In some embodiments, at least one $R_{3S}$ is isopropyl. In some embodiments, at least one $R_{3S}$ is isobutyl. In some embodiments, at least one $R_{3S}$ is isopentyl. In some embodiments, at least one $R_{3S}$ is isohexyl. In some embodiments, at least one $R_{3S}$ is secbutyl. In some embodiments, at least one $R_{3S}$ is secpentyl. In some embodiments, at least one $R_{3S}$ is sechexyl.

In some embodiments, at least one $R_{3S}$ is $C_1$-$C_6$ alkyl, $C_1$-$C_6$ haloalkyl, $C_3$-$C_8$ cycloalkyl, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

In some embodiments, at least one $R_{3S}$ is $C_1$-$C_6$ alkyl optionally substituted with —O($C_1$-$C_6$ alkyl), —N($C_1$-$C_6$ alkyl)$_2$, halo, or —CN.

In some embodiments, at least one $R_{3S}$ is $C_1$-$C_6$ alkyl optionally substituted with —O($C_1$-$C_6$ alkyl) or —N($C_1$-$C_6$ alkyl)$_2$.

In some embodiments, at least one $R_{3S}$ is $C_1$-$C_6$ alkyl optionally substituted with —O($C_1$-$C_6$ alkyl) (e.g. methyl, ethyl, propyl, butyl, pentyl, hexyl).

In some embodiments, at least one $R_{3S}$ is methyl optionally substituted with —O($C_1$-$C_6$ alkyl). In some embodiments, at least one $R_{3S}$ is ethyl optionally substituted with —O($C_1$-$C_6$ alkyl). In some embodiments, at least one $R_{3S}$ is propyl optionally substituted with —O($C_1$-$C_6$ alkyl). In some embodiments, at least one $R_{3S}$ is butyl optionally substituted with —O($C_1$-$C_6$ alkyl). In some embodiments, at least one $R_{3S}$ is pentyl optionally substituted with —O($C_1$-$C_6$ alkyl). In some embodiments, at least one $R_{3S}$ is hexyl optionally substituted with —O($C_1$-$C_6$ alkyl).

In some embodiments, at least one $R_{3S}$ is $C_1$-$C_6$ alkyl optionally substituted with —N($C_1$-$C_6$ alkyl)$_2$ (e.g. methyl, ethyl, propyl, butyl, pentyl, hexyl).

In some embodiments, at least one $R_{3S}$ is methyl optionally substituted with —N($C_1$-$C_6$ alkyl)$_2$. In some embodiments, at least one $R_{3S}$ is ethyl optionally substituted with —N($C_1$-$C_6$ alkyl)$_2$. In some embodiments, at least one $R_{3S}$ is propyl optionally substituted with —N($C_1$-$C_6$ alkyl)$_2$. In some embodiments, at least one $R_{3S}$ is butyl optionally substituted with —N($C_1$-$C_6$ alkyl)$_2$. In some embodiments, at least one $R_{3S}$ is pentyl optionally substituted with —N($C_1$-$C_6$ alkyl)$_2$. In some embodiments, at least one $R_{3S}$ is hexyl optionally substituted with —N($C_1$-$C_6$ alkyl)$_2$.

In some embodiments, at least one $R_{3S}$ is $C_1$-$C_6$ alkyl optionally substituted with —CN.

In some embodiments, at least one $R_{3S}$ is methyl optionally substituted with —CN. In some embodiments, at least one $R_{3S}$ is ethyl optionally substituted with —CN. In some embodiments, at least one $R_{3S}$ is propyl optionally substituted with —CN. In some embodiments, at least one $R_{3S}$ is butyl optionally substituted with —CN. In some embodiments, at least one $R_{3S}$ is pentyl optionally substituted with —CN. In some embodiments, at least one $R_{3S}$ is hexyl optionally substituted with —CN.

In some embodiments, at least one $R_{3S}$ is $C_1$-$C_6$ haloalkyl (e.g. methyl, ethyl, propyl, butyl, pentyl, or hexyl substituted with one or more halogen).

In some embodiments, at least one $R_{3S}$ is $C_1$-$C_6$ haloalkyl optionally substituted with —O($C_1$-$C_6$ alkyl), —N($C_1$-$C_6$ alkyl)$_2$, halo, or —CN.

In some embodiments, at least one $R_{3S}$ is —$CH_2F$, —$CHF_2$, —$CF_3$, —$CH_2CH_2F$, —$CH_2CHF_2$, or —$CH_2CF_3$.

In some embodiments, at least one $R_{3S}$ is —$CHF_2$. In some embodiments, at least one $R_{3S}$ is —$CH_2CHF_2$. In some embodiments, at least one $R_{3S}$ is —$CH_2CF_3$.

In some embodiments, at least one $R_{3S}$ is $C_3$-$C_8$ cycloalkyl.

In some embodiments, at least one $R_{3S}$ is $C_3$-$C_8$ cycloalkyl optionally substituted with —O($C_1$-$C_6$ alkyl), —N($C_1$-$C_6$ alkyl)$_2$, halo, or —CN.

In some embodiments, at least one $R_{3S}$ is $C_3$-$C_7$ cycloalkyl. In some embodiments, at least one $R_{3S}$ is $C_3$-$C_6$ cycloalkyl. In some embodiments, at least one $R_{3S}$ is $C_3$-$C_5$ cycloalkyl. In some embodiments, at least one $R_{3S}$ is $C_3$-$C_4$ cycloalkyl.

In some embodiments, at least one $R_{3S}$ is cyclopropyl.

In some embodiments, at least one $R_{3S}$ is cyclobutyl.

In some embodiments, at least one $R_{3S}$ is $C_3$-$C_8$ heterocycloalkyl.

In some embodiments, at least one $R_{3S}$ is $C_3$-$C_8$ heterocycloalkyl optionally substituted with —O($C_1$-$C_6$ alkyl), —N($C_1$-$C_6$ alkyl)$_2$, halo, or —CN.

In some embodiments, at least one $R_{3S}$ is $C_3$-$C_7$ heterocycloalkyl. In some embodiments, at least one $R_{3S}$ is $C_3$-$C_6$ heterocycloalkyl. In some embodiments, at least one $R_{3S}$ is $C_3$-$C_5$ heterocycloalkyl. In some embodiments, at least one $R_{3S}$ is $C_3$-$C_4$ heterocycloalkyl. In some embodiments, at least one $R_{3S}$ is $C_4$-$C_5$ heterocycloalkyl.

In some embodiments, at least one $R_{3S}$ is oxetanyl.

In some embodiments, at least one $R_{3S}$ is

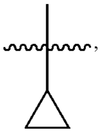,
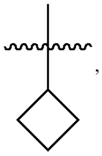, or
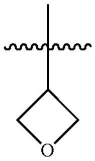.

In some embodiments, at least one $R_{3S}$ is methyl, ethyl, isopropyl, —$CH_2OCH_3P$, —$CH_2CF_3$, —$CH_2CH_2OCH_3$, —$CH_2CN$, $CH_2CF_2$, or —$CH_2CH_2N(CH_3)_2$.

In some embodiments, at least one $R_{3S}$ is halo.

In some embodiments, at least one $R_{3S}$ is F, Cl, Br, or I.

In some embodiments, at least one $R_{3S}$ is F or Cl.

In some embodiments, at least one $R_{3S}$ is F.

In some embodiments, at least one $R_{3S}$ is Cl.

In some embodiments, the compound is of Formula (II-a) or (II-b):

(II-a)

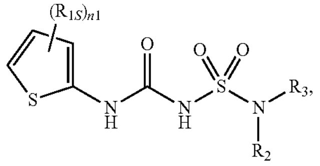

(II-b)

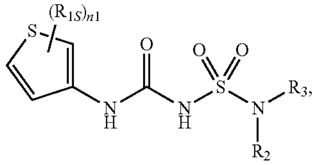

or a prodrug, solvate, or pharmaceutically acceptable salt thereof, wherein $n_1$ is an integer ranging from 0 to 3 (e.g., 0, 1, 2, or 3).

In some embodiments, the compound is of Formula (II-a) or a prodrug, solvate, or pharmaceutically acceptable salt thereof.

In some embodiments, the compound is of Formula (II-b) or a prodrug, solvate, or pharmaceutically acceptable salt thereof.

In some embodiments, the compound is of Formula (II-c), (II-d), (II-e):

(II-c)

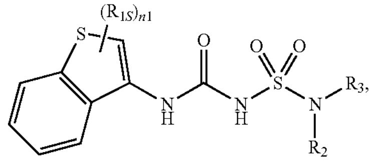

(II-d)

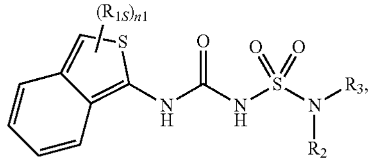

-continued (II-e)

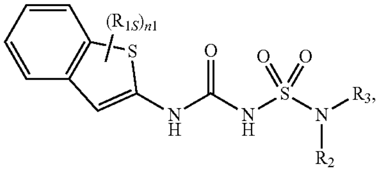

or a prodrug, solvate, or pharmaceutically acceptable salt thereof, wherein $n_1$ is 0 or 1.

In some embodiments, the compound is of Formula (II-c) or a prodrug, solvate, or pharmaceutically acceptable salt thereof.

In some embodiments, the compound is of Formula (II-d) or a prodrug, solvate, or pharmaceutically acceptable salt thereof.

In some embodiments, the compound is of Formula (II-e) or a prodrug, solvate, or pharmaceutically acceptable salt thereof.

In some embodiments, the compound is of Formula (III):

(III)

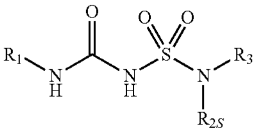

or a prodrug, solvate, or pharmaceutically acceptable salt thereof.

In some embodiments, the compound is of Formula (III-a) or (III-b):

(III-a)

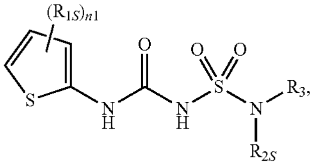

(III-b)

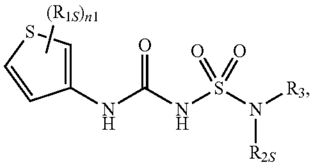

or a prodrug, solvate, or pharmaceutically acceptable salt thereof, wherein $n_1$ is an integer ranging from 0 to 3 (e.g., 0, 1, 2, or 3).

In some embodiments, the compound is of Formula (III-a) or a prodrug, solvate, or pharmaceutically acceptable salt thereof.

In some embodiments, the compound is of Formula (III-b) or a prodrug, solvate, or pharmaceutically acceptable salt thereof.

In some embodiments, the compound is of Formula (III-c), (III-d), (III-e):

(III-c)

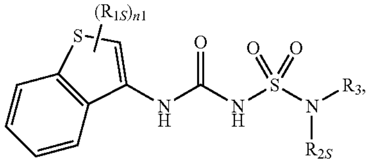

(III-d)

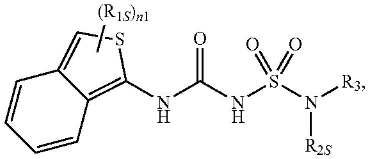

(III-e)

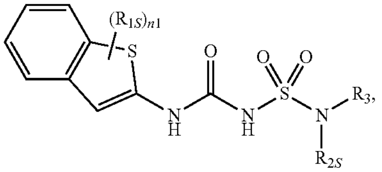

or a prodrug, solvate, or pharmaceutically acceptable salt thereof, wherein $n_1$ is 0 or 1.

In some embodiments, the compound is of Formula (III-c) or a prodrug, solvate, or pharmaceutically acceptable salt thereof.

In some embodiments, the compound is of Formula (III-d) or a prodrug, solvate, or pharmaceutically acceptable salt thereof.

In some embodiments, the compound is of Formula (III-e) or a prodrug, solvate, or pharmaceutically acceptable salt thereof.

In some embodiments, the compound is of Formula (IV):

(IV)

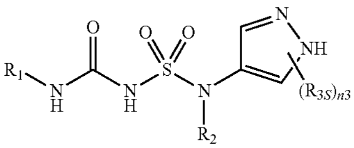

or a prodrug, solvate, or pharmaceutically acceptable salt thereof, wherein $n_1$ is an integer ranging from 0 to 3 (e.g., 0, 1, 2, or 3).

In some embodiments, the compound is of Formula (IV-a):

(IV-a)

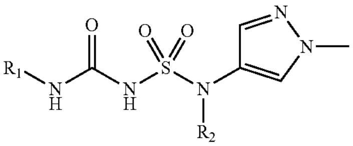

or a prodrug, solvate, or pharmaceutically acceptable salt thereof.

It is understood that, for a compound of any one of the formulae described herein, $R_1$, $R_{1S}$, $R_2$, $R_{2S}$, $R_3$, $R_{3S}$, and $X_2$ can each be, where applicable, selected from the groups described herein, and any group described herein for any of $R_1$, $R_{1S}$, $R_2$, $R_{2S}$, $R_3$, $R_{3S}$, and $X_2$ can be combined, where applicable, with any group described herein for one or more of the remainder of $R_1$, $R_{1S}$, $R_2$, $R_{2S}$, $R_3$, $R_{3S}$, and $X_2$.

In some embodiments, the compound is selected from the compounds described in Table 1 and prodrugs and pharmaceutically acceptable salts thereof.

In some embodiments, the compound is selected from the compounds described in Table 1 and pharmaceutically acceptable salts thereof.

In some embodiments, the compound is selected from the prodrugs of compounds described in Table 1 and pharmaceutically acceptable salts thereof.

In some embodiments, the compound is selected from the compounds described in Table 1.

TABLE 1

| Compound No. | Structure |
|---|---|
| 1 | 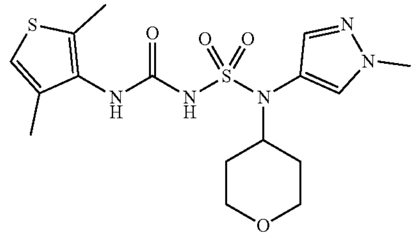 [SMILES: Cc1csc(C)c1NC(=O)NS(=O)(=O)N(c1cnn(C)c1)C1CCOCC1] |
| 2 | 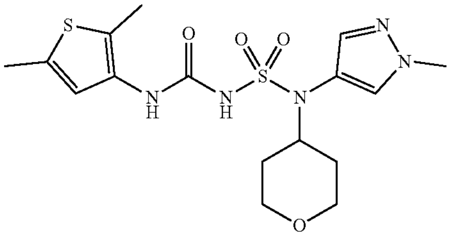 |
| 3 | 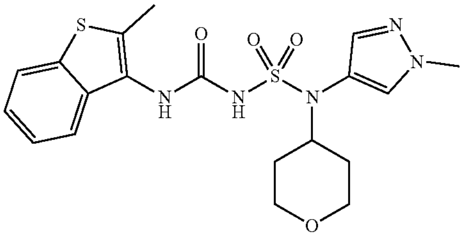 [SMILES: Cc1sc2ccccc2c1NC(=O)NS(=O)(=O)N(c1cnn(C)c1)C1CCOCC1] |
| 4 | 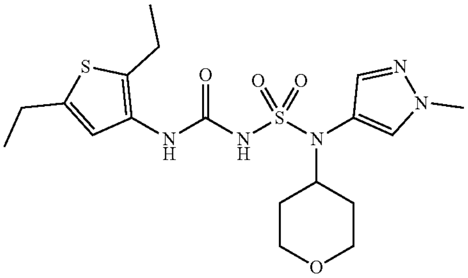 [SMILES: CCc1cc(NC(=O)NS(=O)(=O)N(c2cnn(C)c2)C2CCOCC2)c(CC)s1] |
| 5 | 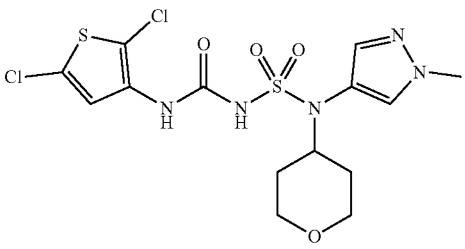 [SMILES: Cn1cc(N(C2CCOCC2)S(=O)(=O)NC(=O)Nc2cc(Cl)sc2Cl)cn1] |

TABLE 1-continued
| Compound No. | Structure |
|---|---|
| 6 | 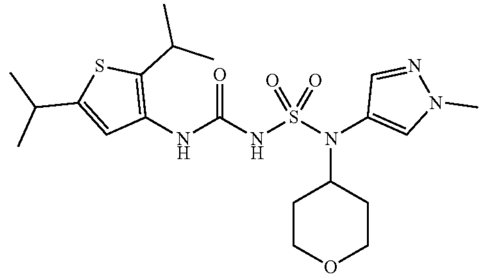 [SMILES: CC(C)c1cc(NC(=O)NS(=O)(=O)N(c2cnn(C)c2)C2CCOCC2)c(C(C)C)s1] |
| 7 | 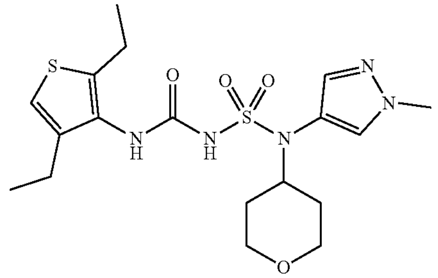 [SMILES: CCc1csc(CC)c1NC(=O)NS(=O)(=O)N(c1cnn(C)c1)C1CCOCC1] |
| 8 | 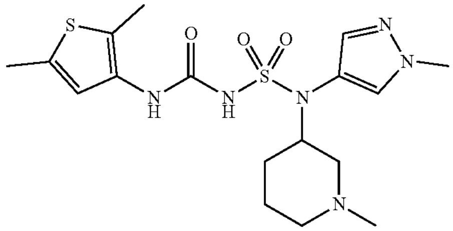 |
| 9 | 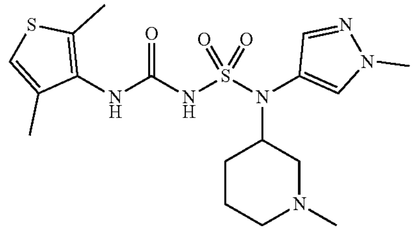 [SMILES: Cc1csc(C)c1NC(=O)NS(=O)(=O)N(c1cnn(C)c1)C1CCCN(C)C1] |
| 10 | 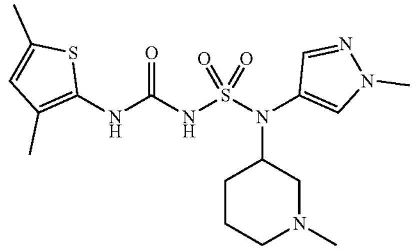 [SMILES: Cc1cc(C)c(NC(=O)NS(=O)(=O)N(c2cnn(C)c2)C2CCCN(C)C2)s1] |
| 11 | 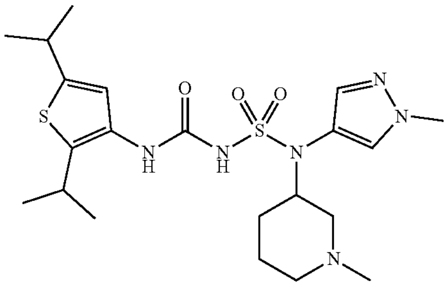 [SMILES: CC(C)c1cc(NC(=O)NS(=O)(=O)N(c2cnn(C)c2)C2CCCN(C)C2)c(C(C)C)s1] |

TABLE 1-continued
| Compound No. | Structure |
| --- | --- |
| 12 | 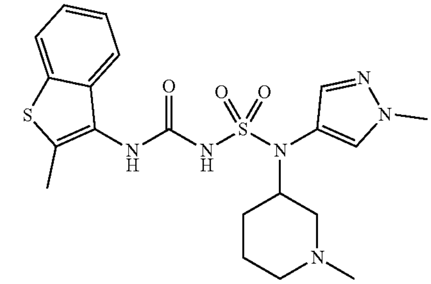 [SMILES: Cc1sc2ccccc2c1NC(=O)NS(=O)(=O)N(c1cnn(C)c1)C1CCCN(C)C1] |
| 13 | 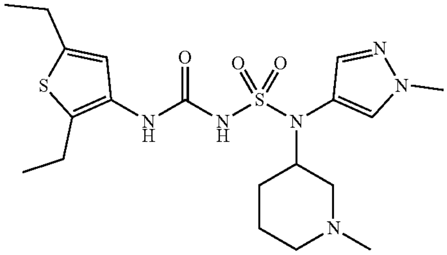 [SMILES: CCc1cc(NC(=O)NS(=O)(=O)N(c2cnn(C)c2)C2CCCN(C)C2)c(CC)s1] |
| 14 | 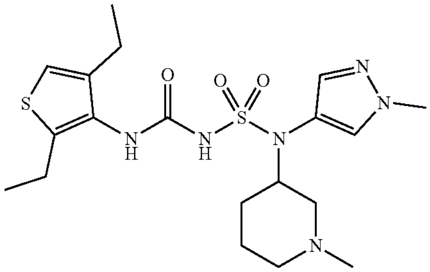 [SMILES: CCc1csc(CC)c1NC(=O)NS(=O)(=O)N(c1cnn(C)c1)C1CCCN(C)C1] |
| 15 | 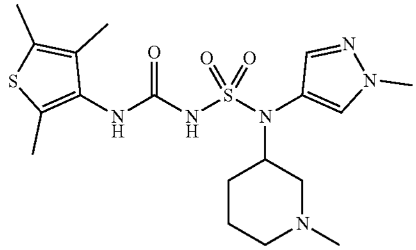 [SMILES: Cc1sc(C)c(NC(=O)NS(=O)(=O)N(c2cnn(C)c2)C2CCCN(C)C2)c1C] |
| 16 | 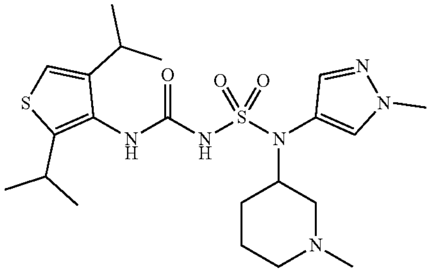 [SMILES: CC(C)c1csc(C(C)C)c1NC(=O)NS(=O)(=O)N(c1cnn(C)c1)C1CCCN(C)C1]

TABLE 1-continued
| Compound No. | Structure |
|---|---|
| 17 | 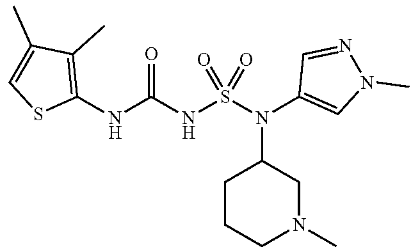 [SMILES: Cc1csc(NC(=O)NS(=O)(=O)N(c2cnn(C)c2)C2CCCN(C)C2)c1C] |
| 18 | 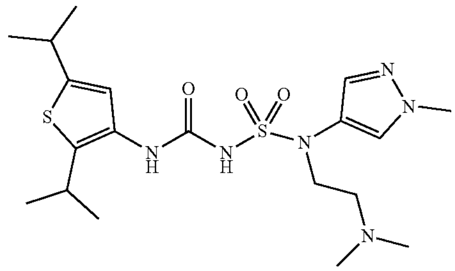 [SMILES: CC(C)c1cc(NC(=O)NS(=O)(=O)N(CCN(C)C)c2cnn(C)c2)c(C(C)C)s1] |
| 19 | 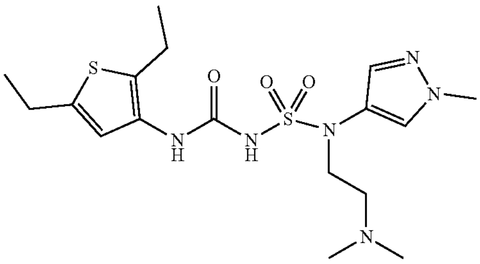 [SMILES: CCc1cc(NC(=O)NS(=O)(=O)N(CCN(C)C)c2cnn(C)c2)c(CC)s1] |
| 20 | 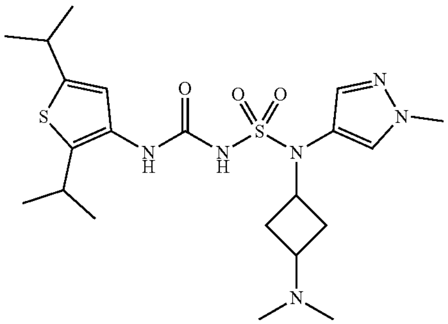 [SMILES: CC(C)c1cc(NC(=O)NS(=O)(=O)N(c2cnn(C)c2)C2CC(N(C)C)C2)c(C(C)C)s1] |
| 21 | 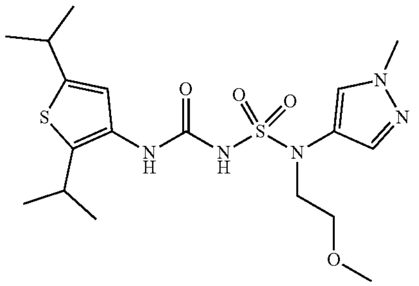 [SMILES: COCCN(c1cnn(C)c1)S(=O)(=O)NC(=O)Nc1cc(C(C)C)sc1C(C)C] |

TABLE 1-continued
| Compound No. | Structure |
| --- | --- |
| 22 | 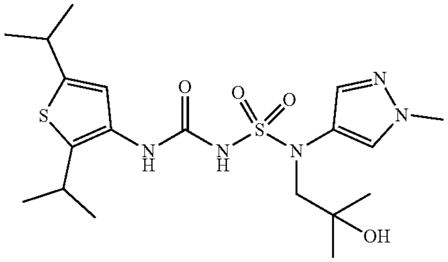 [SMILES: CC(C)c1cc(NC(=O)NS(=O)(=O)N(CC(C)(C)O)c2cnn(C)c2)c(C(C)C)s1] |
| 23 | 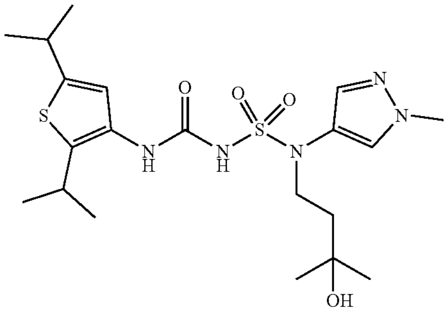 [SMILES: CC(C)c1cc(NC(=O)NS(=O)(=O)N(CCC(C)(C)O)c2cnn(C)c2)c(C(C)C)s1] |
| 24 | 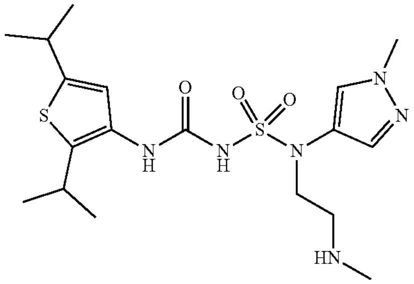 [SMILES: CNCCN(c1cnn(C)c1)S(=O)(=O)NC(=O)Nc1cc(C(C)C)sc1C(C)C] |
| 25 | 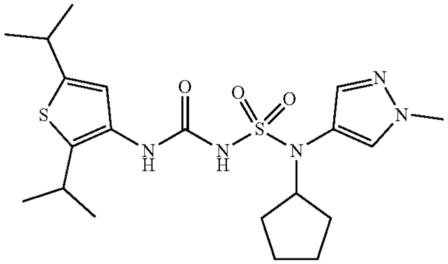 [SMILES: CC(C)c1cc(NC(=O)NS(=O)(=O)N(c2cnn(C)c2)C2CCCC2)c(C(C)C)s1] |
| 26 | 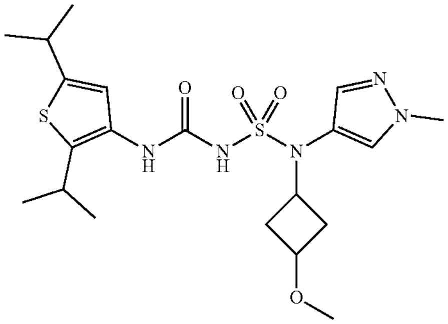 [SMILES: COC1CC(N(c2cnn(C)c2)S(=O)(=O)NC(=O)Nc2cc(C(C)C)sc2C(C)C)C1] |

TABLE 1-continued
| Compound No. | Structure |
| --- | --- |
| 27 | 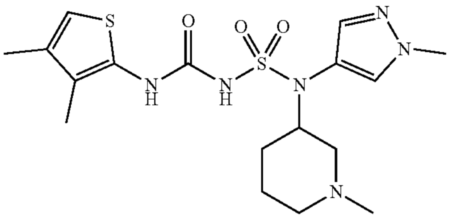 |
| 28 | 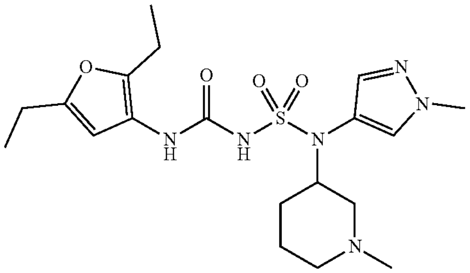 [SMILES: CCc1cc(NC(=O)NS(=O)(=O)N(c2cnn(C)c2)C2CCCN(C)C2)c(CC)o1] |
| 29 | 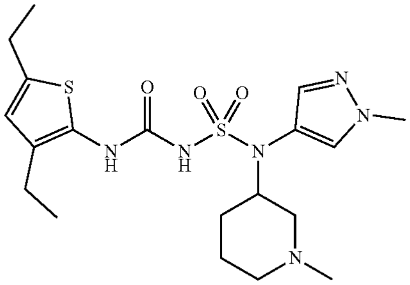 [SMILES: CCc1cc(CC)c(NC(=O)NS(=O)(=O)N(c2cnn(C)c2)C2CCCN(C)C2)s1] |
| 30 | 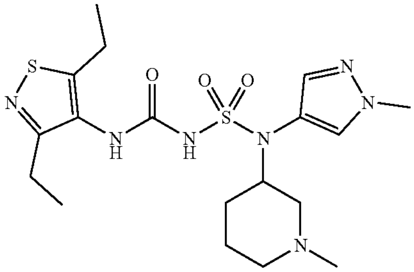 [SMILES: CCc1nsc(CC)c1NC(=O)NS(=O)(=O)N(c1cnn(C)c1)C1CCCN(C)C1] |
| 31 | 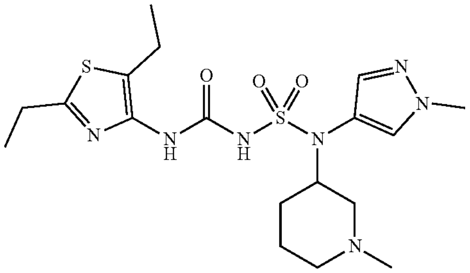 [SMILES: CCc1nc(NC(=O)NS(=O)(=O)N(c2cnn(C)c2)C2CCCN(C)C2)c(CC)s1] |
| 32 | 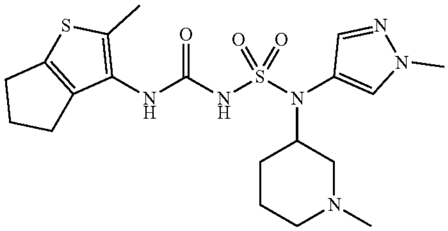 [SMILES: Cc1sc2c(c1NC(=O)NS(=O)(=O)N(c1cnn(C)c1)C1CCCN(C)C1)CCC2] |

TABLE 1-continued
| Compound No. | Structure |
| --- | --- |
| 33 | 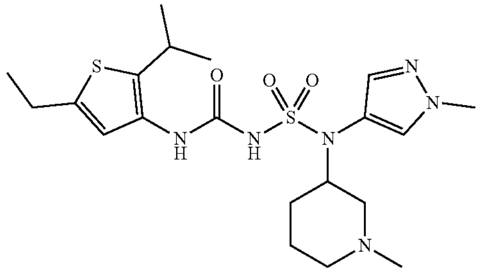 [SMILES: CCc1cc(NC(=O)NS(=O)(=O)N(c2cnn(C)c2)C2CCCN(C)C2)c(C(C)C)s1] |
| 34 | 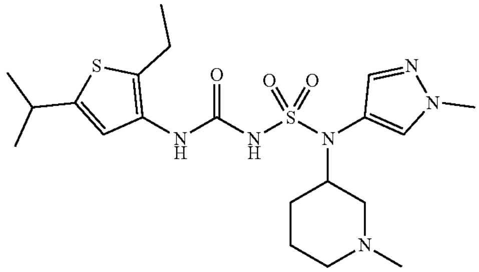 [SMILES: CCc1sc(C(C)C)cc1NC(=O)NS(=O)(=O)N(c1cnn(C)c1)C1CCCN(C)C1] |
| 35 | 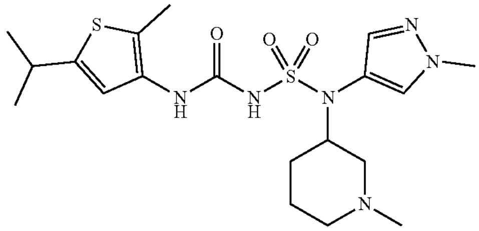 [SMILES: Cc1sc(C(C)C)cc1NC(=O)NS(=O)(=O)N(c1cnn(C)c1)C1CCCN(C)C1] |
| 36 | 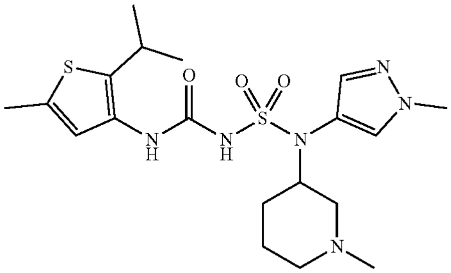 |
| 37 | 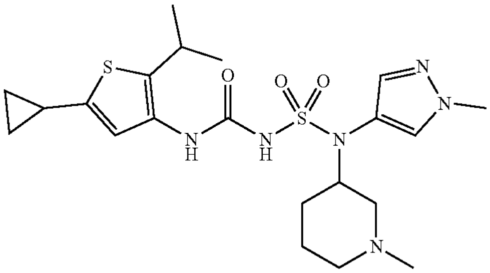 [SMILES: CC(C)c1sc(C2CC2)cc1NC(=O)NS(=O)(=O)N(c1cnn(C)c1)C1CCCN(C)C1] |

TABLE 1-continued
| Compound No. | Structure |
|---|---|
| 38 | 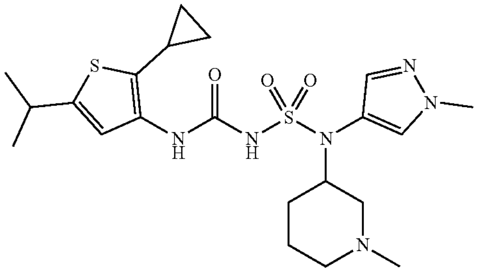 [SMILES: CC(C)c1cc(NC(=O)NS(=O)(=O)N(c2cnn(C)c2)C2CCCN(C)C2)c(C2CC2)s1] |
| 39 | 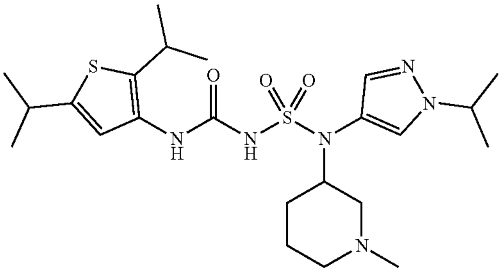 [SMILES: CC(C)c1cc(NC(=O)NS(=O)(=O)N(c2cnn(C(C)C)c2)C2CCCN(C)C2)c(C(C)C)s1] |
| 40 | 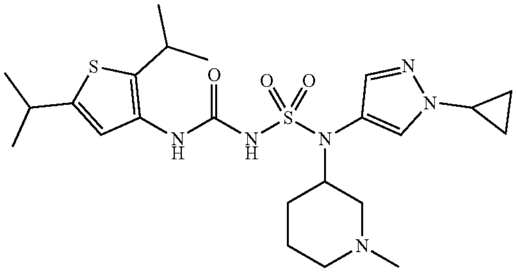 [SMILES: CC(C)c1cc(NC(=O)NS(=O)(=O)N(c2cnn(C3CC3)c2)C2CCCN(C)C2)c(C(C)C)s1] |
| 41 | 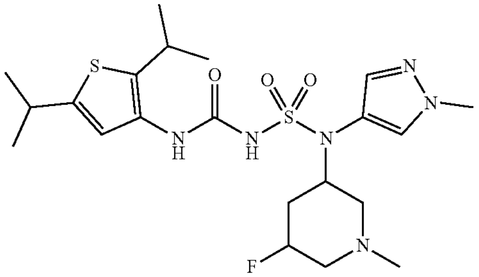 [SMILES: CC(C)c1cc(NC(=O)NS(=O)(=O)N(c2cnn(C)c2)C2CC(F)CN(C)C2)c(C(C)C)s1] |
| 42 | 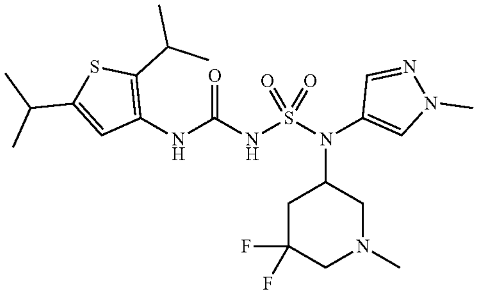 [SMILES: CC(C)c1cc(NC(=O)NS(=O)(=O)N(c2cnn(C)c2)C2CN(C)CC(F)(F)C2)c(C(C)C)s1] |

TABLE 1-continued
| Compound No. | Structure |
|---|---|
| 43 | 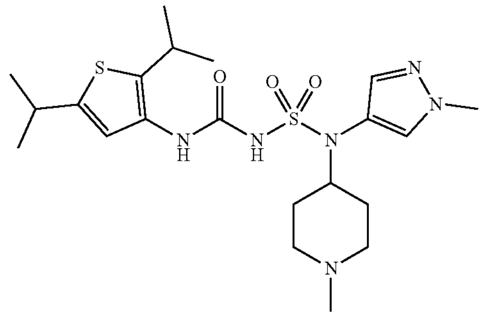 [SMILES: CC(C)c1cc(NC(=O)NS(=O)(=O)N(c2cnn(C)c2)C2CCN(C)CC2)c(C(C)C)s1] |
| 44 | 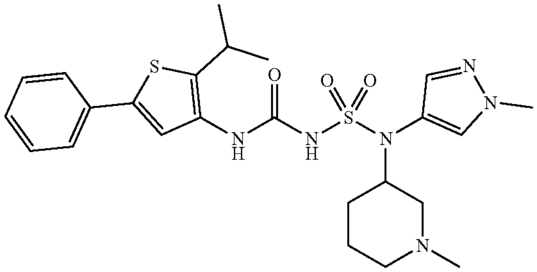 [SMILES: CC(C)c1sc(-c2ccccc2)cc1NC(=O)NS(=O)(=O)N(c1cnn(C)c1)C1CCCN(C)C1] |
| 45 | 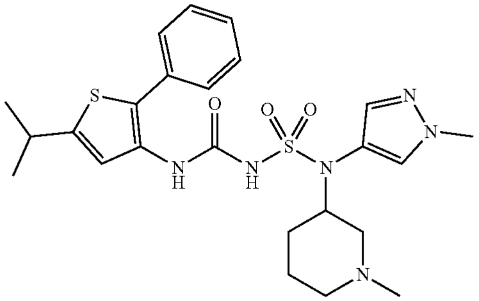 [SMILES: CC(C)c1cc(NC(=O)NS(=O)(=O)N(c2cnn(C)c2)C2CCCN(C)C2)c(-c2ccccc2)s1] |
| 46 | 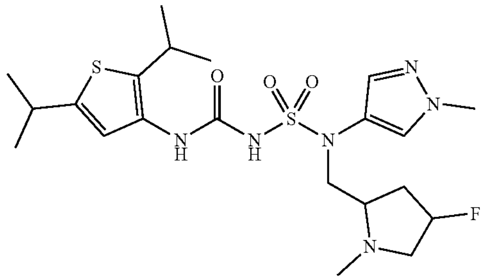 [SMILES: CC(C)c1cc(NC(=O)NS(=O)(=O)N(CC2CC(F)CN2C)c2cnn(C)c2)c(C(C)C)s1] |
| 47 | 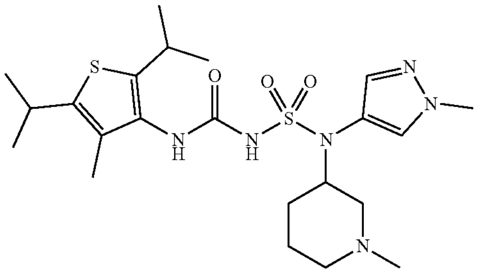 [SMILES: Cc1c(C(C)C)sc(C(C)C)c1NC(=O)NS(=O)(=O)N(c1cnn(C)c1)C1CCCN(C)C1] |

TABLE 1-continued
| Compound No. | Structure |
| --- | --- |
| 48 | 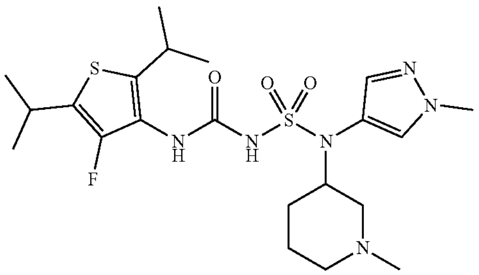 [SMILES: CC(C)c1sc(C(C)C)c(NC(=O)NS(=O)(=O)N(c2cnn(C)c2)C2CCCN(C)C2)c1F] |
| 49 | 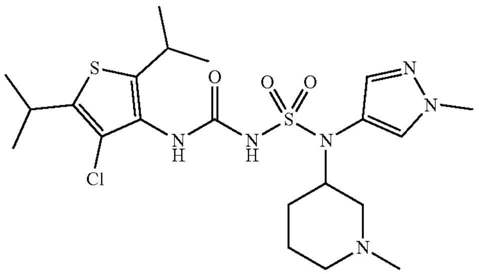 [SMILES: CC(C)c1sc(C(C)C)c(NC(=O)NS(=O)(=O)N(c2cnn(C)c2)C2CCCN(C)C2)c1Cl] |
| 50 | 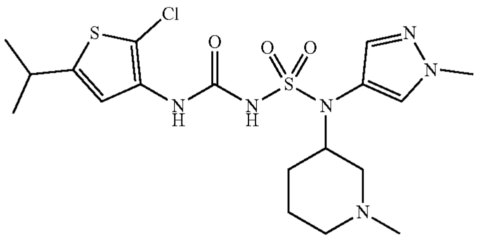 [SMILES: CC(C)c1cc(NC(=O)NS(=O)(=O)N(c2cnn(C)c2)C2CCCN(C)C2)c(Cl)s1] |
| 51 | 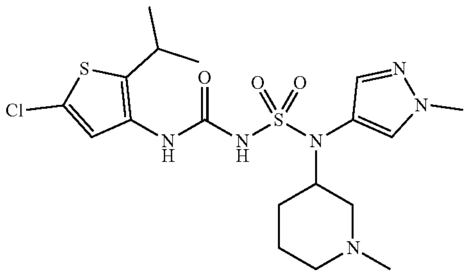 [SMILES: CC(C)c1sc(Cl)cc1NC(=O)NS(=O)(=O)N(c1cnn(C)c1)C1CCCN(C)C1] |
| 52 | 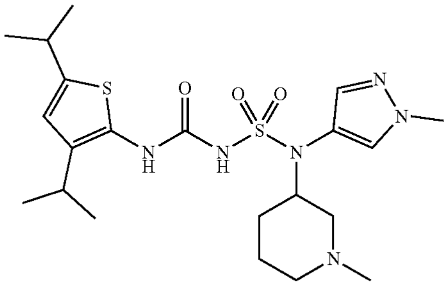 [SMILES: CC(C)c1cc(C(C)C)c(NC(=O)NS(=O)(=O)N(c2cnn(C)c2)C2CCCN(C)C2)s1] |

TABLE 1-continued
| Compound No. | Structure |
|---|---|
| 53 | 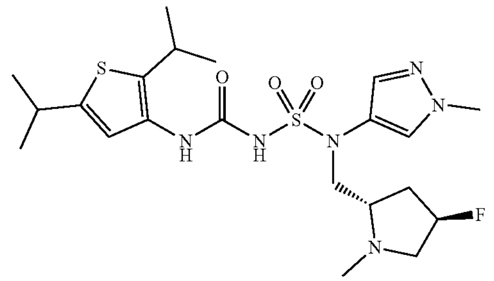 [SMILES: CC(C)c1cc(NC(=O)NS(=O)(=O)N(C[C@@H]2C[C@@H](F)CN2C)c2cnn(C)c2)c(C(C)C)s1] |
| 54 | 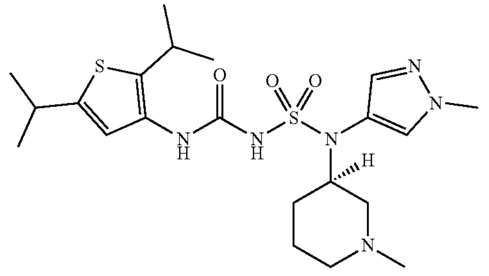 [SMILES: CC(C)c1cc(NC(=O)NS(=O)(=O)N(c2cnn(C)c2)[C@@H]2CCCN(C)C2)c(C(C)C)s1] |
| 55 | 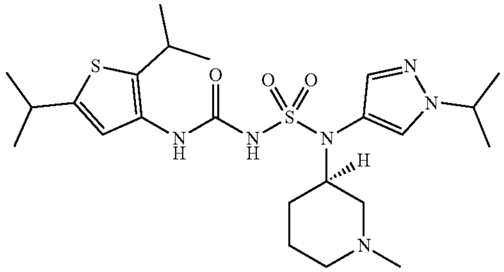 [SMILES: CC(C)c1cc(NC(=O)NS(=O)(=O)N(c2cnn(C(C)C)c2)[C@@H]2CCCN(C)C2)c(C(C)C)s1] |
| 56 | 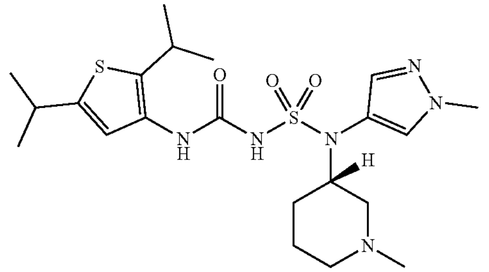 [SMILES: CC(C)c1cc(NC(=O)NS(=O)(=O)N(c2cnn(C)c2)[C@H]2CCCN(C)C2)c(C(C)C)s1] |
| 57 | 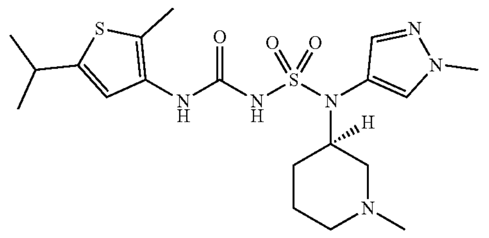 [SMILES: Cc1sc(C(C)C)cc1NC(=O)NS(=O)(=O)N(c1cnn(C)c1)[C@@H]1CCCN(C)C1] |

TABLE 1-continued
| Compound No. | Structure |
| --- | --- |
| 58 | 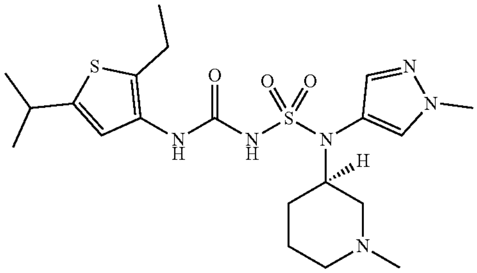 [SMILES: CCc1sc(C(C)C)cc1NC(=O)NS(=O)(=O)N(c1cnn(C)c1)[C@@H]1CCCN(C)C1] |
| 59 | 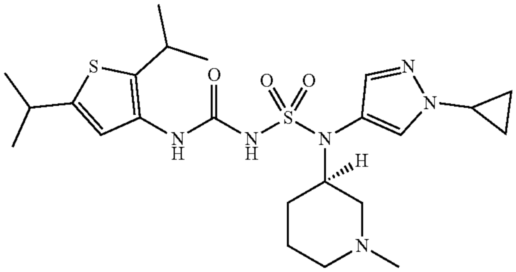 [SMILES: CC(C)c1cc(NC(=O)NS(=O)(=O)N(c2cnn(C3CC3)c2)[C@@H]2CCCN(C)C2)c(C(C)C)s1] |
| 60 | 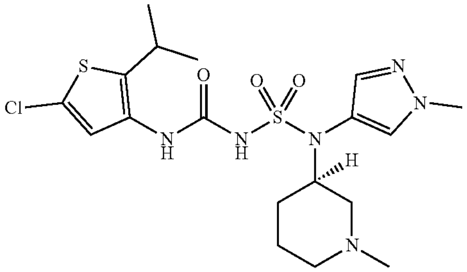 [SMILES: CC(C)c1sc(Cl)cc1NC(=O)NS(=O)(=O)N(c1cnn(C)c1)[C@@H]1CCCN(C)C1] |
| 61 | 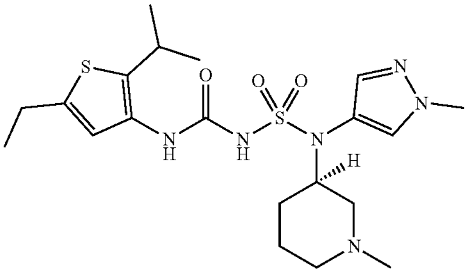 [SMILES: CCc1cc(NC(=O)NS(=O)(=O)N(c2cnn(C)c2)[C@@H]2CCCN(C)C2)c(C(C)C)s1] |
| 62 | 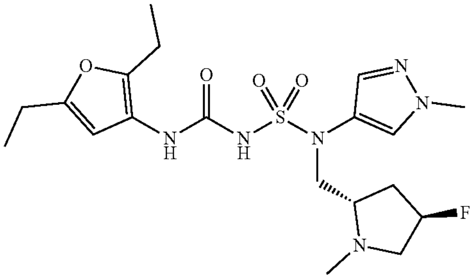 [SMILES: CCc1cc(NC(=O)NS(=O)(=O)N(C[C@@H]2C[C@@H](F)CN2C)c2cnn(C)c2)c(CC)o1] |

TABLE 1-continued
| Compound No. | Structure |
| --- | --- |
| 63 | 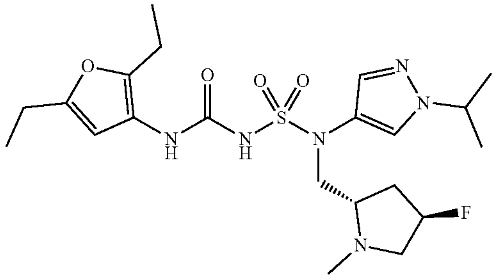 [SMILES: CCc1cc(NC(=O)NS(=O)(=O)N(C[C@@H]2C[C@@H](F)CN2C)c2cnn(C(C)C)c2)c(CC)o1] |
| 64 | 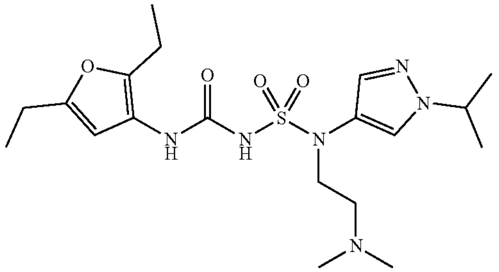 [SMILES: CCc1cc(NC(=O)NS(=O)(=O)N(CCN(C)C)c2cnn(C(C)C)c2)c(CC)o1] |
| 65 | 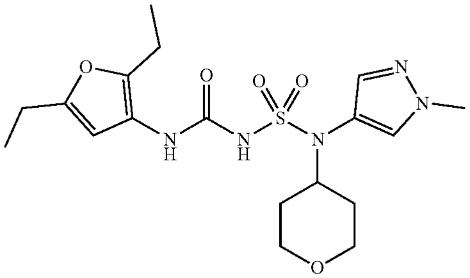 |
| 66 | 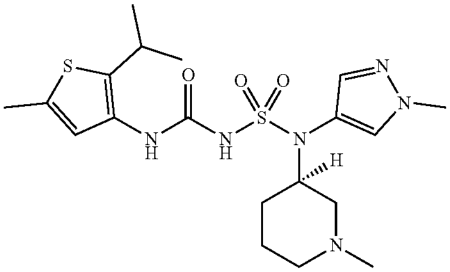 |
| 67 | 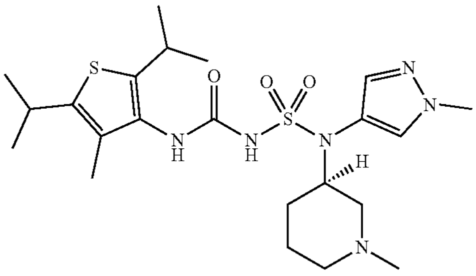 [SMILES: Cc1c(C(C)C)sc(C(C)C)c1NC(=O)NS(=O)(=O)N(c1cnn(C)c1)[C@@H]1CCCN(C)C1] |

TABLE 1-continued
| Compound No. | Structure |
| --- | --- |
| 68 | 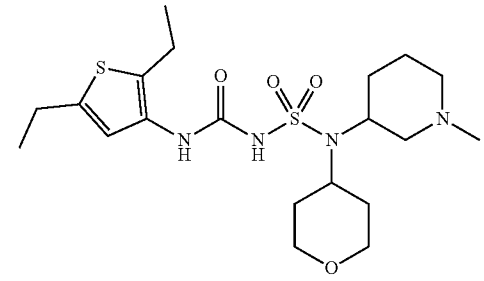 [SMILES: CCc1cc(NC(=O)NS(=O)(=O)N(C2CCOCC2)C2CCCN(C)C2)c(CC)s1] |
| 69 | 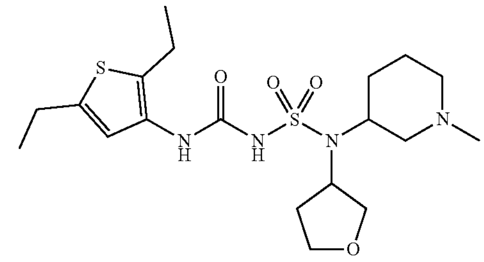 [SMILES: CCc1cc(NC(=O)NS(=O)(=O)N(C2CCOC2)C2CCCN(C)C2)c(CC)s1] |
| 70 | 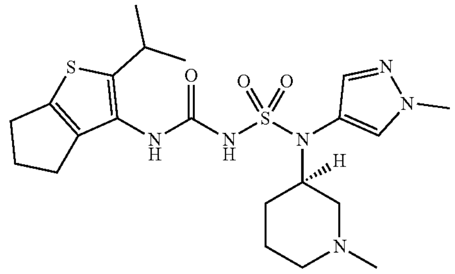 [SMILES: CC(C)c1sc2c(c1NC(=O)NS(=O)(=O)N(c1cnn(C)c1)[C@@H]1CCCN(C)C1)CCC2] |
| 71 | 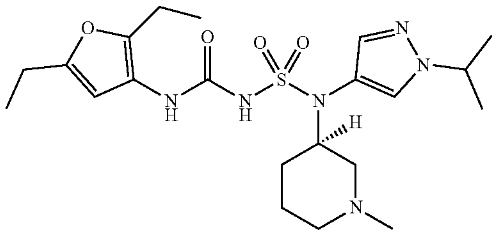 [SMILES: CCc1cc(NC(=O)NS(=O)(=O)N(c2cnn(C(C)C)c2)[C@@H]2CCCN(C)C2)c(CC)o1] |
| 72 | 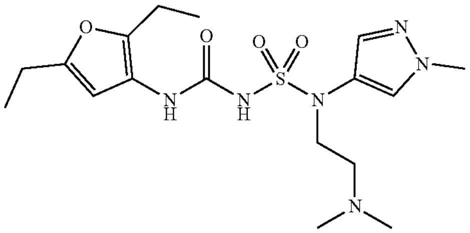 [SMILES: CCc1cc(NC(=O)NS(=O)(=O)N(CCN(C)C)c2cnn(C)c2)c(CC)o1] |
| 73 | 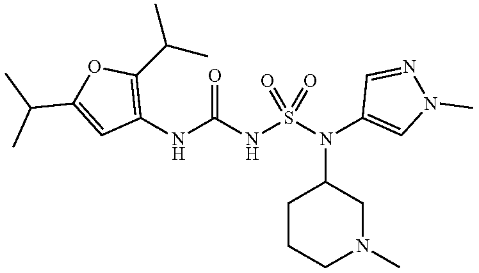 [SMILES: CC(C)c1cc(NC(=O)NS(=O)(=O)N(c2cnn(C)c2)C2CCCN(C)C2)c(C(C)C)o1] |

TABLE 1-continued
| Compound No. | Structure |
| --- | --- |
| 74 | 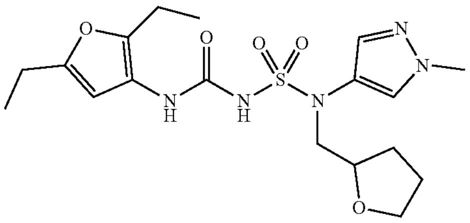 [SMILES: CCc1cc(NC(=O)NS(=O)(=O)N(CC2CCCO2)c2cnn(C)c2)c(CC)o1] |
| 75 | 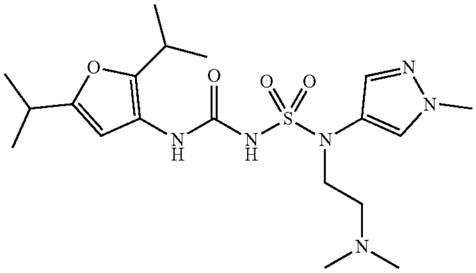 [SMILES: CC(C)c1cc(NC(=O)NS(=O)(=O)N(CCN(C)C)c2cnn(C)c2)c(C(C)C)o1] |
| 76 | 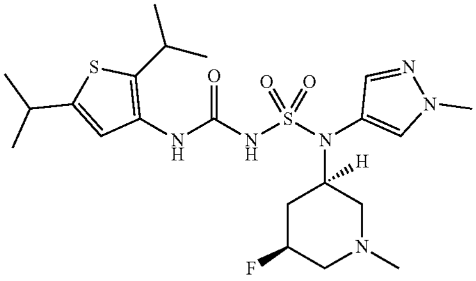 [SMILES: CC(C)c1cc(NC(=O)NS(=O)(=O)N(c2cnn(C)c2)[C@@H]2C[C@H](F)CN(C)C2)c(C(C)C)s1] |
| 77 | 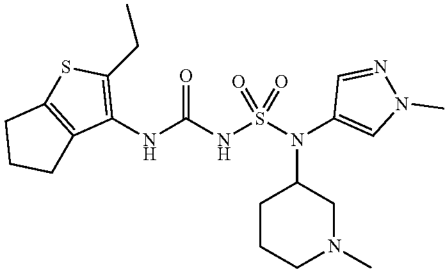 [SMILES: CCc1sc2c(c1NC(=O)NS(=O)(=O)N(c1cnn(C)c1)C1CCCN(C)C1)CCC2] |
| 78 | 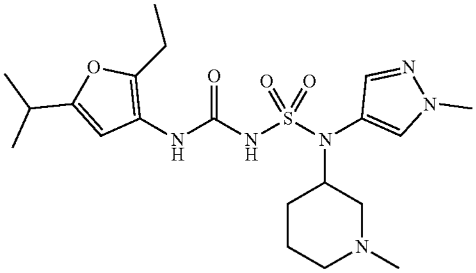 [SMILES: CCc1oc(C(C)C)cc1NC(=O)NS(=O)(=O)N(c1cnn(C)c1)C1CCCN(C)C1] |

TABLE 1-continued
| Compound No. | Structure |
|---|---|
| 79 | 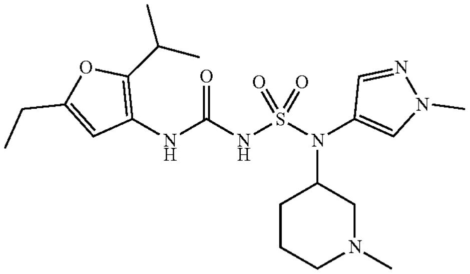 [SMILES: CCc1cc(NC(=O)NS(=O)(=O)N(c2cnn(C)c2)C2CCCN(C)C2)c(C(C)C)o1] |
| 80 | 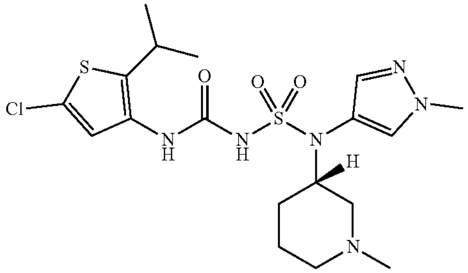 [SMILES: CC(C)c1sc(Cl)cc1NC(=O)NS(=O)(=O)N(c1cnn(C)c1)[C@H]1CCCN(C)C1] |
| 81 | 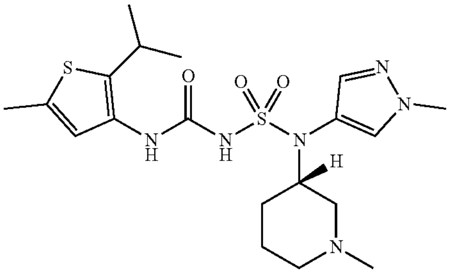 |
| 82 | 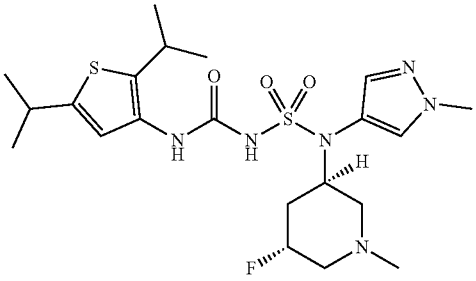 [SMILES: CC(C)c1cc(NC(=O)NS(=O)(=O)N(c2cnn(C)c2)[C@@H]2C[C@@H](F)CN(C)C2)c(C(C)C)s1] |
| 83 | 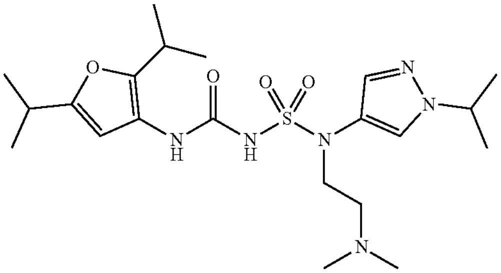 [SMILES: CC(C)c1cc(NC(=O)NS(=O)(=O)N(CCN(C)C)c2cnn(C(C)C)c2)c(C(C)C)o1] |

TABLE 1-continued
| Compound No. | Structure |
| --- | --- |
| 84 | 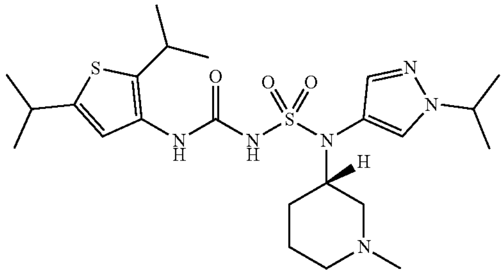 [SMILES: CC(C)c1cc(NC(=O)NS(=O)(=O)N(c2cnn(C(C)C)c2)[C@H]2CCCN(C)C2)c(C(C)C)s1] |
| 85 | 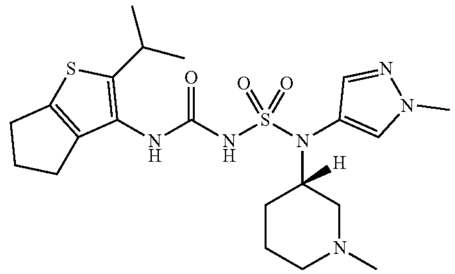 [SMILES: CC(C)c1sc2c(c1NC(=O)NS(=O)(=O)N(c1cnn(C)c1)[C@H]1CCCN(C)C1)CCC2] |
| 86 | 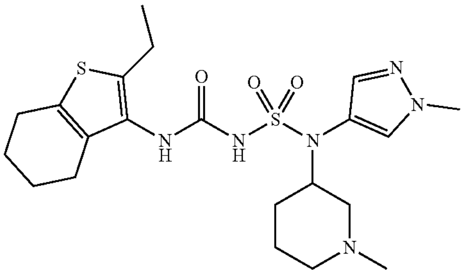 |
| 87 | 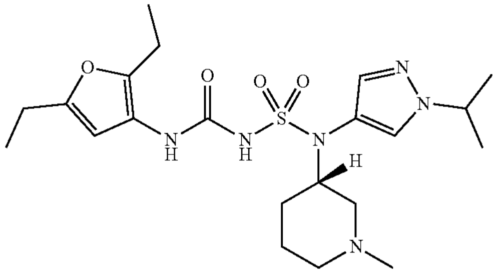 [SMILES: CCc1cc(NC(=O)NS(=O)(=O)N(c2cnn(C(C)C)c2)[C@H]2CCCN(C)C2)c(CC)o1] |
| 88 | 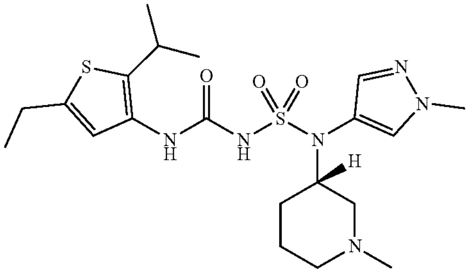 [SMILES: CCc1cc(NC(=O)NS(=O)(=O)N(c2cnn(C)c2)[C@H]2CCCN(C)C2)c(C(C)C)s1] |

TABLE 1-continued
| Compound No. | Structure |
| --- | --- |
| 89 | 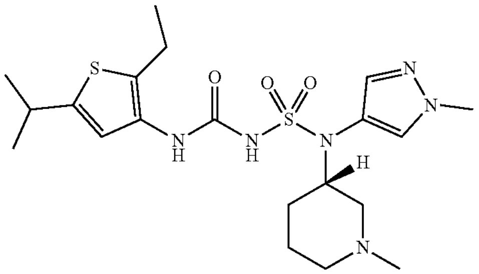 [SMILES: CCc1sc(C(C)C)cc1NC(=O)NS(=O)(=O)N(c1cnn(C)c1)[C@H]1CCCN(C)C1] |
| 90 | 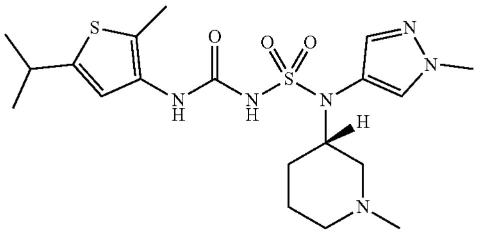 [SMILES: Cc1sc(C(C)C)cc1NC(=O)NS(=O)(=O)N(c1cnn(C)c1)[C@H]1CCCN(C)C1] |
| 91 | 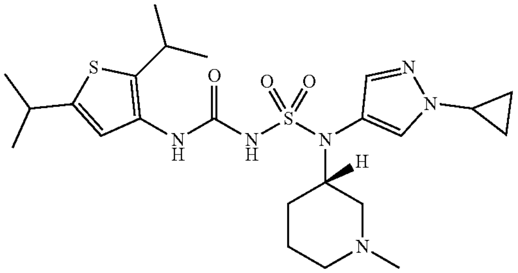 [SMILES: CC(C)c1cc(NC(=O)NS(=O)(=O)N(c2cnn(C3CC3)c2)[C@H]2CCCN(C)C2)c(C(C)C)s1] |
| 92 | 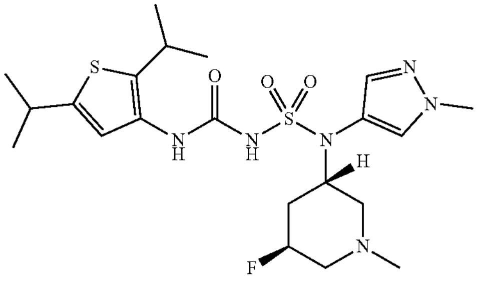 [SMILES: CC(C)c1cc(NC(=O)NS(=O)(=O)N(c2cnn(C)c2)[C@H]2C[C@H](F)CN(C)C2)c(C(C)C)s1] |
| 93 | 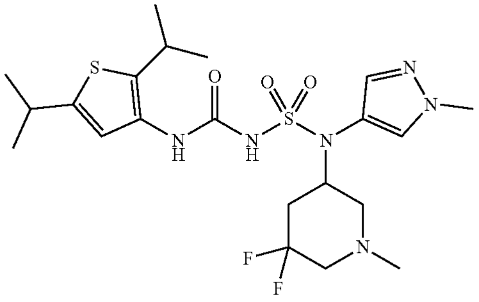 [SMILES: CC(C)c1cc(NC(=O)NS(=O)(=O)N(c2cnn(C)c2)C2CN(C)CC(F)(F)C2)c(C(C)C)s1] |

TABLE 1-continued
| Compound No. | Structure |
| --- | --- |
| 94 | 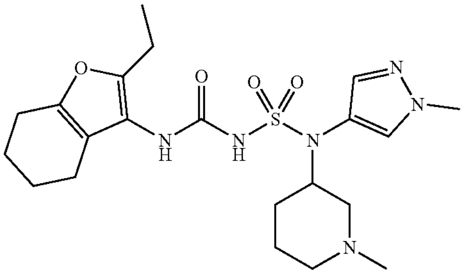 [SMILES: CCc1oc2c(c1NC(=O)NS(=O)(=O)N(c1cnn(C)c1)C1CCCN(C)C1)CCCC2] |
| 95 | 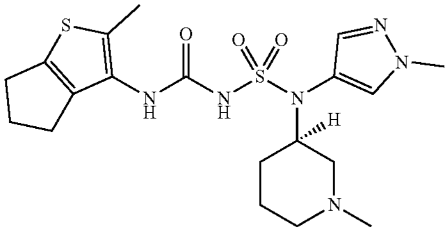 [SMILES: Cc1sc2c(c1NC(=O)NS(=O)(=O)N(c1cnn(C)c1)[C@@H]1CCCN(C)C1)CCC2] |
| 96 | 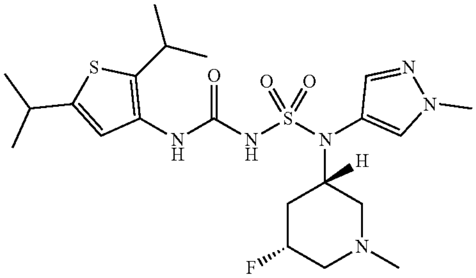 [SMILES: CC(C)c1cc(NC(=O)NS(=O)(=O)N(c2cnn(C)c2)[C@H]2C[C@@H](F)CN(C)C2)c(C(C)C)s1] |
| 97 | 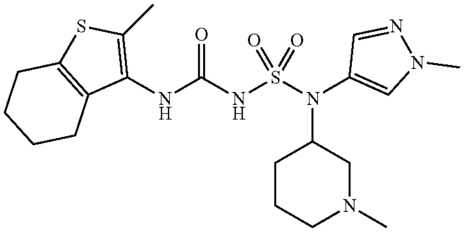 [SMILES: Cc1sc2c(c1NC(=O)NS(=O)(=O)N(c1cnn(C)c1)C1CCCN(C)C1)CCCC2] |
| 98 | 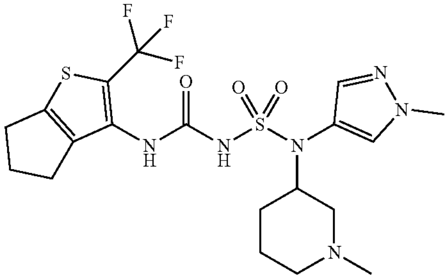 [SMILES: CN1CCCC(N(c2cnn(C)c2)S(=O)(=O)NC(=O)Nc2c(C(F)(F)F)sc3c2CCC3)C1] |
| 99 | 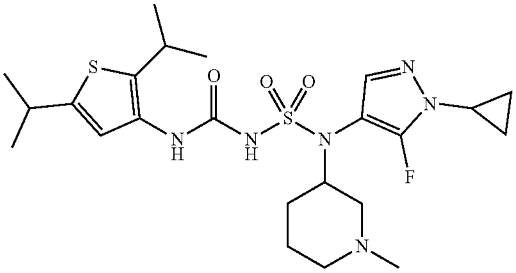 [SMILES: CC(C)c1cc(NC(=O)NS(=O)(=O)N(c2cnn(C3CC3)c2F)C2CCCN(C)C2)c(C(C)C)s1] |

TABLE 1-continued
| Compound No. | Structure |
| --- | --- |
| 100 | 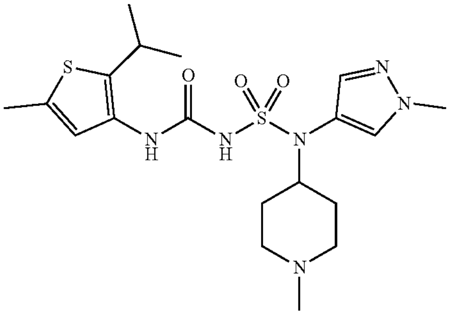 |
| 101 | 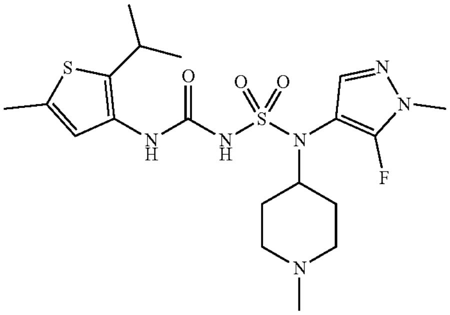 |
| 102 | 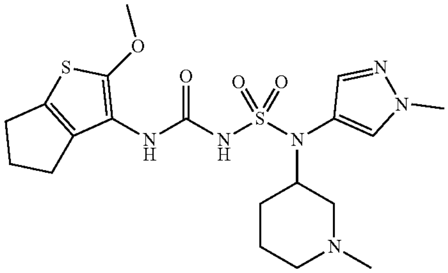 [SMILES: COc1sc2c(c1NC(=O)NS(=O)(=O)N(c1cnn(C)c1)C1CCCN(C)C1)CCC2] |
| 103 | 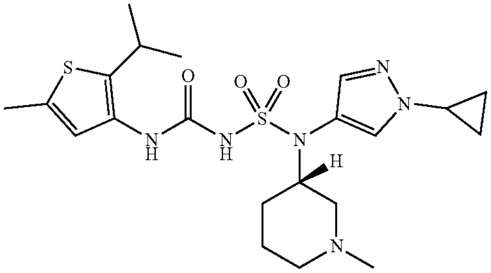 [SMILES: Cc1cc(NC(=O)NS(=O)(=O)N(c2cnn(C3CC3)c2)[C@H]2CCCN(C)C2)c(C(C)C)s1] |
| 104 | 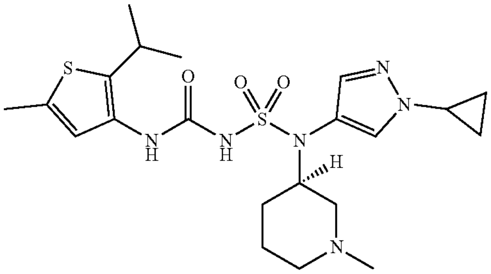 [SMILES: Cc1cc(NC(=O)NS(=O)(=O)N(c2cnn(C3CC3)c2)[C@@H]2CCCN(C)C2)c(C(C)C)s1] |

TABLE 1-continued
| Compound No. | Structure |
|---|---|
| 105 | 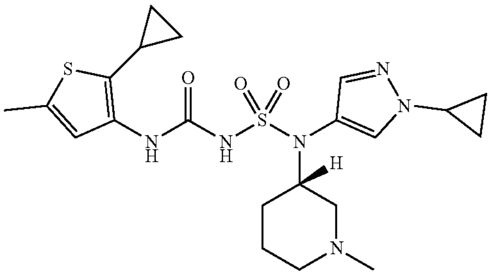 [SMILES: Cc1cc(NC(=O)NS(=O)(=O)N(c2cnn(C3CC3)c2)[C@H]2CCCN(C)C2)c(C2CC2)s1] |
| 106 | 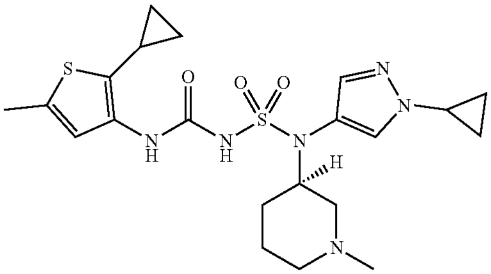 [SMILES: Cc1cc(NC(=O)NS(=O)(=O)N(c2cnn(C3CC3)c2)[C@@H]2CCCN(C)C2)c(C2CC2)s1] |
| 107 | 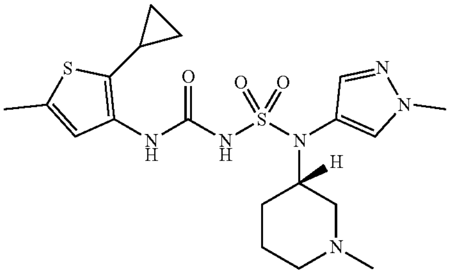 |
| 108 | 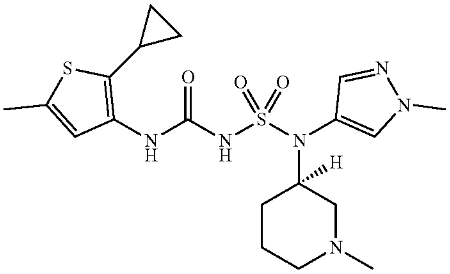 |
| 109 | 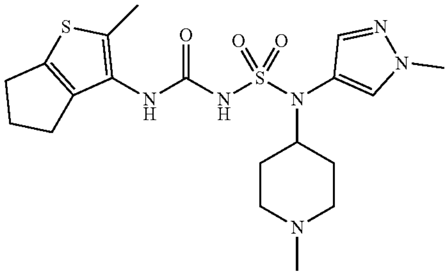 [SMILES: Cc1sc2c(c1NC(=O)NS(=O)(=O)N(c1cnn(C)c1)C1CCN(C)CC1)CCC2] |

TABLE 1-continued
| Compound No. | Structure |
|---|---|
| 110 | 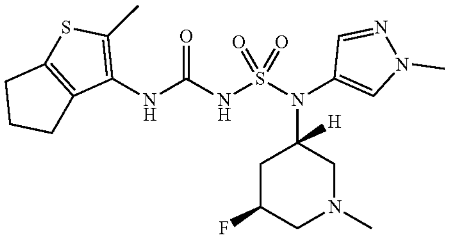 [SMILES: Cc1sc2c(c1NC(=O)NS(=O)(=O)N(c1cnn(C)c1)[C@H]1C[C@H](F)CN(C)C1)CCC2] |
| 111 | 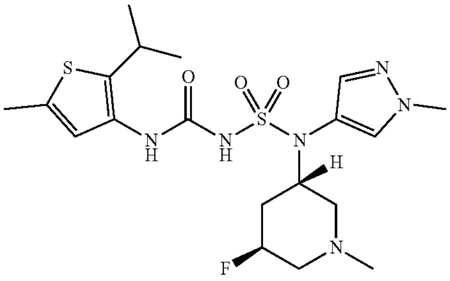 |
| 112 | 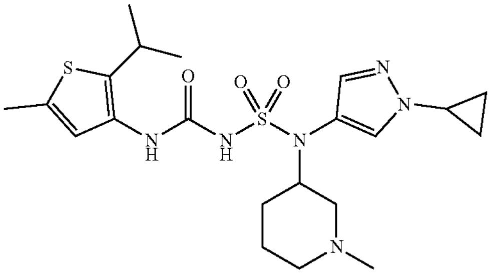 [SMILES: Cc1cc(NC(=O)NS(=O)(=O)N(c2cnn(C3CC3)c2)C2CCCN(C)C2)c(C(C)C)s1] |
| 113 | 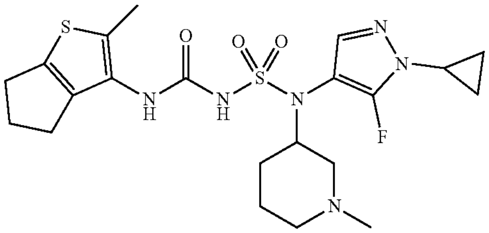 [SMILES: Cc1sc2c(c1NC(=O)NS(=O)(=O)N(c1cnn(C3CC3)c1F)C1CCCN(C)C1)CCC2] |
| 114 | 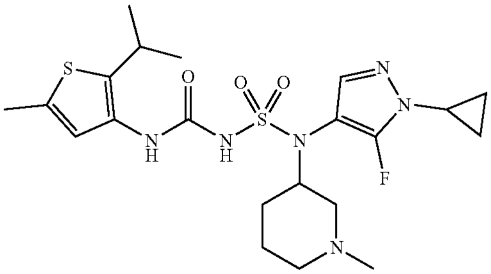 [SMILES: Cc1cc(NC(=O)NS(=O)(=O)N(c2cnn(C3CC3)c2F)C2CCCN(C)C2)c(C(C)C)s1] |
| 115 | 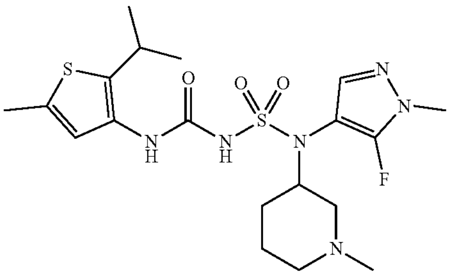 |

TABLE 1-continued
| Compound No. | Structure |
|---|---|
| 116 | 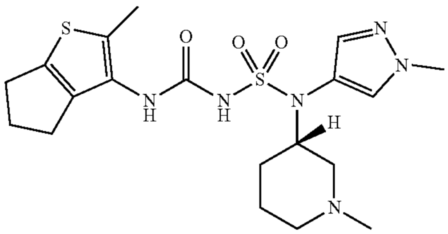 [SMILES: Cc1sc2c(c1NC(=O)NS(=O)(=O)N(c1cnn(C)c1)[C@H]1CCCN(C)C1)CCC2] |
| 117 | 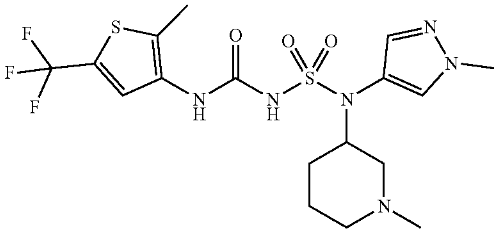 [SMILES: Cc1sc(C(F)(F)F)cc1NC(=O)NS(=O)(=O)N(c1cnn(C)c1)C1CCCN(C)C1] |
| 118 | 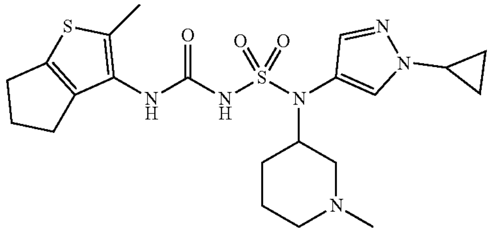 [SMILES: Cc1sc2c(c1NC(=O)NS(=O)(=O)N(c1cnn(C3CC3)c1)C1CCCN(C)C1)CCC2] |
| 119 | 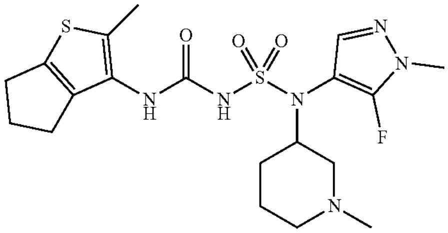 [SMILES: Cc1sc2c(c1NC(=O)NS(=O)(=O)N(c1cnn(C)c1F)C1CCCN(C)C1)CCC2] |
| 120 | 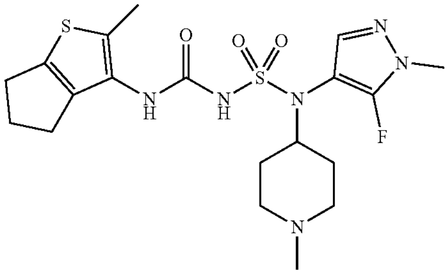 [SMILES: Cc1sc2c(c1NC(=O)NS(=O)(=O)N(c1cnn(C)c1F)C1CCN(C)CC1)CCC2] |
| 121 | 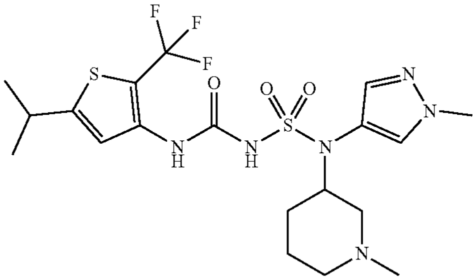 [SMILES: CC(C)c1cc(NC(=O)NS(=O)(=O)N(c2cnn(C)c2)C2CCCN(C)C2)c(C(F)(F)F)s1] |

TABLE 1-continued
| Compound No. | Structure |
|---|---|
| 122 | 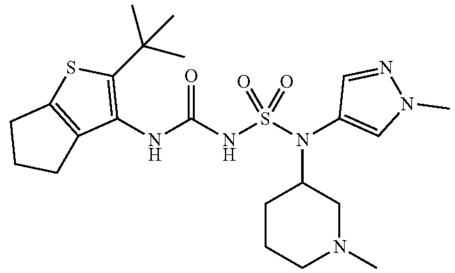 [SMILES: CN1CCCC(N(c2cnn(C)c2)S(=O)(=O)NC(=O)Nc2c(C(C)(C)C)sc3c2CCC3)C1] |
| 123 | 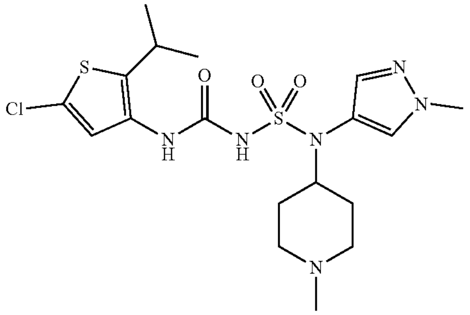 [SMILES: CC(C)c1sc(Cl)cc1NC(=O)NS(=O)(=O)N(c1cnn(C)c1)C1CCN(C)CC1] |
| 124 | 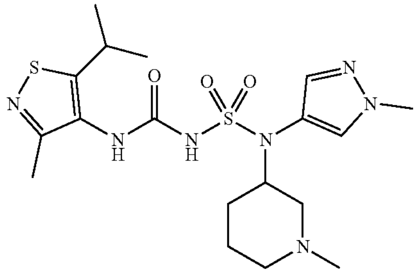 [SMILES: Cc1nsc(C(C)C)c1NC(=O)NS(=O)(=O)N(c1cnn(C)c1)C1CCCN(C)C1] |
| 125 | 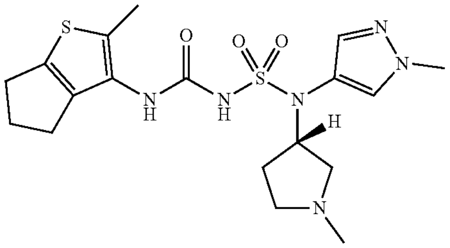 [SMILES: Cc1sc2c(c1NC(=O)NS(=O)(=O)N(c1cnn(C)c1)[C@H]1CCN(C)C1)CCC2] |
| 126 | 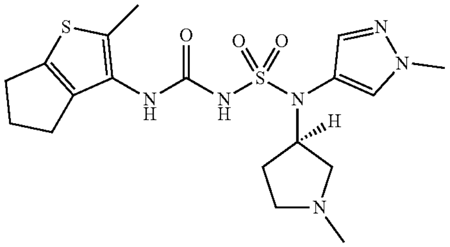 [SMILES: Cc1sc2c(c1NC(=O)NS(=O)(=O)N(c1cnn(C)c1)[C@@H]1CCN(C)C1)CCC2] |

TABLE 1-continued
| Compound No. | Structure |
|---|---|
| 127 | 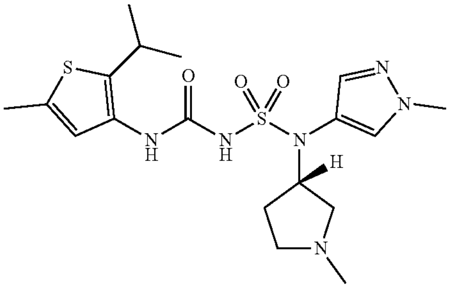 |
| 128 | 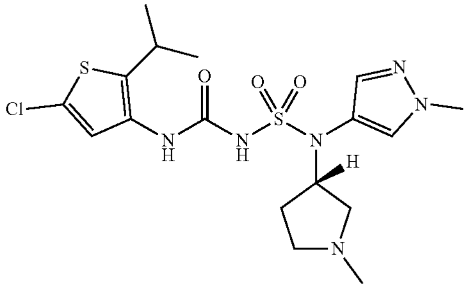 [SMILES: CC(C)c1sc(Cl)cc1NC(=O)NS(=O)(=O)N(c1cnn(C)c1)[C@H]1CCN(C)C1] |
| 129 | 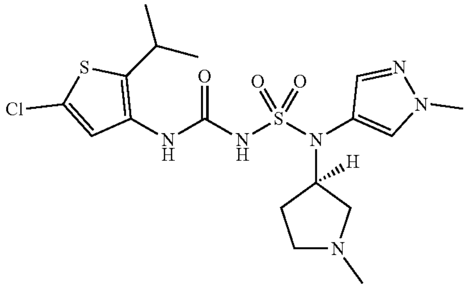 [SMILES: CC(C)c1sc(Cl)cc1NC(=O)NS(=O)(=O)N(c1cnn(C)c1)[C@@H]1CCN(C)C1] |
| 130 | 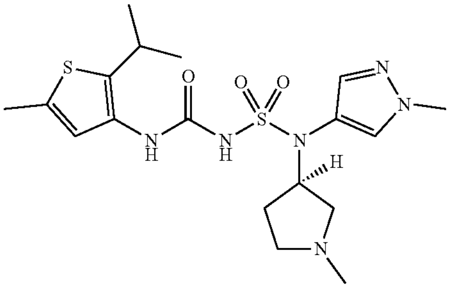 |
| 131 | 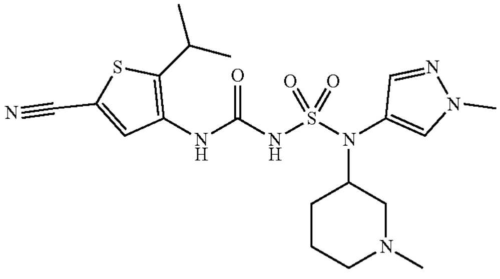 [SMILES: CC(C)c1sc(C#N)cc1NC(=O)NS(=O)(=O)N(c1cnn(C)c1)C1CCCN(C)C1] |

In some embodiments, the compound is a pharmaceutically acceptable salt of any one of the compounds described in Table 1.

In some embodiments, the compound is a lithium salt, sodium salt, potassium salt, calcium salt, or magnesium salt of any one of the compounds described in Table 1.

In some embodiments, the compound is a sodium salt or potassium salt of any one of the compounds described in Table 1.

In some embodiments, the compound is a sodium salt of any one of the compounds described in Table 1. For example, the sodium salt of Compound No. 131 could be

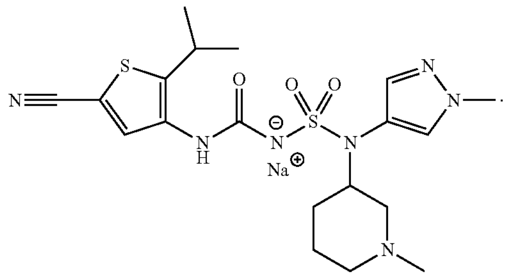 [SMILES: CC(C)c1sc(C#N)cc1NC(=O)[N-]S(=O)(=O)N(c1cnn(C)c1)C1CCCN(C)C1 ; [Na+]]

In some embodiments, the compound is a potassium salt of any one of the compounds described in Table 1.

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Table 1 and prodrugs and pharmaceutically acceptable salts thereof.

In some embodiments, the compound is an isotopic derivative of any one of the compounds described in Table 1 and pharmaceutically acceptable salts thereof.

In some embodiments, the compound is an isotopic derivative of any one of prodrugs of the compounds described in Table 1 and pharmaceutically acceptable salts thereof.

In some embodiments, the compound is an isotopic derivative of any one of the compounds described in Table 1.

It is understood that the isotopic derivative can be prepared using any of a variety of art-recognised techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound of Formula (I) is isotopically enriched with regard to, or labelled with, one or more isotopes as compared to the corresponding compound of Formula (I). In some embodiments, the isotopic derivative is enriched with regard to, or labelled with, one or more atoms selected from $^{2}H$, $^{13}C$, $^{14}C$, $^{15}N$, $^{18}O$, $^{29}Si$, $^{31}P$, and $^{34}S$. In some embodiments, the isotopic derivative is a deuterium labeled compound (i.e., being enriched with $^{2}H$ with regard to one or more atoms thereof).

In some embodiments, the compound is a deuterium labeled compound of any one of the compounds described in Table 1 and prodrugs and pharmaceutically acceptable salts thereof.

In some embodiments, the compound is a deuterium labeled compound of any one of the compounds described in Table 1 and pharmaceutically acceptable salts thereof.

In some embodiments, the compound is a deuterium labeled compound of any one of the prodrugs of the compounds described in Table 1 and pharmaceutically acceptable salts thereof.

In some embodiments, the compound is a deuterium labeled compound of any one of the compounds described in Table 1.

It is understood that the deuterium labeled compound comprises a deuterium atom having an abundance of deuterium that is substantially greater than the natural abundance of deuterium, which is 0.015%.

In some embodiments, the deuterium labeled compound has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). As used herein, the term "deuterium enrichment factor" means the ratio between the deuterium abundance and the natural abundance of a deuterium.

It is understood that the deuterium labeled compound can be prepared using any of a variety of art-recognised techniques. For example, the deuterium labeled compound can generally be prepared by carrying out the procedures disclosed in the Schemes and/or in the Examples described herein, by substituting a deuterium labeled reagent for a non-deuterium labeled reagent.

A compound of the invention or a pharmaceutically acceptable salt or solvate thereof that contains the aforementioned deuterium atom(s) is within the scope of the invention. Further, substitution with deuterium (i.e., $^{2}H$) may afford certain therapeutic advantages resulting from greater metabolic stability, e.g., increased in vivo half-life or reduced dosage requirements.

In some embodiments, the compound is a $^{18}F$ labeled compound.

In some embodiments, the compound is a $^{123}I$ labeled compound, a $^{124}I$ labeled compound, a $^{125}I$ labeled compound, a $^{129}I$ labeled compound, a $^{131}I$ labeled compound, a $^{135}I$ labeled compound, or any combination thereof.

In some embodiments, the compound is a $^{33}S$ labeled compound, a $^{34}S$ labeled compound, a $^{35}S$ labeled compound, a $^{16}S$ labeled compound, or any combination thereof.

It is understood that the $^{18}F$, $^{123}I$, $^{124}I$, $^{125}I$, $^{129}I$, $^{131}I$, $^{135}I$, $^{32}S$, $^{34}S$, $^{35}S$, and/or $^{36}S$ labeled compound, can be prepared using any of a variety of art-recognised techniques. For example, the deuterium labeled compound can generally be prepared by carrying out the procedures disclosed in the Schemes and/or in the Examples described herein, by substituting a $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$ labeled reagent for a non-isotope labeled reagent.

A compound of the invention or a pharmaceutically acceptable salt or solvate thereof that contains one or more of the aforementioned $^{18}F$, $^{123}I$, $^{124}I$, $^{125}I$, $^{129}I$, $^{131}I$, $^{135}I$, $^{3}S$, $^{34}S$, $^{35}S$, and $^{36}S$ atom(s) is within the scope of the invention. Further, substitution with isotope (e.g., $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$) may afford certain therapeutic advantages resulting from greater metabolic stability, e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

The various functional groups and substituents making up the compounds of the Formula (I) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

A suitable pharmaceutically acceptable salt of a compound of the disclosure is, for example, an acid-addition salt of a compound of the disclosure which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral centre" refers to a carbon atom bonded to four nonidentical substituents.

As used herein, the term "chiral isomer" means a compound with at least one chiral centre. Compounds with more than one chiral centre may exist either as an individual diastereomer or as a mixture of diastereomers, termed "diastereomeric mixture." When one chiral centre is present, a stereoisomer may be characterised by the absolute configuration (R or S) of that chiral centre. Absolute configuration refers to the arrangement in space of the substituents attached to the chiral centre. The substituents attached to the chiral centre under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerisation is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterised by the absolute configuration of its asymmetric centre and is described by the R- and S-sequencing rules of Cahn and Prelog, or by the manner in which the molecule rotates the plane of polarised light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this disclosure may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centres (E- and Z-isomers). It is to be understood that the present disclosure encompasses all optical, diastereoisomers and geometric isomers and mixtures thereof that possess inflammasome inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonamides, tetrazoles, sulfonates and phosphonates. See, e.g., Patani and LaVoie, *Chem. Rev.* 96, 3147-3176, 1996.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess inflammasome inhibitory activity.

It is also to be understood that certain compounds of any one of the Formulae disclosed herein may exhibit polymorphism, and that the disclosure encompasses all such forms, or mixtures thereof, which possess inflammasome inhibitory activity. It is generally known that crystalline materials may be analysed using conventional techniques such as X-Ray Powder Diffraction analysis, Differential Scanning Calorimetry, Thermal Gravimetric Analysis, Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of Formula (I) include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

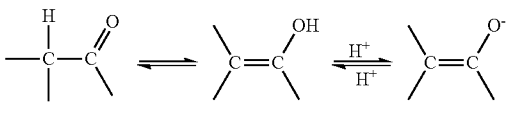

keto enol enolate

Compounds of any one of the Formulae disclosed herein containing an amine function may also form N-oxides. A reference herein to a compound of Formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidising agent such as hydrogen peroxide or a peracid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substitutents at the ester or amide group in any one of the Formulae disclosed herein.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p. 113-191 (1991); d) H. Bundgaard, Advanced Drug Delivery Reviews, 8, 1-38 (1992); e) H. Bundgaard, et al., Journal of Pharmaceutical Sciences, 77,285 (1988); f) N. Kakeya, et al., Chem. Pharm. Bull., 32, 692 (1984); g) T. Higuchi and V. Stella, "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any one of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine, N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof.

It is understood that a compound of any one of the Formulae disclosed herein, wherein $R_3$ is not H, may be used as a prodrug of the corresponding compound, wherein $R_3$ is H. For example, a compound of any one of the Formulae disclosed herein, wherein $R_3$ is $C_1$-$C_6$ alkyl, $C_2$-$C_6$ alkenyl, or $C_2$-$C_6$ alkynyl; wherein the $C_1$-$C_6$ alkyl, $C_2$-$C_6$ alkenyl, or $C_2$-$C_6$ alkynyl is optionally substituted with one or more $C_1$-$C_6$ alkyl, $C_2$-$C_6$ alkenyl, $C_2$-$C_6$ alkynyl, $C_3$-$C_8$ cycloalkyl, $C_5$-$C_6$ aryl, 5- or 6-membered heteroaryl, $C_3$-$C_8$ heterocycloalkyl, $C_1$-$C_6$ haloalkyl, —O($C_1$-$C_6$ alkyl), —O($C_1$-$C_6$ haloalkyl), halo, —CN, —OH, —$NH_2$, —NH($C_1$-$C_6$ alkyl), —N($C_1$-$C_6$ alkyl)$_2$, oxo, or $R_{3S}$, may be used as a prodrug of the corresponding compound, wherein $R_3$ is H.

A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl,morpholinomethyl,piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, ‘Protective Groups in Organic Synthesis’ by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) has been synthesised by any one of the processes defined herein, the processes may then further comprise the additional steps of: (i) removing any protecting groups present; (ii) converting the compound Formula (I) into another compound of Formula (I); (iii) forming a pharmaceutically acceptable salt, hydrate or solvate thereof; and/or (iv) forming a prodrug thereof.

The resultant compounds of Formula (I) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilising the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

General routes for the preparation of a compound of the application are described in Schemes 1-6 herein.

Scheme 1

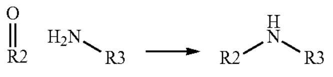

1a 1b 1c

Compound 1a (R2 substituent containing an aldehyde or ketone functional group) is reacted with Compound 1b in the presence of a reducing agent (e.g., sodium triacetoxyborohydride) in a solvent (e.g., dichloromethane) and, optionally, with an acid catalyst (e.g., acetic acid) to yield Compound 1c.

Scheme 2

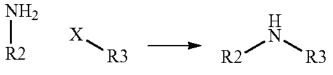

2a 2b 2c

Compound 2a is reacted with Compound 2b (R3 substituent where X is a leaving group such as bromide, iodide or mesylate etc) in the presence of a base (e.g., sodium tert-butoxide, or cesium carbonate), a precatalyst (e.g., tris(dibenzylideneacetone)dipalladium(0)) and a ligand (e.g., 2-dicyclohexylphosphino-2',4',6'-triisopropylbiphenyl), in a solvent (e.g., toluene or 1,4-dioxane) and at an elevated temperature (e.g., 100° C.) to yield Compound 2c.

Scheme 3

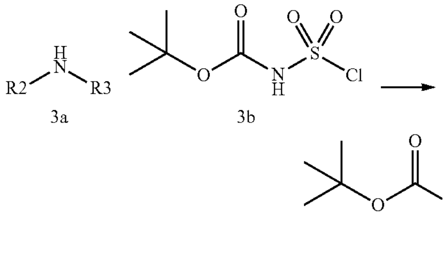

3a 3b 3c

Compound 3a is reacted with Compound 3b in the presence of abase (e.g., triethylamine), in a solvent (e.g., dichloromethane) and, optionally, at a reduced temperature (e.g., 0° C.) to yield Compound 3c.

Scheme 4

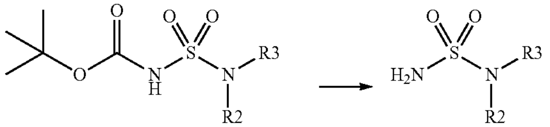

4a 4b

Compound 4a is reacted with an acid (e.g., hydrochloric acid or trifluoroacetic acid) in a suitable solvent (e.g., dichloromethane, 1,4-dioxane or ethyl acetate) and, optionally, at a reduced temperature (e.g., 0° C.) to yield Compound 4b.

Scheme 5

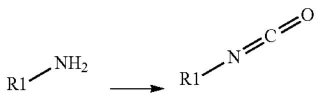

5a 5b

Compound 5a is reacted with a suitable isocyanate-forming reagent (e.g., diphosgene or triphosgene) in a solvent (e.g., dichloromethane or 1,4-dioxane) and, optionally, in the presence of a base (e.g., triethylamine) to yield Compound 5b.

Scheme 6

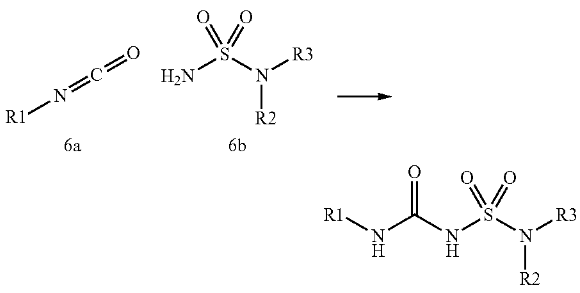

6a 6b 6c

Compound 6a is reacted with Compound 6b in the presence of a base (e.g., sodium hydroxide or sodium hydride) in a solvent (e.g., tetrahydrofuran) and, optionally, at a reduced temperature (e.g., 0° C.) to yield Compound 6c.

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

In some embodiments, the compounds of the present disclosure may be tested for their inhibitory activity in various cell lines (e.g., peripheral blood mononuclear cells). In some embodiments, the compounds of the present disclosure may be tested for their inhibitory activity in peripheral blood mononuclear cells. In some embodiments, the compounds of the present disclosure may be tested for their inhibitory activity against IL-1β release upon NLRP3 activation.

In some embodiments, a PBMC $IC_{50}$ determination assay may be used to characterize the compounds of the present disclosure.

PBMC may be isolated, seeded into the wells of a plate, and incubated with a saccharide. Following medium exchange, the compounds of the present disclosure may be added to a well and incubated. The cells may be stimulated and the cell culture media collected for analysis.

PBMC may be isolated by density gradient centrifugation, seeded into the wells of a plate, and incubated with a saccharide. The compounds of the present disclosure may be added to a well and incubated. The cells may be stimulated and the cell culture media collected for analysis.

In some embodiments, release of IL-1β may be determined by a quantitative detection. In some embodiments, release of IL-1β may be determined by a quantitative detection of IL-1β using an IL-1β enzyme-linked immunosorbent assay (ELISA). A microplate spectrophotometer may be used to detect signals (e.g., at 450 nm).

In some embodiments, release of IL-1β may be determined by quantitative detection of IL-1β using Homogenous Time-Resolved Fluorescence (HTRF®). A microplate spectrophotometer may be used to detect signals (e.g., at 655 nm and 620 nm).

In some embodiments, the biological assay is described in the Examples herein.

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising at least one compound selected from Table 1.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilise the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present disclosure for use in therapy is an amount sufficient to treat or prevent an inflammasome related condition referred to herein, slow its progression and/or reduce the symptoms associated with the condition.

An effective amount of a compound of the present disclosure for use in therapy is an amount sufficient to treat an inflammasome related condition referred to herein, slow its progression and/or reduce the symptoms associated with the condition.

The size of the dose for therapeutic or prophylactic purposes of a compound of Formula (I) will naturally vary according to the nature and severity of the conditions, the age and sex of the animal or patient and the route of administration, according to well-known principles of medicine.

Methods of Use

In some aspects, the present disclosure provides a method of inhibiting inflammasome (e.g., the NLRP3 inflammasome) activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some embodiments, the disease or disorder is associated with an implicated inflammasome activity. In some embodiments, the disease or disorder is a disease or disorder in which inflammasome activity is implicated.

In some embodiments, the disease or disorder is an inflammatory disorder, autoinflammatory disorder, an autoimmune disorder, a neurodegenerative disease, or cancer.

In some embodiments, the disease or disorder is an inflammatory disorder, autoinflammatory disorder and/or an autoimmune disorder.

In some embodiments, the disease or disorder is selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disease (e.g. acne) and neuroinflammation occurring in protein misfolding diseases (e.g., Prion diseases).

In some embodiments, the disease or disorder is a neurodegenerative disease.

In some embodiments, the disease or disorder is Parkinson's disease or Alzheimer's disease.

In some embodiments, the disease or disorder is a dermatological disease.

In some embodiments, the dermatological disease is acne.

In some embodiments, the disease or disorder is cancer.

In some embodiments, the cancer is metastasising cancer, gastrointestinal cancer, skin cancer, non-small-cell lung carcinoma, brain cancer (e.g. glioblastoma) or colorectal adenocarcinoma.

In some aspects, the present disclosure provides a method of treating or preventing an autoinflammatory disorder, an autoimmune disorder, a neurodegenerative disease or cancer in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating an autoinflammatory disorder, an autoimmune disorder, a neurodegenerative disease or cancer in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing an inflammatory disorder, autoinflammatory disorder and/or an autoimmune disorder selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disease (e.g. acne) and neuroinflammation occurring in protein misfolding diseases (e.g., Prion diseases) in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating an inflammatory disorder, autoinflammatory disorder and/or an autoimmune disorder selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disease (e.g. acne) and neuroinflammation occurring in protein misfolding diseases (e.g., Prion diseases) in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a neurodegenerative disease (e.g., Parkinson's disease or Alzheimer's disease) in a subject in need thereof, said method comprising administering to the subject a therapeutically effective amount of a compound of the present disclosure or a pharmaceutically acceptable salt thereof, or a pharmaceutical composition of the present disclosure.

In some aspects, the present disclosure provides a method of treating a neurodegenerative disease (e.g., Parkinson's disease or Alzheimer's disease) in a subject in need thereof, said method comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing cancer in a subject in need thereof, said method comprising administering to the subject a therapeutically effective amount of a compound of the present disclosure or a pharmaceutically acceptable salt thereof, or a pharmaceutical composition of the present disclosure.

In some aspects, the present disclosure provides a method of treating cancer in a subject in need thereof, said method comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in inhibiting inflammasome (e.g., the NLRP3 inflammasome) activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides a compound of the present disclosure or a pharmaceutically acceptable salt thereof for use in treating or preventing an inflammatory disorder, an autoinflammatory disorder, an autoimmune disorder, a neurodegenerative disease or cancer in a subject in need thereof.

In some aspects, the present disclosure provides a compound of the present disclosure or a pharmaceutically acceptable salt thereof for use in treating an inflammatory disorder, an autoinflammatory disorder, an autoimmune disorder, a neurodegenerative disease or cancer in a subject in need thereof.

In some aspects, the present disclosure provides a compound of the present disclosure or a pharmaceutically acceptable salt thereof for use in treating or preventing an inflammatory disorder, an autoinflammatory disorder and/or an autoimmune disorder selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis and neuroinflammation occurring in protein misfolding diseases (e.g., Prion diseases) in a subject in need thereof.

In some aspects, the present disclosure provides a compound of the present disclosure or a pharmaceutically acceptable salt thereof for use in treating an inflammatory disorder, an autoinflammatory disorder and/or an autoimmune disorder selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis and neuroinflammation occurring in protein misfolding diseases (e.g., Prion diseases) in a subject in need thereof.

In some aspects, the present disclosure provides a compound of the present disclosure or a pharmaceutically acceptable salt thereof for use in treating or preventing a neurodegenerative disease (e.g., Parkinson's disease or Alzheimer's disease) in a subject in need thereof.

In some aspects, the present disclosure provides a compound of the present disclosure or a pharmaceutically acceptable salt thereof for use in treating a neurodegenerative disease (e.g., Parkinson's disease or Alzheimer's disease) in a subject in need thereof.

In some aspects, the present disclosure provides a compound of the present disclosure or a pharmaceutically acceptable salt thereof for use in treating or preventing cancer in a subject in need thereof.

In some aspects, the present disclosure provides a compound of the present disclosure or a pharmaceutically acceptable salt thereof for use in treating cancer in a subject in need thereof.

In some aspects, the present disclosure provides use of a compound of the present disclosure or a pharmaceutically acceptable salt thereof in the manufacture of a medicament for inhibiting inflammasome (e.g., the NLRP3 inflammasome) activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides use of a compound of the present disclosure or a pharmaceutically acceptable salt thereof in the manufacture of a medicament for treating or preventing an inflammatory disorder, an autoinflammatory disorder, an autoimmune disorder, a neurodegenerative disease or cancer in a subject in need thereof.

In some aspects, the present disclosure provides use of a compound of the present disclosure or a pharmaceutically acceptable salt thereof in the manufacture of a medicament for treating an inflammatory disorder, an autoinflammatory disorder, an autoimmune disorder, a neurodegenerative disease or cancer in a subject in need thereof.

In some aspects, the present disclosure provides use of a compound of the present disclosure or a pharmaceutically acceptable salt thereof in the manufacture of a medicament for treating or preventing an inflammatory disorder, an autoinflammatory disorder and/or an autoimmune disorder selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disorders (e.g., acne) and neuroinflammation occurring in protein misfolding diseases (e.g., Prion diseases) in a subject in need thereof.

In some aspects, the present disclosure provides use of a compound of the present disclosure or a pharmaceutically acceptable salt thereof in the manufacture of a medicament for treating an inflammatory disorder, an autoinflammatory disorder and/or an autoimmune disorder selected from cryopyrin-associated autoinflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disorders (e.g., acne) and neuroinflammation occurring in protein misfolding diseases (e.g., Prion diseases) in a subject in need thereof.

In some aspects, the present disclosure provides use of a compound of the present disclosure or a pharmaceutically acceptable salt thereof in the manufacture of a medicament for treating or preventing a neurodegenerative disease (e.g., Parkinson's disease or Alzheimer's disease) in a subject in need thereof.

In some aspects, the present disclosure provides use of a compound of the present disclosure or a pharmaceutically acceptable salt thereof in the manufacture of a medicament for treating a neurodegenerative disease (e.g., Parkinson's disease or Alzheimer's disease) in a subject in need thereof.

In some aspects, the present disclosure provides use of a compound of the present disclosure or a pharmaceutically acceptable salt thereof in the manufacture of a medicament for treating or preventing cancer in a subject in need thereof.

In some aspects, the present disclosure provides use of a compound of the present disclosure or a pharmaceutically acceptable salt thereof in the manufacture of a medicament for treating cancer in a subject in need thereof.

The present disclosure provides compounds that function as inhibitors of inflammasome activity. The present disclosure therefore provides a method of inhibiting inflammasome activity in vitro or in vivo, said method comprising contacting a cell with an effective amount of a compound, or a pharmaceutically acceptable salt thereof, as defined herein.

Effectiveness of compounds of the disclosure can be determined by industry-accepted assays/disease models according to standard practices of elucidating the same as described in the art and are found in the current general knowledge.

The present disclosure also provides a method of treating a disease or disorder in which inflammasome activity is implicated in a patient in need of such treatment, said method comprising administering to said patient a therapeutically effective amount of a compound, or a pharmaceutically acceptable salt thereof, or a pharmaceutical composition as defined herein.

On a general level, the compounds of the present disclosure, which inhibit the maturation of cytokines of the IL-1 family, are effective in all therapeutic indications that are mediated or associated with elevated levels of active forms of cytokines belonging to IL-1 family of cytokines (Sims J. et al. Nature Reviews Immunology 10, 89-102 (February 2010).

Exemplary diseases and the corresponding references will be given in the following: inflammatory, autoinflammatory and autoimmune diseases like CAPS (Dinarello C A. Immunity. 2004 March; 20(3):243-4; Hoffman H M. al. Reumatología 2005; 21(3)), gout, rheumatoid arthritis (Gabay C et al. Arthritis Research & Therapy 2009, 11:230; Schett G. et al. Nat Rev Rheumatol. 2016 January; 12(1):14-24.), Crohn's disease (Jung Mogg Kim Korean J Gastroenterol Vol. 58 No. 6, 300-310), COPD (Mortaz E. et al. Tanaffos. 2011; 10(2): 9-14.), fibrosis (Gasse P. et al. Am J Respir Crit Care Med. 2009 May 15; 179(10):903-13), obesity, type 2 diabetes ((Dinarello C A. et al. Curr Opin Endocrinol Diabetes Obes. 2010 August; 17(4):314-21)) multiple sclerosis (see EAE-model in Coll R C. et al. Nat Med. 2015 March; 21(3):248-55) and many others (Martinon F. et al. Immunol. 2009. 27:229-65) like Parkinson's disease or Alzheimer's disease (Michael T. et al. Nature 493, 674-678 (31 Jan. 2013); Halle A. et al., Nat Immunol. 2008 August; 9(8):857-65; Saresella M. et al. Mol Neurodegener. 2016 Mar. 3; 11:23) and some oncological disorders.

Suitably, the compounds according to the present disclosure can be used for the treatment of a disease selected from the group consisting of an inflammatory disease, an autoinflammatory disease, an autoimmune disease, a neurodegenerative disease and cancer. Said inflammatory, autoinflammatory and autoimmune disease is suitably selected from the group consisting of a cryopyrin-associated autoinflammatory syndrome (CAPS, such as for example familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), chronic kidney disease (CKD), gout, rheumatoid arthritis, osteoarthritis, Crohn's disease, COPD, fibrosis, obesity, type 2 diabetes, multiple sclerosis, dermatological diseases (e.g., acne) and neuroinflammation occurring in protein misfolding diseases, such as Prion diseases. Said neurodegenerative disease includes, but is not limited, to Parkinson's disease and Alzheimer's disease.

Accordingly, the compounds of the present disclosure can be used for the treatment of a disease selected from the group consisting of cryopyrin-associated autoinflammatory syndrome (CAPS, such as for example familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), nonalcoholic steatohepatitis (NASH), chronic kidney disease (CKD), gout, rheumatoid arthritis, osteoarthritis, Crohn's disease, COPD, fibrosis, obesity, type 2 diabetes, multiple sclerosis, dermatological diseases (e.g., acne) neuroinflammation occurring in protein misfolding diseases, such as Prion diseases, neurogenerative diseases (e.g., Parkinson's disease, Alzheimer's disease) and oncological disorders.

Treatment in Cancer; Links with Inflammasome

Chronic inflammation responses have long been observed to be associated with various types of cancer. During malignant transformation or cancer therapy inflammasomes may become activated in response to danger signals and this activation may be both beneficial and detrimental in cancer.

IL-1β expression is elevated in a variety of cancers (including breast, prostate, colon, lung, head and neck cancers and melanomas) and patients with IL-1β producing tumours generally have a worse prognosis (Lewis, Anne M., et al. "Interleukin-1 and cancer progression: the emerging role of interleukin-1 receptor antagonist as a novel therapeutic agent in cancer treatment." Journal of translational medicine 4.1 (2006): 48).

Cancers derived from epithelial cells (carcinoma) or epithelium in glands (adenocarcinoma) are heterogeneous; consisting of many different cell types. This may include fibroblasts, immune cells, adipocytes, endothelial cells and pericytes amongst others, all of which may be cytokine/chemokine secreting (Grivennikov, Sergei I., Florian R. Greten, and Michael Karin. "Immunity, inflammation, and cancer." Cell 140.6 (2010): 883-899). This can lead to cancer-associated inflammation through the immune cell infiltration. The presence of leukocytes in tumours is known but it has only recently become evident that an inflammatory microenvironment is an essential component of all tumours. Most tumours (>90%) are the result of somatic mutations or environmental factors rather than germline mutations and many environmental causes of cancer are associated with chronic inflammation (20% of cancers are related to chronic infection, 30% to smoking/inhaled pollutants and 35% to dietary factors (20% of all cancers are linked to obesity) (Aggarwal, Bharat B., R. V. Vijayalekshmi, and Bokyung Sung. "Targeting inflammatory pathways for prevention and therapy of cancer: short-term friend, long-term foe." Clinical Cancer Research 15.2 (2009): 425-430).

GI Cancer

Cancers of the gastrointestinal (GI) tract are frequently associated with chronic inflammation. For example, *H. pylori* infection is associated with gastric cancer (Amieva, Manuel, and Richard M. Peek. "Pathobiology of *Helicobacter pylori*-Induced Gastric Cancer." Gastroenterology 150.1 (2016): 64-78). Colorectal cancer is associated with inflammatory bowel disease (Bernstein, Charles N., et al.

"Cancer risk in patients with inflammatory bowel disease." Cancer 91.4 (2001): 854-862). Chronic inflammation in stomach leads to the upregulation of IL-1 and other cytokines (Basso D, et al., (1996) *Helicobacter pylori* infection enhances mucosal interleukin-1 beta, interleukin-6, and the soluble receptor of interleukin-2. Int J Clin Lab Res 26:207-210) and polymorphisms in IL-1β gene can increase risk of gastric cancer (Wang P, et al., (2007) Association of interleukin-1 gene polymorphisms with gastric cancer: a meta-analysis. Int J Cancer 120:552-562).

In 19% of gastric cancer cases, caspase-1 expression is decreased which correlates with stage, lymph node metastasis and survival (Jee et al., 2005). *Mycoplasma hyorhinis* is associated with the development of gastric cancer its activation of the NLRP3 inflammasome may be associated with its promotion of gastric cancer metastasis (Xu et al., 2013).

Skin Cancers

Ultraviolet radiation is the greatest environmental risk for skin cancer which is promoted by causing DNA damage, immunosuppression and inflammation. The most malignant skin cancer, melanoma, is characterised by the upregulation of inflammatory cytokines, all of which can be regulated by IL-1β (Lázár-Molnár, Eszter, et al. "Autocrine and paracrine regulation by cytokines and growth factors in melanoma." Cytokine 12.6 (2000): 547-554). Systemic inflammation induces an enhancement of melanoma cell metastasis and growth by IL-1-dependent mechanisms in vivo. Using thymoquinone inhibition of metastasis in a B16F10 mouse melanoma model was shown to be dependent on inhibition of the NLRP3 inflammasome (Ahmad, Israr, et al. "Thymoquinone suppresses metastasis of melanoma cells by inhibition of NLRP3 inflammasome." Toxicology and applied pharmacology 270.1 (2013): 70-76).

Glioblastoma

NLRP3 contributes to radiotherapy resistance in glioma. Ionising radiation can induce NLRP3 expression whereas NLRP3 inhibition reduced tumour growth and prolonged mouse survival following radiation therapy. NLRP3 inflammasome inhibition can therefore provide a therapeutic strategy for radiation-resistant glioma (Li, Lianling, and Yuguang Liu. "Aging-related gene signature regulated by Nlrp3 predicts glioma progression." American journal of cancer research 5.1 (2015): 442).

Metastasis

More widely, NLRP3 is considered by the applicants to be involved in the promotion of metastasis and consequently modulation of NLRP3 should plausibly block this. IL-1 is involved in tumour genesis, tumour invasiveness, metastasis, tumour host interactions (Apte, Ron N., et al. "The involvement of IL-1 in tumorigenesis, tumour invasiveness, metastasis and tumour-host interactions." Cancer and Metastasis Reviews 25.3 (2006): 387-408) and angiogenesis (Voronov, Elena, et al. "IL-1 is required for tumor invasiveness and angiogenesis." Proceedings of the National Academy of Sciences 100.5 (2003): 2645-2650).

The IL-1 gene is frequently expressed in metastases from patients with several types of human cancers. For example, IL-1mRNA was highly expressed in more than half of all tested metastatic human tumour specimens including specifically non-small-cell lung carcinoma, colorectal adenocarcinoma, and melanoma tumour samples (Elaraj, Dina M., et al. "The role of interleukin 1 in growth and metastasis of human cancer xenografts." Clinical Cancer Research 12.4 (2006): 1088-1096) and IL-1RA inhibits xenograft growth in IL-1 producing tumours but without anti-proliferative effects in vitro.

Further, IL-1 signalling is a biomarker for predicting breast cancer patients at increased risk for developing bone metastasis. In mouse models IL-1β and its receptor are upregulated in breast cancer cells that metastasize to bone compared with cells that do not. In a mouse model the IL-1 receptor antagonist anakinra reduced proliferation and angiogenesis in addition to exerting significant effects on the tumour environment reducing bone turnover markers, IL-1β and TNF alpha (Holen, Ingunn, et al. "IL-1 drives breast cancer growth and bone metastasis in vivo." Oncotarget (2016).

IL-18 induced the production of MMP-9 in the human leukaemia cell line HL-60, thus favouring degradation of the extracellular matrix and the migration and invasiveness of cancer cells (Zhang, Bin, et al. "IL-18 increases invasiveness of HL-60 myeloid leukemia cells: upregulation of matrix metalloproteinases-9 (MMP-9) expression." Leukemia research 28.1 (2004): 91-95). Additionally IL-18 can support the development of tumour metastasis in the liver by inducing expression of VCAM-1 on hepatic sinusoidal endothelium (Carrascal, Maria Teresa, et al. "Interleukin-18 binding protein reduces b16 melanoma hepatic metastasis by neutralizing adhesiveness and growth factors of sinusoidal endothelium." Cancer Research 63.2 (2003): 491-497).

CD36

The fatty acid scavenger receptor CD36 serves a dual role in priming gene transcription of pro-IL-1β and inducing assembly of the NLRP3 inflammasome complex. CD36 and the TLR4-TLR6 heterodimer recognise oxLDL, which initiates a signalling pathway leading to transcriptional upregulation of NLRP3 and pro-IL-1β (signal 1). CD36 also mediates the internalisation of oxLDL into the lysosomal compartment, where crystals are formed that induce lysosomal rupture and activation of the NLRP3 inflammasome (signal 2) (Kagan, J. and Horng T., "NLRP3 inflammasome activation: CD36 serves double duty." Nature immunology 14.8 (2013): 772-774).

A subpopulation of human oral carcinoma cells express high levels of the fatty acid scavenger receptor CD36 and are unique in their ability to initiate metastasis. Palmitic acid or a high fat diet boosted the metastatic potential of the CD36+ cells. Neutralising anti-CD36 antibodies blocked metastasis in orthotopic mouse models of human oral cancer. The presence of CD36+ metastasis-initiating cells correlates with a poor prognosis for numerous types of carcinomas. It is suggested that dietary lipids may promote metastasis (Pasqual, G, Avgustinova, A., Mejetta, S, Martin, M, Castellanos, A, Attolini, CS-O, Berenguer, A., Prats, N, Toll, A, Hueto, J A, Bescos, C, Di Croce, L, and Benitah, S A. 2017 "Targeting metastasis-initiating cells through the fatty acid receptor CD36" Nature 541:41-45).

In hepatocellular carcinoma exogenous palmitic acid activated an epithelial-mesenchymal transition (EMT)-like program and induced migration that was decreased by the CD36 inhibitor, sulfo-N-succinimidyl oleate (Nath, Aritro, et al. "Elevated free fatty acid uptake via CD36 promotes epithelial-mesenchymal transition in hepatocellular carcinoma." Scientific reports 5 (2015). Body mass index was not associated with the degree of EMT highlighting that it is actually CD36 and free fatty acids that are important.

Cancer stems cells (CSCs) use CD36 to promote their maintenance. Oxidised phospholipids, ligands of CD36, were present in glioblastoma and the proliferation of CSCs but not non-CSCs increased with exposure to oxidised LDL. CD36 also correlated with patient prognosis.

Chemotherapy Resistance

In addition to direct cytotoxic effects, chemotherapeutic agents harness the host immune system which contributes to anti-tumour activity. However, gemcitabine and 5-FU were shown to activate NLRP3 in myeloid-derived suppressor cells leading to production of IL-1β which curtails anti-tumour efficacy. Mechanistically these agents destabilised the lysosome to release cathepsin B to activate NLRP3. IL-1β drove the production of IL-17 from CD4+ T cells which in turn blunted the efficacy of the chemotherapy. Higher anti-tumoral effects for both gemcitabine and 5-FU were observed when tumours were established in NLRP3−/− or Caps1−/− mice, or WT mice treated with IL-1RA. Myeloid-derived suppressor cell NLRP3 activation therefore limits the anti-tumour efficacy of gemcitabine and 5-FU (Bruchard, Melanie, et al. "Chemotherapy-triggered cathepsin B release in myeloid-derived suppressor cells activates the Nlrp3 inflammasome and promotes tumour growth." Nature medicine 19.1 (2013): 57-64.). Compounds of the present disclosure may therefore be useful in chemotherapy to treat a range of cancers.

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which inflammasome activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with a suitable, in association with a pharmaceutically acceptable diluent or carrier.

In addition to its use in therapeutic medicine, compounds of Formula (I) and pharmaceutically acceptable salts thereof are also useful as pharmacological tools in the development and standardisation of in vitro and in vivo test systems for the evaluation of the effects of inhibitors of inflammasome in laboratory animals such as dogs, rabbits, monkeys, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

Routes of Administration

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXEMPLARY EMBODIMENTS

Embodiment No. 1: A compound of Formula (I):

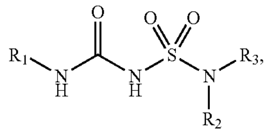

(I)

or a prodrug, solvate, or pharmaceutically acceptable salt thereof, wherein:

- $R_1$ is 5- to 12-membered heterocycloalkyl or 5- to 12-membered heteroaryl optionally substituted with one or more $R_{1S}$;
- each $R_{1S}$ is independently $C_1$-$C_6$ alkyl, $C_1$-$C_6$ haloalkyl, —O($C_1$-$C_6$ alkyl), —O($C_1$-$C_6$ haloalkyl), —($C_1$-$C_6$ alkyl)-O($C_1$-$C_6$ alkyl), cyano, halo, $C_3$-$C_8$ cycloalkyl, $C_3$-$C_8$ aryl, 3- to 8-membered heterocycloalkyl, or 3- to 8-membered heteroaryl;
- $R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;
- $R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 5- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

Embodiment No. 2: The compound of Embodiment 1, wherein:

$R_1$ is 5- to 12-membered heterocycloalkyl or 5- to 12-membered heteroaryl optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), —($C_1$-$C_6$ alkyl)-O($C_1$-$C_6$ alkyl), cyano, halo, $C_3$-$C_8$ cycloalkyl, $C_3$-$C_8$ aryl, 3- to 8-membered heterocycloalkyl, or 3- to 8-membered heteroaryl;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH ($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

Embodiment No. 3: The compound of any one of the preceding Embodiments, wherein:

$R_1$ is 5- to 12-membered heterocycloalkyl or 5- to 12-membered heteroaryl, wherein at least one heteroatom in the 5- to 12-membered heterocycloalkyl or 5- to 12-membered heteroaryl is O or S, and wherein the 5- to 12-membered heterocycloalkyl or 5- to 12-membered heteroaryl is optionally substituted with one or more $R_{1S}$;

each $R_{1S}$ is independently $C_1$-$C_6$ alkyl, $C_1$-$C_6$ haloalkyl, —O($C_1$-$C_6$ alkyl), cyano, halo, $C_3$-$C_8$ cycloalkyl, or $C_3$-$C_8$ aryl;

$R_2$ is —$(CH_2)_n$—$R_{2S}$, wherein n is 0, 1, or 2;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, halo, —OH, —O($C_1$-$C_6$ alkyl), —$NH_2$, —NH ($C_1$-$C_6$ alkyl), or —N($C_1$-$C_6$ alkyl)$_2$; and $R_3$ is 5- to 6-membered heterocycloalkyl or 5- or 6-membered heteroaryl, wherein the 5- to 12-membered heterocycloalkyl or 5- or 6-membered heteroaryl is optionally substituted with one or more $C_1$-$C_6$ alkyl, $C_3$-$C_8$ cycloalkyl, or halo.

Embodiment No. 4: The compound of any one of the preceding Embodiments, wherein:

$R_1$ is 5- to 12-membered heterocycloalkyl or 5- to 12-membered heteroaryl, wherein at least one heteroatom in the 5- to 12-membered heterocycloalkyl or 5- to 12-membered heteroaryl is O or S, and wherein the 5- to 12-membered heterocycloalkyl or 5- to 12-membered heteroaryl is optionally substituted with one or more $R_{1S}$;

each $R_{1S}$ is independently $C_1$-$C_6$ alkyl, $C_1$-$C_6$ haloalkyl, —O($C_1$-$C_6$ alkyl), cyano, halo, $C_3$-$C_8$ cycloalkyl, or $C_3$-$C_8$ aryl;

$R_2$ is —$(CH_2)_n$—$R_{2S}$, wherein n is 0, 1, or 2;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, halo, —OH, —O($C_1$-$C_6$ alkyl), —$NH_2$, —NH ($C_1$-$C_6$ alkyl), or —N($C_1$-$C_6$ alkyl)$_2$; and $R_3$ is 5- or 6-membered heteroaryl optionally substituted with one or more $C_1$-$C_6$ alkyl, $C_3$-$C_8$ cycloalkyl or halo.

Embodiment No. 5: The compound of any one of the preceding Embodiments, wherein:

$R_1$ is 5- to 12-membered heteroaryl optionally substituted with one or more $R_{1S}$, wherein at least one heteroatom in the 5- to 12-membered heteroaryl is S;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH ($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

Embodiment No. 6: The compound of any one of the preceding Embodiments, wherein:

$R_1$ is 5- to 12-membered heteroaryl optionally substituted with one or more $R_{1S}$, wherein at least one heteroatom in the 5- to 12-membered heteroaryl is S;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is $C_1$-$C_6$ alkyl, $C_3$-$C_{16}$ cycloalkyl, or 4- to 8-membered heterocycloalkyl, wherein the $C_1$-$C_6$ alkyl, $C_3$-$C_{16}$ cycloalkyl, or 4- to 8-membered heterocycloalkyl is optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH ($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

Embodiment No. 7: The compound of any one of the preceding Embodiments, wherein:

$R_1$ is 5- to 12-membered heteroaryl optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

Embodiment No. 8: The compound of any one of the preceding Embodiments, wherein:

$R_1$ is 5- to 12-membered heteroaryl optionally substituted with one or more $R_{1S}$, wherein the heteroaryl comprises at least one S;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is —$(CX_2X_2)_n$—$R_{2S}$, wherein n is 0, 1, or 2, and each $X_2$ is independently H, $C_1$-$C_6$ alkyl, $C_2$-$C_6$ alkenyl, or $C_2$-$C_6$ alkynyl, wherein the $C_1$-$C_6$ alkyl, $C_2$-$C_6$ alkenyl, or $C_2$-$C_6$ alkynyl is optionally substituted with one or more halo, —CN, —OH, —O($C_1$-$C_6$ alkyl), —$NH_2$, —NH($C_1$-$C_6$ alkyl), —N($C_1$-$C_6$ alkyl)$_2$, or oxo;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

Embodiment No. 9: The compound of any one of the preceding Embodiments, wherein:

$R_1$ is $C_5$-$C_{12}$ heteroaryl optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is $R_{2S}$;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

Embodiment No. 10: The compound of any one of the preceding Embodiments, wherein:

$R_1$ is thiophenyl or benzothiophenyl, wherein the thiophenyl or benzothiophenyl is optionally substituted with one or more $R_{1S}$;

each $R_{1S}$ is independently $C_1$-$C_6$ alkyl, $C_1$-$C_6$ haloalkyl, —O($C_1$-$C_6$ alkyl), —O($C_1$-$C_6$ haloalkyl), or halo;

$R_2$ is $R_{2S}$;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

Embodiment No. 11: The compound of any one of the preceding Embodiments, wherein:

$R_1$ is thiophenyl or benzothiophenyl, wherein the thiophenyl or benzothiophenyl is optionally substituted with one or more $R_{1S}$;

each $R_{1S}$ is $C_1$-$C_6$ alkyl or halo;

$R_2$ is $R_{2S}$;

$R_{2S}$ is 4- to 8-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), —$NH_2$, —NH($C_1$-$C_6$ alkyl), —N($C_1$-$C_6$ alkyl)$_2$, or oxo; and $R_3$ is 7- to 12-membered heterocycloalkyl or 5- or 6-membered heteroaryl optionally substituted with one or more $R_{3S}$, wherein each $R_{3S}$ is independently $C_1$-$C_6$ alkyl, $C_1$-$C_6$ haloalkyl, $C_3$-$C_8$ cycloalkyl, halo, or $C_3$-$C_8$ heterocycloalkyl wherein the $C_1$-$C_6$ alkyl, $C_1$-$C_6$ haloalkyl, $C_3$-$C_8$ cycloalkyl, or $C_3$-$C_8$ heterocycloalkyl is optionally substituted with —O($C_1$-$C_6$ alkyl), —N($C_1$-$C_6$ alkyl)$_2$, halo, or —CN.

Embodiment No. 12: The compound of any one of the preceding Embodiments, wherein $R_1$ is 5- to 12-membered heterocycloalkyl optionally substituted with one or more $R_{1S}$.

Embodiment No. 13: The compound of any one of the preceding Embodiments, wherein $R_1$ is 5,6-dihydro-4H-cyclopenta[b]thiophenyl optionally substituted with one or more $R_{1S}$.

Embodiment No. 14: The compound of any one of the preceding Embodiments, wherein $R_1$ is

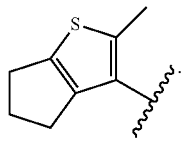 [SMILES: *c1c(C)sc2c1CCC2]

Embodiment No. 15: The compound of any one of the preceding Embodiments, wherein $R_1$ is 5- to 12-membered heteroaryl optionally substituted with one or more $R_{1S}$.

Embodiment No. 16: The compound of any one of the preceding Embodiments, wherein $R_1$ is 5- to 12-membered heteroaryl optionally substituted with one or more $R_{1S}$, wherein $R_1$ is attached to the rest of Formula (I) via a carbon atom in $R_1$.

Embodiment No. 17: The compound of any one of the preceding Embodiments, wherein $R_1$ is 5- to 12-membered heteroaryl optionally substituted with one or more $C_1$-$C_6$ alkyl or halo.

Embodiment No. 18: The compound of any one of the preceding Embodiments, wherein $R_1$ is 5- to 12-membered heteroaryl optionally substituted with one or more $R_{1S}$, wherein at least one heteroatom in the $C_5$-$C_{12}$ heteroaryl is S.

Embodiment No. 19: The compound of any one of the preceding Embodiments, wherein $R_1$ is 5-membered monocyclic heteroaryl optionally substituted with one or more $R_{1S}$, wherein the $C_5$ monocyclic heteroaryl comprises one heteroatom being O.

Embodiment No. 20: The compound of any one of the preceding Embodiments, wherein $R_1$ is furanyl optionally substituted with one or more $R_{1S}$.

Embodiment No. 21: The compound of any one of the preceding Embodiments, wherein $R_1$ is

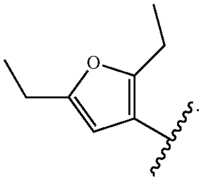 [SMILES: *c1cc(CC)oc1CC].

Embodiment No. 22: The compound of any one of the preceding Embodiments, wherein $R_1$ is 5-membered monocyclic heteroaryl optionally substituted with one or more $R_{1S}$, wherein at least one heteroatom in the $C_5$ monocyclic heteroaryl is S.

Embodiment No. 23: The compound of any one of the preceding Embodiments, wherein $R_1$ is thiophenyl optionally substituted with one or more $R_{1S}$.

Embodiment No. 24: The compound of any one of the preceding Embodiments, wherein $R_1$ is

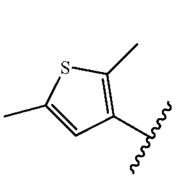,

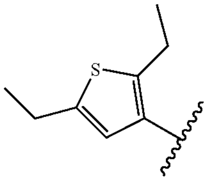,

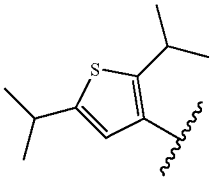,

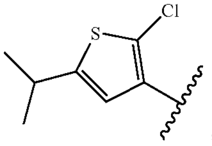,

-continued

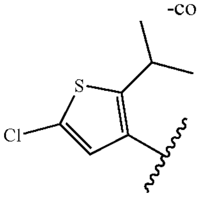,

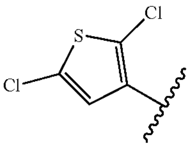,

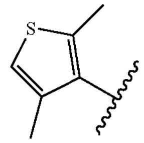,

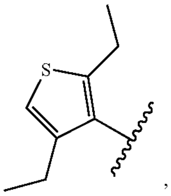,

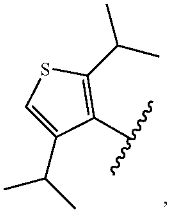,

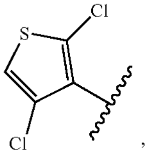,

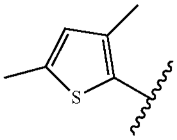,

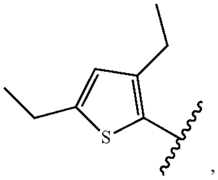,

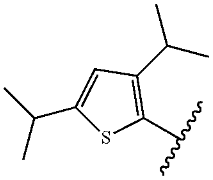,

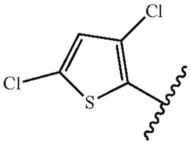,

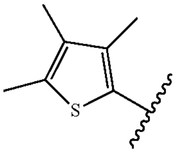,

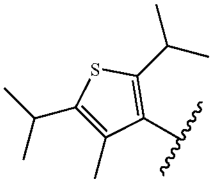,

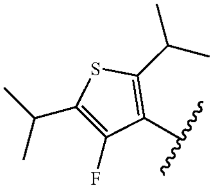,

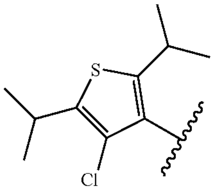,

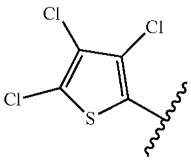,

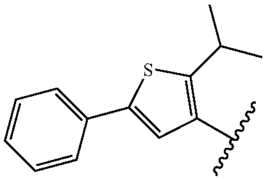, or

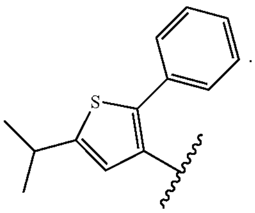.

Embodiment No. 25: The compound of any one of the preceding Embodiments, wherein $R_1$ is -continued
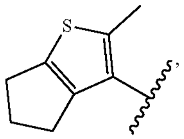,
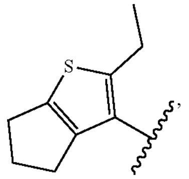,
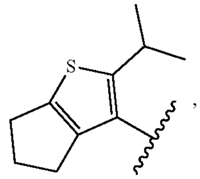,
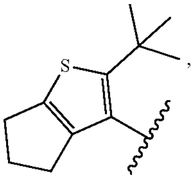,
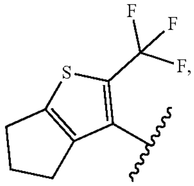,
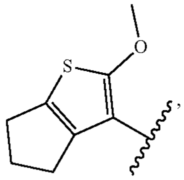,
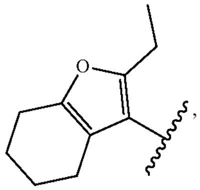,
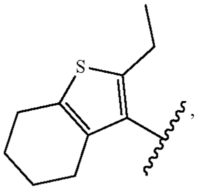,
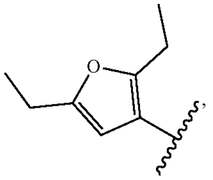,
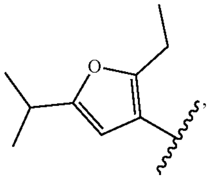,
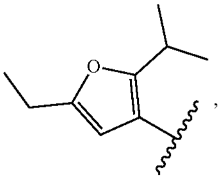,
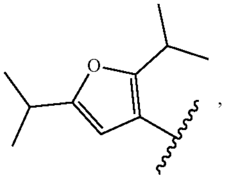,
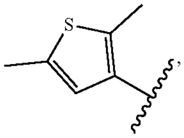,
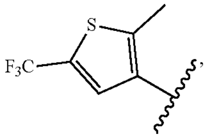,
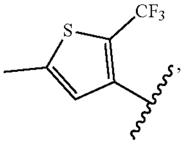,
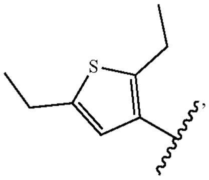,
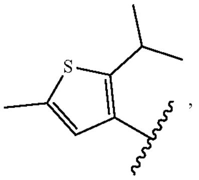,
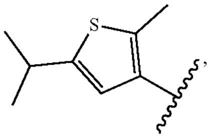,
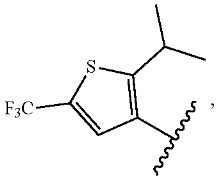,
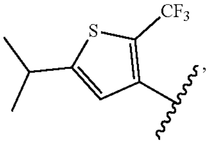,
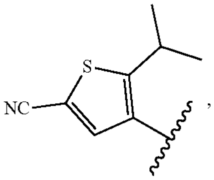,
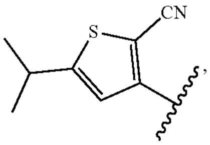,
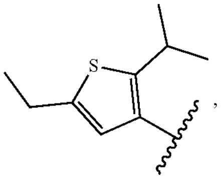,
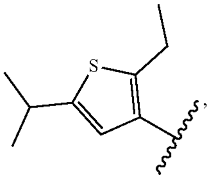,
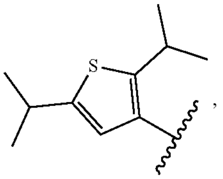,
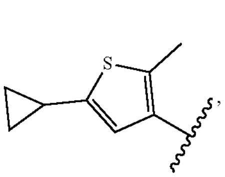,
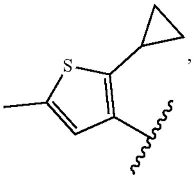,
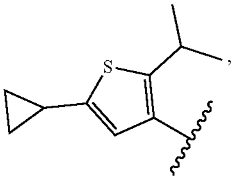,
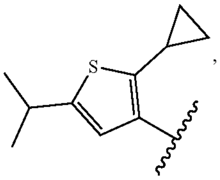,
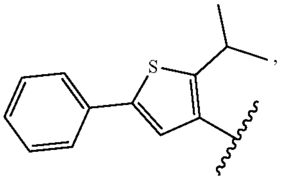,
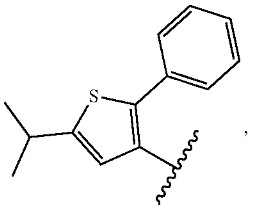,
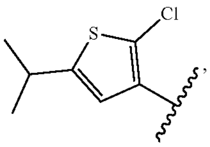,
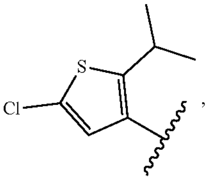,
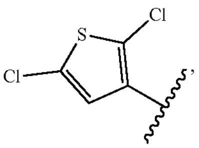,
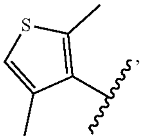,
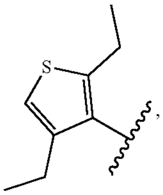,
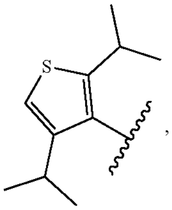, -continued
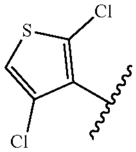, 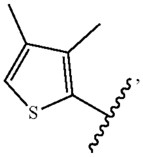, 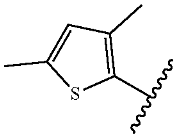,
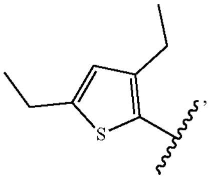, 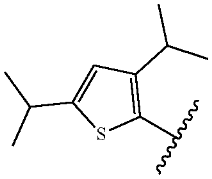,
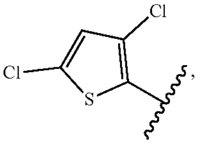, 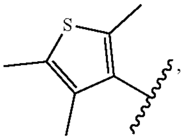,
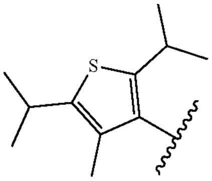, 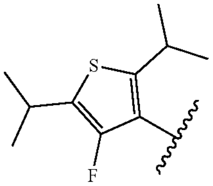,
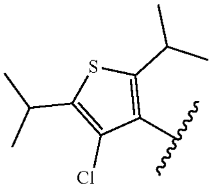, 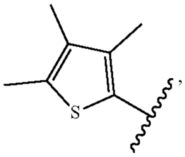,
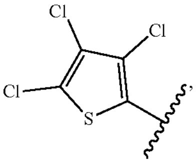, 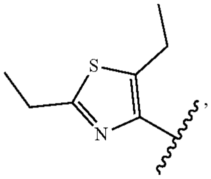,
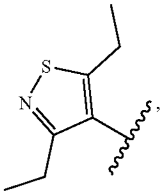, 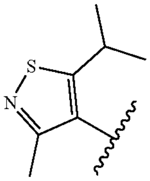, or 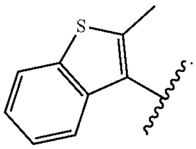.
Embodiment No. 26: The compound of any one of the preceding Embodiments, wherein $R_1$ is
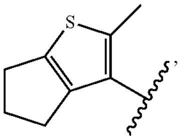, 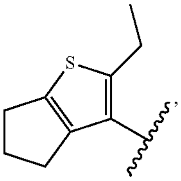,
-continued
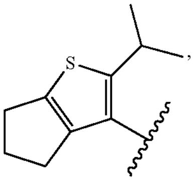, 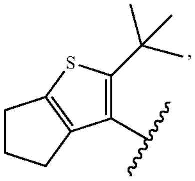,
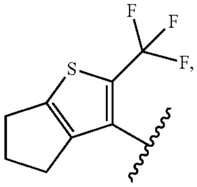, 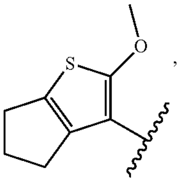,
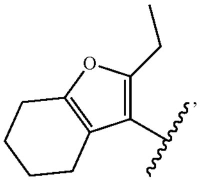, or 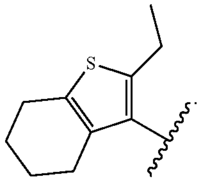.
Embodiment No. 27: The compound of any one of the preceding Embodiments, wherein $R_1$ is
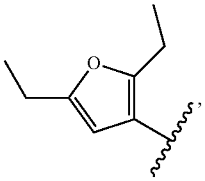, 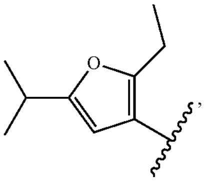,
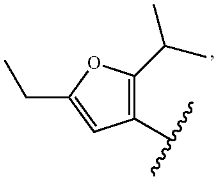, or 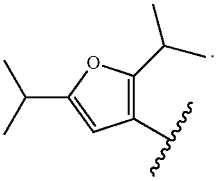.
Embodiment No. 28: The compound of any one of the preceding Embodiments, wherein $R_1$ is
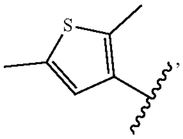, 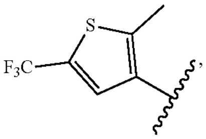,
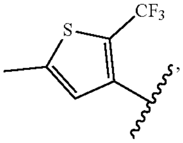, 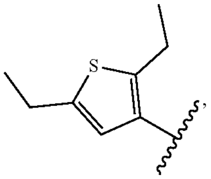,
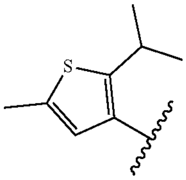, 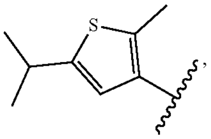, -continued
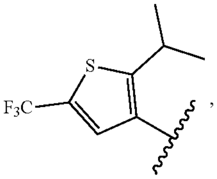, 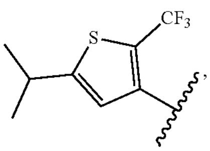,
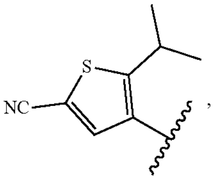, 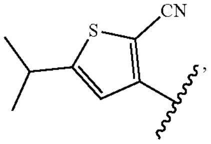,
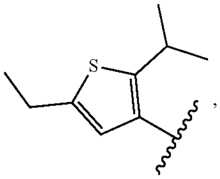, 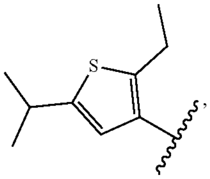,
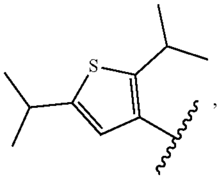, 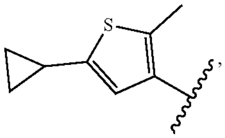,
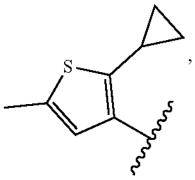, 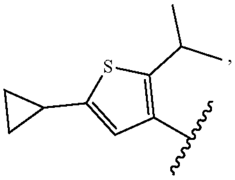,
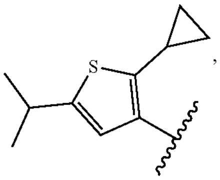, 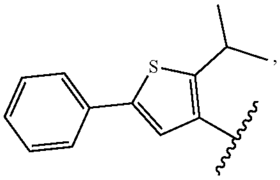,
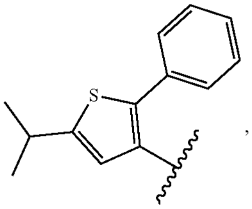, 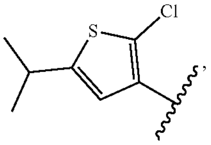,
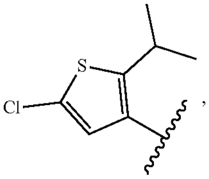, 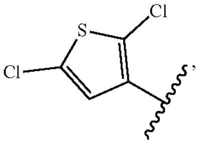,
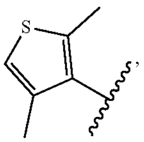, 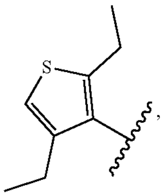, 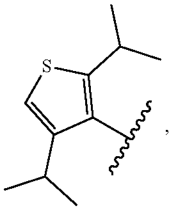,
-continued
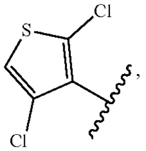, 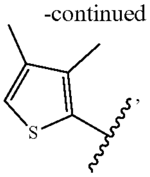, 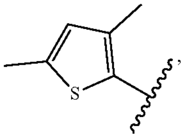,
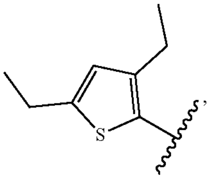, 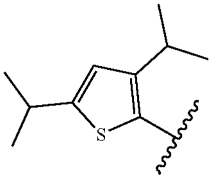,
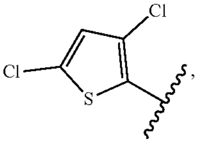, 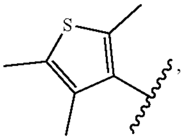,
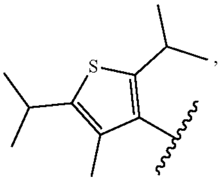, 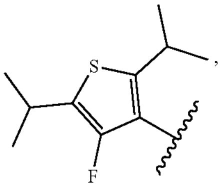,
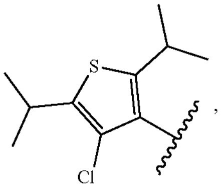, 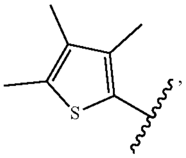, or
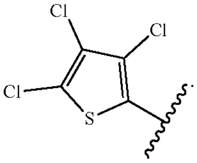.
Embodiment No. 29: The compound of any one of the preceding Embodiments, wherein $R_1$ is
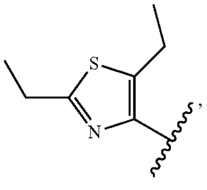, 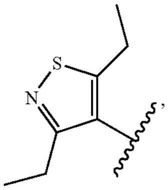, or 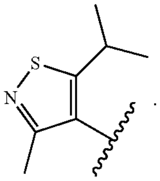.
Embodiment No. 30: The compound of any one of the preceding Embodiments, wherein $R_1$ is
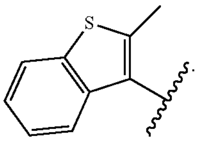 [SMILES: *c1c(C)sc2ccccc12].
Embodiment No. 31: The compound of any one of the preceding Embodiments, wherein $R_1$ is 5-membered monocyclic heteroaryl optionally substituted with one or more $R_{1S}$, wherein the $C_5$ monocyclic heteroaryl comprises two heteroatoms, wherein one heteroatom is S and the other heteroatom is N.

Embodiment No. 32: The compound of any one of the preceding Embodiments, wherein $R_1$ is thiazolyl optionally substituted with one or more $R_{1S}$.

Embodiment No. 33: The compound of any one of the preceding Embodiments, wherein $R_1$ is

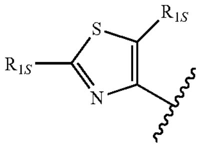
or
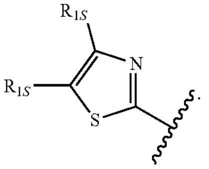

Embodiment No. 34: The compound of any one of the preceding Embodiments, wherein $R_1$ is

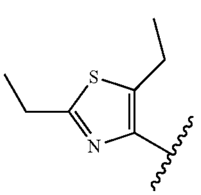
or
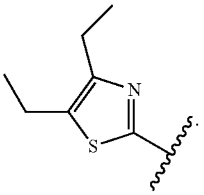

Embodiment No. 35: The compound of any one of the preceding Embodiments, wherein $R_1$ is isothiazolyl optionally substituted with one or more $R_{1S}$.

Embodiment No. 36: The compound of any one of the preceding Embodiments, wherein $R_1$ is

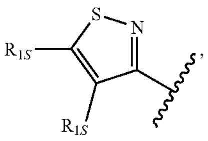
,
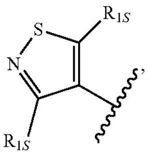
, or
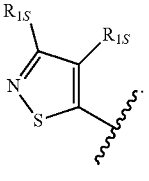

Embodiment No. 37: The compound of any one of the preceding Embodiments, wherein $R_1$ is

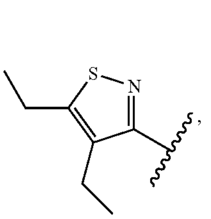
,
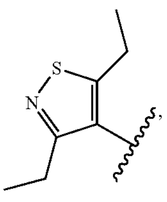
, or
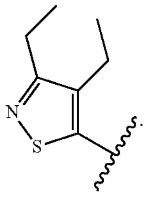

Embodiment No. 38: The compound of any one of the preceding Embodiments, wherein $R_1$ is 9-membered bicyclic heteroaryl optionally substituted with one or more $R_{1S}$, wherein at least one heteroatom in the 9-membered bicyclic heteroaryl is S.

Embodiment No. 39: The compound of any one of the preceding Embodiments, wherein $R_1$ is benzothiophenyl optionally substituted with one or more $R_{1S}$.

Embodiment No. 40: The compound of any one of the preceding Embodiments, wherein $R_1$ is

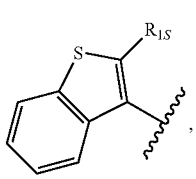
,
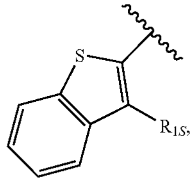
, or
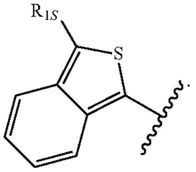

Embodiment No. 41: The compound of any one of the preceding Embodiments, wherein $R_1$ is

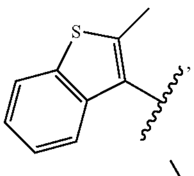
,
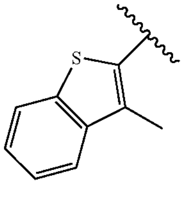
, or
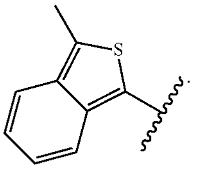

Embodiment No. 42: The compound of any one of the preceding Embodiments, wherein at least one $R_{1S}$ is $C_1$-$C_6$ alkyl, $C_1$-$C_6$ haloalkyl, —O($C_1$-$C_6$ alkyl), —O($C_1$-$C_6$ haloalkyl), or halo.

Embodiment No. 43: The compound of any one of the preceding Embodiments, wherein at least one $R_{1S}$ is $C_1$-$C_6$ alkyl or halo.

Embodiment No. 44: The compound of any one of the preceding Embodiments, wherein $R_2$ is $R_{2S}$.

Embodiment No. 45: The compound of any one of the preceding Embodiments, wherein $R_2$ is $—(CX_2)_n—R_{2S}$, wherein n is 1 or 2.

Embodiment No. 46: The compound of any one of the preceding Embodiments, wherein $R_{2S}$ is 6-membered heterocycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), $—NH_2$, —NH($C_1$-$C_6$ alkyl), —N($C_1$-$C_6$ alkyl)$_2$, or oxo.

Embodiment No. 47: The compound of any one of the preceding Embodiments, wherein $R_{2S}$ is $C_1$-$C_6$ alkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), $—NH_2$, —NH($C_1$-$C_6$ alkyl), —N($C_1$-$C_6$ alkyl)$_2$, or oxo.

Embodiment No. 48: The compound of any one of the preceding Embodiments, wherein $R_{2S}$ is $C_3$-$C_{16}$ cycloalkyl optionally substituted with one or more $C_1$-$C_6$ alkyl, $C_2$-$C_6$ alkenyl, $C_2$-$C_6$ alkynyl, $C_1$-$C_6$ haloalkyl, halo, —CN, —OH, —O($C_1$-$C_6$ alkyl), $—NH_2$, —NH($C_1$-$C_6$ alkyl), —N($C_1$-$C_6$ alkyl)$_2$, or oxo.

Embodiment No. 49: The compound of any one of the preceding Embodiments, wherein $R_{2S}$ is 6-membered heterocycloalkyl optionally substituted with one or more $C_1$-$C_6$ alkyl.
Embodiment No. 50: The compound of any one of the preceding Embodiments, wherein $R_{2S}$ is
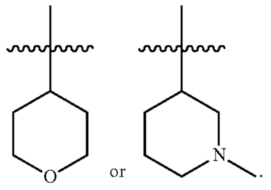
Embodiment No. 51: The compound of any one of the preceding Embodiments, wherein $R_2$ is
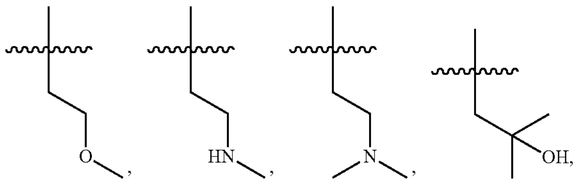
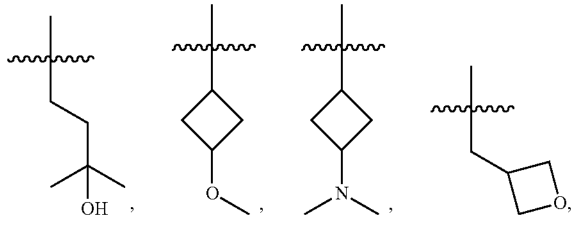
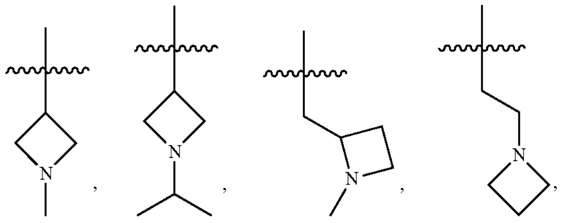
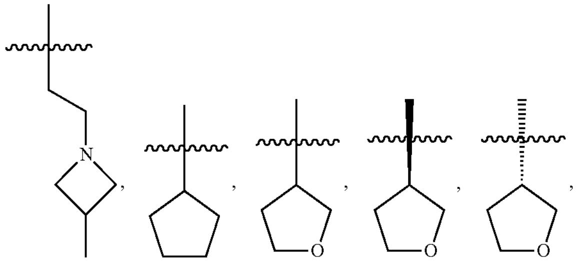
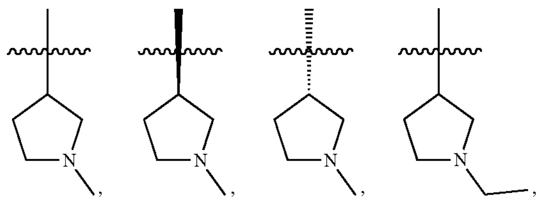
-continued
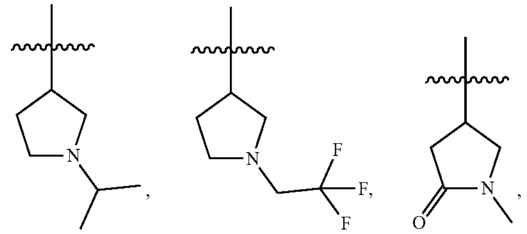
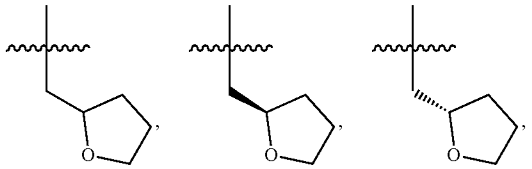
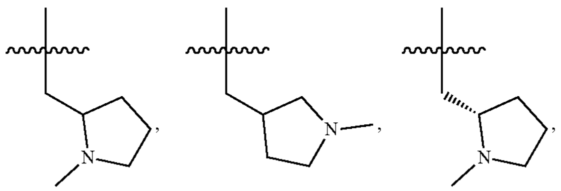
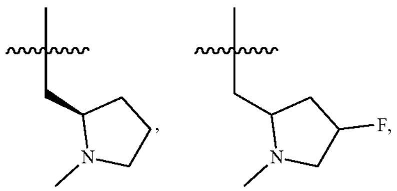
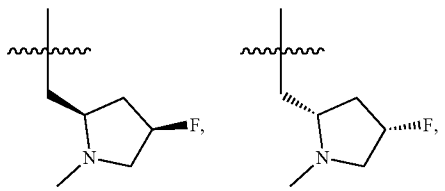
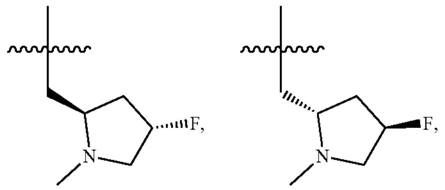
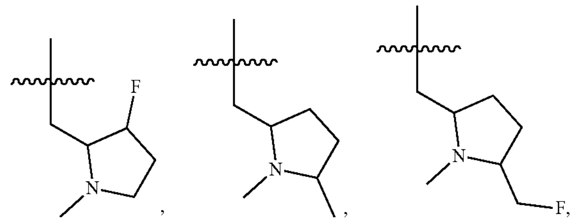
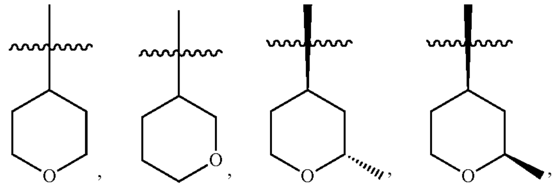

-continued
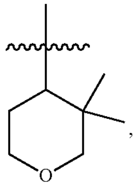, 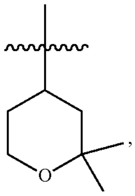, 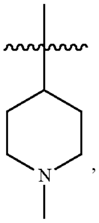, 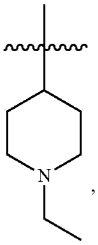,
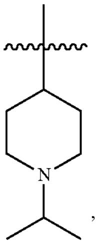, 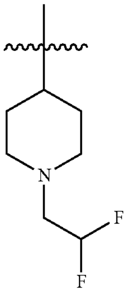, 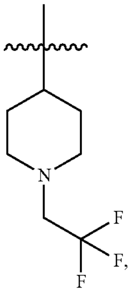 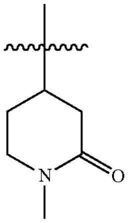,
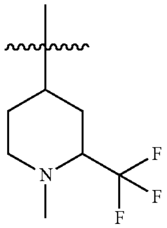, 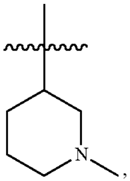, 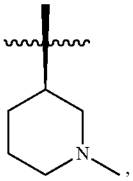,
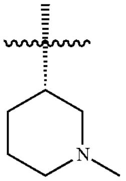, 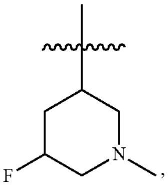, 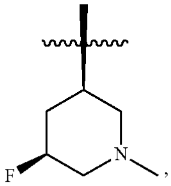,
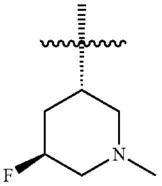, 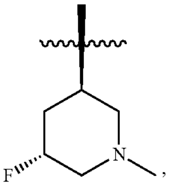, 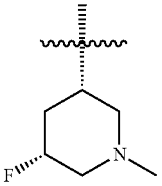,
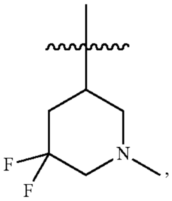, 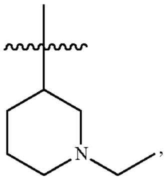, 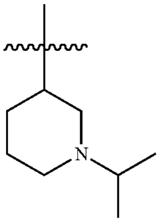,
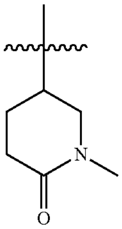, 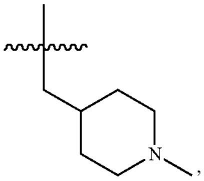, 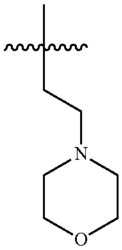,
-continued
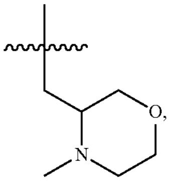 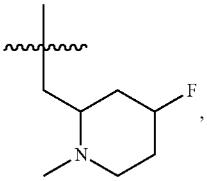,
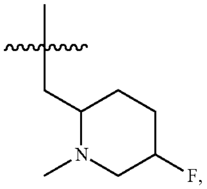 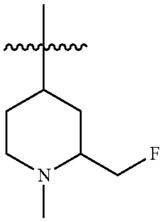, 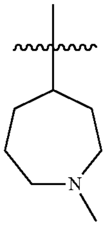,
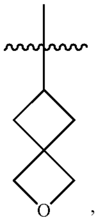, 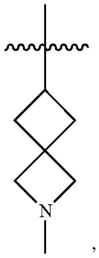, 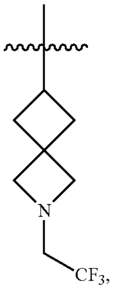 or 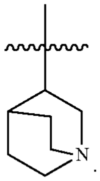
Embodiment No. 52: The compound of any one of the preceding Embodiments, wherein $R_2$ is
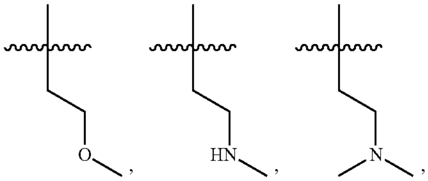
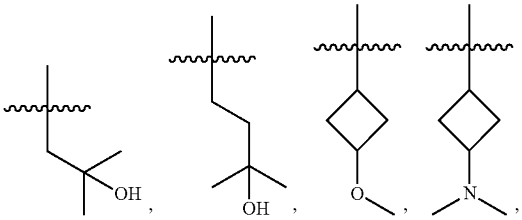
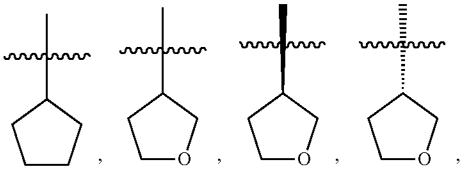
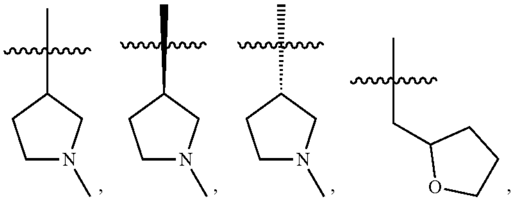

-continued
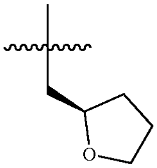 , 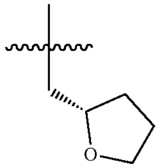 ,
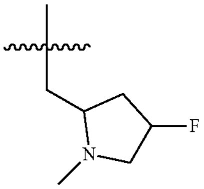 , 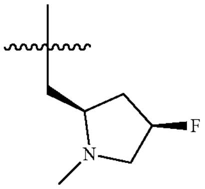 ,
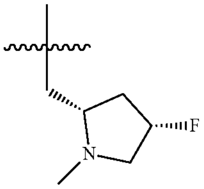 , 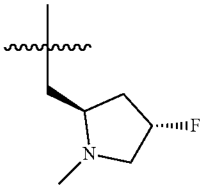 ,
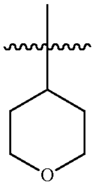 , 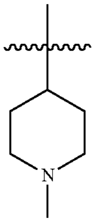 , 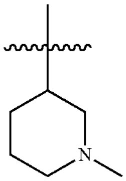 ,
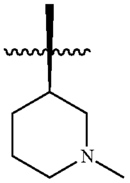 , 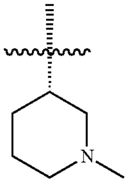 , 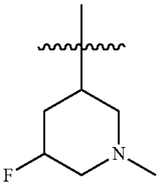 ,
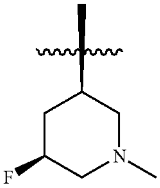 , 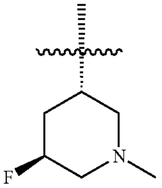 ,
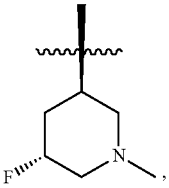 , 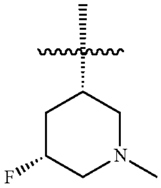 , or
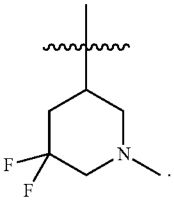 .
Embodiment No. 53: The compound of any one of the preceding Embodiments, wherein $R_2$ is
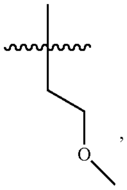 , 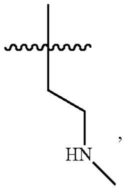 , 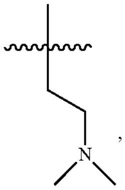 , 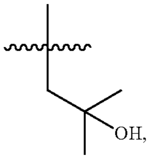 , or
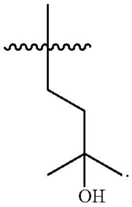 .
Embodiment No. 54: The compound of any one of the preceding Embodiments, wherein $R_2$ is
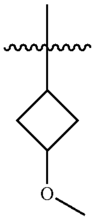 or 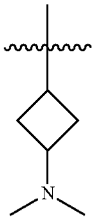 .
Embodiment No. 55: The compound of any one of the preceding Embodiments, wherein $R_2$ is
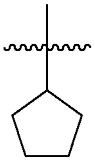 , 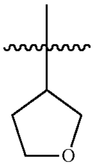 , 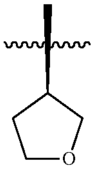 , 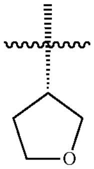 ,
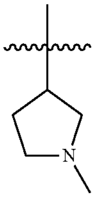 , 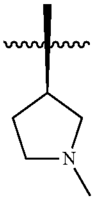 , 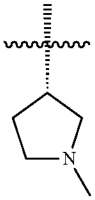 , 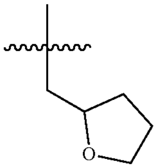 ,
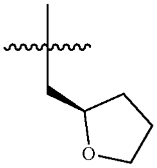 , 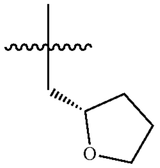 ,
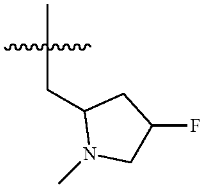 , 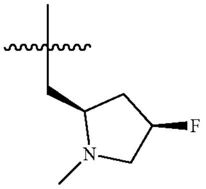 , -continued

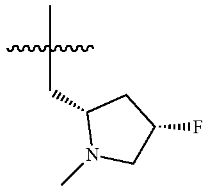

, or

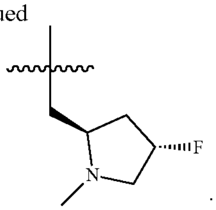

.

Embodiment No. 56: The compound of any one of the preceding Embodiments, wherein $R_2$ is

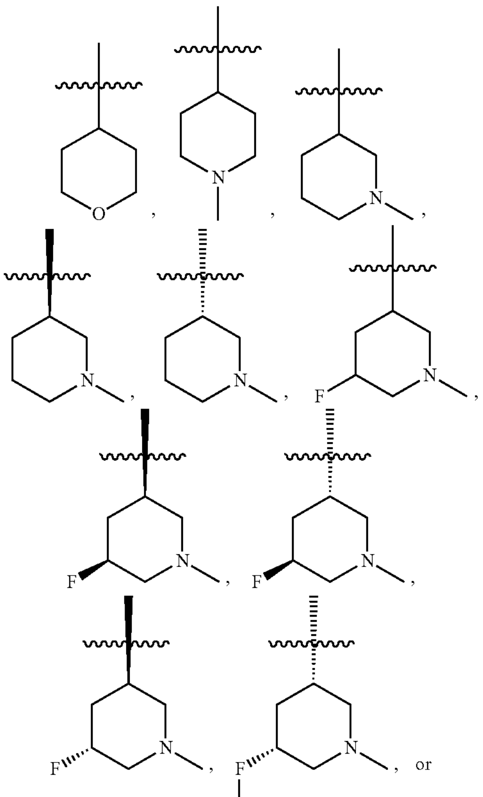

or

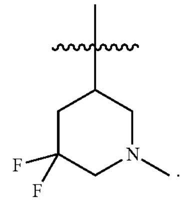

.

Embodiment No. 57: The compound of any one of the preceding Embodiments, wherein $R_2$ is

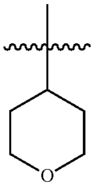

or

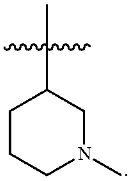

.

Embodiment No. 58: The compound of any one of the preceding Embodiments, wherein $R_3$ is 5- to 6-membered heterocycloalkyl or 5-membered heteroaryl, wherein the 5- to 6-membered heterocycloalkyl or 5-membered heteroaryl is optionally substituted with one or more $R_{3S}$.

Embodiment No. 59: The compound of any one of the preceding Embodiments, wherein $R_3$ is 5- to 6-membered heterocycloalkyl optionally substituted with one or more $R_{3S}$.

Embodiment No. 60: The compound of any one of the preceding Embodiments, wherein $R_3$ is

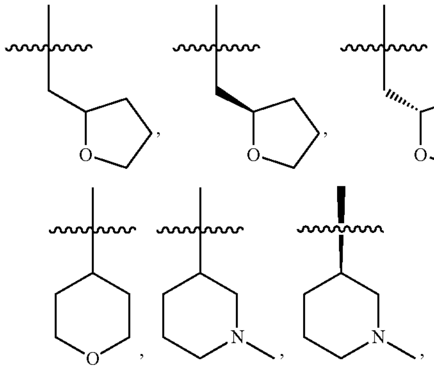

or

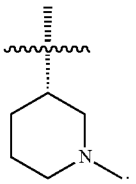

.

Embodiment No. 61: The compound of any one of the preceding Embodiments, wherein $R_3$ is 5-membered heteroaryl optionally substituted with one or more $R_{3S}$.

Embodiment No. 62: The compound of any one of the preceding Embodiments, wherein $R_3$ is pyrazolyl optionally substituted with one or more $R_{3S}$.

Embodiment No. 63: The compound of any one of the preceding Embodiments, wherein $R_3$ is

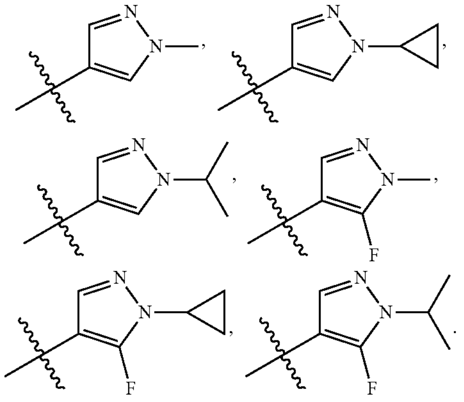

Embodiment No. 64: The compound of any one of the preceding Embodiments, wherein $R_3$ is

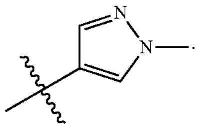 [SMILES: *c1cnn(C)c1]

Embodiment No. 65: The compound of any one of the preceding Embodiments, wherein at least one $R_{3S}$ is $C_1$-$C_6$ alkyl, $C_1$-$C_6$ haloalkyl, $C_3$-$C_8$ cycloalkyl, halo, or $C_3$-$C_8$ heterocycloalkyl.

Embodiment No. 66: The compound of any one of the preceding Embodiments, wherein at least one $R_{3S}$ is $C_1$-$C_6$ alkyl.

Embodiment No. 67: The compound of any one of the preceding Embodiments, wherein at least one $R_{3S}$ is methyl.

Embodiment No. 68: The compound of any one of the preceding Embodiments, being of Formula (II-a) or (II-b), or a prodrug, solvate, or pharmaceutically acceptable salt thereof, wherein $n_1$ is an integer ranging from 0 to 3 (e.g., 0, 1, 2, or 3).

Embodiment No. 69: The compound of any one of the preceding Embodiments, being of Formula (II-c), (II-d), (II-e), or a prodrug, solvate, or pharmaceutically acceptable salt thereof, wherein $n_1$ is 0 or 1.

Embodiment No. 70: The compound of any one of the preceding Embodiments, being of Formula (III), or a prodrug, solvate, or pharmaceutically acceptable salt thereof.

Embodiment No. 71: The compound of any one of the preceding Embodiments, being of Formula (III-a) or (III-b), or a prodrug, solvate, or pharmaceutically acceptable salt thereof, wherein $n_1$ is an integer ranging from 0 to 3 (e.g., 0, 1, 2, or 3).

Embodiment No. 72: The compound of any one of the preceding Embodiments, being of Formula (III-c), (III-d), (III-e), or a prodrug, solvate, or pharmaceutically acceptable salt thereof, wherein $n_1$ is 0 or 1.

Embodiment No. 73: The compound of any one of the preceding Embodiments, being of Formula (IV), or a prodrug, solvate, or pharmaceutically acceptable salt thereof, wherein $n_1$ is an integer ranging from 0 to 3 (e.g., 0, 1, 2, or 3).

Embodiment No. 74: The compound of any one of the preceding Embodiments, being of Formula (IV-a), or a prodrug, solvate, or pharmaceutically acceptable salt thereof.

Embodiment No. 75: The compound of any one of the preceding Embodiments, being selected from Compound Nos. 1-131 and prodrugs and pharmaceutically acceptable salts thereof.

Embodiment No. 76: The compound of any one of the preceding Embodiments, being selected from Compound Nos. 1-131 and pharmaceutically acceptable salts thereof.

Embodiment No. 77: The compound of any one of the preceding Embodiments, being selected from Compound Nos. 1-131.

Embodiment No. 78: A compound being an isotopic derivative of the compound of any one of the preceding Embodiments.

Embodiment No. 79: The compound of Embodiment 77, being a deuterium labeled compound of any one of Compound Nos. 1-131 and prodrugs and pharmaceutically acceptable salts thereof.

Embodiment No. 80: The compound of Embodiment 77 or Embodiment 78, being a deuterium labeled compound of any one of Compound Nos. 1-131.

Embodiment No. 81: A compound obtainable by, or obtained by, a method described herein; optionally, the method comprises one or more steps described in Schemes 1-6.

Embodiment No. 82: A compound, or an intermediate obtained by a method for preparing the compound of any one of Embodiments 1-79; optionally, the intermediate is selected from the intermediates described in Examples 1-107.

Embodiment No. 83: A pharmaceutical composition comprising the compound of any one of Embodiments 1-79 or a pharmaceutically acceptable salt thereof, and a pharmaceutically acceptable diluent or carrier.

Embodiment No. 84: The pharmaceutical composition of Embodiment 82, wherein the compound is selected from Compound Nos. 1-131.

Embodiment No. 85: A method of inhibiting inflammasome activity, comprising contacting a cell with an effective amount of the compound of any one of Embodiments 1-79 or a pharmaceutically acceptable salt thereof, optionally, the inflammasome is NLRP3 inflammasome, and the activity is in vitro or in vivo.

Embodiment No. 86: A method of treating or preventing a disease or disorder in a subject in need thereof, comprising administering to the subject a therapeutically effective amount of the compound of any one of Embodiments 1-79 or a pharmaceutically acceptable salt thereof, or the pharmaceutical composition of Embodiment 82 or Embodiment 83.

Embodiment No. 87: The compound of any one of Embodiments 1-79, or the pharmaceutical composition of Embodiment 82 or Embodiment 83, for use in inhibiting inflammasome activity; optionally, the inflammasome is NLRP3 inflammasome, and the activity is in vitro or in vivo.

Embodiment No. 88: The compound of any one of Embodiments 1-79, or the pharmaceutical composition of Embodiment 82 or Embodiment 83, for use in treating or preventing a disease or disorder.

Embodiment No. 89: Use of the compound of any one of Embodiments 1-79 or a pharmaceutically acceptable salt thereof in the manufacture of a medicament for inhibiting inflammasome activity; optionally, the inflammasome is NLRP3 inflammasome, and the activity is in vitro or in vivo.

Embodiment No. 90: Use of the compound of any one of Embodiments 1-79 or a pharmaceutically acceptable salt thereof in the manufacture of a medicament for treating or preventing a disease or disorder.

Embodiment No. 91: The method, compound, pharmaceutical composition, or use of any one of the preceding Embodiments, wherein the disease or disorder is associated with an implicated inflammasome activity; optionally, the disease or disorder is a disease or disorder in which inflammasome activity is implicated.

Embodiment No. 92: The method, compound, pharmaceutical composition, or use of any one of the preceding Embodiments, wherein the disease or disorder is an inflammatory disorder, an autoinflammatory disorder, an autoimmune disorder, a neurodegenerative disease, or cancer.

Embodiment No. 93: The method, compound, pharmaceutical composition, or use of any one of the preceding Embodiments, wherein the disease or disorder is an inflammatory disorder, an autoinflammatory disorder or an autoimmune disorder; optionally, the disease or disorder is selected from cryopyrin-associated auto-inflammatory syndrome (CAPS; e.g., familial cold autoinflammatory syndrome (FCAS), Muckle-Wells syndrome (MWS), chronic infantile neurological cutaneous and articular (CINCA) syndrome/neonatal-onset multisystem inflammatory disease (NOMID)), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disease (e.g., acne) and neuroinflammation occurring in protein misfolding diseases (e.g., Prion diseases).

Embodiment No. 94: The method, compound, pharmaceutical composition, or use of any one of the preceding Embodiments, wherein disease or disorder is a neurodegenerative disease; optionally, the disease or disorder is Parkinson's disease or Alzheimer's disease.

Embodiment No. 95: The method, compound, pharmaceutical composition, or use of any one of the preceding Embodiments, wherein the disease or disorder is cancer; optionally, the cancer is metastasising cancer, brain cancer, gastrointestinal cancer, skin cancer, non-small-cell lung carcinoma, head and neck squamous cell carcinoma or colorectal adenocarcinoma.

EXAMPLES

For exemplary purpose, neutral compounds of Formula (I) are synthesized and tested in the examples. It is understood that the neutral compounds of Formula (I) may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Nuclear magnetic resonance (NMR) spectra were recorded at 400 MHz or 300 MHz as stated and at 300.3 K unless otherwise stated; the chemical shifts (6) are reported in parts per million (ppm). Spectra were recorded using a Bruker or Varian instrument with 8, 16 or 32 scans.

LC-MS chromatograms and spectra were recorded using an Agilent 1200 or Shimadzu LC-20 AD&MS 2020 instrument using a C-18 column such as a Luna-C18 2.0×30 mm or Xbridge Shield RPC18 2.1×50 mm. Injection volumes were 0.7-8.0 µl and the flow rates were typically 0.8 or 1.2 ml/min. Detection methods were diode array (DAD) or evaporative light scattering (ELSD) as well as positive ion electrospray ionisation. MS range was 100-1000 Da. Solvents were gradients of water and acetonitrile both containing a modifier (typically 0.01-0.04%) such as trifluoroacetic acid or ammonium carbonate.

Abbreviations

ACN acetonitrile
AcOH acetic acid
DCE 1,2-dichloroethane
DCM dichloromethane
DIAD diisopropyl azodicarboxylate
DIPEA N,N-diisopropylethylamine
DMAP N,N-dimethylaminopyridine
DMF N,N-dimethylformamide
DPPA diphenylphosphoryl azide
dppf 1,1'-bis(diphenylphosphino)ferrocene
EDCI N-(3-dimethylaminopropyl)-N'-ethylcarbodiimide hydrochloride
ESI electrospray ionisation
EtOAc ethyl acetate
EtOH ethanol
h hour(s)
HATU N-[(dimethylamino)-1H-1,2,3-triazolo-[4,5-b]pyridin-1-ylmethylene]-N-methylmethanaminium hexafluorophosphate N-oxide
HMPA hexamethylphosphoramide
HOBt hydroxybenzotriazole
Jones reagent $CrO_3$ in aqueous $H_2SO_4$
Lawesson's reagent 2,4-Bis(4-methoxyphenyl)-1,3,2,4-dithiadiphosphetane-2,4-dithione
LCMS Liquid Chromatography—Mass Spectrometry
MeCN acetonitrile
MeOD methanol-$d_4$
MeOH methanol
$Me_2S$ dimethylsulfide
min minute(s)
m/z mass/charge
NBS N-bromosuccinimide
NCS N-chlorosuccinimide
Pd/C palladium on carbon
$Pd_2(dba)_3$ tris(dibenzylideneacetone)dipalladium(O)
$Pd(PPh_3)_4$ tetrakis(triphenylphosphine)palladium(0)
$PPh_3$ triphenylphosphine
prep-HPLC preparative high-performance liquid chromatography
prep-TLC preparative thin-layer chromatography
psi pound-force per square inch
Pt/C platinum on carbon
RM reaction mixture
rt room temperature
TFA trifluoroacetic acid
THF tetrahydrofuran
XPhos 2-dicyclohexylphosphino-2',4',6'-triisopropylbiphenyl
Y yield

Synthesis of Intermediates

Intermediate 1. N-(1-Methyl-1H-pyrazol-4-yl)-N-(oxan-4-yl)aminosulfonamide

Step 1: 1-Methyl-N-(oxan-4-yl)-1H-pyrazol-4-amine

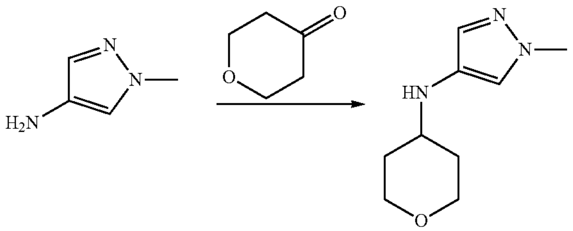

To a solution of 1-methylpyrazol-4-amine (10 g, 103 mmol) in DCE (205 ml) were added AcOH (23.6 ml, 412 mmol) and tetrahydropyran-4-one (11.35 ml, 124 mmol). The RM was stirred at rt for 1 h. The reaction was cooled to 0° C. then sodium triacetoxyborohydride (43.7 g, 206 mmol) was added to the mixture, maintaining the reaction temperature between 0 and 10° C. The reaction was allowed to warm to rt and stirred for 11 h. Saturated $Na_2CO_3$ aqueous solution (200 ml) was added to the mixture. The resulting mixture was extracted with DCM (3×50 ml) and the combined organic phases concentrated under reduced pressure to give a residue. The residue was purified by flash column chromatography (silica, 20-100% EtOAc in petroleum ether) to give 1-methyl-N-(oxan-4-yl)-1H-pyrazol-4-amine as a red oil. Y=86%. $^1$H NMR (400 MHz, MeOD) δ 7.22 (s, 1H), 7.15 (s, 1H), 3.98-3.93 (m, 2H), 3.78 (s, 3H), 3.49-3.40 (m, 2H), 3.10-3.01 (m, 1H), 1.97-1.88 (m, 2H), 1.47-1.36 (m, 2H).

Step 2: Tert-butyl N-(chlorosulfonyl)carbamate

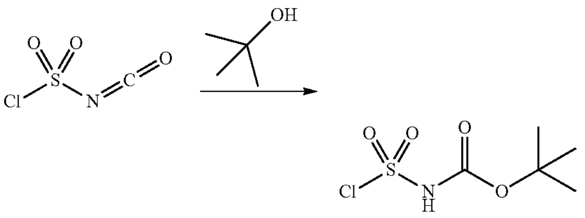

To a solution of N-(oxomethylene)sulfamoyl chloride (6.13 ml, 70.7 mmol) in DCM (100 ml) cooled to 0° C. was added tert-butanol (6.76 ml, 70.7 mmol). The mixture was stirred at 0° C. for 0.5 h to give tert-butyl N-(chlorosulfonyl) carbamate as a solution (100 ml, 70.7 mmol, 0.71 M in DCM). The tert-butyl N-(chlorosulfonyl)carbamate was used directly in the next step.

Step 3: Tert-butyl N-[(1-methyl-1H-pyrazol-4-yl) (oxan-4-yl)sulfamoyl]carbamate

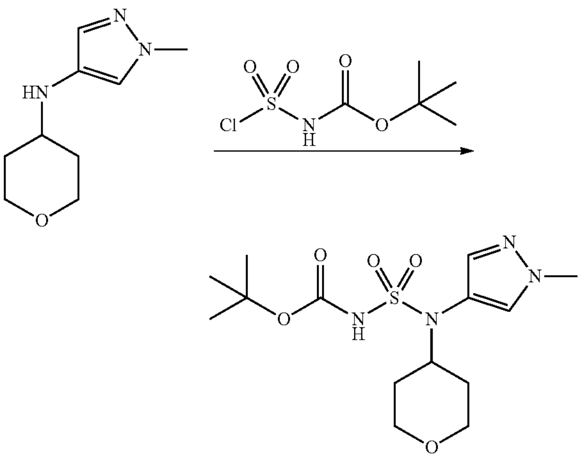

To a solution of 1-methyl-N-tetrahydropyran-4-yl-pyrazol-4-amine (7.0 g, 38.6 mmol) in DCM (70 ml) cooled to 0° C. was added DIPEA (20.2 ml, 116 mmol). The resulting solution was treated dropwise with a solution of tert-butyl N-chlorosulfonylcarbamate in DCM (0.71 M, 54.4 ml, 38.6 mmol. The mixture was stirred at 0° C. for 2 h. The solution was concentrated under vacuum. The resulting residue was purified by prep-HPLC (column: Phenomenex Luna C18 10 μm, 250×100 mm; mobile phase: [water (0.1% TFA)-ACN]; B: 5-35%, 20 min) to give tert-butyl N-[(1-methyl-1H-pyrazol-4-yl)(oxan-4-yl)sulfamoyl]carbamate as a yellow oil. Y=26%. LCMS (ESI): m/z: [M+H]$^+$=361.1.

Step 3: N-(1-Methyl-1H-pyrazol-4-yl)-N-(oxan-4-yl)aminosulfonamide

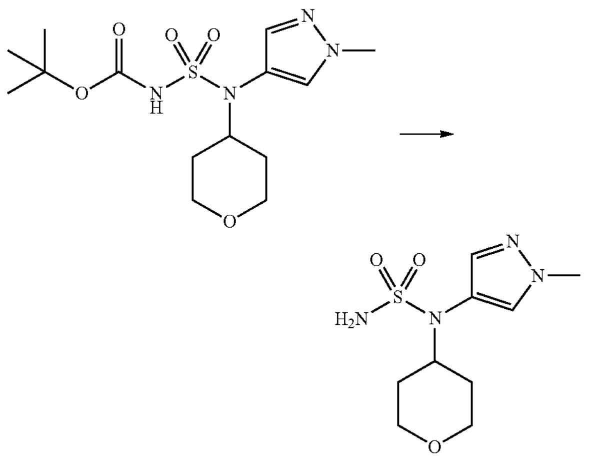

Tert-butyl N-[(1-methylpyrazol-4-yl)-tetrahydropyran-4-yl-sulfamoyl]carbamate (560 mg, 1.55 mmol, 1 eq) was dissolved in 4 M hydrochloric acid in EtOAc (10 ml). The mixture was stirred at rt for 12 h. The solution was concentrated under vacuum to give N-(1-methyl-1H-pyrazol-4-yl)-N-(oxan-4-yl)aminosulfonamide as a white solid. This was used without further purification. LCMS (ESI): m/z: [M+H]$^+$=261.1

Intermediate 2. 1-Methyl-3-[(I-methyl-1H-pyrazol-4-yl)(sulfamoyl)amino]piperidin-1-ium Trifluoroacetate Step 1. Tert-butyl 3-[(1-methyl-1H-pyrazol-4-yl) amino]piperidine-1-carboxylate

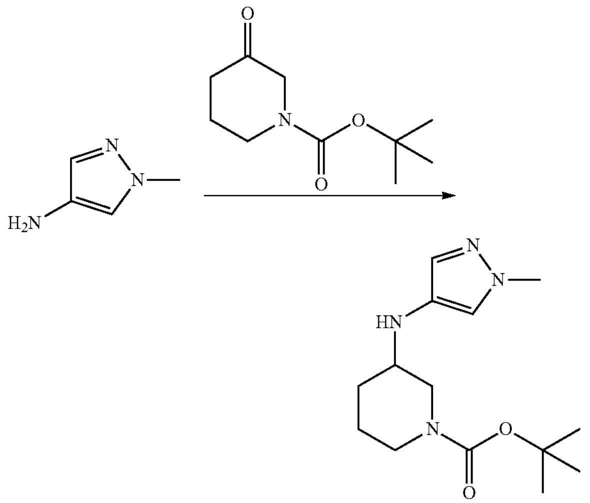

To a solution of 1-methylpyrazol-4-amine (2.0 g, 20.6 mmol) in DCE (41 ml) was added AcOH (4.71 ml, 82 mmol) and tert-butyl 3-oxopiperidine-1-carboxylate (4.10 g, 20.6 mmol). The mixture was stirred at rt for 1 h. The reaction was cooled to 0° C. and sodium triacetoxyborohydride (8.73 g, 41.2 mmol) was added. The reaction was stirred at between 0 and 10° C. for 12 h. The solvent was removed under reduced pressure and the resulting residue was purified by flash column chromatography (silica, 9-100% EtOAc in petroleum ether) to give tert-butyl 3-[(1-methyl-1H-pyrazol-4-yl)amino]piperidine-1-carboxylate as a red liquid. Y=78%.

Step 2. 1-Methyl-N-(1-methyl-1H-pyrazol-4-yl) piperidin-3-amine

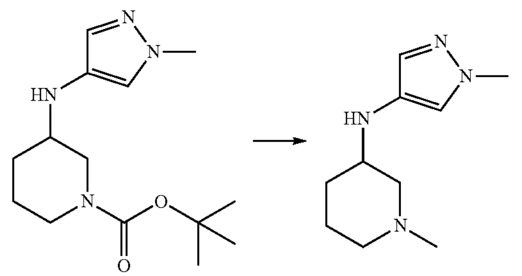 [SMILES: Cn1cc(NC2CCCN(C(=O)OC(C)(C)C)C2)cn1 ; CN1CCCC(Nc2cnn(C)c2)C1]

To a solution of tert-butyl 3-[(1-methyl-1H-pyrazol-4-yl) amino]piperidine-1-carboxylate (4.1 g, 14.6 mmol) in THF (30 ml) cooled to 0° C. was added lithium aluminium hydride (5.55 g, 146 mmol). The mixture was stirred at 0° C. for 0.5 h, then heated at 80° C. for 2 h. The RM was cooled, then $H_2O$ (5.55 ml) and 10% aqueous NaOH (5.55 ml) were added. The mixture was filtered and the filtrate concentrated under reduced pressure to give 1-methyl-N-(1-methyl-1H-pyrazol-4-yl)piperidin-3-amine as an oil. This was used without further purification. Y=95%.

Step 3. 3-[({[(Tert-butoxy)carbonyl]amino}sulfonyl) (1-methyl-1H-pyrazol-4-yl)amino]-1-methylpiperidin-1-ium Trifluoroacetate

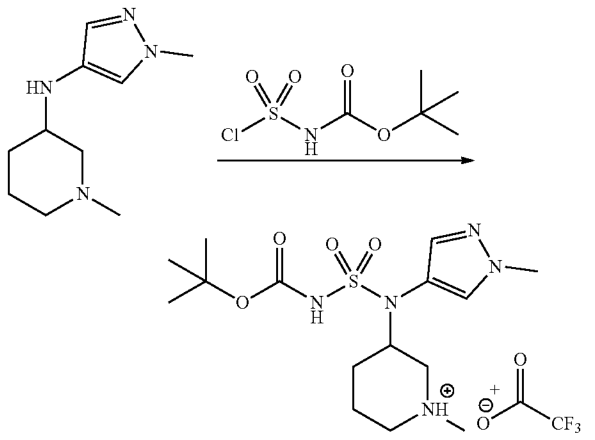

To a solution of 1-methyl-N-(1-methylpyrazol-4-yl)piperidin-3-amine (200 mg, 1.03 mmol) in DCM (2 ml) cooled to 0° C. was added a solution of 0.59 M tert-butyl N-chlorosulfonylcarbamate in DCM (1.75 ml, 1.03 mmol) and DIPEA (538 μl, 3.09 mmol). The mixture was stirred at 0° C. for 5 h. The reaction was concentrated under vacuum and the resulting residue purified by prep-HPLC (column: Phenomenex Luna C18 10 μm, 250×50 mm; mobile phase: [water (0.1% TFA)-ACN]; B: 15-45%, 20 min) to give 3-[({[(Tert-butoxy)carbonyl]amino}sulfonyl)(1-methyl-1H-pyrazol-4-yl)amino]-1-methylpiperidin-1-ium trifluoroacetate as a white solid. Y=40%. LCMS (ESI): m/z: $[M+H]^+$=374.2

Step 4. 1-Methyl-3-[(1-methyl-1H-pyrazol-4-yl) (sulfamoyl)amino]piperidin-1-ium Trifluoroacetate

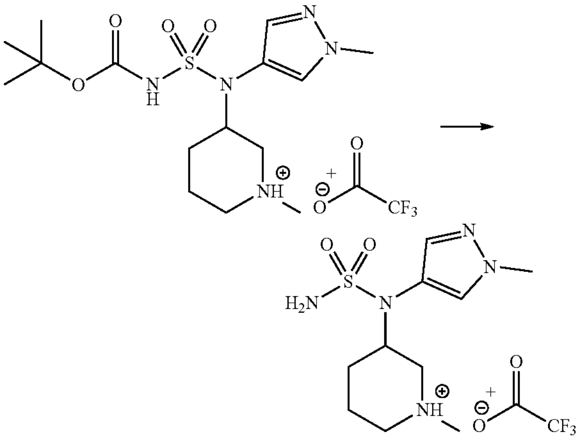

A mixture of 3-[({[(tert-butoxy)carbonyl] amino}sulfonyl)(1-methyl-1H-pyrazol-4-yl)amino]-1-methylpiperidin-1-ium trifluoroacetate (131 mg, 0.27 mmol) in DCM (2 ml) and TFA (0.4 ml) was stirred at rt for 3 h. The residue was concentrated under vacuum to 1-methyl-3-[(1-methyl-1H-pyrazol-4-yl)(sulfamoyl)amino]piperidin-1-ium trifluoroacetate as a white solid. This was used without further purification. Y=96%. LCMS (ESI): m/z: $[M+H]^+$=274.3

Intermediate 3. 3-Isocyanato-2,4-dimethylthiophene

Step 1: 2,4-Dimethylthiophen-3-amine

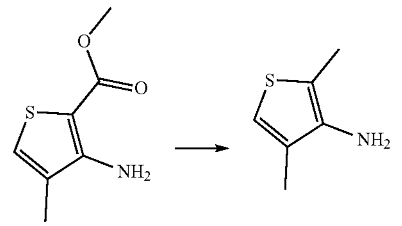

To a solution of lithium aluminium hydride (2.93 g, 77 mmol) in THF (30 ml) cooled to 0° C. was added dropwise a solution of methyl 3-amino-4-methyl-thiophene-2-carboxylate (6.00 g, 35 mmol) in THF (30 ml). The solution was stirred under nitrogen at rt for 30 min, then heated at 80° C. for 3 h. The reaction was cooled and then quenched with water (3 ml) and 15% aqueous NaOH (3 ml). The mixture was stirred at rt for 0.5 h and then filtered. The filtrate was concentrated under reduced pressure to give 2,4-dimethylthiophen-3-amine as a yellow oil. Y=96%. $^1$H NMR (400 MHz, chloroform-d) δ 6.60 (s, 1H), 3.12-3.32 (br. s, 2H), 2.24 (s, 3H), 2.07 (s, 3H)

Step 2. 3-Isocyanato-2,4-dimethylthiophene

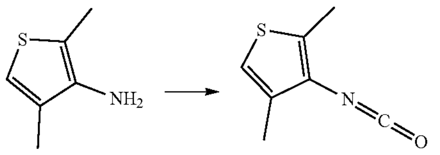

To a solution of 2,4-dimethylthiophen-3-amine (200 mg, 1.57 mmol) in DCM (2 ml) cooled to 0° C. was added triphosgene (209 μl, 1.57 mmol). The reaction was treated dropwise with triethylamine (438 μl, 3.14 mmol), maintaining the temperature at 0° C. The solution was allowed to warm to rt and stirred 3 h. The mixture was concentrated under reduced pressure to give 3-isocyanato-2,4-dimethylthiophene as a white solid. This was used without further purification.

Intermediate 4. 3-Isocyanato-2,5-dimethylthiophene

Step 1: 2,5-Dimethylthiophene-3-carboxylic Acid

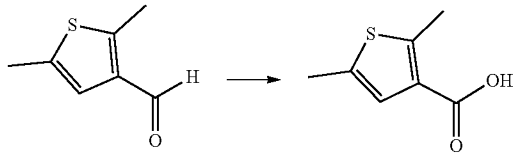

To a solution of 2,5-dimethylthiophene-3-carbaldehyde (1.0 g, 7.13 mmol) in acetone (4 ml) cooled to 0° C. was added 6 M Jones reagent (1.18 ml, 7.13 mmol). The mixture was allowed to warm to rt and stirred for 6 h. The solution was acidified to pH 5 with 1 M hydrochloric acid, then the resulting mixture was extracted with EtOAc (3×10 ml). The combined organic phases were concentrated under reduced pressure to give 2,5-dimethylthiophene-3-carboxylic acid as a brown solid. This was used directly without purification. $^1$H NMR (400 MHz, chloroform-d) δ 7.09 (s, 1H), 2.70 (s, 3H), 2.40 (s, 3H).

Step 2: Tert-butyl N-(2,5-dimethylthiophen-3-yl)carbamate

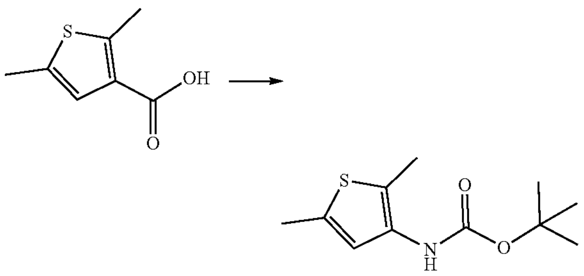

To a solution of 2,5-dimethylthiophene-3-carboxylic acid (500 mg, 3.20 mmol) in tert-butanol (2 ml) was added DPPA (694 μl, 3.20 mmol) and DIPEA (0.84 ml, 4.80 mmol). The mixture was stirred at 90° C. for 12 h. The solution was filtered and concentrated under reduced pressure. The residue was purified by prep-HPLC (column: Huapu C8 Extreme BDS 5 μm 150×30 mm; mobile phase: [water (10 mM $NH_4HCO_3$)-ACN]; B: 40-60%, 10 min) to give tert-butyl N-(2,5-dimethylthiophen-3-yl)carbamate as a white solid. Y=4%. $^1$H NMR (400 MHz, chloroform-d) δ 6.96 (s, 1H), 6.04 (s, 1H), 2.38 (s, 3H), 2.23 (s, 3H), 1.51 (s, 9H).

Step 3: 2,5-Dimethylthiophen-3-amine Hydrochloride

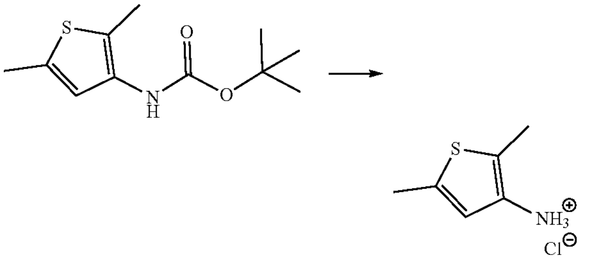

A solution of tert-butyl N-(2,5-dimethylthiophen-3-yl) carbamate (50 mg, 0.22 mmol) in 4 M HCl in EtOAc (4 ml) was stirred at rt for 1 h. The solution was concentrated under reduced pressure to give 2,5-dimethylthiophen-3-amine hydrochloride. LCMS (ESI): m/z: $[M+H]^+$=128.1

Step 4: 3-Isocyanato-2,5-dimethylthiophene

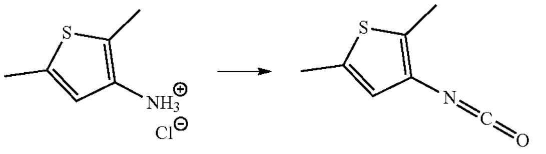

To a solution of 2,5-dimethylthiophen-3-amine hydrochloride (50 mg, 0.31 mmol) in dioxane (1.5 ml) heated to 40° C. was added dropwise trichloromethyl carbonochloridate (37 μl, 0.31 mmol). The solution was heated at 70° C. for 3 h. The solution was concentrated under reduced pressure to give 3-isocyanato-2,5-dimethylthiophene as a white solid. This was used directly without purification. LCMS in methanol (ESI): m/z: $[M+MeOH+H]^+$=186.2.

Intermediate 5. 3-Isocyanato-2-methyl-1-benzothiophene

Step 1. 2-Methyl-1-benzothiophen-3-amine

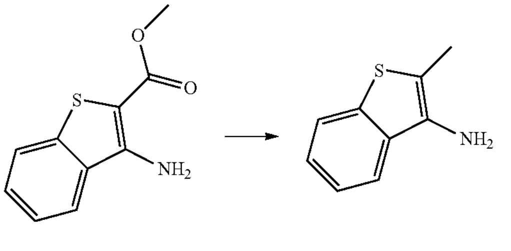

To a solution of lithium aluminium hydride (121 mg, 3.18 mmol) in THF (2 ml) cooled to 0° C. was added dropwise a solution of methyl 3-aminobenzothiophene-2-carboxylate (300 mg, 1.45 mmol) in THF (2 ml). The solution was stirred at 0° C. under nitrogen for 30 min, then heated at 80° C. for 2 h. The reaction was cooled, then quenched with water (0.12 ml), followed by 15% aq. NaOH (0.12 ml). The mixture was filtered and the filtrate concentrated under reduced pressure to give 2-methyl-1-benzothiophen-3-amine as a yellow solid. Y=97%. $^1$H NMR (400 MHz, chloroform-d) δ 7.70 (d, J=8 Hz, 1H), 7.49 (d, J=8 Hz, 1H), 7.36-7.31 (m, 1H), 7.29-7.24 (m, 1H), 3.55 (s, 2H), 2.37 (s, 3H).

Step 2. 3-Isocyanato-2-methyl-1-benzothiophene

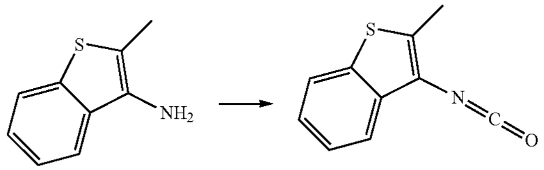

To a solution of 2-methylbenzothiophen-3-amine (100 mg, 0.61 mmol) in dioxane (3 ml) heated to 40° C. was added dropwise a solution of triphosgene (89 μl, 0.74 mmol) in dioxane (3 ml). The solution was heated at 70° C. for 1 h. The solution was concentrated under reduced pressure to give 3-isocyanato-2-methyl-1-benzothiophene as a yellow solid. LCMS in methanol (ESI): m/z: $[M+CH_3OH+H]^+$ =222.1

Intermediate 6. 2,5-Diethyl-3-isocyanatothiophene

Step 1. Tert-butyl N-(2,5-dibromothiophen-3-yl)carbamate

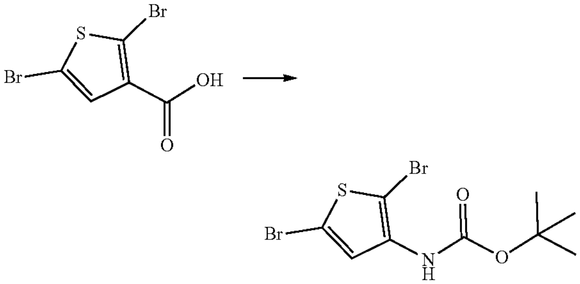

To a solution of 2,5-dibromothiophene-3-carboxylic acid (3.0 g, 10.5 mmol) in tert-butanol (30 ml) was added DPPA (2.27 ml, 10.5 mmol) and DIPEA (2.74 ml, 15.7 mmol). The RM was heated at 90° C. for 1 h. The reaction was concentrated under reduced pressure to give a residue. The residue was purified by flash column chromatography (silica, 9-100% EtOAc in petroleum ether) to give tert-butyl N-(2,5-dibromothiophen-3-yl)carbamate as a yellow solid. Y=29%. $^1$H NMR (400 MHz, chloroform-d) δ 7.65 (s, 1H), 6.54 (s, 1H), 1.53 (s, 9H).

Step 2. Tert-butyl N-(2,5-diethenylthiophen-3-yl)carbamate

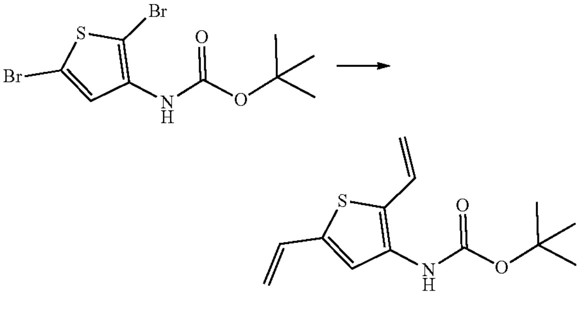

To a solution of tert-butyl N-(2,5-dibromo-3-thienyl)carbamate (350 mg, 0.98 mmol) and potassium ethenyltrifluoroboranuide (1.31 g, 9.80 mmol) in THF (6.3 ml) and $H_2O$ (0.7 ml) under $N_2$ were added $Cs_2CO_3$ (958 mg, 2.94 mmol), triphenylphosphine (15 mg, 59 μmol) and $PdCl_2$ (3.5 mg, 20 μmol). The mixture was stirred at 85° C. for 12 h. The reaction was diluted with EtOAc (10 ml) and water (3 ml), the resulting mixture was separated and the organic phase was concentrated under reduced pressure to give a residue. The residue was purified by prep-TLC (20% EtOAc in petroleum ether) to give tert-butyl N-(2,5-diethenylthiophen-3-yl)carbamate as a yellow solid. Y=73%. $^1$H NMR (400 MHz, chloroform-d) δ 7.32 (s, 1H), 6.73-6.62 (m, 2H), 6.36 (s, 1H), 5.58-5.43 (m, 2H), 5.18-5.12 (m, 2H), 1.52 (s, 9H).

Step 3. Tert-butyl N-(2,5-diethylthiophen-3-yl)carbamate

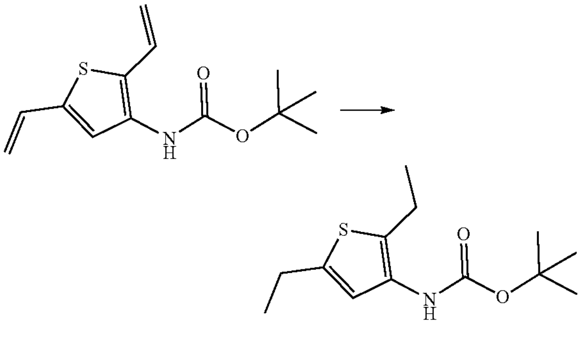

To a solution of tert-butyl N-(2,5-diethenylthiophen-3-yl) carbamate (180 mg, 0.72 mmol) in methanol (1 ml) was added 10% Pd on Carbon (50 mg, 50% in water). The solution was stirred at rt under hydrogen atmosphere at 15 psi for 10 min. The reaction was diluted with EtOAc (3 ml) and water (2 ml), the resulting mixture separated and the organic phase concentrated under reduced pressure to give a residue. The residue was purified by prep-TLC (17% EtOAc in petroleum ether) to give tert-butyl N-(2,5-diethylthiophen-3-yl)carbamate as a yellow oil. Y=71%. $^1$H NMR (400 MHz, chloroform-d) δ 7.01 (s, 1H), 6.05 (s, 1H), 2.79-2.60 (m, 4H), 1.51 (s, 9H), 1.30-1.22 (m, 6H).

Step 4. 2,5-Diethylthiophen-3-amine Hydrochloride

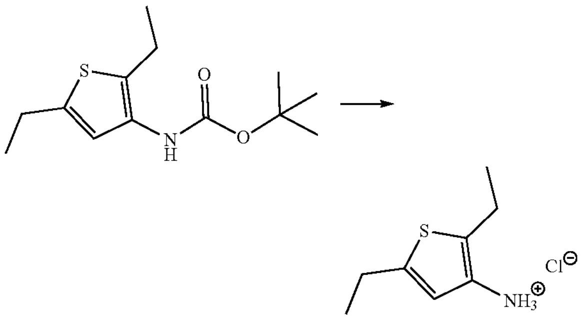

A solution of tert-butyl N-(2,5-diethylthiophen-3-yl)carbamate (130 mg, 0.51 mmol) in 4 M HCl in EtOAc (2 ml, 8.0 mmol) was stirred at rt for 2 h. The solution was concentrated under reduced pressure to give 2,5-diethylthiophen-3-amine hydrochloride as a red solid. This was used directly without purification. LCMS (ESI): m/z: $[M+H]^+$=156.3

Step 5. 2,5-Diethyl-3-isocyanatothiophene

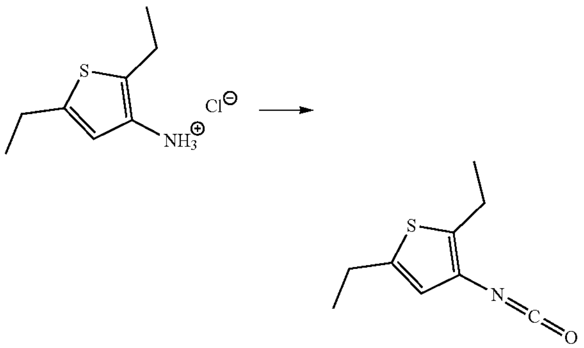

To a solution of 2,5-diethylthiophen-3-amine hydrochloride (100 mg 0.64 mmol) in dioxane (10 ml) heated to 40° C. was added trichloromethyl carbonochloridate (85 µl, 0.71 mmol). The mixture was heated at 70° C. for 1 h. The solution was concentrated under reduced pressure to give 2,5-diethyl-3-isocyanatothiophene as an oil. This was used directly without purification. LCMS in methanol (ESI): m/z: $[M+MeOH+H]^+$=214.2

Intermediate 7. 2,5-Dichloro-3-isocyanatothiophene

Step 1. Tert-butyl N-(2,5-dichlorothiophen-3-yl)carbamate

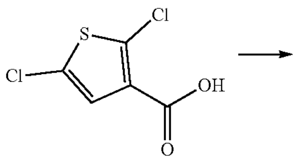

-continued

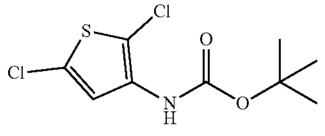

To a solution of 2,5-dichlorothiophene-3-carboxylic acid (500 mg, 2.54 mmol) in tert-butanol (10 ml) was added DPPA (0.55 ml, 2.54 mmol) and DIPEA (0.66 ml, 3.81 mmol). The mixture was heated at 90° C. for 12 h. The solution was concentrated under vacuum. The residue was purified by prep-TLC (petroleum ether), to give tert-butyl N-(2,5-dichlorothiophen-3-yl)carbamate as a white solid. Y=56%. $^1$H NMR (400 MHz, chloroform-d) δ 7.50 (s, 1H), 6.52 (s, 1H), 1.52 (s, 9H).

Step 2. 2,5-Dichlorothiophen-3-amine Hydrochloride

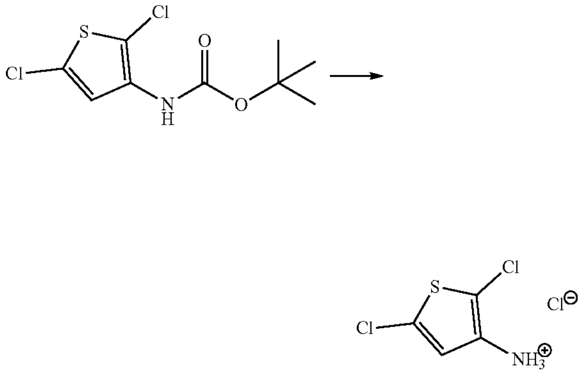

A mixture of tert-butyl N-(2,5-dichlorothiophen-3-yl)carbamate (190 mg, 0.71 mmol) in 4 M HCl in EtOAc (20 ml) was stirred at rt for 30 min. The solution was concentrated under vacuum to give 2,5-dichlorothiophen-3-amine hydrochloride as a yellow solid. This was used directly without purification.

Step 3. 2,5-Dichloro-3-isocyanatothiophene

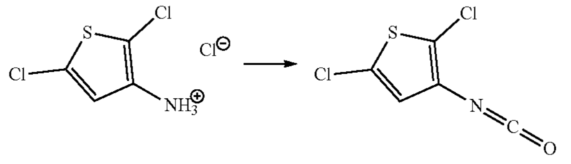 [SMILES: [NH3+]c1cc(Cl)sc1Cl ; [Cl-] ; O=C=Nc1cc(Cl)sc1Cl]

To a solution of 2,5-dichlorothiophen-3-amine hydrochloride (120 mg, 0.59 mmol) in dioxane (3 ml) heated to 40° C. was added trichloromethyl carbonochloridate (95 µl, 0.79 mmol). The mixture was heated at 70° C. for 0.5 h. The solution was concentrated under vacuum to give 2,5-dichloro-3-isocyanatothiophene as a yellow solid. This was used directly without purification. LCMS (ESI): m/z: $[M+MeOH+H]^+$226.0

Intermediate 8. 3-Isocyanato-2,5-bis(propan-2-yl)thiophene

Step 1. Tert-butyl N-(2,5-dibromothiophen-3-yl)carbamate

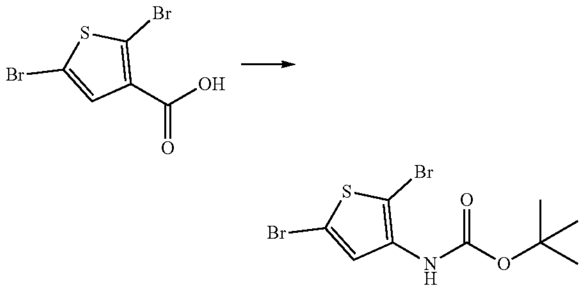

To a solution of 2,5-dibromothiophene-3-carboxylic acid (3.0 g, 10.5 mmol) in tert-butanol (30 ml) was added DPPA (2.27 ml, 10.5 mmol) and DIPEA (2.74 ml, 15.7 mmol). The RM was heated at 90° C. for 1 h. The reaction was concentrated under reduced pressure to give a residue. The residue was purified by flash column chromatography (silica, 9-100% EtOAc in petroleum ether) to give tert-butyl N-(2,5-dibromothiophen-3-yl)carbamate as a yellow solid. Y=29%. $^{1}H$ NMR (400 MHz, chloroform-d) δ 7.65 (s, 1H), 6.54 (s, 1H), 1.53 (s, 9H).

Step 2. Tert-butyl N-[2,5-bis(prop-1-en-2-yl)thiophen-3-yl]carbamate

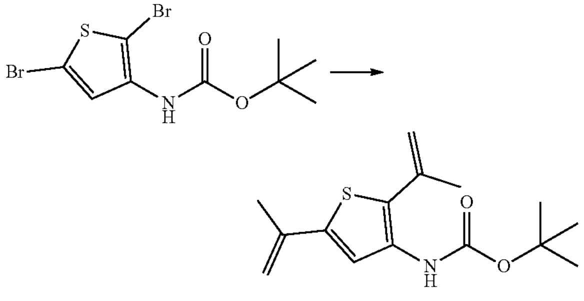

To a solution of tert-butyl N-(2,5-dibromothiophen-3-yl) carbamate (400 mg, 1.12 mmol) and 2-isopropenyl-4,4,5,5-tetramethyl-1,3,2-dioxaborolane (0.94 g, 5.60 mmol) in THF (8 ml) and $H_2O$ (1.6 ml) under nitrogen were added $Pd(PPh_3)_4$ (13 mg, 11.2 μmol) and $Na_2CO_3$ (356 mg, 3.36 mmol). The mixture was stirred at 90° C. for 12 h under $N_2$. The reaction was cooled, diluted with EtOAc (10 ml) and water (5 ml), and the organic phase was collected and concentrated under reduced pressure to give a residue. The residue was purified by prep-TLC (5:1 petroleum ether/EtOAc) to give tert-butyl N-[2,5-bis(prop-1-en-2-yl)thiophen-3-yl]carbamate as a yellow oil. Y=58%. $^{1}H$ NMR (400 MHz, chloroform-d) δ 7.58-7.50 (br. s, 1H), 6.73-6.65 (br. s, 1H), 5.34 (s, 1H), 5.29-5.24 (m, 1H), 5.18 (s, 1H), 4.94 (s, 1H), 2.12 (d, J=11 Hz, 6H), 1.52 (s, 9H)

Step 3. Tert-butyl N-[2,5-bis(propan-2-yl)thiophen-3-yl]carbamate

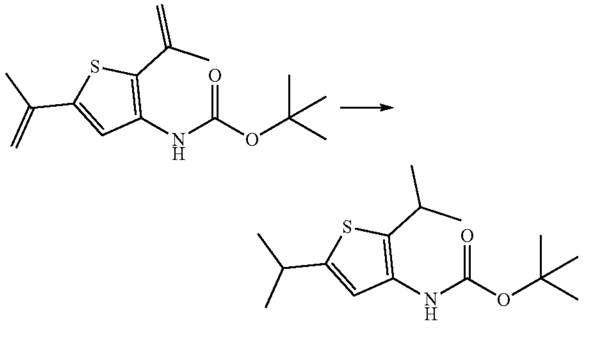

To a solution of tert-butyl N-[2,5-bis(prop-1-en-2-yl)thiophen-3-yl]carbamate (90 mg, 0.32 mmol) in MeOH (1 ml) was added 10% Pd/C (50% in water, 90 mg). The reaction was stirred at rt under $H_2$ (15 psi) for 10 min. The reaction was filtered and the filtrate concentrated under reduced pressure to give tert-butyl N-[2,5-bis(propan-2-yl)thiophen-3-yl]carbamate as a yellow oil. Y=99%. $^{1}H$ NMR (400 MHz, chloroform-d) δ 7.06-7.00 (br. s, 1H), 6.10-6.04 (br. s, 1H), 3.12-3.02 (m, 2H), 1.51 (s, 9H), 1.31-1.24 (m, 12H).

Step 4. 2,5-Bis(propan-2-yl)thiophen-3-amine Hydrochloride

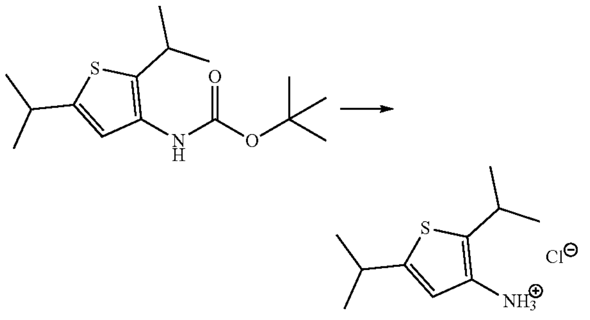

The solution of tert-butyl N-[2,5-bis(propan-2-yl)thiophen-3-yl]carbamate (100 mg, 0.35 mmol) in 4 M HCl in EtOAc (1.5 ml) was stirred at rt for 0.5 h. The solution was concentrated under reduced pressure to give 2,5-bis(propan-2-yl)thiophen-3-amine hydrochloride as a red solid. This was used directly without purification.

Step 5. 3-Isocyanato-2,5-bis(propan-2-yl)thiophene

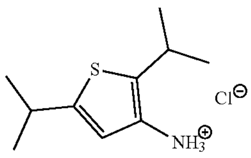

-continued

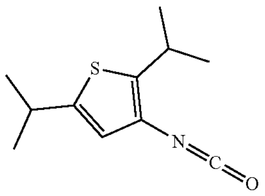

To a solution of 2,5-bis(propan-2-yl)thiophen-3-amine hydrochloride (80 mg, 0.36 mmol) in dioxane (3 ml) warmed to 40° C. was added trichloromethyl carbonochloridate (48 μl, 0.40 mmol). The mixture was stirred at 70° C. for 0.5 h. The solution was cooled and concentrated under reduced pressure to give 3-isocyanato-2,5-bis(propan-2-yl)thiophene as an oil. This was used directly without purification. LCMS in MeOH (ESI): m/z: $[M+CH_3OH+H]^+$=242.1

Intermediate 9. 2,4-Diethyl-3-isocyanatothiophene

Step 1. Tert-butyl N-(4-bromothiophen-3-yl)carbamate

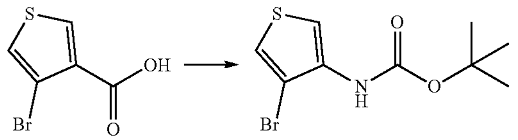

To a solution of 4-bromothiophene-3-carboxylic acid (0.50 g, 2.41 mmol) in tert-butanol (20 ml) was added DPPA (523 μl, 2.41 mmol) and DIPEA (631 μl, 3.62 mmol). The mixture was stirred at 90° C. for 12 h. The solution was cooled and concentrated under vacuum and the resulting residue purified by flash chromatography (silica, 10:1 petroleum ether/EtOAc) to give tert-butyl N-(4-bromothiophen-3-yl)carbamate as a colourless oil. Y=82%. $^1H$ NMR (400 MHz, DMSO-$d_6$) δ 8.51 (s, 1H), 7.64 (d, J=3 Hz, 1H), 7.41 (d, J=3 Hz, 1H), 1.45 (s, 9H).

Step 2. Tert-butyl N-(2,4-dibromothiophen-3-yl)carbamate

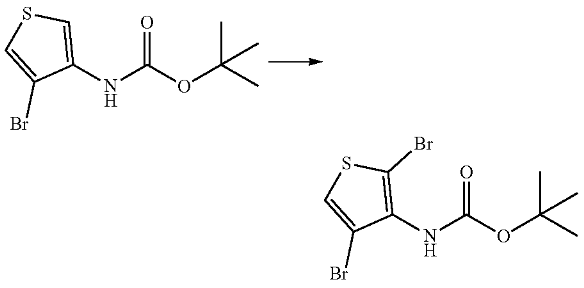

To a solution of tert-butyl N-(4-bromothiophen-3-yl)carbamate (1.1 g, 3.95 mmol) in THF (15 ml) cooled to 0° C. was added NBS (845 mg, 4.75 mmol). The mixture was stirred at rt for 2 h. The solution was concentrated under vacuum and the resulting residue was purified by prep-TLC (10:1 petroleum ether/EtOAc) to give tert-butyl N-(2,4-dibromothiophen-3-yl)carbamate as a colourless oil. Y=64%. LCMS (ESI): m/z: $[M-H]^-$=353.7

Step 3. Tert-butyl N-(2,4-diethenylthiophen-3-yl)carbamate

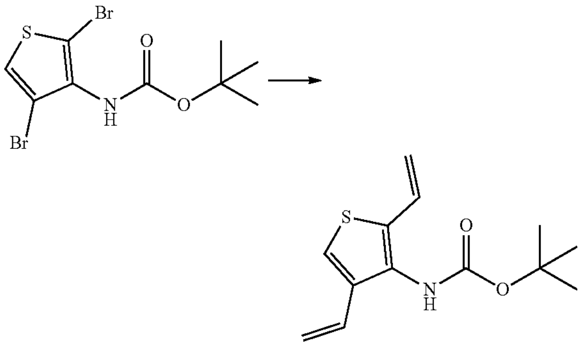

To a solution of tert-butyl N-(2,4-dibromothiophen-3-yl) carbamate (900 mg, 2.52 mmol) in THF (9 ml) and $H_2O$ (1 ml) under nitrogen was added potassium ethenyltrifluoroboranuide (3.38 g, 25.2 mmol), $Cs_2CO_3$ (2.46 g, 7.56 mmol), $PdCl_2$ (9 mg, 50 μmol) and triphenylphosphine (40 mg, 0.15 mmol). The mixture was heated at 85° C. for 12 h. The solution was cooled and concentrated under vacuum. The residue was purified by prep-TLC (10:1 petroleum ether/EtOAc) to give tert-butyl N-(2,4-diethenylthiophen-3-yl) carbamate as a yellow solid. Y=39%. $^1H$ NMR (400 MHz, DMSO-$d_6$) δ 8.71-8.61 (br. s, 1H), 7.54 (s, 1H), 6.75-6.63 (m, 1H), 6.46-6.38 (m, 1H), 5.66 (d, J=17 Hz, 1H), 5.47 (d, J=18 Hz, 1H), 5.22-5.14 (m, 2H), 1.42 (s, 9H).

Step 4 Tert-butyl N-(2,4-diethylthiophen-3-yl)carbamate

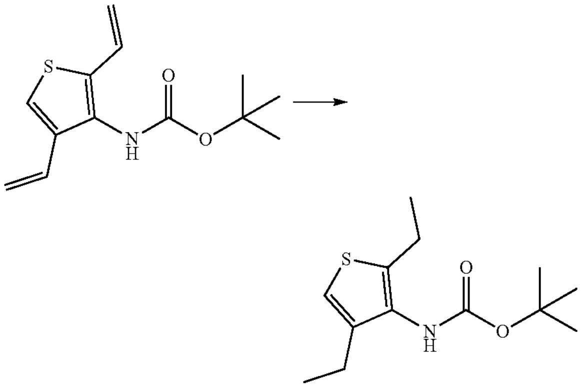

To a solution of tert-butyl N-(2,4-diethenylthiophen-3-yl) carbamate (100 mg, 0.40 mmol) in MeOH (8 ml) was added 10% Pd on carbon (50% in water, 60 mg). The reaction was stirred at rt under $H_2$ (15 psi) for 30 min. The solution was filtered and the filtrate was concentrated under vacuum to give tert-butyl N-(2,4-diethylthiophen-3-yl)carbamate as a yellow oil. This was used directly without purification.

Step 5. 2,4-Diethylthiophen-3-amine Hydrochloride

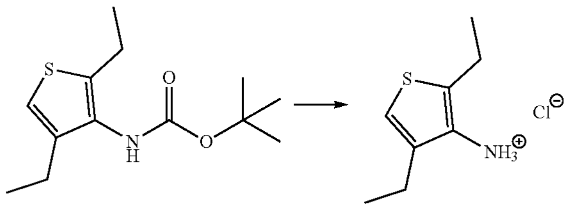

A solution of tert-butyl N-(2,4-diethylthiophen-3-yl)carbamate (80 mg, 0.31 mmol) in 4 M HCl in EtOAc (20 ml) was stirred at rt for 15 min. The solution was concentrated under vacuum to give 2,4-diethylthiophen-3-amine hydrochloride as a white solid. This was used directly without purification.

Step 6. 2,4-Diethyl-3-isocyanatothiophene

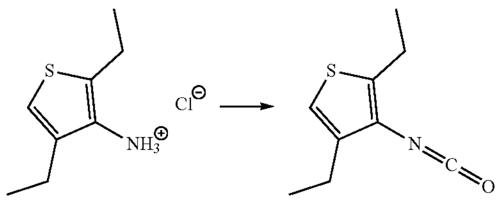

To a solution of 2,4-diethylthiophen-3-amine hydrochloride (80 mg, 0.42 mmol) in dioxane (3 ml) warmed to 40° C. was added trichloromethyl carbonochloridate (62 μl, 0.52 mmol). The mixture was stirred at 70° C. for 1 h. The solution was cooled and concentrated under vacuum to give 2,4-diethyl-3-isocyanatothiophene as a liquid. LCMS in MeOH (ESI): m/z: $[M+MeOH+H]^+$=214.0.

Intermediate 10. 2-Isocyanato-3,5-dimethylthiophene

Step 1. 3,5-Dimethylthiophen-2-amine

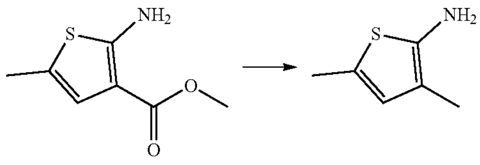

To a solution of methyl 2-amino-5-methyl-thiophene-3-carboxylate (300 mg, 1.75 mmol) in THF (5 ml) cooled to 0° C. was added lithium aluminium hydride (200 mg, 5.3 mmol). The RM was stirred at 80° C. for 3 h. The reaction was quenched with ice-water (0.2 ml), stirred for 20 min and then treated with 10% aqueous NaOH (0.2 ml). The mixture was filtered through Celite and the filtrate concentrated under vacuum to give 3,5-dimethylthiophen-2-amine as a yellow liquid. This was used directly without purification. LCMS (ESI): m/z: $[M+H]^+$=128.2.

Step 2. 2-Isocyanato-3,5-dimethylthiophene

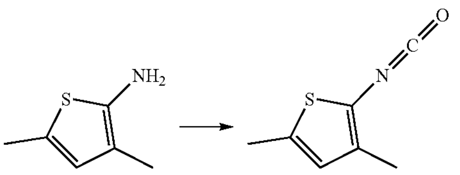

To a solution of 3,5-dimethylthiophen-2-amine (140 mg, 1.10 mmol) in dioxane (5 ml) warmed to 40° C. was added trichloromethyl carbonochloridate (146 μl, 1.21 mmol). The mixture was stirred at 70° C. for 1 h. The solution was concentrated under vacuum to give 2-isocyanato-3,5-dimethylthiophene as a yellow oil. This was used directly without purification. LCMS in MeOH (ESI): m/z: $[M+MeOH+H]^+$=186.0.

Intermediate 11. 3-Isocyanato-2,4,5-trimethylthiophene

Step 1. Tert-butyl N-(2,4-dimethylthiophen-3-yl)carbamate

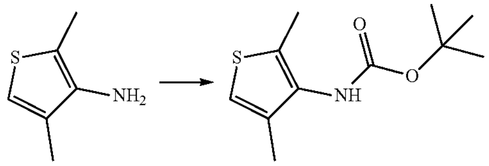

To a solution of 2,4-dimethylthiophen-3-amine (200 mg, 1.57 mmol) [for synthesis refer to Intermediate 3] in DCM (5 ml) was added di-tert-butyl dicarbonate (433 μl, 1.89 mmol) and TEA (438 μl, 3.14 mmol). The RM was stirred at rt for 12 h, then concentrated under vacuum. The resulting residue was purified by silica gel chromatography (25% EtOAc in petroleum ether) to give tert-butyl N-(2,4-dimethylthiophen-3-yl)carbamate as a yellow oil. Y=36%. $^1$H NMR (400 MHz, chloroform-d) δ 6.67 (s, 1H), 5.79-5.69 (br. s, 1H), 2.33 (s, 3H), 2.10 (s, 3H), 1.50 (s, 9H).

Step 2. Tert-butyl N-(5-bromo-2,4-dimethylthiophen-3-yl)carbamate

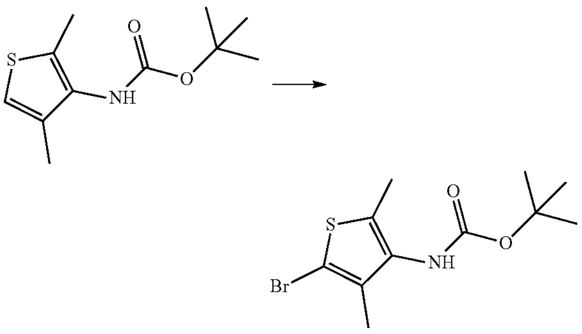

To a solution of tert-butyl N-(2,4-dimethylthiophen-3-yl) carbamate (65 mg, 0.29 mmol) in THF (3 ml) cooled to 0° C. was added NBS (61 mg, 0.34 mmol). The solution was stirred at 0° C. for 2 h, then concentrated under vacuum. The residue was purified by silica gel chromatography (25% EtOAc in petroleum ether) to give tert-butyl N-(5-bromo-2,4-dimethylthiophen-3-yl)carbamate as a yellow oil. Y=80%. $^{1}$H NMR (400 MHz, chloroform-d) δ 5.79-5.71 (br. s, 1H), 2.27 (s, 3H), 2.04 (s, 3H), 1.49 (s, 9H).

Step 3. Tert-butyl N-(2,4,5-trimethylthiophen-3-yl)carbamate

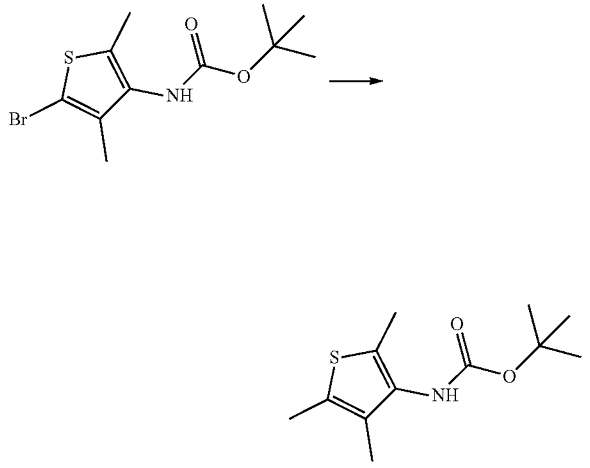

To a solution of tert-butyl N-(5-bromo-2,4-dimethylthiophen-3-yl)carbamate (70 mg, 0.23 mmol) in dioxane (3 ml) and water (1 ml) was added methylboronic acid (37 mg, 0.62 mmol), $Pd(PPh_3)_4$ (26 mg, 0.023 mmol) and $Cs_2CO_3$ (223 mg, 0.69 mmol) at rt under $N_2$. The mixture was stirred at 90° C. for 18 h. The solution was cooled and concentrated under vacuum and the resulting residue purified by prep-TLC (10:1 petroleum ether/EtOAc) to give tert-butyl N-(2,4,5-trimethylthiophen-3-yl)carbamate as a white solid. $^{1}$H NMR (400 MHz, chloroform-d) δ 5.79-5.69 (br. s, 1H), 2.33 (s, 3H), 2.10 (s, 3H), 1.56 (s, 9H).

Step 4. Trimethylthiophen-3-amine Hydrochloride

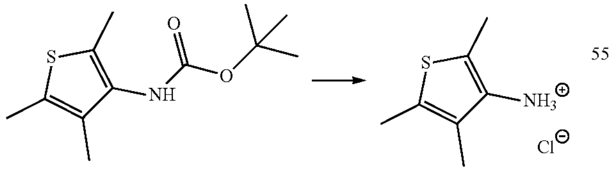

A mixture of tert-butyl N-(2,4,5-trimethylthiophen-3-yl) carbamate (140 mg, 0.58 mmol) in 4 M HCl in EtOAc (10 ml) was stirred at rt for 1 h. The solution was concentrated under vacuum to give trimethylthiophen-3-amine hydrochloride as a yellow gum. This was used directly without purification.

Step 5. 3-Isocyanato-2,4,5-trimethylthiophene

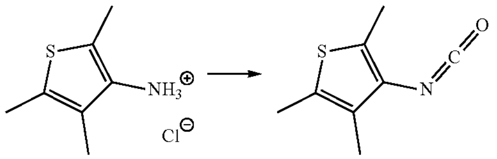

To a mixture of trimethylthiophen-3-amine hydrochloride (140 mg, 0.79 mmol) in dioxane (3 ml) warmed to 40° C. was added dropwise trichloromethyl carbonochloridate (132 μl, 1.09 mmol). The mixture was stirred at 70° C. for 1 h. The solution was cooled and concentrated under vacuum to give 3-isocyanato-2,4,5-trimethylthiophene as an oil. LCMS (ESI): m/z: $[M+MeOH+H]^{+}$=200.1

Intermediate 12. 3-Isocyanato-2,4-bis(propan-2-yl)thiophene

Step 1. Tert-butyl N-[2,4-bis(prop-1-en-2-yl)thiophen-3-yl]carbamate

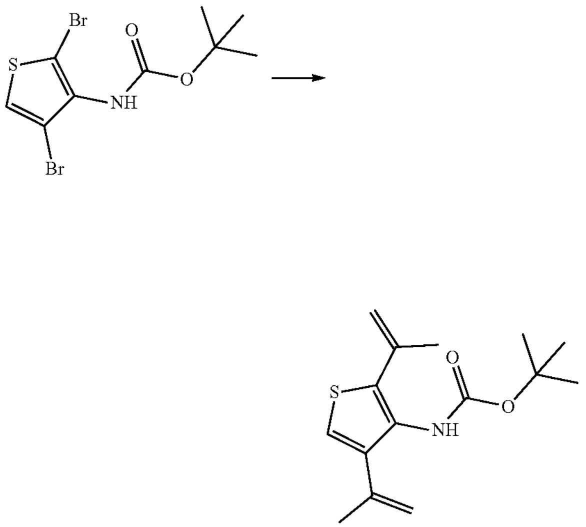

To a solution of tert-butyl N-(2,4-dibromothiophen-3-yl) carbamate (1.0 g, 2.80 mmol) [for synthesis refer to Intermediate 9] in THF (20 ml) and $H_2O$ (10 ml) were added $Pd(PPh_3)_4$ (32 mg, 28 μmol), $Na_2CO_3$ (0.89 g, 8.40 mmol) and 2-isopropenyl-4,4,5,5-tetramethyl-1,3,2-dioxaborolane (2.35 g, 14.0 mmol). The solution was stirred at 90° C. for 12 h. The solution was cooled and concentrated under reduced pressure. The residue was purified by flash column chromatography (silica, 0-17% EtOAc in petroleum ether) to give tert-butyl N-[2,4-bis(prop-1-en-2-yl)thiophen-3-yl] carbamate as a white solid. LCMS (ESI): m/z: $[M-56+H]^{+}$=224.1

Step 2. Tert-butyl N-[2,4-bis(propan-2-yl)thiophen-3-yl]carbamate

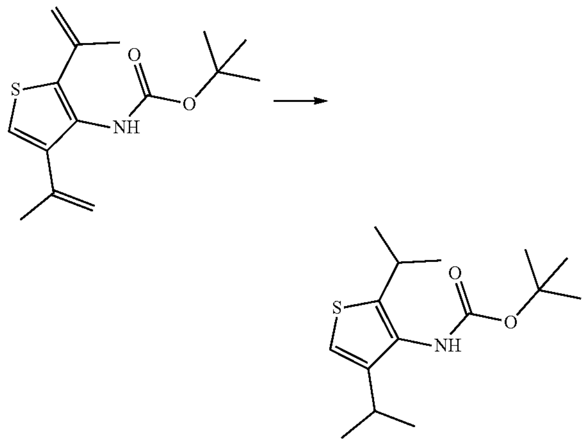

To a solution of tert-butyl N-[2,4-bis(prop-1-en-2-yl)thiophen-3-yl]carbamate (300 mg, 1.07 mmol) in MeOH (6 ml) was added 10% Pd/C (50% water, 100 mg). The solution was stirred at rt under $H_2$ (15 psi) for 10 min. The solution was concentrated under reduced pressure to give tert-butyl N-[2,4-bis(propan-2-yl)thiophen-3-yl]carbamate as a white solid. This was used directly without purification. LCMS (ESI): m/z: $[M-56+H]^+=228.1$ Step 3. 2,4-Bis(propan-2-yl)thiophen-3-amine Hydrochloride

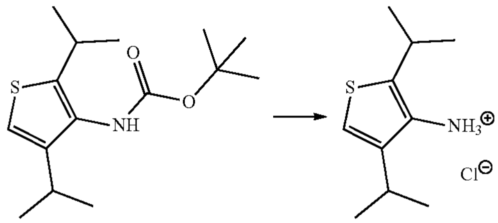 [SMILES: CC(C)c1csc(C(C)C)c1NC(=O)OC(C)(C)C ; CC(C)c1csc(C(C)C)c1[NH3+] ; [Cl-]]

A solution of tert-butyl N-[2,4-bis(propan-2-yl)thiophen-3-yl]carbamate (180 mg, 0.64 mmol) in 4 M HCl in EtOAc (3 ml) was stirred at rt for 30 min. The solution was concentrated under reduced pressure to give 2,4-bis(propan-2-yl)thiophen-3-amine hydrochloride as a white solid. This was used directly without purification. LCMS (ESI): m/z: $[M+H]^+=184.2$ Step 4. 3-Isocyanato-2,4-bis(propan-2-yl)thiophene

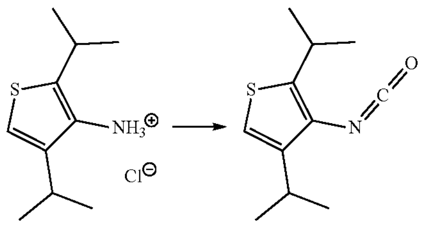

To a solution of 2,4-bis(propan-2-yl)thiophen-3-amine hydrochloride (116 mg, 0.53 mmol) in dioxane (3 ml) warmed to 40° C. was added trichloromethyl carbonochloridate (92 μl, 0.76 mmol). The solution was stirred at 70° C. for 1 h. The solution was concentrated under reduced pressure to give 3-isocyanato-2,4-bis(propan-2-yl)thiophene as a white solid. This was used directly without purification. LCMS (ESI): m/z: $[M+MeOH+H]^+=242.2$ Intermediate 13. 2-Isocyanato-3,4-dimethylthiophene Step 1. 3,4-Dimethylthiophen-2-amine

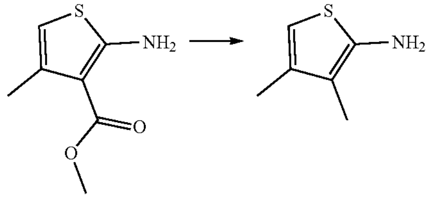

To a solution of lithium aluminium hydride (122 mg, 3.21 mmol) in THF (10 ml) cooled to 0° C. was added dropwise a solution of methyl 2-amino-4-methyl-thiophene-3-carboxylate (250 mg, 1.46 mmol) in THF (10 ml). The solution was stirred at 0° C. for 30 min, then heated at 75° C. for 2 h. The reaction was cooled and quenched by addition of water (0.12 ml), followed by 15% aq. NaOH (0.12 ml). The resulting mixture was filtered and the filtrate concentrated under reduced pressure to give 3,4-dimethylthiophen-2-amine as a yellow oil. This was used directly without purification. $^1H$ NMR (400 MHz, chloroform-d) δ 6.19 (s, 1H), 2.08 (s, 3H), 1.96 (s, 3H).

Step 2. 2-Isocyanato-3,4-dimethylthiophene

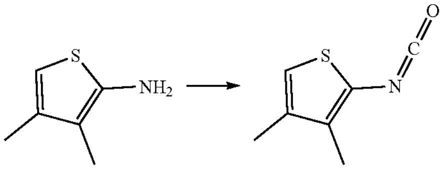

To a solution of 3,4-dimethylthiophen-2-amine (200 mg, 1.57 mmol) in dioxane (6 ml) warmed to 40° C. was added trichloromethyl carbonochloridate (209 μl, 1.73 mmol). The mixture was stirred at 70° C. for 0.5 h, then concentrated under reduced pressure to give 2-isocyanato-3,4-dimethylthiophene as a red oil. This was used directly without purification. LCMS in MeOH (ESI): m/z: $[M+CH_3OH+H]^+=186.1$ Intermediate 14. (3S,5R)-3-Fluoro-1-methyl-5-[(1-methyl-1H-pyrazol-4-yl)(sulfamoyl)amino]-piperidin-1-ium Trifluoroacetate Step 1. Tert-butyl (3S,5R)-3-fluoro-5-[(1-methyl-1H-pyrazol-4-yl)amino]piperidine-1-carboxylate

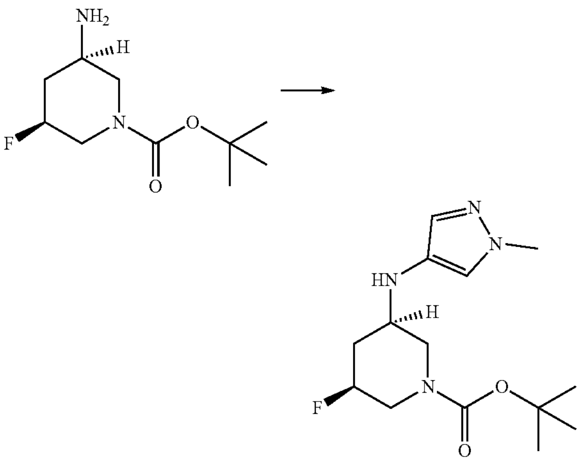

To a solution of tert-butyl (3R,5S)-3-amino-5-fluoro-piperidine-1-carboxylate (200 mg, 0.92 mmol) in toluene (3 ml) was added 4-iodo-1-methyl-pyrazole (229 mg, 1.10 mmol), [2-(2-aminoethyl)phenyl]-chloro-palladium; ditert-butyl-[2-(2,4,6-triisopropylphenyl)phenyl]-phosphane (63 mg, 92 μmol) and sodium tert-butoxide (176 mg, 1.83 mmol) and the reaction was stirred under $N_2$ atmosphere at 100° C. for 4 h. The mixture was filtered and concentrated in vacuo. The residue was purified by silica gel chromatography (0-100% EtOAc in petrol) to give the title compound as an oil. Y=91%.

Step 2. Tert-butyl (3S,5R)-3-fluoro-5-[2,2,2-trifluoro-N-(1-methyl-1H-pyrazol-4-yl)acetamido]piperidine-1-carboxylate

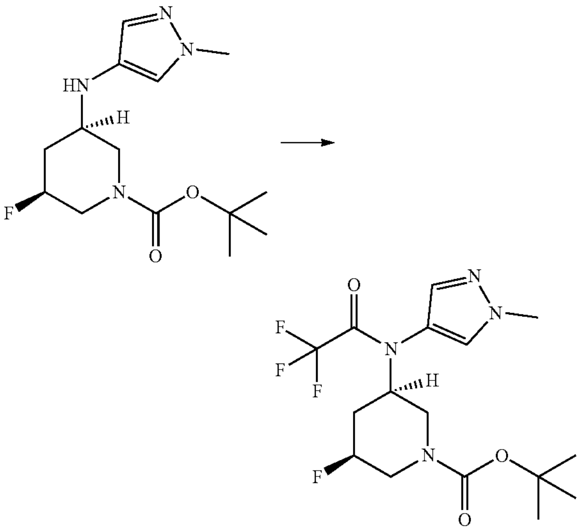

To a solution of tert-butyl (3S,5R)-3-fluoro-5-[(1-methylpyrazol-4-yl)amino]piperidine-1-carboxylate (170 mg, 0.57 mmol) in DCM (3 ml) was added triflic anhydride (119 μl, 0.85 mmol) and $Et_3N$ (159 μl, 1.14 mmol), then the mixture was stirred under $N_2$ atmosphere at rt for 4 h. The mixture was diluted with water (5 ml) and extracted with DCM (3×5 ml). The combined organic phase was washed with brine (2×3 ml), dried with anhydrous $Na_2SO_4$, filtered and concentrated under vacuum to give the title compound as an oil. Y=98%. LCMS (ESI): m/z: $[M+H]^+$=395.2.

Step 3. (3S,5R)-3-Fluoro-5-[2,2,2-trifluoro-N-(1-methyl-1H-pyrazol-4-yl)acetamido]-piperidin-1-ium Trifluoroacetate

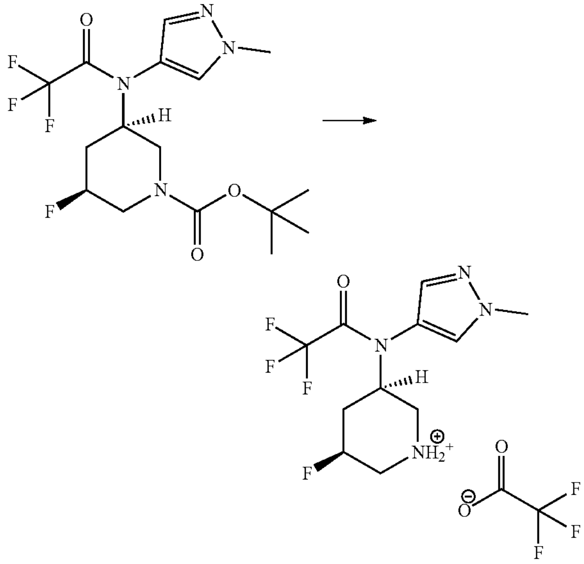

To a solution of tert-butyl (3S,5R)-3-fluoro-5-[(1-methylpyrazol-4-yl)-(2,2,2-trifluoroacetyl)amino]piperidine-1-carboxylate (200 mg, 0.51 mmol) in DCM (2.5 ml) was added TFA (488 μl, 6.59 mmol). The RM was stirred under $N_2$ at rt for 1.5 h. The mixture was concentrated under vacuum to give the title compound as an oil. LCMS (ESI): m/z: $[M+H]^+$=295.1.

Step 4. 2,2,2-Trifluoro-N-[(3R,5S)-5-fluoro-1-methylpiperidin-3-yl]-N-(1-methyl-1H-pyrazol-4-yl)acetamide

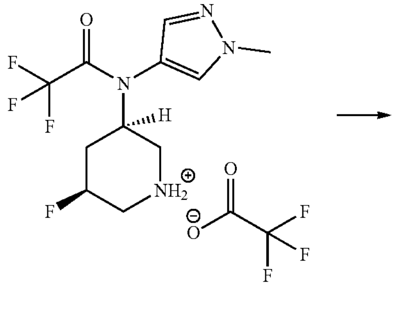

-continued

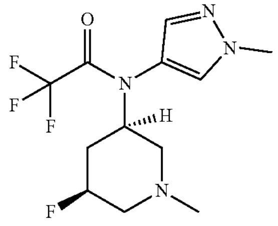

To a solution of 2,2,2-trifluoro-N-[(3R,5S)-5-fluoro-3-piperidyl]-N-(1-methylpyrazol-4-yl)acetamide trifluoroacetate (200 mg, 0.49 mmol) in MeOH (3 ml) was added $NaBH_3CN$ (92 mg, 1.47 mmol) and formaldehyde (37% wt. in water, 146 µl, 1.96 mmol). The reaction was stirred under $N_2$ at rt for 3 h. The mixture was concentrated under vacuum to give the title compound as an oil. LCMS (ESI): m/z: $[M+H]^+$=309.2.

Step 5. (3R,5S)-5-Fluoro-1-methyl-N-(1-methyl-1H-pyrazol-4-yl)piperidin-3-amine

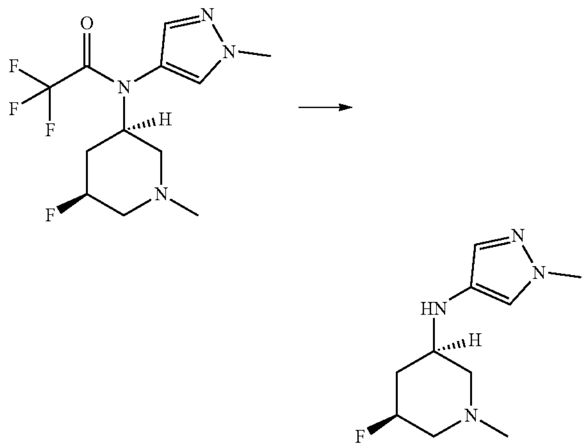

To a solution of 2,2,2-trifluoro-N-[(3R,5S)-5-fluoro-1-methyl-3-piperidyl]-N-(1-methylpyrazol-4-yl)acetamide (150 mg, 0.49 mmol) in MeOH (2 ml) was added a solution of NaOH (58 mg, 1.46 mmol) in $H_2O$ (0.7 ml). The RM was stirred under $N_2$ at rt for 2 h. The mixture was concentrated under vacuum and the resulting residue purified by silica gel chromatography (0-100% methanol in EtOAc) to give the title compound as an oil.

Step 6. (3R,5S)-3-[({[(Tert-butoxy)carbonyl]amino}sulfonyl)(1-methyl-1H-pyrazol-4-yl)amino]-5-fluoro-1-methylpiperidin-1-ium Trifluoroacetate

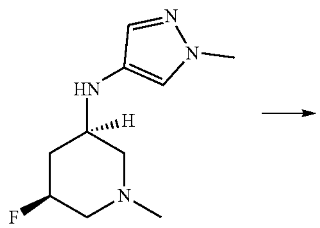

-continued

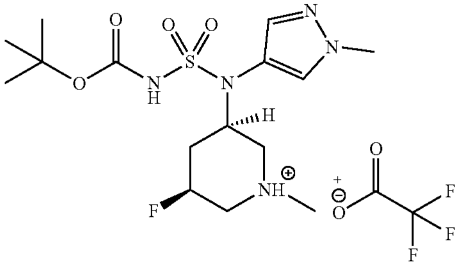

To a solution of (3R,5S)-5-fluoro-1-methyl-N-(1-methylpyrazol-4-yl)piperidin-3-amine (90 mg, 0.42 mmol) in THF (3 ml) cooled to 0° C. was added DIPEA (222 µl, 1.27 mmol) and a solution of tert-butyl N-chlorosulfonylcarbamate (274 mg, 1.27 mmol) in THF (2 ml). The RM was stirred under $N_2$ at 0° C. for 2 h. The mixture was concentrated in vacuo and the resulting residue purified by prep-HPLC (column: Nano-micro Kromasil C18 80x25 mm, 3 µm; mobile phase: [water (0.1% TFA)-ACN]; B: 6-36%, 7 min) to give the title compound as a white solid. Y=33%. LCMS (ESI): m/z: $[M+H]^+$=392.2.

Step 7. (3S,5R)-3-Fluoro-1-methyl-5-[(1-methyl-1H-pyrazol-4-yl)(sulfamoyl)-amino]-piperidin-1-ium Trifluoroacetate

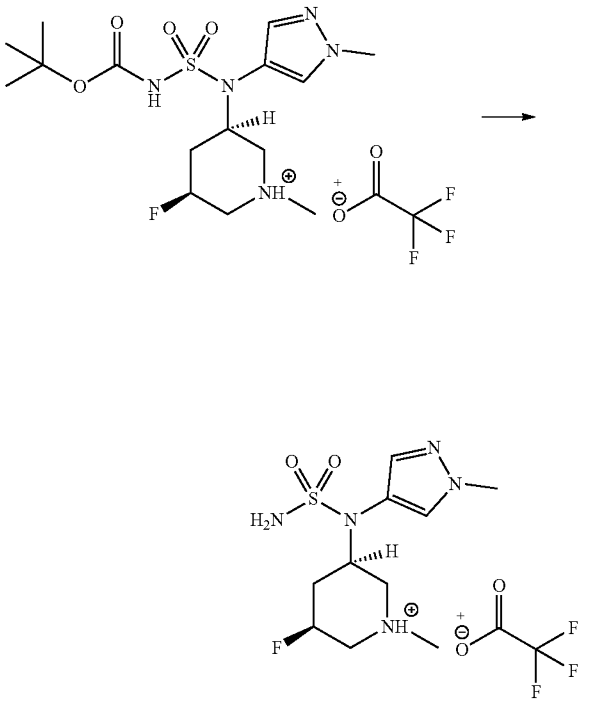

To a solution of (3S,5R)-3-fluoro-1-methyl-5-[(1-methyl-1H-pyrazol-4-yl)(sulfamoyl)amino]piperidin-1-ium triflate (50 mg, 99 µmol) in DCM (0.5 ml) was added TFA (95 µl, 1.29 mmol). The RM was stirred under $N_2$ at rt for 1.5 h and then evaporated under vacuum to give the title compound as an oil. LCMS (ESI): m/z: $[M+H]^+$=292.2.

Intermediate 15. (3R,5R)-3-Fluoro-1-methyl-5-[(1-methyl-1H-pyrazol-4-yl)(sulfamoyl)amino]-piperidin-1-ium Trifluoroacetate

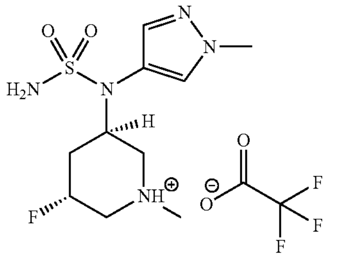 [SMILES: Cn1cc(N([C@@H]2C[C@@H](F)C[NH+](C)C2)S(N)(=O)=O)cn1 ; O=C([O-])C(F)(F)F]

Prepared using an analogous method to Intermediate 14, but starting with tert-butyl (3R,5R)-3-amino-5-fluoropiperidine-1-carboxylate. LCMS (ESI): m/z: $[M+H]^+$=292.1.

Intermediate 16. (3S,5S)-3-Fluoro-1-methyl-5-[(I-methyl-1H-pyrazol-4-yl)(sulfamoyl)amino]-piperidin-1-ium Trifluoroacetate

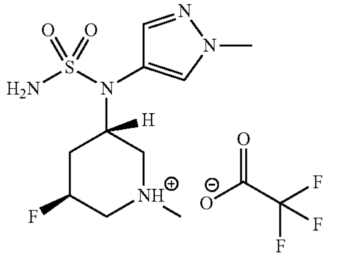 [SMILES: Cn1cc(N([C@H]2C[C@H](F)C[NH+](C)C2)S(N)(=O)=O)cn1 ; O=C([O-])C(F)(F)F]

Prepared using an analogous method to Intermediate 14, but starting with tert-butyl (3S,5S)-3-amino-5-fluoropiperidine-1-carboxylate. LCMS (ESI): m/z: $[M+H]^+$=292.1.

Intermediate 17. (3R,5S)-3-Fluoro-1-methyl-5-[(I-methyl-1H-pyrazol-4-yl)(sulfamoyl)amino]-piperidin-1-ium Trifluoroacetate

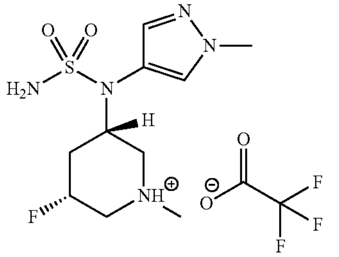 [SMILES: Cn1cc(N([C@H]2C[C@@H](F)C[NH+](C)C2)S(N)(=O)=O)cn1 ; O=C([O-])C(F)(F)F]

Prepared using an analogous method to Intermediate 14, but starting with tert-butyl (3R,5S)-3-amino-5-fluoropiperidine-1-carboxylate. LCMS (ESI): m/z: $[M+H]^+$=292.1.

Intermediate 18. 3,3-Difluoro-1-methyl-5-[(1-methyl-1H-pyrazol-4-yl)(sulfamoyl)amino]-piperidin-1-ium Trifluoroacetate Step 1. Tert-butyl 3,3-difluoro-5-[(1-methyl-1H-pyrazol-4-yl)amino]piperidine-1-carboxylate

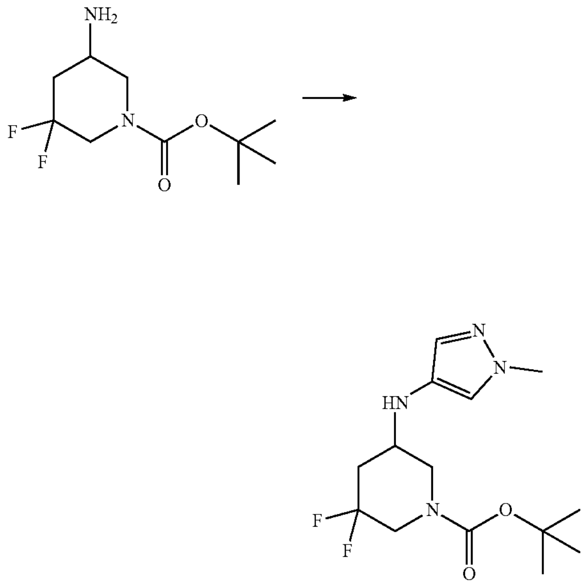

To a solution of tert-butyl 5-amino-3,3-difluoro-piperidine-1-carboxylate (250 mg, 1.06 mmol) in toluene (5 ml) was added 4-iodo-1-methyl-pyrazole (330 mg, 1.59 mmol), sodium tert-butoxide (203 mg, 2.12 mmol) and [2-(2-aminoethyl)phenyl]-chloro-palladium; ditert-butyl-[2-(2,4,6-triisopropylphenyl)phenyl]phosphane (73 mg, 106 μmol). The mixture was stirred under nitrogen at 100° C. for 3 h. The RM was concentrated under reduced pressure to give a residue. The residue was purified by column chromatography (silica, 0-100% EtOAc in petrol) to give the title compound as a gum. Y=60%. $^1H$ NMR (400 MHz, MeOD) δ 7.21 (s, 1H), 7.13 (s, 1H), 4.31-4.15 (m, 1H), 4.11-3.95 (m, 2H), 3.79 (s, 3H), 3.25-3.12 (m, 1H), 3.06-2.58 (m, 1H), 2.50-2.31 (m, 1H), 1.95-1.76 (m, 1H), 1.45 (s, 9H).

Step 2. Tert-butyl 3,3-difluoro-5-[2,2,2-trifluoro-N-(1-methyl-1H-pyrazol-4-yl)acetamido]piperidine-1-carboxylate

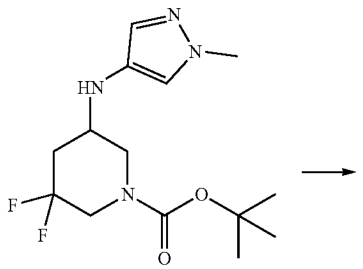

-continued

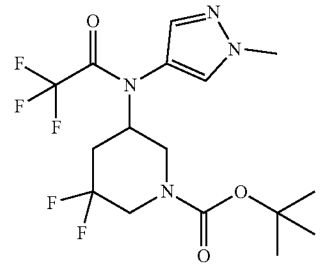

To a solution of tert-butyl 3,3-difluoro-5-[(1-methylpyrazol-4-yl)amino]piperidine-1-carboxylate (200 mg, 0.63 mmol) in DCM (4 ml), cooled to 0° C. was added triethylamine (264 μl, 1.90 mmol) and trifluoroacetic anhydride (176 μl, 1.26 mmol). The mixture was stirred at 0° C. for 3 h. The RM was diluted with water (5 ml) and extracted with DCM (3×5 ml). The combined organic layers were washed with brine (5 ml), dried over $Na_2SO_4$, filtered and concentrated under reduced pressure to give the title compound as a gum. The product was used for the next step directly. LCMS (ESI): m/z: $[M+H-56]^+$=357.0

Step 3. 3,3-Difluoro-5-[2,2,2-trifluoro-N-(1-methyl-1H-pyrazol-4-yl)acetamido]-piperidin-1-ium Trifluoroacetate

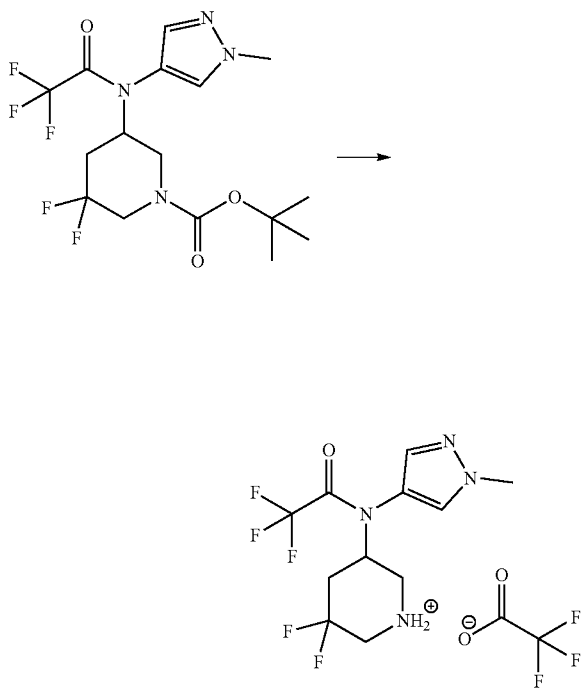

To a solution of tert-butyl 3,3-difluoro-5-[(1-methylpyrazol-4-yl)-(2,2,2-trifluoroacetyl)amino] piperidine-1-carboxylate (260 mg, 631 μmol,) in DCM (5 ml) was added TFA (1.0 ml, 13.5 mmol). The mixture was stirred at rt for 1 h, then concentrated under reduced pressure to give the title compound as a gum. Y=99%. LCMS (ESI): m/z: $[M+H]^+$=313.0.

Step 4. N-(5,5-Difluoro-1-methylpiperidin-3-yl)-2,2,2-trifluoro-N-(1-methyl-1H-pyrazol-4-yl)acetamide

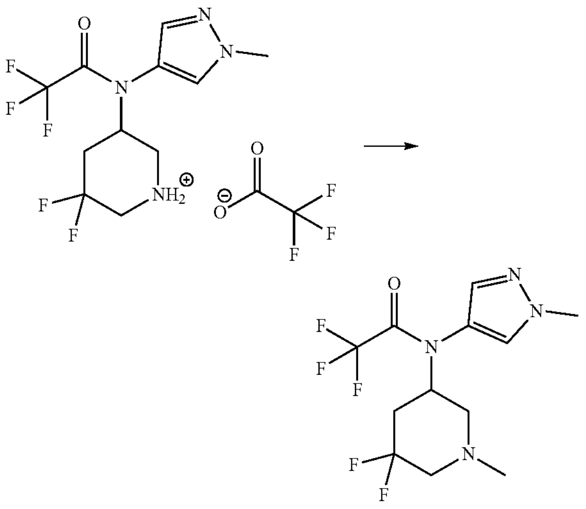

To a solution of 3,3-difluoro-5-[2,2,2-trifluoro-N-(1-methyl-1H-pyrazol-4-yl)acetamido]piperidin-1-ium trifluoroacetate (265 mg, 0.62 mmol) in MeOH (3 ml) cooled to 0° C. was added $NaBH_3CN$ (78 mg, 1.24 mmol) and 37% wt. formaldehyde (139 μl, 1.87 mmol). The mixture was stirred at 0° C. for 3 h then concentrated under reduced pressure to give the title compound as a gum. This was used for the next step directly. LCMS (ESI): m/z: $[M+H]^+$=327.0

Step 5. 5,5-Difluoro-1-methyl-N-(1-methyl-1H-pyrazol-4-yl)piperidin-3-amine

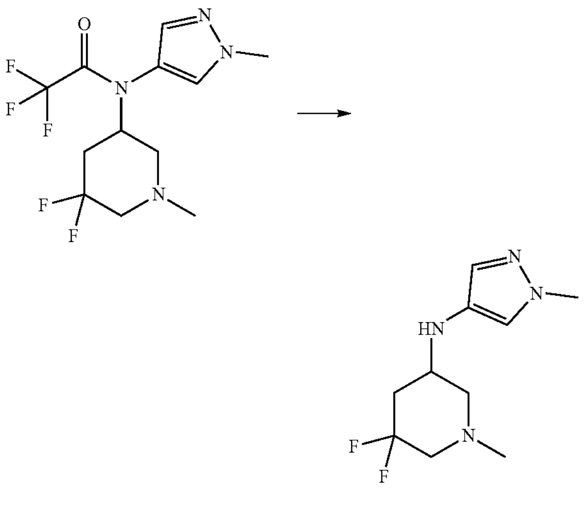

To a solution of N-(5,5-difluoro-1-methyl-3-piperidyl)-2,2,2-trifluoro-N-(1-methylpyrazol-4-yl) acetamide (200 mg, 0.61 mmol) in MeOH (6 ml) and $H_2O$ (2 ml) was added NaOH (74 mg, 1.84 mmol). The mixture was stirred at rt for 3 h. The RM was concentrated under reduced pressure and the resulting residue purified by column chromatography (silica, 0-10% MeOH in EtOAc) to give the title compound as a gum. Y=99%. $^1H$ NMR (400 MHz, MeOD) δ 7.19 (s, 1H), 7.12 (s, 1H), 3.78 (s, 3H), 3.15-3.04 (m, 2H), 2.37 (s, 3H), 2.33-2.21 (m, 2H), 1.97 (s, 3H).

Step 6. 5-[({[(Tert-butoxy)carbonyl]amino}sulfonyl)(1-methyl-1H-pyrazol-4-yl)amino]-3,3-difluoro-1-methylpiperidin-1-ium Trifluoroacetate

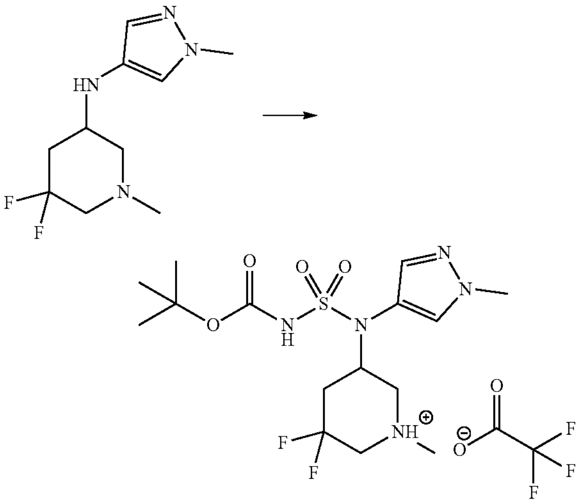

To a solution of 5,5-difluoro-1-methyl-N-(1-methylpyrazol-4-yl)piperidin-3-amine (140 mg, 0.61 mmol) in THF (2 ml) cooled to 0° C. was added DIPEA (212 μl, 1.22 mmol) and 0.7 M tert-butyl N-chlorosulfonylcarbamate in THF (1.3 ml, 0.92 mmol). The mixture was stirred at 0° C. for 1 h. The RM was concentrated under reduced pressure and the resulting residue purified by prep-HPLC (column: Welch Ultimate AQ-C18 150×30 mm, 5 μm; mobile phase: [water (0.1% TFA)-ACN]; B: 23-53%, 12 min) to give the title compound as a yellow gum. Y=31%. LCMS (ESI): m/z: $[M+H]^+$=410.1.

Step 7. 3,3-Difluoro-1-methyl-5-[(1-methyl-1H-pyrazol-4-yl)(sulfamoyl)-amino]-piperidin-1-ium Trifluoroacetate

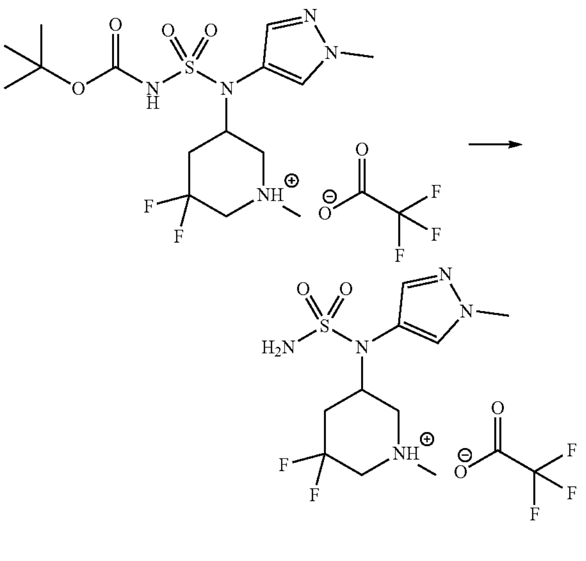

To a solution of 5-[({[(tert-butoxy)carbonyl]amino}sulfonyl)(1-methyl-1H-pyrazol-4-yl)amino]-3,3-difluoro-1-methylpiperidin-1-ium trifluoroacetate (100 mg, 191 μmol) in DCM (1 ml) was added trifluoroacetic acid (0.20 ml, 2.70 mmol). The mixture was stirred at rt for 1 h. The RM was concentrated under reduced pressure to give the title compound as a gum. This was used for the next step directly. LCMS (ESI): m/z: $[M+H]^+$=310.2.

Intermediate 19. 3-Isocyanato-2-methyl-4,5,6,7-tetrahydro-1-benzothiophene

Step 1. Ethyl 2-amino-4,5,6,7-tetrahydro-1-benzothiophene-3-carboxylate

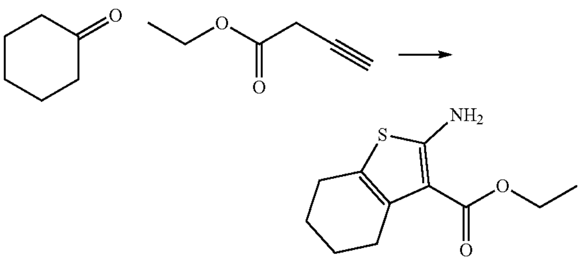

To a solution of ethyl 2-cyanoacetate (1.27 g, 11.2 mmol) in EtOH (10 ml) was added cyclohexanone (1.0 g, 10.2 mmol), diethylamine (1.05 ml, 10.2 mmol) and sulfur (0.33 g, 10.2 mmol). The RM was placed in an ultrasonic bath at 25° C. for 1 h. The solution was concentrated under reduced pressure and the resulting residue purified by column chromatography (silica, Petroleum ether/Ethyl acetate=10/1 to 5/1) to give the title compound as a yellow solid. Y=42%. LCMS (ESI): m/z: $[M+H]^+$=226.0.

Step 2. Ethyl 2-bromo-4,5,6,7-tetrahydro-1-benzothiophene-3-carboxylate

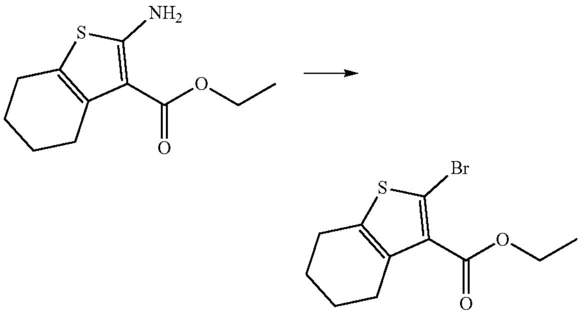

To a solution of tert-butyl nitrite (4.09 ml, 34.4 mmol) in MeCN (58 ml) cooled to 0° C. was added $CuBr_2$ (8.54 g, 38.2 mmol). To this mixture was added portionwise ethyl 2-amino-4,5,6,7-tetrahydrobenzothiophene-3-carboxylate (6.24 g, 27.7 mmol). The resulting mixture was stirred at 0° C. for 2 h, then allowed to warm to rt and stirred for 3 h. The RM was concentrated under reduced pressure to remove MeCN. The residue was diluted with $H_2O$ (40 ml) and extracted with EtOAc (3×20 ml). The combined organic layers were washed with brine (3×20 ml), dried over $Na_2SO_4$, filtered and the filtrate concentrated under reduced pressure to give a residue. The residue was purified by column chromatography (silica, Petroleum ether:Ethyl acetate=5:1) to give the title compound as a white solid. Y=44%. $^1$H NMR (400 MHz, MeOD) δ 4.30 (q, J=7 Hz, 2H), 2.70 (t, J=7 Hz, 2H), 2.63 (t, J=7 Hz, 2H), 1.80-1.74 (m, 4H), 1.36 (t, J=7 Hz, 3H).

Step 3. Ethyl 2-methyl-4,5,6,7-tetrahydro-1-benzothiophene-3-carboxylate

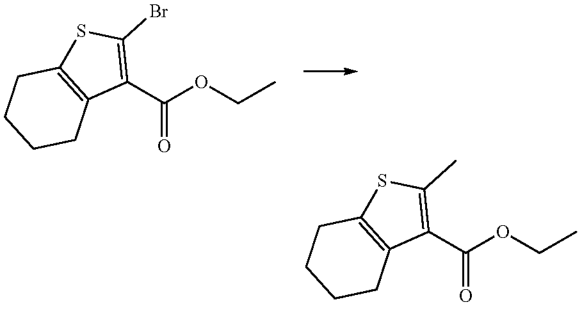

To a solution of ethyl 2-bromo-4,5,6,7-tetrahydrobenzothiophene-3-carboxylate (0.5 g, 1.73 mmol) in dioxane (5 ml) and $H_2O$ (1 ml) was added $K_2CO_3$ (597 mg, 4.32 mmol), $Pd(PPh_3)_4$ (100 mg, 86.5 μmol) and 2,4,6-trimethyl-1,3,5,2,4,6-trioxatriborinane (1.09 g, 8.64 mmol). The mixture was stirred at 80° C. under $N_2$ for 12 h. The RM was diluted with $H_2O$ (6 ml) and extracted with EtOAc (3×5 ml). The combined organic layers were washed with brine (3×4 ml), dried over $Na_2SO_4$, filtered and the filtrate concentrated under reduced pressure to give a residue. The residue was purified by column chromatography (silica, Petroleum ether: Ethyl acetate=10:1) to give the title compound as a white solid. Y=72%. $^1$H NMR (400 MHz, chloroform-d) δ 4.33 (q, J=7 Hz, 2H), 2.80-2.78 (m, 2H), 2.67-2.65 (m, 2H), 2.63 (s, 3H), 1.82-1.78 (m, 4H), 1.37 (t, J=7 Hz, 3H).

Step 4. 2-Methyl-4,5,6,7-tetrahydro-1-benzothiophene-3-carboxylic Acid

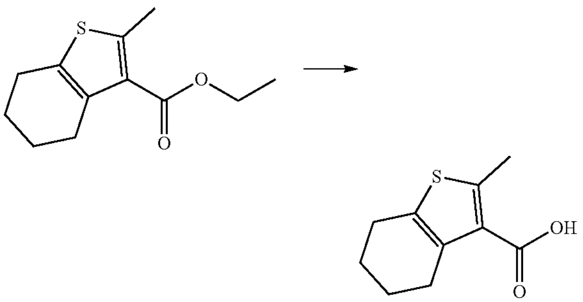

To a solution of ethyl 2-methyl-4,5,6,7-tetrahydrobenzothiophene-3-carboxylate (570 mg, 2.54 mmol) in MeOH (6 ml) and $H_2O$ (3 ml) was added NaOH (152 mg, 3.81 mmol). The resulting mixture was stirred at 50° C. for 12 h. To the RM was slowly added dilute 2M HCl until pH=5. The resulting mixture was diluted with $H_2O$ (6 ml) and extracted with EtOAc (3×6 ml). The combined organic layers were washed with brine (3×6 ml), dried over $Na_2SO_4$, filtered and the filtrate concentrated under reduced pressure to give a residue. The residue was purified by column chromatography (silica, Petroleum ether:Ethyl acetate=3:1) to give the title compound as a white solid. Y=60%. $^1$H NMR (400 MHz, chloroform-d) δ 2.91-2.83 (m, 2H), 2.75-2.59 (m, 5H), 1.90-1.70 (m, 4H).

Step 5. Tert-butyl N-(2-methyl-4,5,6,7-tetrahydro-1-benzothiophen-3-yl)carbamate

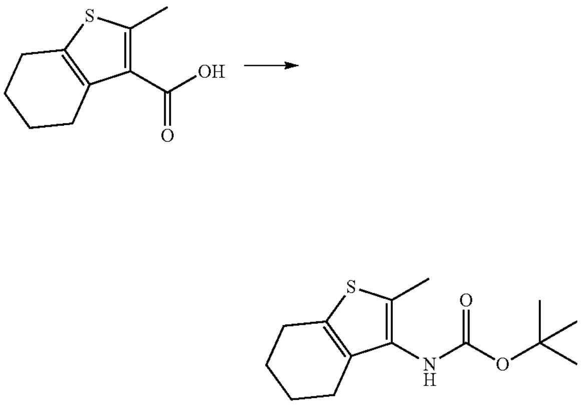

To a solution of 2-methyl-4,5,6,7-tetrahydrobenzothiophene-3-carboxylic acid (150 mg, 0.76 mmol) in tert-butanol (2 ml) were added DPPA (210 mg, 0.76 mmol) and DIPEA (0.20 ml, 1.15 mmol). The mixture was stirred at 90° C. for 12 h. The RM was diluted with $H_2O$ (4 ml) and extracted with EtOAc (3×3 ml). The combined organic layers were washed with brine (3×3 ml), dried over $Na_2SO_4$, filtered and concentrated under reduced pressure to give a residue. The residue was purified by column chromatography (silica, Petroleum ether/Ethyl acetate=3:1) to give the title compound as a white solid. Y=34%. $^1$H NMR (400 MHz, chloroform-d) δ 5.68 (s, 1H), 2.70-2.63 (m, 2H), 2.41 (t, J=6 Hz, 2H), 2.28 (s, 3H), 1.83-1.76 (m, 4H), 1.49 (s, 9H).

Step 6. 2-Methyl-4,5,6,7-tetrahydro-1-benzothiophen-3-amine Hydrochloride

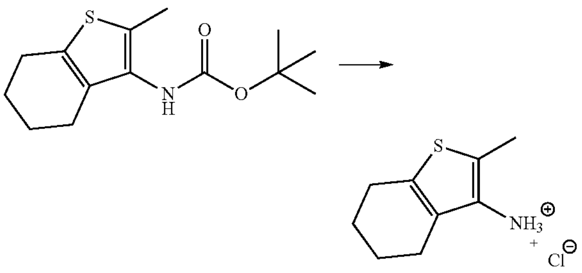

A solution of tert-butyl N-(2-methyl-4,5,6,7-tetrahydrobenzothiophen-3-yl)carbamate (50 mg, 187 μmol) in 4M HCl in EtOAc (1 ml) was stirred at rt for 1 h. The RM was filtered, and the solid collected and dried to give the title compound as a white solid. This was used for the next step directly. LCMS (ESI): m/z: $[M+H]^+$=168.0.

Step 7. 3-Isocyanato-2-methyl-4,5,6,7-tetrahydro-1-benzothiophene

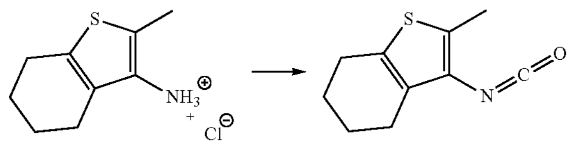

To a solution of 2-methyl-4,5,6,7-tetrahydro-1-benzothiophen-3-amine hydrochloride (38 mg, 187 μmol) in dioxane (1 ml) at 40° C. was added trichloromethyl carbonochloridate (55 mg, 0.28 mmol). The mixture was stirred at 70° C. for 0.5 h. The RM was concentrated under reduced pressure to give the title compound as a yellow oil. This was used for the next step directly. LCMS in MeOH (ESI): m/z: $[M+MeOH+H]^+$ 226.0.

Intermediate 20. N-[2-(Dimethylamino)ethyl]-N-(1-methyl-1H-pyrazol-4-yl)aminosulfonamide Hydrochloride Step 1. 2-(Dimethylamino)-N-(1-methyl-1H-pyrazol-4-yl)acetamide

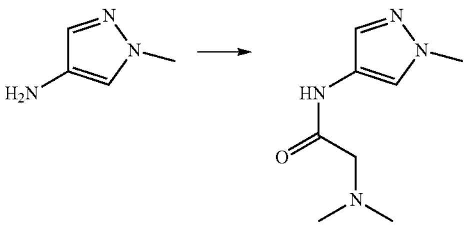

To a solution of 2-(dimethylamino)acetic acid (1.06 g, 10.3 mmol) in DMF (10 ml) cooled to 0° C. was added HOBt (2.09 g, 15.5 mmol) and N-(3-dimethylaminopropyl)-N'-ethylcarbodiimide hydrochloride (2.96 g, 15.5 mmol). The mixture was stirred at 0° C. for 0.5 h, then treated with 1-methylpyrazol-4-amine (1.0 g, 10.3 mmol) and DIPEA (5.4 ml, 30.9 mmol). The RM was stirred at 15° C. for 1 h. The mixture was diluted with $H_2O$ (10 ml) and extracted with EtOAc (7×10 ml). The combined organic layers were washed with brine (2×10 ml), dried over $Na_2SO_4$, filtered and the filtrate concentrated under reduced pressure to give the title compound as a yellow oil. $^1H$ NMR (400 MHz, chloroform-d) δ 7.94 (s, 1H), 7.41 (s, 1H), 3.87 (s, 3H), 3.07 (s, 2H), 2.36 (s, 6H).

Step 2. N-[2-(Dimethylamino)ethyl]-1-methyl-1H-pyrazol-4-amine

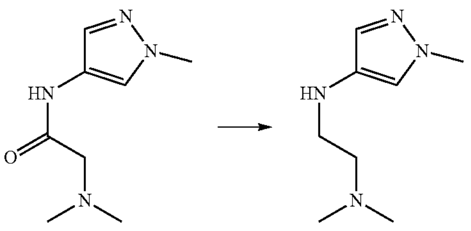

A solution of 2-(dimethylamino)-N-(1-methylpyrazol-4-yl)acetamide (3.0 g, 16.5 mmol) in 1M $BH_3$·THF (50 ml, 50 mmol) was stirred at 50° C. for 1 h. The mixture was cooled to 0° C. and quenched by addition of MeOH (10 ml). The mixture was concentrated under reduced pressure and the resulting residue purified by prep-HPLC (column: Welch Xtimate C18 250×50 mm, 10 μm; mobile phase: [water (10 mM $NH_4HCO_3$)-ACN]; B: 0-10%, 22 min) to give the title compound as a colourless gum. Y=7%.

Step 3. Tert-butyl N-{[2-(dimethylamino)ethyl](1-methyl-1H-pyrazol-4-yl)sulfamoyl}-carbamate

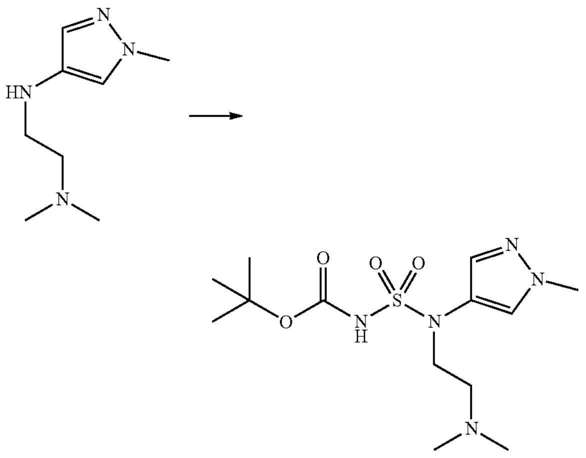

To a solution of N',N'-dimethyl-N-(1-methylpyrazol-4-yl) ethane-1,2-diamine (250 mg, 1.49 mmol) in DCM (3 ml) at 0° C. under $N_2$ was added DIPEA (0.46 ml, 2.66 mmol) and the mixture was stirred at 0° C. for 0.5 h. The RM was treated dropwise with a solution of tert-butyl N-chlorosulfonylcarbamate (2.52 ml, 0.89 mmol, 0.35 M in DCM) and stirred at 0° C. for 0.5 h. The RM was concentrated under reduce pressure and the resulting residue purified by prep-HPLC (column: Nano-micro Kromasil C18 80×25 mm, 3 μm; mobile phase: [water (0.1% TFA)-ACN]; B: 1-32%, 7 min) to give the title as a white solid. Y=33%. $^1H$ NMR (400 MHz, chloroform-d) δ 7.67-7.65 (m, 2H), 7.48 (s, 1H), 4.23 (t, J=6 Hz, 2H), 3.91 (s, 3H), 3.33 (t, J=6 Hz, 2H), 3.00 (s, 3H), 2.96 (s, 6H), 1.50 (s, 9H).

Step 4. N-[2-(Dimethylamino)ethyl]-N-(1-methyl-1H-pyrazol-4-yl)aminosulfonamide Hydrochloride

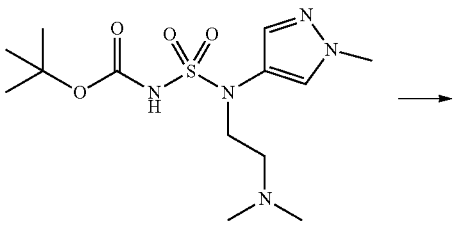

-continued

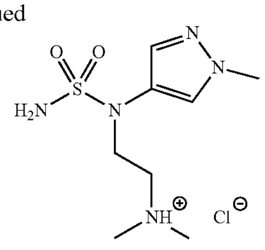

A solution of tert-butyl N-[2-(dimethylamino) ethyl-(1-methylpyrazol-4-yl)sulfamoyl]carbamate (200 mg, 0.58 mmol) in 4M HCl in EtOAc (10 ml) was stirred at rt for 0.5 h. The mixture was concentrated under reduce pressure to give the title compound as a white solid. Y=98%. $^1$H NMR (400 MHz, DMSO-$d_6$) δ 7.85 (s, 1H), 7.52 (s, 1H), 7.21 (s, 2H), 3.84 (s, 3H), 3.75-3.68 (m, 2H), 3.16-3.12 (m, 2H), 2.78-2.70 (m, 6H).

Intermediate 21. 3,5-Diethyl-2-isocyanatothiophene

Step 1. Tert-butyl N-(3,5-dibromothiophen-2-yl)carbamate

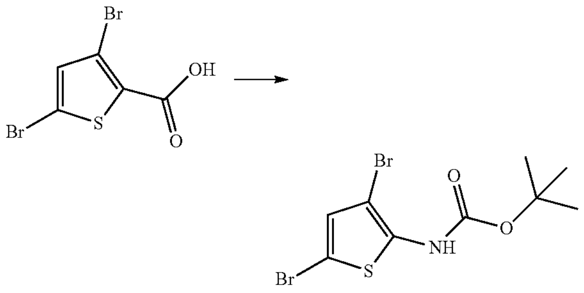

To a solution of 3,5-dibromothiophene-2-carboxylic acid (1.24 g, 4.34 mmol) in tert-butanol (20 ml) was added DPPA (1.19 g, 4.34 mmol) and DIPEA (1.13 ml, 6.50 mmol). The mixture was stirred at 90° C. for 12 h then concentrated under reduced pressure to give a residue. The residue was purified by silica gel chromatography (Petroleum ether: Ethyl acetate=5:1) to give the title compound as a yellow solid. Y=84%. $^1$H NMR (400 MHz, MeOD) δ 6.86 (s, 1H), 1.52 (s, 9H).

Step 2. Tert-butyl N-(3,5-diethenylthiophen-2-yl)carbamate

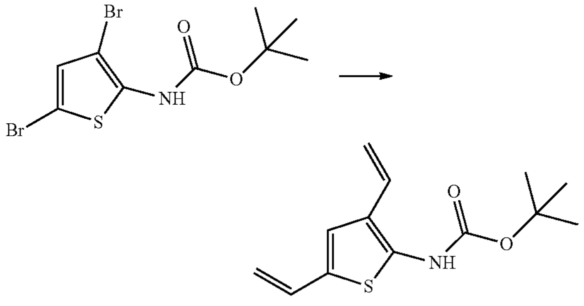

To a solution of tert-butyl N-(3,5-dibromo-2-thienyl)carbamate (350 mg, 0.98 mmol) in THF (7 ml) and $H_2O$ (0.7 ml) under $N_2$ was added difluoro-[(Z)-vinylboranylidene-fluoranyl]potassium (1.31 g, 9.80 mmol), $PPh_3$ (15 mg, 59 μmol), $Cs_2CO_3$ (0.96 g, 2.94 mmol) and $PdCl_2$ (3.5 mg, 19.6 μmol). The mixture was stirred at 85° C. for 48 h. The RM was concentrated under reduced pressure and the resulting residue was purified by prep-TLC (Petroleum ether:Ethyl acetate=5:1) to give the title compound as a yellow gum. Y=22%. $^1$H NMR (400 MHz, MeOD) δ 6.96 (s, 1H), 6.77-6.65 (m, 2H), 5.54-5.37 (m, 2H), 5.20-5.00 (m, 2H), 1.52 (s, 9H).

Step 3. Tert-butyl N-(3,5-diethylthiophen-2-yl)carbamate

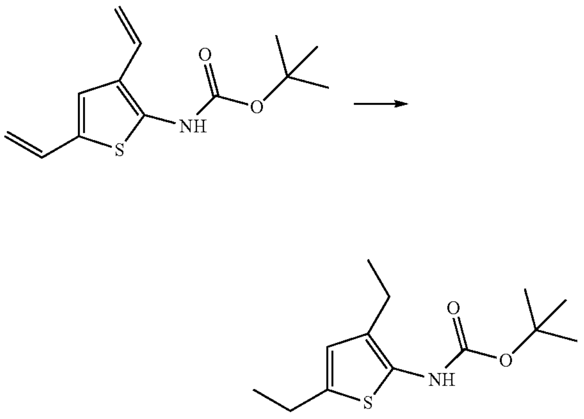

A solution of tert-butyl N-(3,5-diethenylthiophen-2-yl) carbamate (75 mg, 0.30 mmol) and 10% Pd/C (50% in water, 40 mg) in EtOAc (10 ml) was stirred under $H_2$ (15 psi) at rt for 1 h. The solution was filtered through a pad of Celite and the filtrate concentrated under reduced pressure to give the title compound as a yellow oil. LCMS (ESI): m/z: $[M+H]^+$=256.0.

Step 4. 3,5-diethylthiophen-2-amine Hydrochloride

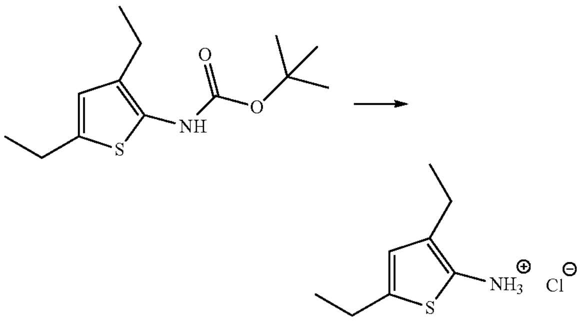

A solution of tert-butyl N-(3,5-diethyl-2-thienyl)carbamate (180 mg, 0.70 mmol) in 4 M HCl/EtOAc (10 ml) and the mixture was stirred for 0.5 h. The solution was concentrated under reduced pressure to give the title compound as a yellow solid. LCMS (ESI): m/z: $[M+H]^+$=156.1.

Step 5. 3,5-Diethyl-2-isocyanatothiophene

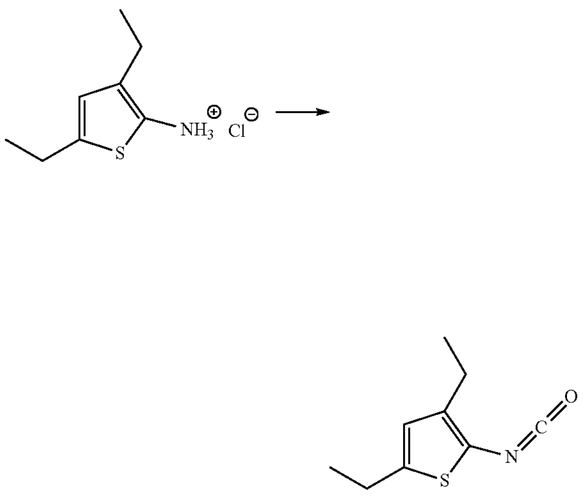

To a solution of 3,5-diethylthiophen-2-amine hydrochloride (110 mg, 0.57 mmol) in dioxane (2 ml) at 40° C. was added trichloromethyl carbonochloridate (94 μl, 0.78 mmol). The RM was stirred at 70° C. for 1 h. The solution was concentrated under reduced pressure to give the title compound as an oil. This was used directly in the next step. LCMS in MeOH (ESI): m/z: $[M+MeOH+H]^+=214.0$.

Intermediate 22. N-(1-Methyl-1H-pyrazol-4-yl)-N-(1-methylpiperidin-4-yl)aminosulfonamide Hydrochloride Step 1. 1-Methyl-N-(1-methyl-1H-pyrazol-4-yl)piperidin-4-amine

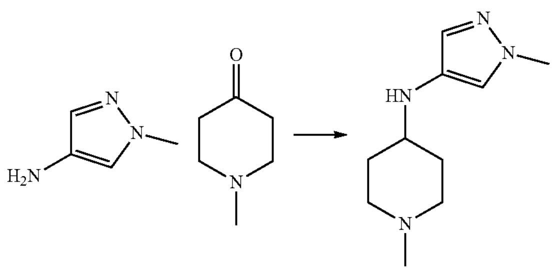

To a solution of 1-methylpyrazol-4-amine (2.0 g, 20.6 mmol, 1 eq) in DCE (20 ml) cooled to 0° C. was added 1-methylpiperidin-4-one (2.39 ml, 2.33 g, 20.6 mmol) and AcOH (2.0 ml, 35.0 mmol). The RM was stirred at 0° C. for 1 h, then treated with $NaBH(OAc)_3$ (13.1 g, 61.8 mmol). The RM was stirred at rt for 1 h then concentrated under reduced pressure. The residue was purified by column chromatography (silica, 17-100% EtOAc in petrol) to give the title compound as an oil. Y=80%. $^1H$ NMR (400 MHz, MeOD) δ 7.18 (s, 1H), 7.12 (s, 1H), 3.77 (s, 3H), 2.89-2.80 (m, 3H), 2.27 (s, 3H), 2.16-2.06 (m, 2H), 2.01-1.92 (m, 2H), 1.52-1.38 (m, 2H).

Step 2. 4-[({[(Tert-butoxy)carbonyl]amino}sulfonyl)(1-methyl-1H-pyrazol-4-yl)amino]-1-methylpiperidin-1-ium Trifluoroacetate

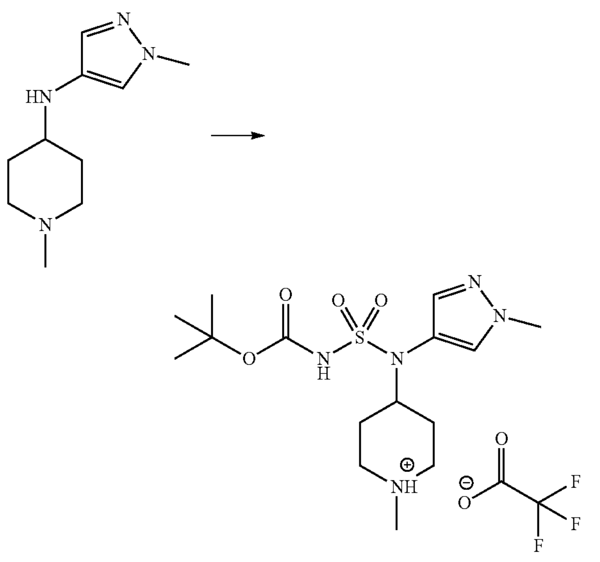

To a solution of 1-methyl-N-(1-methylpyrazol-4-yl)piperidin-4-amine (1.0 g, 5.15 mmol) in DCM (10 ml) at 0° C. was added a solution of 0.45 M tert-butyl N-chlorosulfonylcarbamate in DCM (13.67 ml, 6.18 mmol). The RM was stirred at 0° C. for 1 h, treated with DIPEA (4.48 ml, 25.7 mmol) and stirred at rt for 1 h. The solution was concentrated under reduced pressure and the resulting residue purified by prep-HPLC (column: Phenomenex Luna C18 250×100 mm, 10 m; mobile phase: [water (0.1% TFA)-ACN]; B: 0-25%, 45 min) to give the title compound as a white solid. Y=60%. LCMS (ESI): m/z: $[M+H]^+=374.1$.

Step 3. N-(1-Methyl-1H-pyrazol-4-yl)-N-(1-methylpiperidin-4-yl)aminosulfonamide Hydrochloride

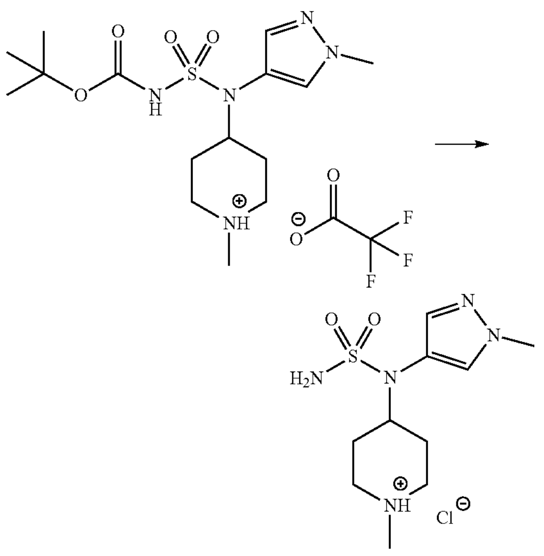

A solution of 4-[({[(tert-butoxy)carbonyl]amino}sulfonyl)(1-methyl-1H-pyrazol-4-yl)amino]-1-methylpiperidin-1-ium trifluoroacetate (300 mg, 0.62 mmol) in 4 M HCl/EtOAc (3 ml) was stirred at rt for 1 h, then concentrated under reduced pressure to give the title compound as a white solid. LCMS (ESI): m/z: $[M+H]^+$=274.1.

Intermediate 23. 2-Isocyanato-3,5-bis(propan-2-yl)thiophene

Step 1. Tert-butyl N-[3,5-bis(prop-1-en-2-yl)thiophen-2-yl]carbamate

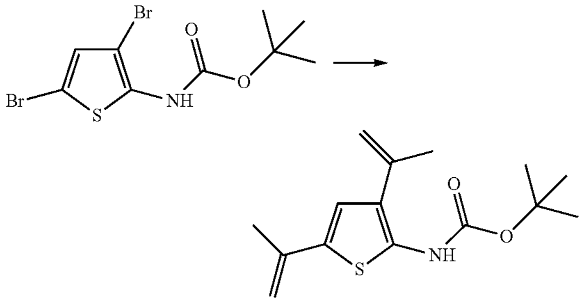

To a solution of tert-butyl N-(3,5-dibromo-2-thienyl)carbamate (0.50 g, 1.40 mmol) [for synthesis refer to Intermediate 21] in dioxane (4 ml) under $N_2$ was added 2-isopropenyl-4,4,5,5-tetramethyl-1,3,2-dioxaborolane (0.94 g, 5.60 mmol), $Pd(dppf)Cl_2 \cdot CH_2Cl_2$ (57 mg, 70 μmol) and 2M $Na_2CO_3$ in water (1.40 ml, 2.80 mmol). The mixture was stirred at 100° C. for 2 h. The solution was allowed to cool and concentrated in vacuo. The residue was purified by silica gel chromatography (17% EtOAc in petrol) to give the title compound as a yellow oil. Y=92%. $^1H$ NMR (400 MHz, MeOD) δ 6.80 (s, 1H), 5.69-5.60 (m, 2H), 5.23 (s, 1H), 5.15-5.08 (m, 2H), 2.08 (s, 3H), 2.04 (s, 3H), 1.50 (s, 9H).

Step 2. Tert-butyl N-[3,5-bis(propan-2-yl)thiophen-2-yl]carbamate

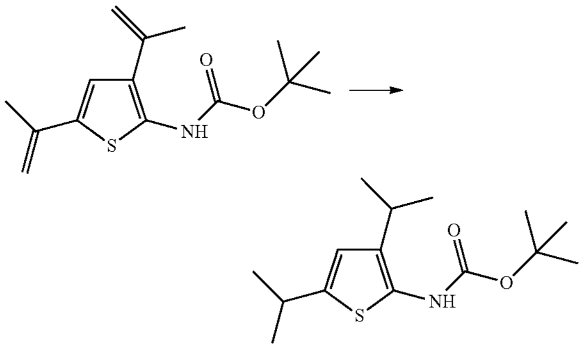

To a solution of tert-butyl N-[3,5-bis(prop-1-en-2-yl)thiophen-2-yl]carbamate (150 mg, 0.54 mmol) in EtOAc (10 ml) under $N_2$ was added 10% Pd/C (50% in water, 30 mg,). The RM was stirred under $H_2$ (15 psi) at rt for 2 h. The RM was filtered through Celite and the filtrate concentrated in vacuo to give the title compound as a yellow oil. LCMS (ESI): m/z: $[M+H]^+$=284.2.

Step 3. 3,5-Bis(propan-2-yl)thiophen-2-amine Hydrochloride

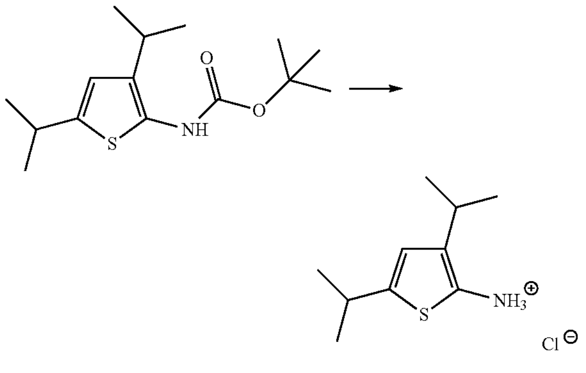

A mixture of tert-butyl N-[3,5-bis(propan-2-yl)thiophen-2-yl]carbamate (90 mg, 0.32 mmol) in 4 M HCl in EtOAc (10 ml) was stirred at rt for 1 h. The mixture was concentrated in vacuo to give the title compound as a yellow solid.

Step 4. 2-Isocyanato-3,5-bis(propan-2-yl)thiophene

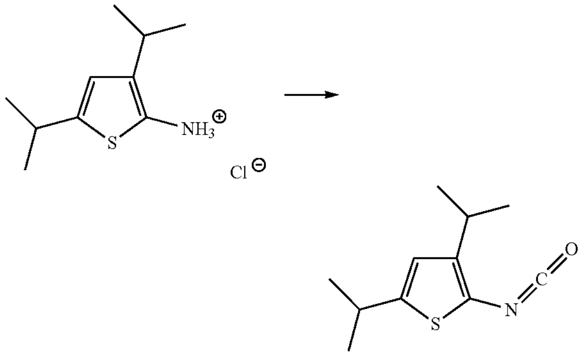

To a solution of 3,5-bis(propan-2-yl)thiophen-2-amine hydrochloride (100 mg, 0.46 mmol) in dioxane (2 ml) warmed to 40° C. was added trichloromethyl carbonochloridate (72 μl, 0.60 mmol). The RM was heated at 70° C. for 1 h. The solution was concentrated in vacuo to give the title compound as a yellow oil. LCMS in MeOH (ESI): m/z: $[M+MeOH+H]^+$=242.1.

Intermediate 24. N-{[(2S,4R)-4-Fluoro-1-methylpyrrolidin-2-yl]methyl}-N-(1-methyl-1H-pyrazol-4-yl)aminosulfonamide Hydrochloride Step 1. Tert-butyl (2S,4R)-4-fluoro-2-[(1-methyl-1H-pyrazol-4-yl)carbamoyl]-pyrrolidine-1-carboxylate

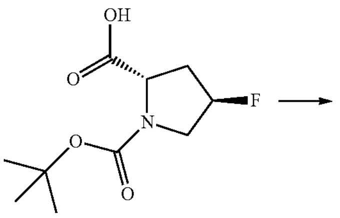

-continued

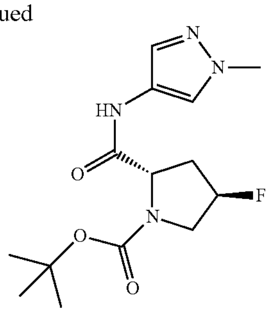

To a solution of (2S,4R)-1-tert-butoxycarbonyl-4-fluoro-pyrrolidine-2-carboxylic acid (5.04 g, 21.6 mmol) in DMF (50 ml) cooled to 0° C. was added HATU (9.04 g, 23.8 mmol). The mixture was stirred at 0° C. for 1 h, then treated with 1-methylpyrazol-4-amine (2.1 g, 21.6 mmol) and DIPEA (7.53 ml, 43.2 mmol). The RM was stirred at rt for 2 h. The mixture was diluted with $H_2O$ (50 ml) and extracted with EtOAc (3×50 ml). The organics were combined, washed sequentially with $H_2O$ (2×50 ml) and brine (20 ml), dried over $Na_2SO_4$ and concentrated under vacuum. The residue was purified by column chromatography (silica, 9-100% EtOAc in petrol) to give the title compound as a white solid. Y=74%. $^1H$ NMR (400 MHz, MeOD) δ 7.91 (s, 1H), 7.50 (s, 1H), 5.35-5.22 (m, 2H), 4.38-4.34 (m, 1H), 3.82-3.56 (m, 3H), 2.62-2.49 (m, 2H), 2.27-2.06 (m, 1H), 1.36 (s, 9H).

Step 2. (2S,4R)-4-Fluoro-N-(1-methyl-1H-pyrazol-4-yl)pyrrolidine-2-carboxamide Hydrochloride

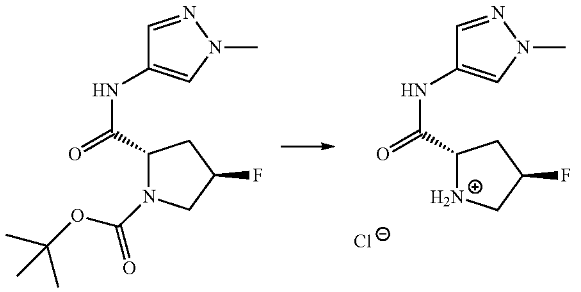 [SMILES: Cn1cc(NC(=O)[C@@H]2C[C@@H](F)CN2C(=O)OC(C)(C)C)cn1 ; [Cl-] ; Cn1cc(NC(=O)[C@@H]2C[C@@H](F)C[NH2+]2)cn1]

A solution of tert-butyl (2S,4R)-4-fluoro-2-[(1-methylpyrazol-4-yl)carbamoyl]pyrrolidine-1-carboxylate (3.0 g, 9.60 mmol) in 4 M HCl/EtOAc (40 ml) was stirred at rt for 2 h. The mixture was filtered and the solid dried to give the title compound as a white solid. Y=100%.

Step 3. (2S,4R)-4-Fluoro-1-methyl-N-(1-methyl-1H-pyrazol-4-yl)pyrrolidine-2-carboxamide

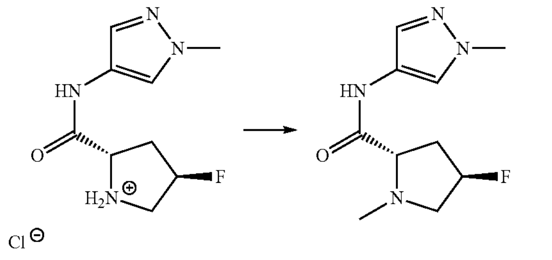 [SMILES: Cn1cc(NC(=O)[C@@H]2C[C@@H](F)C[NH2+]2)cn1 ; CN1C[C@H](F)C[C@H]1C(=O)Nc1cnn(C)c1 ; [Cl-]]

To a solution of (2S,4R)-4-fluoro-N-(1-methyl-1H-pyrazol-4-yl)pyrrolidine-2-carboxamide hydrochloride (2.39 g, 9.61 mmol) in MeOH (20 ml) was added formaldehyde (37% in water, 1.43 ml, 19.2 mmol) then $NaBH_3CN$ (0.91 g, 14.4 mmol). The mixture was stirred at rt for 30 min. The mixture was concentrated under reduced pressure and the resulting residue purified by column chromatography (silica, 0-9% MeOH in EtOAc) to give the title compound as a yellow oil. Y=69%. $^1H$ NMR (400 MHz, MeOD) δ 7.91 (s, 1H), 7.55 (s, 1H), 5.27-5.13 (m, 1H), 3.85 (s, 3H), 3.68-3.51 (m, 1H), 2.78-2.65 (m, 1H), 2.48-2.34 (m, 5H), 2.18-1.99 (m, 1H).

Step 4. N-{[(2S,4R)-4-Fluoro-1-methylpyrrolidin-2-yl]methyl}-1-methyl-1H-pyrazol-4-amine

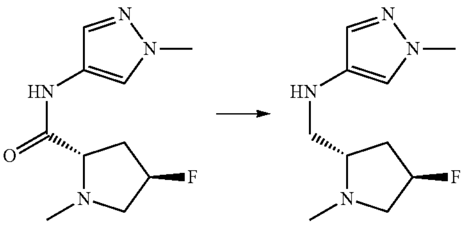 [SMILES: CN1C[C@H](F)C[C@H]1C(=O)Nc1cnn(C)c1 ; CN1C[C@H](F)C[C@H]1CNc1cnn(C)c1]

To a solution of (2S,4R)-4-fluoro-1-methyl-N-(1-methylpyrazol-4-yl)pyrrolidine-2-carboxamide (1.0 g, 4.42 mmol) in THF (15 ml) at 0° C. was added 10 M $BH_3$-$Me_2S$ (4.42 ml, 44 mmol). The mixture was stirred at 0° C. for 1 h, then warmed to 50° C. and stirred at this temperature for 5 h. The mixture was cooled to 0° C. and quenched by dropwise addition of MeOH (10 ml). The resulting solution was concentrated under vacuum to give the title compound as a white gum. LCMS (ESI): m/z: $[M+H]^+$=213.1.

Step 5. (2S,4R)-2-{[({[(Tert-butoxy)carbonyl]amino}sulfonyl)(1-methyl-1H-pyrazol-4-yl)amino]methyl}-4-fluoro-1-methylpyrrolidin-1-ium Trifluoroacetate

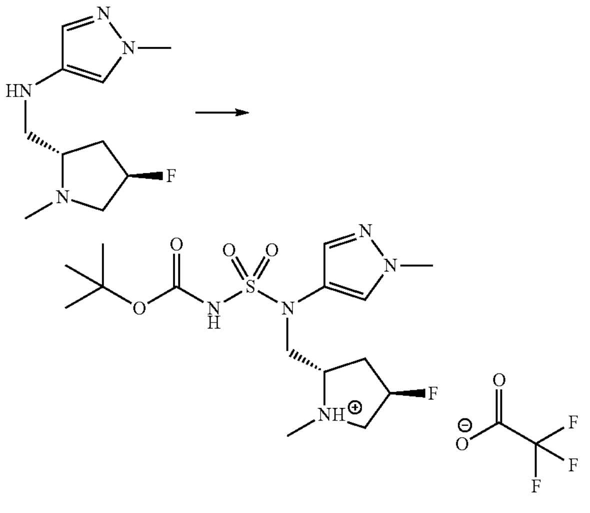

To a solution of N-{[(2S,4R)-4-fluoro-1-methylpyrrolidin-2-yl]methyl}-1-methyl-1H-pyrazol-4-amine (1.0 g, 4.71 mmol) in DCM (10 ml) cooled to 0° C. was added DIPEA (1.64 ml, 9.42 mmol) then a solution of 0.71 M tert-butyl N-chlorosulfonylcarbamate in DCM (13.32 ml 9.42 mmol). The RM was stirred at 0° C. for 2 h. The mixture was concentrated under vacuum and the resulting residue purified by prep-HPLC (column: Phenomenex Luna C18 250×50 mm, 10 μm; mobile phase: [water (0.1% TFA)-ACN]; B: 1-30%, 20 min) to give the title compound as a colourless gum. Y=42%. LCMS (ESI): m/z: $[M+H]^+$=392.1.

Step 6. N-{[(2S,4R)-4-Fluoro-1-methylpyrrolidin-2-yl]methyl}-N-(1-methyl-1H-pyrazol-4-yl)aminosulfonamide Hydrochloride

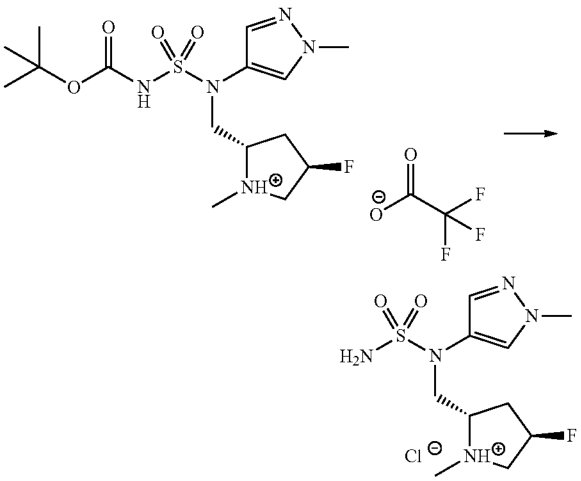

A mixture of (2S,4R)-2-{[({[(tert-butoxy)carbonyl]amino}sulfonyl)(1-methyl-1H-pyrazol-4-yl)amino]methyl}-4-fluoro-1-methylpyrrolidin-1-ium trifluoroacetate (3.2 g, 6.33 mmol) in 4 M HCl/EtOAc (25 ml) was stirred at rt for 2 h. The mixture was filtered and the solid collected and dried to give the title compound as a white solid.

Intermediate 25. N-[(3R)-1-Methylpiperidin-3-yl]-N-[1-(propan-2-yl)-1H-pyrazol-4-yl]aminosulfonamide Hydrochloride

Step 1. Tert-butyl (3R)-3-{[1-(propan-2-yl)-1H-pyrazol-4-yl]amino}piperidine-1-carboxylate

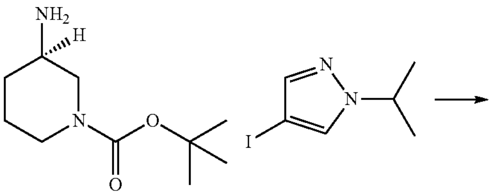

-continued

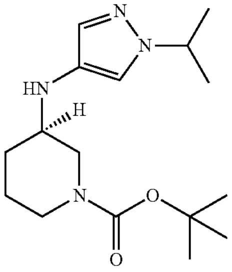

To a solution of 4-iodo-1-isopropyl-pyrazole (1.18 g, 5.0 mmol) in toluene (10 ml) at rt under $N_2$ was added tert-butyl (3R)-3-aminopiperidine-1-carboxylate (1.0 g, 5.0 mmol), t-BuONa (0.96 g, 10.0 mmol) and [2-(2-aminoethyl)phenyl]-chloro-palladium; ditert-butyl-[2-(2,4,6-triisopropylphenyl)phenyl]phosphane (343 mg, 0.50 mmol). The mixture was stirred at 100° C. for 4 h. The solution was concentrated in vacuo and the resulting residue was purified by silica gel chromatography (100% EtOAc) to give the title compound tert-butyl (3R)-3-[(1-isopropylpyrazol-4-yl)amino]piperidine-1-carboxylate as a yellow oil. Y=42%. $^1H$ NMR (400 MHz, MeOD) δ 7.26 (s, 1H), 7.15 (s, 1H), 4.46-4.34 (m, 1H), 3.99-3.61 (m, 2H), 3.05-2.95 (m, 3H), 2.05-1.95 (m, 2H), 1.80-1.70 (m, 1H), 1.46-1.44 (m, 6H), 1.44-1.42 (m, 10H).

Step 2. (3R)-1-Methyl-N-[1-(propan-2-yl)-1H-pyrazol-4-yl]piperidin-3-amine

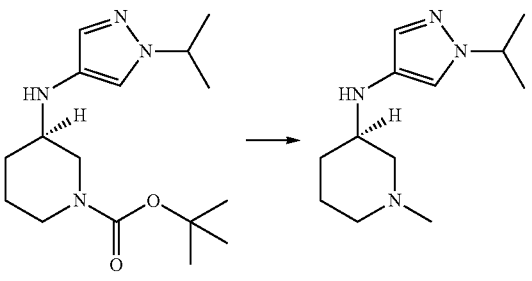 [SMILES: CC(C)n1cc(N[C@@H]2CCCN(C(=O)OC(C)(C)C)C2)cn1 ; CC(C)n1cc(N[C@@H]2CCCN(C)C2)cn1]

To a solution of tert-butyl (3R)-3-[(1-isopropylpyrazol-4-yl)amino]piperidine-1-carboxylate (650 mg, 2.11 mmol) in THF (20 ml) cooled to 0° C. was added lithium aluminium hydride (800 mg, 21.1 mmol). The RM was stirred at 0° C. for 20 min, then heated at 85° C. for 3 h. The RM was treated dropwise with ice-cold water (1 ml) and the resulting mixture stirred for 10 min, then 10% NaOH (1 ml) was added dropwise. The resulting mixture was filtered through Celite and the filtrate concentrated in vacuo to give the title compound as a yellow liquid. LCMS (ESI): m/z: $[M+H]^+$=223.2.

Step 3. Tert-butyl N-{[(3R)-1-methylpiperidin-3-yl][1-(propan-2-yl)-1H-pyrazol-4-yl]sulfamoyl}carbamate

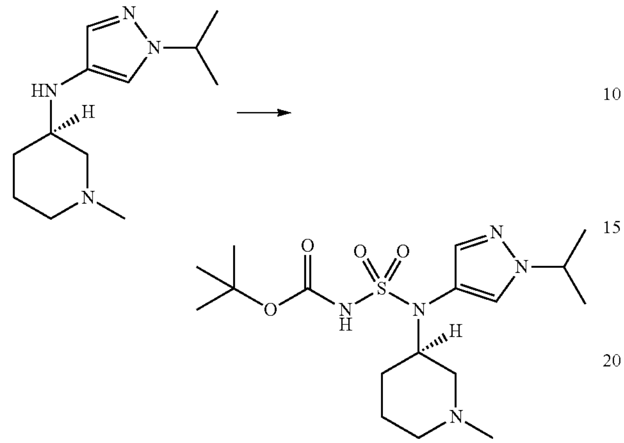

To a solution of (3R)—N-(1-isopropylpyrazol-4-yl)-1-methyl-piperidin-3-amine (700 mg, 3.15 mmol) in DCM (5 ml) cooled to 0° C. was added DIPEA (1.65 ml, 9.45 mmol) and the solution stirred for 20 min. To the RM was added a solution of tert-butyl N-chlorosulfonylcarbamate (0.94 M in DCM, 3.34 ml) and the RM stirred at 0° C. for 4 h. The solution was concentrated in vacuo and the resulting residue purified by prep-HPLC (column: Phenomenex Luna C18 250×50 mm, 10 m; mobile phase: [water (0.1% TFA)-ACN]; B: 15-45%, 20 min) to give the title compound as a white solid. Y=24%. $^1$H NMR (400 MHz, MeOD) δ 7.75 (s, 1H), 7.40 (s, 1H), 4.57-4.48 (m, 2H), 3.73 (d, J=8 Hz, 1H), 3.40 (d, J=11 Hz, 1H), 2.90 (s, 3H), 2.85-2.71 (m, 2H), 2.15-2.01 (m, 2H), 1.90-1.80 (m, 1H), 1.54 (s, 9H), 1.51-1.48 (m, 6H), 1.40-1.25 (m, 1H).

Step 4. N-[(3R)-1-Methylpiperidin-3-yl]-N-[1-(propan-2-yl)-1H-pyrazol-4-yl]aminosulfonamide Hydrochloride

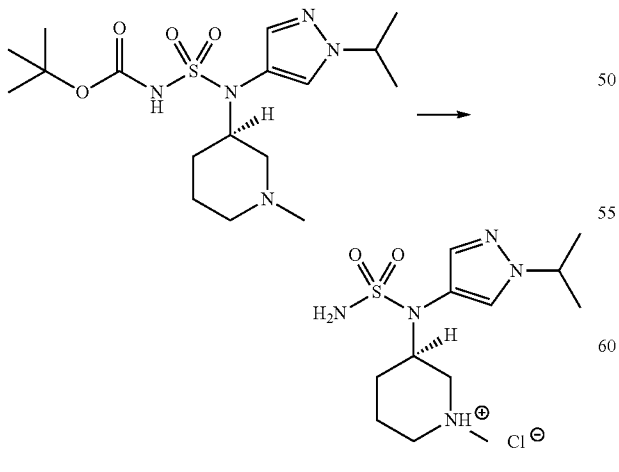

A solution of tert-butyl N-{[(3R)-1-methylpiperidin-3-yl][1-(propan-2-yl)-1H-pyrazol-4-yl]sulfamoyl}carbamate (100 mg, 0.21 mmol) in 4 M HCl/EtOAc (20 ml) was stirred at rt for 1 h. The solution was concentrated in vacuo to give the title compound as a yellow solid. LCMS (ESI): m/z: $[M+H]^+$=302.2.

Intermediate 26. 2,5-Diethyl-3-isocyanatofuran

Step 1. Ethyl 2,5-diethylfuran-3-carboxylate

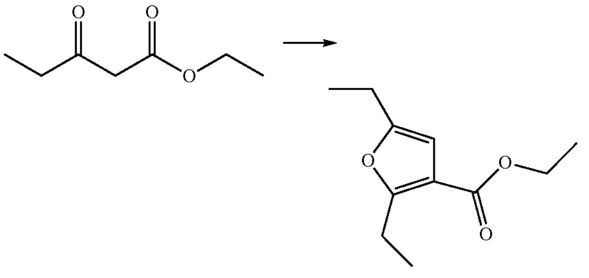

To a solution of butanal (2.54 ml, 28.8 mmol) in MeCN (50 ml) was added ethyl 3-oxopentanoate (4.95 ml, 34.7 mmol), N-bromosuccinimide (6.17 g, 34.7 mmol) and $AlCl_3$ (231 mg, 1.73 mmol). The RM was stirred at 80° C. for 4 h. The solution was concentrated under reduced pressure and the resulting residue purified by column chromatography (silica, 9-17% EtOAc in petrol) to give the title compound as a white solid. Y=46%. $^1$H NMR (400 MHz, chloroform-d) δ 6.22 (s, 1H), 4.27 (q, J=7 Hz, 2H), 2.97 (q, J=7 Hz, 2H), 2.60 (q, J=7 Hz, 2H), 1.34 (t, J=7 Hz, 3H), 1.26-1.20 (m, 6H).

Step 2. 2,5-Diethylfuran-3-carboxylic Acid

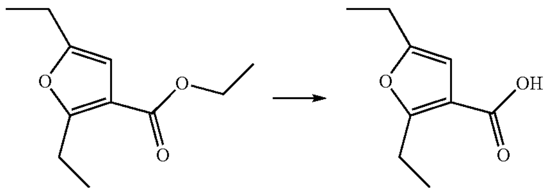

To a solution of ethyl 2,5-diethylfuran-3-carboxylate (3.1 g, 15.8 mmol) in EtOH (24 ml) and $H_2O$ (6 ml) was added NaOH (632 mg, 15.8 mmol). The RM was stirred at 80° C. for 1 h. The solution was concentrated under reduced pressure to remove EtOH and the aqueous phase was adjusted to pH~3 with addition of 1 M HCl (aq.). The mixture was filtered and the solid dried to give the title compound as a white solid. Y=75%.

Step 3. Tert-butyl N-(2,5-diethylfuran-3-yl)carbamate

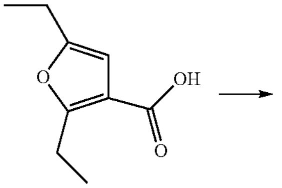

-continued

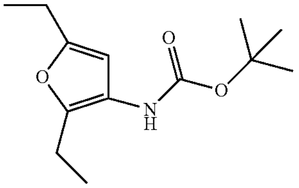

To a solution of 2,5-diethylfuran-3-carboxylic acid (1.0 g, 5.95 mmol) in tert-butanol (10 ml) were added DPPA (1.29 ml, 5.95 mmol) and DIPEA (1.55 ml, 8.92 mmol). The RM was stirred at 90° C. for 12 h. The solution was concentrated under reduced pressure and the resulting residue purified by column chromatography (silica, 5-10% EtOAc in petrol) to give the title compound as a yellow oil. Y=37%.

Step 4. 2,5-Diethylfuran-3-amine Hydrochloride

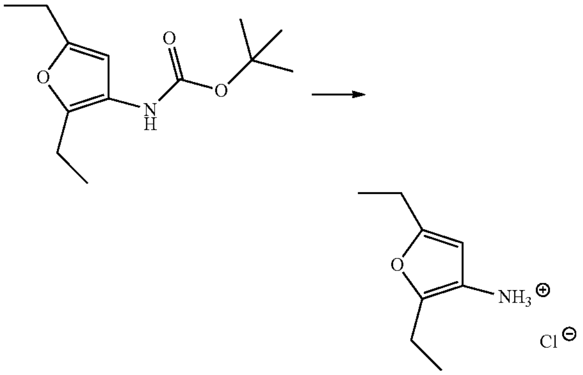

A solution of tert-butyl N-(2,5-diethyl-3-furyl)carbamate (140 mg, 0.59 mmol) in 4 M HCl in EtOAc (2 ml) was stirred at rt for 1 h. The solution was concentrated under reduced pressure to give the title compound as a white solid. Y=100%.

Step 5. 2,5-Diethyl-3-isocyanatofuran

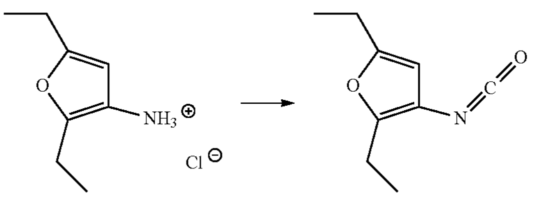

To a solution of 2,5-diethylfuran-3-amine hydrochloride (103 mg, 0.59 mmol) in dioxane (1 ml) at 40° C. was added trichloromethyl carbonochloridate (85 μl 0.70 mmol). The RM was stirred at 70° C. for 1 h, then concentrated under reduced pressure to give the title compound as an oil. This was used directly. LCMS in MeOH (ESI): m/z: $[M+MeOH+H]^+$=198.2.

Intermediate 27. 2,5-Diethyl-4-isocyanato-1,3-thiazole

Step 1. Methyl 2-(hydroxyimino)-3-oxopentanoate

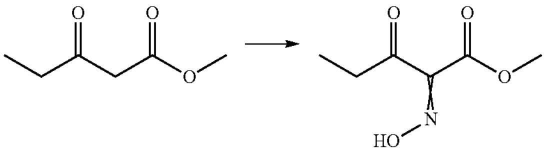

To a solution of methyl 3-oxopentanoate (1.90 ml, 15.4 mmol) in acetic acid (2.4 ml) was added dropwise a solution of 6.2 M $NaNO_2$ in water (2.60 ml, 16.1 mmol) while the reaction temperature was kept near 15° C. The RM was stirred at 15° C. for 2 h. The RM was extracted with EtOAc (3×5 ml). The combined organic phase was washed with brine (3 ml), dried with anhydrous $Na_2SO_4$, filtered and concentrated under vacuum to give the title compound as a yellow oil. LCMS (ESI): m/z: $[M+H]^+$=160.0.

Step 2. Methyl 2-amino-3-oxopentanoate Hydrochloride

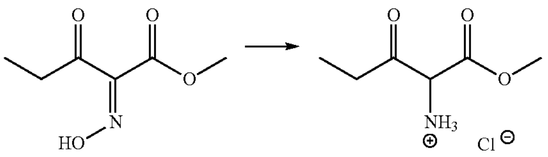

To a solution of methyl-2-hydroxyimino-3-oxo-pentanoate (2.5 g, 15.7 mmol) and 12 M HCl (1.31 ml) in MeOH (14.4 ml) under $N_2$ was added 10% Pd/C (50% in water, 1.2 g). The RM was stirred at rt under $H_2$ (15 psi) for 5 h. The solution was filtered through Celite and the filtrate concentrated under vacuum to give the title compound as a yellow liquid. LCMS (ESI): m/z: $[M+H]^+$=146.1.

Step 3. Methyl 3-oxo-2-propanamidopentanoate

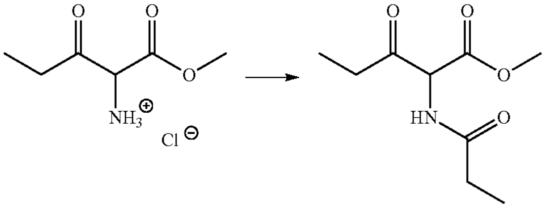

To a solution of methyl 2-amino-3-oxo-pentanoate hydrochloride (3.0 g, 16.5 mmol) in THF (40 ml) was added propanoyl chloride (1.91 ml, 20.7 mmol) and N-methylmorpholine (3.41 ml, 31.0 mmol) and the reaction stirred at rt for 5 h. The solution was concentrated under vacuum and the resulting residue purified by silica gel chromatography (9-100% EtOAc in petrol) to give the title compound as a yellow oil. Y=60%. LCMS (ESI): m/z: $[M+H]^+$ 202.1.

Step 4. Methyl 2,5-diethyl-1,3-thiazole-4-carboxylate

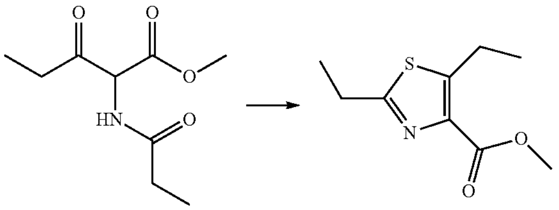

To a solution of methyl 3-oxo-2-(propanoylamino)pentanoate (2.0 g, 9.94 mmol) in THF (30 ml) was added Lawesson's reagent (8.04 g, 19.9 mmol). The RM was stirred at 60° C. for 5 h. The solution was concentrated under vacuum and the resulting residue purified by silica gel chromatography (9-25% EtOAc in petrol) to give the title compound as a yellow oil. Y=70%. LCMS (ESI): m/z: $[M+H]^+$=200.2.

Step 5. Diethyl-1,3-thiazole-4-carboxylic Acid

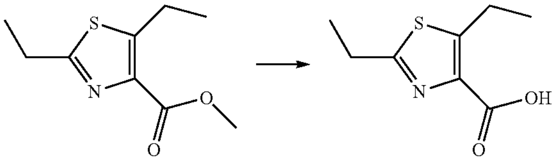

To a solution of methyl 2,5-diethylthiazole-4-carboxylate (1.0 g, 5.02 mmol) in THF (8 ml) and $H_2O$ (2 ml) cooled to 0° C. was added lithium hydroxide monohydrate (632 mg, 15.1 mmol). The mixture was stirred at rt for 2 h. The RM was diluted with EtOAc (5 ml) and washed with water (3×3 ml). The combined aqueous phases were acidified to pH 3-4 with addition of 1 M HCl. The resulting mixture was extracted with EtOAc (3×3 ml). The combined organic phases were washed with brine (2 ml), dried by anhydrous $Na_2SO_4$ and concentrated under reduced pressure to give the title compound 2,5-diethylthiazole-4-carboxylic acid as a yellow oil. LCMS (ESI): m/z: $[M+H]^+$=186.1.

Step 6. Tert-butyl N-(2,5-diethyl-1,3-thiazol-4-yl)carbamate

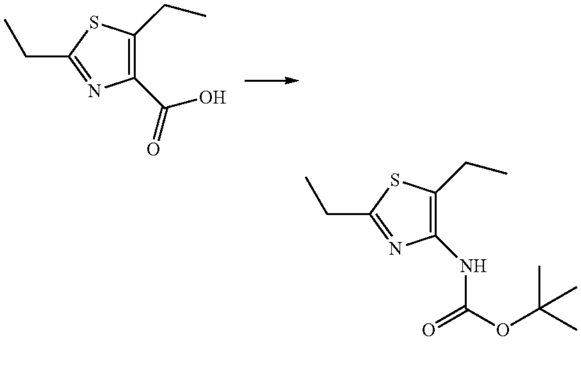

To a solution of 2,5-diethylthiazole-4-carboxylic acid (1.1 g, 5.94 mmol) in tert-butanol (25 ml) at rt was added diphenylphosphorylazide (1.29 ml, 5.94 mmol) and DIPEA (1.55 ml, 8.91 mmol). The RM was stirred at 85° C. for 4 h. The solution was concentrated under vacuum and the resulting residue purified by silica gel chromatography (9-50% EtOAc in petrol) to give the title compound as a yellow solid. Y=72%. H NMR (400 MHz, MeOD) δ 2.94-2.88 (m, 2H), 2.73-2.66 (m, 2H), 1.49 (s, 9H), 1.32 (t, J=8 Hz, 3H), 1.24 (t, J=8 Hz, 3H).

Step 7. Diethyl-1,3-thiazol-4-amine

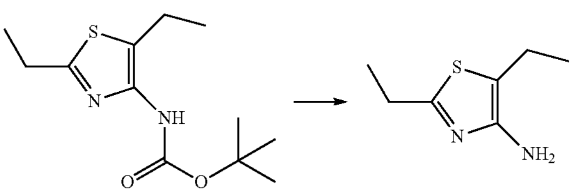

A solution of tert-butyl N-(2,5-diethylthiazol-4-yl)carbamate (150 mg, 0.59 mmol) in TFA (1 ml) and DCM (5 ml) was stirred at rt for 1 h. The solution was concentrated under vacuum and the resulting residue purified by prep-TLC (9-50% EtOAc in petrol) to give the title compound as a yellow oil. Y=66%. LCMS (ESI): m/z: $[M+H]^+$=157.3.

Step 8. 2,5-Diethyl-4-isocyanato-1,3-thiazole

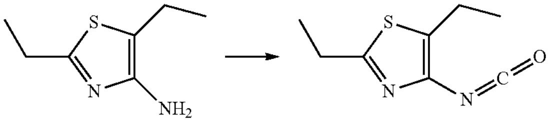

To a solution of 2,5-diethylthiazol-4-amine (60 mg, 0.38 mmol) in DCM (2 ml) cooled to 0° C. was added a solution of triphosgene (66 mg, 0.22 mmol) in DCM (1 ml), followed by a solution of triethylamine (93 μl, 0.67 mmol) in DCM (1 ml). The RM was stirred at 0° C. for 1 h. The solution was concentrated under vacuum to give the title compound as a yellow oil. LCMS in MeOH (ESI): m/z: $[M+MeOH+H]^+$=215.2.

Intermediate 28. 3-Isocyanato-2-methyl-4H,5H,6H-cyclopenta[b]thiophene

Step 1. Methyl 2-amino-4H,5H,6H-cyclopenta[b] thiophene-3-carboxylate

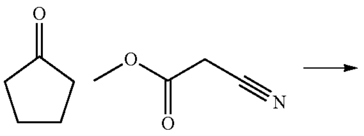

-continued

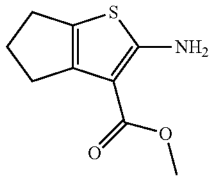

To a solution of cyclopentanone (1.05 ml, 11.9 mmol) in MeOH (100 ml) was added methyl 2-cyanoacetate (1.16 ml, 13.1 mmol), diethylamine (1.35 ml, 13.1 mmol) and sulfur (419 mg, 13.1 mmol). The RM was sonicated in an ultrasound bath at 25° C. for 1 h. The RM was concentrated under reduced pressure and the resulting residue purified by column chromatography (silica, 0-16% EtOAc in petrol) to give the title compound as a white solid. Y=26%. $^1$H NMR (400 MHz, chloroform-d) δ 5.86 (s, 2H), 3.79 (s, 3H), 2.84-2.77 (m, 2H), 2.75-2.68 (m, 2H), 2.36-2.26 (m, 2H).

Step 2. Methyl 2-bromo-4H,5H,6H-cyclopenta[b]thiophene-3-carboxylate

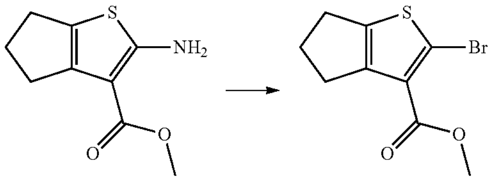

To a mixture of $CuBr_2$ (5.23 g, 23.4 mmol) in MeCN (32 ml) cooled to 0° C. was added tert-butyl nitrite (2.50 ml, 21.1 mmol). The RM was treated portionwise with methyl 2-amino-5,6-dihydro-4H-cyclopenta[b]thiophene-3-carboxylate (3.35 g, 17.0 mmol). The RM was stirred at 0° C. for 2 h, then at rt for a further 3 h. The RM was poured into water (100 ml) and the resulting mixture extracted with EtOAc (3×50 ml). The combined organic phase was washed with brine, dried with anhydrous $Na_2SO_4$, filtered and concentrated in vacuo. The resulting residue was purified by column chromatography (silica, 0-17% EtOAc in petrol) to give the title compound as a white solid. Y=23%. $^1$H NMR (400 MHz, chloroform-d) δ 3.86 (s, 3H), 2.97-2.91 (m, 2H), 2.88-2.82 (m, 2H), 2.45-2.35 (m, 2H).

Step 3. Methyl 2-methyl-4H,5H,6H-cyclopenta[b]thiophene-3-carboxylate

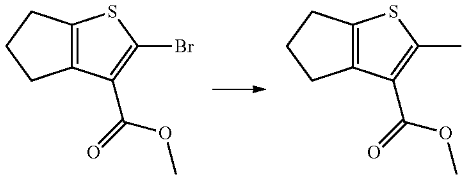

To a solution of methyl 2-bromo-5,6-dihydro-4H-cyclopenta[b]thiophene-3-carboxylate (500 mg, 1.91 mmol) in dioxane (10 ml) under $N_2$ was added methylboronic acid (229 mg, 3.83 mmol), CsF (1.02 g, 6.70 mmol) and Pd(dppf) $Cl_2 \cdot CH_2Cl_2$ (172 mg, 0.21 mmol). The RM was stirred at 90° C. for 12 h. The RM was allowed to cool and treated with water (10 ml). The mixture was extracted with EtOAc (3×20 ml). The combined organic phase was concentrated under reduced pressure and the resulting residue purified by column chromatography (silica, 9-17% EtOAc in petrol), to give the title compound as a white solid. Y=28%. $^1$H NMR (400 MHz, chloroform-d) δ 3.82 (s, 3H), 2.91-2.88 (m, 2H), 2.82 (t, J=7 Hz, 2H), 2.70 (s, 3H), 2.40 (m, 2H).

Step 4. 2-Methyl-4H,5H,6H-cyclopenta[b]thiophene-3-carboxylic Acid

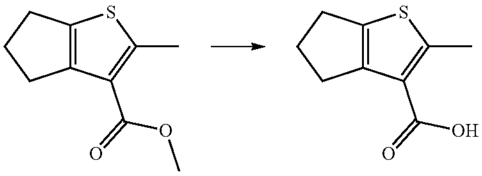

To a solution of methyl 2-methyl-5,6-dihydro-4H-cyclopenta[b]thiophene-3-carboxylate (210 mg, 1.07 mmol) in $H_2O$ (1 ml) and MeOH (2 ml) was added NaOH (86 mg, 2.14 mmol). The RM was stirred at 50° C. for 12 h. The solution was adjusted to pH~4 with addition of 4 M HCl (aq.). The mixture was extracted with EtOAc (3×5 ml) and the combined organic phase concentrated under reduced pressure to give the title compound as a white solid.

Step 5. Tert-butyl N-{2-methyl-4H,5H,6H-cyclopenta[b]thiophen-3-yl}carbamate

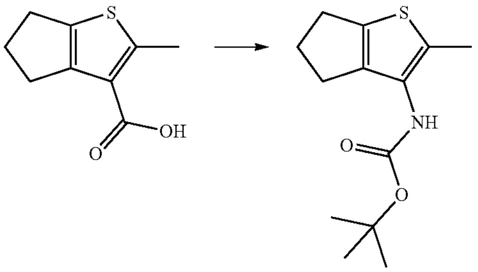 [SMILES: Cc1sc2c(c1C(=O)O)CCC2 ; Cc1sc2c(c1NC(=O)OC(C)(C)C)CCC2]

To a solution of 2-methyl-5,6-dihydro-4H-cyclopenta[b]thiophene-3-carboxylic acid (180 mg, 0.99 mmol) in tert-butanol (3 ml) was added DPPA (214 μl, 0.99 mmol) and DIPEA (258 μl, 1.48 mmol). The RM was stirred at 90° C. for 12 h. The solution was concentrated under reduced pressure and the resulting residue purified by prep-TLC (17% EtOAc in petrol) to give the title compound as a white solid. Y=48%. $^1$H NMR (400 MHz, chloroform-d) δ 5.90 (s, 1H), 2.82 (t, J=7 Hz, 2H), 2.67 (t, J=7 Hz, 2H), 2.43-2.34 (m, 2H), 2.29 (s, 3H), 1.50 (s, 9H).

Step 6. 2-Methyl-4H,5H,6H-cyclopenta[b]thiophen-3-amine Hydrochloride

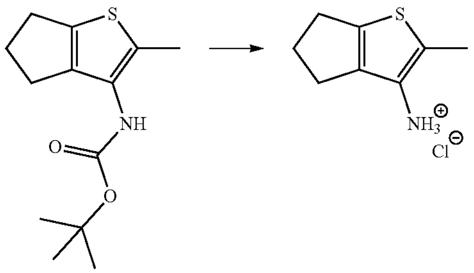

Tert-butyl N-(2-methyl-5,6-dihydro-4H-cyclopenta[b]thiophen-3-yl)carbamate (100 mg, 0.39 mmol) was dissolved in 4 M HCl in EtOAc (10 ml) and the mixture stirred at rt for 3 h. The RM was filtered and the filtrate concentrated under reduced pressure to give the title compound as a light yellow solid.

Step 7. 3-Isocyanato-2-methyl-4H,5H,6H-cyclopenta[b]thiophene

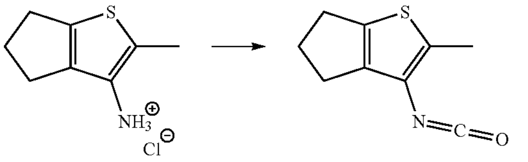

To a solution of 2-methyl-4H,5H,6H-cyclopenta[b]thiophen-3-amine hydrochloride (100 mg 0.53 mmol) in dioxane (2 ml) at 40° C. was added trichloromethyl carbonochloridate (63.6 µl, 0.53 mmol). The mixture was heated at 70° C. for 1 h. The RM was filtered and the filtrate concentrated under reduced pressure to give the title compound as an oil. This was used into the next step without further purification.

Intermediate 29. 5-Cyclopropyl-3-isocyanato-2-(propan-2-yl)thiophene

Step 1. Tert-butyl N-(5-cyclopropylthiophen-3-yl)carbamate

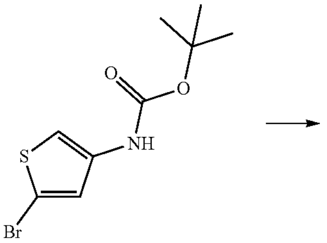

-continued

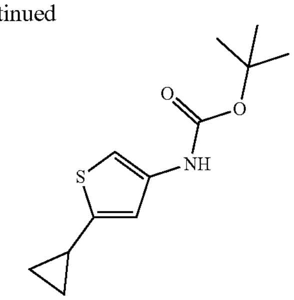

To a solution of tert-butyl N-(5-bromo-3-thienyl)carbamate (1.0 g, 3.59 mmol) in $H_2O$ (3 ml) and dioxane (15 ml) under nitrogen was added cyclopropylboronic acid (3.09 g, 35.9 mmol), $Pd_2(dba)_3$ (658 mg, 0.72 mmol), XPhos (686 mg, 1.44 mmol) and $K_2CO_3$ (2.98 g, 21.6 mmol). The solution was stirred at 110° C. for 12 h. The RM was diluted with water (10 ml) and extracted with EtOAc (3×10 ml). The combined organic phase was concentrated under reduced pressure and the resulting residue purified by column chromatography (silica, 9-17% EtOAc in petrol) to give the title compound as a yellow solid. Y=81%. LCMS (ESI): m/z: $[M+H]^+$=240.0.

Step 2. Tert-butyl N-(2-bromo-5-cyclopropylthiophen-3-yl)carbamate

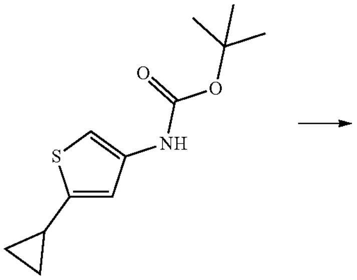

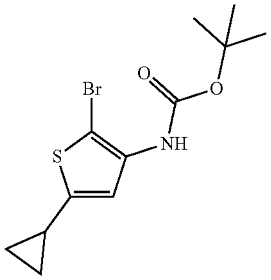

To a solution of tert-butyl N-(5-cyclopropyl-3-thienyl) carbamate (400 mg, 1.67 mmol) in THF (10 ml) at 0° C. under nitrogen was added NBS (297 mg, 1.67 mmol) and the RM stirred at rt for 2 h. The solution was concentrated under reduced pressure and the resulting residue purified by column chromatography (silica, 9-17% EtOAc in petrol) to give the title as a yellow solid. Y=79%. LCMS (ESI): m/z: $[M+H]^+$=319.9.

Step 3. Tert-butyl N-[5-cyclopropyl-2-(prop-1-en-2-yl)thiophen-3-yl]carbamate

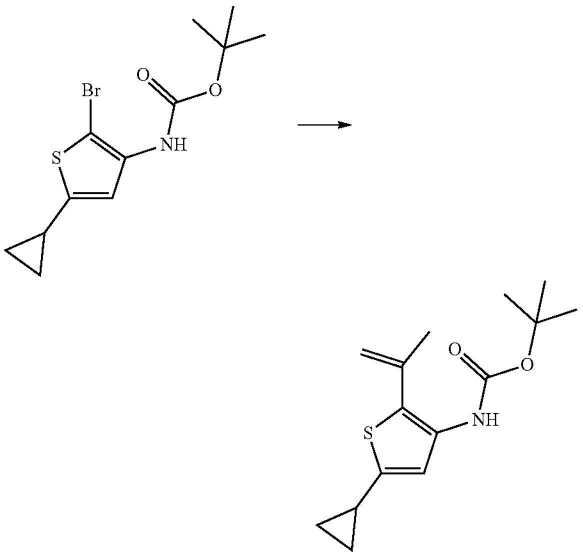

To a solution of tert-butyl N-(2-bromo-5-cyclopropyl-3-thienyl)carbamate (420 mg, 1.32 mmol) in THF (10 ml) and $H_2O$ (2 ml) under $N_2$ atmosphere were added 2-isopropenyl-4,4,5,5-tetramethyl-1,3,2-dioxaborolane (1.11 g, 6.60 mmol), $Na_2CO_3$ (420 mg, 3.96 mmol) and $Pd(PPh_3)_4$ (15 mg, 13.2 μmol). The RM was heated at 90° C. for 12 h. The RM was diluted with water (20 ml) and extracted with EtOAc (3x25 ml). The combined organic phase was concentrated under reduced pressure and the resulting residue purified by column chromatography (silica, 9-17% EtOAc in petrol) to give the title compound as a yellow solid. Y=89%. LCMS (ESI): m/z: $[M+H]^+$=280.1.

Step 4. Tert-butyl N-[5-cyclopropyl-2-(propan-2-yl) thiophen-3-yl]carbamate

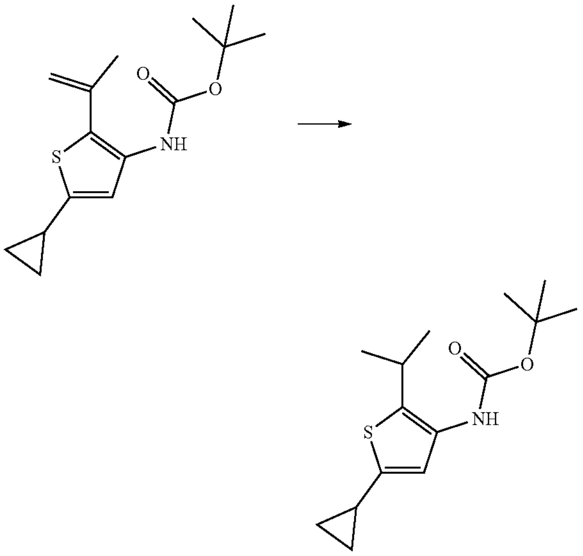

To a solution of tert-butyl N-(5-cyclopropyl-2-isopropenyl-3-thienyl)carbamate (320 mg, 1.15 mmol) in MeOH (15 ml) was added 10% Pd/C (50% in water, 90 mg). The RM was stirred under $H_2$ (15 psi) at rt for 1 h. The RM was filtered through Celite and the filtrate was concentrated under reduced pressure. The resulting residue was purified by prep-HPLC (column: Nano-micro Kromasil C18 100×40 mm, 3 μm; mobile phase: [water (0.1% TFA)-ACN]; B: 42-72%, 8 min) to give the title compound as a white solid. Y=53%. LCMS (ESI): m/z: $[M+H]^+$=282.1.

Step 5. 5-Cyclopropyl-2-(propan-2-yl)thiophen-3-amine Hydrochloride

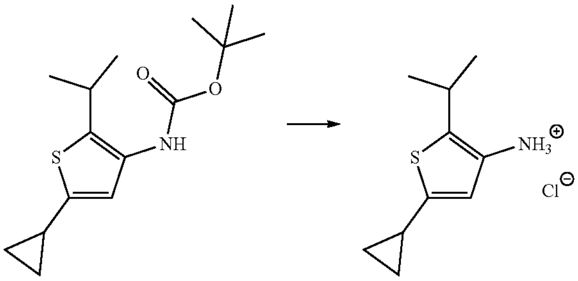 [SMILES: CC(C)c1sc(C2CC2)cc1NC(=O)OC(C)(C)C ; CC(C)c1sc(C2CC2)cc1[NH3+] ; [Cl-]]

A solution of tert-butyl N-(5-cyclopropyl-2-isopropyl-3-thienyl)carbamate (80 mg, 0.28 mmol) in 4 M HCl in EtOAc (4 ml) was stirred at rt for 1 h. The solution was concentrated under reduced pressure to give the title compound as a yellow solid. Y=99%. LCMS (ESI): m/z: $[M+H]^+$=182.0.

Step 6. 5-Cyclopropyl-3-isocyanato-2-(propan-2-yl) thiophene

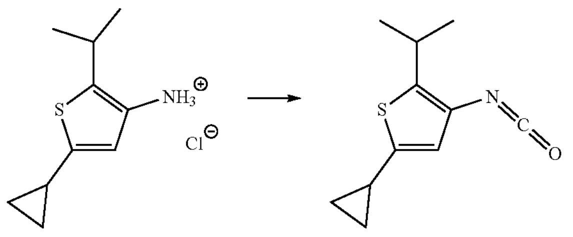

To a solution of 5-cyclopropyl-2-isopropyl-thiophen-3-amine hydrochloride (61 mg, 0.28 mmol) in dioxane (3 ml) warmed to 40° C. was added trichloromethyl carbonochloridate (40.6 μl, 0.34 mmol). The RM was stirred at 70° C. for 1 h. The solution was concentrated under reduced pressure to give the title compound as a yellow solid, which was used for the next step directly. LCMS in MeOH (ESI): m/z: $[M+MeOH+H]^+$=240.0.

Intermediate 30. 2-Cyclopropyl-3-isocyanato-5-(propan-2-yl)thiophene

Step 1. Tert-butyl N-(2,5-dibromothiophen-3-yl)carbamate

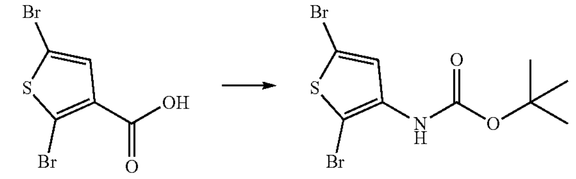

To a solution of 2,5-dibromothiophene-3-carboxylic acid (1.0 g, 3.50 mmol) in tert-butanol (10 ml) was added DPPA (758 μl, 3.50 mmol) and DIPEA (914 μl, 5.25 mmol). The RM was stirred at 90° C. for 12 h. The RM was filtered and the filtrate concentrated under reduced pressure to give a residue. This was purified by column chromatography (silica, 9% EtOAc in petrol) to give the title compound as a yellow solid. Y=64%. $^1$H NMR (400 MHz, chloroform-d) δ 7.66 (s, 1H), 6.54 (s, 1H), 1.54 (d, J=11 Hz, 9H).

Step 2. Tert-butyl N-[2-bromo-5-(prop-1-en-2-yl)thiophen-3-yl]carbamate

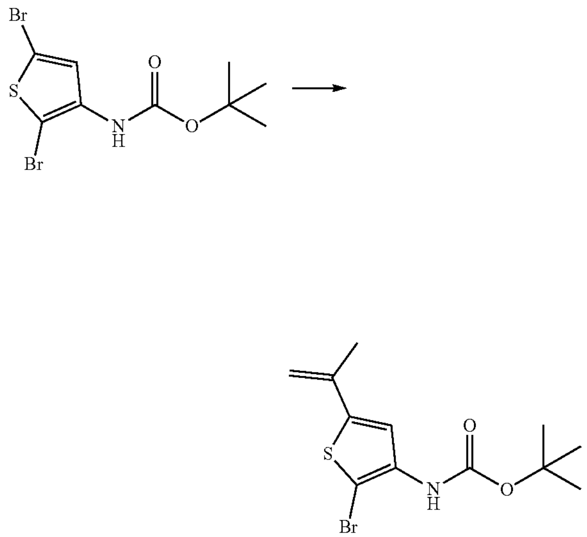

To a solution of tert-butyl N-(2,5-dibromo-3-thienyl)carbamate (200 mg, 0.56 mmol) in THF (4 ml) and $H_2O$ (0.8 ml) under $N_2$ was added 2-isopropenyl-4,4,5,5-tetramethyl-1,3,2-dioxaborolane (282 mg, 1.68 mmol), $Pd(PPh_3)_4$ (6.5 mg, 5.6 μmol) and $Na_2CO_3$ (178 mg, 1.68 mmol). The resulting mixture was stirred at 90° C. for 8 h. The RM was concentrated under reduced pressure and the resulting residue purified by prep-TLC (9% EtOAc in petrol) to give the title compound as a yellow solid. Y=28%. $^1$H NMR (400 MHz, chloroform-d) δ 7.52 (s, 1H), 6.54 (s, 1H), 5.30 (s, 1H), 4.96 (s, 1H), 2.11 (s, 3H), 1.53 (s, 9H).

Step 3. Tert-butyl N-[2-cyclopropyl-5-(prop-1-en-2-yl)thiophen-3-yl]carbamate

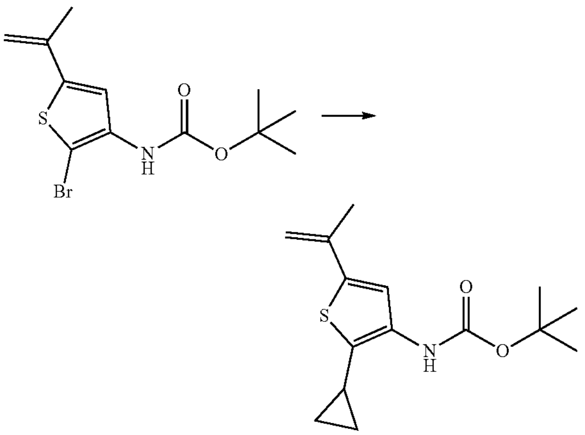

To a solution of tert-butyl N-(2-bromo-5-isopropenyl-3-thienyl)carbamate (150 mg, 0.47 mmol) in dioxane (3 ml) and $H_2O$ (0.6 ml) was added cyclopropylboronic acid (405 mg, 4.71 mmol), $Pd_2(dba)_3$ (86 mg, 94 μmol), XPhos (90 mg, 0.19 mmol) and $K_2CO_3$ (391 mg, 2.83 mmol). The resulting mixture was stirred at 110° C. for 12 h. The mixture was concentrated under reduced pressure and the resulting residue purified by prep-TLC (9% EtOAc in petrol) to give the title compound as a yellow solid. Y=46%. $^1$H NMR (400 MHz, chloroform-d) δ 7.39 (s, 1H), 6.48 (s, 1H), 5.26 (s, 1H), 4.86 (s, 1H), 2.10 (s, 3H), 1.82-1.71 (m, 1H), 1.53 (s, 9H), 1.02-0.94 (m, 2H), 0.72-0.66 (m, 2H).

Step 4. Tert-butyl N-[2-cyclopropyl-5-(propan-2-yl)thiophen-3-yl]carbamate

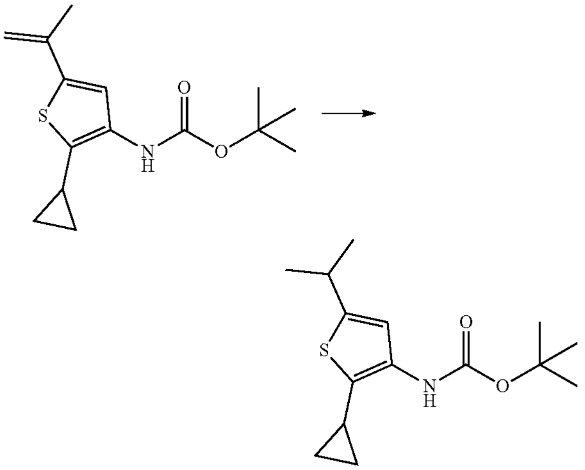 [SMILES: C=C(C)c1cc(NC(=O)OC(C)(C)C)c(Br)s1 ; C=C(C)c1cc(NC(=O)OC(C)(C)C)c(C2CC2)s1]

To a solution of tert-butyl N-(2-cyclopropyl-5-isopropenyl-3-thienyl)carbamate (60 mg, 0.21 mmol) in MeOH (3 ml) under $N_2$ atmosphere was added 10% Pd/C (50% in water, 20 mg). The mixture was degassed and purged with $H_2$ three times. The mixture was stirred under $H_2$ (15 Psi) at rt for 10 min. The mixture was filtered through Celite and the filtrate concentrated under reduced pressure to give the title compound as a white solid. The solid was used in the next step without further purification. Y=83%. $^{1}H$ NMR (400 MHz, chloroform-d) δ 7.18 (s, 1H), 6.48 (s, 1H), 3.10-2.97 (m, 1H), 1.78-1.69 (m, 1H), 1.53 (s, 9H), 1.28 (d, J=7 Hz, 6H), 0.96-0.91 (m, 2H), 0.68-0.63 (m, 2H).

Step 5. 2-Cyclopropyl-5-(propan-2-yl)thiophen-3-amine Hydrochloride

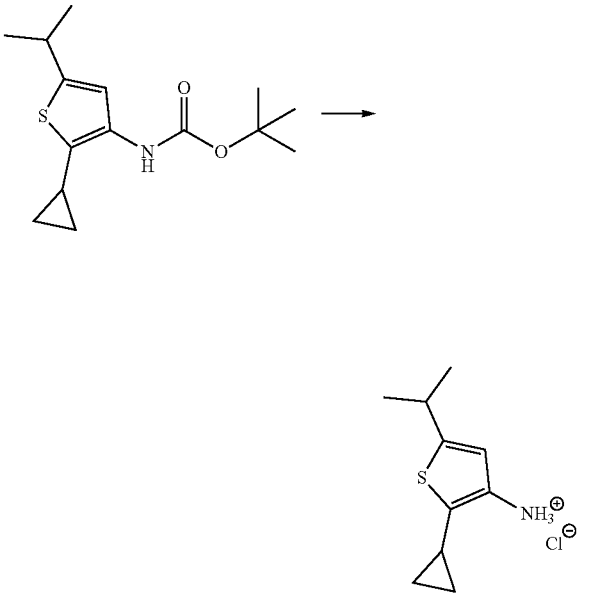

A solution of tert-butyl N-(2-cyclopropyl-5-isopropyl-3-thienyl)carbamate (50 mg, 0.18 mmol) in 4 M HCl in EtOAc (2 ml) was stirred at rt for 0.5 h. The mixture was concentrated under reduced pressure to give the title compound as a white solid. LCMS (ESI): m/z: $[M+H]^+$=182.1.

Step 6. 2-Cyclopropyl-3-isocyanato-5-(propan-2-yl) thiophene

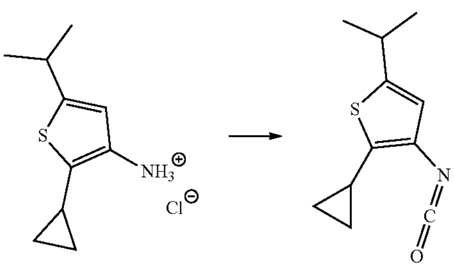

To a solution of 2-cyclopropyl-5-(propan-2-yl)thiophen-3-amine hydrochloride (38 mg, 175 μmol) in dioxane (2 ml) at 40° C. was added trichloromethyl carbonochloridate (23 μl, 192 μmol). The resulting mixture was stirred at 70° C. for 1 h. The mixture was concentrated under reduced pressure to give the title compound as a yellow solid. This was used directly without further purification. LCMS in MeOH (ESI): m/z: $[M+H+MeOH]^+$=240.1.

Intermediate 31. 2-Chloro-3-isocyanato-5-(propan-2-yl)thiophene

Step 1. Tert-butyl N-(5-bromothiophen-3-yl)carbamate

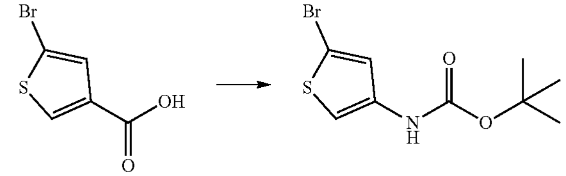

To a solution of 5-bromothiophene-3-carboxylic acid (3.0 g, 14.5 mmol) in tert-butanol (30 ml) was add DPPA (3.14 ml, 14.5 mmol) and DIPEA (3.79 ml, 21.7 mmol). The RM was stirred at 85° C. under $N_2$ for 12 h, then concentrated in vacuo. The resulting residue was purified by silica gel chromatography (9-17% EtOAc in petrol) to give the title compound as a white solid. Y=62%.

Step 2. Tert-butyl N-(5-bromo-2-chlorothiophen-3-yl)carbamate

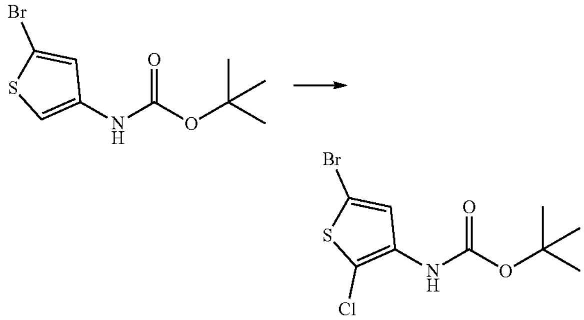

To a mixture of tert-butyl N-(5-bromothiophen-3-yl)carbamate (600 mg, 2.16 mmol) in DMF (25 ml) was added NCS (432 mg, 3.24 mmol). The mixture was stirred at 60° C. for 2 h. The RM was diluted with water (30 ml) and extracted with EtOAc (3×20 ml). The combined organic phase was washed with brine (3×20 ml), dried with anhydrous $Na_2SO_4$, filtered and concentrated under vacuum to give a residue. This was purified by silica gel chromatography (9-17% EtOAc in petrol) to give the title compound as yellow oil. Y=89%. $^{1}H$ NMR (400 MHz, MeOD) δ 7.26 (s, 1H), 1.52 (s, 9H).

Step 3. Tert-butyl N-[2-chloro-5-(prop-1-en-2-yl) thiophen-3-yl]carbamate

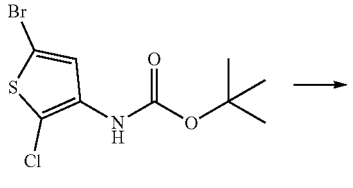

-continued

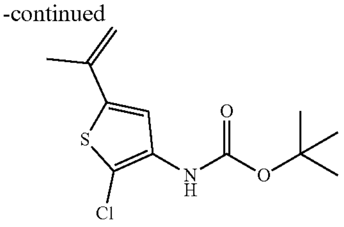

To a solution of tert-butyl N-(5-bromo-2-chloro-3-thienyl)carbamate (600 mg, 1.92 mmol) in THF (10 ml) and $H_2O$ (2 ml) under $N_2$ atmosphere were added 2-isopropenyl-4,4,5,5-tetramethyl-1,3,2-dioxaborolane (1.61 g, 9.60 mmol), $Pd(PPh_3)_4$ (22 mg, 19.2 μmol) and $Na_2CO_3$ (610 mg, 5.76 mmol). The mixture was stirred at 90° C. for 8 h. The mixture was concentrated in vacuo and the resulting residue purified by silica gel chromatography (9-17% EtOAc in petrol) to give the title as a white solid. $^1H$ NMR (400 MHz, MeOD) δ 7.27 (s, 1H), 5.69 (s, 1H), 5.60 (s, 1H), 1.51 (s, 3H), 1.26 (s, 9H).

Step 4. Tert-butyl N-[2-chloro-5-(propan-2-yl)thiophen-3-yl]carbamate

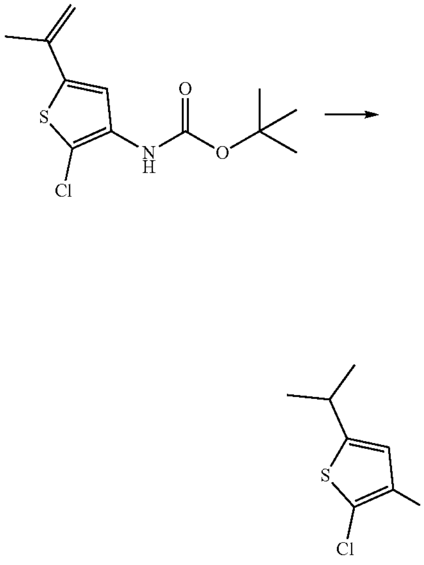

To a solution of tert-butyl N-[2-chloro-5-(prop-1-en-2-yl)thiophen-3-yl]carbamate (400 mg crude, 1.46 mmol) in EtOAc (25 ml) under $N_2$ was added 10% Pd/C (50% in water, 200 mg). The suspension was degassed under vacuum and purged with $H_2$ three times. The mixture was stirred under $H_2$ (15 psi) atmosphere at rt for 2 h. The RM was filtered and the filtrate concentrated under reduced pressure. The residue was purified by prep-HPLC (column: Phenomenex Luna C18 250×50 mm, 10 μm; mobile phase: [water (0.1% TFA)-ACN]; B: 65-95%, 10 min) to give the title compound as yellow oil. Y=12%. $^1H$ NMR (400 MHz, MeOD) δ 7.01 (s, 1H), 3.10-3.00 (m, 1H), 1.51 (s, 9H), 1.30-1.26 (d, J=7 Hz, 6H).

Step 5. 2-Chloro-5-(propan-2-yl)thiophen-3-amine Hydrochloride

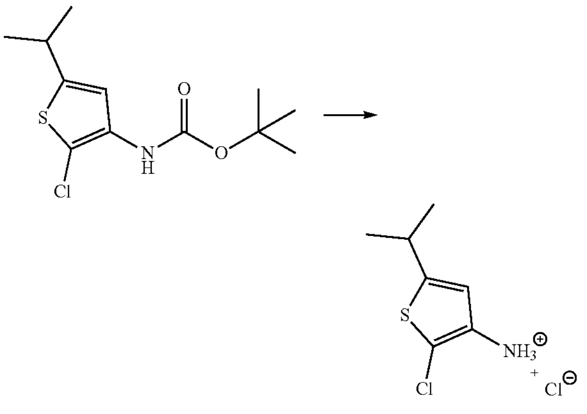

The solution of tert-butyl N-(2-chloro-5-isopropyl-3-thienyl)carbamate (50 mg, 0.18 mmol) in 4 M HCl in EtOAc (2 ml) was stirred at rt for 1 h. The solution was concentrated in vacuo to give the title compound as a white solid.

Step 6. 2-Chloro-3-isocyanato-5-(propan-2-yl)thiophene

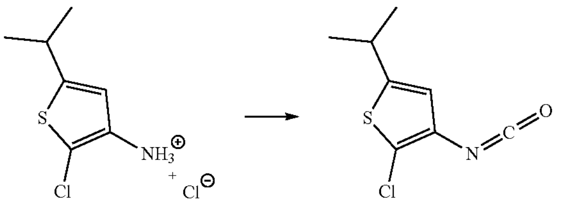

To a solution of 2-chloro-5-(propan-2-yl)thiophen-3-amine hydrochloride (40 mg, 0.19 mmol) in dioxane (2 ml) at 40° C. was added trichloromethyl carbonochloridate (25.0 μl, 0.21 mmol). The RM was stirred at 70° C. for 1 h, then concentrated in vacuo to give the title compound as an oil. This was used for the next step directly.

Intermediate 32. N-(1-Methyl-1H-pyrazol-4-yl)-N-[(3R)-1-methylpiperidin-3-yl]aminosulfonamide Hydrochloride Step 1. Tert-butyl (3R)-3-[(1-methyl-1H-pyrazol-4-yl)amino]piperidine-1-carboxylate

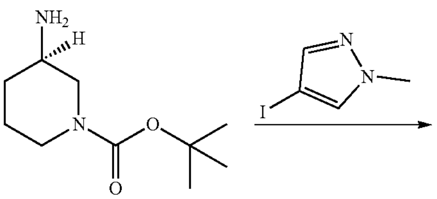

-continued

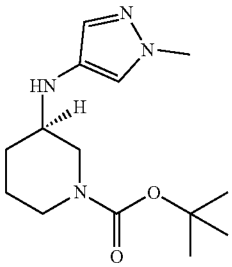

To a solution of 4-iodo-1-methyl-pyrazole (3.12 g, 15.0 mmol) in toluene (20 ml) under $N_2$ was added tert-butyl (3R)-3-aminopiperidine-1-carboxylate (2.0 g, 10.0 mmol), sodium tert-butoxide (1.92 g, 20.0 mmol) and [2-(2-aminoethyl)phenyl]-chloro-palladium; ditert-butyl-[2-(2,4,6-triisopropylphenyl)phenyl]phosphane (686 mg, 1.0 mmol). The RM was stirred at 100° C. for 3 h. The solution was concentrated under reduced pressure and the resulting residue purified by prep-HPLC (column: Agela DuraShell C18 250×50 mm, 10 μm; mobile phase: [water (10 mM $NH_4HCO_3$)-ACN]; B: 15-45%, 22 min) to give the title compound as a yellow solid. Y=360%.

Step 2. (3R)-1-Methyl-N-(1-methyl-1H-pyrazol-4-yl)piperidin-3-amine

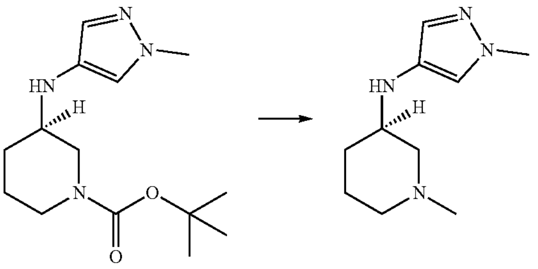 [SMILES: Cn1cc(N[C@@H]2CCCN(C(=O)OC(C)(C)C)C2)cn1 ; CN1CCC[C@@H](Nc2cnn(C)c2)C1]

To a solution of tert-butyl (3R)-3-[(1-methylpyrazol-4-yl)amino]piperidine-1-carboxylate (1.0 g, 3.57 mmol) in THF (20 ml) cooled to 0° C. was added lithium aluminium hydride (1.35 g, 35.7 mmol). The RM was stirred at 0° C. for 20 min, then heated at reflux for 4 h. The reaction was quenched with dropwise addition of ice-cold water (1.4 ml). The RM was stirred for 10 min then treated dropwise with 10% NaOH aq. (1.4 ml). The resulting mixture was filtered through Celite and the filtrate concentrated under reduced pressure to give the title compound as a yellow oil. LCMS (ESI): m/z: $[M+H]^+$=195.1.

Step 3. Tert-butyl N-[(1-methyl-1H-pyrazol-4-yl)[(3R)-1-methylpiperidin-3-yl]-sulfamoyl]carbamate

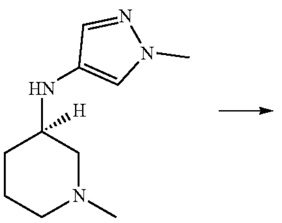

-continued

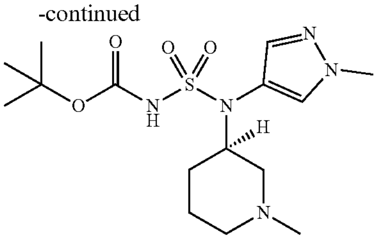

To a solution of (3R)-1-methyl-N-(1-methylpyrazol-4-yl)piperidin-3-amine (560 mg, 2.88 mmol) in DCM (4 ml) at 0° C. was added DIPEA (1.51 ml, 8.65 mmol) and the mixture stirred for 20 min. A solution of tert-butyl N-chlorosulfonylcarbamate (0.471 M in DCM, 6.1 ml, 2.88 mmol) was added and the resulting mixture stirred at rt for 2 hr The solution was concentrated under reduced pressure and the resulting residue purified by prep-HPLC (column: Phenomenex Luna C18 250×80 mm, 10 μm; mobile phase: [water (0.1% TFA)-ACN]; B: 1-30%, 22 min) to give the title compound as a white solid. Y=46%. LCMS (ESI): m/z: $[M+H]^+$=374.2.

Step 4. N-(1-Methyl-1H-pyrazol-4-yl)-N-[(3R)-1-methylpiperidin-3-yl]aminosulfonamide Hydrochloride

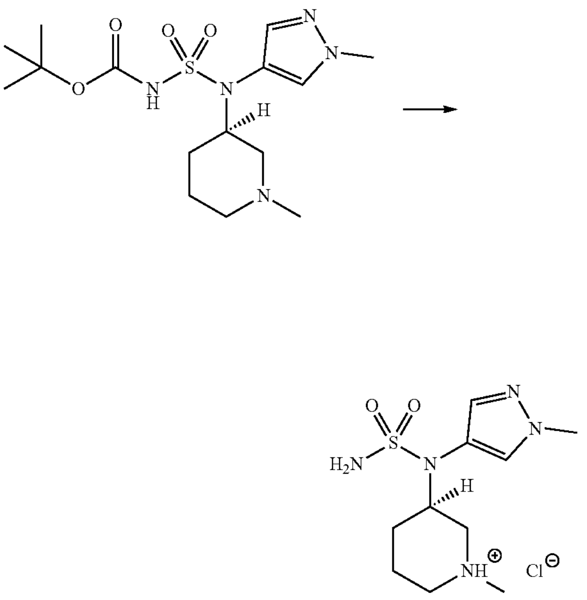

Tert-butyl N-[[(3R)-1-methyl-3-piperidyl]-(1-methylpyrazol-4-yl)sulfamoyl]carbamate (400 mg, 1.07 mmol) was dissolved into 4 M HCl in EtOAc (20 ml) and the mixture stirred at rt for 2 h. The solution was concentrated under reduced pressure to give the title compound as yellow solid. LCMS (ESI): m/z: $[M+H]^+$=274.1.

Intermediate 33. N-(1-Methyl-1H-pyrazol-4-yl)-N-[(3S)-1-methylpiperidin-3-yl]aminosulfonamide Hydrochloride Step 1. Tert-butyl (3S)-3-[(1-methyl-1H-pyrazol-4-yl)amino]piperidine-1-carboxylate

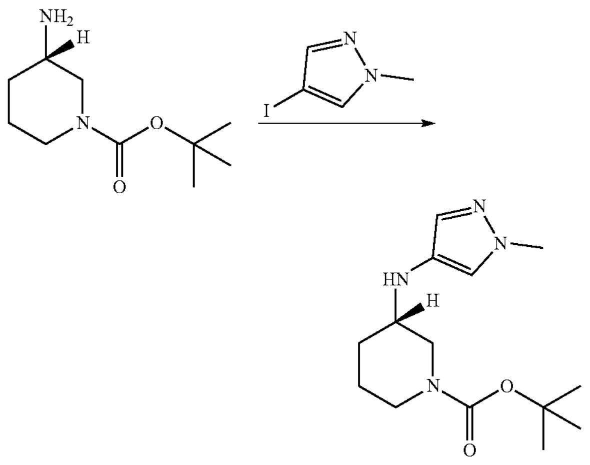

To a solution of 4-iodo-1-methyl-pyrazole (1.56 g, 7.5 mmol) in toluene (8 ml) under $N_2$ was added tert-butyl (3S)-3-aminopiperidine-1-carboxylate (1.0 g, 5.0 mmol), sodium tert-butoxide (0.96 g, 10.0 mmol) and [2-(2-aminoethyl)phenyl]-chloro-palladium; ditert-butyl-[2-(2,4,6-triisopropylphenyl)phenyl]phosphane (343 mg, 0.50 mmol). The RM was heated at 100° C. for 3 h under $N_2$ atmosphere. The RM was concentrated in vacuo and the resulting residue purified by prep-HPLC (column: Welch Xtimate C18 250×50 mm, 10 μm; mobile phase: [water (10 mM $NH_4HCO_3$)-ACN]; B: 20-50%, 10 min) to give the title compound as a white solid. Y=36%. LCMS (ESI): m/z: $[M+H]^+$=281.2.

Step 2. Tert-butyl (3S)-3-[({[(tert-butoxy)carbonyl]amino}sulfonyl)(1-methyl-1H-pyrazol-4-yl)amino]piperidine-1-carboxylate

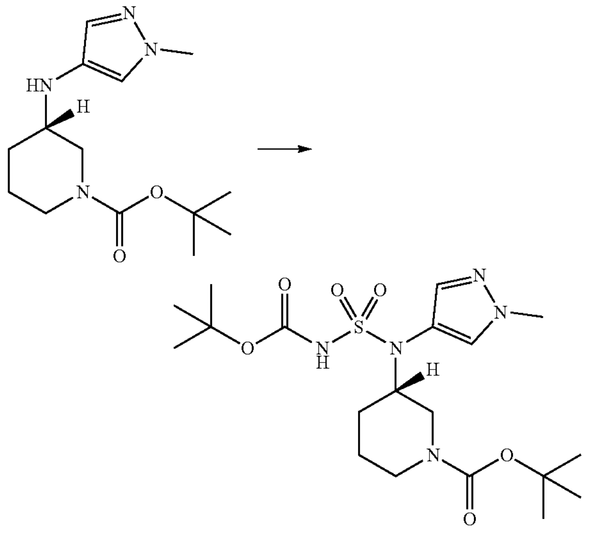

To a solution of tert-butyl (3S)-3-[(1-methylpyrazol-4-yl)amino]piperidine-1-carboxylate (500 mg, 1.78 mmol) in DCM (2 ml) cooled to 0° C. was added DIPEA (0.93 ml, 5.35 mmol) and the RM stirred for 20 min. A solution of tert-butyl N-chlorosulfonylcarbamate (1.41 M in DCM, 1.26 ml, 1.78 mmol) was added and the resulting solution stirred at 0° C. for 3 h. The solution was concentrated under vacuum and the resulting residue purified by prep-HPLC (column: Nano-micro Kromasil C18 80×25 mm, 3 μm; mobile phase: [water (0.1% TFA)-ACN]; B: 30-66%, 7 min), to give the title compound as a white solid. Y=7%. LCMS (ESI): m/z: $[M+H]^+$=460.2.

Step 3. N-(1-Methyl-1H-pyrazol-4-yl)-N-[(3S)-piperidin-3-yl]aminosulfonamide Hydrochloride

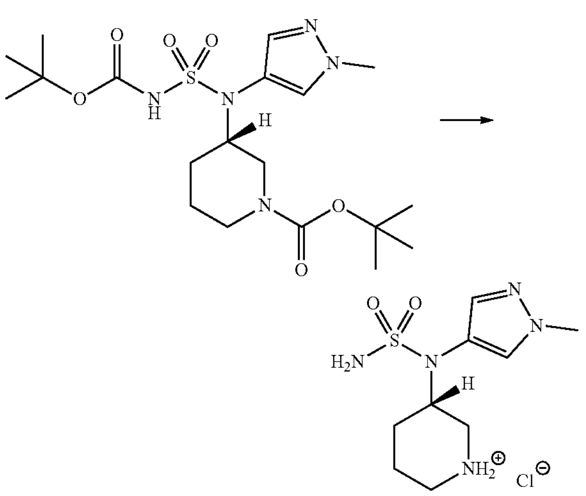

A mixture of tert-butyl (3S)-3-[({[(tert-butoxy)carbonyl]amino}sulfonyl)(1-methyl-1H-pyrazol-4-yl)amino]piperidine-1-carboxylate (60 mg, 131 μmol) in 4 M HCl in EtOAc (20 ml) was stirred at rt for 1 h. The solution was concentrated under vacuum to give the title compound as a yellow solid. LCMS (ESI): m/z: $[M+H]^+$=260.2.

Step 4. N-(1-methyl-1H-pyrazol-4-yl)-N-[(3S)-1-methylpiperidin-3-yl]aminosulfonamide

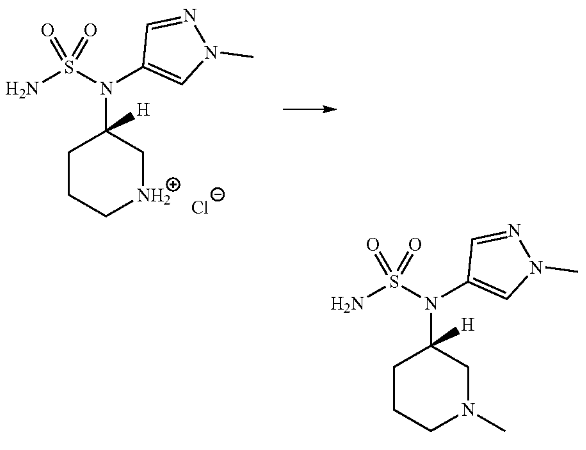

To a solution of N-(1-methyl-1H-pyrazol-4-yl)-N-[(3S)-piperidin-3-yl]aminosulfonamide hydrochloride (55 mg, 186 μmol) in MeOH (4 ml) cooled to 0° C. was added $NaBH_3CN$ (26 mg, 413 μmol) and formaldehyde (37% in water, 31 μl, 413 μmol) and the resulting solution stirred for 2 h. The reaction was diluted dropwise with water (2 ml) and the resulting mixture concentrated under vacuum to give the title compound as a yellow gum. LCMS (ESI): m/z: $[M+H]^+$ =274.1 $^1H$ NMR (400 MHz, MeOD) δ 7.70 (s, 1H), 7.45 (s, 1H), 4.22-4.14 (m, 1H), 3.89 (s, 3H), 3.41-3.33 (m, 1H), 3.16-3.07 (m, 1H), 3.06-2.98 (m, 1H), 2.53 (s, 3H), 2.17-2.12 (m, 1H), 1.91-1.82 (m, 2H), 1.80-1.68 (m, 2H).

Intermediate 34. 3-Isocyanato-2-methyl-5-(propan-2-yl)thiophene

Step 1. Tert-butyl N-[2-methyl-5-(prop-1-en-2-yl) thiophen-3-yl]carbamate

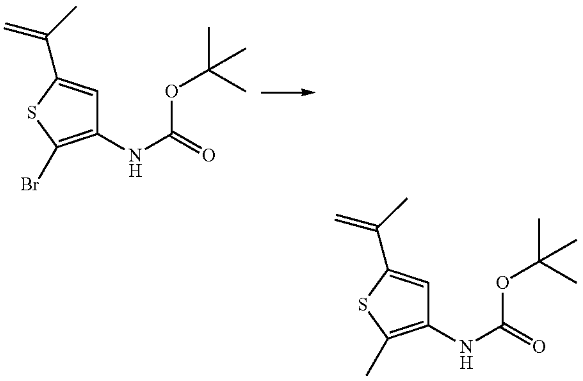

To a solution of tert-butyl N-(2-bromo-5-isopropenyl-3-thienyl)carbamate (293 mg, 0.92 mmol) (for synthesis refer to Intermediate 30) in dioxane (5 ml) under $N_2$ was added methylboronic acid (110 mg, 1.84 mmol), Pd(dppf) $Cl_2 \cdot CH_2Cl_2$ (83 mg, 101 μmol) and CsF (490 mg, 3.22 mmol). The RM was stirred at 90° C. for 12 h. The RM was concentrated under reduced pressure and the resulting residue diluted with $H_2O$ (10 ml) and extracted with EtOAc (3×3 ml). The combined organic layers were washed with brine (2×2 ml), dried over $Na_2SO_4$, filtered and the filtrate concentrated under reduced pressure. The resulting residue was purified by prep-TLC (silica, 9% EtOAc in petrol) to give the title compound as a white solid. Y=12%. $^1H$ NMR (400 MHz, chloroform-d) δ 7.70 (s, 1H), 6.48 (s, 1H), 5.40 (s, 1H), 5.01 (s, 1H), 2.17 (s, 3H), 1.51 (s, 12H).

Step 2. Tert-butyl N-[2-methyl-5-(propan-2-yl)thiophen-3-yl]carbamate

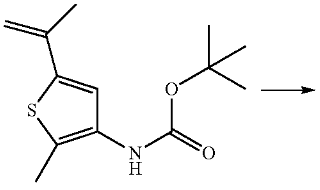

-continued

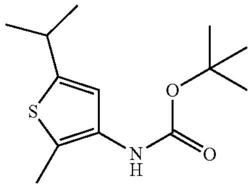

To a solution of tert-butyl N-[2-methyl-5-(prop-1-en-2-yl)thiophen-3-yl]carbamate (31 mg, 0.12 mmol) in MeOH (1 ml) under $N_2$ was added 10% Pd/C (50% in water, 1 mg). The suspension was degassed under vacuum and purged with $H_2$ several times. The mixture was stirred under $H_2$ (15 psi) at rt for 15 min. The RM was filtered through Celite and concentrated under reduced pressure to give the title compound as a yellow solid. LCMS (ESI): m/z: $[M+H]^+$=256.1.

Step 3. 2-Methyl-5-(propan-2-yl)thiophen-3-amine Hydrochloride

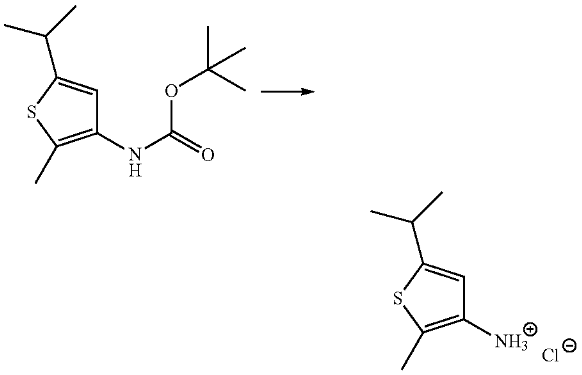

A solution of tert-butyl N-[2-methyl-5-(propan-2-yl)thiophen-3-yl]carbamate (31 mg, 122 μmol) in 4 M HCl in EtOAc (2 ml) was stirred at rt for 10 min. The RM was concentrated under reduced pressure to give the title compound as a yellow solid. $^1H$ NMR (400 MHz, chloroform-d) δ 6.79 (s, 1H), 3.09-3.01 (m, 1H), 2.55 (s, 3H), 1.28-1.26 (m, 6H).

Step 4. 3-Isocyanato-2-methyl-5-(propan-2-yl)thiophene

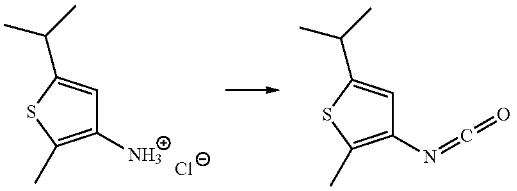

To a solution of 2-methyl-5-(propan-2-yl)thiophen-3-amine hydrochloride (23.5 mg, 122 μmol) in dioxane (3 ml) warmed to 40° C. was added trichloromethyl carbonochloridate (17.7 μl, 147 μmol). The RM was heated at 70° C. for 1 h, then concentrated under reduced pressure to give the title compound as a yellow solid. LCMS in MeOH (ESI): m/z: $[M+MeOH+H]^+$=214.1.

Intermediate 35. 2-Ethyl-3-isocyanato-5-(propan-2-yl)thiophene

Step 1. Tert-butyl N-[2-ethenyl-5-(prop-1-en-2-yl)thiophen-3-yl]carbamate

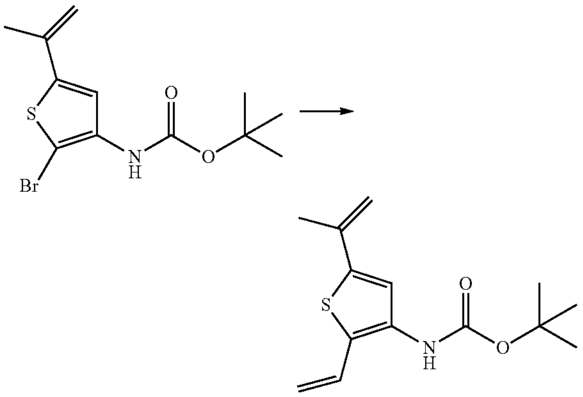

To a solution of tert-butyl N-(2-bromo-5-isopropenyl-3-thienyl)carbamate (200 mg, 0.63 mmol) (for synthesis refer to Intermediate 30) and potassium ethenyltrifluoroboranuide (842 mg, 6.28 mmol) in THF (7.2 ml) and $H_2O$ (0.8 ml) under $N_2$ were added $Cs_2CO_3$ (614 mg, 1.89 mmol), $PPh_3$ (10 mg, 38 μmol) and $PdCl_2$ (2.2 mg, 13 μmol). The RM was stirred at 85° C. for 12 h. The mixture was concentrated under reduced pressure and the resulting residue purified by prep-TLC (9% EtOAc in petrol) to give the title compound as a white solid. Y=42%. LCMS (ESI): m/z: $[M+H]^+$=266.1.

Step 2. Tert-butyl N-[2-ethyl-5-(propan-2-yl)thiophen-3-yl]carbamate

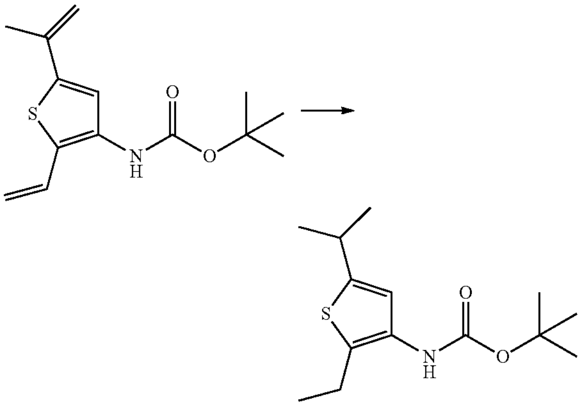

To a solution of tert-butyl N-[2-ethenyl-5-(prop-1-en-2-yl)thiophen-3-yl]carbamate (70 mg, 0.26 mmol) in MeOH (3 ml) under $N_2$ atmosphere was added 10% Pd/C (50% in water, 5 mg). The suspension was degassed and purged with $H_2$ for 3 times. The mixture was stirred under $H_2$ (15 Psi) at rt for 10 min. The mixture was filtered through Celite and the filtrate concentrated under reduced pressure to give the title compound as a white solid. Y=84%. LCMS (ESI): m/z: $[M+H]^+$=270.2.

Step 3. 2-Ethyl-5-(propan-2-yl)thiophen-3-amine Hydrochloride

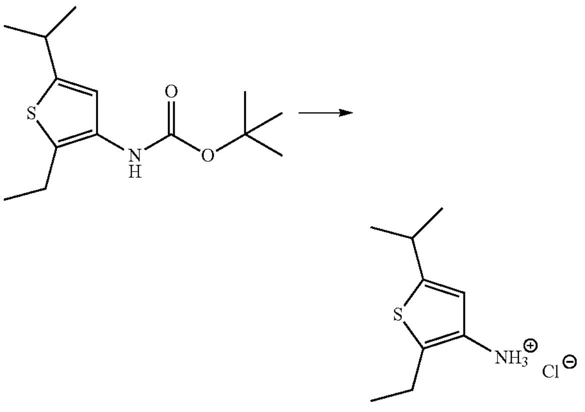

A solution of tert-butyl N-[2-ethyl-5-(propan-2-yl)thiophen-3-yl]carbamate (60 mg, 0.22 mmol) in 4 M HCl in EtOAc (4 ml) was stirred at rt for 10 min. The mixture was concentrated under reduced pressure to give the title compound as a white solid. LCMS (ESI): m/z: $[M+H]^+$=170.1.

Step 4. 2-Ethyl-3-isocyanato-5-(propan-2-yl)thiophene

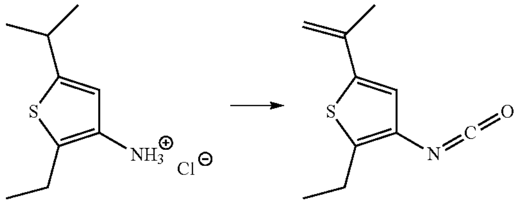

To a solution of 2-ethyl-5-(propan-2-yl)thiophen-3-amine hydrochloride (60 mg, 0.29 mmol) in dioxane (2 ml) warmed to 40° C. was added trichloromethyl carbonochloridate (38.7 μL, 0.32 mmol) and the resulting mixture stirred at 70° C. for 1 h. The mixture was concentrated under reduced pressure to give the title compound as a yellow solid. LCMS in MeOH (ESI): m/z: $[M+H+MeOH]^+$=228.1.

Intermediate 36. N-(1-Cyclopropyl-1H-pyrazol-4-yl)-N-[(3R)-1-methylpiperidin-3-yl]aminosulfonamide Hydrochloride Step 1. 1-Cyclopropyl-4-iodo-1H-pyrazole

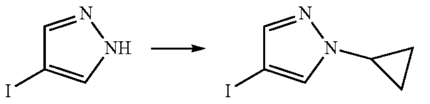 [SMILES: Ic1cn[nH]c1 ; Ic1cnn(C2CC2)c1]

To a solution of 4-iodo-1H-pyrazole (5.0 g, 25.8 mmol) in dioxane (100 ml) was added copper(II)acetate (4.68 g, 25.8 mmol), DMAP (9.45 g, 77.3 mmol), cyclopropylboronic acid (4.43 g, 51.6 mmol) and pyridine (2.08 ml, 25.8 mmol).

The RM was stirred at 100° C. for 12 h. The solution was concentrated under reduced pressure and the resulting residue diluted with EtOAc (100 ml), washed with 1 M HCl (aq.) (25 ml), dried and concentrated under reduced pressure. The residue was purified by column chromatography (silica, 5-17% EtOAc in petrol) to give the title compound as a yellow oil. Y=60%. $^1$H NMR (400 MHz, chloroform-d) δ 7.50 (s, 1H), 7.48 (s, 1H), 3.68-3.54 (m, 1H), 1.14-1.00 (m, 4H).

Step 2. Tert-butyl (3R)-3-[(1-cyclopropyl-1H-pyrazol-4-yl)amino]piperidine-1-carboxylate

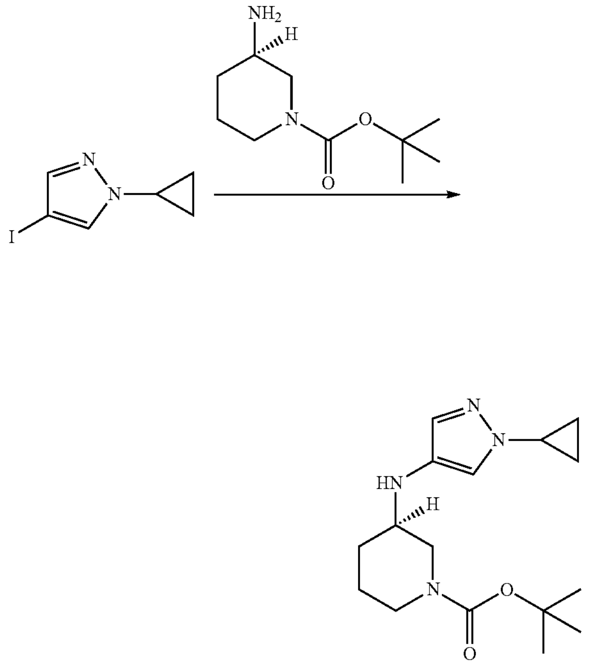

To a solution of tert-butyl (3R)-3-aminopiperidine-1-carboxylate (300 mg, 1.50 mmol) in toluene (5 ml) under $N_2$ was added 1-cyclopropyl-4-iodo-pyrazole (526 mg, 2.25 mmol), [2-(2-aminoethyl)phenyl]-chloro-palladium; ditert-butyl-[2-(2,4,6-triisopropylphenyl)phenyl]-phosphane (103 mg, 0.15 mmol) and sodium tert-butoxide (288 mg, 3.00 mmol). The RM was stirred under $N_2$ atmosphere at 100° C. for 3 h. The mixture was concentrated under reduced pressure and the resulting residue diluted with water (3 ml) and extracted with EtOAc (3×5 ml), dried over $Na_2SO_4$ and concentrated under reduced pressure. The residue was purified by prep-HPLC (column: Nano-micro Kromasil C18 80×25 mm, 3 μm; mobile phase: [water (0.1% TFA)-ACN]; B: 20-40%, 7 min) to give the title compound as a white solid. Y=39%. $^1$H NMR (400 MHz, chloroform-d) δ 7.65 (s, 1H), 7.51 (s, 1H), 4.19-3.94 (m, 1H), 3.92-3.65 (m, 1H), 3.64-3.51 (m, 1H), 3.26-3.10 (m, 1H), 3.08-2.73 (m, 2H), 2.17-1.99 (m, 1H), 1.87-1.71 (m, 1H), 1.70-1.52 (m, 1H), 1.51-1.46 (m, 1H), 1.43 (s, 9H), 1.19-1.07 (m, 2H), 1.04-0.99 (m, 2H).

Step 3. (3R)—N-(1-Cyclopropyl-1H-pyrazol-4-yl)-1-methylpiperidin-3-amine

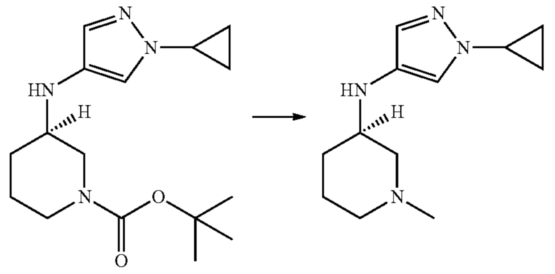 [SMILES: CC(C)(C)OC(=O)N1CCC[C@@H](Nc2cnn(C3CC3)c2)C1 ; CN1CCC[C@@H](Nc2cnn(C3CC3)c2)C1]

To a solution of tert-butyl (3R)-3-[(1-cyclopropyl-1H-pyrazol-4-yl)amino]piperidine-1-carboxylate (220 mg, 0.72 mmol) in THF (4 ml) cooled to 0° C. was added $LiAlH_4$ (273 mg, 7.2 mmol). The RM was heated at 85° C. for 12 h. The RM allowed to cool and quenched with $H_2O$ (0.5 ml) and then treated with 10% NaOH (aq.)(0.2 ml). The resulting mixture was filtered and the filtrate concentrated under reduced pressure to give the title compound as a white solid. LCMS (ESI): m/z: $[M+H]^+$=221.3.

Step 4. Tert-butyl N-[(1-cyclopropyl-1H-pyrazol-4-yl)[(3R)-1-methylpiperidin-3-yl]sulfamoyl]carbamate

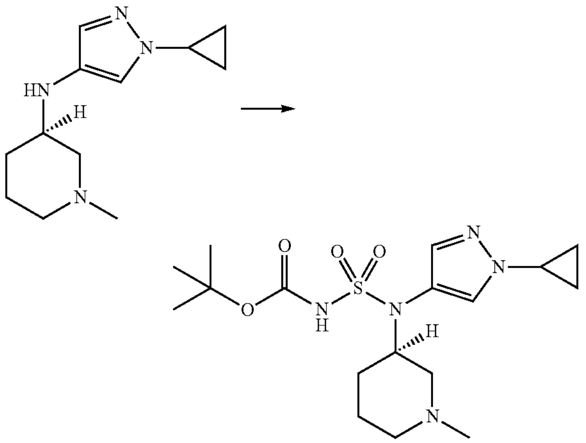

To a solution of (3R)—N-(1-cyclopropyl-1H-pyrazol-4-yl)-1-methylpiperidin-3-amine (160 mg, 0.73 mmol) in DCM (2 ml) was added DIPEA (253 μl, 1.45 mmol) and the RM stirred at rt for 0.5 h. The RM was treated with a solution of 0.88 M tert-butyl N-chlorosulfonylcarbamate in DCM (0.99 ml, 0.87 mmol) and the RM stirred at rt for 1 h. The solution was concentrated under reduced pressure and the resulting residue purified by prep-HPLC (column: Nano-micro Kromasil C18 80×25 mm, 3 μm; mobile phase: [water (0.1% TFA)-ACN]; B: 5-33%, 7 min) to give the title compound as a white solid. Y=28%. $^1$H NMR (400 MHz, chloroform-d) δ 7.64 (s, 1H), 7.41 (s, 1H), 4.58-4.44 (m, 1H), 3.82-3.77 (m, 1H), 3.66-3.55 (m, 1H), 3.53-3.43 (m, 1H), 2.80 (s, 3H), 2.53 (t, J=12 Hz, 1H), 2.46-2.37 (m, 1H), 2.22-2.08 (m, 2H), 2.01-1.87 (m, 2H), 1.52 (s, 9H), 1.20-1.15 (m, 2H), 1.09-1.02 (m, 2H).

Step 5. N-(1-Cyclopropyl-1H-pyrazol-4-yl)-N-[(3R)-1-methylpiperidin-3-yl]aminosulfonamide Hydrochloride

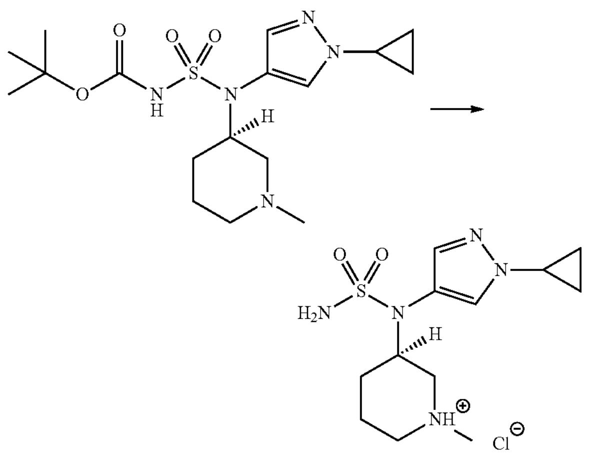

A solution of tert-butyl N-[(1-cyclopropyl-1H-pyrazol-4-yl)[(3R)-1-methylpiperidin-3-yl]sulfamoyl]carbamate (70 mg, 175 μmol) in 4 M HCl in EtOAc (2 ml) was stirred at rt for 1 h. The solution was concentrated under reduced pressure to give the title compound as a white solid. LCMS (ESI): m/z: $[M+H]^+$=300.1.

Intermediate 37. 5-Chloro-3-isocyanato-2-(propan-2-yl)thiophene

Step 1. Tert-butyl N-(2-bromo-5-chlorothiophen-3-yl)carbamate

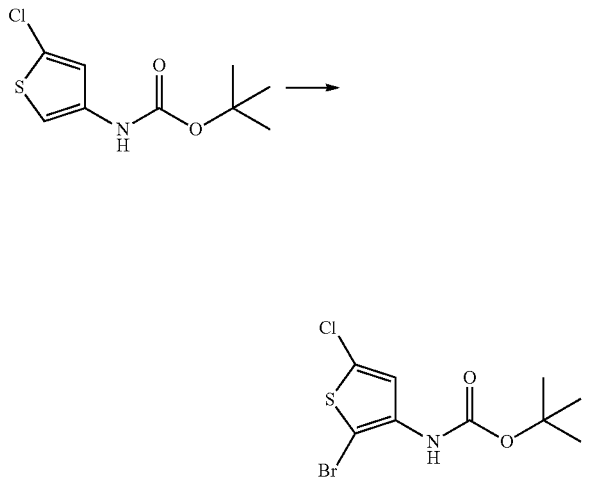

To a mixture of tert-butyl N-(5-chloro-3-thienyl) carbamate (1.7 g, 7.27 mmol) in THF (17 ml) cooled to 0° C. was added NBS (1.36 g, 7.64 mmol). The mixture was stirred at rt for 2 h. The solution was concentrated under vacuum and the resulting residue purified by silica gel chromatography (17% EtOAc in petrol) to give the title compound as a white solid. Y=57%. LCMS: m/z: $[M+H-56]^+$=257.8.

Step 2. Tert-butyl N-[5-chloro-2-(prop-1-en-2-yl) thiophen-3-yl]carbamate

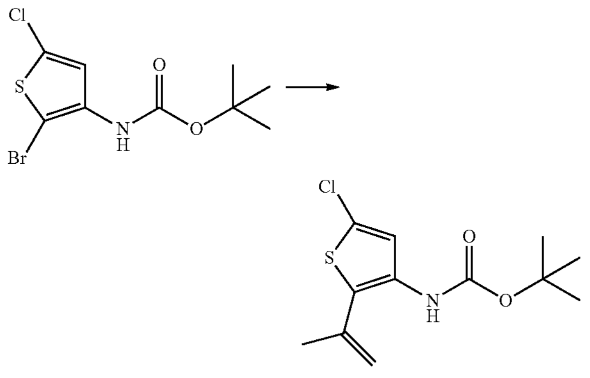

To a solution of tert-butyl N-(2-bromo-5-chloro-3-thienyl) carbamate (1.3 g, 4.16 mmol) in $H_2O$ (3 ml) and THF (15 ml) under $N_2$ were added 2-isopropenyl-4,4,5,5-tetramethyl-1,3,2-dioxaborolane (1.40 g, 8.32 mmol), $Pd(PPh_3)_4$ (48 mg, 41.6 μmol) and $Na_2CO_3$ (1.32 g, 12.5 mmol) and the mixture stirred at 90° C. for 8 h. The solution was concentrated in vacuo and the resulting residue purified by silica gel chromatography (17% EtOAc in petrol) to give the title compound as a yellow oil. $^1H$ NMR (400 MHz, MeOD) δ 7.21 (s, 1H), 6.99 (s, 1H) 5.22 (s, 1H) 5.15 (s, 1H) 2.07 (s, 3H) 1.48 (s, 9H).

Step 3. Tert-butyl N-[5-chloro-2-(propan-2-yl)thiophen-3-yl]carbamate

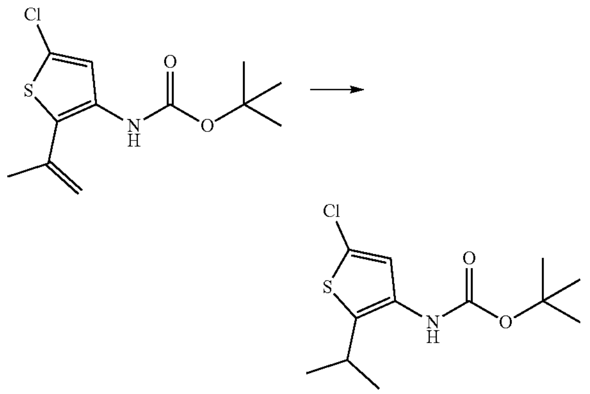

To a solution of tert-butyl N-(5-chloro-2-isopropenyl-3-thienyl) carbamate (250 mg, 0.91 mmol) in EtOH (20 ml) under $N_2$ was added 5% Pt/C (2.5 g). The suspension was degassed under vacuum and purged with $H_2$ several times. The mixture was stirred under $H_2$ (15 psi) at rt for 12 h. The reaction solution was filtered and the filtrate concentrated under reduced pressure. The residue was purified by prep-HPLC (column: Phenomenex Luna C18 150×30 mm, 5 μm; mobile phase: Y=47%. $^1H$ NMR (400 MHz, MeOD) δ 6.90 (s, 1H), 3.28-3.22 (m, 1H), 1.49 (s, 9H), 1.22 (d, J=7 Hz, 6H).

Step 4. 5-Chloro-2-(propan-2-yl)thiophen-3-amine Hydrochloride

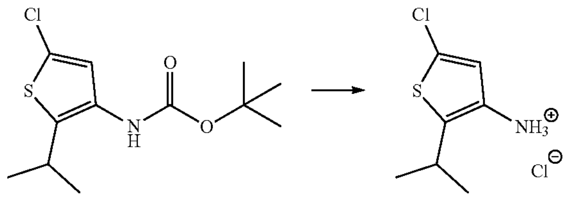

The solution of tert-butyl N-(5-chloro-2-isopropyl-3-thienyl) carbamate (150 mg, 0.54 mmol) in 4 M HCl in EtOAc (3 ml) was stirred at rt for 1 h. The solution was concentrated under vacuum to give the title compound as a white solid.

Step 5. 5-Chloro-3-isocyanato-2-(propan-2-yl)thiophene

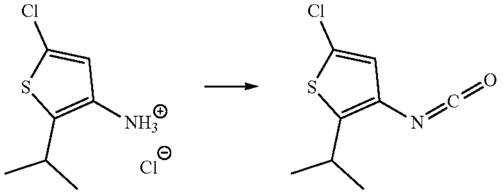

To the solution of 5-chloro-2-isopropyl-thiophen-3-amine (115 mg, 0.65 mmol) in dioxane (3 ml) warmed to 40° C. was added trichloromethyl carbonochloridate (79 µl, 0.65 mmol). The RM was stirred at 70° C. for 1 h. The solution was concentrated under vacuum to give the title compound as a yellow oil. LCMS in MeOH: m/z: $[M+MeOH+H]^+$ =234.1.

Intermediate 38. 5-Ethyl-3-isocyanato-2-(propan-2-yl)thiophene

Step 1. Tert-butyl N-(2-bromo-5-ethenylthiophen-3-yl)carbamate

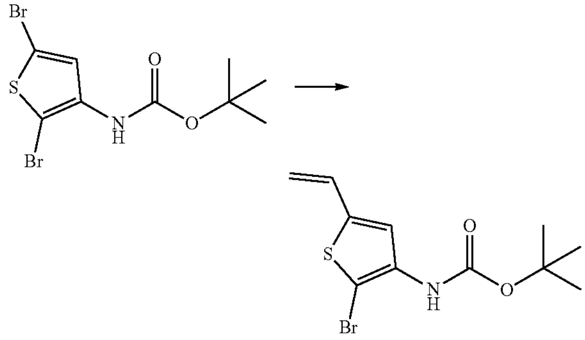

To a solution of tert-butyl N-(2,4-dibromo-3-thienyl)carbamate (300 mg, 0.84 mmol) (for synthesis refer to Intermediate 30) in THF (10 ml) under $N_2$ was added potassium ethenyltrifluoroboranuide (563 mg, 4.20 mmol), $PPh_3$ (13.2 mg, 50.4 µmol), $Cs_2CO_3$ (0.82 g, 2.52 mmol) and $PdCl_2$ (3.0 mg, 16.8 µmol). The RM was stirred at 90° C. for 12 h. The solution was filtered and the filtrate concentrated under reduced pressure. The resulting residue was purified by prep-HPLC (column: Phenomenex Luna C18 250×50 mm, 10 µm; mobile phase: [water (0.1% TFA)-ACN]; B: 50-80%, 10 min) to give the title compound as a white solid. Y=39%. $^1$H NMR (400 MHz, chloroform-d) δ 7.52-7.43 (s, 1H), 6.71-6.63 (m, 1H), 6.53 (s, 1H), 5.50 (d, J=17 Hz, 1H), 5.16 (d, J=11 Hz, 1H), 1.53 (s, 9H).

Step 2. Tert-butyl N-[5-ethenyl-2-(prop-1-en-2-yl)thiophen-3-yl]carbamate

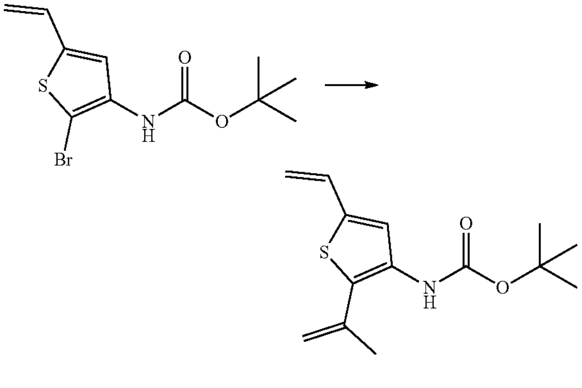

To a solution of tert-butyl N-(2-bromo-5-ethenylthiophen-3-yl)carbamate (100 mg, 0.33 mmol) in THF (2 ml) and $H_2O$ (0.4 ml) was added $Pd(PPh_3)_4$ (3.8 mg, 3.3 µmol), $Na_2CO_3$ (105 mg, 0.99 mmol) and 2-isopropenyl-4,4,5,5-tetramethyl-1,3,2-dioxaborolane (276 mg, 1.64 mmol). The RM was stirred at 90° C. for 12 h. The RM was concentrated under reduced pressure and the resulting residue purified by prep-TLC (silica, 9% EtOAc in petrol) to give the title compound as a white solid. Y=69%. LCMS (ESI): m/z: $[M+H]^+$=266.1.

Step 3. Tert-butyl N-[5-ethyl-2-(propan-2-yl)thiophen-3-yl]carbamate

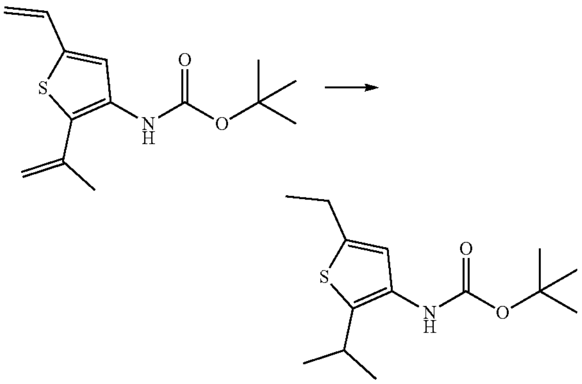

To a solution of tert-butyl N-[5-ethenyl-2-(prop-1-en-2-yl)thiophen-3-yl]carbamate (60 mg, 0.23 mmol) in MeOH (3 ml) was added 10% Pd/C (50% in water, 30 mg). The RM was degassed and stirred under $H_2$ (15 psi) at rt for 5 min.

The RM was filtered through Celite and the filtrate concentrated under reduced pressure to give the title compound as a white solid. Y=82%. LCMS (ESI): m/z: $[M+H]^+$=270.1.

Step 4. 5-Ethyl-2-(propan-2-yl)thiophen-3-amine Hydrochloride

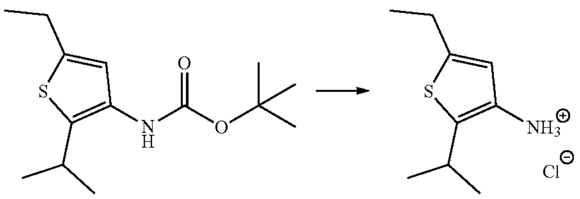 [SMILES: CCc1cc(NC(=O)OC(C)(C)C)c(C(C)C)s1 ; CCc1cc([NH3+])c(C(C)C)s1 ; [Cl-]]

A solution of tert-butyl N-[5-ethyl-2-(propan-2-yl)thiophen-3-yl]carbamate (50 mg, 186 μmol) in 4 M HCl in EtOAc (2 ml) was stirred at rt for 1 h. The solution was concentrated under vacuum to give the title compound as a white solid. LCMS (ESI): m/z: $[M+H]^+$=170.2.

Step 5. 5-Ethyl-3-isocyanato-2-(propan-2-yl)thiophene

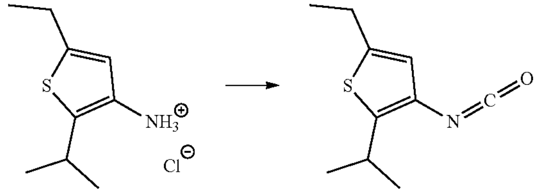

To a solution of 5-ethyl-2-(propan-2-yl)thiophen-3-amine hydrochloride (40 mg, 194 μmol) in dioxane (3 ml) warmed to 40° C. was added trichloromethyl carbonochloridate (28.1 μl, 233 μmol). The RM was stirred at 70° C. for 1 h. The solution was concentrated under reduced pressure to give the title compound as a white solid, which was used to next step directly. LCMS in MeOH (ESI): m/z: $[M+MeOH+H]^+$ 228.2.

Intermediate 39. N-{[(2S,4R)-4-Fluoro-1-methylpyrrolidin-2-yl]methyl}-N-(1-methyl-1H-pyrazol-4-yl)aminosulfonamide Hydrochloride Step 1. Tert-butyl (2S,4R)-4-fluoro-2-[(1-methyl-1H-pyrazol-4-yl)carbamoyl]-pyrrolidine-1-carboxylate

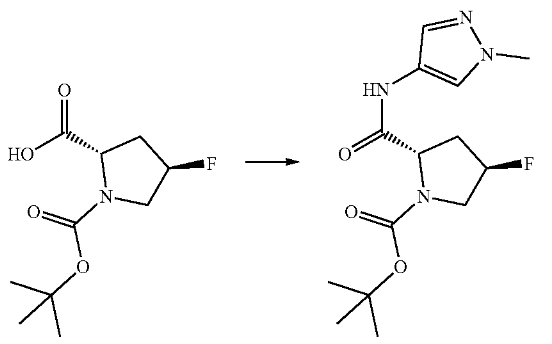 [SMILES: CC(C)(C)OC(=O)N1C[C@H](F)C[C@H]1C(=O)O ; Cn1cc(NC(=O)[C@@H]2C[C@@H](F)CN2C(=O)OC(C)(C)C)cn1]

To a solution of (2S,4R)-1-tert-butoxycarbonyl-4-fluoro-pyrrolidine-2-carboxylic acid (5.04 g, 21.6 mmol) in DMF (50 ml) cooled to 0° C. was added HATU (9.04 g, 23.8 mmol). The mixture was stirred at 0° C. for 1 h, then 1-methylpyrazol-4-amine (2.1 g, 21.6 mmol) and DIPEA (7.53 ml, 43.3 mmol) were added. The RM was stirred at rt for 2 h. The mixture was diluted with $H_2O$ (50 ml) and extracted with EtOAc (3×50 ml). The combined organic layers were washed with $H_2O$ (2×50 ml) and brine (20 ml), dried over $Na_2SO_4$ and concentrated under vacuum. The residue was purified by column chromatography (silica, 9-100% EtOAc in petrol) to give the title compound as a white solid. Y=74%. $^1H$ NMR (400 MHz, MeOD) δ 7.91 (s, 1H), 7.50 (s, 1H), 5.35-5.22 (m, 2H), 4.38-4.34 (m, 1H), 3.82-3.56 (m, 3H), 2.62-2.49 (m, 2H), 2.27-2.06 (m, 1H), 1.36 (s, 9H).

Step 2. (2S,4R)-4-Fluoro-N-(1-methyl-1H-pyrazol-4-yl)pyrrolidine-2-carboxamide Hydrochloride

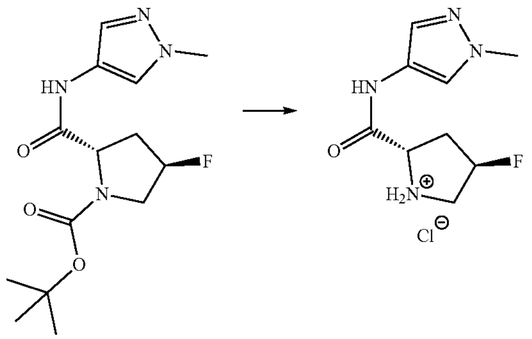 [SMILES: Cn1cc(NC(=O)[C@@H]2C[C@@H](F)CN2C(=O)OC(C)(C)C)cn1 ; Cn1cc(NC(=O)[C@@H]2C[C@@H](F)C[NH2+]2)cn1 ; [Cl-]]

A mixture of tert-butyl (2S,4R)-4-fluoro-2-[(1-methyl-1H-pyrazol-4-yl)carbamoyl]pyrrolidine-1-carboxylate (3.0 g, 9.60 mmol) in 4 M HCl in EtOAc (40 ml) was stirred at rt for 2 h. The mixture was filtered and the solid dried to give the title compound as a white solid.

Step 3. (2S,4R)-4-Fluoro-1-methyl-N-(1-methyl-1H-pyrazol-4-yl)pyrrolidine-2-carboxamide

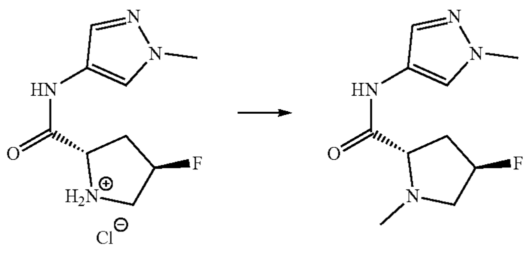 [SMILES: Cn1cc(NC(=O)[C@@H]2C[C@@H](F)C[NH2+]2)cn1 ; CN1C[C@H](F)C[C@H]1C(=O)Nc1cnn(C)c1 ; [Cl-]]

To a solution of (2S,4R)-4-fluoro-N-(1-methyl-1H-pyrazol-4-yl)pyrrolidine-2-carboxamide hydrochloride (2.39 g, 9.61 mmol) in MeOH (20 ml) was added 37% formaldehyde (aq.) (1.43 ml, 19.2 mmol) and $NaBH_3CN$ (906 mg, 14.4 mmol). The mixture was stirred at rt for 30 min. The RM was concentrated under reduced pressure and the resulting residue purified by column chromatography (silica, 0-9% EtOAc in MeOH) to give the title compound as a yellow oil. Y=70%. $^1H$ NMR (400 MHz, MeOD) δ 7.91 (s, 1H), 7.55

(s, 1H), 5.27-5.13 (m, 1H), 3.85 (s, 3H), 3.68-3.51 (m, 1H), 2.78-2.65 (m, 1H), 2.48-2.34 (m, 5H), 2.18-1.99 (m, 1H).

Step 4. N-{[(2S,4R)-4-Fluoro-1-methylpyrrolidin-2-yl]methyl}-1-methyl-1H-pyrazol-4-amine

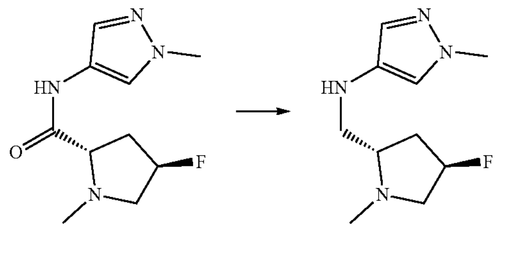 [SMILES: CN1C[C@H](F)C[C@H]1C(=O)Nc1cnn(C)c1 ; CN1C[C@H](F)C[C@H]1CNc1cnn(C)c1]

To a solution of (2S,4R)-4-fluoro-1-methyl-N-(1-methyl-1H-pyrazol-4-yl)pyrrolidine-2-carboxamide (1.0 g, 4.42 mmol) in THF (15 ml) cooled to 0° C. was added 10 M $BH_3$-$Me_2S$ (4.42 ml). The RM was stirred at 0° C. for 1 h, then warmed to 50° C. for 5 h. The mixture was cooled to 0° C. and quenched by dropwise addition of MeOH (10 ml). The resulting solution was concentrated under vacuum to give the title compound as a white gum. LCMS (ESI): m/z: $[M+H]^+$=213.1.

Step 5. (2S,4R)-2-{[({[(Tert-butoxy)carbonyl]amino}sulfonyl)(1-methyl-1H-pyrazol-4-yl)amino]methyl}-4-fluoro-1-methylpyrrolidin-1-ium Trifluoroacetate

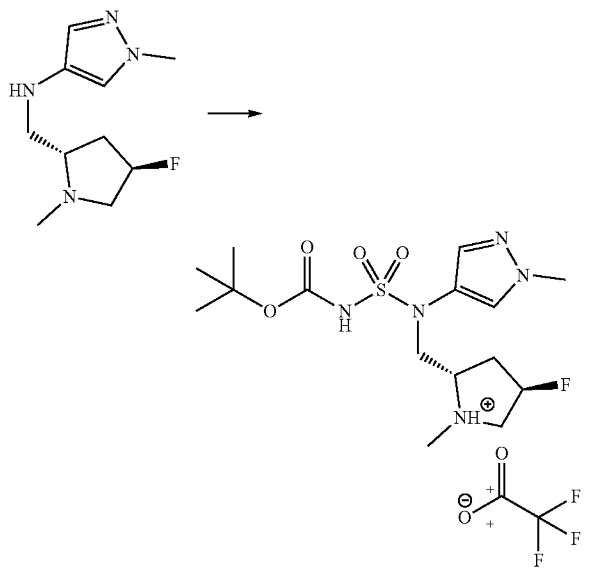

To a solution of N-{[(2S,4R)-4-fluoro-1-methylpyrrolidin-2-yl]methyl}-1-methyl-1H-pyrazol-4-amine (1.0 g crude, 4.71 mmol) in DCM (10 ml) cooled to 0° C. was added DIPEA (1.64 ml, 9.42 mmol) and a solution of tert-butyl N-chlorosulfonylcarbamate (0.71 M in DCM, 13.32 ml, 9.42 mmol). The RM was stirred at 0° C. for 2 h. The mixture was concentrated under vacuum and the resulting residue purified by prep-HPLC (column: Phenomenex Luna C18 250×50 mm, 10 μm; mobile phase: [water (0.1% TFA)-ACN]; B: 1-30%, 20 min) to give the title compound as a colourless gum. Y=42%. LCMS (ESI): m/z: $[M+H]^+$=392.1.

Step 6. N-{[(2S,4R)-4-Fluoro-1-methylpyrrolidin-2-yl]methyl}-N-(1-methyl-1H-pyrazol-4-yl)aminosulfonamide Hydrochloride

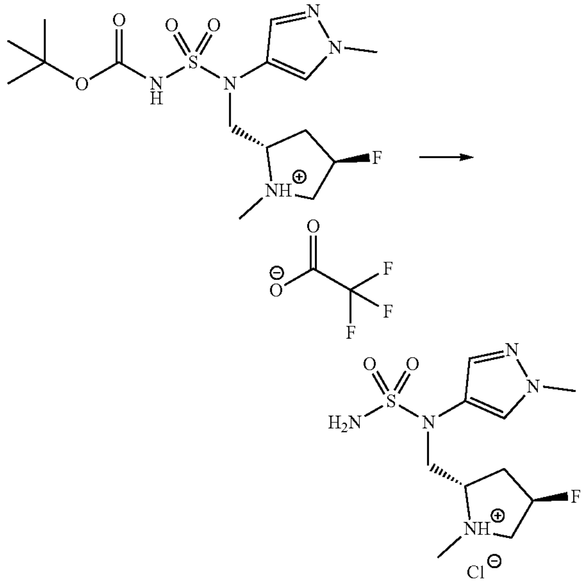

A mixture of (2S,4R)-2-{[({[(tert-butoxy)carbonyl]amino}sulfonyl)(1-methyl-1H-pyrazol-4-yl)amino]methyl}-4-fluoro-1-methylpyrrolidin-1-ium trifluoroacetate (3.2 g, 6.33 mmol) in 4 M HCl in EtOAc (25 ml) was stirred at rt for 2 h. The mixture was filtered and the solid dried under vacuum to give the title compound as a white solid.

Intermediate 40. N-{[(2S,4R)-4-Fluoro-1-methylpyrrolidin-2-yl]methyl}-N-[1-(propan-2-yl)-1H-pyrazol-4-yl]aminosulfonamide Hydrochloride Step 1. 4-Nitro-1-(propan-2-yl)-1H-pyrazole

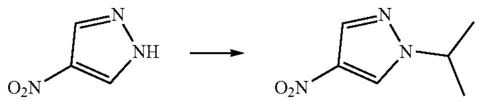

To a solution of 4-nitro-1H-pyrazole (15 g, 133 mmol) in THF (300 ml) cooled to 0° C. was added propan-2-ol (12.2 ml, 159 mmol), $PPh_3$ (52.2 g, 199 mmol) and DIAD (31.0 ml, 159 mmol). The resulting mixture was stirred at rt for 12 h. The solution was concentrated under reduced pressure and the resulting residue purified by column chromatography (silica, 9-33% EtOAc in petrol) to give the title compound as a white solid. Y=99%. $^1H$ NMR (400 MHz, chloroform-d) δ 8.17 (s, 1H), 8.08 (s, 1H), 4.61-4.46 (m, 1H), 1.56 (d, J=7 Hz, 6H).

Step 2. 1-(Propan-2-yl)-1H-pyrazol-4-amine

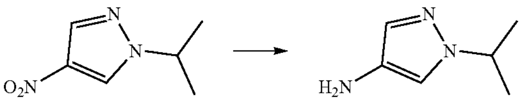

To a solution of 4-nitro-1-(propan-2-yl)-1H-pyrazole (5.0 g, 32.2 mmol) in MeOH (60 ml) was added 10% Pd/C (50% in water, 1.0 g). The RM was degassed and stirred under $H_2$ (15 psi) atmosphere at rt for 1 h. The RM was filtered through Celite and the filtrate concentrated under reduced pressure to give the title compound as a solid. Y=100%. $^1$H NMR (400 MHz, chloroform-d) δ 7.14 (s, 1H), 7.03 (s, 1H), 4.40-4.26 (m, 1H), 2.75 (s, 2H), 1.44 (d, J=7 Hz, 6H).

Step 3. Tert-butyl (2S,4R)-4-fluoro-2-{[1-(propan-2-yl)-1H-pyrazol-4-yl]carbamoyl}-pyrrolidine-1-carboxylate

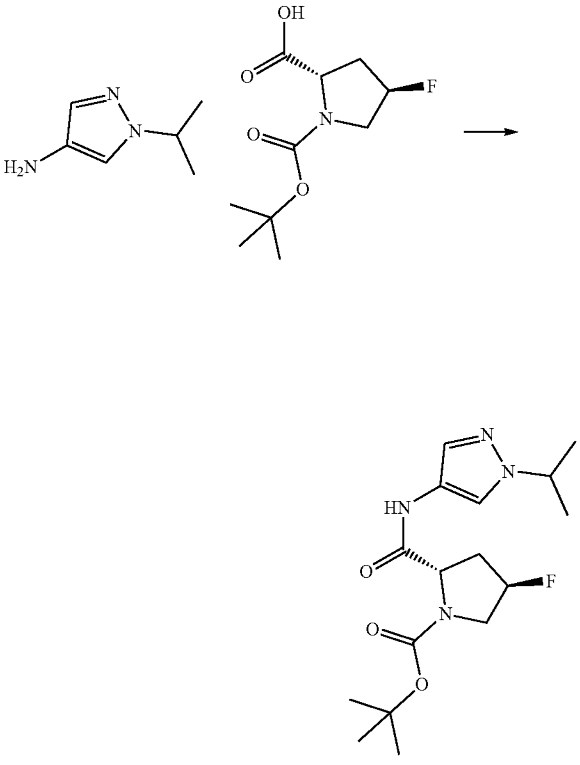

To a solution of (2S,4R)-1-tert-butoxycarbonyl-4-fluoro-pyrrolidine-2-carboxylic acid (2.0 g, 8.58 mmol) in DCM (10 ml) cooled to 0° C. was added EDCI (2.47 g, 12.9 mmol) and HOBt (1.74 g, 12.9 mmol). The RM was stirred at 0° C. for 30 min, then treated with DIPEA (4.48 ml, 25.7 mmol) and 1-isopropylpyrazol-4-amine (1.61 g, 12.9 mmol). The RM was stirred at rt for 12 h. The mixture was concentrated under reduced pressure and the resulting residue purified by column chromatography (silica, 50-100% EtOAc in petrol) to give the title compound as a white solid. LCMS (ESI): m/z: $[M+H]^+$=341.2.

Step 4. (2S,4R)-4-Fluoro-N-[1-(propan-2-yl)-1H-pyrazol-4-yl]pyrrolidine-2-carboxamide Hydrochloride

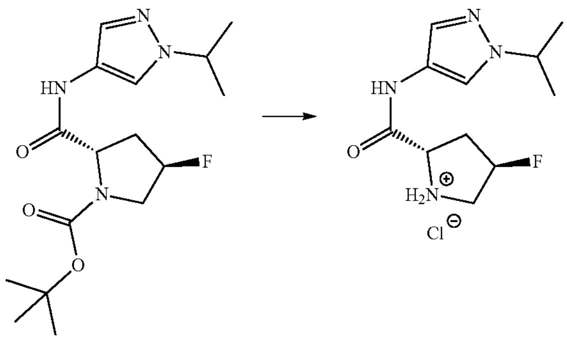 [SMILES: CC(C)n1cc(NC(=O)[C@@H]2C[C@@H](F)CN2C(=O)OC(C)(C)C)cn1 ; CC(C)n1cc(NC(=O)[C@@H]2C[C@@H](F)C[NH2+]2)cn1 ; [Cl-]]

A solution of tert-butyl (2S,4R)-4-fluoro-2-{[1-(propan-2-yl)-1H-pyrazol-4-yl]carbamoyl}pyrrolidine-1-carboxylate (2.92 g, 8.58 mmol) in 4 M HCl in EtOAc (20 ml) was stirred at rt for 1 h. The solution was concentrated under reduced pressure to give the title compound as a white solid.

Step 5. (2S,4R)-4-Fluoro-1-methyl-N-[1-(propan-2-yl)-1H-pyrazol-4-yl]pyrrolidine-2-carboxamide

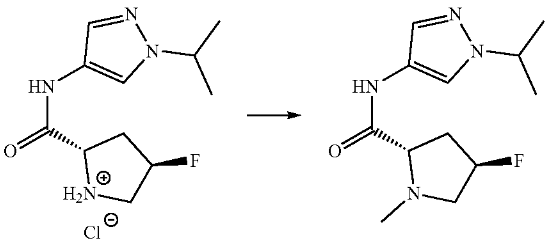 [SMILES: CC(C)n1cc(NC(=O)[C@@H]2C[C@@H](F)C[NH2+]2)cn1 ; CC(C)n1cc(NC(=O)[C@@H]2C[C@@H](F)CN2C)cn1 ; [Cl-]]

To a solution of (2S,4R)-4-fluoro-N-[1-(propan-2-yl)-1H-pyrazol-4-yl]pyrrolidine-2-carboxamide hydrochloride (1.5 g, 5.42 mmol) in MeOH (15 ml) at 0° C. was added $NaBH_3CN$ (511 mg, 8.13 mmol). The RM was stirred at 0° C. for 30 min, then treated with 37% aq. formaldehyde (0.81 ml, 10.8 mmol). The RM was stirred at rt for 1 h, quenched with water (5 ml) and extracted with EtOAc (3×5 ml). The combined organic phase was washed with brine (5 ml), dried with anhydrous $Na_2SO_4$, filtered and concentrated under vacuum. The residue was purified by column chromatography (silica, 50-100% EtOAc in petrol) to give the title compound as a white solid. Y=80%. $^1$H NMR (400 MHz, MeOD) δ 7.96 (s, 1H), 7.57 (s, 1H), 5.34-5.09 (m, 2H), 4.52-4.46 (m, 1H), 3.69-3.56 (m, 1H), 3.39-3.29 (m, 1H), 2.80-2.66 (m, 1H), 2.45 (s, 3H), 2.41-2.33 (m, 1H), 2.19-2.03 (m, 1H), 1.47 (d, J=7 Hz, 6H).

Step 6. N-{[(2S,4R)-4-Fluoro-1-methylpyrrolidin-2-yl]methyl}-1-(propan-2-yl)-1H-pyrazol-4-amine Hydrochloride

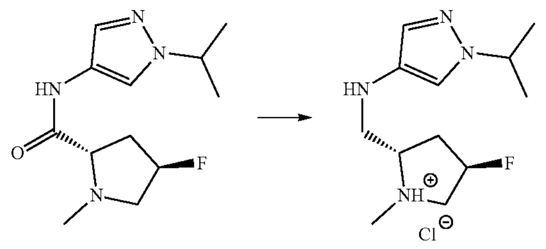 [SMILES: CC(C)n1cc(NC(=O)[C@@H]2C[C@@H](F)CN2C)cn1 ; CC(C)n1cc(NC[C@@H]2C[C@@H](F)C[NH+]2C)cn1 ; [Cl-]]

To a solution of (2S,4R)-4-fluoro-1-methyl-N-[1-(propan-2-yl)-1H-pyrazol-4-yl]pyrrolidine-2-carboxamide (500 mg, 1.97 mmol) in THF (6 ml) at 0° C. was added 10 M $BH_3 \cdot Me_2S$ (1.97 ml, 19.7 mmol). The RM was heated at 80° C. for 12 h. The RM was concentrated under reduced pressure, then the residue dissolved in 4 M HCl in EtOAc (5 ml). The mixture was stirred at rt for 12 h and concentrated under reduced pressure to give the title compound as a white solid. LCMS (ESI): m/z: $[M+H]^+$=241.2.

Step 7. (2S,4R)-2-{[({[(Tert-butoxy)carbonyl]amino}sulfonyl)[1-(propan-2-yl)-1H-pyrazol-4-yl]amino]methyl}-4-fluoro-1-methylpyrrolidin-1-ium Trifluoroacetate

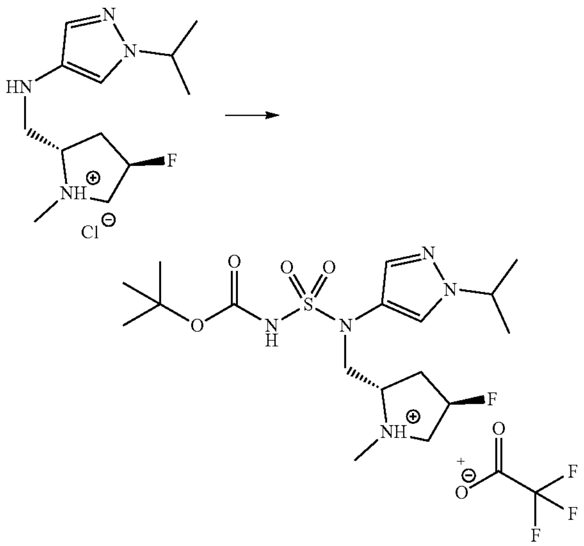

To a solution of N-{[(2S,4R)-4-fluoro-1-methylpyrrolidin-2-yl]methyl}-1-(propan-2-yl)-1H-pyrazol-4-amine hydrochloride (1.09 g, 3.94 mmol) in DCM (10 ml) at 0° C. was added DIPEA (3.43 ml, 19.7 mmol). The RM was stirred at 0° C. for 30 min, then treated with 0.45 M tert-butyl N-chlorosulfonylcarbamate in DCM (10.5 ml DCM, 4.73 mmol). The resulting mixture was stirred at rt for 1 h then concentrated under reduced pressure. The residue was purified by prep-HPLC (column: Phenomenex Luna C18 250×100 mm, 10 μm; mobile phase: [water (0.1% TFA)-ACN]; B: 10-36%, 20 min) to give the title compound as a white solid. Y=29%. $^1$H NMR (400 MHz, MeOD) δ 7.88 (s, 1H), 7.56 (s, 1H), 5.51-5.29 (m, 1H), 4.58-4.42 (m, 1H), 4.35-4.25 (m, 2H), 4.24-4.04 (m, 1H), 3.98-3.85 (m, 1H), 3.69-3.52 (m, 1H), 3.15 (s, 3H), 2.63-2.48 (m, 1H), 2.32-2.10 (m, 1H), 1.52 (s, 9H), 1.49 (d, J=7 Hz, 6H).

Step 8. N-{[(2S,4R)-4-Fluoro-1-methylpyrrolidin-2-yl]methyl}-N-[1-(propan-2-yl)-1H-pyrazol-4-yl]aminosulfonamide Hydrochloride

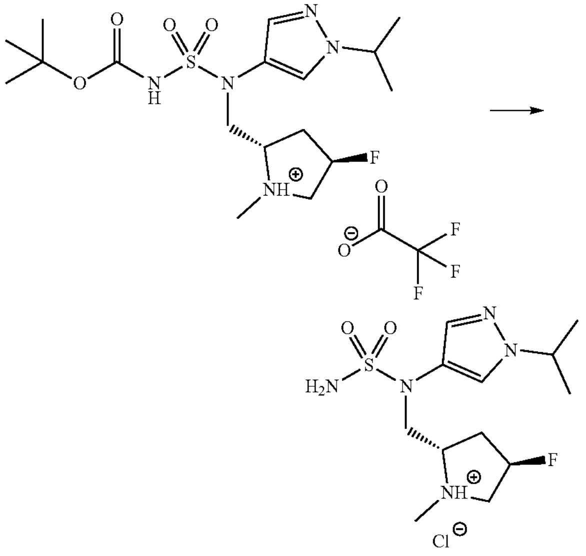

A solution of (2S,4R)-2-{[({[(tert-butoxy)carbonyl]amino}sulfonyl)[1-(propan-2-yl)-1H-pyrazol-4-yl]amino]methyl}-4-fluoro-1-methylpyrrolidin-1-ium trifluoroacetate (500 mg, 1.19 mmol) in 4 M HCl in EtOAc (10 ml) was stirred at rt for 1 h. The RM was concentrated under reduced pressure to give the title compound as a white solid. LCMS (ESI): m/z: $[M+H]^+$=320.2.

Intermediate 41. 3-Isocyanato-5-methyl-2-(propan-2-yl)thiophene

Step 1. Tert-butyl N-(5-methylthiophen-3-yl)carbamate

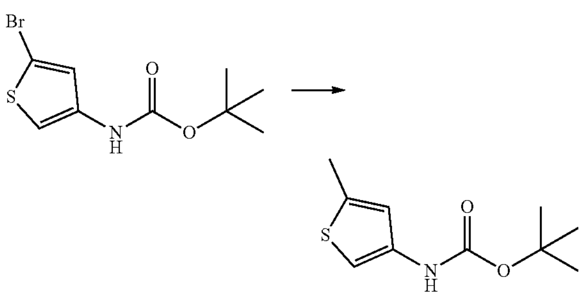

To a solution of tert-butyl N-(5-bromo-3-thienyl)carbamate (100 mg, 0.36 mmol) [for synthesis refer to Example 31] in dioxane (2 ml) was added methylboronic acid (43 mg, 0.72 mmol), CsF (191 mg, 1.26 mmol) and [1,1'-bis(diphenylphosphino)ferrocene]-dichloropalladium(II), complex with dichloromethane (32 mg, 39.5 μmol). The RM was stirred at 90° C. for 12 h. The RM was concentrated under reduced pressure and the resulting residue purified by prep-TLC (silica, 9% EtOAc in petrol) to give the title compound as a white solid. Y=25%.

Step 2. Tert-butyl N-(2-bromo-5-methylthiophen-3-yl)carbamate

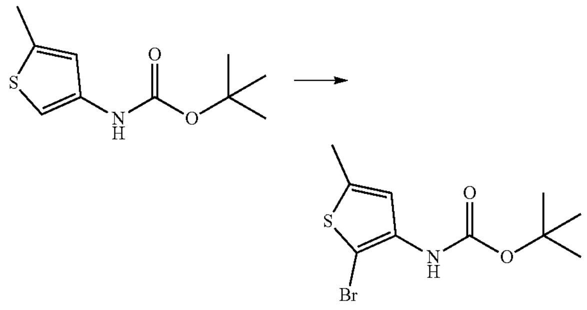

To a solution of tert-butyl N-(5-methylthiophen-3-yl) carbamate (170 mg, 0.80 mmol) in THF (8 ml) cooled to 0° C. was added portionwise NBS (142 mg, 0.80 mmol). The RM was stirred at rt for 30 min. The solution was concentrated under reduced pressure and the resulting residue purified by prep-TLC (silica, 9% EtOAc in petrol) to give the title compound as a white solid. Y=77%.

Step 3. Tert-butyl N-[5-methyl-2-(prop-1-en-2-yl) thiophen-3-yl]carbamate

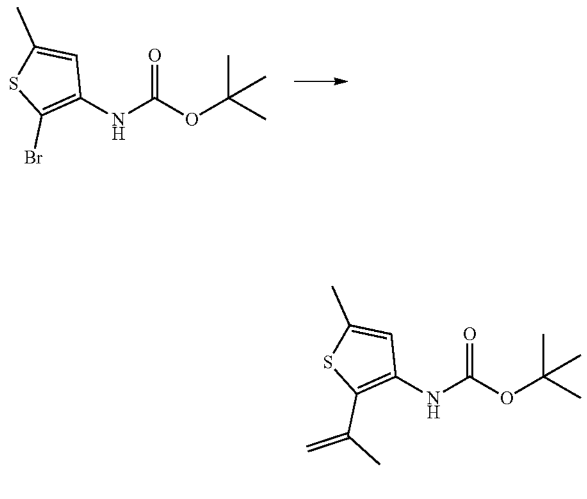

To a solution of tert-butyl N-(2-bromo-5-methylthiophen-3-yl)carbamate (180 mg, 0.62 mmol) in THF (4 ml) and $H_2O$ (0.8 ml) was added isopropenyl-(4,4,5,5-tetramethyl-1,3-dioxolan-2-yl)borane (561 mg, 3.08 mmol), $Pd(PPh_3)_4$ (7.1 mg, 6.2 μmol) and $Na_2CO_3$ (196 mg, 1.85 mmol). The RM was stirred at 90° C. for 12 h. The mixture was concentrated under reduced pressure and the resulting residue purified by prep-TLC (silica, 9% EtOAc in petrol) to give the title compound as a white solid. Y=77%. LCMS (ESI): m/z: $[M+H]^+$=254.2.

Step 4. Tert-butyl N-[5-methyl-2-(propan-2-yl)thiophen-3-yl]carbamate

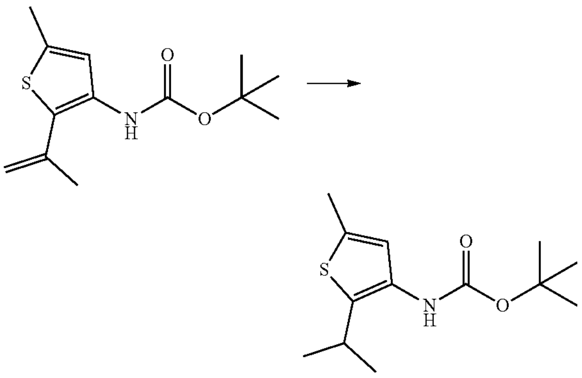

To a solution of tert-butyl N-[5-methyl-2-(prop-1-en-2-yl)thiophen-3-yl]carbamate (120 mg, 0.47 mmol) in MeOH (3 ml) was added 10% Pd/C (50% in water, 60 mg). The RM was degassed and stirred under $H_2$ (15 psi) atmosphere at rt for 5 min. The solution was filtered and the filtrate concentrated under reduced pressure to give the title compound as a white solid. $^1$H NMR (400 MHz, chloroform-d) δ 6.97 (s, 1H), 6.05 (s, 1H), 3.12-3.05 (m, 1H), 2.39 (s, 3H), 1.51 (s, 9H), 1.30-1.25 (m, 6H).

Step 5. 5-Methyl-2-(propan-2-yl)thiophen-3-amine Hydrochloride

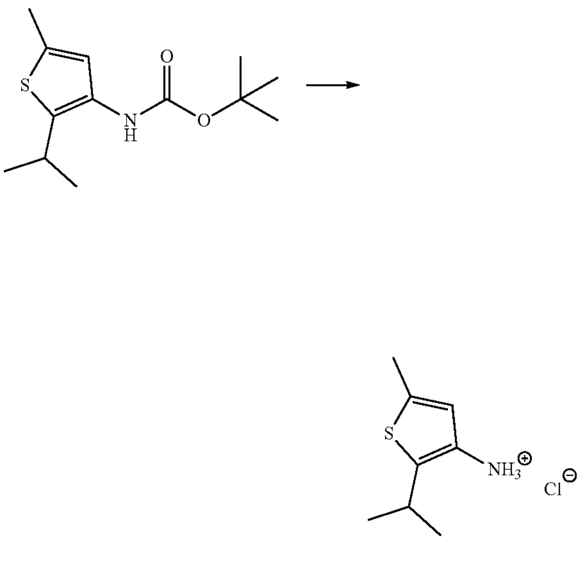

A solution of tert-butyl N-[5-methyl-2-(propan-2-yl)thiophen-3-yl]carbamate (140 mg, 0.55 mmol) in 4 M HCl in EtOAc (2 ml) was stirred at rt for 1 h. The solution was concentrated under reduced pressure to give the title compound as a white solid. LCMS (ESI): m/z: $[M+H]^+$=156.2.

Step 6. 3-Isocyanato-5-methyl-2-(propan-2-yl)thiophene

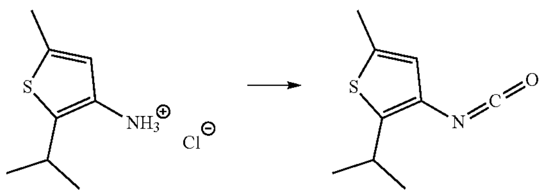

To a solution of 5-methyl-2-(propan-2-yl)thiophen-3-amine hydrochloride (110 mg, 0.57 mmol) in dioxane (3 ml) at 40° C. was added trichloromethyl carbonochloridate (69.2 μl, 0.57 mmol), then the mixture was heated at 70° C. for 1 h. The solution was concentrated under reduced pressure to give the title compound as a white solid. LCMS in MeOH (ESI): m/z: $[M+MeOH+H]^+$=214.1.

Intermediate 42. 3-Isocyanato-4-methyl-2,5-bis(propan-2-yl)thiophene

Step 1. Tert-butyl N-(4-bromothiophen-3-yl)carbamate

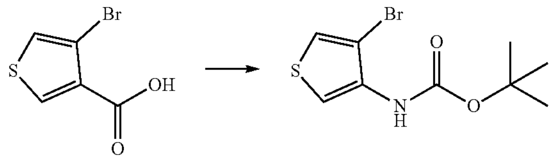

To a solution of 4-bromothiophene-3-carboxylic acid (3.0 g, 14.5 mmol) in tert-butanol (40 ml) under $N_2$ was added DPPA (3.14 ml, 14.5 mmol) and DIPEA (3.79 ml, 21.7 mmol). The RM was stirred at 90° C. for 12 h. The RM was concentrated under reduced pressure and the resulting residue purified by column chromatography (silica, 5-9% EtOAc in petrol) to give the title compound as a solid Y=74%. $^1$H NMR (400 MHz, chloroform-d) δ 7.51 (s, 1H), 7.21 (d, J=4 Hz, 1H), 6.83 (s, 1H), 1.54 (s, 9H).

Step 2. Tert-butyl N-(4-methylthiophen-3-yl)carbamate

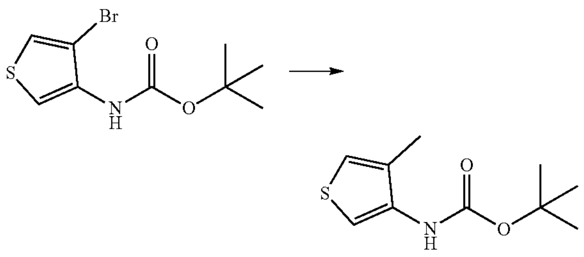

To a solution of tert-butyl N-(4-bromothiophen-3-yl)carbamate (2.0 g, 7.19 mmol) in dioxane (20 ml) under $N_2$ was added methylboronic acid (861 mg, 14.4 mmol), CsF (3.82 g, 25.1 mmol) and $Pd(dppf)Cl_2 \cdot CH_2Cl_2$ (646 mg, 791 μmol). The RM was stirred at 90° C. for 12 h. The RM was concentrated under reduced pressure and the resulting residue diluted with $H_2O$ (30 ml). The mixture was extracted with EtOAc (3×20 ml). The combined organic layers were washed with brine (2×20 ml), dried over $Na_2SO_4$, filtered and concentrated under reduced pressure to give a residue. This was purified by column chromatography (silica, 9% EtOAc in petrol) to give the title compound as a yellow solid. Y=38%. $^1$H NMR (400 MHz, chloroform-d) δ 7.41 (s, 1H), 6.87 (s, 1H), 6.37 (s, 1H), 2.14 (s, 3H), 1.54 (s, 9H).

Step 3. Tert-butyl N-(2,5-dibromo-4-methylthiophen-3-yl)carbamate

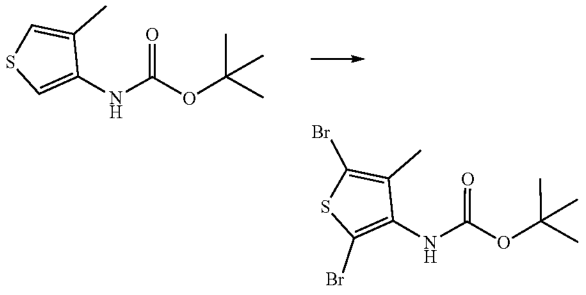

To a solution of tert-butyl N-(4-methylthiophen-3-yl)carbamate (578 mg, 2.71 mmol) in ACN (5 ml) was added NBS (1.01 g, 5.69 mmol). The mixture was stirred at rt for 12 h. The RM was concentrated under reduced pressure and the resulting residue purified by column chromatography (silica, 9% EtOAc in petrol) to give the title compound as a yellow solid. Y=65%. $^1$H NMR (400 MHz, chloroform-d) δ 5.90 (s, 1H), 2.11 (s, 3H), 1.50 (s, 9H).

Step 4. Tert-butyl N-[4-methyl-2,5-bis(prop-1-en-2-yl)thiophen-3-yl]carbamate

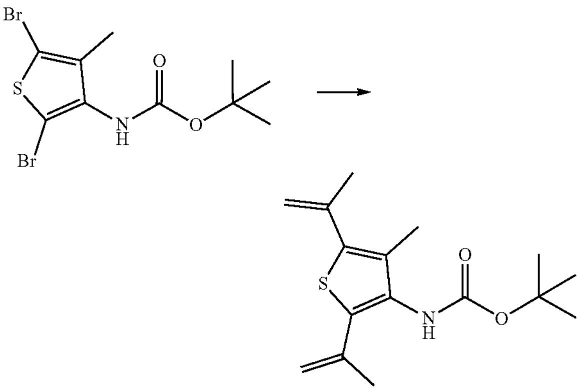

To a solution of tert-butyl N-(2,5-dibromo-4-methylthiophen-3-yl)carbamate (651 mg, 1.75 mmol) and 2-isopropenyl-4,4,5,5-tetramethyl-1,3,2-dioxaborolane (1.47 g, 8.77 mmol) in THF (9 ml) and $H_2O$ (1 ml) under $N_2$ were added $Pd(PPh_3)_4$ (20 mg, 17.5 μmol) and $Na_2CO_3$ (0.56 g, 5.26 mmol). The RM was stirred at 90° C. for 12 h. The RM was concentrated under reduced pressure and the resulting residue purified by column chromatography (silica, 9% EtOAc in petrol) to give the title compound as a yellow solid. Y=80%. LCMS (ESI): m/z: $[M+H-56]^+=238.0$.

Step 5. Tert-butyl N-[4-methyl-2,5-bis(propan-2-yl) thiophen-3-yl]carbamate

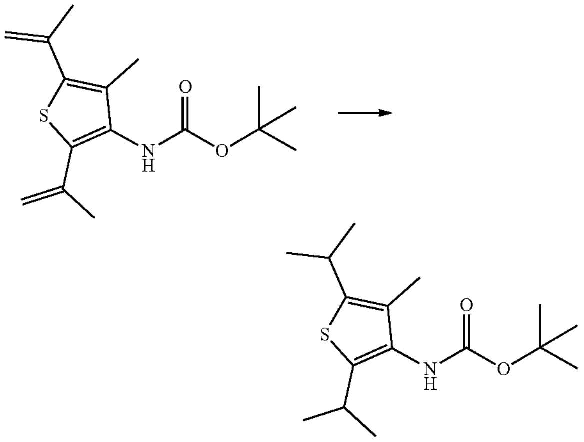

To a solution of tert-butyl N-[4-methyl-2,5-bis(prop-1-en-2-yl)thiophen-3-yl]carbamate (413 mg, 1.41 mmol) in MeOH (5 ml) was added 10% Pd/C (50% in water, 500 mg). The suspension was degassed under vacuum and purged with $H_2$ several times. The mixture was stirred under $H_2$ (15 psi) at rt for 0.5 h. The RM was filtered through Celite and concentrated under reduced pressure. The resulting residue was purified by prep-TLC (silica, 9% EtOAc in petrol) to give the title compound as a yellow solid. LCMS (ESI): m/z: $[M+H]^+=298.1$.

Step 6. 4-Methyl-2,5-bis(propan-2-yl)thiophen-3-amine Hydrochloride

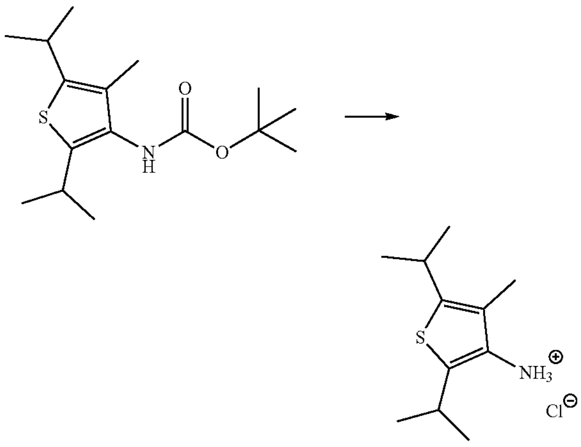

A solution of tert-butyl N-[4-methyl-2,5-bis(propan-2-yl) thiophen-3-yl]carbamate (282 mg, 0.95 mmol in 4 M HCl in EtOAc (5 ml) was stirred at rt for 0.5 h. The RM was concentrated under reduced pressure to give the title compound as a yellow solid. LCMS (ESI): m/z: $[M+H]^+=198.0$.

Step 7. 3-Isocyanato-4-methyl-2,5-bis(propan-2-yl) thiophene

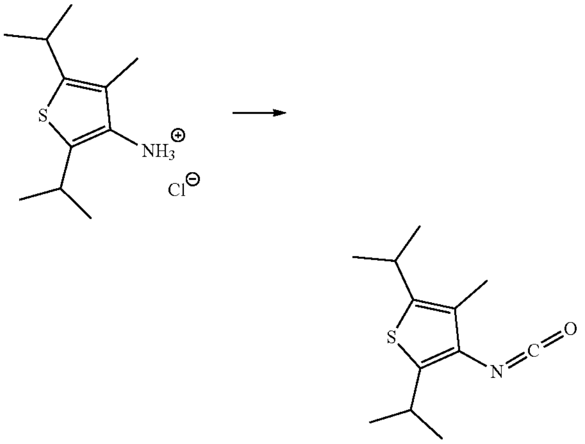

To a solution of 4-methyl-2,5-bis(propan-2-yl)thiophen-3-amine hydrochloride (222 mg, 0.95 mmol) in dioxane (5 ml) warmed to 40° C. was added trichloromethyl carbonochloridate (137 μl, 1.1 mmol). The RM was heated at 70° C. for 0.5 h. The RM was concentrated under reduced pressure to give the title compound as a yellow solid. LCMS in MeOH (ESI): m/z: $[M+H+MeOH]^+=256.2$.

Intermediate 43. N-(1-Methylpiperidin-3-yl)-N-(oxan-4-yl)aminosulfonamide Hydrochloride Step 1. Tert-butyl 3-[(oxan-4-yl)amino]piperidine-1-carboxylate

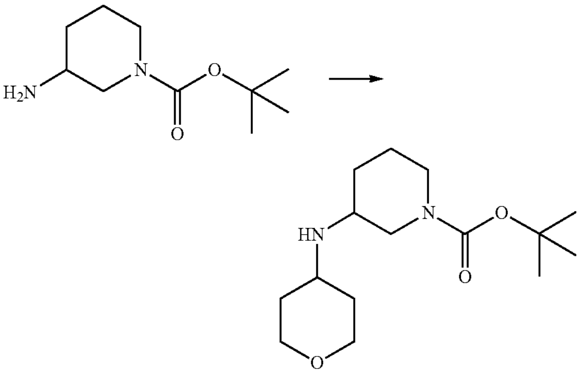

To a solution of tert-butyl 3-aminopiperidine-1-carboxylate (1.0 g, 5.0 mmol) in DCE (20 ml) was added tetrahydropyran-4-one (0.45 g, 4.5 mmol) and the resulting mixture stirred at rt for 0.5 h. The mixture was treated with $NaBH(OAc)_3$ (1.38 g, 6.5 mmol) and stirred at rt for 1 h. The RM was diluted with $H_2O$ (10 ml) and extracted with DCM (3×10 ml). The combined organic layers were washed with brine (2×10 ml), dried over $Na_2SO_4$, filtered and concentrated under reduced pressure to give the title compound as a white solid. $^1H$ NMR (400 MHz, MeOD) δ 4.13-4.07 (m, 1H), 4.00-3.97 (m, 2H), 3.88-3.85 (m, 1H), 3.47-3.40 (m, 2H), 3.21-3.08 (m, 1H), 3.03-2.83 (m, 2H), 2.12-1.84 (m, 5H), 1.79-1.72 (m, 1H), 1.58-1.48 (m, 3H), 1.46 (s, 9H).

Step 2. 1-Methyl-N-(oxan-4-yl)piperidin-3-amine

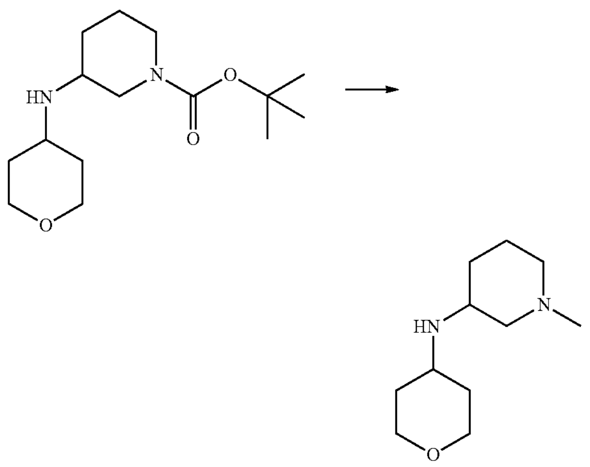

To a solution of tert-butyl 3-[(oxan-4-yl)amino]piperidine-1-carboxylate (500 mg, 1.76 mmol) in THF (10 ml) at 0° C. was added lithium aluminium hydride (667 mg, 17.6 mmol). The RM was stirred at 80° C. for 2 h. The mixture was allowed to cool to rt and quenched by addition of $H_2O$ (7 ml). The mixture was filtered and the filtrate concentrated under reduced pressure to give the title compound as a colourless oil. $^1H$ NMR (400 MHz, MeOD) δ 3.95-3.91 (m, 2H), 3.46-3.36 (m, 2H), 3.01-2.70 (m, 4H), 2.27 (s, 3H), 2.05-1.67 (m, 6H), 1.65-1.51 (m, 1H), 1.45-1.30 (m, 2H), 1.16-0.99 (m, 1H).

Step 3. Tert-butyl N-[(1-methylpiperidin-3-yl)(oxan-4-yl)sulfamoyl]carbamate

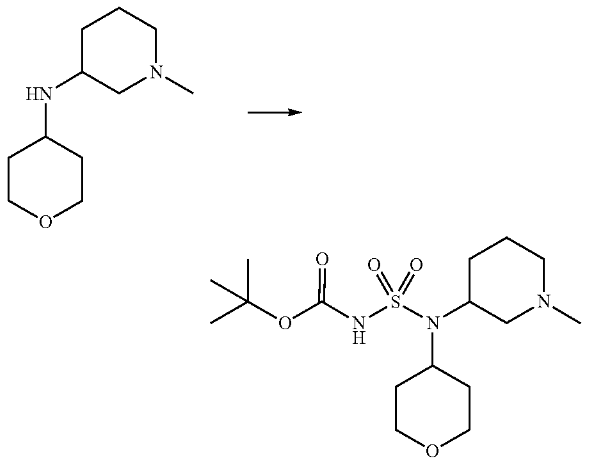

To a solution of 1-methyl-N-(oxan-4-yl)piperidin-3-amine (100 mg, 0.50 mmol) in DCM (1 ml) cooled to 0° C. under $N_2$ was added DIPEA (264 µl, 1.50 mmol). The RM was stirred at 0° C. for 0.5 h then treated dropwise with 0.70 M tert-butyl N-chlorosulfonylcarbamate in DCM (713 µl, 0.50 mmol). The resulting mixture was stirred at 0° C. for 0.5 h. The mixture was concentrated under reduced pressure and the resulting residue purified by column chromatography (silica, 50-100% EtOAc in petrol) to give the title compound as a white solid. Y=53%.

Step 4. N-(1-Methylpiperidin-3-yl)-N-(oxan-4-yl)aminosulfonamide Hydrochloride

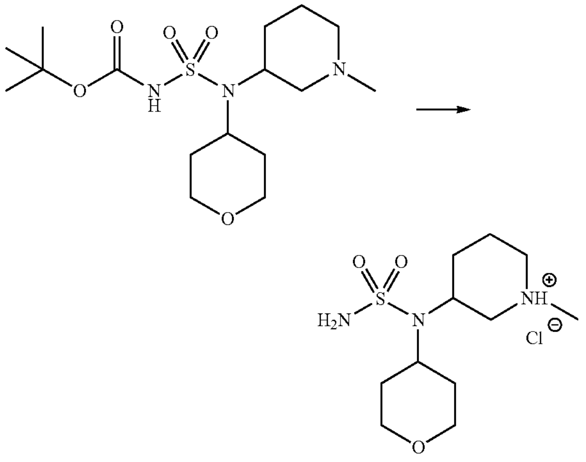

A solution of tert-butyl N-[(1-methylpiperidin-3-yl)(oxan-4-yl)sulfamoyl]carbamate (100 mg, 265 µmol) in 4 M HCl in EtOAc (10 ml) was stirred at rt for 0.5 h. The mixture was concentrated under reduced pressure to give the title compound as a white solid. LCMS (ESI): m/z: $[M+H]^+$=278.2.

Intermediate 44. N-(1-Methylpiperidin-3-yl)-N-(oxolan-3-yl)aminosulfonamide Hydrochloride Step 1. Tert-butyl 3-[(oxolan-3-yl)amino]piperidine-1-carboxylate

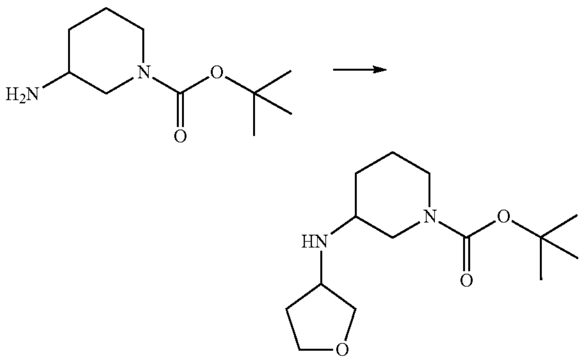

To a solution of tert-butyl 3-aminopiperidine-1-carboxylate (1 g, 5.0 mmol) in DCE (20 ml) under $N_2$ was added tetrahydrofuran-3-one (430 mg, 5.0 mmol) and the mixture stirred at rt for 0.5 h. The RM was treated with $NaBH(OAc)_3$ (1.38 g, 6.5 mmol) and stirred at rt for 3 h. The RM was concentrated under reduced pressure and the resulting residue purified by column chromatography (silica, 100% EtOAc) to give the title compound as a yellow solid.

Y=95%. ¹H NMR (400 MHz, MeOD) δ 4.10 (s, 1H), 4.00-3.95 (m, 1H), 3.90-3.85 (m, 2H), 3.80-3.75 (m, 1H), 3.60-3.48 (m, 2H), 2.92-2.82 (m, 1H), 2.72-2.60 (m, 2H), 2.30-2.20 (m, 1H), 2.10-1.95 (m, 1H), 1.94-1.65 (m, 2H), 1.46 (s, 9H), 1.44-1.25 (m, 2H).

Step 2. 1-Methyl-N-(oxolan-3-yl)piperidin-3-amine

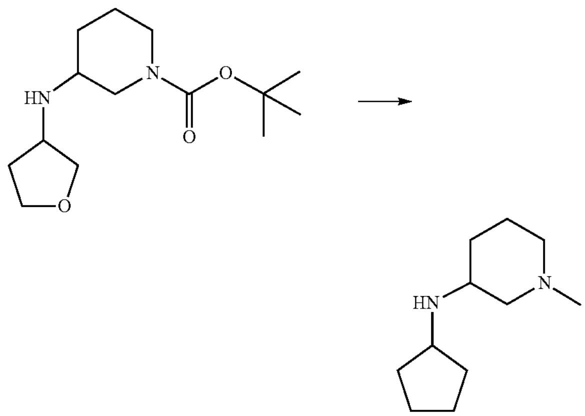

To a solution of tert-butyl 3-[(oxolan-3-yl)amino]piperidine-1-carboxylate (1.28 g, 4.73 mmol) in THF (30 ml) was added lithium aluminium hydride (1.80 g, 47.3 mmol). The RM was stirred at 80° C. for 3 h. The RM cooled to 0° C. was quenched by addition of $H_2O$ (1.8 ml) and NaOH aq. (1.8 ml). The mixture was filtered and the filtrate concentrated under reduced pressure to give a residue. This was purified by column chromatography (silica, 9% MeOH in DCM) to give the title compound as a yellow solid. Y=57%. ¹HNMR (400 MHz, MeOD) δ 3.95-3.80 (m, 2H), 3.70-3.65 (m, 1H), 3.60-3.45 (m, 2H), 3.05-2.95 (m, 1H), 2.80-2.75 (m, 1H), 2.70-2.60 (m, 1H), 2.25 (s, 3H), 2.20-2.10 (m, 1H), 2.05-1.90 (m, 2H), 1.80-1.65 (m, 3H), 1.63-1.50 (m, 1H), 1.15-0.95 (m, 1H).

Step 3. Tert-butyl N-[(1-methylpiperidin-3-yl)(oxolan-3-yl)sulfamoyl]carbamate

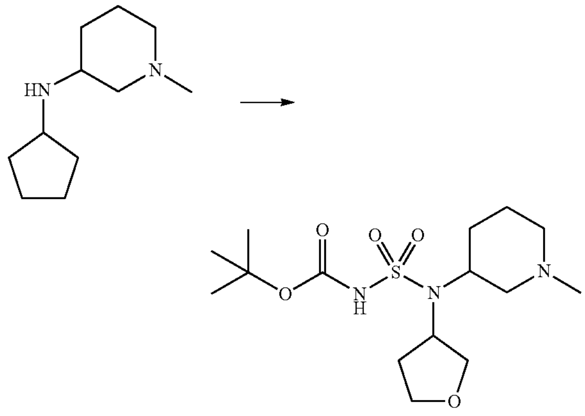

To a solution of 1-methyl-N-(oxolan-3-yl)piperidin-3-amine (200 mg, 1.09 mmol) in THF (2 ml) under $N_2$ was added DIPEA (567 μl, 3.26 mmol). The RM was stirred at rt for 0.5 h, cooled to 0° C. and treated with 0.47 M tert-butyl N-chlorosulfonylcarbamate in DCM (6.92 ml). The RM was stirred at 0° C. for 3 h. The RM was concentrated under reduced pressure and the resulting residue purified by prep-TLC (silica, 25% EtOAc in petrol) to give the title compound as a yellow solid. Y=27%. ¹H NMR (400 MHz, MeOD) δ 4.55-4.40 (m, 1H), 4.05-3.98 (m, 1H), 3.90-3.85 (m, 1H), 3.70-3.60 (m, 3H), 3.49-3.40 (m, 1H), 3.30-3.00 (m, 2H), 2.95-2.65 (m, 1H), 2.54 (d, J=4 Hz, 3H), 2.35-2.25 (m, 1H), 2.23-2.10 (m, 1H), 1.95-1.85 (m, 2H), 1.80-1.65 (m, 1H), 1.63-1.60 (m, 1H), 1.50 (s, 9H).

Step 4. N-(1-Methylpiperidin-3-yl)-N-(oxolan-3-yl)aminosulfonamide Hydrochloride

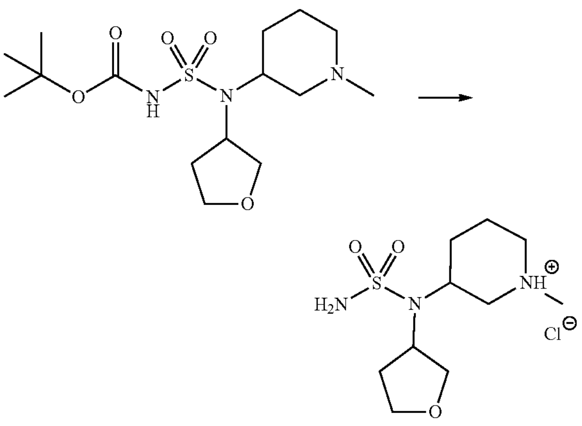

A solution of tert-butyl N-[(1-methylpiperidin-3-yl)(oxolan-3-yl)sulfamoyl]carbamate (105 mg, 0.29 mmol) in 4 M HCl in EtOAc (2 ml) was stirred at rt for 0.5 h. The RM was concentrated under reduced pressure to give the title compound as a yellow solid. LCMS (ESI): m/z: $[M+H]^+$=264.1.

Intermediate 45. 3-Isocyanato-2-(propan-2-yl)-4H,5H,6H-cyclopenta[b]thiophene

Step 1. Methyl 2-amino-4H,5H,6H-cyclopenta[b]thiophene-3-carboxylate

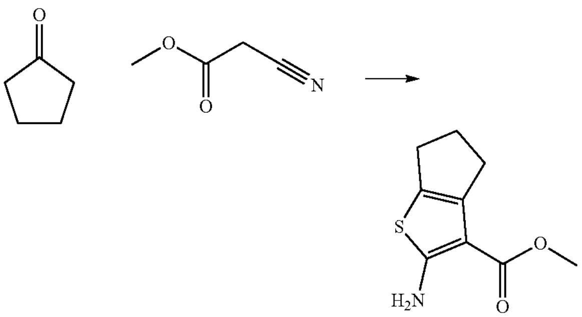

To a solution of methyl 2-cyanoacetate (1.30 g, 13.1 mmol) in MeOH (10 ml) was added cyclopentanone (1.0 g, 11.9 mmol), diethylamine (1.35 ml, 13.1 mmol) and sulfur (419 mg, 13.1 mmol). The RM was sonicated in an ultrasound bath at rt for 1 h. The RM was concentrated under reduced pressure and the resulting residue purified by column chromatography (silica, 9-17% EtOAc in petrol) to give the title compound as a yellow solid. Y=20%. $^1$H NMR (400 MHz, chloroform-d) δ 5.87 (s, 2H), 3.79 (s, 3H), 2.83-2.78 (m, 2H), 2.74-2.68 (m, 2H), 2.35-2.27 (m, 2H).

Step 2. Methyl 2-bromo-4H,5H,6H-cyclopenta[b]thiophene-3-carboxylate

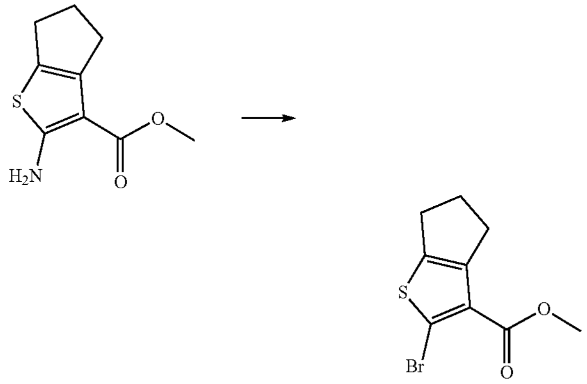

To a mixture of $CuBr_2$ (7.81 g, 35.0 mmol) in MeCN (50 ml) cooled to 0° C. was added tert-butyl nitrite (3.24 g, 31.4 mmol) and, portionwise, methyl 2-amino-4H,5H,6H-cyclopenta[b]thiophene-3-carboxylate (5.0 g, 25.4 mmol). The RM was stirred at 0° C. for 2 h, then the mixture was allowed to warm to rt and stirred for 3 h. The RM was diluted with water (40 ml) and extracted with EtOAc (3×50 ml). The combined organic phase was washed with brine (25 ml), dried with anhydrous $Na_2SO_4$, filtered and concentrated in vacuo. The resulting residue was purified by column chromatography (silica, 9-17% EtOAc in petrol) to give the title compound as a solid. Y=32%. $^1$H NMR (400 MHz, chloroform-d) δ 3.87 (s, 3H), 2.95 (t, J=7 Hz, 2H), 2.85 (t, J=7 Hz, 2H), 2.44-2.37 (m, 2H).

Step 3. Methyl 2-(prop-1-en-2-yl)-4H,5H,6H-cyclopenta[b]thiophene-3-carboxylate

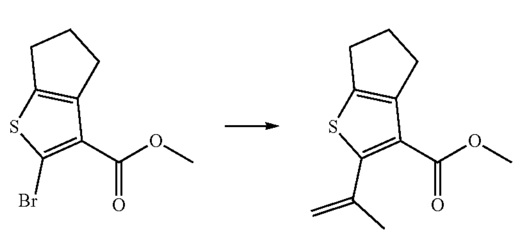

To a solution of methyl 2-bromo-4H,5H,6H-cyclopenta[b]thiophene-3-carboxylate (500 mg, 1.91 mmol) and 2-isopropenyl-4,4,5,5-tetramethyl-1,3,2-dioxaborolane (1.61 g, 9.57 mmol) in THF (10 ml) and $H_2O$ (2 ml) under $N_2$ were added $Na_2CO_3$ (609 mg, 5.74 mmol) and $Pd(PPh_3)_4$ (22 mg, 19 μmol). The RM was stirred at 90° C. for 12 h. The solution was concentrated under reduced pressure to give a residue which was purified by preparative-HPLC (column: Welch Ultimate AQ-C18 150×30 mm, 5 μm; mobile phase: [water (0.1% TFA)-ACN]; B: 55-80%, 12 min) to give the title compound as a white solid. Y=38%. $^1$H NMR (400 MHz, chloroform-d) δ 5.20-5.14 (m, 2H), 3.82 (s, 3H), 2.92-2.84 (m, 4H), 2.45-2.38 (m, 2H), 2.14 (s, 3H).

Step 4. Methyl 2-(propan-2-yl)-4H,5H,6H-cyclopenta[b]thiophene-3-carboxylate

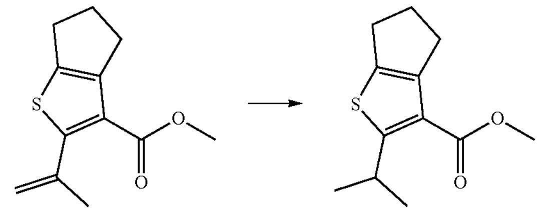

To a solution of methyl 2-(prop-1-en-2-yl)-4H,5H,6H-cyclopenta[b]thiophene-3-carboxylate (160 mg, 0.72 mmol) in MeOH (4 ml) was added 10% Pd/C (50% in water, 100 mg). The RM was degassed and stirred under $H_2$ atmosphere at rt for 1 h. The RM was filtered through Celite and the filtrate concentrated under reduced pressure to give the title compound as a white solid. Y=81%. $^1$H NMR (400 MHz, chloroform-d) δ 4.12-4.05 (m, 1H), 3.82 (s, 3H), 2.90 (t, J=7 Hz, 2H), 2.84 (t, J=7 Hz, 2H), 2.43-2.36 (m, 2H), 1.31 (d, J=7 Hz, 6H).

Step 5. 2-(Propan-2-yl)-4H,5H,6H-cyclopenta[b]thiophene-3-carboxylic Acid

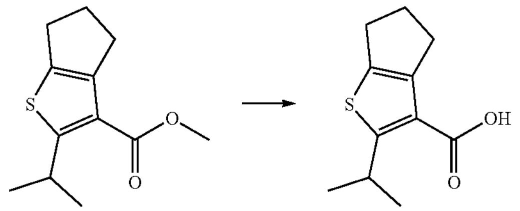

To a solution of methyl 2-(propan-2-yl)-4H,5H,6H-cyclopenta[b]thiophene-3-carboxylate (130 mg, 0.58 mmol) in $H_2O$ (1 ml) and MeOH (2 ml) was added NaOH (28 mg, 0.70 mmol). The RM was stirred at 50° C. for 12 h. The solution was filtered and the filtrate concentrated under reduced pressure. The residue was diluted with $H_2O$ (5 ml). The solution was acidified to pH~2 with 6 M HCl, then extracted with EtOAc (3×15 ml). The combined organic phase was concentrated under reduced pressure to give the title compound as a white solid. Y=89%. $^1$H NMR (400 MHz, chloroform-d) δ 4.16-4.08 (m, 1H), 2.98-2.83 (m, 4H), 2.45-2.38 (m, 2H), 1.33 (d, J=7 Hz, 6H).

Step 6. Tert-butyl N-[2-(propan-2-yl)-4H,5H,6H-cyclopenta[b]thiophen-3-yl]carbamate

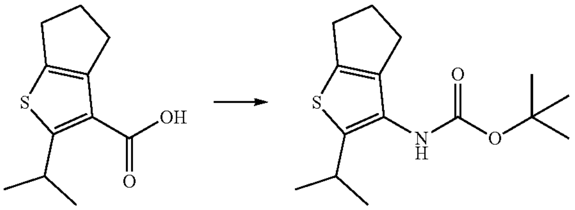 [SMILES: CC(C)c1sc2c(c1C(=O)O)CCC2 ; CC(C)c1sc2c(c1NC(=O)OC(C)(C)C)CCC2]

To a solution of 2-(propan-2-yl)-4H,5H,6H-cyclopenta[b]thiophene-3-carboxylic acid (108 mg, 0.51 mmol) in tert-butanol (3 ml) under $N_2$ were added DPPA (111 μl, 0.51 mmol) and DIPEA (134 μl, 6 0.77 mmol). The RM was stirred at 90° C. for 12 h. The solution was concentrated under reduced pressure and the resulting residue purified by column chromatography (silica, 9-17% EtOAc in petrol) to give the title compound as a yellow solid. Y=35%. $^1$H NMR (400 MHz, chloroform-d) δ 5.74 (s, 1H), 3.20-3.14 (m, 1H), 2.83 (t, J=7 Hz, 2H), 2.68 (t, J=7 Hz, 2H), 2.42-2.35 (m, 2H), 1.49 (s, 9H), 1.26 (d, J=7 Hz, 6H).

Step 7. 2-(Propan-2-yl)-4H,5H,6H-cyclopenta[b]thiophen-3-amine Hydrochloride

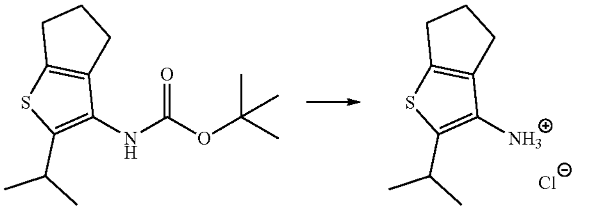 [SMILES: CC(C)c1sc2c(c1NC(=O)OC(C)(C)C)CCC2 ; CC(C)c1sc2c(c1[NH3+])CCC2 ; [Cl-]]

A mixture of tert-butyl N-[2-(propan-2-yl)-4H,5H,6H-cyclopenta[b]thiophen-3-yl]carbamate (50 mg, 178 μmol) and 4 M HCl in EtOAc (3 ml) was stirred at rt for 1 h. The solution was concentrated under reduced pressure to give the title compound as a yellow solid. Y=83%. LCMS (ESI): m/z: $[M+H]^+$=182.2.

Step 8. 3-Isocyanato-2-(propan-2-yl)-4H,5H,6H-cyclopenta[b]thiophene

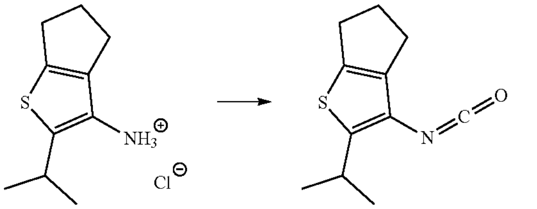

To a solution of 2-(propan-2-yl)-4H,5H,6H-cyclopenta[b]thiophen-3-amine hydrochloride (32 mg, 0.15 mmol) in dioxane (3 ml) warmed to 40° C. was added trichloromethyl carbonochloridate (21 μl, 0.18 mmol). The RM was heated at 70° C. for 0.5 h. The RM was concentrated under reduced pressure to give the title compound as a solid. LCMS in MeOH (ESI): m/z: $[M+MeOH+H]^+$=240.2.

Intermediate 46.
3-Isocyanato-2,5-bis(propan-2-yl)furan

Step 1. Methyl
2,5-bis(propan-2-yl)furan-3-carboxylate

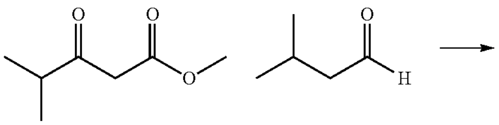

-continued

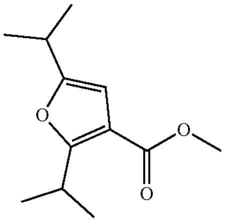

To a solution of 3-methylbutanal (1.98 g, 23.0 mmol) in ACN (40 ml) was added methyl 4-methyl-3-oxo-pentanoate (4.0 g, 27.8 mmol), $AlCl_3$ (185 mg, 1.39 mmol) and NBS (4.94 g, 27.8 mmol). The RM was heated at 80° C. for 12 h. The solution was concentrated in vacuo and the resulting residue purified by silica gel chromatography (9% EtOAc in petrol) to give the title compound as a yellow oil. Y=43%. $^1$H NMR (400 MHz, chloroform-d) δ 6.19 (s, 1H), 3.80 (s, 3H), 3.77-3.67 (m, 1H), 2.94-2.84 (m, 1H), 1.30-1.17 (m, 12H).

Step 2. 2,5-Bis(propan-2-yl)furan-3-carboxylic Acid

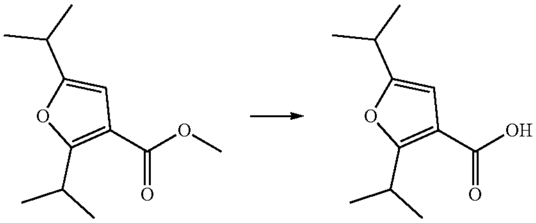

To a solution of methyl 2,5-bis(propan-2-yl)furan-3-carboxylate (2.5 g, 11.9 mmol) in EtOH (32 ml) and $H_2O$ (4 ml) cooled to 0° C. was added NaOH (476 mg, 11.9 mmol). The RM was stirred at 80° C. for 12 h. The RM was diluted with EtOAc (5 ml) and extracted with water (3×3 ml). The combined aqueous phase was acidified to pH~4 with 1 M HCl. The mixture was extracted with EtOAc (3×3 ml) and the combined organics washed with brine (2 ml), dried over anhydrous $Na_2SO_4$ and concentrated under reduced pressure to give the title compound as a yellow oil. LCMS (ESI): m/z: $[M+H]^+$=197.2.

Step 3. Tert-butyl N-[2,5-bis(propan-2-yl)furan-3-yl]carbamate

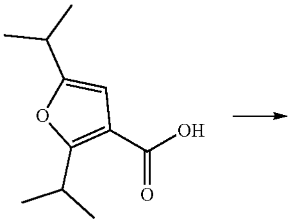

-continued

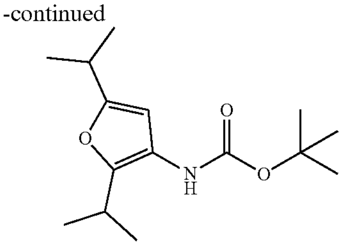

To a solution of 2,5-bis(propan-2-yl)furan-3-carboxylic acid (2.6 g, 13.3 mmol) in tert-butanol (30 ml) was added DIPEA (3.46 ml, 19.9 mmol) and DPPA (3.65 g, 13.3 mmol). The RM was heated at 85° C. for 12 h. The solution was concentrated in vacuo and the resulting residue purified by silica gel chromatography (17% EtOAc in petrol) to give the title as a yellow solid. Y=28%. LCMS (ESI): m/z: $[M+H]^+$=268.1.

Step 4. 2,5-Bis(propan-2-yl)furan-3-amine Hydrochloride

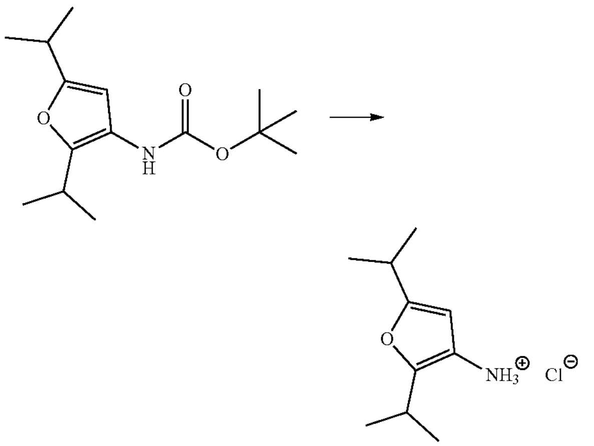

A solution of tert-butyl N-[2,5-bis(propan-2-yl)furan-3-yl]carbamate (500 mg, 1.87 mmol) in 4 M HCl in EtOAc (20 ml) was stirred at rt for 2 h. The solution was concentrated in vacuo to give the title compound as a yellow oil. LCMS (ESI): m/z: $[M+H]^+$=168.1.

Step 5. 3-Isocyanato-2,5-bis(propan-2-yl)furan

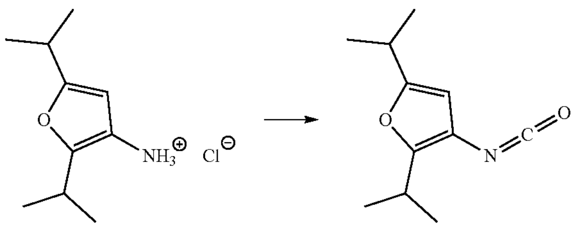

To a solution of 2,5-bis(propan-2-yl)furan-3-amine hydrochloride (300 mg, 1.79 mmol) in dioxane (6 ml) warmed to 40° C. was added trichloromethyl carbonochloridate (216 µl, 1.79 mmol). The RM was heated at 70° C. for 1 h. The solution was concentrated in vacuo to give the title compound as a liquid. LCMS in MeOH (ESI): m/z: $[M+MeOH+H]^+$=226.2.

Intermediate 47. N-(1-methyl-1H-pyrazol-4-yl)-N-[(oxolan-2-yl)methyl]aminosulfonamide Step 1. N-(1-Methyl-1H-pyrazol-4-yl)oxolane-2-carboxamide

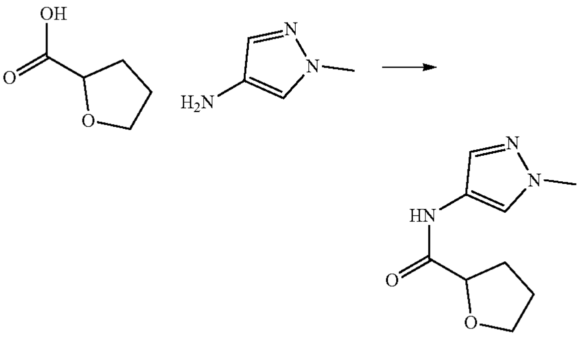

To a solution of tetrahydrofuran-2-carboxylic acid (500 mg, 4.31 mmol) in DCM (5 ml) cooled to 0° C. was added HATU (2.46 g, 6.46 mmol) and the mixture was stirred for 0.5 h. The RM was treated with 1-methylpyrazol-4-amine (418 mg, 4.31 mmol) and DIPEA (2.25 ml, 12.9 mmol). The mixture was stirred at rt for 12 h. The RM was diluted with water (10 ml) and the resulting mixture was extracted with DCM (3×10 ml). The organic phase was collected, washed with brine (10 ml), dried over $Na_2SO_4$, filtered and the filtrate concentrated under reduced pressure. The resulting residue was purified by column chromatography (silica, 5-9% MeOH in DCM) to give the title compound as a white solid. Y=83%. $^1$H NMR (400 MHz, chloroform-d) δ 8.33 (s, 1H), 7.94 (s, 1H), 7.42 (s, 1H), 4.49-4.44 (m, 1H), 4.07-4.00 (m, 1H), 3.97-3.90 (m, 1H), 3.88 (s, 3H), 2.38-2.33 (m, 1H), 2.15-2.14 (m, 1H), 1.97-1.91 (m, 2H).

Step 2. 1-Methyl-N-[(oxolan-2-yl)methyl]-1H-pyrazol-4-amine

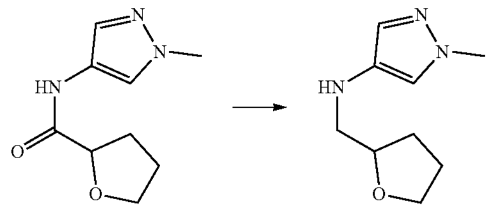

To a solution of N-(1-methyl-1H-pyrazol-4-yl)oxolane-2-carboxamide (400 mg, 2.05 mmol) in THF (4 ml) at 0° C. was added 10 M $BH_3$-$Me_2S$ (2.05 ml, 20.5 mmol). The mixture was heated at 80° C. for 12 h. The reaction was quenched with MeOH (5 ml) and stirred at rt for 10 min. The mixture was diluted with water (10 ml) and extracted by EtOAc (3×10 ml). The organic phase was collected, washed with brine (10 ml) dried over $Na_2SO_4$, filtered and the filtrate concentrated under reduced pressure to give the title compound as a yellow solid. LCMS (ESI): m/z: $[M+H]^+$=182.1.

Step 3. Tert-butyl N-[(1-methyl-1H-pyrazol-4-yl)[(oxolan-2-yl)methyl]sulfamoyl]-carbamate

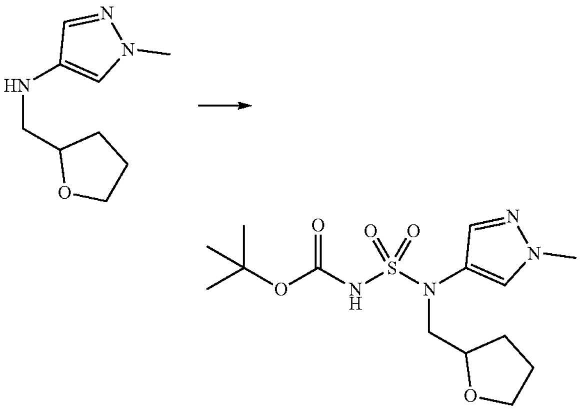

To a solution of 1-methyl-N-[(oxolan-2-yl)methyl]-1H-pyrazol-4-amine (380 mg, 2.10 mmol) in DCM (4 ml) cooled to 0° C. was added DIPEA (1.10 ml, 6.29 mmol) and 0.70 M tert-butyl N-chlorosulfonylcarbamate in DCM (3.86 ml, 2.70 mmol). The mixture was stirred at rt for 0.5 h. The RM was filtered and the filtrate concentrated under reduced pressure to give a residue. This was purified by prep-HPLC (column: Phenomenex Luna C18 250×50 mm, 10 μm; mobile phase: [water (0.05% HCl)-ACN]; B: 20-50%, 10 min) to give the title compound as a pale yellow oil. Y=46%. $^1$H NMR (400 MHz, chloroform-d) δ 7.52 (s, 1H), 7.45 (s, 1H), 4.07-3.99 (m, 1H), 3.87 (s, 3H), 3.84-3.68 (m, 4H), 2.00-1.84 (m, 3H), 1.68-1.62 (m, 1H), 1.50 (s, 9H).

Step 4. N-(1-Methyl-1H-pyrazol-4-yl)-N-[(oxolan-2-yl)methyl]aminosulfonamide

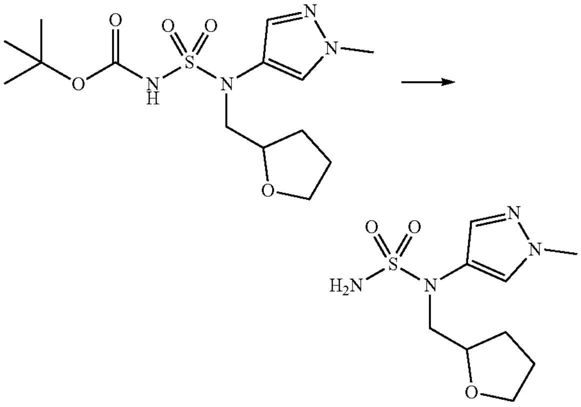

A solution of tert-butyl N-[(1-methyl-1H-pyrazol-4-yl)[(oxolan-2-yl)methyl]sulfamoyl]-carbamate (350 mg, 0.97 mmol) in 4 M HCl in EtOAc (10 ml) was stirred at rt for 1 h. The mixture was concentrated under reduced pressure to give the title compound as a white solid. $^1$H NMR (400 MHz, MeOD) δ 7.94 (s, 1H), 7.82 (s, 1H), 4.14-4.00 (m, 1H), 3.96 (s, 3H), 3.88-3.69 (m, 2H), 3.65-3.43 (m, 2H), 2.07-1.81 (m, 3H), 1.72-1.57 (m, 1H).

Intermediate 48. N-[2-(Dimethylamino)ethyl]-N-[1-(propan-2-yl)-1H-pyrazol-4-yl]aminosulfonamide Hydrochloride Step 1. 2-(Dimethylamino)-N-[1-(propan-2-yl)-1H-pyrazol-4-yl]acetamide

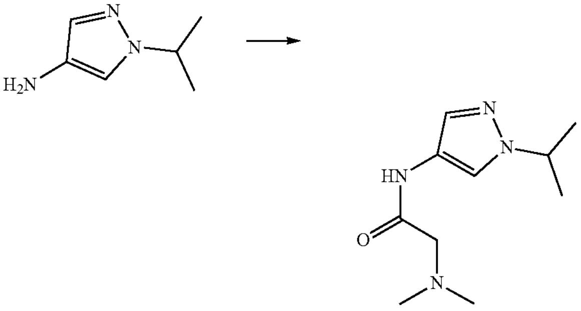

To a solution of 2-(dimethylamino)acetic acid (1.24 g, 12.0 mmol) in DCM (20 ml) at 0° C. was added HOBt (2.43 g, 18.0 mmol) and EDCI (3.45 g, 18.0 mmol). The solution was stirred at 0° C. for 0.5 h then treated with 1-isopropylpyrazol-4-amine (1.5 g, 12.0 mmol) [for synthesis refer to Intermediate 40] and DIPEA (6.26 ml, 36.0 mmol). The RM was stirred at rt for 6 h. The solution was concentrated under vacuum and the resulting residue purified by silica gel chromatography (9-33% MeOH in EtOAc) to give the title compound as a yellow oil. Y=46%. $^1$H NMR (400 MHz, MeOD) δ 7.95 (s, 1H), 7.55 (s, 1H), 4.53-4.42 (m, 1H), 3.10 (s, 2H), 2.34 (s, 6H), 1.50-1.45 (m, 6H).

Step 2. N-[2-(Dimethylamino)ethyl]-1-(propan-2-yl)-1H-pyrazol-4-amine

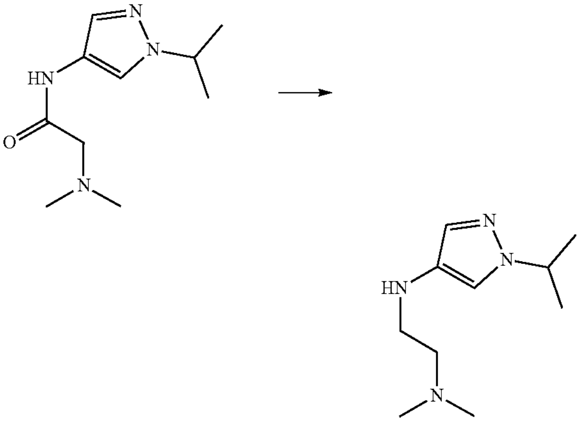

A solution of 2-(dimethylamino)-N-(1-isopropylpyrazol-4-yl)acetamide (580 mg, 2.76 mmol) in 1 M $BH_3$ in THF (10 ml) was stirred at 50° C. for 6 h. The RM was cooled to 0° C. and treated with 10 M $BH_3$·$Me_2S$ (1.38 ml, 13.8 mmol). The RM was heated at 60° C. for 12 h. The solution was cooled to 0° C. and quenched by addition of MeOH (20 ml). The solution was concentrated under vacuum to give the title compound as a yellow gum. LCMS (ESI): m/z: $[M+H]^+$=197.2.

Step 3. Tert-butyl N-{[2-(dimethylamino)ethyl][1-(propan-2-yl)-1H-pyrazol-4-yl]sulfamoyl}carbamate

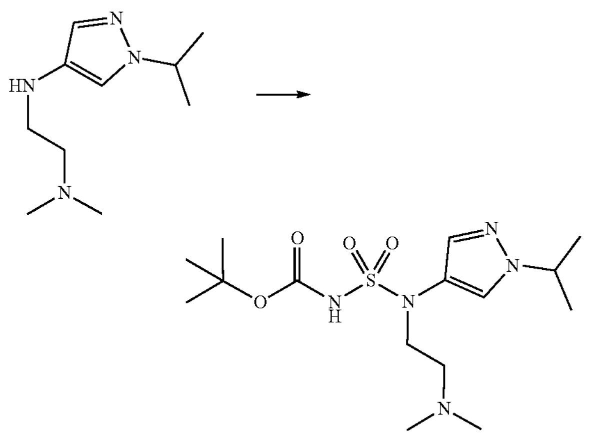

To a solution of N-[2-(dimethylamino)ethyl]-1-(propan-2-yl)-1H-pyrazol-4-amine (500 mg, 2.55 mmol) in DCM (2 ml) cooled to 0° C. was added DIPEA (1.33 ml, 7.64 mmol) and the solution was stirred for 20 min. The RM was treated with 0.99 M tert-butyl N-chlorosulfonylcarbamate in DCM (2.70 ml, 2.55 mmol) and the resulting solution stirred at 0° C. for 4 h. The solution was concentrated in vacuo and the resulting residue purified by prep-HPLC (column: Phenomenex Luna C18 250×50 mm, 10 μm; mobile phase: [water (0.1% TFA)-ACN]; B: 5-35%, 20 min) to give the title compound as a yellow gum. Y=53%. $^{1}$H NMR (400 MHz, MeOD) δ 7.62 (s, 1H), 7.56 (s, 1H), 4.55-4.51 (m, 1H), 4.21-4.18 (m, 1H), 3.90-3.88 (m, 2H), 3.36-3.35 (m, 1H), 3.30-3.25 (m, 1H), 3.01 (s, 6H), 1.52 (s, 9H), 1.51-1.47 (m, 6H).

Step 4. N-[2-(Dimethylamino)ethyl]-N-[1-(propan-2-yl)-1H-pyrazol-4-yl]aminosulfonamide Hydrochloride

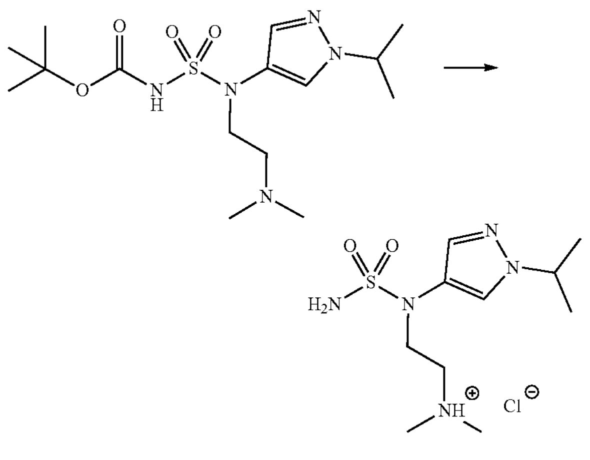

A solution of tert-butyl N-{[2-(dimethylamino)ethyl][1-(propan-2-yl)-1H-pyrazol-4-yl]sulfamoyl}carbamate (100 mg, 266 μmol, 1 eq) in 4 M HCl in EtOAc (5 ml) was stirred at rt for 1 h. The solution was concentrated in vacuo to give the title compound as a yellow oil. LCMS (ESI): m/z: $[M+H]^+$=276.1.

Intermediate 49. 2-Ethyl-3-isocyanato-4H,5H,6H-cyclopenta[b]thiophene

Step 1. Methyl 2-ethenyl-4H,5H,6H-cyclopenta[b]thiophene-3-carboxylate

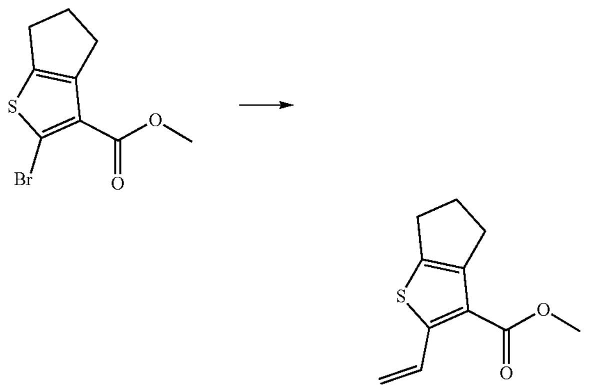

To a solution of methyl 2-bromo-5,6-dihydro-4H-cyclopenta[b]thiophene-3-carboxylate (300 mg, 1.15 mmol) [for synthesis refer to Intermediate 28] in THF (5 ml) and $H_2O$ (0.5 ml) were added potassium ethenyltrifluoroboranuide (769 mg, 5.74 mmol), triphenylphosphine (18 mg, 69 μmol), $Cs_2CO_3$ (1.12 g, 3.45 mmol) and $PdCl_2$ (4.1 mg, 23 μmol). The RM was degassed and placed under nitrogen atmosphere. The RM was heated at 90° C. for 12 h. The RM was concentrated under reduced pressure and the resulting residue purified by column chromatography (silica, 5-9% EtOAc in petrol) to give the title compound as a solid. Y=30%.

Step 2. Methyl 2-ethyl-4H,5H,6H-cyclopenta[b]thiophene-3-carboxylate

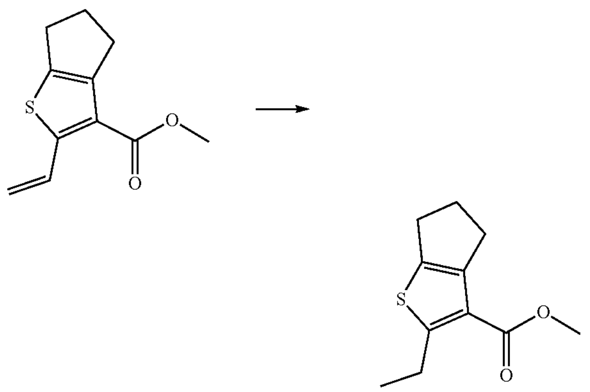

To a solution of methyl 2-ethenyl-4H,5H,6H-cyclopenta[b]thiophene-3-carboxylate (203 mg, 0.97 mmol) in MeOH (6 ml) was added 10% Pd/C (50% in water, 100 mg). The RM was degassed and stirred under $H_2$ (15 psi) at rt for 1 h. The RM was filtered through Celite and the filtrate concentrated under reduced pressure to give the title compound as a yellow solid. LCMS (ESI): m/z: $[M+H]^+$=211.0.

Step 3. 2-Ethyl-4H,5H,6H-cyclopenta[b]thiophene-3-carboxylic Acid

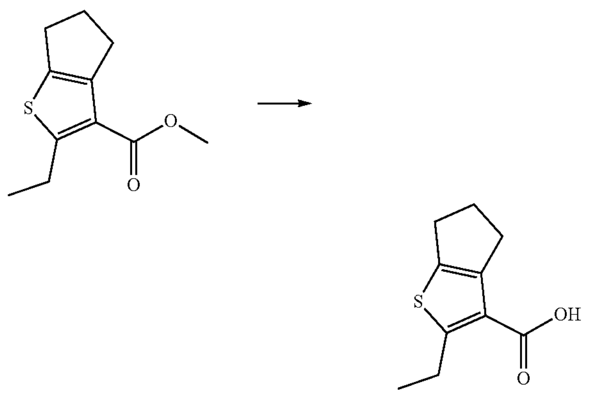

To a solution of methyl 2-ethyl-4H,5H,6H-cyclopenta[b]thiophene-3-carboxylate (183 mg, 0.87 mmol) in MeOH (4 ml) and $H_2O$ (2 ml) was added NaOH (52 mg, 1.31 mmol). The RM was stirred at 50° C. for 12 h. The RM was concentrated under reduced pressure. The residue was diluted with $H_2O$ (5 ml) and the solution acidified to pH~2 with 1 M HCl aq. The mixture was extracted with EtOAc (3×5 ml). The combined organic phase was concentrated under reduced pressure to give the title compound as a yellow solid. LCMS (ESI): m/z: $[M-H]^+$=195.1.

Step 4. Tert-butyl N-{2-ethyl-4H,5H,6H-cyclopenta[b]thiophen-3-yl}carbamate

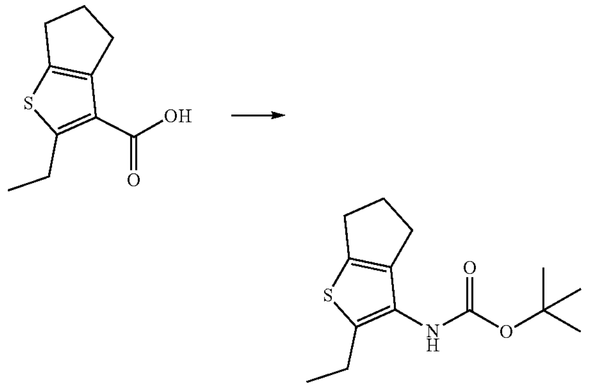

To a solution of 2-ethyl-4H,5H,6H-cyclopenta[b]thiophene-3-carboxylic acid (245 mg, 1.25 mmol) in tert-butanol (6 ml) under $N_2$ was added DPPA (344 mg, 1.25 mmol) and DIPEA (326 μl, 1.87 mmol). The RM was heated at 90° C. for 12 h. The solution was concentrated under reduced pressure and the resulting residue purified by column chromatography (silica, 5-9% EtOAc in petrol) to give the title compound as a yellow solid. Y=21%. $^1H$ NMR (400 MHz, chloroform-d) δ 2.83 (t, J=7 Hz, 2H), 2.70-2.66 (m, 3H), 2.42-2.36 (m, 2H), 1.49 (s, 9H), 1.23 (t, J=7 Hz, 3H).

Step 5. 2-Ethyl-4H,5H,6H-cyclopenta[b]thiophen-3-amine Hydrochloride

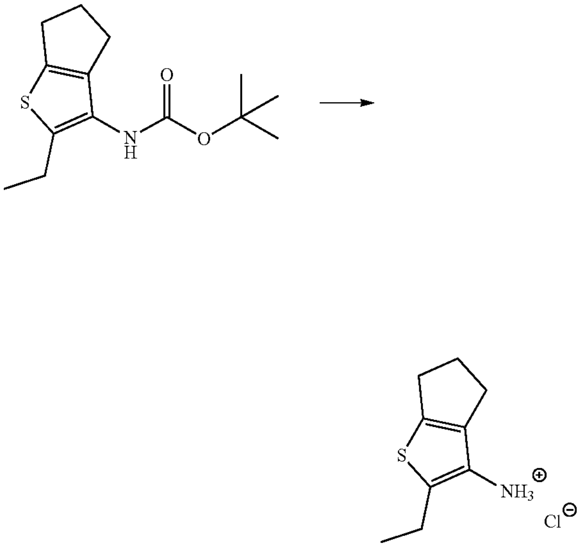 [SMILES: CCc1sc2c(c1NC(=O)OC(C)(C)C)CCC2 ; CCc1sc2c(c1[NH3+])CCC2 ; [Cl-]]

A solution of tert-butyl N-{2-ethyl-4H,5H,6H-cyclopenta[b]thiophen-3-yl}carbamate (70 mg, 0.26 mmol) in 4 M HCl in EtOAc (7 ml) was stirred at rt for 1 h. The solution was concentrated under reduced pressure to give the title compound as a yellow solid. LCMS (ESI): m/z: $[M+H]^+$=168.2.

Step 6. 2-Ethyl-3-isocyanato-4H,5H,6H-cyclopenta[b]thiophene

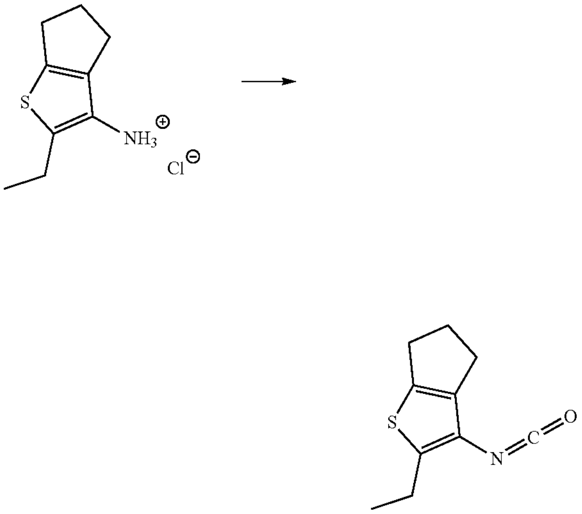

To a solution of 2-ethyl-4H,5H,6H-cyclopenta[b]thiophen-3-amine hydrochloride (55 mg, 0.27 mmol) in dioxane (3 ml) warmed to 40° C. was added trichloromethyl carbonochloridate (95 mg, 0.48 mmol). The RM was stirred at 70° C. for 0.5 h. The solution was concentrated under reduced pressure to give the title compound as a yellow solid, which was used for the next step directly. LCMS in MeOH (ESI): m/z: $[M+MeOH+H]^+$=226.1.

Intermediate 50. 2-Ethyl-3-isocyanato-5-(propan-2-yl)furan

Step 1. Methyl 2-ethyl-5-(propan-2-yl)furan-3-carboxylate

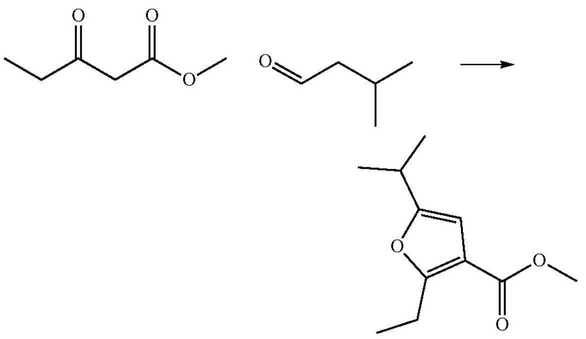

To a solution of 3-methyl butanal (1.10 g, 12.8 mmol) in ACN (40 ml) was add methyl 3-oxopentanoate (2.0 g, 15.4 mmol), $AlCl_3$ (102 mg, 0.77 mmol) and NBS (2.74 g, 15.4 mmol). The RM was stirred at 80° C. for 12 h. The mixture was concentrated in vacuo and the resulting residue purified by silica gel chromatography (9% EtOAc in petrol) to give the title compound as a yellow oil. Y=70%. $^1H$ NMR (400 MHz, chloroform-d) δ 6.12 (s, 1H), 3.73 (s, 3H), 2.89 (q, J=7 Hz, 2H), 2.85-2.75 (m, 1H), 1.21-1.10 (m, 9H).

Step 2. 2-Ethyl-5-(propan-2-yl)furan-3-carboxylic Acid

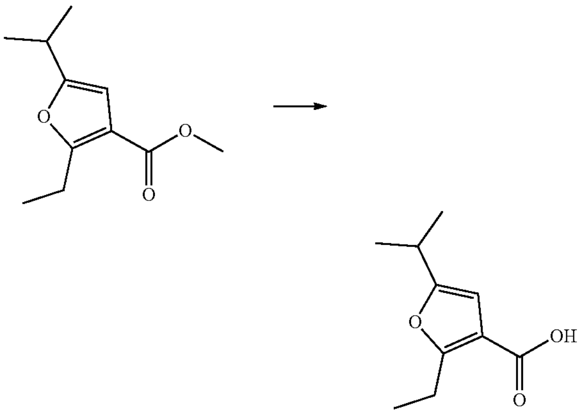

To a solution of methyl 2-ethyl-5-(propan-2-yl)furan-3-carboxylate (2.1 g, 10.7 mmol) in EtOH (20 ml) and $H_2O$ (4 ml) cooled to 0° C. was add NaOH (428 mg, 10.7 mmol). The RM was heated at 80° C. for 12 h. The RM was concentrated then diluted with EtOAc (5 ml). The mixture was extracted with water (3×3 ml) and the combined aqueous phases acidified to pH~4 with 1 M HCl aq. The resulting aqueous phase was extracted with EtOAc (3×3 ml). The combined organic phase was washed with brine (2 ml), dried over anhydrous $Na_2SO_4$, filtered and the filtrate concentrated under reduced pressure to give the title compound as a yellow liquid. $^1H$ NMR (400 MHz, chloroform-d) δ 6.25 (s, 1H), 3.00 (q, J=8 Hz, 2H), 2.90-2.80 (m, 1H), 1.31-1.18 (m, 9H).

Step 3. Tert-butyl N-[2-ethyl-5-(propan-2-yl)furan-3-yl]carbamate

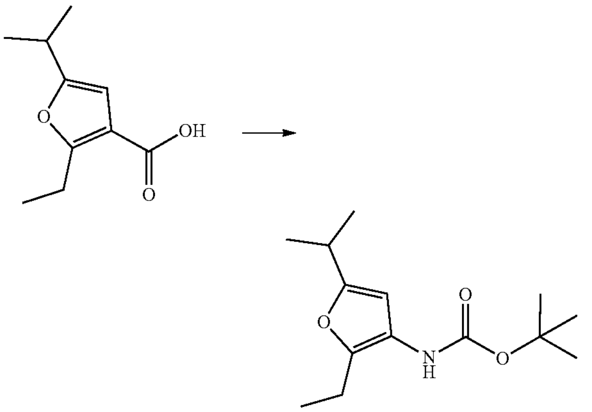

To a solution of 2-ethyl-5-(propan-2-yl)furan-3-carboxylic acid (2.0 g, 11.0 mmol) in tert-butanol (30 ml) was add DPPA (3.02 g, 11.0 mmol) and DIPEA (2.87 ml, 16.5 mmol). The RM was heated at 85° C. for 3 h. The solution was concentrated in vacuo and the resulting residue purified by silica gel chromatography (17% EtOAc in petrol) to give the title compound as a white solid. Y=76%. LCMS: m/z: $[M+H]^+$=254.1.

Step 4. 2-Ethyl-5-(propan-2-yl)furan-3-amine Hydrochloride

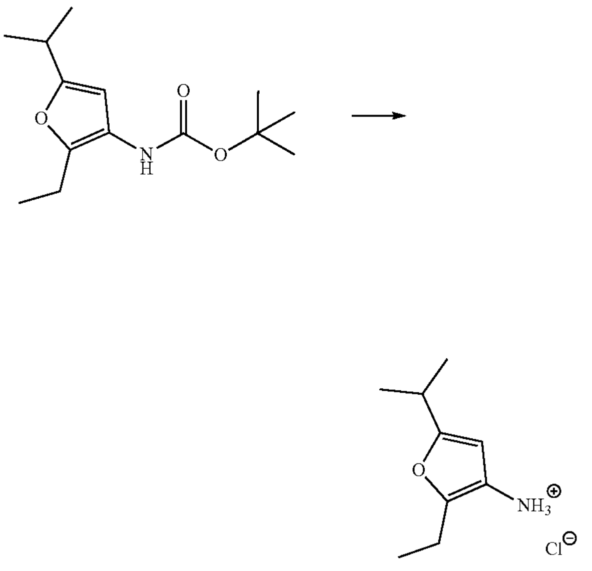

A solution of tert-butyl N-[2-ethyl-5-(propan-2-yl)furan-3-yl]carbamate (100 mg, 0.39 mmol) in 4 M HCl in EtOAc (3 ml) was stirred at rt for 12 h. The solution was concentrated in vacuo to give the title compound as a yellow oil. LCMS: m/z: $[M+H]^+$ 154.1.

Step 5. 2-Ethyl-3-isocyanato-5-(propan-2-yl)furan

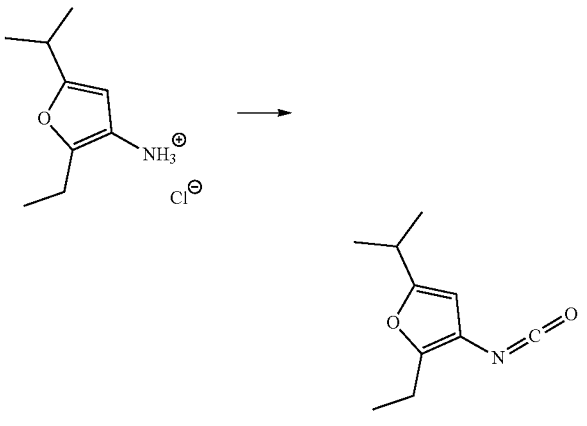

To a solution of 2-ethyl-5-(propan-2-yl)furan-3-amine hydrochloride (90 mg, 0.47 mmol) in dioxane (3 ml) warmed to 40° C. was added trichloromethyl carbonochloridate (116 mg, 0.59 mmol). The RM was heated at 70° C. for 1 h. The solution was concentrated in vacuo to give the title compound as an oil. LCMS in MeOH: m/z: $[M+MeOH+H]^+=212.2$.

Intermediate 51. 5-Ethyl-3-isocyanato-2-(propan-2-yl)furan

Step 1. Methyl 5-ethyl-2-(propan-2-yl)furan-3-carboxylate

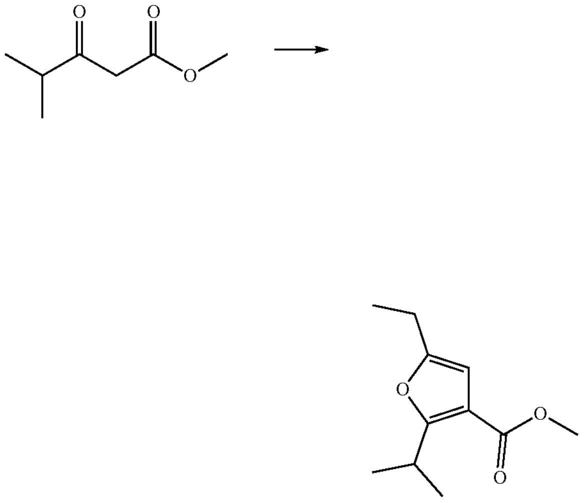

To a solution of butanal (2.5 g, 34.7 mmol) in MeCN (60 ml) were added methyl 4-methyl-3-oxo-pentanoate (6.02 g, 41.8 mmol), NBS (7.43 g, 41.8 mmol) and $AlCl_3$ (279 mg, 2.09 mmol). The RM was stirred at 80° C. for 12 h. The solution was concentrated under reduced pressure and the resulting residue purified by column chromatography (silica, 5-9% EtOAc in petrol) to give the title compound as a white solid. Y=56%. $^1H$ NMR (400 MHz, chloroform-d) δ 6.25 (s, 1H), 3.75 (m, 1H), 2.62 (m, 2H), 1.29-1.21 (m, 9H).

Step 2. 5-Ethyl-2-(propan-2-yl)furan-3-carboxylic Acid

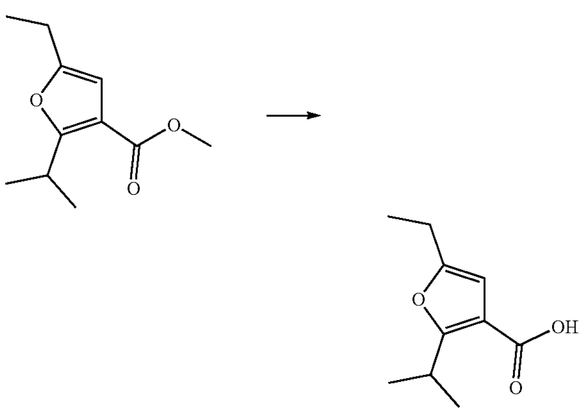

To a solution of methyl 5-ethyl-2-(propan-2-yl)furan-3-carboxylate (4.5 g, 22.9 mmol) in EtOH (40 ml) and $H_2O$ (10 ml) cooled to 0° C. was added NaOH (1.10 g, 27.5 mmol). The solution was heated at 80° C. for 12 h. The solution was concentrated under reduce pressure and the residue acidified to pH~4 with 1 M HCl aq. The mixture was extracted with EtOAc (3x30 ml). The combined organics were dried and concentrated under reduced pressure to give the title compound as a white solid. Y=91%. $^1H$ NMR (400 MHz, chloroform-d) δ 6.25 (s, 1H), 3.79-3.71 (m, 1H), 2.64-2.58 (m, 2H), 1.28-1.21 (m, 9H).

Step 3. Tert-butyl N-[5-ethyl-2-(propan-2-yl)furan-3-yl]carbamate

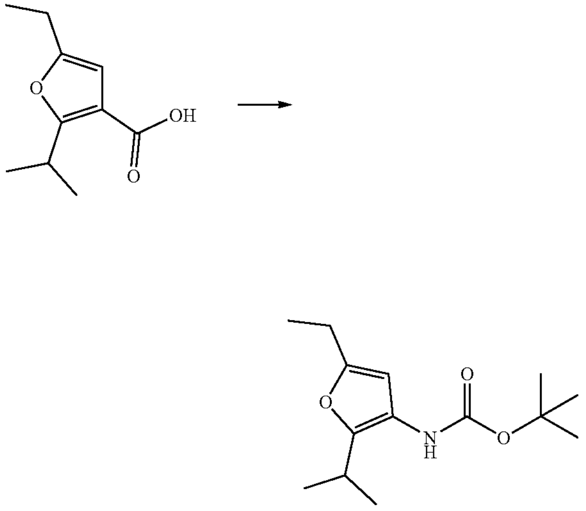

To a solution of 5-ethyl-2-(propan-2-yl)furan-3-carboxylic acid (500 mg, 2.74 mmol) in tert-butanol (10 ml) were added DPPA (755 mg, 2.74 mmol) and DIPEA (717 μl, 4.12 mmol). The RM was stirred at 90° C. for 12 h. The mixture was concentrated under reduced pressure and the resulting residue purified by column chromatography (silica, 5-9% EtOAc in petrol) to give the title compound as a white solid. Y=33%. LCMS (ESI): m/z: $[M+H]^+=254.1$.

Step 4. 5-Ethyl-2-(propan-2-yl)furan-3-amine Hydrochloride

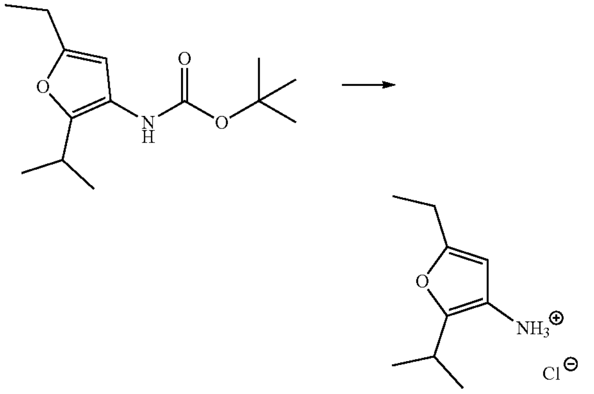

A solution of tert-butyl N-[5-ethyl-2-(propan-2-yl)furan-3-yl]carbamate (200 mg, 0.79 mmol) in 4 M HCl in EtOAc (3 ml) was stirred at rt for 1 h. The solution was concentrated under reduced pressure to give the title compound as a white solid.

Step 5. 5-Ethyl-3-isocyanato-2-(propan-2-yl)furan

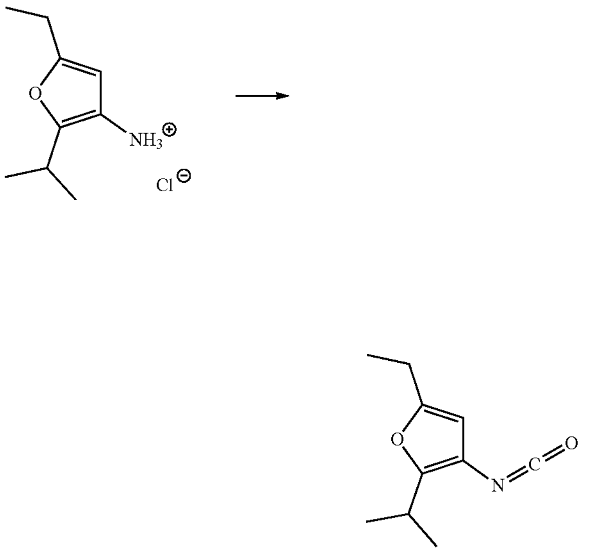

To a solution of 5-ethyl-2-(propan-2-yl)furan-3-amine hydrochloride (150 mg, 0.79 mmol) in dioxane (3 ml) at 40° C. was added trichloromethyl carbonochloridate (188 mg, 0.95 mmol). The RM was stirred at 70° C. for 1 h. The solution was concentrated under reduced pressure to give the title compound as a white solid. Y=52%. LCMS in MeOH (ESI): m/z: $[M+MeOH+H]^+$=212.2.

Intermediate 52. N-[(3S)-1-Methylpiperidin-3-yl]-N-[1-(propan-2-yl)-1H-pyrazol-4-yl]aminosulfonamide Hydrochloride

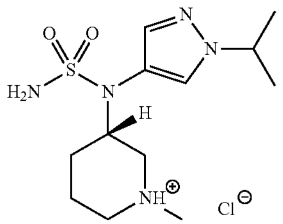 [SMILES: CC(C)n1cc(N([C@H]2CCC[NH+](C)C2)S(N)(=O)=O)cn1 ; [Cl-]]

Prepared using an analogous method to Intermediate 25, but starting with tert-butyl (3S)-3-aminopiperidine-1-carboxylate. LCMS (ESI): m/z: $[M+H]^+$=281.2.

Intermediate 53. 2-Ethyl-3-isocyanato-4,5,6,7-tetrahydro-1-benzothiophene

Step 1. Ethyl 2-amino-4,5,6,7-tetrahydro-1-benzothiophene-3-carboxylate

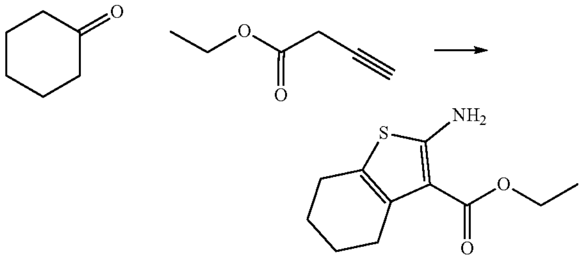

To a solution of ethyl 2-cyanoacetate (1.27 g, 11.2 mmol) in EtOH (10 ml) was added cyclohexanone (1.0 g, 10.2 mmol), diethylamine (1.05 ml, 10.2 mmol) and sulfur (0.33 g, 10.2 mmol). The RM was placed in an ultrasonic bath at 25° C. for 1 h. The solution was concentrated under reduced pressure and the resulting residue purified by column chromatography (silica, Petroleum ether/Ethyl acetate=10/1 to 5/1) to give the title compound as a yellow solid. Y=42%. LCMS (ESI): m/z: $[M+H]^+$=226.0.

Step 2. Ethyl 2-bromo-4,5,6,7-tetrahydro-1-benzothiophene-3-carboxylate

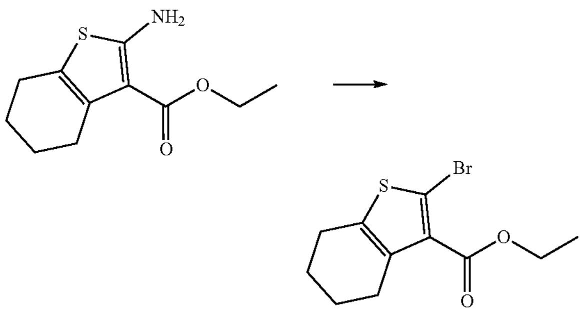

To a solution of tert-butyl nitrite (4.09 ml, 34.4 mmol) in MeCN (58 ml) cooled to 0° C. was added $CuBr_2$ (8.54 g, 38.2 mmol). To this mixture was added portionwise ethyl 2-amino-4,5,6,7-tetrahydrobenzothiophene-3-carboxylate (6.24 g, 27.7 mmol). The resulting mixture was stirred at 0° C. for 2 h, then allowed to warm to rt and stirred for 3 h. The RM was concentrated under reduced pressure to remove MeCN. The residue was diluted with $H_2O$ (40 ml) and extracted with EtOAc (3×20 ml). The combined organic layers were washed with brine (3×20 ml), dried over $Na_2SO_4$, filtered and the filtrate concentrated under reduced pressure to give a residue. The residue was purified by column chromatography (silica, Petroleum ether:Ethyl acetate=5:1) to give the title compound as a white solid. Y=44%. $^1$H NMR (400 MHz, MeOD) δ 4.30 (q, J=7 Hz, 2H), 2.70 (t, J=7 Hz, 2H), 2.63 (t, J=7 Hz, 2H), 1.80-1.74 (m, 4H), 1.36 (t, J=7 Hz, 3H).

Step 3. 2-Bromo-4,5,6,7-tetrahydro-1-benzothiophene-3-carboxylic Acid

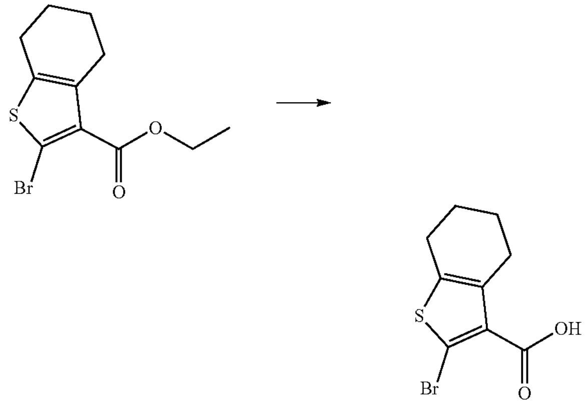

To a solution of ethyl 2-bromo-4,5,6,7-tetrahydro-1-benzothiophene-3-carboxylate (2.1 g, 7.27 mmol) in MeOH (20 ml) and $H_2O$ (10 ml) was added NaOH (436 mg, 10.9 mmol). The RM was stirred at 50° C. for 12 h. The solution was concentrated under reduced pressure. The residue was diluted with water (10 ml) and the solution acidified to pH~4 with 6 M HCl aq. The mixture was extracted with EtOAc (3×20 ml) and the combined organic phase dried and concentrated under reduced pressure to give the title compound as a white solid. Y=90%. $^1$H NMR (400 MHz, chloroform-d) δ 4.87 (s, 4H), 2.75-2.65 (m, 2H), 1.83-1.79 (m, 2H).

Step 4. Tert-butyl N-(2-bromo-4,5,6,7-tetrahydro-1-benzothiophen-3-yl)carbamate

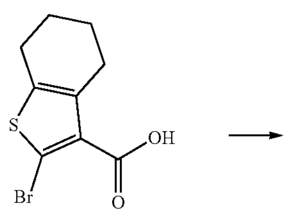

-continued

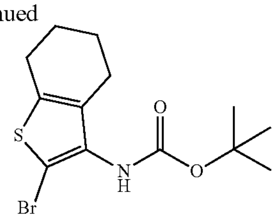

To a solution of 2-bromo-4,5,6,7-tetrahydro-1-benzothiophene-3-carboxylic acid (1.7 g, 6.51 mmol) in tert-butanol (20 ml) were added DPPA (1.79 g, 6.51 mmol) and DIPEA (1.70 ml, 9.77 mmol). The RM was stirred at 90° C. for 12 h. The solution was concentrated under reduced pressure and the resulting residue purified by column chromatography (silica, 5-9% EtOAc in petrol) to give the title compound as a yellow solid. Y=38%. $^1$H NMR (400 MHz, chloroform-d) δ 5.82 (s, 1H), 2.64 (t, J=6 Hz, 2H), 2.49 (t, J=6 Hz, 2H), 1.85-1.74 (m, 4H), 1.50 (s, 9H).

Step 5. Tert-butyl N-(2-ethenyl-4,5,6,7-tetrahydro-1-benzothiophen-3-yl)carbamate

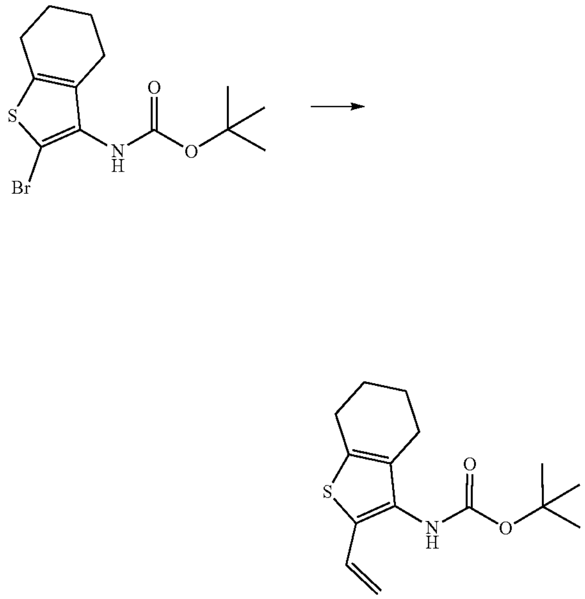

To a solution of potassium ethenyltrifluoroboranuide (806 mg, 6.02 mmol) in THF (10 ml) under $N_2$ were added tert-butyl N-(2-bromo-4,5,6,7-tetrahydro-1-benzothiophen-3-yl)carbamate (400 mg, 1.20 mmol), triphenylphosphine (19 mg, 72 μmol), $Cs_2CO_3$ (1.18 g, 3.61 mmol) and $PdCl_2$ (4.3 mg, 24 μmol). The RM was heated at 90° C. for 12 h. The RM was allowed to cool, filtered and the filtrate concentrated under reduced pressure to give a residue. This was purified by prep-HPLC (column: Phenomenex Luna C18 250×50 mm, 10 μm; mobile phase: [water (0.1% TFA)-ACN]; B: 50-80%, 10 min) to give the title compound as a white solid. Y=30%. $^1$H NMR (400 MHz, chloroform-d) δ 6.75 (dd, J=11, 17 Hz, 1H), 5.42 (d, J=17 Hz, 1H), 5.07 (d, J=11 Hz, 1H), 2.68 (t, J=6 Hz, 2H), 2.42 (t, J=6 Hz, 2H), 1.87-1.73 (m, 4H), 1.49 (s, 9H).

Step 6. Tert-butyl N-(2-ethyl-4,5,6,7-tetrahydro-1-benzothiophen-3-yl)carbamate

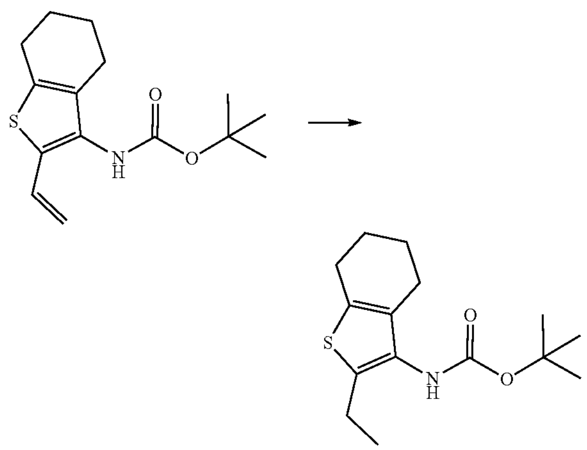

To a solution of tert-butyl N-(2-ethenyl-4,5,6,7-tetrahydro-1-benzothiophen-3-yl)carbamate (100 mg, 0.36 mmol) in MeOH (3 ml) was added 10% Pd/C (50% in water, 50 mg). The RM was stirred under $H_2$ (15 psi) atmosphere at rt for 1 h. The RM was filtered and the filtrate concentrated under reduced pressure to give the title compound as a white solid. LCMS (ESI): m/z: $[M+H]^+$=282.2.

Step 7. 2-Ethyl-4,5,6,7-tetrahydro-1-benzothiophen-3-amine Hydrochloride

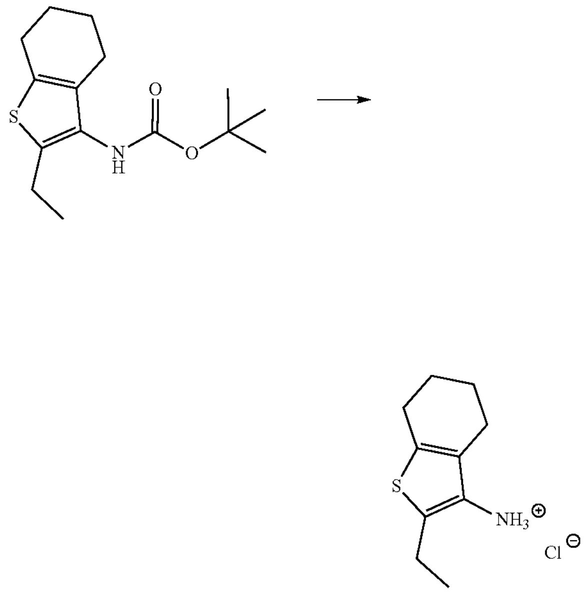

A solution of tert-butyl N-(2-ethyl-4, 5, 6, 7-tetrahydrobenzothiophen-3-yl)carbamate (130 mg, 0.46 mmol) in 4 M HCl in EtOAc (2 ml) was stirred at rt for 1 h. The solution was concentrated under reduced pressure to give the title compound as a white solid. LCMS (ESI): m/z: $[M+H]^+$=182.0.

Step 8. 2-Ethyl-3-isocyanato-4,5,6,7-tetrahydro-1-benzothiophene

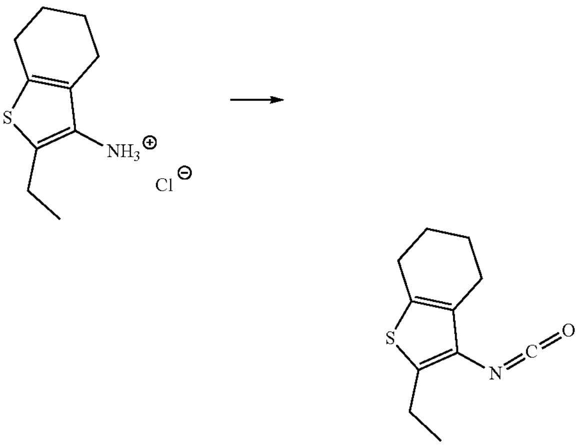

To a solution of 2-ethyl-4,5,6,7-tetrahydro-1-benzothiophen-3-amine hydrochloride (90 mg, 0.41 mmol) in dioxane (3 ml) warmed to 40° C. was added trichloromethyl carbonochloridate (98 mg, 0.50 mmol). The RM was stirred at 70° C. for 1 h. The solution was concentrated under reduced pressure to give the title compound as a white solid. LCMS in MeOH (ESI): m/z: $[M+MeOH+H]^+$=240.2.

Intermediate 54. N-(1-cyclopropyl-1H-pyrazol-4-yl)-N-[(3S)-1-methylpiperidin-3-yl]aminosulfonamide Hydrochloride

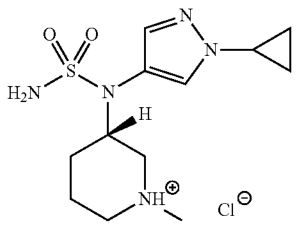 [SMILES: C[NH+]1CCC[C@H](N(c2cnn(C3CC3)c2)S(N)(=O)=O)C1 ; [Cl-]]

Prepared using an analogous method to Intermediate 36, but starting with tert-butyl (3S)-3-aminopiperidine-1-carboxylate. LCMS (ESI): m/z: $[M+H]^+$=300.1.

Intermediate 55. 2-Ethyl-3-isocyanato-4,5,6,7-tetrahydro-1-benzofuran

Step 1. 2-Hydroxycyclohexan-1-one

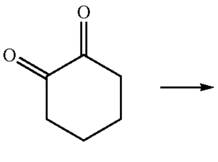

-continued

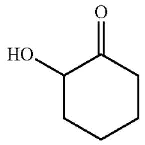

A mixture of zinc (4.67 g, 71.4 mmol), NaCl (4.17 g, 71.4 mmol) and cyclohexane-1,2-dione (4.0 g, 35.7 mmol) in MeOH (40 ml) and $H_2O$ (40 ml) was heated at 90° C. for 1 h. The reaction was filtered and the filtrate extracted with EtOAc (3×60 ml). The combined organic phase was concentrated under reduced pressure to give the title compound as a white solid, which was used directly in the next step.

Step 2. Methyl 2-ethyl-4,5,6,7-tetrahydro-1-benzofuran-3-carboxylate

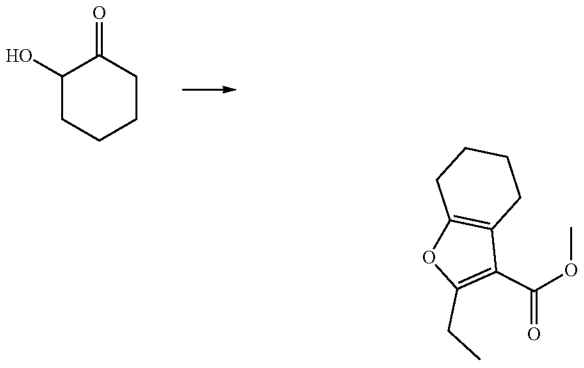

To a solution of methyl 3-oxopentanoate (1.5 g, 11.5 mmol) and 2-hydroxycyclohexan-lone (2.63 g, 11.5 mmol) in MeOH (20 ml) was added $ZnCl_2$ (1.10 g, 8.07 mmol). The RM was stirred at 90° C. for 12 h. The reaction was concentrated under reduced pressure and the resulting residue purified by column chromatography (silica, 0-17% EtOAc in petrol) to give the title compound as a yellow oil. Y=16%. $^1H$ NMR (400 MHz, chloroform-d) δ 3.78 (s, 3H), 3.00-2.90 (m, 2H), 2.61-2.46 (m, 4H), 1.87-1.77 (m, 2H), 1.76-1.67 (m, 2H), 1.25-1.15 (m, 3H).

Step 3. 2-Ethyl-4,5,6,7-tetrahydro-1-benzofuran-3-carboxylic Acid

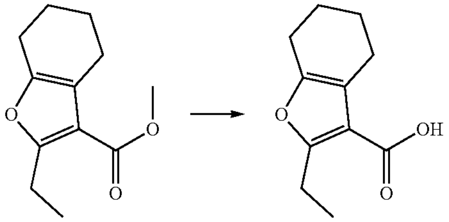

To a solution of methyl 2-ethyl-4,5,6,7-tetrahydro-1-benzofuran-3-carboxylate (390 mg, 1.87 mmol) in $H_2O$ (1.75 ml) and EtOH (7 ml) cooled to 0° C. was added NaOH (112 mg, 2.81 mmol). The RM was heated at 80° C. for 12 h. The solution was concentrated under reduced pressure. The residue was diluted with water (3 ml) and the aqueous acidified to pH~2 with 6 M HCl (aq.). The resulting mixture was extracted with EtOAc (3×8 ml). The combined organic phase was washed with brine (10 ml), dried over anhydrous $Na_2SO_4$ and concentrated under reduced pressure to give the title compound as a yellow solid.

Step 4. Tert-butyl N-(2-ethyl-4,5,6,7-tetrahydro-1-benzofuran-3-yl)carbamate

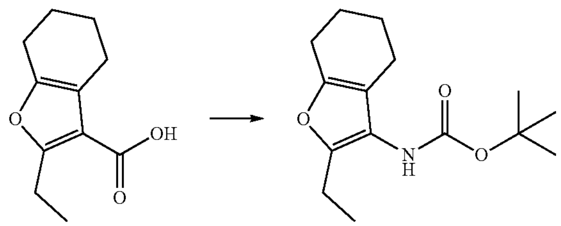 [SMILES: CCc1oc2c(c1C(=O)O)CCCC2 ; CCc1oc2c(c1NC(=O)OC(C)(C)C)CCCC2]

To a solution of 2-ethyl-4,5,6,7-tetrahydro-1-benzofuran-3-carboxylic acid (300 mg, 1.54 mmol) in tert-butanol (6 ml) under $N_2$ were added DPPA (425 mg, 1.54 mmol) and DIPEA (404 μl, 2.32 mmol). The RM was heated at 90° C. for 12 h. The solution was concentrated under reduced pressure and the resulting residue purified by prep-TLC (silica, 9% EtOAc in petrol) to give the title compound as a white solid. Y=24%. $^1H$ NMR (400 MHz, chloroform-d) δ 5.55 (s, 1H), 2.60-2.46 (m, 4H), 2.35-2.30 (m, 2H), 1.84-1.76 (m, 2H), 1.74-1.66 (m, 2H), 1.49 (s, 9H), 1.19 (t, J=7 Hz, 3H).

Step 5. 2-Ethyl-4,5,6,7-tetrahydro-1-benzofuran-3-amine Hydrochloride

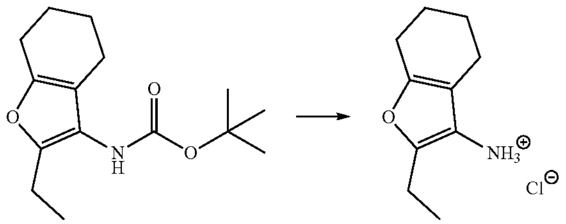 [SMILES: CCc1oc2c(c1NC(=O)OC(C)(C)C)CCCC2 ; CCc1oc2c(c1[NH3+])CCCC2 ; [Cl-]]

The solution of tert-butyl N-(2-ethyl-4,5,6,7-tetrahydro-1-benzofuran-3-yl)carbamate (100 mg, 0.38 mmol) in 4 M HCl in EtOAc (3 ml) was stirred at rt for 5 h. The solution was concentrated under reduced pressure to give the title compound as a yellow oil. LCMS (ESI): m/z: $[M+H]^+$=166.1.

Step 6. 2-Ethyl-3-isocyanato-4,5,6,7-tetrahydro-1-benzofuran

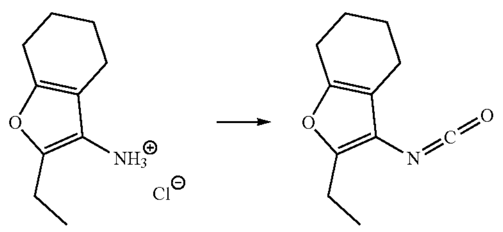

To a solution of 2-ethyl-4,5,6,7-tetrahydro-1-benzofuran-3-amine hydrochloride (75 mg, 0.37 mmol) in dioxane (3 ml) warmed to 40° C. was added trichloromethyl carbonochloridate (53.8 μL 0.45 mmol) and the solution stirred at 70° C. for 1 h. The solution was concentrated under reduced pressure to give the title compound as an oil, which was used to next step directly. LCMS in MeOH (ESI): m/z: $[M+MeOH+H]^+$=224.2.

Intermediate 56. 3-Isocyanato-2-(trifluoromethyl)-4H,5H,6H-cyclopenta[b]thiophene Step 1. Methyl 2-iodo-4H,5H,6H-cyclopenta[b]thiophene-3-carboxylate

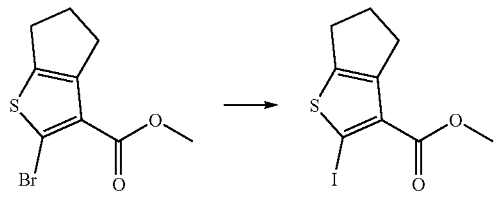

To a mixture of methyl 2-bromo-4H,5H,6H-cyclopenta[b]thiophene-3-carboxylate (500 mg, 1.91 mmol) [for synthesis refer to Intermediate 28], NaI (574 mg, 3.83 mmol) and CuI (36.5 mg, 0.19 mmol) in dioxane (10 ml) was added N,N'-dimethylethane-1,2-diamine (41.2 μl, 0.38 mmol). The RM was heated at reflux for 16 h. The mixture was filtered and the filtrate concentrated under reduced pressure to give a residue. This was purified by column chromatography (silica, 5-9% EtOAc in petrol) to give the title compound as a white solid. LCMS (ESI): m/z: $[M+H]^+$=308.9.

Step 2. Methyl 2-(trifluoromethyl)-4H,5H,6H-cyclopenta[b]thiophene-3-carboxylate

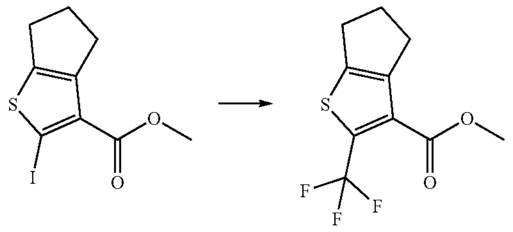 [SMILES: COC(=O)c1c(I)sc2c1CCC2 ; COC(=O)c1c(C(F)(F)F)sc2c1CCC2]

To a solution of methyl 2-iodo-4H,5H,6H-cyclopenta[b]thiophene-3-carboxylate (950 mg, 3.08 mmol) in DMF (10 ml) under $N_2$ were added CuI (0.76 g, 4.01 mmol) and hexamethylphosphoramide (2.76 g, 15.4 mmol). The RM was stirred at rt for 5 min, then treated with methyl 2,2-difluoro-2-fluorosulfonyl acetate (2.96 g, 15.4 mmol). The mixture was heated to 100° C. for 1 h. The solution was concentrated under reduced pressure and the resulting residue purified by prep-HPLC (column: Phenomenex Luna C18 250×50 mm, 10 μm; mobile phase: [water (0.1% TFA)-ACN]; B: 60-90%, 10 min) to give the title compound as a white solid. Y=39%. $^1$H NMR (400 MHz, chloroform-d) δ 3.89 (s, 3H), 2.99-2.92 (m, 4H), 2.52-2.43 (m, 2H).

Step 3. 2-(Trifluoromethyl)-4H,5H,6H-cyclopenta[b]thiophene-3-carboxylic Acid

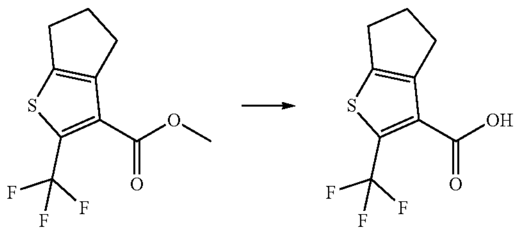 [SMILES: COC(=O)c1c(C(F)(F)F)sc2c1CCC2 ; O=C(O)c1c(C(F)(F)F)sc2c1CCC2]

To a solution of methyl 2-(trifluoromethyl)-5,6-dihydro-4H-cyclopenta[b]thiophene-3-carboxylate (300 mg, 1.20 mmol) in MeOH (2 ml) and $H_2O$ (1 ml) was added NaOH (72 mg, 1.80 mmol). The RM was stirred at 50° C. for 12 h. The solution was concentrated under reduced pressure. The residue was diluted with water (3 ml) and acidified to pH~2 with 1 M HCl (aq.). The mixture was extracted with EtOAc (3×3 ml). The combined organic phase was concentrated under reduced pressure to give the title compound as a white solid. Y=85%. $^1$H NMR (400 MHz, chloroform-d) δ 3.05-2.94 (m, 4H), 2.51-2.47 (m, 2H).

Step 4. Tert-butyl N-[2-(trifluoromethyl)-4H,5H,6H-cyclopenta[b]thiophen-3-yl]-carbamate

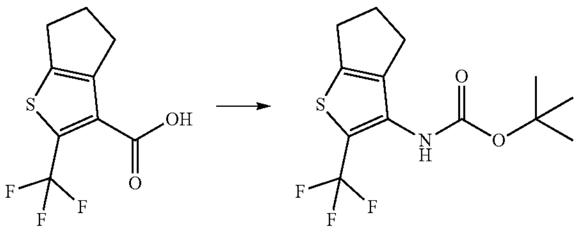 [SMILES: O=C(O)c1c(C(F)(F)F)sc2c1CCC2 ; CC(C)(C)OC(=O)Nc1c(C(F)(F)F)sc2c1CCC2]

To a solution of 2-(trifluoromethyl)-5,6-dihydro-4H-cyclopenta[b]thiophene-3-carboxylic acid (190 mg, 0.80 mmol) in tert-butanol (5 ml) were added DPPA (221 mg, 0.80 mmol) and DIPEA (210 μl, 1.2 mmol). The RM was heated at 90° C. for 12 h. The solution was concentrated under reduced pressure and the resulting residue purified by prep-TLC (silica, 9% EtOAc in petrol) to give the title compound as a white solid. Y=74%. $^1$H NMR (400 MHz, chloroform-d) δ 6.42 (s, 1H), 2.90 (t, J=7 Hz, 2H), 2.82 (t, J=7 Hz, 2H), 2.45-2.39 (m, 2H), 1.51 (s, 9H).

Step 5. 2-(Trifluoromethyl)-4H,5H,6H-cyclopenta[b]thiophen-3-amine Hydrochloride

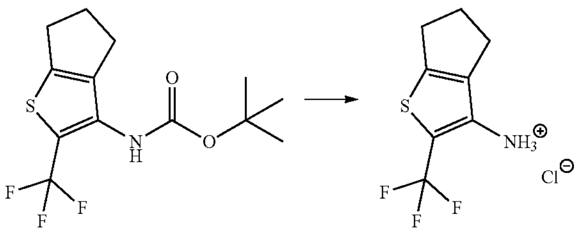 [SMILES: CC(C)(C)OC(=O)Nc1c(C(F)(F)F)sc2c1CCC2 ; [NH3+]c1c(C(F)(F)F)sc2c1CCC2 ; [Cl-]]

A solution of tert-butyl N-[2-(trifluoromethyl)-4H,5H,6H-cyclopenta[b]thiophen-3-yl]carbamate (130 mg, 0.42 mmol) in 4 M HCl in EtOAc (2 ml) was stirred at rt for 30 min. The solution was concentrated under reduced pressure to give the title compound as a white solid. LCMS (ESI): m/z: $[M+H]^+$=208.1.

Step 6. 3-Isocyanato-2-(trifluoromethyl)-4H,5H,6H-cyclopenta[b]thiophene

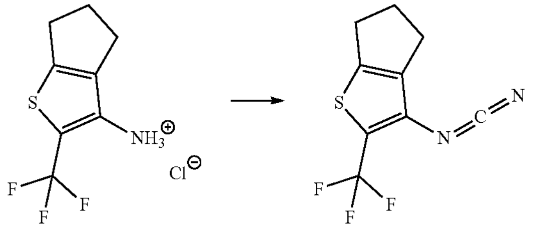 [SMILES: [NH3+]c1c(C(F)(F)F)sc2c1CCC2 ; [Cl-] ; N=C=Nc1c(C(F)(F)F)sc2c1CCC2]

To a solution of 2-(trifluoromethyl)-4H,5H,6H-cyclopenta[b]thiophen-3-amine hydrochloride (104 mg, 0.43 mmol) in dioxane (3 ml) warmed to 40° C. was added trichloromethyl carbonochloridate (101 mg, 0.51 mmol). The RM was stirred at 70° C. for 1 h. The solution was concentrated under reduced pressure to give the title compound as a white solid. LCMS in MeOH (ESI): m/z: $[M+MeOH+H]^+$=266.0.

Intermediate 57. N-(1-Cyclopropyl-5-fluoro-1H-pyrazol-4-yl)-N-(1-methylpiperidin-3-yl)aminosulfonamide Step 1. 1-Cyclopropyl-4-nitro-1H-pyrazole

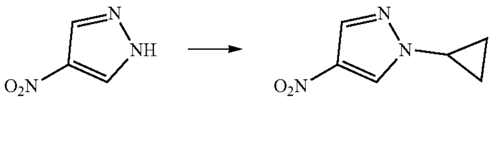 [SMILES: O=[N+]([O-])c1cn[nH]c1 ; O=[N+]([O-])c1cnn(C2CC2)c1]

To a solution of 4-nitro-1H-pyrazole (8.0 g, 71 mmol) in DCE (6 ml) under $N_2$ were added cyclopropylboronic acid (12.2 g, 142 mmol), 4-tert-butyl-2-(4-tert-butyl-2-pyridyl)pyridine (18.0 g, 67 mmol), $CuSO_4$ (12.4 g, 78 mmol) and $Na_2CO_3$ (15.0 g, 142 mmol). The RM was heated at 70° C. for 12 h. The solution was concentrated in vacuo and the resulting residue purified by silica gel chromatography (5-9% EtOAc in petrol) to give the title compound as a yellow solid. Y=46%.

Step 2. 1-Cyclopropyl-1H-pyrazol-4-amine

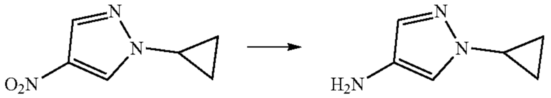

To a solution of 1-cyclopropyl-4-nitro-pyrazole (5.0 g, 32.7 mmol) in EtOH (50 ml) under $N_2$ was added 10% Pd/C (50% in water, 800 mg). The suspension was degassed under vacuum and purged with $H_2$ several times. The mixture was stirred under $H_2$ (15 psi) at rt for 2 h. The RM was filtered and the filtrate concentrated in vacuo to give the title compound as a yellow oil. LCMS (ESI): m/z: $[M+H]^+$=124.2.

Step 3. Tert-butyl N-(1-cyclopropyl-1H-pyrazol-4-yl)carbamate

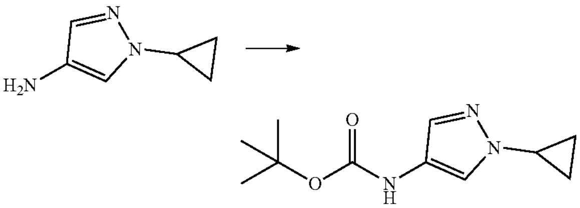

To a solution of 1-cyclopropyl-1H-pyrazol-4-amine (3.7 g, 30.0 mmol) in DCM (50 ml) were added di-tert-butyl dicarbonate (7.21 g, 33.1 mmol) and triethylamine (12.5 ml, 90.1 mmol). The RM was stirred at rt for 12 h. The reaction solution was concentrated in vacuo and the resulting residue purified by silica gel chromatography (17% EtOAc in petrol) to give the title compound as a yellow solid. Y=58%. LCMS (ESI): m/z: $[M+H]^+$=224.2.

Step 4. Tert-butyl N-(1-cyclopropyl-5-fluoro-1H-pyrazol-4-yl)carbamate

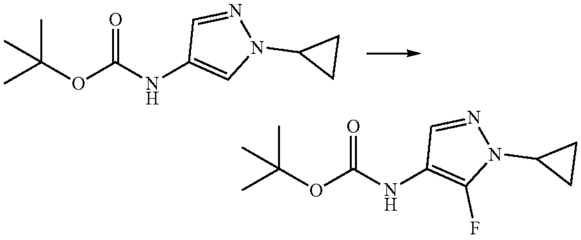

To a solution tert-butyl N-(1-cyclopropyl-1H-pyrazol-4-yl)carbamate (3.9 g, 17.5 mmol) in DMF (30 ml) and DCM (30 ml) was added 1-chloromethyl-4-fluoro-1,4-diazoniabicyclo[2.2.2]octane bis(tetrafluoroborate)(Selectfluor) (8.66 g, 24.5 mmol). The RM was stirred for 12 h. The reaction was poured into $H_2O$ (50 ml), then the mixture extracted with DCM (3×30 ml). The combined organic phase was washed with brine (10 ml), dried over anhydrous $Na_2SO_4$, filtered and concentrated in vacuo. The residue was purified by silica gel chromatography (0-50% EtOAc in petrol) to give the title compound as a yellow oil. Y=12%. $^1H$ NMR (400 MHz, chloroform-d) δ 7.43 (s, 1H), 5.78 (s, 1H), 3.37-3.31 (m, 1H), 1.49 (s, 9H), 1.17-1.11 (m, 2H), 1.05-0.98 (m, 2H).

Step 5. 1-Cyclopropyl-5-fluoro-1H-pyrazol-4-amine Hydrochloride

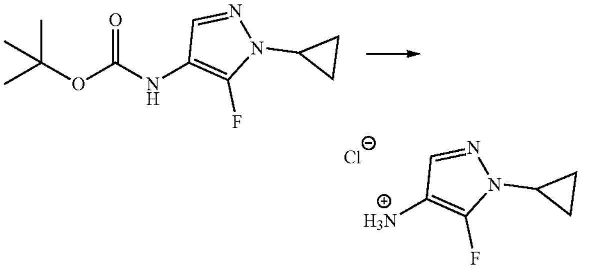

A solution of tert-butyl N-(1-cyclopropyl-5-fluoro-1H-pyrazol-4-yl)carbamate (500 mg, 2.07 mmol, 1 eq) in 4 M HCl in EtOAc (10 ml) was stirred at rt for 2 h. The solution was concentrated in vacuo to give the title compound as a yellow oil.

Step 6. Tert-butyl 3-[(1-cyclopropyl-5-fluoro-1H-pyrazol-4-yl)amino]piperidine-1-carboxylate

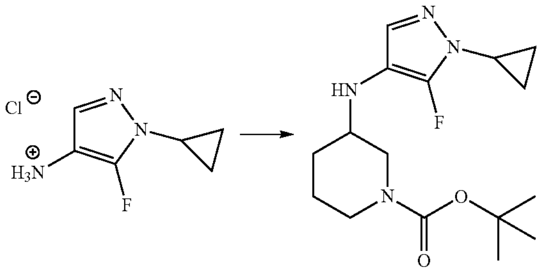 [SMILES: [Cl-] ; [NH3+]c1cnn(C2CC2)c1F ; CC(C)(C)OC(=O)N1CCCC(Nc2cnn(C3CC3)c2F)C1]

To a solution of 1-cyclopropyl-5-fluoro-1H-pyrazol-4-amine hydrochloride (500 mg, 2.82 mmol) in DCE (15 ml) and AcOH (1.6 ml) was added tert-butyl 3-oxopiperidine-1-carboxylate (706 mg, 3.54 mmol). The RM was stirred at rt for 1 h, then cooled to 0° C. The RM was treated with $NaBH(OAc)_3$ (1.50 g, 7.08 mmol) and the resulting RM stirred at rt for 12 h. The solution was concentrated in vacuo and the resulting residue purified by silica gel chromatography (0-25% EtOAc in petrol), to give the title compound as a yellow solid. Y=55%. LCMS (ESI): m/z: $[M+H]^+$=325.2.

Step 7. Tert-butyl 3-[({[(tert-butoxy)carbonyl]amino}sulfonyl)(1-cyclopropyl-5-fluoro-1H-pyrazol-4-yl)amino]piperidine-1-carboxylate

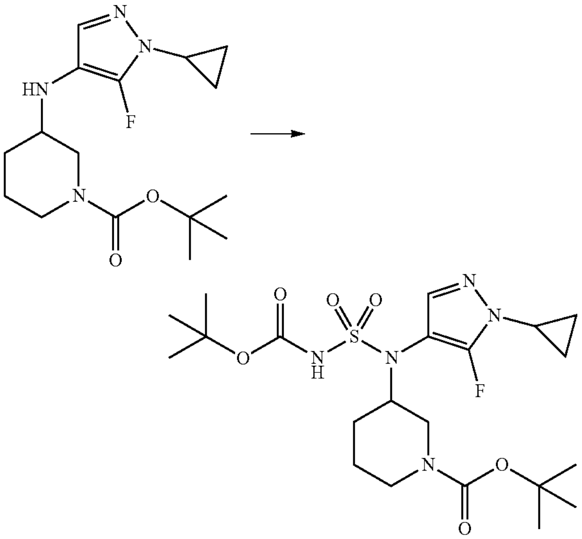

To a solution of tert-butyl 3-[(1-cyclopropyl-5-fluoro-1H-pyrazol-4-yl)amino]piperidine-1-carboxylate (500 mg, 1.54 mmol) in DCM (5 ml) at 0° C. was added DIPEA (805 μl, 4.62 mmol) and the solution stirred for 30 min. A solution of 0.71 M tert-butyl N-chlorosulfonylcarbamate in DCM (2.18 ml, 1.54 mmol) was added and the resulting RM stirred at 0° C. for 2 h. The solution was concentrated in vacuo and the resulting residue was purified by prep-HPLC (column: Kromasil C18 (250×50 mm, 10 m); mobile phase: [water (0.05% $NH_3 \cdot H_2O$+10 mM $NH_4HCO_3$)-ACN]; B: 20-45%, 10 min) to give the title compound as a white solid. Y=52%. LCMS (ESI): m/z: $[M+H]^+$=504.2.

Step 8. N-(1-Cyclopropyl-5-fluoro-1H-pyrazol-4-yl)-N-(piperidin-3-yl)aminosulfonamide Hydrochloride

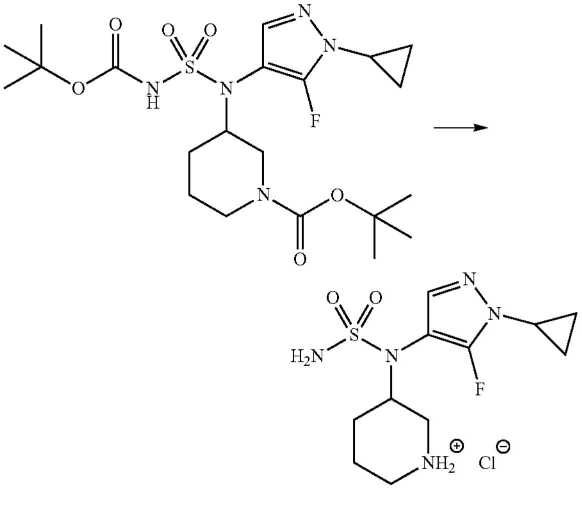

A solution of tert-butyl 3-[({[(tert-butoxy)carbonyl]amino}sulfonyl)(1-cyclopropyl-5-fluoro-1H-pyrazol-4-yl)amino]piperidine-1-carboxylate (400 mg, 0.79 mmol) in 4 M HCl in EtOAc (10 ml) was stirred at rt for 1 h. The solution was concentrated in vacuo to give the title compound as a yellow oil.

Step 9. N-(1-Cyclopropyl-5-fluoro-1H-pyrazol-4-yl)-N-(1-methylpiperidin-3-yl)aminosulfonamide

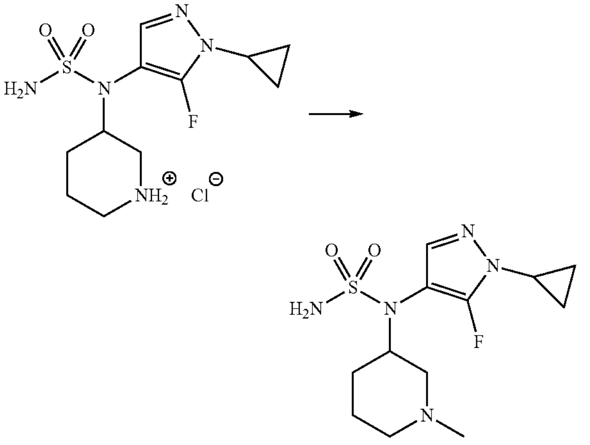

To a solution of N-(1-cyclopropyl-5-fluoro-1H-pyrazol-4-yl)-N-(piperidin-3-yl)aminosulfonamide hydrochloride (350 mg, 1.15 mmol) in MeOH (8 ml) at 0° C. was added $NaBH_3CN$ (129 mg, 2.06 mmol). To this mixture was added 37% formaldehyde (aq.) (153 μl, 2.06 mmol) and the solution was stirred for 2 h. The solution was concentrated in vacuo to give the title compound as a yellow oil. LCMS (ESI): m/z: $[M+H]^+$=318.1.

Intermediate 58. N-(1-methyl-1H-pyrazol-4-yl)-N-(1-methylpiperidin-4-yl)aminosulfonamide Hydrochloride Step 1. 1-Methyl-N-(1-methyl-1H-pyrazol-4-yl)piperidin-4-amine

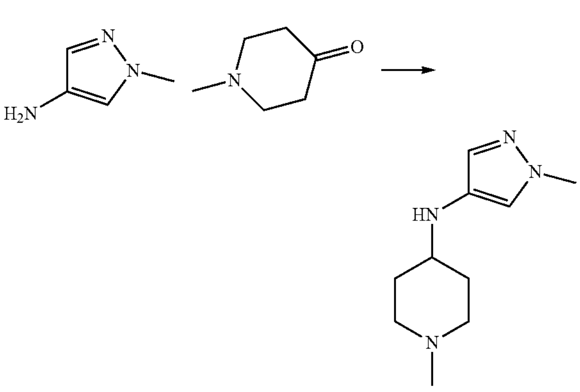

To a solution of 1-methylpyrazol-4-amine (2.0 g, 20.6 mmol) in DCE (20 ml) at 0° C. was added 1-methylpiperidin-4-one (2.33 g, 20.6 mmol) and AcOH (2.00 ml, 35.0 mmol). The RM was stirred at 0° C. for 1 h, then $NaBH(OAc)_3$ (13.09 g, 61.8 mmol) was added. The RM was stirred at rt for 1 h. The solution was concentrated under reduced pressure and the resulting residue purified by column chromatography (silica, 17-100% EtOAc in petrol) to give the title compound as an oil. Y=80%. $^1H$ NMR (400 MHz, MeOD) δ 7.18 (s, 1H), 7.12 (s, 1H), 3.77 (s, 3H), 2.89-2.80 (m, 3H), 2.27 (s, 3H), 2.16-2.06 (m, 2H), 2.01-1.92 (m, 2H), 1.52-1.38 (m, 2H).

Step 2. 4-[({[(Tert-butoxy)carbonyl]amino}sulfonyl)(1-methyl-1H-pyrazol-4-yl)amino]-1-methylpiperidin-1-ium Trifluoroacetate

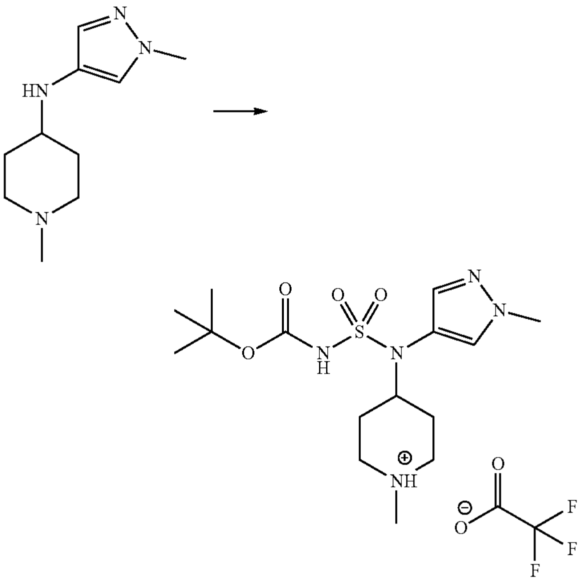

To a solution of 1-methyl-N-(1-methyl-1H-pyrazol-4-yl)piperidin-4-amine (1.0 g, 5.15 mmol) in DCM (10 ml) at 0° C. was added DIPEA (4.48 ml, 25.7 mmol). The RM was stirred at 0° C. for 1 h and then treated with 0.45 M tert-butyl N-chlorosulfonylcarbamate in DCM (13.67 ml, 6.18 mmol). The RM was stirred at rt for 1 h. The solution was concentrated under reduced pressure and the resulting residue was purified by prep-HPLC (column: Phenomenex Luna C18 250×100 mm, 10 μm; mobile phase: [water (0.1% TFA)-ACN]; B: 0-25%, 45 min) to give the title compound as a white solid. Y=60%. LCMS (ESI): m/z: $[M+H]^+$=374.1.

Step 3. N-(1-methyl-1H-pyrazol-4-yl)-N-(1-methylpiperidin-4-yl)aminosulfonamide Hydrochloride

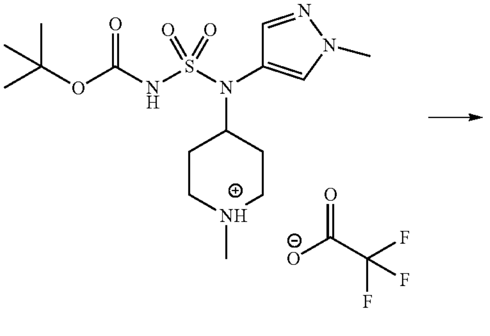

-continued

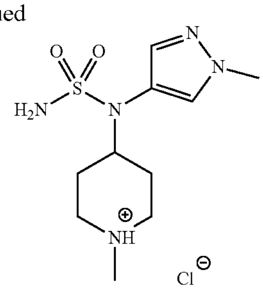

A solution of 4-[({[(tert-butoxy)carbonyl]amino}sulfonyl)(1-methyl-1H-pyrazol-4-yl)amino]-1-methylpiperidin-1-ium trifluoroacetate (300 mg, 616 μmol) in 4 M HCl in EtOAc (3 ml) was stirred at rt for 1 h. The solution was concentrated under reduced pressure to give the title compound as a white solid. LCMS (ESI): m/z: $[M+H]^+$=274.1.

Intermediate 59. N-(5-Fluoro-1-methyl-1H-pyrazol-4-yl)-N-(1-methylpiperidin-4-yl)aminosulfonamide Hydrochloride Step 1. Tert-butyl N-(1-methyl-1H-pyrazol-4-yl)carbamate

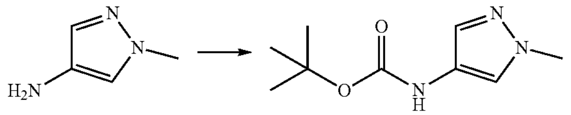

To a mixture of 1-methylpyrazol-4-amine (10 g, 103 mmol) in DCM (100 ml) were added di-tert-butyl dicarbonate (24.7 g, 113 mmol) and triethylamine (43 ml, 309 mmol). The mixture was stirred at rt for 12 h. The solution was concentrated in vacuo and the resulting residue purified by silica gel chromatography (50% EtOAc in petrol) to give the title compound as a yellow solid. Y=65%. $^1$H NMR (400 MHz, MeOD) δ 7.60 (s, 1H) 7.34 (s, 1H) 3.82 (s, 3H) 1.49 (s, 9H).

Step 2. Tert-butyl N-(5-fluoro-1-methyl-1H-pyrazol-4-yl)carbamate

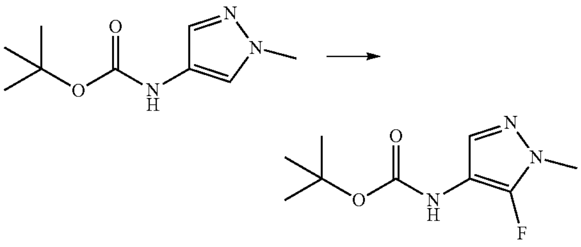

To a mixture of tert-butyl N-(1-methylpyrazol-4-yl)carbamate (13 g, 65.9 mmol) in DMF (70 ml) and DCM (70 ml) was added 1-chloromethyl-4-fluoro-1,4-diazoniabicyclo[2.2.2]octane bis(tetrafluoroborate)(Selectfluor) (32.7 g, 92.3 mmol) in one portion. The mixture was stirred at rt for 8 h. The RM was concentrated under reduced pressure and diluted with water (50 ml). The mixture was extracted with EtOAc (3×40 ml). The combined organic phase was washed with brine (2×20 ml), dried over anhydrous $Na_2SO_4$, filtered and concentrated in vacuo to give a residue. This was purified by silica gel chromatography (50% EtOAc in petrol) to give the title compound as a yellow oil. Y=14%. $^1$H NMR (400 MHz, MeOD) δ 7.38 (s, 1H) 3.70 (s, 3H) 1.48 (s, 9H).

Step 3. 5-Fluoro-1-methyl-1H-pyrazol-4-aminium Chloride

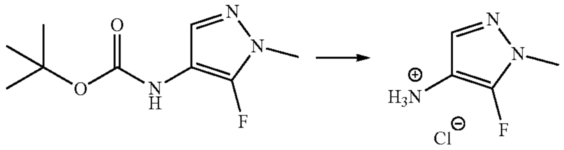

The solution of tert-butyl N-(5-fluoro-1-methyl-1H-pyrazol-4-yl)carbamate (1.4 g, 6.50 mmol) in 4 M HCl in EtOAc (13 ml) was stirred at rt for 1 h. The solution was concentrated in vacuo to give the title compound as a white solid. LCMS: m/z: $[M+H]^+$=116.3.

Step 4. N-(5-Fluoro-1-methyl-1H-pyrazol-4-yl)-1-methylpiperidin-4-amine

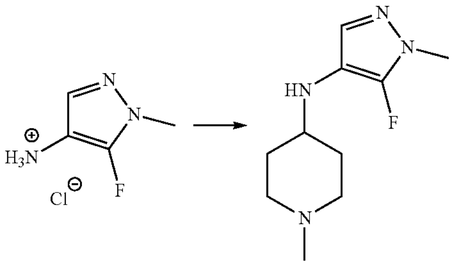

To a solution of 5-fluoro-1-methyl-1H-pyrazol-4-aminium chloride (700 mg, 4.62 mmol) in DCE (10 ml) and AcOH (1.14 ml) was added 1-methylpiperidin-4-one (707 μl, 6.08 mmol). The RM was stirred at rt for 2 h. The RM was cooled to 0° C., treated with $NaBH(OAc)_3$ (2.58 g, 12.2 mmol) and stirred at this temperature for 12 h. The solution was concentrated in vacuo and the resulting residue purified by silica gel chromatography (0-100% EtOAc in petrol) to give the title compound as a yellow oil. LCMS: m/z: $[M+H]^+$=213.2.

Step 5. Tert-butyl N-[(5-fluoro-1-methyl-1H-pyrazol-4-yl)(1-methylpiperidin-4-yl)sulfamoyl]carbamate

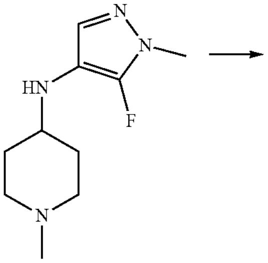

-continued

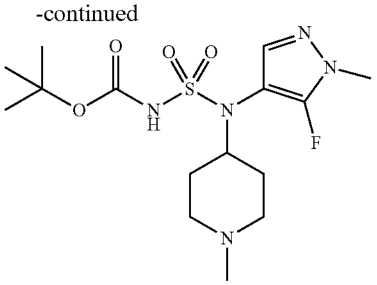

To a solution of N-(5-fluoro-1-methyl-1H-pyrazol-4-yl)-1-methylpiperidin-4-amine (1.0 g, 4.71 mmol) in DCM (10 ml) under $N_2$ at 0° C. was added DIPEA (821 μl, 4.71 mmol) and the RM stirred for 15 min. The RM was treated with 0.51 M tert-butyl N-chlorosulfonylcarbamate in DCM (9.33 ml, 4.71 mmol) and the mixture stirred for 1 h. The solution was concentrated in vacuo and the resulting residue purified by prep-HPLC (column: Agela DuraShell C18 250×70 mm, 10 μm; mobile phase: [water (10 mM $NH_4HCO_3$)-ACN]; B: 3-20%, 22 min) to give the title compound as a white solid. LCMS (ESI): m/z: $[M+H]^+$ 392.1.

Step 6. N-(5-Fluoro-1-methyl-1H-pyrazol-4-yl)-N-(1-methylpiperidin-4-yl)aminosulfonamide Hydrochloride

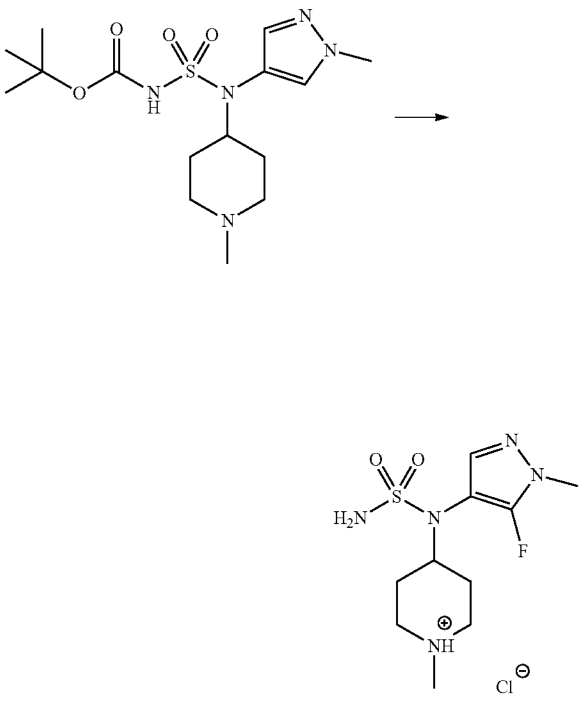

A solution of tert-butyl N-[(5-fluoro-1-methyl-1H-pyrazol-4-yl)(1-methylpiperidin-4-yl)sulfamoyl]carbamate (100 mg, 0.26 mmol) in 4 M HCl in EtOAc (1 ml) was stirred at rt for 1 h. The solution was concentrated in vacuo to give the title compound as a yellow oil. LCMS (ESI): m/z: $[M+H]^+$=292.1.

Intermediate 60. 3-Isocyanato-2-methoxy-4H,5H,6H-cyclopenta[b]thiophene

Step 1. 2-Methoxy-4H,5H,6H-cyclopenta[b]thiophene-3-carboxylic Acid

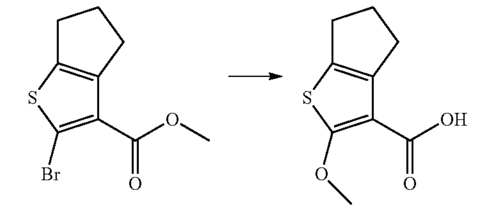

To a solution of methyl 2-bromo-5,6-dihydro-4H-cyclopenta[b]thiophene-3-carboxylate (1.0 g, 3.83 mmol) (for synthesis refer to Example 28) in THF (4 ml) was added 50 wt. % sodium methoxide in MeOH (4.14 g, 38.3 mmol), CuO (101 mg, 1.26 mmol) and NaI (20 mg, 133 μmol,). The RM was heated at 80° C. for 12 h. The RM was concentrated under reduced pressure and the resulting residue diluted with $H_2O$ (15 ml). The solution was acidified to pH~2 with 6 M HCl (aq.) and the resulting mixture extracted with EtOAc (3×30 ml). The organic phase was concentrated under reduced pressure and the resulting residue purified by column chromatography (silica, 9-25% EtOAc in petrol) to give the title compound as a white solid. Y=40%. LCMS (ESI): m/z: $[M+H]^+$=199.0.

Step 2. Tert-butyl N-{2-methoxy-4H,5H,6H-cyclopenta[b]thiophen-3-yl}carbamate

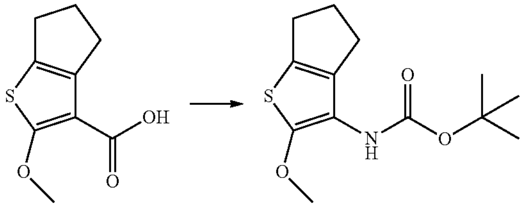 [SMILES: COc1sc2c(c1C(=O)O)CCC2 ; COc1sc2c(c1NC(=O)OC(C)(C)C)CCC2]

To a solution of 2-methoxy-4H,5H,6H-cyclopenta[b]thiophene-3-carboxylic acid (140 mg, 0.71 mmol) in tert-butanol (4 ml) under nitrogen were added DPPA (194 mg, 0.71 mmol) and DIPEA (185 μl, 1.06 mmol). The RM was heated at 90° C. for 12 h. The solution was concentrated under reduced pressure and the resulting residue purified by column chromatography (silica, 9-17% EtOAc in petrol) to give the title compound as a white solid. Y=42%. LCMS (ESI): m/z: $[M+H]^+$=270.1.

Step 3. 2-Methoxy-4H,5H,6H-cyclopenta[b]thiophen-3-aminium Chloride

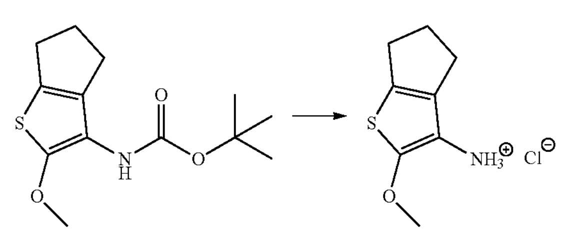 [SMILES: COc1sc2c(c1NC(=O)OC(C)(C)C)CCC2 ; COc1sc2c(c1[NH3+])CCC2 ; [Cl-]]

A solution of trimethylsilyl chloride (583 μl, 4.60 mmol) in 2,2,2-trifluoroethanol (3 ml) was stirred at 0° C. for 0.5 h. This was treated with tert-butyl N-{2-methoxy-4H,5H,6H-cyclopenta[b]thiophen-3-yl}carbamate (70 mg, 0.26 mmol) and the resulting solution stirred at rt for 1 h. The solution was concentrated under reduced pressure to give the title compound as a yellow solid. LCMS (ESI): m/z: $[M+H]^+$=170.0.

Step 4. 3-Isocyanato-2-methoxy-4H,5H,6H-cyclopenta[b]thiophene

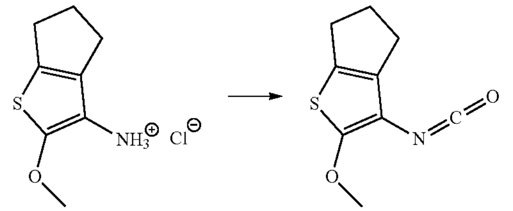

To a solution 2-Methoxy-4H,5H,6H-cyclopenta[b]thiophen-3-aminium chloride (53 mg, 0.26 mmol) in DCM (3 ml) cooled to 0° C. were added triethylamine (35.6 μl, 0.26 mmol) and triphosgene (23 mg, 77.3 μmol). The RM was stirred at 0° C. for 1 h. The solution was concentrated under reduced pressure to give the title compound as a yellow solid. LCMS in MeOH (ESI): m/z: $[M+MeOH+H]^+$=228.0.

Intermediate 61. 2-Cyclopropyl-3-isocyanato-5-methylthiophene

Step 1. Tert-butyl N-(2-cyclopropyl-5-methylthiophen-3-yl)carbamate

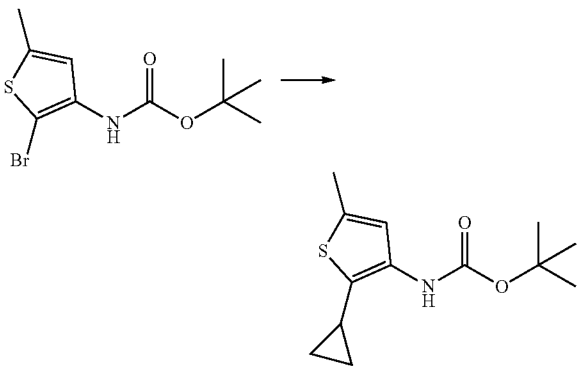

To a solution of tert-butyl N-(2-bromo-5-methylthiophen-3-yl)carbamate (600 mg, 2.05 mmol) (for synthesis refer to Example 41) in $H_2O$ (2 ml) and dioxane (10 ml) was added cyclopropylboronic acid (1.76 g, 20.5 mmol), $Pd_2(dba)_3$ (376 mg, 0.41 mmol), XPhos (392 mg, 0.82 mmol) and $K_2CO_3$ (1.70 g, 12.3 mmol). The RM was heated at reflux for 12 h. The mixture was concentrated under reduced pressure and the resulting residue purified by prep-TLC (9% EtOAc in petrol) to give the title compound as a yellow solid. Y=58%. $^1$H NMR (400 MHz, chloroform-d) δ 7.12 (s, 1H), 6.43 (s, 1H), 2.37 (s, 3H), 1.76-1.70 (m, 1H), 1.52 (s, 9H), 0.96-0.90 (m, 2H), 0.67-0.61 (m, 2H).

Step 2. 2-Cyclopropyl-5-methylthiophen-3-amine Hydrochloride

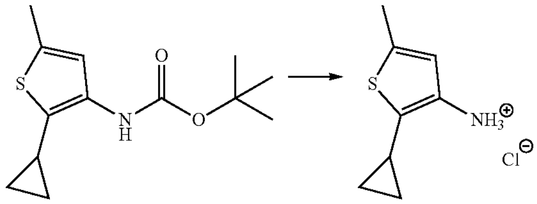

A mixture of tert-butyl N-(2-cyclopropyl-5-methylthiophen-3-yl)carbamate (300 mg, 1.18 mmol) in 4 M HCl in EtOAc (10 ml) was stirred at rt for 1 h. The mixture was concentrated under reduced pressure to give the title compound as a white solid. LCMS (ESI): m/z: $[M+H]^+$=154.1.

Step 3. 2-Cyclopropyl-3-isocyanato-5-methylthiophene

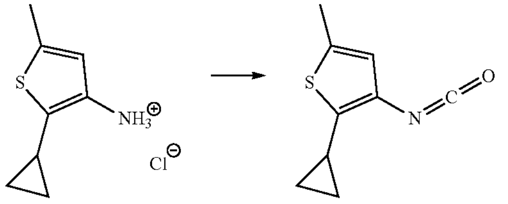

To a solution of 2-cyclopropyl-5-methylthiophen-3-amine hydrochloride (250 mg, 1.63 mmol) in dioxane (2 ml) warmed to 40° C. was added trichloromethyl carbonochloridate (355 mg, 1.79 mmol). The RM was heated at 70° C. for 1 h. The mixture was concentrated under reduced pressure to give the title compound as a yellow solid. LCMS in MeOH (ESI): m/z: $[M+H+MeOH]^+$=212.1.

Intermediate 62. N-(1-Cyclopropyl-1H-pyrazol-4-yl)-N-(1-methylpiperidin-3-yl)aminosulfonamide Hydrochloride Step 1. Tert-butyl 3-[(1-cyclopropyl-1H-pyrazol-4-yl)amino]piperidine-1-carboxylate

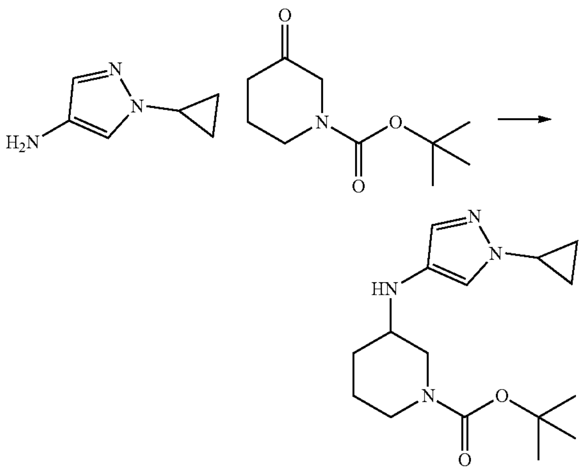

To a solution of 1-cyclopropyl-1H-pyrazol-4-amine (1.0 g, 8.12 mmol) [for synthesis refer to Intermediate 57] in DCM (10 ml) cooled to 0° C. was added tert-butyl 3-oxopiperidine-1-carboxylate (1.62 g, 8.12 mmol) and acetic acid (1 ml). The RM was stirred at 0° C. for 0.5 h, then treated with $NaBH(OAc)_3$ (3.44 g, 16.2 mmol). The RM was stirred at rt for 12 h. The solution was concentrated under reduced pressure. The residue was purified by column chromatography (silica, 50-100% EtOAc in petrol) to give the title compound as a white solid. Y=40%.

Step 2. N-(1-Cyclopropyl-1H-pyrazol-4-yl)-1-methylpiperidin-3-amine

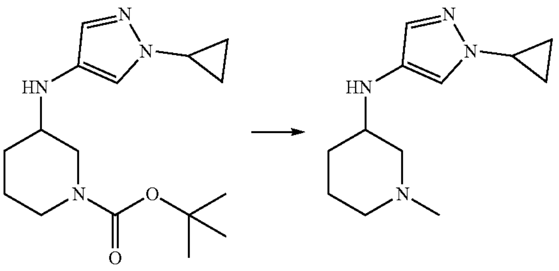 [SMILES: CC(C)(C)OC(=O)N1CCCC(Nc2cnn(C3CC3)c2)C1 ; CN1CCCC(Nc2cnn(C3CC3)c2)C1]

To a solution of tert-butyl 3-[(1-cyclopropyl-1H-pyrazol-4-yl)amino]piperidine-1-carboxylate (1.0 g, 3.26 mmol) in THF (20 ml) at 0° C. was added $LiAlH_4$ (1.24 g, 32.6 mmol). The RM was heated at 85° C. for 12 h. The solution was quenched with water (1 ml) and 10% NaOH (aq.) (1 ml). The resulting mixture was filtered and the filtrate concentrated under reduced pressure to give the title compound as an oil. LCMS (ESI): m/z: $[M+H]^+$=221.1.

Step 3. 3-[({[(Tert-butoxy)carbonyl]amino}sulfonyl)(1-cyclopropyl-1H-pyrazol-4-yl)amino]-1-methylpiperidin-1-ium Trifluoroacetate

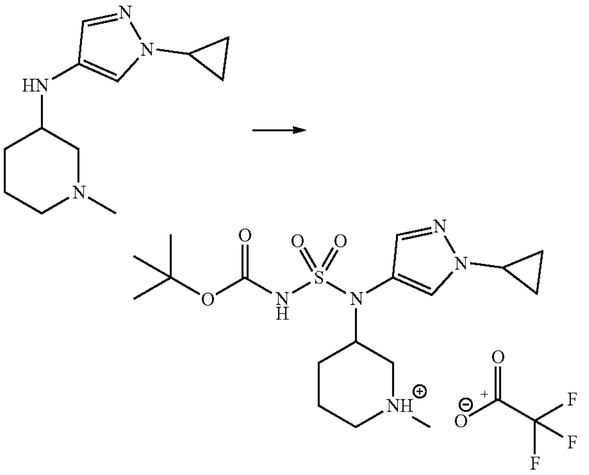

To a solution of N-(1-cyclopropyl-1H-pyrazol-4-yl)-1-methylpiperidin-3-amine (720 mg, 3.27 mmol) in DCM (10 ml) was added DIPEA (1.14 ml, 6.54 mmol). The RM was stirred at rt for 0.5 h and treated with 0.71 M tert-butyl N-chlorosulfonylcarbamate in DCM (5.54 ml, 3.92 mmol). The RM was stirred at rt for 1 h. The solution was concentrated under reduced pressure and the resulting residue purified by prep-HPLC (column: Phenomenex Luna C18 250×50 mm, m; mobile phase: [water (0.1% TFA)-ACN]; B: 1-30%, 10 min) to give the title compound as a white solid. Y=24%. LCMS (ESI): m/z: $[M+H]^+$=400.2.

Step 4. N-(1-Cyclopropyl-1H-pyrazol-4-yl)-N-(1-methylpiperidin-3-yl)aminosulfonamide Hydrochloride

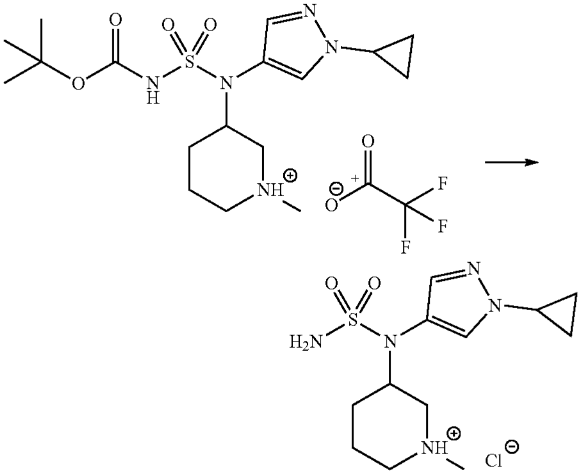

A solution of 3-[({[(tert-butoxy)carbonyl]amino}sulfonyl)(1-cyclopropyl-1H-pyrazol-4-yl)amino]-1-methylpiperidin-1-ium trifluoroacetate (100 mg, 195 μmol) in 4 M HCl in EtOAc (2 ml) was stirred at rt for 0.5 h. The solution was concentrated under reduced pressure to give the title compound as a white solid. LCMS (ESI): m/z: $[M+H]^+=300.1$.

Intermediate 63. N-(5-Fluoro-1-methyl-1H-pyrazol-4-yl)-N-(1-methylpiperidin-3-yl)aminosulfonamide Step 1. Tert-butyl 3-[(5-fluoro-1-methyl-1H-pyrazol-4-yl)amino]piperidine-1-carboxylate

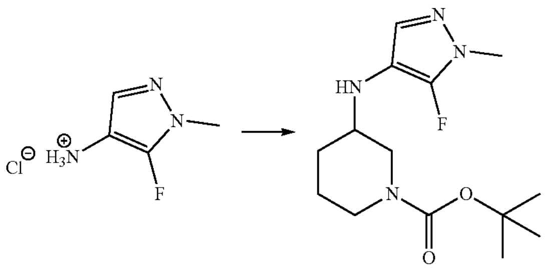

To a solution of 5-fluoro-1-methyl-1H-pyrazol-4-amine hydrochloride (3.0 g, 19.8 mmol) [for synthesis refer to Intermediate 59] in AcOH (3.42 ml) and DCE (30 ml) was added tert-butyl 3-oxopiperidine-1-carboxylate (3.94 g, 19.8 mmol). The mixture was stirred at rt for 2 h, then cooled to 0° C. The RM was treated with $NaBH(OAc)_3$ (8.39 g, 39.6 mmol) and stirred at rt for 12 h. The mixture was concentrated in vacuo and the resulting residue purified by silica gel chromatography (0-100% EtOAc in petrol) to give the title compound as a yellow oil. Y=34%. LCMS: m/z: $[M+H]^+=299.1$.

Step 2. Tert-butyl 3-[({[(tert-butoxy)carbonyl]amino}sulfonyl)(5-fluoro-1-methyl-1H-pyrazol-4-yl)amino]piperidine-1-carboxylate

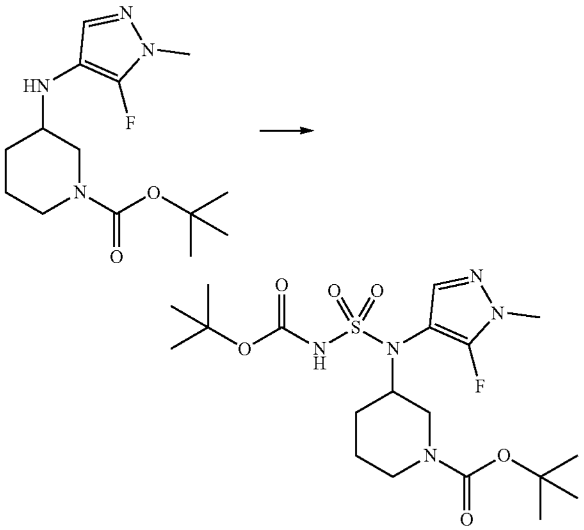

To a solution of tert-butyl 3-[(5-fluoro-1-methyl-1H-pyrazol-4-yl)amino]piperidine-1-carboxylate (2.0 g, 6.70 mmol) in DCM (20 ml) under $N_2$ at 0° C. was added DIPEA (1.17 ml, 6.70 mmol) and the RM stirred for 15 min. This was treated with 0.71 M tert-butyl N-chlorosulfonylcarbamate in DCM (9.48 ml, 6.70 mmol) and stirred at 0° C. for 1 h. The solution was concentrated in vacuo and the resulting residue purified by prep-HPLC (column: Phenomenex Luna C18 250×50 mm, 10 μm; mobile phase: [water (0.1% TFA)-ACN]; B: 40-70%, 20 min) to give the title compound as a white solid. Y=53%. LCMS: m/z: $[M+H]^+=478.2$.

Step 3. N-(5-Fluoro-1-methyl-1H-pyrazol-4-yl)-N-(piperidin-3-yl)aminosulfonamide Hydrochloride

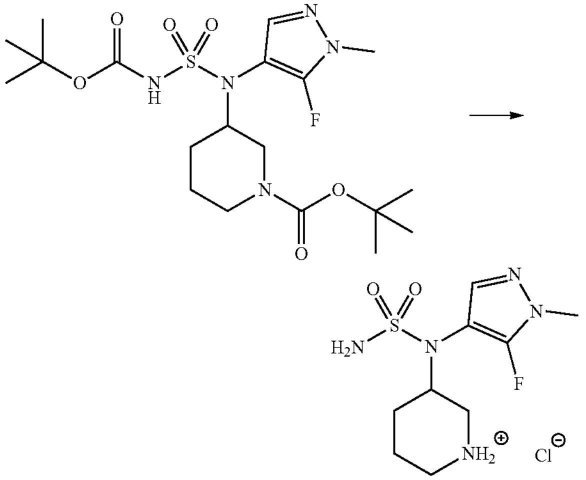

A solution of tert-butyl 3-[({[(tert-butoxy)carbonyl]amino}sulfonyl)(5-fluoro-1-methyl-1H-pyrazol-4-yl)amino]piperidine-1-carboxylate (800 mg, 1.68 mmol) in 4 M HCl in EtOAc (10 ml) was stirred at rt for 1 h. The solution was concentrated in vacuo to give the title compound as a white solid. LCMS: m/z: $[M+H]^+=278.2$.

Step 4. N-(5-Fluoro-1-methyl-1H-pyrazol-4-yl)-N-(1-methylpiperidin-3-yl)aminosulfonamide

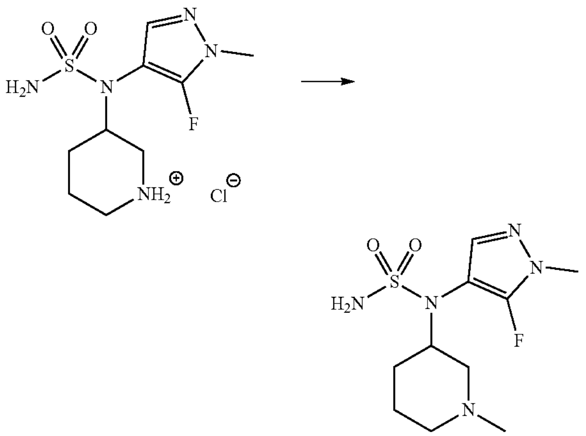

To a mixture of N-(5-fluoro-1-methyl-1H-pyrazol-4-yl)-N-(piperidin-3-yl)aminosulfonamide hydrochloride (800 mg, 2.55 mmol) in MeOH (10 ml) cooled to 0° C. was added 37 wt. % formaldehyde (aq.) (153 mg, 1.89 mmol) and $NaBH_3CN$ (320 mg, 5.10 mmol). The RM was stirred at 0°

C. for 2 h. The RM was concentrated in vacuo to give the title product as a white solid. This was used directly in the next step. LCMS: m/z: $[M+H]^+$=292.2.

Intermediate 64. 3-Isocyanato-2-methyl-5-(trifluoromethyl)thiophene

Step 1. Tert-butyl N-(2-methylthiophen-3-yl)carbamate

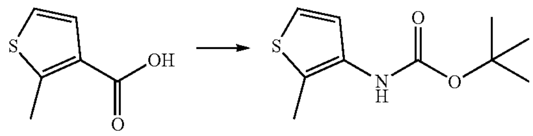

To a solution of 2-methylthiophene-3-carboxylic acid (3.0 g, 21.1 mmol) in tert-butanol (50 ml) was added DPPA (5.81 g, 21.1 mmol) and DIPEA (5.51 ml, 31.7 mmol). The RM was heated at 85° C. for 12 h. The RM was concentrated under reduced pressure and the resulting residue purified by column chromatography (silica, 9% EtOAc in petrol) to give the title compound as a white solid. Y=56%. $^{1}$H NMR (400 MHz, MeOD) δ 7.49-7.38 (m, 1H), 7.34-7.30 (m, 1H), 7.04-6.97 (m, 1H), 2.28 (s, 3H), 1.50 (s, 9H).

Step 2. Tert-butyl N-(5-bromo-2-methylthiophen-3-yl)carbamate

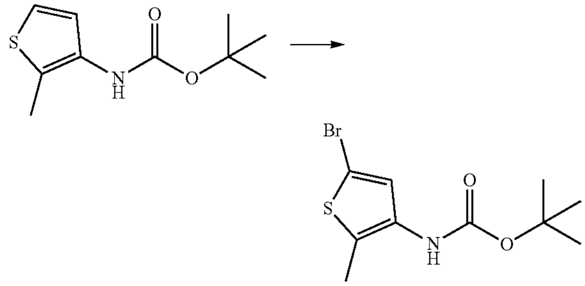

To a solution of tert-butyl N-(2-methylthiophen-3-yl) carbamate (500 mg, 2.34 mmol) in THF (8 ml) was added NBS (417 mg, 2.34 mmol). The RM was stirred at rt for 0.5 h. The RM was diluted with $H_2O$ (20 ml) and extracted with EtOAc (3×5 ml). The combined organic layers were washed with brine (2×5 ml), dried over $Na_2SO_4$, filtered and concentrated under reduced pressure to give a residue. This was purified by column chromatography (silica, 9% EtOAc in petrol) to give the title compound as a yellow solid. Y=70%. LCMS: m/z: $[M+H-56]^-$=237.9.

Step 3. Tert-butyl N-(5-iodo-2-methylthiophen-3-yl)carbamate

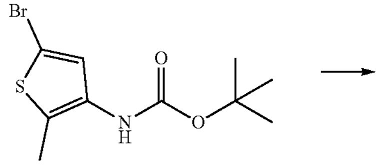

-continued

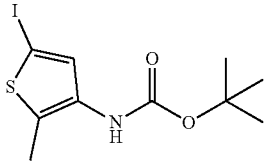

To a mixture of tert-butyl N-(5-bromo-2-methylthiophen-3-yl)carbamate (1.0 g, 3.42 mmol), NaI (1.03 g, 6.84 mmol) and CuI (65 mg, 342 μmol) in dioxane (10 ml) was added N,N'-dimethylethane-1,2-diamine (60 mg, 0.68 mmol). The resulting mixture was heated to 110° C. and stirred for 16 h. The solution was concentrated in vacuo and the resulting residue purified by column chromatography (silica, 9-17% EtOAc in petrol) to give the title compound as a yellow oil. $^{1}$H NMR (400 MHz, MeOD) δ 7.18 (s, 1H) 2.25 (s, 3H) 1.49 (s, 9H).

Step 4. Tert-butyl N-[2-methyl-5-(trifluoromethyl) thiophen-3-yl]carbamate

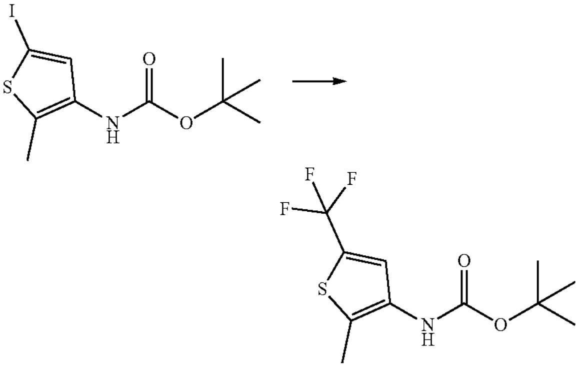

To a solution of tert-butyl N-(5-iodo-2-methylthiophen-3-yl)carbamate (1.2 g, 3.54 mmol) in DMF (10 ml) under $N_2$ were added CuI (876 mg, 4.60 mmol) and HMPA (3.17 g, 17.7 mmol). The RM was stirred at rt for 5 min, then treated with methyl 2,2-difluoro-2-fluorosulfonyl-acetate (3.40 g, 17.7 mmol). The RM was heated at 100° C. for 1 h. The reaction was concentrated under reduced pressure and the resulting residue purified by silica gel column chromatography (17% EtOAc in petrol) to give the title compound as a white solid. Y=65%. $^{1}$H NMR (400 MHz, MeOD) δ 7.53 (s, 1H) 2.34 (s, 3H) 1.51 (s, 9H).

Step 5. 2-Methyl-5-(trifluoromethyl)thiophen-3-amine Hydrochloride

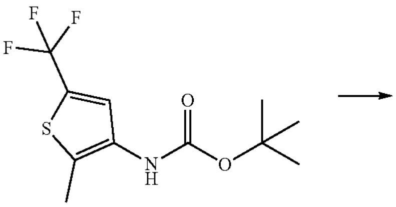

-continued

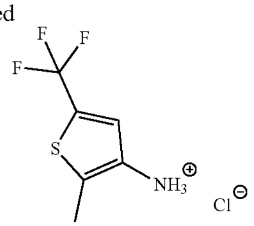

A solution of tert-butyl N-[2-methyl-5-(trifluoromethyl)thiophen-3-yl]carbamate (300 mg, 1.07 mmol) in 4 M HCl in EtOAc (3 ml) was stirred at rt for 1 h. The mixture was concentrated in vacuo to give the title compound as a white solid. This was used in the next step directly.

Step 6. 3-Isocyanato-2-methyl-5-(trifluoromethyl)thiophene

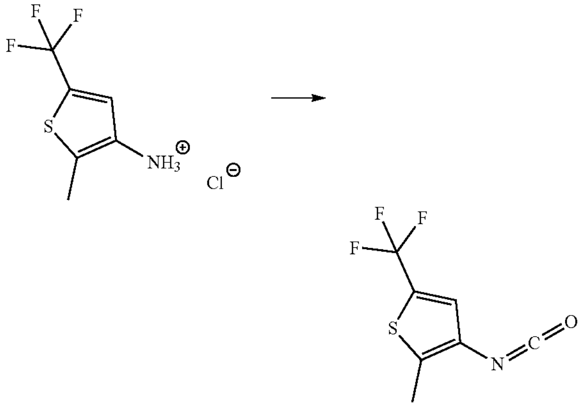

To a solution of 2-methyl-5-(trifluoromethyl)thiophen-3-amine hydrochloride (300 mg, 1.38 mmol) in dioxane (3 ml) warmed to 40° C. was added trichloromethyl carbonochloridate (122 mg, 0.62 mmol). The RM was heated at 70° C. for 1 h. The solution was concentrated in vacuo to give the title compound as a yellow oil. This was used directly without purification. LCMS in MeOH: m/z: $[M+MeOH+H]^+$=240.1.

Intermediate 65. 3-Isocyanato-5-(propan-2-yl)-2-(trifluoromethyl)thiophene

Step 1. Tert-butyl N-[5-(prop-1-en-2-yl)thiophen-3-yl]carbamate

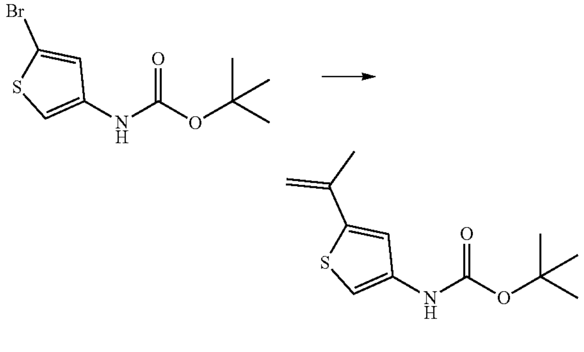

To a solution of tert-butyl N-(5-bromothiophen-3-yl)carbamate (2.0 g, 7.19 mmol) [for synthesis refer to Intermediate 31] in THF (25 ml) and $H_2O$ (5 ml) under $N_2$ was added 2-isopropenyl-4,4,5,5-tetramethyl-1,3,2-dioxaborolane (6.04 g, 36.0 mmol), $Pd(PPh_3)_4$ (83 mg, 71.9 mol) and $Na_2CO_3$ (2.29 g, 21.6 mmol). The RM was heated at 90° C. for 12 h. The RM was concentrated in vacuo and the resulting residue purified by silica gel chromatography (0-17% EtOAc in petrol) to give the title compound as a yellow solid. LCMS (ESI): m/z: $[M+H]^+$=240.1.

Step 2. Tert-butyl N-[5-(propan-2-yl)thiophen-3-yl] carbamate

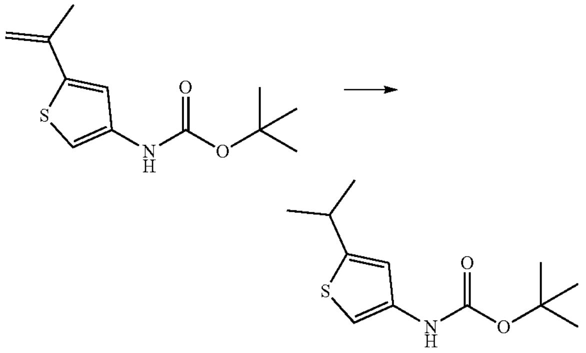

To a solution of tert-butyl N-[5-(prop-1-en-2-yl)thiophen-3-yl]carbamate (1.8 g, 7.52 mmol) in MeOH (3 ml) was added 10% Pd/C (50% in water, 1 g). The RM was degassed under vacuum and purged with $H_2$ several times. The mixture was stirred under $H_2$ (15 psi) at rt for 2 h. The RM was filtered through Celite and the filtrate concentrated in vacuo to give the title compound as a yellow solid. LCMS (ESI): m/z: $[M+H]^+$=242.3.

Step 3. Tert-butyl N-[5-(propan-2-yl)-2-(trifluoromethyl)thiophen-3-yl]carbamate

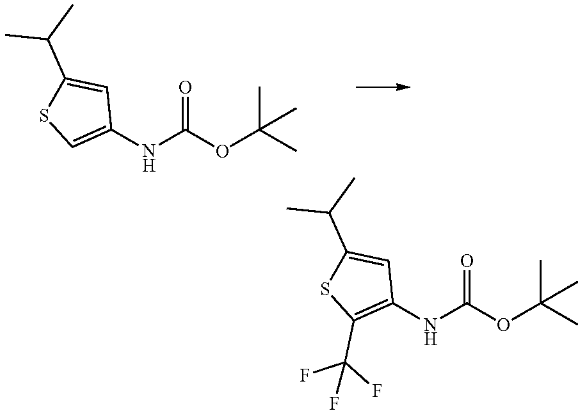

To a solution of tert-butyl N-[5-(propan-2-yl)thiophen-3-yl]carbamate (150 mg, 0.62 mmol) in tert-butanol (5 ml) were added 1-(trifluoromethyl)-1,2-benziodoxol-3-one (393 mg, 1.24 mmol) and CuCl (12.3 mg, 124 μmol). The mixture was stirred at 115° C. for 8 h. The solution was concentrated in vacuo and the resulting residue purified by silica gel chromatography (0-17% EtOAc in petrol) to give the title compound as a white solid. Y=42%.

Step 4. 5-(Propan-2-yl)-2-(trifluoromethyl)thiophen-3-amine Hydrochloride

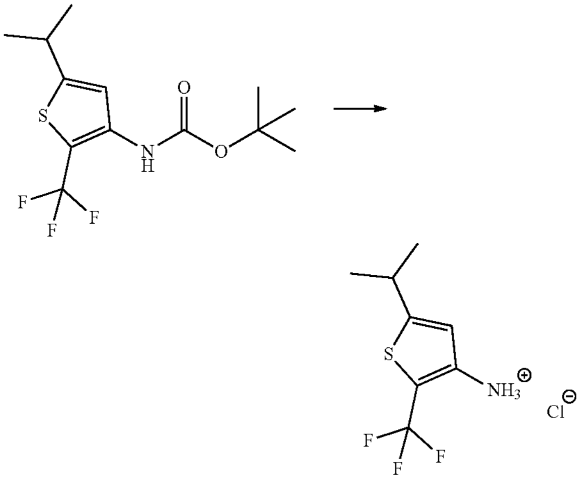

A mixture of tert-butyl N-[5-(propan-2-yl)-2-(trifluoromethyl)thiophen-3-yl]carbamate (80 mg, 0.26 mmol) in 4 M HCl in EtOAc (5 ml) was stirred at rt for 1 h. The solution was concentrated in vacuo to give the title compound as a solid. This was used directly in the next step.

Step 5. 3-Isocyanato-5-(propan-2-yl)-2-(trifluoromethyl)thiophene

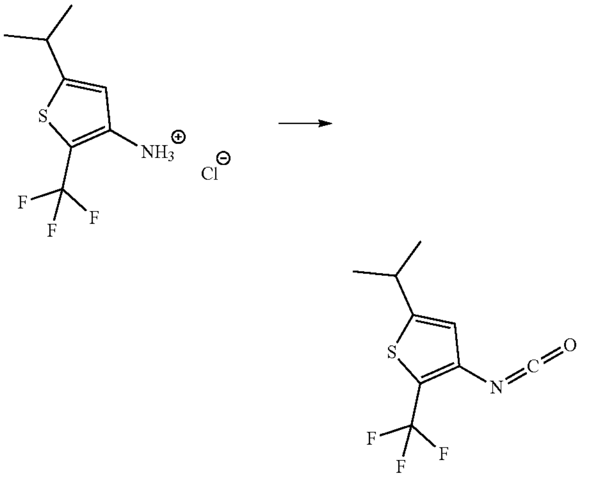

To a solution of 5-isopropyl-2-(trifluoromethyl)thiophen-3-amine (80 mg, 0.38 mmol) in dioxane (6 ml) warmed to 40° C. was added trichloromethyl carbonochloridate (83 mg, 0.42 mmol). The mixture was heated at 70° C. for 1 h. The solution was concentrated in vacuo to give the title compound as an oil. LCMS in MeOH (ESI): m/z: $[M+MeOH+H]^+=268.0$.

Intermediate 66. 2-Tert-butyl-3-isocyanato-4H,5H,6H-cyclopenta[b]thiophene

Step 1. Methyl 4H,5H,6H-cyclopenta[b]thiophene-3-carboxylate

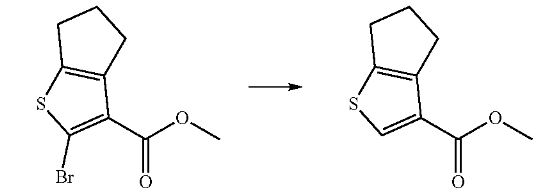

To a solution of methyl 2-bromo-4H,5H,6H-cyclopenta[b]thiophene-3-carboxylate (1.0 g, 3.83 mmol) [for synthesis refer to Intermediate 28] in MeOH (20 ml) was added 10% Pd/C (50% in water, 500 mg). The RM was degassed and stirred under $H_2$ (15 psi) at rt for 1 h. The RM was filtered through Celite and the filtrate concentrated under reduced pressure to give the title compound as a yellow solid. Y=quantitative.

Step 2. 4H,5H,6H-Cyclopenta[b]thiophene-3-carboxylic Acid

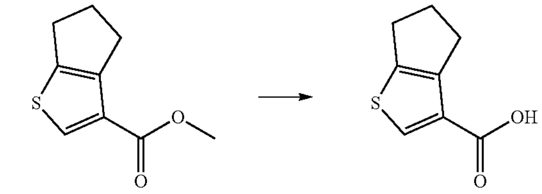

To a solution of methyl 4H,5H,6H-cyclopenta[b]thiophene-3-carboxylate (690 mg, 3.79 mmol) in MeOH (10 ml) and $H_2O$ (5 ml) was added NaOH (227 mg, 5.68 mmol) and the solution stirred at 50° C. for 12 h. The RM was concentrated under reduced pressure to remove MeOH and diluted with $H_2O$ (30 ml). The pH of the resulting solution was adjusted to 5 by addition of 6 M HCl (aq.) and the resulting mixture was extracted with EtOAc (3×60 ml). The combined organic phase was concentrated under reduced pressure and the resulting residue purified by column chromatography (silica, 9-17% EtOAc in petrol) to give the title compound as a yellow solid.

Step 3. Tert-butyl N-{4H,5H,6H-cyclopenta[b]thiophen-3-yl}carbamate

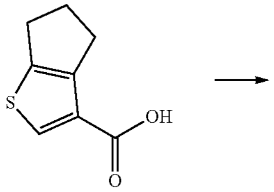

-continued

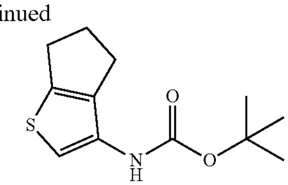

To a solution of 4H,5H,6H-Cyclopenta[b]thiophene-3-carboxylic acid (720 mg, 4.28 mmol) in tert-butanol (15 ml) under $N_2$ were added DPPA (1.18 g, 4.28 mmol) and DIPEA (1.12 ml, 6.42 mmol). The RM was stirred at 90° C. for 12 h. The solution was concentrated under reduced pressure and the resulting residue purified by column chromatography (silica, 9-17% EtOAc in petrol) to give the title compound as a white solid. Y=69%. LCMS (ESI): m/z: $[M+H]^+$=240.0.

Step 4. 2-Tert-butyl-4H,5H,6H-cyclopenta[b]thiophen-3-amine

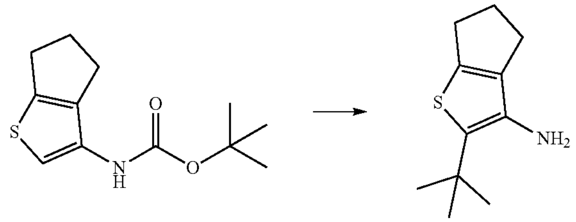 [SMILES: CC(C)(C)OC(=O)Nc1csc2c1CCC2 ; CC(C)(C)c1sc2c(c1N)CCC2]

To a solution of tert-butyl N-{4H,5H,6H-cyclopenta[b]thiophen-3-yl}carbamate (500 mg, 2.09 mmol) in DCE (10 ml) cooled to 0° C. were added 2-methylpropan-2-ol (599 μl, 6.27 mmol) and boron trifluoride etherate (387 μl, 3.13 mmol). The RM was gradually warmed to 85° C. and stirred at this temperature for 12 h. The reaction was concentrated under reduced pressure and the resulting residue purified by prep-HPLC (column: Phenomenex Luna C18 250×50 mm, 10 μm; mobile phase: [water (0.1% TFA)-ACN]; B: 10-20%, 10 min) to give the title compound as a white solid. Y=25%. $^1H$ NMR (400 MHz, MeOD) δ 2.85-2.83 (m, 2H), 2.73-2.70 (m, 1H), 2.60-2.53 (m, 2H), 2.46-2.41 (m, 1H), 1.44-1.40 (m, 9H).

Step 5. 2-Tert-butyl-3-isocyanato-4H,5H,6H-cyclopenta[b]thiophene

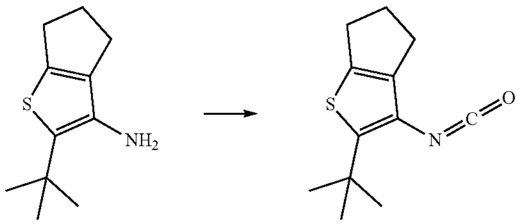

To a solution of 2-tert-butyl-4H,5H,6H-cyclopenta[b]thiophen-3-amine (40 mg, 0.20 mmol) in dioxane (2 ml) warmed to 40° C. was added trichloromethyl carbonochloridate (48.6 mg, 0.25 mmol). The RM was heated at 70° C. for 1 h. The solution was concentrated under reduced pressure to give the title compound as an oil. LCMS in MeOH (ESI): m/z: $[M+MeOH+H]^+$=254.2.

Intermediate 67. 4-Isocyanato-3-methyl-5-(propan-2-yl)-1,2-thiazole

Step 1. 3-Methyl-1,2-thiazole-4-carboxylic Acid

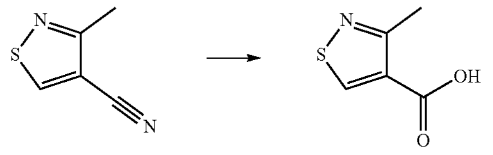

In a sealed tube, a solution of 3-methyl-1,2-thiazole-4-carbonitrile (500 mg, 4.03 mmol) in ethylene glycol (12.6 ml) and $H_2O$ (0.9 ml) under $N_2$ was treated with KOH (520 mg, 9.26 mmol). The RM was heated at 120° C. for 12 h. The residue was diluted with $H_2O$ (20 ml), the resulting solution acidified to pH~2 by addition of 6 M HCl (aq.), and the mixture extracted with EtOAc (3×15 ml). The organic phase was concentrated under reduced pressure to give the title compound as a yellow solid. Y=78%. LCMS (ESI): m/z: $[M+H]^+$ 144.0.

Step 2. Tert-butyl N-(3-methyl-1,2-thiazol-4-yl)carbamate

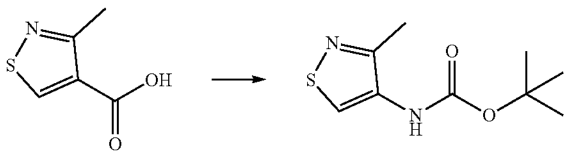

To a solution of 3-methyl-1,2-thiazole-4-carboxylic acid (390 mg, 2.72 mmol) in tert-butanol (20 ml) under $N_2$ were added DPPA (750 mg, 2.72 mmol) and DIPEA (0.71 ml, 4.09 mmol). The RM was heated at 90° C. for 12 h. The solution was concentrated under reduced and the resulting residue purified by column chromatography (silica, 9-17% EtOAc in petrol) to give the title compound as a yellow solid. Y=74%. LCMS (ESI): m/z: $[M+H]^+$=215.0.

Step 3. Tert-butyl N-(5-bromo-3-methyl-1,2-thiazol-4-yl)carbamate

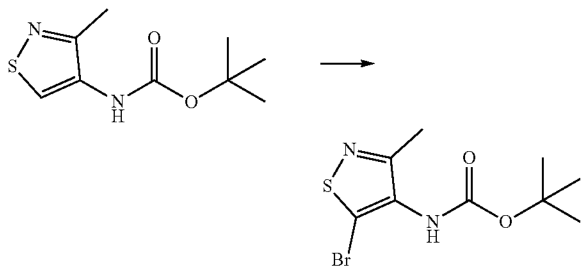

To a solution of tert-butyl N-(3-methyl-1,2-thiazol-4-yl) carbamate (400 mg, 1.87 mmol) in THF (8 ml) under $N_2$ at 0° C. was added NBS (399 mg, 2.24 mmol). The RM was stirred at rt for 12 h. The mixture was concentrated under reduced pressure and the resulting residue purified by column chromatography (silica, 9-17% EtOAc in petrol) to give the title compound as a yellow solid. Y=75%. LCMS (ESI): m/z: $[M+H]^+$=295.0.

Step 4. Tert-butyl N-[3-methyl-5-(prop-1-en-2-yl)-1,2-thiazol-4-yl]carbamate

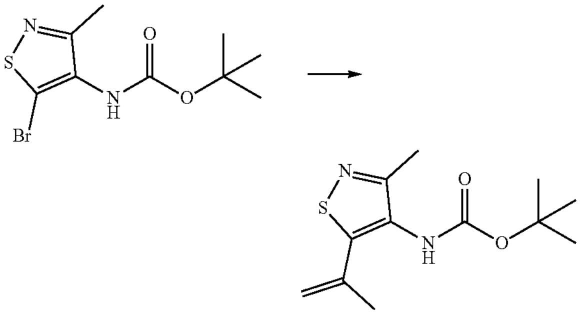

To a mixture of tert-butyl N-(5-bromo-3-methyl-1,2-thiazol-4-yl)carbamate (400 mg, 1.36 mmol) and 2-isopropenyl-4,4,5,5-tetramethyl-1,3,2-dioxaborolane (573 mg, 3.41 mmol) in THF (10 ml) and $H_2O$ (2 ml) was added $Na_2CO_3$ (434 mg, 4.09 mmol) and $Pd(PPh_3)_4$ (15.8 mg, 13.6 mol). The RM was degassed and heated under $N_2$ at 90° C. for 12 h. The RM was diluted with water (5 ml) and extracted with EtOAc (3×10 ml). The combined organic phase was concentrated under reduced pressure and the resulting residue purified by column chromatography (silica, 9-17% EtOAc in petrol) to give the title compound as a yellow solid. Y=95%. LCMS (ESI): m/z: $[M+H]^+$=255.1.

Step 5. Tert-butyl N-[3-methyl-5-(propan-2-yl)-1,2-thiazol-4-yl]carbamate

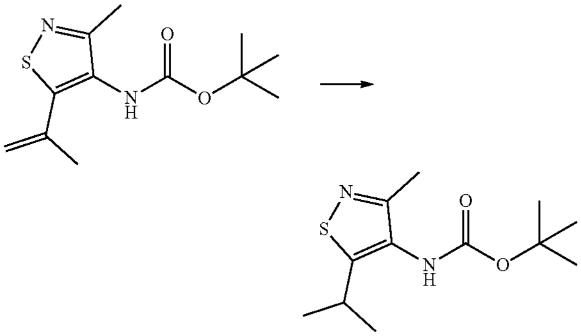

To a solution of tert-butyl N-[3-methyl-5-(prop-1-en-2-yl)-1,2-thiazol-4-yl]carbamate (100 mg, 0.39 mmol) in MeOH (10 ml) was added 10% Pd/C (50% in water, 55 mg). The RM was degassed and purged with hydrogen several times. The RM was stirred under $H_2$ (15 psi) at rt for 1 h. The RM was filtered through Celite and the filtrate concentrated under reduced pressure to give the title compound as a yellow solid. Y=91%. LCMS (ESI): m/z: $[M+H]^+$=257.0.

Step 6. 3-Methyl-5-(propan-2-yl)-1,2-thiazol-4-amine Hydrochloride

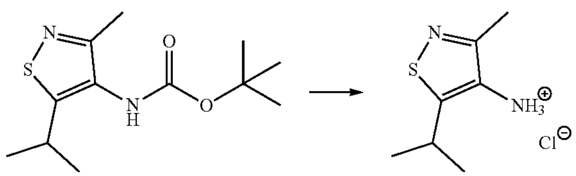

A solution of tert-butyl N-[3-methyl-5-(propan-2-yl)-1,2-thiazol-4-yl]carbamate (92 mg, 0.36 mmol) in 4 M HCl in EtOAc (4 ml) was stirred at rt for 1 h. The solution was concentrated under reduced pressure to give the title compound as a yellow solid. Y=quantitative. LCMS (ESI): m/z: $[M+H]^+$=157.1.

Step 7. 4-Isocyanato-3-methyl-5-(propan-2-yl)-1,2-thiazole

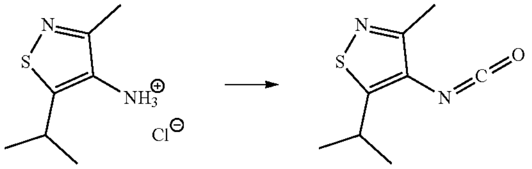

To a solution of 3-methyl-5-(propan-2-yl)-1,2-thiazol-4-amine hydrochloride (69 mg, 0.36 mmol) in dioxane (4 ml) warmed to 40° C. was added trichloromethyl carbonochloridate (85 mg, 0.43 mmol). The RM was heated at 70° C. for 1 h. The solution was concentrated under reduced pressure to give the title compound as a white solid. This was used in the next step directly. LCMS in MeOH (ESI): m/z: $[M+MeOH+H]^+$=215.0.

Intermediate 68. N-(1-methyl-1H-pyrazol-4-yl)-N-[(3S)-1-methylpyrrolidin-3-yl]aminosulfonamide Hydrochloride Step 1. Tert-butyl (3S)-3-[(1-methyl-1H-pyrazol-4-yl)amino]pyrrolidine-1-carboxylate

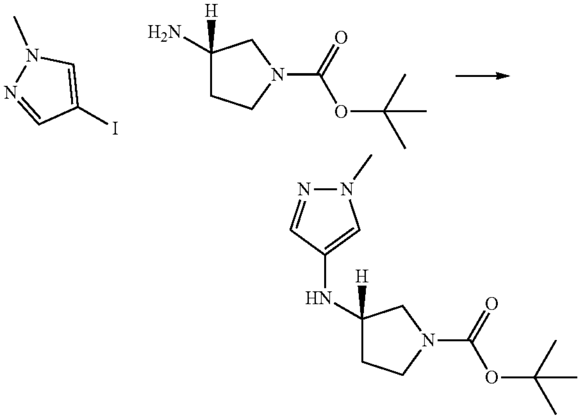

To a solution of 4-iodo-1-methyl-pyrazole (1.68 g, 8.05 mmol) in toluene (20 ml) was added tert-butyl (3S)-3-aminopyrrolidine-1-carboxylate (1.0 g, 5.37 mmol) and [2-(2-aminoethyl)phenyl]-chloro-palladium; ditert-butyl-[2-(2,4,6-triisopropylphenyl)phenyl]phosphane (369 mg, 0.54 mmol), sodium tert-butoxide (1.03 g, 10.74 mmol). The RM was stirred at 100° C. under $N_2$ for 12 h. The solution was concentrated in vacuo and the resulting residue purified by silica gel chromatography (0-100% EtOAc in petrol) to give the title compound as a yellow oil. Y=35%. LCMS (ESI): m/z: $[M+H]^+$=267.2.

Step 2. 1-Methyl-N-[(3S)-1-methylpyrrolidin-3-yl]-1H-pyrazol-4-amine

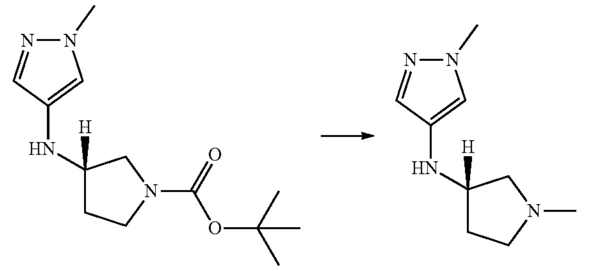 [SMILES: Cn1cc(N[C@H]2CCN(C(=O)OC(C)(C)C)C2)cn1 ; CN1CC[C@H](Nc2cnn(C)c2)C1]

To a solution of tert-butyl (3S)-3-[(1-methyl-1H-pyrazol-4-yl)amino]pyrrolidine-1-carboxylate (500 mg, 1.88 mmol) in THF (20 ml) at 0° C. was added lithium aluminium hydride (713 mg, 18.8 mmol). The RM was stirred at 0° C. for 10 min, then heated at 80° C. for 12 h. The RM was treated dropwise with ice-cold water (0.7 ml) and the resulting mixture stirred for 10 min. This was treated with 10% NaOH (aq.) (0.7 ml). The resulting mixture was filtered through Celite and the filtrate concentrated in vacuo to give the title compound as a yellow gum. LCMS (ESI): m/z: $[M+H]^+$=181.2.

Step 3. Tert-butyl N-[(1-methyl-1H-pyrazol-4-yl)[(3S)-1-methylpyrrolidin-3-yl]sulfamoyl]carbamate

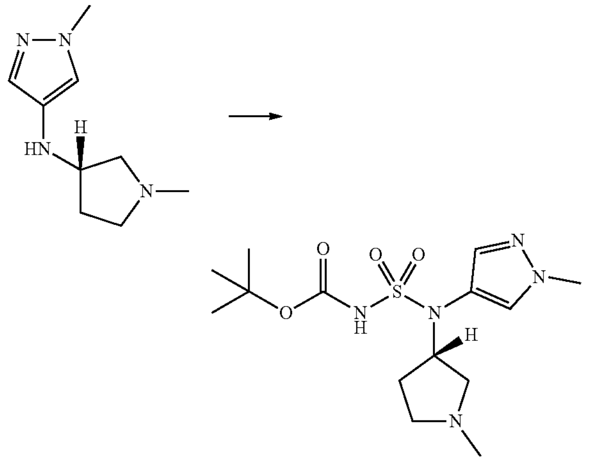

To a solution of 1-methyl-N-[(3S)-1-methylpyrrolidin-3-yl]-1H-pyrazol-4-amine (340 mg, 1.89 mmol) in DCM (5 ml) cooled to 0° C. was added DIPEA (0.99 ml, 5.66 mmol). The RM was stirred for 30 min, then treated with 0.71 M tert-butyl N-chlorosulfonylcarbamate in DCM (2.67 ml, 1.89 mmol). The resulting solution was stirred at 0° C. for 12 h. The solution was concentrated in vacuo and the resulting residue purified by prep-HPLC (column: Phenomenex Luna C18 250×50 mm, 10 μm; mobile phase: [water (0.1% TFA)-ACN]; B: 5-25%, 20 min) to give the title compound as a white solid. Y=49%. $^1H$ NMR (400 MHz, chloroform-d) δ 7.52 (s, 1H), 7.33 (s, 1H), 5.39-5.34 (m, 1H), 3.94-3.83 (m, 3H), 3.79-3.60 (m, 2H), 3.40-3.25 (m, 1H), 2.85-2.75 (m, 4H), 2.50-2.30 (m, 1H), 2.20-1.95 (m, 1H), 1.52 (s, 9H).

Step 4. N-(1-methyl-1H-pyrazol-4-yl)-N-[(3S)-1-methylpyrrolidin-3-yl]aminosulfonamide Hydrochloride

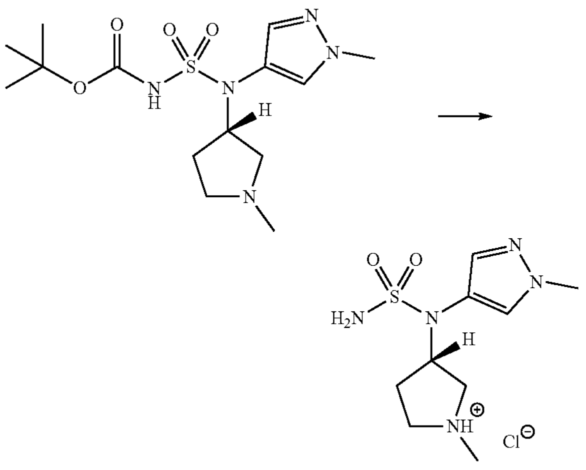

A solution of tert-butyl N-[(1-methyl-1H-pyrazol-4-yl)[(3S)-1-methylpyrrolidin-3-yl]sulfamoyl]carbamate (160 mg, 445 μmol) in 4 M HCl in EtOAc (5 ml) was stirred at rt for 1 h. The solution was concentrated in vacuo to give the title compound as a yellow solid. LCMS (ESI): m/z: $[M+H]^+$=260.0.

Intermediate 69. N-(1-methyl-1H-pyrazol-4-yl)-N-[(3R)-1-methylpyrrolidin-3-yl]aminosulfonamide Hydrochloride

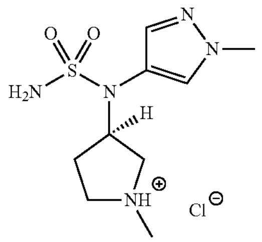 [SMILES: Cn1cc(N([C@@H]2CC[NH+](C)C2)S(N)(=O)=O)cn1 ; [Cl-]]

Prepared using an analogous method to Intermediate 68, but starting with tert-butyl (3R)-3-aminopyrrolidine-1-carboxylate. LCMS (ESI): m/z: $[M+H]^+$=360.2.

Intermediate 70. 4-Isocyanato-5-(propan-2-yl)thiophene-2-carbonitrile

Step 1. 5-Bromo-4-nitrothiophene-2-carbonitrile

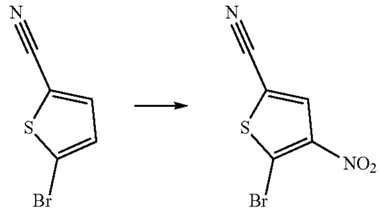 [SMILES: N#Cc1ccc(Br)s1 ; N#Cc1cc([N+](=O)[O-])c(Br)s1]

To a stirred solution of fuming nitric acid (9.0 ml, 200 mmol) and acetic anhydride (17.80 ml, 190 mmol) cooled to 0° C. was added dropwise 5-bromothiophene-2-carbonitrile (1.0 g, 5.32 mmol). The mixture was stirred at 0° C. for 0.5 h, then at 15° C. for 4 h. The RM was poured onto crushed ice and stirred. The resulting mixture was extracted with EtOAc (3×20 ml). The combined organics were washed with brine (20 ml), dried and concentrated under reduced pressure. The resulting oil was purified by column chromatography (silica, 2-4% EtOAc in petrol) to give the title compound as a yellow solid. Y=31%. $^1$H NMR (400 MHz, MeOD) δ 8.30 (s, 1H).

Step 2. 4-Nitro-5-(prop-1-en-2-yl)thiophene-2-carbonitrile

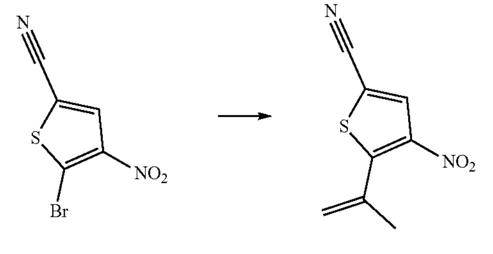

To a solution of 5-bromo-4-nitrothiophene-2-carbonitrile (500 mg, 2.15 mmol) in THF (5 ml) and $H_2O$ (1.25 ml) under $N_2$ was added 2-isopropenyl-4,4,5,5-tetramethyl-1,3,2-dioxaborolane (1.80 g, 10.7 mmol), $Na_2CO_3$ (682 mg, 6.44 mmol) and $Pd(PPh_3)_4$ (50 mg, 42.9 μmol). The RM was heated at 70° C. for 3 h. The RM was diluted with water (10 ml) and brine (5 ml), then extracted with EtOAc (3×20 ml). The combined organic phase was dried over anhydrous $Na_2SO_4$, filtered and the filtrate concentrated under reduced pressure. The resulting oil was purified by column chromatography (silica, 2-4% EtOAc in petrol) to give the title compound as a yellow solid. Y=77%. $^1$H NMR (400 MHz, MeOD) δ 8.27 (s, 1H), 5.50 (s, 1H), 5.38 (s, 1H), 2.16 (s, 3H).

Step 3. 4-Amino-5-(propan-2-yl)thiophene-2-carbonitrile

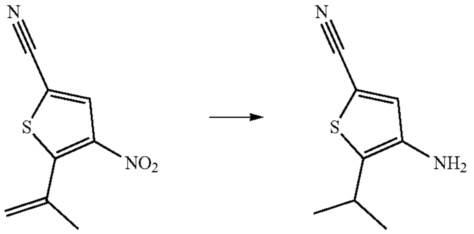

To a solution of 4-nitro-5-(prop-1-en-2-yl)thiophene-2-carbonitrile (160 mg, 0.82 mmol) in MeOH (6 ml) was added 10% Pd/C (50% in water, 160 mg). The suspension was degassed under vacuum and purged with $H_2$ several times. The mixture was stirred under $H_2$ (15 psi) at rt for 12 h. The RM was filtered through Celite and the filtrate concentrated to give the title compound as yellow oil. Y=88%. $^1$H NMR (400 MHz, MeOD) δ 7.16 (s, 1H), 3.28-3.18 (m, 1H), 1.27 (d, J=7 Hz, 6H).

Step 4. 4-Isocyanato-5-(propan-2-yl)thiophene-2-carbonitrile

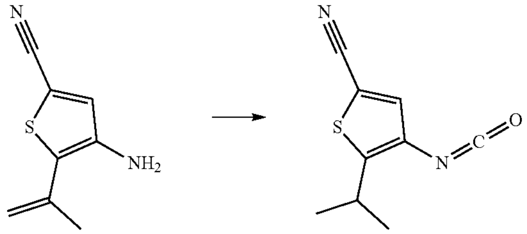

To a solution of 4-amino-5-(propan-2-yl)thiophene-2-carbonitrile (60 mg, 0.36 mmol) in dioxane (1 ml) warmed to 40° C. was added trichloromethyl carbonochloridate (107 mg, 0.54 mmol). The resulting mixture was heated at 70° C. for 1 h. The RM was concentrated under reduced pressure to give the title compound as a yellow oil. This was used in the next step without further purification. LCMS in MeOH (ESI): m/z: $[M+MeOH+H]^+$=225.0.

Example 1. 3-(2,4-Dimethylthiophen-3-yl)-1-[(1-methyl-1H-pyrazol-4-yl)(oxan-4-yl)-sulfamoyl]urea [Compound 1]

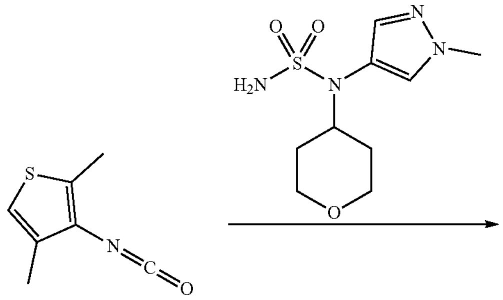

-continued

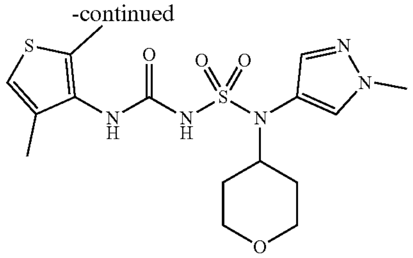

To a solution of 1-methyl-4-[sulfamoyl(tetrahydropyran-4-yl)amino]pyrazole (Intermediate 1, 100 mg, 0.38 mmol) in THF (1 ml) cooled to 0° C. was added NaH (60% suspension in mineral oil, 20 mg, 0.50 mmol). The reaction was then treated with 3-isocyanato-2,4-dimethyl-thiophene (Intermediate 3, 59 mg, 0.38 mmol), maintaining the temperature at 0° C. The solution was allowed to warm to rt and stirred for 1 h. The solution was filtered and the filtrate concentrated under vacuum. The residue was purified by prep-HPLC (column: Waters Xbridge Prep OBD C18 10 μm, 150×40 mm; mobile phase: [water (10 mM $NH_4HCO_3$)-ACN]; B: 1-2 5%, 11 min) to give 3-(2,4-dimethylthiophen-3-yl)-1-[(1-methyl-1H-pyrazol-4-yl)(oxan-4-yl)sulfamoyl]urea as a white solid, isolated as the sodium salt. Y=38%. $^1$H NMR (400 MHz, MeOD) δ 7.67 (s, 1H), 7.42 (s, 1H), 6.75 (s, 1H), 4.38-4.22 (m, 1H), 3.96-3.85 (m, 5H), 3.47 (t, J=11 Hz, 2H), 2.29 (s, 3H), 2.08 (s, 3H), 1.94-1.83 (m, 2H), 1.51-1.34 (m, 2H). LCMS (ESI): m/z: $[M+H]^+$=414.1

Example 2. 3-(2,5-Dimethylthiophen-3-yl)-1-[(1-methyl-1H-pyrazol-4-yl)(oxan-4-yl)sulfamoyl]urea [Compound 2]

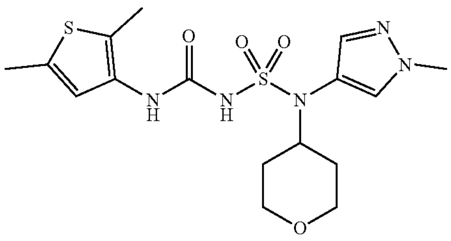

3-(2,5-Dimethylthiophen-3-yl)-1-[(1-methyl-1H-pyrazol-4-yl)(oxan-4-yl)sulfamoyl]urea was prepared following a procedure similar to Example 1 using Intermediate 1 and Intermediate 4, isolated as the sodium salt. $^1$H NMR (400 MHz, MeOD) δ 7.64 (s, 1H), 7.40 (s, 1H), 6.84 (s, 1H), 4.31-4.21 (m, 1H), 3.93-3.89 (m, 2H), 3.85 (s, 3H), 3.47 (t, J=12 Hz, 2H), 2.35 (s, 3H), 2.17 (s, 3H), 1.92-1.85 (m, 2H), 1.49-1.37 (m, 2H). LCMS (ESI): m/z: $[M+H]^+$=414.0.

Example 3. 3-(2-Methyl-1-benzothiophen-3-yl)-1-[(1-methyl-1H-pyrazol-4-yl)(oxan-4-yl)sulfamoyl]urea [Compound 3]

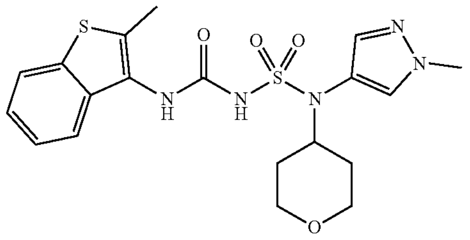 [SMILES: Cc1sc2ccccc2c1NC(=O)NS(=O)(=O)N(c1cnn(C)c1)C1CCOCC1]

3-(2-Methyl-1-benzothiophen-3-yl)-1-[(1-methyl-1H-pyrazol-4-yl)(oxan-4-yl)sulfamoyl]urea was prepared following a procedure similar to Example 1 using Intermediate 1 and Intermediate 5, isolated as the sodium salt. $^1$H NMR (400 MHz, MeOD) δ 7.74 (d, J=8 Hz, 1H), 7.69 (s, 1H), 7.49 (d, J=8 Hz, 1H), 7.44 (s, 1H), 7.39-7.34 (m, 1H), 7.32-7.27 (m, 1H), 4.38-4.28 (m, 1H), 3.92-3.85 (m, 5H), 3.49-3.41 (m, 2H), 2.45 (s, 3H), 1.90-1.82 (m, 2H), 1.50-1.37 (m, 2H). LCMS (ESI): m/z: $[M+H]^+$=450.1.

Example 4. 3-(2,5-Diethylthiophen-3-yl)-1-[(1-methyl-1H-pyrazol-4-yl)(oxan-4-yl)sulfamoyl]urea [Compound 4]

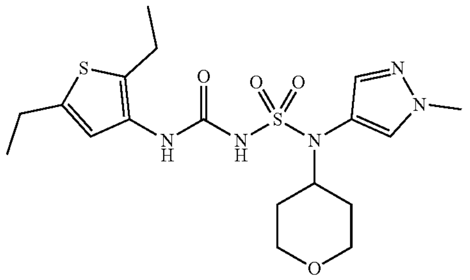 [SMILES: CCc1cc(NC(=O)NS(=O)(=O)N(c2cnn(C)c2)C2CCOCC2)c(CC)s1]

3-(2,5-Diethylthiophen-3-yl)-1-[(1-methyl-1H-pyrazol-4-yl)(oxan-4-yl)sulfamoyl]urea was prepared following a procedure similar to Example 1 using Intermediate 1 and Intermediate 6, isolated as the sodium salt. $^1$H NMR (400 MHz, MeOD) δ 7.70 (s, 1H), 7.41 (s, 1H), 6.88 (s, 1H), 4.40-4.25 (m, 1H), 3.96-3.89 (m, 2H), 3.87 (s, 3H), 3.55-3.42 (m, 2H), 2.75 (q, J=8 Hz, 2H), 2.61 (q, J=8 Hz, 2H), 1.91-1.82 (m, 2H), 1.52-1.39 (m, 2H), 1.26 (t, J=8 Hz, 3H), 1.20 (t, J=8 Hz, 3H). LCMS (ESI): m/z: $[M+H]^+$=442.1.

Example 5. 3-(2,5-Dichlorothiophen-3-yl)-1-[(1-methyl-1H-pyrazol-4-yl)(oxan-4-yl)sulfamoyl]urea [Compound 5]

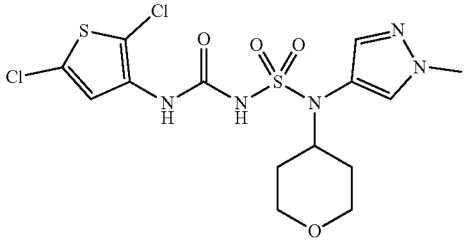 [SMILES: Cn1cc(N(C2CCOCC2)S(=O)(=O)NC(=O)Nc2cc(Cl)sc2Cl)cn1]

3-(2,5-Dichlorothiophen-3-yl)-1-[(1-methyl-1H-pyrazol-4-yl)(oxan-4-yl)sulfamoyl]urea was prepared following a procedure similar to Example 1 using Intermediate 1 and Intermediate 7, isolated as the sodium salt. $^1$H NMR (400 MHz, MeOD) δ 7.66 (s, 1H), 7.50 (s, 1H), 7.40 (s, 1H), 4.33-4.24 (m, 1H), 3.96-3.88 (m, 2H), 3.86 (s, 3H), 3.51-3.44 (m, 2H), 1.92-1.84 (m, 2H), 1.47-1.41 (m, 2H). LCMS (ESI): m/z: $[M+H]^+$ 454.0.

Example 6. 3-[2,5-Bis(propan-2-yl)thiophen-3-yl]-1-[(1-methyl-1H-pyrazol-4-yl)(oxan-4-yl)sulfamoyl] urea [Compound 6]

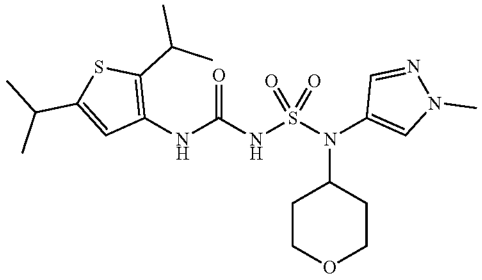 [SMILES: CC(C)c1cc(NC(=O)NS(=O)(=O)N(c2cnn(C)c2)C2CCOCC2)c(C(C)C)s1]

3-[2,5-Bis(propan-2-yl)thiophen-3-yl]-1-[(1-methyl-1H-pyrazol-4-yl)(oxan-4-yl)sulfamoyl]urea was prepared following a procedure similar to Example 1 using Intermediate 1 and Intermediate 8, isolated as the sodium salt. $^1$H NMR (400 MHz, MeOD) δ 7.71 (s, 1H), 7.41 (s, 1H), 6.88 (s, 1H), 4.38-4.27 (m, 1H), 3.94-3.90 (m, 2H), 3.87 (s, 3H), 3.48 (t, J=11 Hz, 2H), 3.13-3.01 (m, 2H), 1.88 (dd, J=2, 12 Hz, 2H), 1.52-1.40 (m, 2H), 1.29 (d, J=7 Hz, 6H), 1.24 (d, J=7 Hz, 6H). LCMS (ESI): m/z: $[M+H]^+$=470.2.

Example 7. 3-(2,4-Diethylthiophen-3-yl)-1-[(1-methyl-1H-pyrazol-4-yl)(oxan-4-yl)sulfamoyl]urea [Compound 7]

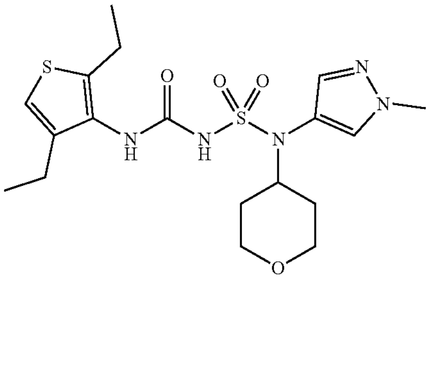 [SMILES: CCc1csc(CC)c1NC(=O)NS(=O)(=O)N(c1cnn(C)c1)C1CCOCC1]

3-(2,4-Diethylthiophen-3-yl)-1-[(1-methyl-1H-pyrazol-4-yl)(oxan-4-yl)sulfamoyl]urea was prepared following a procedure similar to Example 1 using Intermediate 1 and Intermediate 9, isolated as the sodium salt. $^1$H NMR (400 MHz, MeOD) δ 7.71 (s, 1H), 7.42 (s, 1H), 6.84 (s, 1H), 4.35-4.30 (m, 1H), 3.93-3.89 (m, 5H), 3.50-3.43 (m, 2H), 2.72 (q, J=7 Hz, 2H), 2.46 (q, J=7 Hz, 2H), 1.88-1.84 (m, 2H), 1.51-1.41 (m, 2H), 1.28-1.19 (m, 6H). LCMS (ESI): m/z: $[M+H]^+$=442.1.

Example 8. 3-(2,5-Dimethylthiophen-3-yl)-1-[(1-methyl-1H-pyrazol-4-yl)(1-methyl-piperidin-3-yl) sulfamoyl]urea [Compound 8]

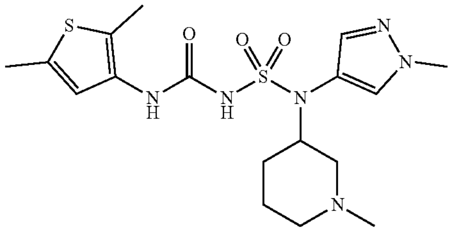

3-(2,5-Dimethylthiophen-3-yl)-1-[(1-methyl-1H-pyrazol-4-yl)(1-methylpiperidin-3-yl)sulfamoyl]urea was prepared following a procedure similar to Example 1 using Intermediate 2 and Intermediate 4, isolated as the sodium salt. $^1$H NMR (400 MHz, MeOD) δ 7.64 (s, 1H), 7.41 (s, 1H), 6.83 (s, 1H), 4.35-4.29 (m, 1H), 3.84 (s, 3H), 3.50 (d, J=11 Hz, 1H), 3.07 (d, J=12 Hz, 1H), 2.59 (s, 3H), 2.45-2.25 (m, 5H), 2.18 (s, 3H), 2.06-1.98 (m, 1H), 1.90-1.85 (m, 1H), 1.80-1.73 (m, 1H), 1.26-1.13 (m, 1H). LCMS (ESI): m/z: $[M+H]^+$=427.0.

Example 9. 3-(2,4-Dimethylthiophen-3-yl)-1-[(1-methyl-1H-pyrazol-4-yl)(1-methyl-piperidin-3-yl) sulfamoyl]urea [Compound 9]

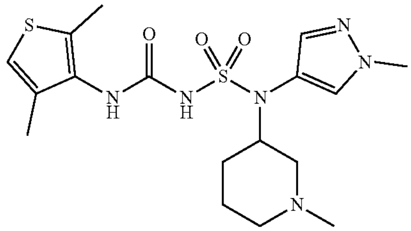 [SMILES: Cc1csc(C)c1NC(=O)NS(=O)(=O)N(c1cnn(C)c1)C1CCCN(C)C1]

3-(2,4-Dimethylthiophen-3-yl)-1-[(1-methyl-1H-pyrazol-4-yl)(1-methylpiperidin-3-yl)sulfamoyl]urea was prepared following a procedure similar to Example 1 using Intermediate 2 and Intermediate 3, isolated as the sodium salt. $^1$H NMR (400 MHz, MeOD) δ 7.65 (s, 1H), 7.42 (s, 1H), 6.74 (s, 1H), 4.39-4.29 (m, 1H), 3.86 (s, 3H), 3.58-3.48 (m, 1H), 3.13-3.03 (m, 1H), 2.61 (s, 3H), 2.45-2.36 (m, 1H), 2.30 (s, 3H), 2.09 (s, 3H), 2.05-1.97 (m, 1H), 1.89-1.85 (m, 1H), 1.77-1.73 (m, 1H), 1.28-1.09 (m, 2H). LCMS (ESI): m/z: $[M+H]^+$=427.0.

Example 10. 3-(3,5-Dimethylthiophen-2-yl)-1-[(1-methyl-1H-pyrazol-4-yl)(1-methyl-piperidin-3-yl) sulfamoyl]urea [Compound 10]

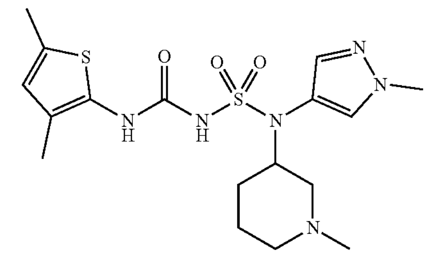 [SMILES: Cc1cc(C)c(NC(=O)NS(=O)(=O)N(c2cnn(C)c2)C2CCCN(C)C2)s1]

3-(3,5-Dimethylthiophen-2-yl)-1-[(1-methyl-1H-pyrazol-4-yl)(1-methylpiperidin-3-yl)sulfamoyl]urea was prepared following a procedure similar to Example 1 using Intermediate 2 and Intermediate 10, isolated as the sodium salt. $^1$H NMR (400 MHz, MeOD) δ 7.65 (s, 1H), 7.42 (s, 1H), 6.74 (s, 1H), 4.39-4.29 (m, 1H), 3.86 (s, 3H), 3.58-3.48 (m, 1H), 3.13-3.03 (m, 1H), 2.61 (s, 3H), 2.45-2.36 (m, 1H), 2.30 (s, 3H), 2.09 (s, 3H), 2.05-1.97 (m, 1H), 1.89-1.85 (m, 1H), 1.77-1.73 (m, 1H), 1.28-1.09 (m, 2H). LCMS (ESI): m/z: $[M+H]^+$=427.0.

Example 11. 3-[2,5-Bis(propan-2-yl)thiophen-3-yl]-1-[(1-methyl-1H-pyrazol-4-yl)(1-methyl-piperidin-3-yl)sulfamoyl]urea [Compound 11]

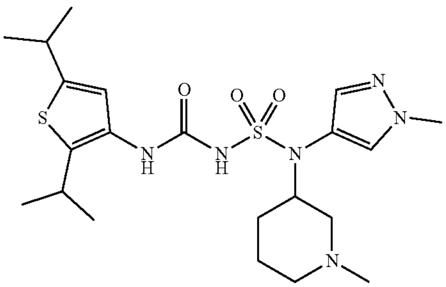 [SMILES: CC(C)c1cc(NC(=O)NS(=O)(=O)N(c2cnn(C)c2)C2CCCN(C)C2)c(C(C)C)s1]

3-[2,5-Bis(propan-2-yl)thiophen-3-yl]-1-[(1-methyl-1H-pyrazol-4-yl)(1-methylpiperidin-3-yl)sulfamoyl]urea was prepared following a procedure similar to Example 1 using Intermediate 2 and Intermediate 8, isolated as the sodium salt. $^1$H NMR (400 MHz, MeOD) δ 7.65 (s, 1H), 7.41 (s, 1H), 6.88 (s, 1H), 4.47-4.32 (m, 1H), 3.84 (s, 3H), 3.61-3.53 (m, 1H), 3.18-2.99 (m, 3H), 2.63 (s, 3H), 2.45-2.33 (m, 2H), 2.09-2.00 (m, 1H), 1.93-1.74 (m, 2H), 1.30-1.17 (m, 13H). LCMS (ESI): m/z: $[M+H]^+$=483.2.

Example 12. 3-(2-Methyl-1-benzothiophen-3-yl)-1-[(1-methyl-1H-pyrazol-4-yl)(1-methyl-piperidin-3-yl)sulfamoyl]urea [Compound 12]

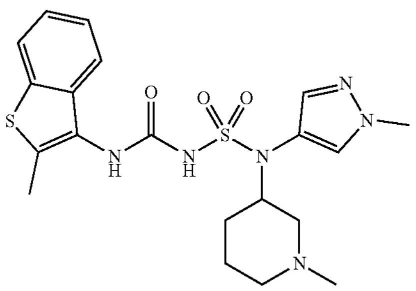 [SMILES: Cc1sc2ccccc2c1NC(=O)NS(=O)(=O)N(c1cnn(C)c1)C1CCCN(C)C1]

3-(2-Methyl-1-benzothiophen-3-yl)-1-[(1-methyl-1H-pyrazol-4-yl)(1-methylpiperidin-3-yl)sulfamoyl]urea was prepared following a procedure similar to Example 1 using Intermediate 2 and Intermediate 5, isolated as the sodium salt. $^1$H NMR (400 MHz, MeOD) δ 7.72 (d, J=8 Hz, 1H), 7.65-7.54 (m, 2H), 7.46-7.40 (br. s, 1H), 7.34 (t, J=7 Hz, 1H), 7.27 (t, J=7 Hz, 1H), 4.45-4.33 (m, 1H), 3.81 (s, 3H), 3.66-3.58 (m, 1H), 3.04-2.96 (m, 1H), 2.60 (s, 3H), 2.46-2.35 (m, 5H), 2.04-1.96 (m, 1H), 1.82-1.69 (m, 2H), 1.24-1.08 (m, 1H). LCMS (ESI): m/z: $[M+H]^+$=463.0.

Example 13. 3-(2,5-Diethylthiophen-3-yl)-1-[(1-methyl-1H-pyrazol-4-yl)(1-methylpiperidin-3-yl) sulfamoyl]urea [Compound 13]

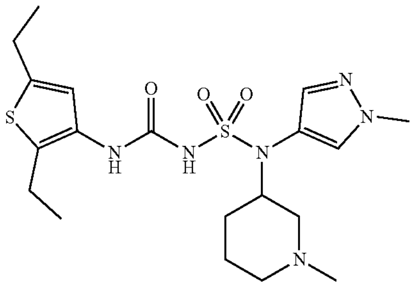 [SMILES: CCc1cc(NC(=O)NS(=O)(=O)N(c2cnn(C)c2)C2CCCN(C)C2)c(CC)s1]

3-(2,5-Diethylthiophen-3-yl)-1-[(1-methyl-1H-pyrazol-4-yl)(1-methylpiperidin-3-yl)sulfamoyl]urea was prepared following a procedure similar to Example 1 using Intermediate 2 and Intermediate 6, isolated as the sodium salt. $^1$H NMR (400 MHz, MeOD) δ 7.65 (s, 1H), 7.41 (s, 1H), 6.88 (s, 1H), 4.41-4.33 (m, 1H), 3.84 (s, 3H), 3.60-3.52 (m, 1H), 3.13-3.05 (m, 1H), 2.74 (q, J=8 Hz, 2H), 2.66-2.59 (m, 5H), 2.47-2.30 (m, 2H), 2.08-2.00 (m, 1H), 1.94-1.72 (m, 2H), 1.29-1.16 (m, 7H). LCMS (ESI): m/z: $[M+H]^+$=455.2.

Example 14. 3-(2,4-Diethylthiophen-3-yl)-1-[(1-methyl-1H-pyrazol-4-yl)(1-methylpiperidin-3-yl)sulfamoyl]urea [Compound 14]

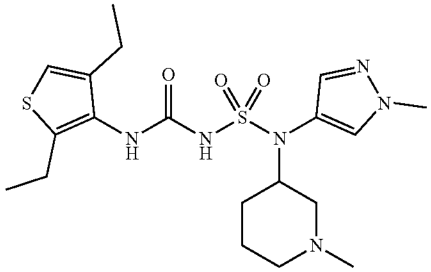 [SMILES: CCc1csc(CC)c1NC(=O)NS(=O)(=O)N(c1cnn(C)c1)C1CCCN(C)C1]

3-(2,4-Diethylthiophen-3-yl)-1-[(1-methyl-1H-pyrazol-4-yl)(1-methylpiperidin-3-yl)sulfamoyl]urea was prepared following a procedure similar to Example 1 using Intermediate 2 and Intermediate 9, isolated as the sodium salt. $^1$H NMR (400 MHz, MeOD) δ 7.65 (s, 1H), 7.42 (s, 1H), 6.80 (s, 1H), 4.38-4.26 (m, 1H), 3.87 (s, 3H), 3.55-3.46 (m, 1H), 3.12-3.00 (m, 1H), 2.73 (q, J=8 Hz, 2H), 2.60 (s, 3H), 2.48 (q, J=8 Hz, 2H), 2.44-2.24 (m, 2H), 2.04-1.95 (m, 1H), 1.92-1.82 (m, 1H), 1.79-1.67 (m, 1H), 1.32-1.10 (m, 7H). LCMS (ESI): m/z: $[M+H]^+$=455.1.

Example 15. 1-[(1-Methyl-1H-pyrazol-4-yl)(1-methylpiperidin-3-yl)sulfamoyl]-3-(2,4,5-trimethylthiophen-3-yl)urea [Compound 15]

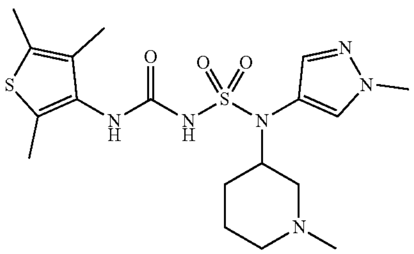 [SMILES: Cc1sc(C)c(NC(=O)NS(=O)(=O)N(c2cnn(C)c2)C2CCCN(C)C2)c1C]

1-[(1-Methyl-1H-pyrazol-4-yl)(1-methylpiperidin-3-yl)sulfamoyl]-3-(2,4,5-trimethylthiophen-3-yl)urea was prepared following a procedure similar to Example 1 using Intermediate 2 and Intermediate 11, isolated as the sodium salt. $^1$H NMR (400 MHz, MeOD) δ 7.65 (s, 1H), 7.42 (s, 1H), 4.38-4.30 (m, 1H), 3.86 (s, 3H), 3.56-3.48 (m, 1H), 3.09-3.01 (m, 1H), 2.59 (s, 3H), 2.38-2.31 (m, 2H), 2.26 (s, 3H), 2.24 (s, 3H), 2.03-1.93 (m, 4H), 1.89-1.72 (m, 2H), 1.26-1.14 (m, 1H). LCMS (ESI): m/z: $[M+H]^+$=441.0.

Example 16. 3-[2,4-Bis(propan-2-yl)thiophen-3-yl]-1-[(1-methyl-1H-pyrazol-4-yl)(1-methyl-piperidin-3-yl)sulfamoyl]urea [Compound 16]

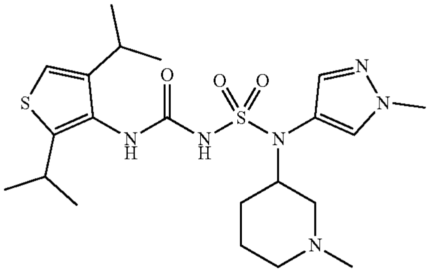 [SMILES: CC(C)c1csc(C(C)C)c1NC(=O)NS(=O)(=O)N(c1cnn(C)c1)C1CCCN(C)C1]

3-[2,4-Bis(propan-2-yl)thiophen-3-yl]-1-[(1-methyl-1H-pyrazol-4-yl)(1-methylpiperidin-3-yl)sulfamoyl]urea was prepared following a procedure similar to Example 1 using Intermediate 2 and Intermediate 12, isolated as the sodium salt. $^1$H NMR (400 MHz, MeOD) δ 7.65 (s, 1H), 7.42 (s, 1H), 6.82 (s, 1H), 4.38-4.30 (m, 1H), 3.87 (s, 3H), 3.53-3.45 (m, 1H), 3.27-3.22 (m, 1H), 3.10-3.02 (m, 1H), 2.89-2.83 (m, 1H), 2.59 (s, 3H), 2.44-2.25 (m, 2H), 2.03-1.95 (m, 1H), 1.91-1.82 (m, 1H), 1.78-1.66 (m, 1H), 1.32-1.16 (m, 13H). LCMS (ESI): m/z: $[M+H]^+$=483.2.

Example 17. 3-(3,4-Dimethylthiophen-2-yl)-1-[(1-methyl-1H-pyrazol-4-yl)(1-methyl-piperidin-3-yl)sulfamoyl]urea [Compound 17]

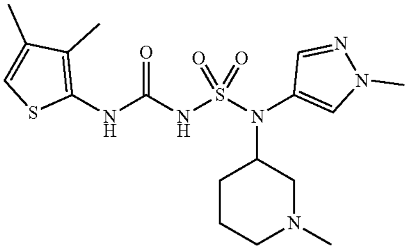 [SMILES: Cc1csc(NC(=O)NS(=O)(=O)N(c2cnn(C)c2)C2CCCN(C)C2)c1C]

3-(3,4-Dimethylthiophen-2-yl)-1-[(1-methyl-1H-pyrazol-4-yl)(1-methylpiperidin-3-yl)sulfamoyl]urea was prepared following a procedure similar to Example 1 using Intermediate 2 and Intermediate 13, isolated as the sodium salt. $^1$H NMR (400 MHz, MeOD) δ 7.60 (s, 1H), 7.40 (s, 1H), 6.51 (s, 1H), 4.37-4.29 (m, 1H), 3.81 (s, 3H), 3.59-3.51 (m, 1H), 3.14-3.06 (m, 1H), 2.62 (s, 3H), 2.45-2.30 (m, 2H), 2.09 (s, 3H), 2.07-2.01 (m, 1H), 1.96 (s, 3H), 1.91-1.74 (m, 2H), 1.27-1.14 (m, 1H). LCMS (ESI): m/z: $[M+H]^+$=427.1.

Example 18. 3-[2,5-Bis(propan-2-yl)thiophen-3-yl]-1-{[2-(dimethylamino)ethyl](1-methyl-1H-pyrazol-4-yl)sulfamoyl}urea [Compound 18]

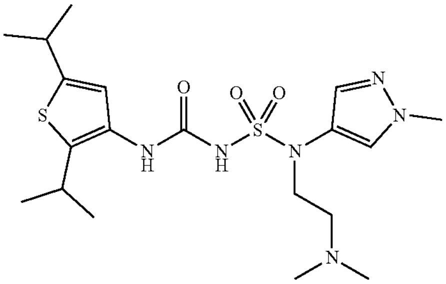 [SMILES: CC(C)c1cc(NC(=O)NS(=O)(=O)N(CCN(C)C)c2cnn(C)c2)c(C(C)C)s1]

To a solution of 4-[2-(dimethylamino) ethyl-sulfamoyl-amino]-1-methyl-pyrazole hydrochloride (100 mg, 0.35 mmol) (Intermediate 20) in THF (3 ml) at 0° C. was added NaOH (42 mg, 1.06 mmol) and the mixture was stirred for 30 min, then 3-isocyanato-2,5-diisopropyl-thiophene (74 mg, 0.35 mmol) (Intermediate 8) was added and the resulting mixture was stirred at rt for 30 min. The solution was concentrated under reduced pressure and the resulting residue purified by prep-HPLC (column: Waters Xbridge BEH C18 100×30 mm, 10 μm; mobile phase: [water (10 mM $NH_4HCO_3$)-ACN]; B: 25-55%, 10 min) to give the title compound as a white solid, isolated as the sodium salt. Y=18%. $^{1}$H NMR (400 MHz, MeOD) δ 7.69 (s, 1H), 7.51 (s, 1H), 6.86 (s, 1H), 3.92-3.84 (m, 2H), 3.84 (s, 3H), 3.25-3.13 (m, 3H), 3.10-3.00 (m, 1H), 2.95 (s, 6H), 1.30-1.20 (m, 12H). LCMS (ESI): m/z: $[M+H]^{+}$=457.2.

Example 19. 3-(2,5-Diethylthiophen-3-yl)-1-{[2-(dimethylamino)ethyl](1-methyl-1H-pyrazol-4-yl) sulfamoyl}urea [Compound 19]

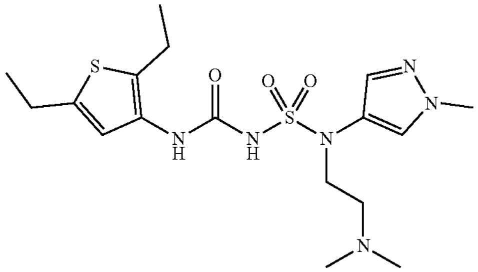 [SMILES: CCc1cc(NC(=O)NS(=O)(=O)N(CCN(C)C)c2cnn(C)c2)c(CC)s1]

3-(2,5-Diethylthiophen-3-yl)-1-{[2-(dimethylamino)ethyl](1-methyl-1H-pyrazol-4-yl)sulfamoyl}urea was prepared following a procedure similar to Example 18 using Intermediate 6 and Intermediate 20, isolated as the sodium salt. $^{1}$H NMR (400 MHz, MeOD) δ 7.69 (s, 1H), 7.51 (s, 1H), 6.85 (s, 1H), 3.92 (t, J=5 Hz, 2H), 3.84 (s, 3H), 3.31 (t, J=5 Hz, 2H), 2.95 (s, 6H), 2.73 (q, J=7 Hz, 2H), 2.64 (q, J=7 Hz, 2H), 1.27-1.18 (m, 6H). LCMS (ESI): m/z: $[M+H]^{+}$=429.2.

Example 20. 3-(2,5-Diethylfuran-3-yl)-1-[(1-methyl-1H-pyrazol-4-yl)(1-methylpiperidin-3-yl) sulfamoyl]urea [Compound 28]

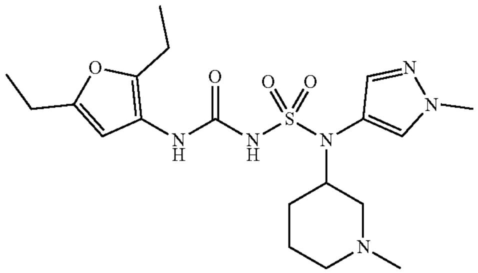 [SMILES: CCc1cc(NC(=O)NS(=O)(=O)N(c2cnn(C)c2)C2CCCN(C)C2)c(CC)o1]

3-(2,5-Diethylfuran-3-yl)-1-[(1-methyl-1H-pyrazol-4-yl)(1-methylpiperidin-3-yl)sulfamoyl]urea was prepared following a procedure similar to Example 18 using Intermediate 2 and Intermediate 26, isolated as the sodium salt. $^{1}$H NMR (400 MHz, MeOD) δ 7.64 (s, 1H), 7.40 (s, 1H), 6.09 (s, 1H), 4.35-4.28 (m, 1H), 3.86 (s, 3H), 3.52-3.49 (m, 1H), 3.10-3.08 (m, 1H), 2.63-2.59 (m, 3H), 2.59-2.50 (m, 4H), 2.45-2.27 (m, 2H), 2.07-1.97 (m, 1H), 1.93-1.69 (m, 2H), 1.36-1.12 (m, 7H). LCMS (ESI): m/z: $[M+H]^{+}$=439.2.

Example 21. 3-(3,5-Diethylthiophen-2-yl)-1-[(1-methyl-1H-pyrazol-4-yl)(1-methylpiperidin-3-yl) sulfamoyl]urea [Compound 29]

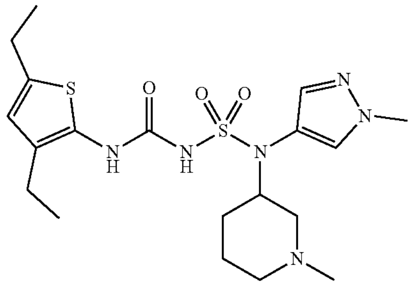 [SMILES: CCc1cc(CC)c(NC(=O)NS(=O)(=O)N(c2cnn(C)c2)C2CCCN(C)C2)s1]

3-(3,5-diethylthiophen-2-yl)-1-[(1-methyl-1H-pyrazol-4-yl)(1-methylpiperidin-3-yl)sulfamoyl]urea was prepared following a procedure similar to Example 1 using Intermediate 2 and Intermediate 21, isolated as the sodium salt. $^{1}$H NMR (400 MHz, MeOD) δ 7.63 (s, 1H), 7.41 (s, 1H), 6.46 (s, 1H), 4.46-4.39 (m, 1H), 3.84 (s, 3H), 3.69-3.65 (m 1H), 3.29-3.21 (m, 1H), 2.73-2.68 (m, 5H), 2.55-2.52 (m, 2H), 2.44-2.38 (m, 2H), 2.09-2.06 (m, 1H), 1.96-1.80 (m, 2H), 1.27-1.22 (m, 4H), 1.13 (t, J=7 Hz, 3H). LCMS (ESI): m/z: $[M+H]^{+}$=455.2.

Example 22. 3-(2,5-Diethyl-1,3-thiazol-4-yl)-1-[(1-methyl-1H-pyrazol-4-yl)(1-methyl-piperidin-3-yl) sulfamoyl]urea [Compound 31]

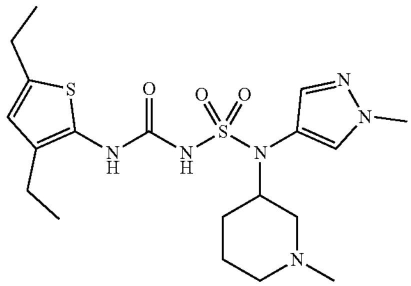 [SMILES: CCc1cc(CC)c(NC(=O)NS(=O)(=O)N(c2cnn(C)c2)C2CCCN(C)C2)s1]

3-(2,5-Diethyl-1,3-thiazol-4-yl)-1-[(1-methyl-1H-pyrazol-4-yl)(1-methylpiperidin-3-yl)sulfamoyl]urea was prepared following a procedure similar to Example 1 using Intermediate 2 and Intermediate 27, isolated as the sodium salt. $^{1}$H NMR (400 MHz, MeOD) δ 7.70 (s, 1H), 7.45 (s, 1H), 4.40-4.32 (m, 1H), 3.87 (s, 3H), 3.57-3.55 (m, 1H), 3.14-3.12 (m, 1H), 2.96-2.89 (m, 2H), 2.76-2.70 (m 2H), 2.67 (s, 3H), 2.50-2.40 (m, 2H), 2.04-2.02 (m, 1H), 1.94-1.86 (m, 1H), 1.78-1.74 (m, 1H), 1.33 (t, J=7 Hz, 3H), 1.27-1.23 (m, 4H). LCMS (ESI): m/z: $[M+H]^{+}$=456.1.

Example 23. 1-[(1-Methyl-1H-pyrazol-4-yl)(1-methylpiperidin-3-yl)sulfamoyl]-3-{2-methyl-4H,5H,6H-cyclopenta[b]thiophen-3-yl}urea [Compound 32]

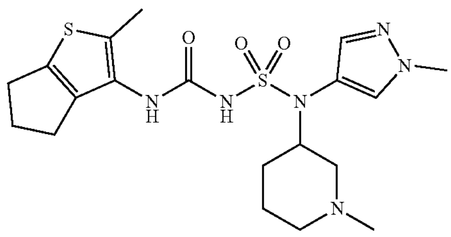 [SMILES: Cc1sc2c(c1NC(=O)NS(=O)(=O)N(c1cnn(C)c1)C1CCCN(C)C1)CCC2]

1-[(1-Methyl-1H-pyrazol-4-yl)(1-methylpiperidin-3-yl)sulfamoyl]-3-{2-methyl-4H,5H,6H-cyclopenta[b]thiophen-3-yl}urea was prepared following a procedure similar to Example 1 using Intermediate 2 and Intermediate 28, isolated as the sodium salt. $^1$H NMR (400 MHz, MeOD) δ 7.64 (s, 1H), 7.41 (s, 1H), 4.40-4.38 (m, 1H), 3.84 (s, 3H), 3.56-3.54 (m, 1H), 3.06-3.03 (m, 1H), 2.87-2.73 (m, 2H), 2.74-2.66 (m, 2H), 2.61 (s, 3H), 2.45-2.39 (m, 4H), 2.25 (s, 3H), 2.03-2.01 (m, 1H), 1.91-1.70 (m, 2H), 1.20-1.18 (m, 1H). LCMS (ESI): m/z: $[M+H]^+$=453.1.

Example 24. 3-[5-Cyclopropyl-2-(propan-2-yl)thiophen-3-yl]-1-[(1-methyl-1H-pyrazol-4-yl)(1-methylpiperidin-3-yl)sulfamoyl]urea [Compound 37]

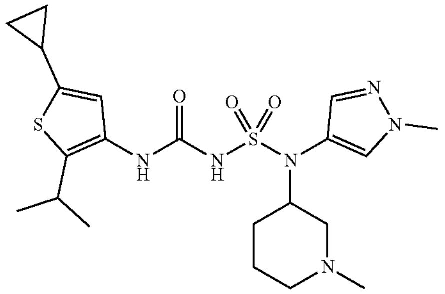 [SMILES: CC(C)c1sc(C2CC2)cc1NC(=O)NS(=O)(=O)N(c1cnn(C)c1)C1CCCN(C)C1]

3-[5-Cyclopropyl-2-(propan-2-yl)thiophen-3-yl]-1-[(1-methyl-1H-pyrazol-4-yl)(1-methylpiperidin-3-yl)sulfamoyl]urea was prepared following a procedure similar to Example 18 using Intermediate 2 and Intermediate 29, isolated as the sodium salt. $^1$H NMR (400 MHz, MeOD) δ 7.64 (s, 1H), 7.41 (s, 1H), 6.84 (s, 1H), 4.40-4.32 (m, 1H), 3.84 (s, 3H), 3.60-3.50 (m, 1H), 3.15-3.05 (m, 2H), 2.63 (s, 3H), 2.45-2.34 (m, 2H), 2.05-1.94 (m, 2H), 1.90-1.75 (m, 2H), 1.25-1.15 (m, 7H), 0.95-0.90 (m, 2H), 0.66-0.62 (m, 2H). LCMS (ESI): m/z: $[M+H]^+$=481.3.

Example 25. 3-[2-Cyclopropyl-5-(propan-2-yl)thiophen-3-yl]-1-[(1-methyl-1H-pyrazol-4-yl)(1-methylpiperidin-3-yl)sulfamoyl]urea [Compound 38]

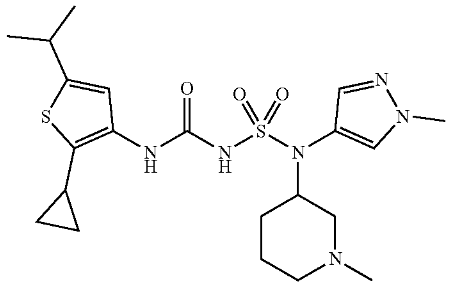 [SMILES: CC(C)c1cc(NC(=O)NS(=O)(=O)N(c2cnn(C)c2)C2CCCN(C)C2)c(C2CC2)s1]

3-[2-Cyclopropyl-5-(propan-2-yl)thiophen-3-yl]-1-[(1-methyl-1H-pyrazol-4-yl)(1-methylpiperidin-3-yl)sulfamoyl]urea was prepared following a procedure similar to Example 18 using Intermediate 2 and Intermediate 30, isolated as the sodium salt. $^1$H NMR (400 MHz, MeOD) δ 7.65 (s, 1H), 7.42 (s, 1H), 7.06 (s, 1H), 4.37-4.30 (m, 1H), 3.83 (s, 3H), 3.59-3.47 (m, 1H), 3.18-2.97 (m, 2H), 2.62 (s, 3H), 2.48-2.25 (m, 2H), 2.11-1.98 (m, 1H), 1.93-1.85 (m, 1H), 1.84-1.70 (m, 2H), 1.27-1.16 (m, 7H), 0.96-0.88 (m, 2H), 0.59-0.51 (m, 2H). LCMS (ESI): m/z: $[M+H]^+$=481.2.

Example 26. 3-[2,5-Bis(propan-2-yl)thiophen-3-yl]-1-[(1-methyl-1H-pyrazol-4-yl)(1-methyl-piperidin-4-yl)sulfamoyl]urea [Compound 43]

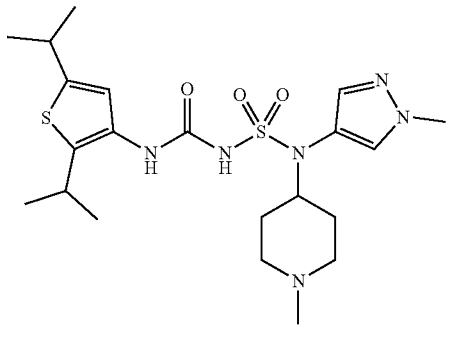 [SMILES: CC(C)c1cc(NC(=O)NS(=O)(=O)N(c2cnn(C)c2)C2CCN(C)CC2)c(C(C)C)s1]

3-(3,5-Diethylthiophen-2-yl)-1-[(1-methyl-1H-pyrazol-4-yl)(1-methylpiperidin-3-yl)sulfamoyl]urea was prepared following a procedure similar to Example 18 using Intermediate 8 and Intermediate 22, isolated as the sodium salt. $^1$H NMR (400 MHz, MeOD) δ 7.66 (s, 1H), 7.41 (s, 1H), 6.89 (s, 1H), 4.27-4.15 (m, 1H), 3.84 (s, 3H), 3.19 (d, J=12 Hz, 2H), 3.14-3.01 (m, 2H), 2.69 (t, J=12 Hz, 2H), 2.52 (s, 3H), 2.09 (d, J=12 Hz, 2H), 1.60-1.50 (m, 2H), 1.30-1.26 (m, 6H), 1.25-1.21 (m, 6H). LCMS (ESI): m/z: $[M+H]^+$=483.2.

Example 27. 3-[2-Chloro-5-(propan-2-yl)thiophen-3-yl]-1-[(1-methyl-1H-pyrazol-4-yl)(1-methylpiperidin-3-yl)sulfamoyl]urea [Compound 50]

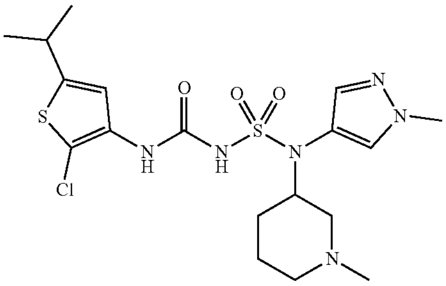 [SMILES: CC(C)c1cc(NC(=O)NS(=O)(=O)N(c2cnn(C)c2)C2CCCN(C)C2)c(Cl)s1]

3-[2-Chloro-5-(propan-2-yl)thiophen-3-yl]-1-[(1-methyl-1H-pyrazol-4-yl)(1-methylpiperidin-3-yl)sulfamoyl]urea was prepared following a procedure similar to Example 18 using Intermediate 2 and Intermediate 31, isolated as the sodium salt. $^1$H NMR (400 MHz, MeOD) δ 7.64 (s, 1H), 7.42 (s, 1H), 7.26 (s, 1H), 4.39-4.32 (m, 1H), 3.84 (s, 3H), 3.65-3.60 (m, 1H), 3.23-3.18 (m, 1H), 3.12-3.05 (m, 1H), 2.72 (s, 3H), 2.55-2.46 (m, 2H), 2.11-1.99 (m, 1H), 1.98-1.89 (m, 1H), 1.87-1.74 (m, 1H), 1.30-1.23 (m, 7H). LCMS (ESI): m/z: $[M+H]^+$=475.2.

Example 28. 3-[3,5-Bis(propan-2-yl)thiophen-2-yl]-1-[(1-methyl-1H-pyrazol-4-yl)(1-methyl-piperidin-3-yl)sulfamoyl]urea [Compound 52]

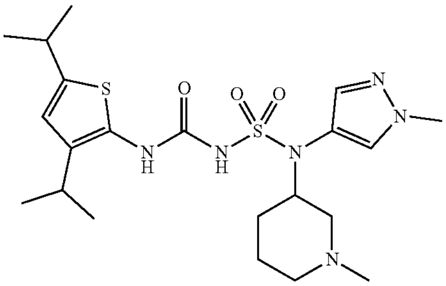 [SMILES: CC(C)c1cc(C(C)C)c(NC(=O)NS(=O)(=O)N(c2cnn(C)c2)C2CCCN(C)C2)s1]

3-[3,5-Bis(propan-2-yl)thiophen-2-yl]-1-[(1-methyl-1H-pyrazol-4-yl)(1-methylpiperidin-3-yl)sulfamoyl]urea was prepared following a procedure similar to Example 1 using Intermediate 2 and Intermediate 23, isolated as the sodium salt. $^1$H NMR (400 MHz, MeOD) δ 7.62 (s, 1H), 7.41 (s, 1H), 6.53 (s, 1H), 4.45-4.35 (m, 1H), 3.84 (s, 3H), 3.70-3.60 (m, 1H), 3.25-3.15 (m, 1H), 3.06-3.01 (m, 1H), 2.88-2.84 (m, 1H), 2.71 (s, 3H), 2.60-2.45 (m, 2H), 2.07-2.01 (m, 1H), 1.91-1.81 (m, 2H), 1.29-1.25 (m, 7H), 1.18-1.14 (m, 6H). LCMS (ESI): m/z: $[M+H]^+$=483.1.

Example 29. 3-[2,5-Bis(propan-2-yl)thiophen-3-yl]-1-{[(2S,4R)-4-fluoro-1-methyl-pyrrolidin-2-yl]methyl}(1-methyl-1H-pyrazol-4-yl)sulfamoyl)urea [Compound 53]

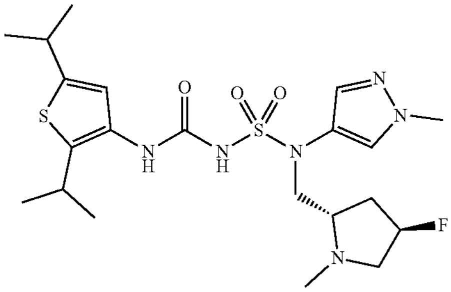 [SMILES: CC(C)c1cc(NC(=O)NS(=O)(=O)N(C[C@@H]2C[C@@H](F)CN2C)c2cnn(C)c2)c(C(C)C)s1]

3-[2,5-Bis(propan-2-yl)thiophen-3-yl]-1-({[(2 S,4R)-4-fluoro-1-methylpyrrolidin-2-yl]methyl} (1-methyl-1H-pyrazol-4-yl)sulfamoyl)urea was prepared following a procedure similar to Example 1 using Intermediate 8 and Intermediate 24, isolated as the sodium salt. $^1$H NMR (400 MHz, MeOD) δ 7.68 (s, 1H), 7.50 (s, 1H), 6.84 (s, 1H), 5.42-5.20 (m, 1H), 4.35-4.25 (m, 1H), 4.20-4.04 (m, 1H), 3.84 (s, 3H), 3.80-3.79 (m, 1H), 3.75-3.65 (m, 1H), 3.48-3.35 (m, 1H), 3.24-3.15 (m, 1H), 3.09-3.03 (m, 1H), 3.01 (s, 3H), 2.35-2.13 (m, 2H), 1.28 (d, J=7 Hz, 6H), 1.23 (d, J=7 Hz, 6H). LCMS (ESI): m/z: $[M+H]^+$=501.1.

Example 30. 3-[2,5-Bis(propan-2-yl)thiophen-3-yl]-1-[(1-methyl-1H-pyrazol-4-yl)[(3R)-1-methylpiperidin-3-yl]sulfamoyl]urea [Compound 54]

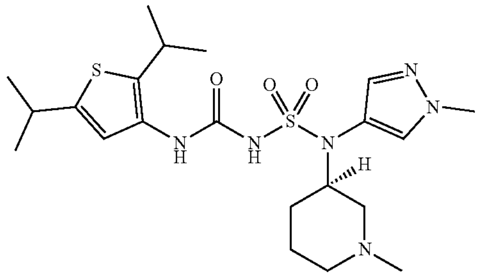 [SMILES: CC(C)c1cc(NC(=O)NS(=O)(=O)N(c2cnn(C)c2)[C@@H]2CCCN(C)C2)c(C(C)C)s1]

3-[2,5-Bis(propan-2-yl)thiophen-3-yl]-1-[(1-methyl-1H-pyrazol-4-yl)[(3R)-1-methylpiperidin-3-yl]sulfamoyl]urea was prepared following a procedure similar to Example 18 using Intermediate 8 and Intermediate 32, isolated as the sodium salt. $^1$H NMR (400 MHz, MeOD) δ 7.65 (s, 1H), 7.41 (s, 1H), 6.89 (s, 1H), 4.54-4.32 (m, 1H), 3.84 (s, 3H), 3.69-3.55 (m, 1H), 3.24-2.99 (m, 3H), 2.65 (s, 3H), 2.53-2.25 (m, 2H), 2.14-1.99 (m, 1H), 1.96-1.75 (m, 2H), 1.35-1.06 (m, 13H). LCMS (ESI): m/z: $[M+H]^+$=483.2.

Example 31. 3-[2,5-Bis(propan-2-yl)thiophen-3-yl]-1-{[(3R)-1-methylpiperidin-3-yl][1-(propan-2-yl)-1H-pyrazol-4-yl]sulfamoyl}urea [Compound 55]

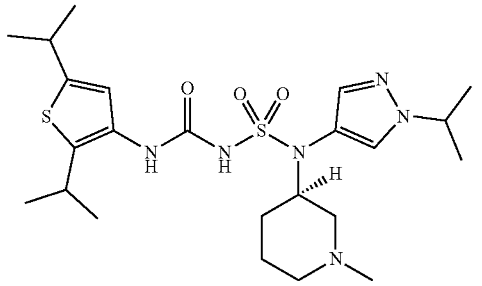 [SMILES: CC(C)c1cc(NC(=O)NS(=O)(=O)N(c2cnn(C(C)C)c2)[C@@H]2CCCN(C)C2)c(C(C)C)s1]

3-[2,5-Bis(propan-2-yl)thiophen-3-yl]-1-{[(3R)-1-methylpiperidin-3-yl][1-(propan-2-yl)-1H-pyrazol-4-yl]sulfamoyl}urea was prepared following a procedure similar to Example 18 using Intermediate 8 and Intermediate 25, isolated as the sodium salt. $^1$H NMR (400 MHz, MeOD) δ 7.69 (s, 1H), 7.43 (s, 1H), 6.92 (s, 1H), 4.52-4.33 (m, 2H), 3.60-3.50 (m, 1H), 3.19-2.99 (m, 3H), 2.63 (s, 3H), 2.48-2.31 (m, 2H), 2.10-2.02 (m, 1H), 1.94-1.77 (m, 2H), 1.50-1.40 (m, 6H), 1.31-1.15 (m, 13H). LCMS (ESI): m/z: $[M+H]^+$=511.2.

Example 32. 3-[2,5-Bis(propan-2-yl)thiophen-3-yl]-1-[(1-methyl-1H-pyrazol-4-yl)[(3S)-1-methylpiperidin-3-yl]sulfamoyl]urea [Compound 56]

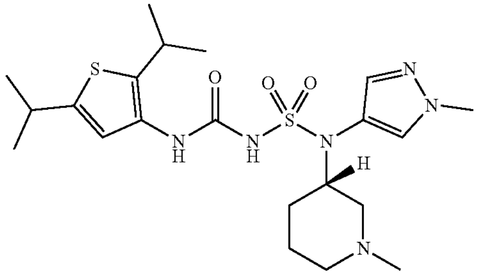 [SMILES: CC(C)c1cc(NC(=O)NS(=O)(=O)N(c2cnn(C)c2)[C@H]2CCCN(C)C2)c(C(C)C)s1]

3-[2,5-Bis(propan-2-yl)thiophen-3-yl]-1-[(1-methyl-1H-pyrazol-4-yl)[(3S)-1-methylpiperidin-3-yl]sulfamoyl]urea was prepared following a procedure similar to Example 18 using Intermediate 8 and Intermediate 33, isolated as the sodium salt. $^1$H NMR (400 MHz, MeOD) δ 7.64 (s, 1H), 7.41 (s, 1H), 6.89 (s, 1H), 4.37-4.28 (m, 1H), 3.84 (s, 3H), 3.55-3.44 (m, 1H), 3.18-3.00 (m, 3H), 2.60 (s, 3H), 2.45-2.25 (m, 2H), 2.05-2.00 (m, 1H), 1.94-1.69 (m, 2H), 1.31-1.14 (m, 13H). LCMS (ESI): m/z: $[M+H]^+$=483.2.

Example 33. 1-[(1-Methyl-1H-pyrazol-4-yl)[(3R)-1-methylpiperidin-3-yl]sulfamoyl]-3-[2-methyl-5-(propan-2-yl)thiophen-3-yl]urea [Compound 57]

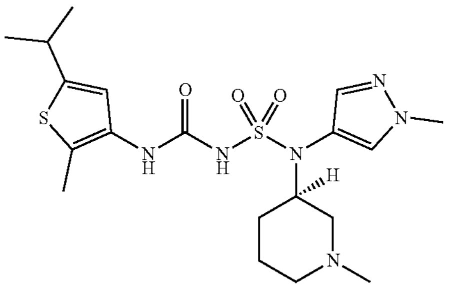 [SMILES: Cc1sc(C(C)C)cc1NC(=O)NS(=O)(=O)N(c1cnn(C)c1)[C@@H]1CCCN(C)C1]

1-[(1-Methyl-1H-pyrazol-4-yl)[(3R)-1-methylpiperidin-3-yl]sulfamoyl]-3-[2-methyl-5-(propan-2-yl)thiophen-3-yl]urea was prepared following a procedure similar to Example 18 using Intermediate 32 and Intermediate 34, isolated as the sodium salt. $^1$H NMR (400 MHz, MeOD) δ 7.72 (s, 1H), 7.43 (s, 1H), 7.40 (s, 1H), 7.02 (s, 1H), 4.43-4.37 (m, 1H), 3.85 (s, 3H), 3.73-3.70 (m, 1H), 3.37-3.24 (m, 1H), 3.07-3.02 (m, 1H), 2.56 (s, 3H), 2.18 (s, 3H), 2.16-2.00 (m, 4H), 1.87-1.83 (m, 1H), 1.28 (d, J=7 Hz, 6H), 1.26-1.22 (m, 1H). LCMS (ESI): m/z: $[M+H]^+$=455.1.

Example 34. 3-[2-Ethyl-5-(propan-2-yl)thiophen-3-yl]-1-[(1-methyl-1H-pyrazol-4-yl)[(3R)-1-methylpiperidin-3-yl]sulfamoyl]urea [Compound 58]

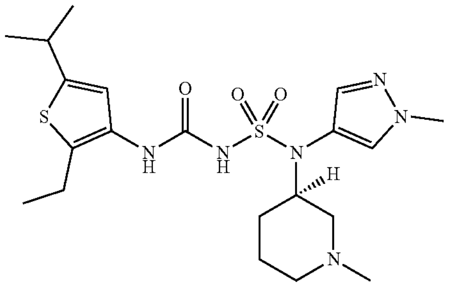 [SMILES: CCc1sc(C(C)C)cc1NC(=O)NS(=O)(=O)N(c1cnn(C)c1)[C@@H]1CCCN(C)C1]

3-[2-Ethyl-5-(propan-2-yl)thiophen-3-yl]-1-[(1-methyl-1H-pyrazol-4-yl)[(3R)-1-methylpiperidin-3-yl]sulfamoyl]urea was prepared following a procedure similar to Example 18 using Intermediate 32 and Intermediate 35, isolated as the sodium salt. $^1$H NMR (400 MHz, MeOD) δ 7.65 (s, 1H), 7.41 (s, 1H), 6.89 (s, 1H), 4.37-4.29 (m, 1H), 3.85 (s, 3H), 3.53-3.48 (m, 1H), 3.13-3.00 (m, 2H), 2.67-2.59 (m, 5H), 2.45-2.31 (m, 2H), 2.04-2.01 (m, 1H), 1.90-1.87 (m, 1H), 1.80-1.71 (m, 1H), 1.28 (d, J=7 Hz, 6H), 1.25-1.15 (m, 4H). LCMS (ESI): m/z: $[M+H]^+$=469.1.

Example 35. 3-[2,5-Bis(propan-2-yl)thiophen-3-yl]-1-[(1-cyclopropyl-1H-pyrazol-4-yl)-[(3R)-1-methylpiperidin-3-yl]sulfamoyl]urea [Compound 59]

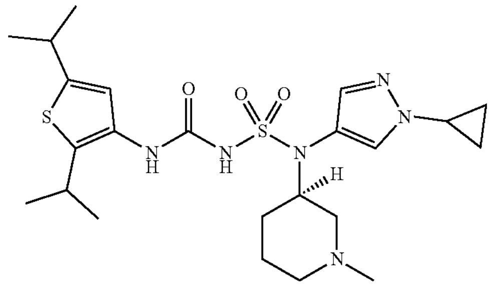 [SMILES: CC(C)c1cc(NC(=O)NS(=O)(=O)N(c2cnn(C3CC3)c2)[C@@H]2CCCN(C)C2)c(C(C)C)s1]

3-[2,5-Bis(propan-2-yl)thiophen-3-yl]-1-[(1-cyclopropyl-1H-pyrazol-4-yl)[(3R)-1-methylpiperidin-3-yl]sulfamoyl]urea was prepared following a procedure similar to Example 18 using Intermediate 8 and Intermediate 36, isolated as the sodium salt. $^1$H NMR (400 MHz, MeOD) δ 7.70 (s, 1H), 7.41 (s, 1H), 6.90 (s, 1H), 4.35-4.25 (m, 1H), 3.65-3.43 (m, 2H), 3.18-2.99 (m, 3H), 2.63 (s, 3H), 2.48-2.26 (m, 2H), 2.07-1.96 (m, 1H), 1.94-1.83 (m, 1H), 1.81-1.67 (m, 1H), 1.30-1.11 (m, 13H), 1.09-0.94 (m, 4H). LCMS (ESI): m/z: $[M+H]^+$=509.3.

Example 36. 3-[5-Chloro-2-(propan-2-yl)thiophen-3-yl]-1-[(1-methyl-1H-pyrazol-4-yl)-[(3R)-1-methylpiperidin-3-yl]sulfamoyl]urea [Compound 60]

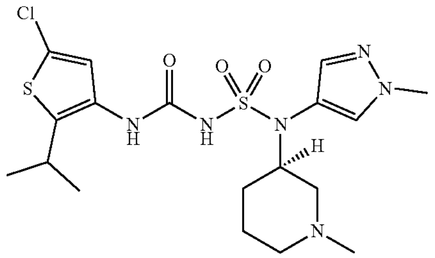 [SMILES: CC(C)c1sc(Cl)cc1NC(=O)NS(=O)(=O)N(c1cnn(C)c1)[C@@H]1CCCN(C)C1]

3-[5-Chloro-2-(propan-2-yl)thiophen-3-yl]-1-[(1-methyl-1H-pyrazol-4-yl)[(3R)-1-methyl-piperidin-3-yl]sulfamoyl]urea was prepared following a procedure similar to Example 18 using Intermediate 32 and Intermediate 37, isolated as the sodium salt. $^1$H NMR (400 MHz, MeOD) δ 7.64 (s, 1H), 7.40 (s, 1H), 7.10 (s, 1H), 4.36-4.33 (m, 1H), 3.84 (s, 3H), 3.63-3.59 (m, 1H), 3.19-3.12 (m, 2H), 2.71 (s, 3H), 2.55-2.45 (m, 2H), 2.06-2.02 (m, 1H), 1.96-1.89 (m, 1H), 1.81-1.76 (m, 1H) 1.30-1.20 (m, 7H). LCMS: m/z: $[M+H]^+$=475.2.

Example 37. 3-[5-Ethyl-2-(propan-2-yl)thiophen-3-yl]-1-[(1-methyl-1H-pyrazol-4-yl)[(3R)-1-methylpiperidin-3-yl]sulfamoyl]urea [Compound 61]

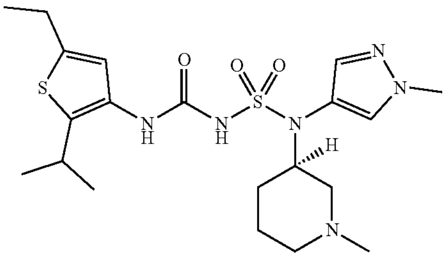 [SMILES: CCc1cc(NC(=O)NS(=O)(=O)N(c2cnn(C)c2)[C@@H]2CCCN(C)C2)c(C(C)C)s1]

3-[5-Ethyl-2-(propan-2-yl)thiophen-3-yl]-1-[(1-methyl-1H-pyrazol-4-yl)[(3R)-1-methylpiperidin-3-yl]sulfamoyl]urea was prepared following a procedure similar to Example 18 using Intermediate 32 and Intermediate 38, isolated as the sodium salt. $^1$H NMR (400 MHz, MeOD) δ 7.65 (s, 1H), 7.41 (s, 1H), 6.87 (s, 1H), 4.38-4.27 (m, 1H), 3.85 (s, 3H), 3.55-3.46 (m, 1H), 3.16-3.03 (m, 2H), 2.78-2.71 (m, 2H), 2.61 (s, 3H), 2.46-2.25 (m, 2H), 2.07-1.97 (m, 1H), 1.94-1.84 (m, 1H), 1.83-1.67 (m, 1H), 1.33-1.13 (m, 10H). LCMS: m/z: $[M+H]^+$=469.2.

Example 38. 1-(2,5-Diethylfuran-3-yl)-3-({[(2S,4R)-4-fluoro-1-methylpyrrolidin-2-yl]methyl}(1-methyl-1H-pyrazol-4-yl)sulfamoyl)urea [Compound 62]

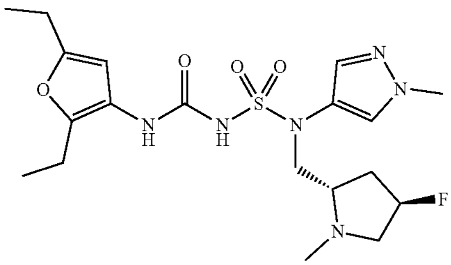 [SMILES: CCc1cc(NC(=O)NS(=O)(=O)N(C[C@@H]2C[C@@H](F)CN2C)c2cnn(C)c2)c(CC)o1]

1-(2,5-Diethylfuran-3-yl)-3-({[(2S,4R)-4-fluoro-1-methylpyrrolidin-2-yl]methyl} (1-methyl-1H-pyrazol-4-yl)sulfamoyl)urea was prepared following a procedure similar to Example 18 using Intermediate 26 and Intermediate 39, isolated as the sodium salt. $^1$H NMR (400 MHz, MeOD) δ 7.66 (s, 1H), 7.49 (s, 1H), 6.10 (s, 1H), 5.39-5.25 (m, 1H), 4.35-4.25 (m, 1H), 4.20-4.08 (m, 1H), 3.84 (s, 3H), 3.79-3.74 (m, 1H), 3.72-3.67 (m, 1H), 3.46-3.37 (m, 1H), 3.02 (s, 3H), 2.58-2.52 (m, 4H), 2.31-2.16 (m, 2H), 1.21-1.15 (m, 6H). LCMS: m/z: $[M+H]^+$=457.1.

Example 39. 3-(2,5-Diethylfuran-3-yl)-1-({[(2S,4R)-4-fluoro-1-methylpyrrolidin-2-yl]methyl}[1-(propan-2-yl)-1H-pyrazol-4-yl]sulfamoyl)urea [Compound 63]

3-(2,5-Diethylfuran-3-yl)-1-({[(2S,4R)-4-fluoro-1-methylpyrrolidin-2-yl]methyl}[1-(propan-2-yl)-1H-pyrazol-4-yl]sulfamoyl)urea was prepared following a procedure similar to Example 18 using Intermediate 26 and Intermediate 40, isolated as the sodium salt. $^1$H NMR (400 MHz, MeOD) δ 7.73 (s, 1H), 7.50 (s, 1H), 6.10 (s, 1H), 5.43-5.24 (m, 1H), 4.50-4.39 (m, 1H), 4.37-4.27 (m, 1H), 4.24-4.07 (m, 1H), 3.84-3.63 (m, 2H), 3.44-3.38 (m, 1H), 3.03 (s, 3H), 2.65 (q, J=8 Hz, 4H), 2.36-2.15 (m, 2H), 1.46 (d, J=7 Hz, 6H), 1.22-1.13 (m, 6H). LCMS: m/z: $[M+H]^+$=485.3.

Example 40. 3-(2,5-Diethylfuran-3-yl)-1-{[2-(dimethylamino)ethyl][1-(propan-2-yl)-1H-pyrazol-4-yl]sulfamoyl}urea [Compound 64]

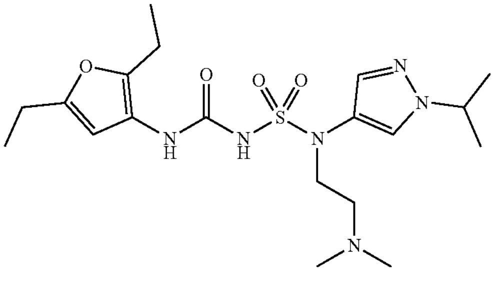 [SMILES: CCc1cc(NC(=O)NS(=O)(=O)N(CCN(C)C)c2cnn(C(C)C)c2)c(CC)o1]

3-(2,5-Diethylfuran-3-yl)-1-{[2-(dimethylamino)ethyl][1-(propan-2-yl)-1H-pyrazol-4-yl]sulfamoyl}urea was prepared following a procedure similar to Example 18 using Intermediate 26 and Intermediate 48, isolated as the sodium salt. $^1$H NMR (400 MHz, MeOD) δ 7.74 (s, 1H), 7.51 (s, 1H), 6.10 (s, 1H), 4.50-4.42 (m, 1H), 3.92 (t, J=5 Hz, 2H), 3.19 (t, J=5 Hz, 2H), 2.94 (s, 6H), 2.58-2.51 (m, 4H), 1.45 (d, J=6 Hz, 6H), 1.20-1.14 (m, 6H). LCMS: m/z: $[M+H]^+$=441.3.

Example 41. 3-(2,5-Diethylfuran-3-yl)-1-[(1-methyl-1H-pyrazol-4-yl)(oxan-4-yl)sulfamoyl]-urea [Compound 65]

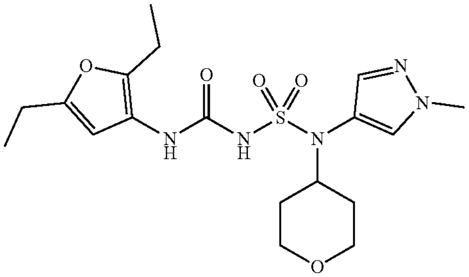

3-(2,5-Diethylfuran-3-yl)-1-[(1-methyl-1H-pyrazol-4-yl)(oxan-4-yl)sulfamoyl]urea was prepared following a procedure similar to Example 18 using Intermediate 26 and Intermediate 1, isolated as the sodium salt. $^1$H NMR (400 MHz, MeOD) δ 7.70 (s, 1H), 7.40 (s, 1H), 6.10 (s, 1H), 4.34-4.31 (m, 1H), 3.95-3.90 (m, 2H), 3.89 (s, 3H), 3.51-3.44 (m, 2H), 2.60-2.48 (m, 4H), 1.89-1.84 (m, 2H), 1.52-1.49 (m, 2H), 1.23-1.15 (m, 6H). LCMS: m/z: $[M+H]^+$=426.2.

Example 42. 1-[(1-Methyl-1H-pyrazol-4-yl)[(3R)-1-methylpiperidin-3-yl]sulfamoyl]-3-[5-methyl-2-(propan-2-yl)thiophen-3-yl]urea [Compound 66]

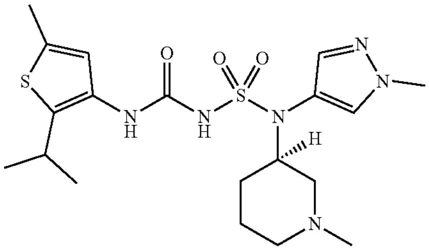 [SMILES: Cc1cc(NC(=O)NS(=O)(=O)N(c2cnn(C)c2)[C@@H]2CCCN(C)C2)c(C(C)C)s1]

1-[(1-Methyl-1H-pyrazol-4-yl)[(3R)-1-methylpiperidin-3-yl]sulfamoyl]-3-[5-methyl-2-(propan-2-yl)thiophen-3-yl]urea was prepared following a procedure similar to Example 18 using Intermediate 32 and Intermediate 41, isolated as the sodium salt. $^1$H NMR (400 MHz, MeOD) δ 7.64 (s, 1H), 7.40 (s, 1H), 6.84 (s, 1H), 4.35-4.32 (m, 1H), 3.84 (s, 3H), 3.52-3.48 (m, 1H), 3.14-3.06 (m, 2H), 2.61 (s, 3H), 2.38-2.21 (m, 5H), 2.05-2.01 (m, 1H), 1.92-1.84 (m, 1H), 1.83-1.68 (m, 1H), 1.33-1.15 (m, 7H). LCMS: m/z: $[M+H]^+$=455.3.

Example 43. 1-[(1-Methyl-1H-pyrazol-4-yl)[(3R)-1-methylpiperidin-3-yl]sulfamoyl]-3-[4-methyl-2,5-bis(propan-2-yl)thiophen-3-yl]urea [Compound 67]

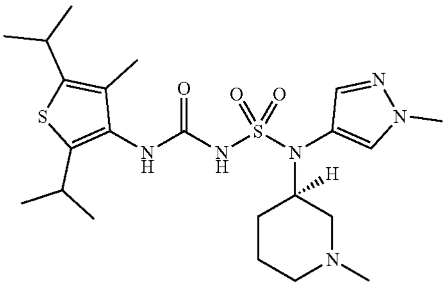 [SMILES: Cc1c(C(C)C)sc(C(C)C)c1NC(=O)NS(=O)(=O)N(c1cnn(C)c1)[C@@H]1CCCN(C)C1]

1-[(1-Methyl-1H-pyrazol-4-yl)[(3R)-1-methylpiperidin-3-yl]sulfamoyl]-3-[4-methyl-2,5-bis(propan-2-yl)thiophen-3-yl]urea was prepared following a procedure similar to Example 18 using Intermediate 32 and Intermediate 42, isolated as the sodium salt. $^1$H NMR (400 MHz, acetonitrile-$d_3$) δ 7.49 (s, 1H), 7.30 (s, 1H), 6.99 (s, 1H), 4.28-4.23 (m, 1H), 3.79 (s, 3H), 3.37-3.34 (m, 1H), 3.26-3.17 (m, 2H), 2.89-2.85 (m, 1H), 2.41 (s, 3H), 2.21-2.17 (m, 3H), 1.95 (s, 3H), 1.75-1.70 (m, 2H), 1.22-1.19 (m, 12H), 1.18-1.11 (m, 1H). LCMS: m/z: $[M+H]^+$=497.3.

Example 44. 3-(2,5-Diethylthiophen-3-yl)-1-[(1-methylpiperidin-3-yl)(oxan-4-yl)sulfamoyl]-urea [Compound 68]

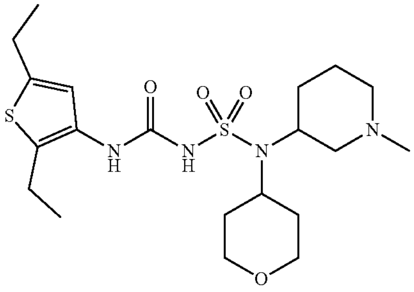 [SMILES: CCc1cc(NC(=O)NS(=O)(=O)N(C2CCOCC2)C2CCCN(C)C2)c(CC)s1]

3-(2,5-Diethylthiophen-3-yl)-1-[(1-methylpiperidin-3-yl)(oxan-4-yl)sulfamoyl]urea was prepared following a procedure similar to Example 18 using Intermediate 6 and Intermediate 43, isolated as the sodium salt. $^1$H NMR (400 MHz, MeOD) δ 6.82 (s, 1H), 3.99-3.82 (m, 2H), 3.89-3.78 (m, 1H), 3.61-3.51 (m, 1H), 3.49-3.40 (m, 2H), 3.25-2.96 (m, 3H), 2.77-2.62 (m, 4H), 2.59 (s, 3H), 2.39 (t, J=12 Hz, 1H), 2.15-1.86 (m, 5H), 1.83-1.64 (m, 3H), 1.27-1.18 (m, 6H). LCMS: m/z: $[M+H]^+$=459.2

Example 45. 3-(2,5-Diethylthiophen-3-yl)-1-[(1-methylpiperidin-3-yl)(oxolan-3-yl)-sulfamoyl]urea [Compound 69]

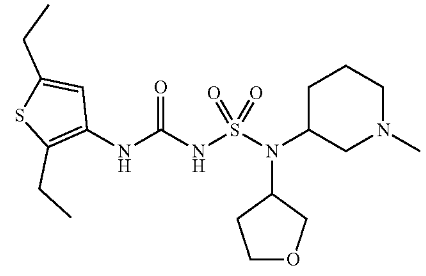 [SMILES: CCc1cc(NC(=O)NS(=O)(=O)N(C2CCOC2)C2CCCN(C)C2)c(CC)s1]

3-(2,5-Diethylthiophen-3-yl)-1-[(1-methylpiperidin-3-yl)(oxolan-3-yl)sulfamoyl]urea was prepared following a procedure similar to Example 18 using Intermediate 6 and Intermediate 44, isolated as the sodium salt. $^1$H NMR (400 MHz, MeOD) δ 6.83 (s, 1H), 4.46-4.42 (m, 1H), 4.00-3.98 (m, 1H), 3.88-3.77 (m, 1H), 3.75-3.67 (m, 3H), 3.35-3.25 (m, 1H), 3.20-3.10 (m, 1H), 3.05-2.95 (m, 1H), 2.80-2.70 (m, 2H), 2.69-2.60 (m, 2H), 2.55 (s, 3H), 2.45-2.35 (m, 1H), 2.25-2.10 (m, 2H), 2.05-1.90 (m, 3H), 1.75-1.60 (m, 1H), 1.32-1.25 (m, 6H). LCMS: m/z: $[M+H]^+$=445.1

Example 46. 1-[(1-Methyl-1H-pyrazol-4-yl)[(3R)-1-methylpiperidin-3-yl]sulfamoyl]-3-[2-(propan-2-yl)-4H,5H,6H-cyclopenta[b]thiophen-3-yl]urea [Compound 70]

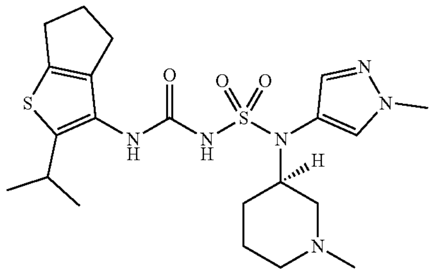 [SMILES: CC(C)c1sc2c(c1NC(=O)NS(=O)(=O)N(c1cnn(C)c1)[C@@H]1CCCN(C)C1)CCC2]

1-[(1-Methyl-1H-pyrazol-4-yl)[(3R)-1-methylpiperidin-3-yl]sulfamoyl]-3-[2-(propan-2-yl)-4H,5H,6H-cyclopenta[b]thiophen-3-yl]urea was prepared following a procedure similar to Example 18 using Intermediate 32 and Intermediate 45, isolated as the sodium salt. $^1$H NMR (400 MHz, MeOD) δ 7.64 (s, 1H), 7.41 (s, 1H), 4.35-4.28 (m, 1H), 3.86 (s, 3H), 3.52-3.45 (m, 1H), 3.21-3.14 (m, 1H), 3.08-3.02 (m, 1H), 2.85-2.80 (m, 2H), 2.69-2.65 (m, 2H), 2.60 (s, 3H), 2.43-2.32 (m, 4H), 2.05-1.96 (m, 1H), 1.89-1.83 (m, 1H), 1.79-1.69 (m, 1H), 1.26-1.20 (m, 7H). LCMS: m/z: $[M+H]^+$=481.2.

Example 47. 3-(2,5-Diethylfuran-3-yl)-1-{[(3R)-1-methylpiperidin-3-yl][1-(propan-2-yl)-1H-pyrazol-4-yl]sulfamoyl}urea [Compound 71]

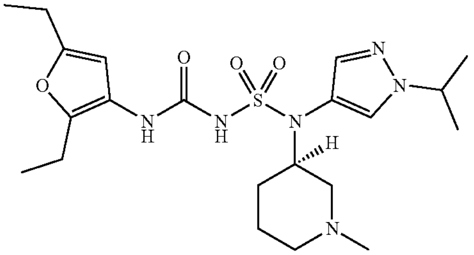 [SMILES: CCc1cc(NC(=O)NS(=O)(=O)N(c2cnn(C(C)C)c2)[C@@H]2CCCN(C)C2)c(CC)o1]

3-(2,5-Diethylfuran-3-yl)-1-{[(3R)-1-methylpiperidin-3-yl][1-(propan-2-yl)-1H-pyrazol-4-yl]sulfamoyl}urea was prepared following a procedure similar to Example 18 using Intermediate 25 and Intermediate 26, isolated as the sodium salt. $^1$H NMR (400 MHz, MeOD) δ 7.69 (s, 1H), 7.42 (s, 1H), 6.11 (s, 1H), 4.50-4.42 (m, 1H), 4.38-4.28 (m, 1H), 3.57-3.47 (m, 1H), 3.11-3.04 (m, 1H), 2.61 (s, 3H), 2.59-2.50 (m, 4H), 2.42-2.28 (m, 2H), 2.06-1.99 (m, 1H), 1.93-1.85 (m, 1H), 1.81-1.69 (m, 1H), 1.46 (d, J=7 Hz, 6H), 1.22-1.14 (m, 7H). LCMS: m/z: $[M+H]^+$=467.3.

Example 48. 3-(2,5-Diethylfuran-3-yl)-1-{[2-(dimethylamino)ethyl](1-methyl-1H-pyrazol-4-yl)sulfamoyl}urea [Compound 72]

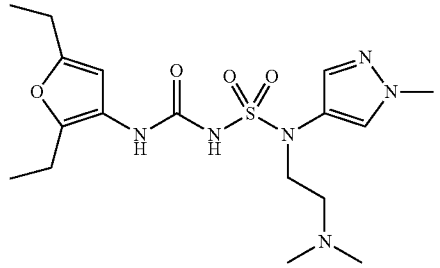 [SMILES: CCc1cc(NC(=O)NS(=O)(=O)N(CCN(C)C)c2cnn(C)c2)c(CC)o1]

3-(2,5-Diethylfuran-3-yl)-1-{[2-(dimethylamino)ethyl](1-methyl-1H-pyrazol-4-yl)sulfamoyl}urea was prepared following a procedure similar to Example 18 using Intermediate 20 and Intermediate 26, isolated as the sodium salt. $^1$H NMR (400 MHz, MeOD) δ 7.68 (s, 1H), 7.50 (s, 1H), 6.10 (s, 1H), 3.93-3.89 (m, 2H), 3.85 (s, 3H), 3.23-3.18 (m, 2H), 2.95 (s, 6H), 2.58-2.52 (m, 4H), 1.20-1.16 (m, 6H). LCMS: m/z: $[M+H]^+$=413.2.

Example 49. 3-[2,5-Bis(propan-2-yl)furan-3-yl]-1-[(1-methyl-1H-pyrazol-4-yl)(1-methylpiperidin-3-yl)sulfamoyl]urea [Compound 73]

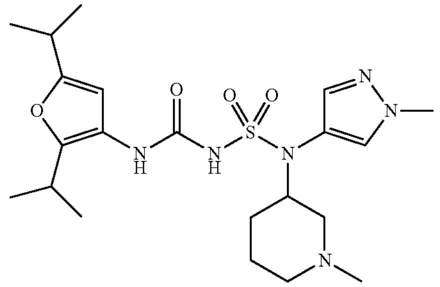 [SMILES: CC(C)c1cc(NC(=O)NS(=O)(=O)N(c2cnn(C)c2)C2CCCN(C)C2)c(C(C)C)o1]

3-[2,5-Bis(propan-2-yl)furan-3-yl]-1-[(1-methyl-1H-pyrazol-4-yl)(1-methylpiperidin-3-yl)sulfamoyl]urea was prepared following a procedure similar to Example 18 using Intermediate 2 and Intermediate 46, isolated as the sodium salt. $^1$H NMR (400 MHz, MeOD) δ 7.64 (s, 1H), 7.40 (s, 1H), 6.07 (s, 1H), 4.38-4.35 (m, 1H), 3.85 (s, 3H), 3.55-3.53 (m, 1H), 3.11-3.08 (m, 1H), 2.95-2.92 (m, 1H), 2.84-2.81 (m, 1H), 2.62 (s, 3H), 2.39-2.35 (m, 2H), 2.04-2.01 (m, 1H), 1.92-1.71 (m, 2H), 1.22-1.19 (m, 13H). LCMS: m/z: $[M+H]^+$=467.3.

Example 50. 1-(2,5-Diethylfuran-3-yl)-3-[(1-methyl-1H-pyrazol-4-yl)[(oxolan-2-yl)methyl]-sulfamoyl]urea [Compound 74]

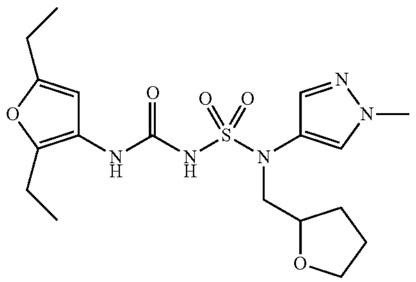 [SMILES: CCc1cc(NC(=O)NS(=O)(=O)N(CC2CCCO2)c2cnn(C)c2)c(CC)o1]

1-(2,5-Diethylfuran-3-yl)-3-[(1-methyl-1H-pyrazol-4-yl)[(oxolan-2-yl)methyl]sulfamoyl]urea was prepared following a procedure similar to Example 18 using Intermediate 26 and Intermediate 47, isolated as the sodium salt. $^1$H NMR (400 MHz, MeOD) δ 7.74 (s, 1H), 7.51 (s, 1H), 6.07 (s, 1H), 4.17-3.93 (m, 1H), 3.85 (s, 3H), 3.83-3.77 (m, 2H), 3.75-3.65 (m, 2H), 2.65-2.45 (m, 4H), 2.05-1.82 (m, 3H), 1.74-1.58 (m, 1H), 1.29-1.09 (m, 6H). LCMS: m/z: $[M+H]^+$=426.3.

Example 51. 3-[2,5-Bis(propan-2-yl)furan-3-yl]-1-{[2-(dimethylamino)ethyl](1-methyl-1H-pyrazol-4-yl)sulfamoyl}urea [Compound 75]

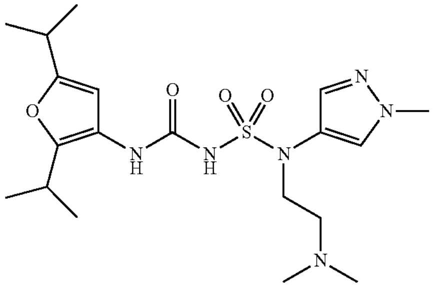 [SMILES: CC(C)c1cc(NC(=O)NS(=O)(=O)N(CCN(C)C)c2cnn(C)c2)c(C(C)C)o1]

3-[2,5-Bis(propan-2-yl)furan-3-yl]-1-{[2-(dimethylamino)ethyl](1-methyl-1H-pyrazol-4-yl)sulfamoyl}urea was prepared following a procedure similar to Example 18 using Intermediate 20 and Intermediate 46, isolated as the sodium salt. $^1$H NMR (400 MHz, MeOD) δ 7.68 (s, 1H), 7.50 (s, 1H), 6.06 (s, 1H), 3.91 (t, J=5 Hz, 2H), 3.85 (s, 3H), 3.21 (t, J=5 Hz, 2H), 3.00-2.94 (m, 7H), 2.86-2.80 (m, 1H), 1.20 (d, J=7 Hz, 12H). LCMS: m/z: $[M+H]^+$=441.3.

Example 52. 3-[2,5-Bis(propan-2-yl)thiophen-3-yl]-1-{[(3R,5S)-5-fluoro-1-methylpiperidin-3-yl](1-methyl-1H-pyrazol-4-yl)sulfamoyl}urea [Compound 76]

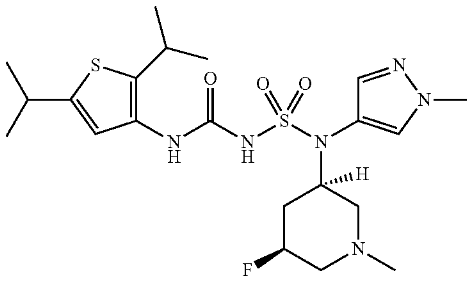 [SMILES: CC(C)c1cc(NC(=O)NS(=O)(=O)N(c2cnn(C)c2)[C@@H]2C[C@H](F)CN(C)C2)c(C(C)C)s1]

3-[2,5-bis(propan-2-yl)thiophen-3-yl]-1-{[(3R,5S)-5-fluoro-1-methylpiperidin-3-yl](1-methyl-1H-pyrazol-4-yl)sulfamoyl}urea was prepared following a procedure similar to Example 1 using Intermediate 8 and Intermediate 14, isolated as the sodium salt. $^1$H NMR (400 MHz, MeOD) δ 7.74 (s, 1H), 7.42 (s, 1H), 6.87 (s, 1H), 4.71 (m, 1H), 4.40-4.27 (m, 1H), 3.87 (s, 3H), 3.17-2.99 (m, 4H), 2.48-2.41 (m, 1H), 2.33 (s, 3H), 1.86-1.72 (m, 2H), 1.29 (d, J=7 Hz, 6H), 1.25 (d, J=7 Hz, 6H), 1.23-1.16 (m, 1H). LCMS (ESI): m/z: $[M+H]^+$=501.2.

Example 53. 3-{2-Ethyl-4H,5H,6H-cyclopenta[b]thiophen-3-yl}-1-[(1-methyl-1H-pyrazol-4-yl)(1-methylpiperidin-3-yl)sulfamoyl]urea [Compound 77]

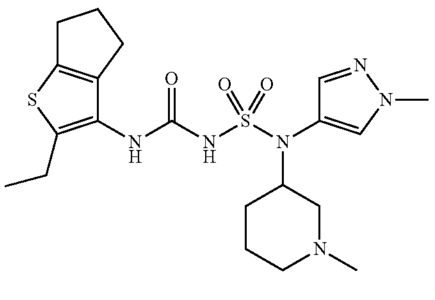 [SMILES: CCc1sc2c(c1NC(=O)NS(=O)(=O)N(c1cnn(C)c1)C1CCCN(C)C1)CCC2]

3-{2-Ethyl-4H,5H,6H-cyclopenta[b]thiophen-3-yl}-1-[(1-methyl-1H-pyrazol-4-yl)(1-methylpiperidin-3-yl)sulfamoyl]urea was prepared following a procedure similar to Example 18 using Intermediate 2 and Intermediate 49, isolated as the sodium salt. $^1$H NMR (400 MHz, MeOD) δ 7.64 (s, 1H), 7.41 (s, 1H), 4.36-4.30 (m, 1H), 3.86 (s, 3H), 3.55-3.45 (m, 1H), 3.10-3.00 (m, 1H), 2.82 (t, J=7 Hz, 2H), 2.70-2.64 (m, 4H), 2.60 (s, 3H), 2.43-2.33 (m, 4H), 2.05-1.96 (m, 1H), 1.90-1.86 (m, 1H), 1.80-1.70 (m, 1H), 1.25-1.18 (m, 4H). LCMS (ESI): m/z: $[M+H]^+$=467.3

Example 54. 3-[2-Ethyl-5-(propan-2-yl)furan-3-yl]-1-[(1-methyl-1H-pyrazol-4-yl)(1-methyl-piperidin-3-yl)sulfamoyl]urea [Compound 78]

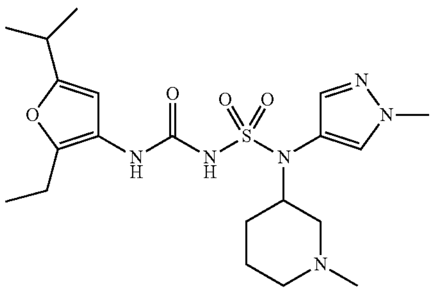 [SMILES: CCc1oc(C(C)C)cc1NC(=O)NS(=O)(=O)N(c1cnn(C)c1)C1CCCN(C)C1]

3-[2-Ethyl-5-(propan-2-yl)furan-3-yl]-1-[(1-methyl-1H-pyrazol-4-yl)(1-methylpiperidin-3-yl)sulfamoyl]urea was prepared following a procedure similar to Example 18 using Intermediate 2 and Intermediate 50, isolated as the sodium salt. $^1$H NMR (400 MHz, MeOD) δ 7.64 (s, 1H), 7.41 (s, 1H), 6.08 (s, 1H), 4.39-4.25 (m, 1H), 3.86 (s, 3H), 3.50 (d, J=13 Hz, 1H), 3.08 (d, J=12 Hz, 1H), 2.88-2.77 (m, 1H), 2.61 (s, 3H), 2.53 (q, J=8 Hz, 2H), 2.48-2.25 (m, 2H), 2.06-1.99 (m, 1H), 1.93-1.84 (m, 1H), 1.81-1.69 (m, 1H), 1.22-1.15 (m, 10H). LCMS (ESI): m/z: $[M+H]^+$=453.3.

Example 55. 3-[5-Ethyl-2-(propan-2-yl)furan-3-yl]-1-[(1-methyl-1H-pyrazol-4-yl)(1-methyl-piperidin-3-yl)sulfamoyl]urea [Compound 79]

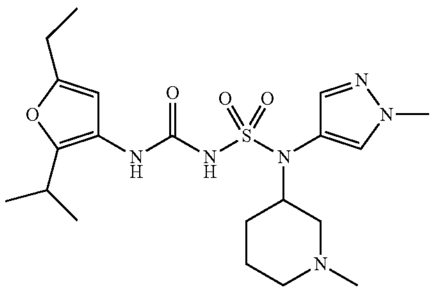 [SMILES: CCc1cc(NC(=O)NS(=O)(=O)N(c2cnn(C)c2)C2CCCN(C)C2)c(C(C)C)o1]

3-[5-Ethyl-2-(propan-2-yl)furan-3-yl]-1-[(1-methyl-1H-pyrazol-4-yl)(1-methylpiperidin-3-yl)sulfamoyl]urea was prepared following a procedure similar to Example 18 using Intermediate 2 and Intermediate 51, isolated as the sodium salt. $^1$H NMR (400 MHz, MeOD) δ 7.65 (s, 1H), 7.41 (s, 1H), 6.09 (s, 1H), 4.41-4.34 (m, 1H), 3.86 (s, 3H), 3.56-3.54 (m, 1H), 3.10-3.05 (m, 1H), 2.97-2.92 (m, 1H), 2.63 (s, 3H), 2.55 (q, J=8 Hz, 2H), 2.43-2.37 (m, 2H), 2.05-2.02 (m, 1H), 1.90-1.79 (m, 2H), 1.22-1.17 (m, 10H). LCMS (ESI): m/z: $[M+H]^+$=453.3.

Example 56. 3-[5-Chloro-2-(propan-2-yl)thiophen-3-yl]-1-[(1-methyl-1H-pyrazol-4-yl)[(3S)-1-methylpiperidin-3-yl]sulfamoyl]urea [Compound 80]

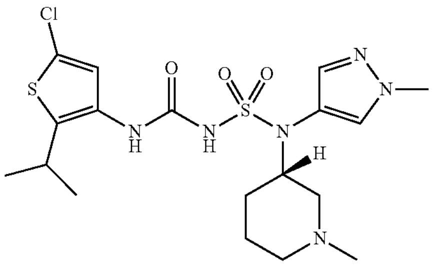 [SMILES: CC(C)c1sc(Cl)cc1NC(=O)NS(=O)(=O)N(c1cnn(C)c1)[C@H]1CCCN(C)C1]

3-[5-Chloro-2-(propan-2-yl)thiophen-3-yl]-1-[(1-methyl-1H-pyrazol-4-yl)[(3S)-1-methylpiperidin-3-yl]sulfamoyl]urea was prepared following a procedure similar to Example 18 using Intermediate 33 and Intermediate 37, isolated as the sodium salt. $^1$H NMR (400 MHz, MeOD) δ 7.63 (s, 1H), 7.40 (s, 1H), 7.10 (s, 1H), 4.42-4.26 (m, 1H), 3.84 (s, 3H), 3.67-3.51 (m, 1H), 3.24-3.06 (m, 2H), 2.69 (s, 3H), 2.61-2.37 (m, 2H), 2.11-1.98 (m, 1H), 1.96-1.86 (m, 1H), 1.85-1.69 (m, 1H), 1.30-1.25 (m, 1H), 1.23 (d, J=7 Hz, 6H). LCMS (ESI): m/z: $[M+H]^+$=475.1.

Example 57. 1-[(1-Methyl-1H-pyrazol-4-yl)[(3S)-1-methylpiperidin-3-yl]sulfamoyl]-3-[5-methyl-2-(propan-2-yl)thiophen-3-yl]urea [Compound 81]

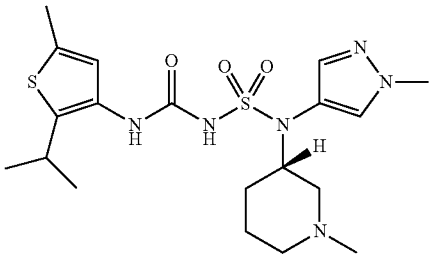 [SMILES: Cc1cc(NC(=O)NS(=O)(=O)N(c2cnn(C)c2)[C@H]2CCCN(C)C2)c(C(C)C)s1]

1-[(1-Methyl-1H-pyrazol-4-yl)[(3S)-1-methylpiperidin-3-yl]sulfamoyl]-3-[5-methyl-2-(propan-2-yl)thiophen-3-yl]urea was prepared following a procedure similar to Example 18 using Intermediate 33 and Intermediate 41, isolated as the sodium salt. $^1$H NMR (400 MHz, MeOD) δ 7.64 (s, 1H), 7.40 (s, 1H), 6.84 (s, 1H), 4.41-4.22 (m, 1H), 3.84 (s, 3H), 3.55-3.45 (m, 1H), 3.13-3.05 (m, 2H), 2.60 (s, 3H), 2.38 (s, 3H), 2.37-2.24 (m, 2H), 2.09-1.97 (m, 1H), 1.93-1.83 (m, 1H), 1.82-1.69 (m, 1H), 1.22 (d, J=7 Hz, 6H), 1.20-1.16 (m, 1H). LCMS (ESI): m/z: $[M+H]^+$=455.2.

Example 58. 3-[2,5-Bis(propan-2-yl)thiophen-3-yl]-1-{[(3R,5R)-5-fluoro-1-methylpiperidin-3-yl](1-methyl-1H-pyrazol-4-yl)sulfamoyl}urea [Compound 82]

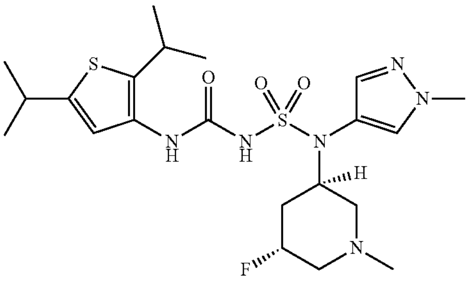 [SMILES: CC(C)c1cc(NC(=O)NS(=O)(=O)N(c2cnn(C)c2)[C@@H]2C[C@@H](F)CN(C)C2)c(C(C)C)s1]

3-[2,5-Bis(propan-2-yl)thiophen-3-yl]-1-{[(3R,5R)-5-fluoro-1-methylpiperidin-3-yl](1-methyl-1H-pyrazol-4-yl) sulfamoyl}urea was prepared following a procedure similar to Example 1 using Intermediate 8 and Intermediate 15, isolated as the sodium salt. $^1$H NMR (400 MHz, MeOD) δ 7.71 (s, 1H), 7.43 (s, 1H), 6.89 (s, 1H), 5.28-5.13 (m, 2H), 3.85 (s, 3H), 3.16-3.01 (m, 3H), 2.36 (s, 3H), 2.33-2.24 (m, 1H), 2.20-1.96 (m, 2H), 1.54-1.33 (m, 2H), 1.29 (d, J=7 Hz, 12H), 1.24 (d, J=7 Hz, 12H). LCMS (ESI): m/z: $[M+H]^+$ =501.1.

Example 59. 1-[2,5-Bis(propan-2-yl)furan-3-yl]-3-{[2-(dimethylamino)ethyl][1-(propan-2-yl)-1H-pyrazol-4-yl]sulfamoyl}urea [Compound 83]

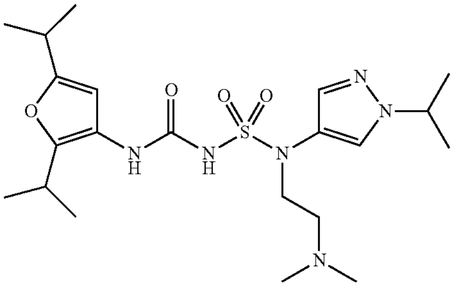 [SMILES: CC(C)c1cc(NC(=O)NS(=O)(=O)N(CCN(C)C)c2cnn(C(C)C)c2)c(C(C)C)o1]

1-[2,5-Bis(propan-2-yl)furan-3-yl]-3-{[2-(dimethylamino)ethyl][1-(propan-2-yl)-1H-pyrazol-4-yl] sulfamoyl}urea was prepared following a procedure similar to Example 18 using Intermediate 46 and Intermediate 48, isolated as the sodium salt. $^1$H NMR (400 MHz, MeOD) δ 7.74 (s, 1H), 7.51 (s, 1H), 6.06 (s, 1H), 4.49-4.42 (m, 1H), 3.92 (t, J=5 Hz, 2H), 3.20 (t, J=5 Hz, 2H), 3.02-2.92 (m, 7H), 2.86-2.76 (m, 1H), 1.50-1.45 (m, 6H), 1.25-1.18 (m, 12H). LCMS (ESI): m/z: $[M+H]^+$=469.3.

Example 60. 3-[2,5-Bis(propan-2-yl)thiophen-3-yl]-1-{[(3S)-1-methylpiperidin-3-yl][1-(propan-2-yl)-1H-pyrazol-4-yl]sulfamoyl}urea [Compound 84]

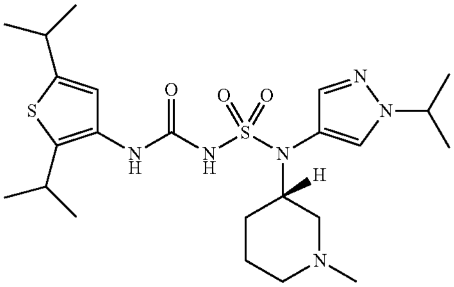 [SMILES: CC(C)c1cc(NC(=O)NS(=O)(=O)N(c2cnn(C(C)C)c2)[C@H]2CCCN(C)C2)c(C(C)C)s1]

3-[2,5-Bis(propan-2-yl)thiophen-3-yl]-1-{[(3S)-1-methylpiperidin-3-yl][1-(propan-2-yl)-1H-pyrazol-4-yl] sulfamoyl}urea was prepared following a procedure similar to Example 18 using Intermediate 8 and Intermediate 52, isolated as the sodium salt. $^1$H NMR (400 MHz, MeOD) δ 7.69 (s, 1H), 7.43 (s, 1H), 6.91 (s, 1H), 4.53-4.42 (m, 1H), 4.40-4.28 (m, 1H), 3.61-3.51 (m, 1H), 3.17-3.00 (m, 3H), 2.64 (s, 3H), 2.46-2.30 (m, 2H), 2.12-1.98 (m, 1H), 1.93-1.71 (m, 2H), 1.44 (d, J=6 Hz, 6H), 1.28 (d, J=7 Hz, 6H), 1.22 (m, 7H). LCMS (ESI): m/z: $[M+H]^+$=511.3.

Example 61. 1-[(1-Methyl-1H-pyrazol-4-yl)[(3S)-1-methylpiperidin-3-yl]sulfamoyl]-3-[2-(propan-2-yl)-4H,5H,6H-cyclopenta[b]thiophen-3-yl]urea [Compound 85]

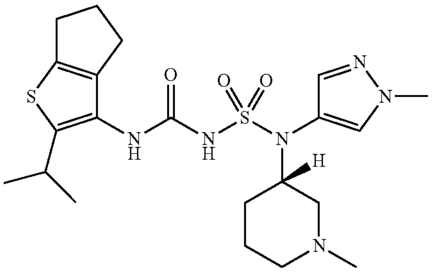 [SMILES: CC(C)c1sc2c(c1NC(=O)NS(=O)(=O)N(c1cnn(C)c1)[C@H]1CCCN(C)C1)CCC2]

1-[(1-Methyl-1H-pyrazol-4-yl)[(3S)-1-methylpiperidin-3-yl]sulfamoyl]-3-[2-(propan-2-yl)-4H,5H,6H-cyclopenta [b]thiophen-3-yl]urea was prepared following a procedure similar to Example 18 using Intermediate 33 and Intermediate 45, isolated as the sodium salt. $^1$H NMR (400 MHz, MeOD) δ 7.64 (s, 1H), 7.41 (s, 1H), 4.39-4.33 (m, 1H), 3.86 (s, 3H), 3.55-3.52 (m, 1H), 3.25-3.15 (m, 1H), 3.12-3.05 (m, 1H), 2.85-2.77 (m, 2H), 2.67-2.62 (m, 5H), 2.43-2.37 (m, 4H), 2.06-2.00 (m, 1H), 1.92-1.69 (m, 2H), 1.25-1.20 (m, 7H). LCMS (ESI): m/z: $[M+H]^+$=481.3.

Example 62. 3-(2-Ethyl-4,5,6,7-tetrahydro-1-benzothiophen-3-yl)-1-[(1-methyl-1H-pyrazol-4-yl)(1-methylpiperidin-3-yl)sulfamoyl]urea [Compound 86]

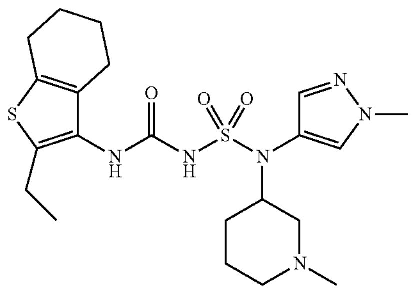 [SMILES: CCc1sc2c(c1NC(=O)NS(=O)(=O)N(c1cnn(C)c1)C1CCCN(C)C1)CCCC2]

3-(2-Ethyl-4,5,6,7-tetrahydro-1-benzothiophen-3-yl)-1-[(1-methyl-1H-pyrazol-4-yl)(1-methylpiperidin-3-yl)sulfamoyl]urea was prepared following a procedure similar to Example 18 using Intermediate 2 and Intermediate 53, isolated as the sodium salt. $^{1}$H NMR (400 MHz, MeOD) δ 7.65 (s, 1H), 7.42 (s, 1H), 4.37-4.28 (m, 1H), 3.87 (s, 3H), 3.51-3.48 (m, 1H), 3.08-3.04 (m, 1H), 2.71-2.65 (m, 4H), 2.59 (s, 3H), 2.42-2.27 (m, 4H), 2.02-1.98 (m, 1H), 1.84-1.67 (m, 6H), 1.24-1.19 (m, 4H). LCMS (ESI): m/z: $[M+H]^{+}$ =481.3.

Example 63. 3-(2,5-Diethylfuran-3-yl)-1-{[(3S)-1-methylpiperidin-3-yl][1-(propan-2-yl)-1H-pyrazol-4-yl]sulfamoyl}urea [Compound 87]

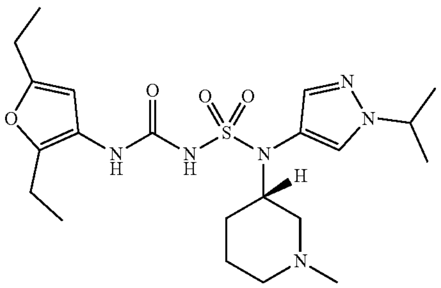 [SMILES: CCc1cc(NC(=O)NS(=O)(=O)N(c2cnn(C(C)C)c2)[C@H]2CCCN(C)C2)c(CC)o1]

3-(2,5-Diethylfuran-3-yl)-1-{[(3S)-1-methylpiperidin-3-yl][1-(propan-2-yl)-1H-pyrazol-4-yl]sulfamoyl}urea was prepared following a procedure similar to Example 18 using Intermediate 26 and Intermediate 52, isolated as the sodium salt. $^{1}$H NMR (400 MHz, MeOD) δ 7.69 (s, 1H), 7.42 (s, 1H), 6.10 (s, 1H), 4.50-4.42 (m, 1H), 4.36-4.28 (m, 1H), 3.56-3.48 (m, 1H), 3.14-3.06 (m, 1H), 2.63 (s, 3H), 2.59-2.49 (m, 4H), 2.47-2.33 (m, 2H), 2.06-1.99 (m, 1H), 1.95-1.69 (m, 2H), 1.46 (d, J=7 Hz, 6H), 1.21-1.14 (m, 7H). LCMS (ESI): m/z: $[M+H]^{+}$=467.3.

Example 64. 3-[5-Ethyl-2-(propan-2-yl)thiophen-3-yl]-1-[(1-methyl-1H-pyrazol-4-yl)[(3S)-1-methylpiperidin-3-yl]sulfamoyl]urea [Compound 88]

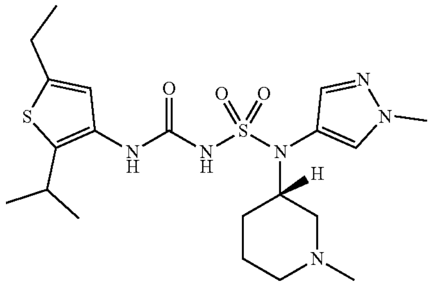 [SMILES: CCc1cc(NC(=O)NS(=O)(=O)N(c2cnn(C)c2)[C@H]2CCCN(C)C2)c(C(C)C)s1]

3-[5-Ethyl-2-(propan-2-yl)thiophen-3-yl]-1-[(1-methyl-1H-pyrazol-4-yl)[(3S)-1-methylpiperidin-3-yl]sulfamoyl]urea was prepared following a procedure similar to Example 18 using Intermediate 33 and Intermediate 38, isolated as the sodium salt. $^{1}$H NMR (400 MHz, MeOD) δ 7.64 (s, 1H), 7.41 (s, 1H), 6.87 (s, 1H), 4.37-4.30 (m, 1H), 3.84 (s, 3H), 3.55-3.50 (m, 1H), 3.14-3.07 (m, 2H), 2.74 (q, J=8 Hz, 2H), 2.62 (s, 3H), 2.49-2.27 (m, 2H), 2.04-2.01 (m, 1H), 1.94-1.68 (m, 2H), 1.28-1.18 (m, 9H). LCMS (ESI): m/z: $[M+H]^{+}$ =469.2.

Example 65. 3-[2-Ethyl-5-(propan-2-yl)thiophen-3-yl]-1-[(1-methyl-1H-pyrazol-4-yl)[(3S)-1-methylpiperidin-3-yl]sulfamoyl]urea [Compound 89]

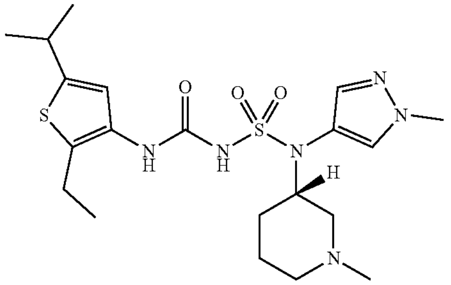 [SMILES: CCc1sc(C(C)C)cc1NC(=O)NS(=O)(=O)N(c1cnn(C)c1)[C@H]1CCCN(C)C1]

3-[2-Ethyl-5-(propan-2-yl)thiophen-3-yl]-1-[(1-methyl-1H-pyrazol-4-yl)[(3S)-1-methylpiperidin-3-yl]sulfamoyl]urea was prepared following a procedure similar to Example 18 using Intermediate 33 and Intermediate 35, isolated as the sodium salt. $^{1}$H NMR (400 MHz, MeOD) δ 7.64 (s, 1H), 7.41 (s, 1H), 6.89 (s, 1H), 4.35-4.28 (m, 1H), 3.84 (s, 3H), 3.59-3.44 (m, 1H), 3.18-2.97 (m, 2H), 2.71-2.56 (m, 5H), 2.46-2.26 (m, 2H), 2.04-2.01 (m, 1H), 1.94-1.84 (m, 1H), 1.82-1.69 (m, 1H), 1.36-1.11 (m, 10H). LCMS (ESI): m/z: $[M+H]^{+}$=469.1.

Example 66. 1-[(1-Methyl-1H-pyrazol-4-yl)[(3S)-1-methylpiperidin-3-yl]sulfamoyl]-3-[2-methyl-5-(propan-2-yl)thiophen-3-yl]urea [Compound 90]

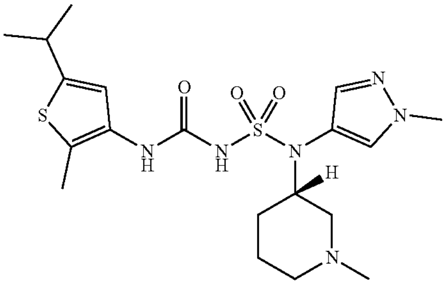 [SMILES: Cc1sc(C(C)C)cc1NC(=O)NS(=O)(=O)N(c1cnn(C)c1)[C@H]1CCCN(C)C1]

1-[(1-Methyl-1H-pyrazol-4-yl)[(3S)-1-methylpiperidin-3-yl]sulfamoyl]-3-[2-methyl-5-(propan-2-yl)thiophen-3-yl]urea was prepared following a procedure similar to Example 18 using Intermediate 33 and Intermediate 34, isolated as the sodium salt. $^1$H NMR (400 MHz, acetonitrile-$d_3$) δ 7.48 (s, 1H), 7.40 (s, 1H), 7.30 (s, 1H), 6.93 (s, 1H), 4.37-4.33 (m, 1H), 3.77 (s, 3H), 3.51-3.46 (m, 1H), 3.06-2.99 (m, 2H), 2.51 (s, 3H), 2.25-2.21 (m, 2H), 2.17 (s, 3H), 2.01-1.94 (m, 1H), 1.85-1.81 (m, 2H), 1.25 (d, J=7 Hz, 6H), 1.18-1.15 (m, 1H). LCMS (ESI): m/z: $[M+H]^+$=455.0.

Example 67. 3-[2,5-Bis(propan-2-yl)thiophen-3-yl]-1-[(1-cyclopropyl-1H-pyrazol-4-yl)[(3S)-1-methylpiperidin-3-yl]sulfamoyl]urea [Compound 91]

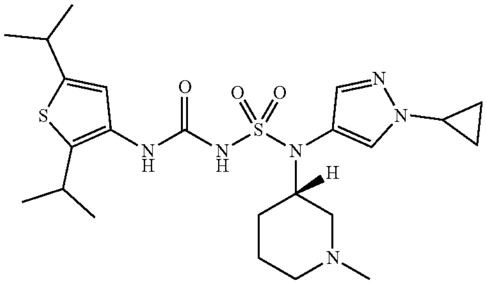 [SMILES: CC(C)c1cc(NC(=O)NS(=O)(=O)N(c2cnn(C3CC3)c2)[C@H]2CCCN(C)C2)c(C(C)C)s1]

3-[2,5-Bis(propan-2-yl)thiophen-3-yl]-1-[(1-cyclopropyl-1H-pyrazol-4-yl)[(3S)-1-methylpiperidin-3-yl]sulfamoyl]urea was prepared following a procedure similar to Example 18 using Intermediate 8 and Intermediate 54, isolated as the sodium salt. $^1$H NMR (400 MHz, MeOD) δ 7.70 (s, 1H), 7.41 (s, 1H), 6.90 (s, 1H), 4.37-4.32 (m, 1H), 3.61-3.56 (m, 2H), 3.14-3.07 (m, 3H), 2.64 (s, 3H), 2.42-2.39 (m, 2H), 2.03-2.01 (m, 1H), 1.89-1.87 (m, 2H), 1.30-1.22 (m, 13H), 1.04-1.00 (m, 4H). LCMS (ESI): m/z: $[M+H]^+$=509.3.

Example 68. 3-[2,5-Bis(propan-2-yl)thiophen-3-yl]-1-{[(3S,5S)-5-fluoro-1-methylpiperidin-3-yl](1-methyl-1H-pyrazol-4-yl)sulfamoyl}urea [Compound 92]

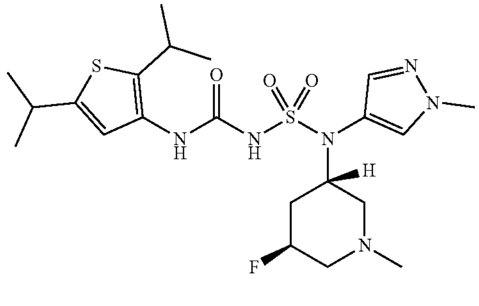 [SMILES: CC(C)c1cc(NC(=O)NS(=O)(=O)N(c2cnn(C)c2)[C@H]2C[C@H](F)CN(C)C2)c(C(C)C)s1]

3-[2,5-Bis(propan-2-yl)thiophen-3-yl]-1-{[(3S,5S)-5-fluoro-1-methylpiperidin-3-yl](1-methyl-1H-pyrazol-4-yl)sulfamoyl}urea was prepared following a procedure similar to Example 1 using Intermediate 8 and Intermediate 16, isolated as the sodium salt. $^1$H NMR (400 MHz, MeOD) δ 7.71 (s, 1H), 7.43 (s, 1H), 6.88 (s, 1H), 4.99-4.93 (m, 2H), 3.85 (s, 3H), 3.17-3.01 (m, 3H), 2.37 (s, 3H), 2.33-2.26 (m, 1H), 2.23-1.94 (m, 2H), 1.51-1.31 (m, 1H), 1.29 (d, J=7 Hz, 6H), 1.24 (d, J=7 Hz, 6H). LCMS (ESI): m/z: $[M+H]^+$=501.1.

Example 69. 3-[2,5-Bis(propan-2-yl)thiophen-3-yl]-1-[(5,5-difluoro-1-methylpiperidin-3-yl)(1-methyl-1H-pyrazol-4-yl)sulfamoyl]urea [Compound 93]

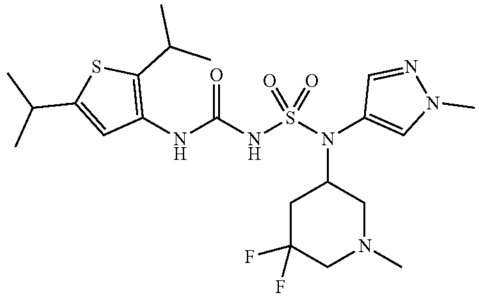 [SMILES: CC(C)c1cc(NC(=O)NS(=O)(=O)N(c2cnn(C)c2)C2CN(C)CC(F)(F)C2)c(C(C)C)s1]

3-[2,5-Bis(propan-2-yl)thiophen-3-yl]-1-[(5,5-difluoro-1-methylpiperidin-3-yl)(1-methyl-1H-pyrazol-4-yl)sulfamoyl]urea was prepared following a procedure similar to Example 1 using Intermediate 8 and Intermediate 18, isolated as the sodium salt. $^1$H NMR (400 MHz, MeOD) δ 7.75 (s, 1H), 7.44 (s, 1H), 6.88 (s, 1H), 4.53-4.43 (m, 1H), 3.87 (s, 3H), 3.20-3.14 (m, 1H), 3.14-3.03 (m, 2H), 2.96 (t, J=11 Hz, 1H), 2.51-2.38 (m, 1H), 2.33 (s, 3H), 2.19-2.02 (m, 1H), 1.92 (t, J=11 Hz, 1H), 1.69-1.46 (m, 1H), 1.29 (d, J=7 Hz, 6H), 1.25 (d, J=7 Hz, 6H). LCMS (ESI): m/z: $[M+H]^+$=519.1.

Example 70. 3-(2-Ethyl-4,5,6,7-tetrahydro-1-benzofuran-3-yl)-1-[(1-methyl-1H-pyrazol-4-yl)(1-methylpiperidin-3-yl)sulfamoyl]urea [Compound 94]

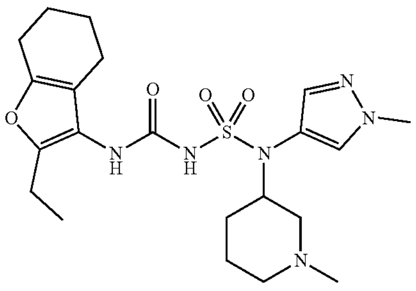 [SMILES: CCc1oc2c(c1NC(=O)NS(=O)(=O)N(c1cnn(C)c1)C1CCCN(C)C1)CCCC2]

3-(2-Ethyl-4,5,6,7-tetrahydro-1-benzofuran-3-yl)-1-[(1-methyl-1H-pyrazol-4-yl)(1-methylpiperidin-3-yl)sulfamoyl]urea was prepared following a procedure similar to Example 18 using Intermediate 2 and Intermediate 55, isolated as the sodium salt. $^1$H NMR (400 MHz, MeOD) δ 7.64 (s, 1H), 7.40 (s, 1H), 4.45-3.35 (m, 1H), 3.86 (s, 3H), 3.54-3.50 (m, 1H), 3.10-3.03 (m, 1H), 2.61 (s, 3H), 2.58-2.46 (m, 4H), 2.45-2.29 (m, 4H), 2.05-1.98 (m, 1H), 1.91-1.77 (m, 4H), 1.74-1.68 (m, 2H), 1.26-1.13 (m, 4H). LCMS (ESI): m/z: $[M+H]^+$=465.3.

Example 71. 1-[(1-Methyl-1H-pyrazol-4-yl)[(3R)-1-methylpiperidin-3-yl]sulfamoyl]-3-{2-methyl-4H,5H,6H-cyclopenta[b]thiophen-3-yl}urea [Compound 95]

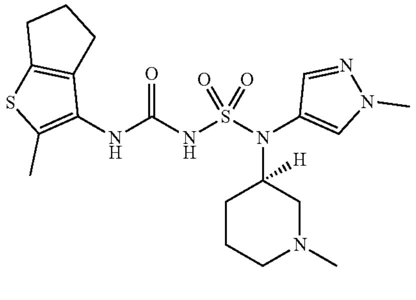 [SMILES: Cc1sc2c(c1NC(=O)NS(=O)(=O)N(c1cnn(C)c1)[C@@H]1CCCN(C)C1)CCC2]

1-[(1-Methyl-1H-pyrazol-4-yl)[(3R)-1-methylpiperidin-3-yl]sulfamoyl]-3-{2-methyl-4H,5H,6H-cyclopenta[b]thiophen-3-yl}urea was prepared following a procedure similar to Example 18 using Intermediate 28 and Intermediate 32, isolated as the sodium salt. $^1$H NMR (400 MHz, MeOD) δ 7.64 (s, 1H), 7.41 (s, 1H), 4.47-4.28 (m, 1H), 3.85 (s, 3H), 3.65-3.49 (m, 1H), 3.10-3.05 (m, 1H), 2.87-2.79 (m, 2H), 2.72-2.64 (m, 2H), 2.61 (s, 3H), 2.47-2.30 (m, 4H), 2.26 (s, 3H), 2.11-1.97 (m, 1H), 1.92-1.69 (m, 2H), 1.26-1.15 (m, 1H). LCMS (ESI): m/z: $[M+H]^+$=453.2.

Example 72. 3-[2,5-Bis(propan-2-yl)thiophen-3-yl]-1-{[(3S,5R)-5-fluoro-1-methylpiperidin-3-yl](1-methyl-1H-pyrazol-4-yl)sulfamoyl}urea [Compound 96]

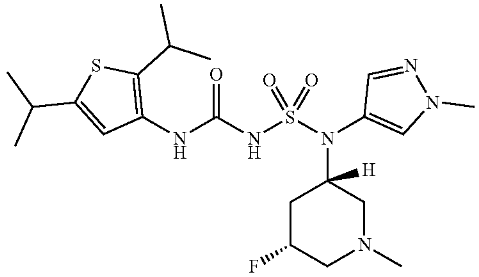 [SMILES: CC(C)c1cc(NC(=O)NS(=O)(=O)N(c2cnn(C)c2)[C@H]2C[C@@H](F)CN(C)C2)c(C(C)C)s1]

3-[2,5-Bis(propan-2-yl)thiophen-3-yl]-1-{[(3S,5R)-5-fluoro-1-methylpiperidin-3-yl](1-methyl-1H-pyrazol-4-yl)sulfamoyl}urea was prepared following a procedure similar to Example 1 using Intermediate 8 and Intermediate 17, isolated as the sodium salt. $^1$H NMR (400 MHz, MeOD) δ 7.74 (s, 1H), 7.42 (s, 1H), 6.87 (s, 1H), 4.73-4.62 (m, 1H), 4.60-4.54 (m, 1H), 4.38-4.22 (m, 1H), 3.88 (s, 3H), 3.16-2.98 (m, 4H), 2.51-2.36 (m, 1H), 2.34 (s, 3H), 1.88-1.71 (m, 2H), 1.29 (d, J=7 Hz, 6H), 1.25 (d, J=7 Hz, 6H). LCMS (ESI): m/z: $[M+H]^+$=501.2.

Example 73. 1-[(1-Methyl-1H-pyrazol-4-yl)(1-methylpiperidin-3-yl)sulfamoyl]-3-(2-methyl-4,5,6,7-tetrahydro-1-benzothiophen-3-yl)urea [Compound 97]

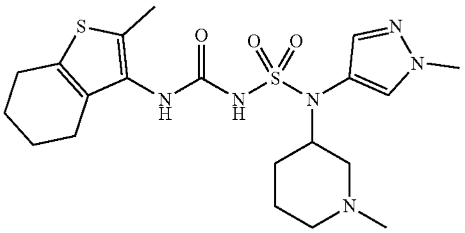 [SMILES: Cc1sc2c(c1NC(=O)NS(=O)(=O)N(c1cnn(C)c1)C1CCCN(C)C1)CCCC2]

1-[(1-Methyl-1H-pyrazol-4-yl)(1-methylpiperidin-3-yl)sulfamoyl]-3-(2-methyl-4,5,6,7-tetrahydro-1-benzothiophen-3-yl)urea was prepared following a procedure similar to Example 1 using Intermediate 19 and Intermediate 2, isolated as the sodium salt. $^1$H NMR (400 MHz, MeOD) δ 7.65 (s, 1H), 7.42 (s, 1H), 4.42-4.26 (m, 1H), 3.86 (s, 3H), 3.56-3.42 (m, 1H), 3.13-2.98 (m, 1H), 2.64-2.62 (m, 2H), 2.59 (s, 3H), 2.40-2.39 (m, 2H), 2.34-2.31 (m, 1H), 2.25 (s, 3H), 2.04-1.99 (m, 1H), 2.89-2.69 (m, 7H), 1.24-1.14 (m, 1H). LCMS (ESI): m/z: $[M+H]^+$=467.2.

Example 74. 1-[(1-Methyl-1H-pyrazol-4-yl)(1-methylpiperidin-3-yl)sulfamoyl]-3-[2-(trifluoromethyl)-4H,5H,6H-cyclopenta[b]thiophen-3-yl]urea [Compound 98]

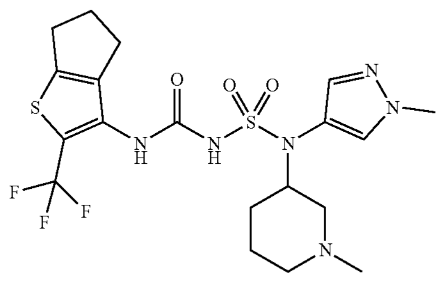 [SMILES: CN1CCCC(N(c2cnn(C)c2)S(=O)(=O)NC(=O)Nc2c(C(F)(F)F)sc3c2CCC3)C1]

1-[(1-Methyl-1H-pyrazol-4-yl)(1-methylpiperidin-3-yl) sulfamoyl]-3-[2-(trifluoromethyl)-4H,5H,6H-cyclopenta[b] thiophen-3-yl]urea was prepared following a procedure similar to Example 18 using Intermediate 2 and Intermediate 56, isolated as the sodium salt. $^1$H NMR (400 MHz, MeOD) δ 7.61 (s, 1H), 7.41 (s, 1H), 4.42-4.37 (m, 1H), 3.85 (s, 3H), 3.63-3.61 (m, 1H), 3.21-3.19 (m, 1H), 2.96-2.90 (m, 2H), 2.82-2.76 (m, 2H), 2.74 (s, 3H), 2.58-2.51 (m, 2H), 2.49-2.42 (m, 2H), 2.03-1.99 (m, 1H), 1.95-1.92 (m, 1H), 1.86-1.80 (m, 1H), 1.29-1.22 (m, 1H). LCMS (ESI): m/z: $[M+H]^+$=507.2.

Example 75. 3-[2,5-Bis(propan-2-yl)thiophen-3-yl]-1-[(1-cyclopropyl-5-fluoro-1H-pyrazol-4-yl)(1-methylpiperidin-3-yl)sulfamoyl]urea [Compound 99]

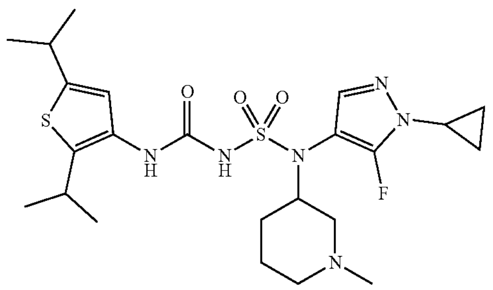 [SMILES: CC(C)c1cc(NC(=O)NS(=O)(=O)N(c2cnn(C3CC3)c2F)C2CCCN(C)C2)c(C(C)C)s1]

3-[2,5-Bis(propan-2-yl)thiophen-3-yl]-1-[(1-cyclopropyl-5-fluoro-1H-pyrazol-4-yl)(1-methylpiperidin-3-yl)sulfamoyl]urea was prepared following a procedure similar to Example 18 using Intermediate 8 and Intermediate 57, isolated as the sodium salt. $^1$H NMR (400 MHz, MeOD) δ 7.35 (d, J=3 Hz, 1H), 6.86 (s, 1H), 4.49-4.35 (m, 1H), 3.65-3.60 (m, 1H), 3.46-3.37 (m, 1H), 3.23-3.10 (m, 2H), 3.08-3.00 (m, 1H), 2.68 (s, 3H), 2.57-2.42 (m, 2H), 2.10-2.06 (m, 1H), 1.94-1.79 (m, 2H), 1.28 (d, J=7 Hz, 6H), 1.25-1.21 (m, 7H), 1.10-1.03 (m, 4H). LCMS (ESI): m/z: $[M+H]^+$=527.3.

Example 76. 1-[(1-Methyl-1H-pyrazol-4-yl)(1-methylpiperidin-4-yl)sulfamoyl]-3-[5-methyl-2-(propan-2-yl)thiophen-3-yl]urea [Compound 100]

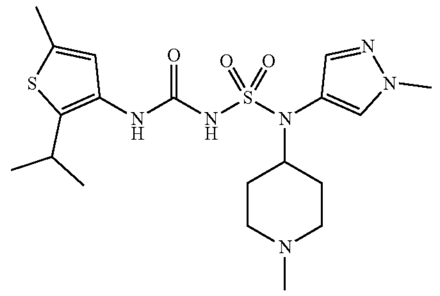 [SMILES: Cc1cc(NC(=O)NS(=O)(=O)N(c2cnn(C)c2)C2CCN(C)CC2)c(C(C)C)s1]

1-[(1-Methyl-1H-pyrazol-4-yl)(1-methylpiperidin-4-yl) sulfamoyl]-3-[5-methyl-2-(propan-2-yl)thiophen-3-yl]urea was prepared following a procedure similar to Example 18 using Intermediate 41 and Intermediate 58, isolated as the sodium salt. $^1$H NMR (400 MHz, MeOD) δ 7.66 (s, 1H), 7.41 (s, 1H), 6.85 (s, 1H), 4.26-4.20 (m, 1H), 3.84 (s, 3H), 3.21-3.17 (m, 2H), 3.12-3.05 (m, 1H), 2.65-2.55 (m, 2H), 2.53 (s, 3H), 2.38 (s, 3H), 2.12-2.07 (m, 2H), 1.60-1.52 (m, 2H), 1.23-1.20 (m, 6H). LCMS (ESI): m/z: $[M+H]^+$=455.2.

Example 77. 1-[(5-Fluoro-1-methyl-1H-pyrazol-4-yl)(1-methylpiperidin-4-yl)sulfamoyl]-3-[5-methyl-2-(propan-2-yl)thiophen-3-yl]urea [Compound 101]

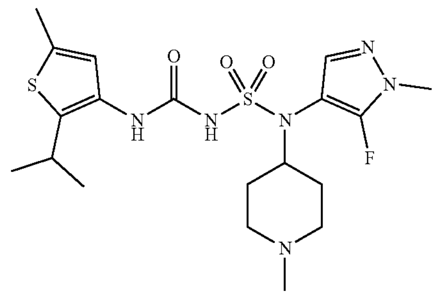 [SMILES: Cc1cc(NC(=O)NS(=O)(=O)N(c2cnn(C)c2F)C2CCN(C)CC2)c(C(C)C)s1]

1-[(5-Fluoro-1-methyl-1H-pyrazol-4-yl)(1-methylpiperidin-4-yl)sulfamoyl]-3-[5-methyl-2-(propan-2-yl)thiophen-3-yl]urea was prepared following a procedure similar to Example 18 using Intermediate 41 and Intermediate 59, isolated as the sodium salt. $^1$H NMR (400 MHz, MeOD) δ 7.37 (d, J=3 Hz, 1H), 6.82 (s, 1H), 4.32-4.25 (m, 1H), 3.70 (s, 3H), 3.26-3.22 (m, 2H), 3.15-3.10 (m, 1H), 2.80-2.73 (m, 2H), 2.58 (s, 3H), 2.37 (s, 3H), 2.15-2.11 (m, 2H), 1.60-1.54 (m, 2H), 1.22 (d, J=7 Hz, 6H). LCMS (ESI): m/z: $[M+H]^+$=473.2.

Example 78. 3-{2-Methoxy-4H,5H,6H-cyclopenta[b]thiophen-3-yl}-1-[(1-methyl-1H-pyrazol-4-yl)(1-methylpiperidin-3-yl)sulfamoyl]urea [Compound 102]

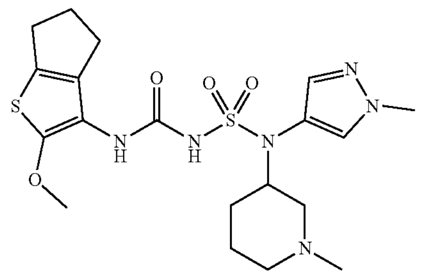 [SMILES: COc1sc2c(c1NC(=O)NS(=O)(=O)N(c1cnn(C)c1)C1CCCN(C)C1)CCC2]

3-{2-Methoxy-4H,5H,6H-cyclopenta[b]thiophen-3-yl}-1-[(1-methyl-1H-pyrazol-4-yl)(1-methylpiperidin-3-yl)sulfamoyl]urea was prepared following a procedure similar to Example 18 using Intermediate 2 and Intermediate 60, isolated as the sodium salt. $^1$H NMR (400 MHz, MeOD) δ 7.65 (s, 1H), 7.43 (s, 1H), 4.40-4.30 (m, 1H), 3.86 (s, 6H), 3.55-3.50 (m, 1H), 3.10-3.06 (m, 1H), 2.82 (t, J=7 Hz, 2H), 2.71 (t, J=7 Hz, 2H), 2.61 (s, 3H), 2.43-2.26 (m, 4H), 2.05-2.01 (m, 1H), 1.88-1.76 (m, 2H), 1.24-1.14 (m, 1H). LCMS (ESI): m/z: [M+H]$^+$=469.2.

Example 79. 1-[(1-Cyclopropyl-1H-pyrazol-4-yl)[(3S)-1-methylpiperidin-3-yl]sulfamoyl]-3-[5-methyl-2-(propan-2-yl)thiophen-3-yl]urea [Compound 103]

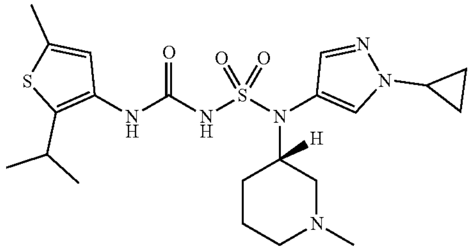 [SMILES: Cc1cc(NC(=O)NS(=O)(=O)N(c2cnn(C3CC3)c2)[C@H]2CCCN(C)C2)c(C(C)C)s1]

1-[(1-Cyclopropyl-1H-pyrazol-4-yl)[(3S)-1-methylpiperidin-3-yl]sulfamoyl]-3-[5-methyl-2-(propan-2-yl)thiophen-3-yl]urea was prepared following a procedure similar to Example 18 using Intermediate 41 and Intermediate 54, isolated as the sodium salt. $^1$H NMR (400 MHz, MeOD) δ 7.70 (s, 1H), 7.41 (s, 1H), 6.85 (s, 1H), 4.39-4.33 (m, 1H), 3.61-3.56 (m, 2H), 3.14-3.08 (m, 2H), 2.64 (s, 3H), 2.45-2.37 (m, 5H), 2.10-2.00 (m, 1H), 1.89-1.86 (m, 2H), 1.27-1.20 (m, 7H), 1.05-1.01 (m, 4H). LCMS (ESI): m/z: [M+H]$^+$=481.3.

Example 80. 1-[(1-Cyclopropyl-1H-pyrazol-4-yl)[(3R)-1-methylpiperidin-3-yl]sulfamoyl]-3-[5-methyl-2-(propan-2-yl)thiophen-3-yl]urea [Compound 104]

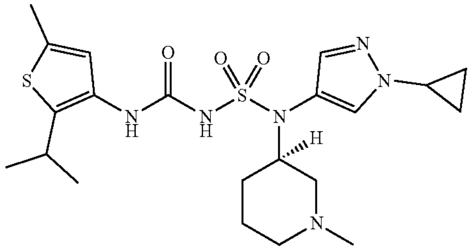 [SMILES: Cc1cc(NC(=O)NS(=O)(=O)N(c2cnn(C3CC3)c2)[C@@H]2CCCN(C)C2)c(C(C)C)s1]

1-[(1-Cyclopropyl-1H-pyrazol-4-yl)[(3R)-1-methylpiperidin-3-yl]sulfamoyl]-3-[5-methyl-2-(propan-2-yl)thiophen-3-yl]urea was prepared following a procedure similar to Example 18 using Intermediate 41 and Intermediate 36, isolated as the sodium salt. $^1$H NMR (400 MHz, MeOD) δ 7.70 (s, 1H), 7.40 (s, 1H), 6.85 (s, 1H), 4.35-4.29 (m, 1H), 3.62-3.57 (m, 1H), 3.55-3.52 (m, 1H), 3.15-3.05 (m, 2H), 2.63 (s, 3H), 2.50-2.47 (m, 5H), 2.06-1.97 (m, 1H), 1.95-1.85 (m, 1H), 1.83-1.69 (m, 1H), 1.22-1.14 (m, 7H), 1.07-0.95 (m, 4H). LCMS (ESI): m/z: [M+H]$^+$=481.2.

Example 81. 1-[(1-Cyclopropyl-1H-pyrazol-4-yl)[(3S)-1-methylpiperidin-3-yl]sulfamoyl]-3-(2-cyclopropyl-5-methylthiophen-3-yl)urea [Compound 105]

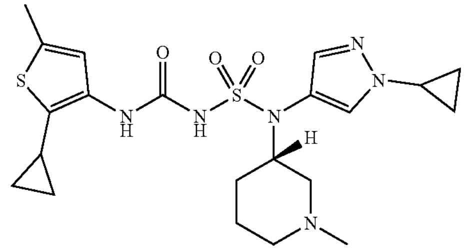 [SMILES: Cc1cc(NC(=O)NS(=O)(=O)N(c2cnn(C3CC3)c2)[C@H]2CCCN(C)C2)c(C2CC2)s1]

1-[(1-Cyclopropyl-1H-pyrazol-4-yl)[(3S)-1-methylpiperidin-3-yl]sulfamoyl]-3-(2-cyclopropyl-5-methylthiophen-3-yl)urea was prepared following a procedure similar to Example 18 using Intermediate 54 and Intermediate 61, isolated as the sodium salt. $^1$H NMR (400 MHz, MeOD) δ 7.70 (s, 1H), 7.41 (s, 1H), 7.02 (s, 1H), 4.37-4.31 (m 1H), 3.60-3.53 (m, 2H), 3.12-3.08 (m, 1H), 2.63 (s, 3H), 2.40-2.32 (m, 5H), 2.05-2.03 (m, 1H), 1.93-1.85 (m, 1H), 1.84-1.68 (m, 2H), 1.24-1.15 (m, 1H), 1.03-0.98 (m, 4H), 0.92-0.89 (m, 2H), 0.54-0.51 (m, 2H). LCMS (ESI): m/z: [M+H]$^+$=479.2.

Example 82. 1-[(1-Cyclopropyl-1H-pyrazol-4-yl)[(3R)-1-methylpiperidin-3-yl]sulfamoyl]-3-(2-cyclopropyl-5-methylthiophen-3-yl)urea [Compound 106]

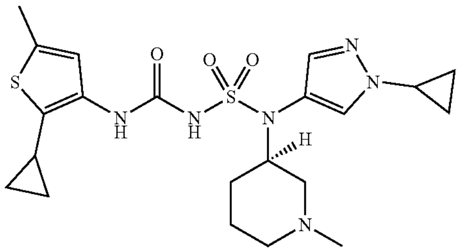 [SMILES: Cc1cc(NC(=O)NS(=O)(=O)N(c2cnn(C3CC3)c2)[C@@H]2CCCN(C)C2)c(C2CC2)s1]

1-[(1-Cyclopropyl-1H-pyrazol-4-yl)[(3R)-1-methylpiperidin-3-yl]sulfamoyl]-3-(2-cyclopropyl-5-methylthiophen-3-yl)urea was prepared following a procedure similar to Example 18 using Intermediate 36 and Intermediate 61, isolated as the sodium salt. $^1$H NMR (400 MHz, MeOD) δ 7.70 (s, 1H), 7.41 (s, 1H), 7.01 (s, 1H), 4.37-4.30 (m, 1H), 3.65-3.50 (m, 2H), 3.13-3.10 (m, 1H), 2.64 (s, 3H), 2.50-2.29 (m, 5H), 2.06-2.03 (m, 1H), 1.95-1.68 (m, 3H), 1.25-1.15 (m, 1H), 1.05-0.96 (m, 4H), 0.94-0.87 (m, 2H), 0.56-0.50 (m, 2H). LCMS (ESI): m/z: $[M+H]^+$=479.2.

Example 83. 3-(2-Cyclopropyl-5-methylthiophen-3-yl)-1-[(1-methyl-1H-pyrazol-4-yl)[(3S)-1-methylpiperidin-3-yl]sulfamoyl]urea [Compound 107]

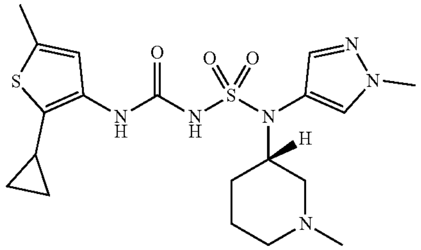 [SMILES: Cc1cc(NC(=O)NS(=O)(=O)N(c2cnn(C)c2)[C@H]2CCCN(C)C2)c(C2CC2)s1]

3-(2-Cyclopropyl-5-methylthiophen-3-yl)-1-[(1-methyl-1H-pyrazol-4-yl)[(3 S)-1-methylpiperidin-3-yl]sulfamoyl]urea was prepared following a procedure similar to Example 18 using Intermediate 33 and Intermediate 61, isolated as the sodium salt. $^1$H NMR (400 MHz, MeOD) δ 7.65 (s, 1H), 7.41 (s, 1H), 7.01 (s, 1H), 4.36-4.26 (m, 1H), 3.83 (s, 3H), 3.55-3.45 (m, 1H), 3.10-3.06 (m, 1H), 2.61 (s, 3H), 2.45-2.31 (m, 5H), 2.06-2.00 (m, 1H), 1.95-1.84 (m, 1H), 1.80-1.60 (m, 2H), 1.26-1.15 (m, 1H), 0.95-0.88 (m, 2H), 0.58-0.51 (m, 2H). LCMS (ESI): m/z: $[M+H]^+$=453.2.

Example 84. 3-(2-Cyclopropyl-5-methylthiophen-3-yl)-1-[(1-methyl-1H-pyrazol-4-yl)[(3R)-1-methylpiperidin-3-yl]sulfamoyl]urea [Compound 108]

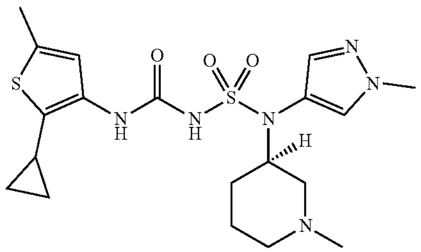 [SMILES: Cc1cc(NC(=O)NS(=O)(=O)N(c2cnn(C)c2)[C@@H]2CCCN(C)C2)c(C2CC2)s1]

3-(2-Cyclopropyl-5-methylthiophen-3-yl)-1-[(1-methyl-1H-pyrazol-4-yl)[(3R)-1-methylpiperidin-3-yl]sulfamoyl]urea was prepared following a procedure similar to Example 18 using Intermediate 32 and Intermediate 61, isolated as the sodium salt. $^1$H NMR (400 MHz, MeOD) δ 7.64 (s, 1H), 7.41 (s, 1H), 7.01 (s, 1H), 4.35-4.29 (m, 1H), 3.83 (s, 3H), 3.53-3.46 (m, 1H), 3.10-3.03 (m, 1H), 2.59 (s, 3H), 2.40-2.30 (m, 5H), 2.09-1.99 (m, 1H), 1.92-1.84 (m, 1H), 1.79-1.70 (m, 2H), 1.23-1.16 (m, 1H), 0.93-0.88 (m, 2H), 0.56-0.53 (m, 2H). LCMS (ESI): m/z: $[M+H]^+$=453.2.

Example 85. 1-[(1-Methyl-1H-pyrazol-4-yl)(1-methylpiperidin-4-yl)sulfamoyl]-3-{2-methyl-4H,5H,6H-cyclopenta[b]thiophen-3-yl}urea [Compound 109]

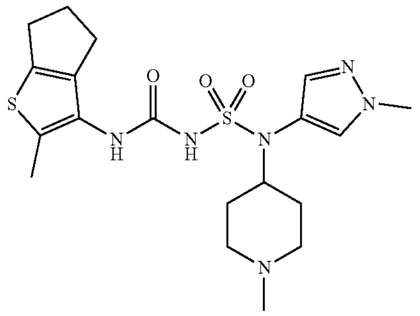 [SMILES: Cc1sc2c(c1NC(=O)NS(=O)(=O)N(c1cnn(C)c1)C1CCN(C)CC1)CCC2]

1-[(1-Methyl-1H-pyrazol-4-yl)(1-methylpiperidin-4-yl)sulfamoyl]-3-{2-methyl-4H,5H,6H-cyclopenta[b]thiophen-3-yl}urea was prepared following a procedure similar to Example 18 using Intermediate 28 and Intermediate 58, isolated as the sodium salt. $^1$H NMR (400 MHz, MeOD) δ 7.64 (s, 1H), 7.40 (s, 1H), 4.25-4.22 (m, 1H), 3.82 (s, 3H), 3.19-3.16 (m, 2H), 2.80 (t, J=7 Hz, 2H), 2.73-2.62 (m, 4H), 2.51 (s, 3H), 2.42-2.35 (m, 2H), 2.23 (s, 3H), 2.09-2.06 (m, 2H), 1.60-1. 51 (m, 2H). LCMS (ESI): m/z: $[M+H]^+$=453.2.

Example 86. 1-{[(3S,5S)-5-Fluoro-1-methylpiperidin-3-yl](1-methyl-1H-pyrazol-4-yl)sulfamoyl}-3-{2-methyl-4H,5H,6H-cyclopenta[b]thiophen-3-yl}urea [Compound 110]

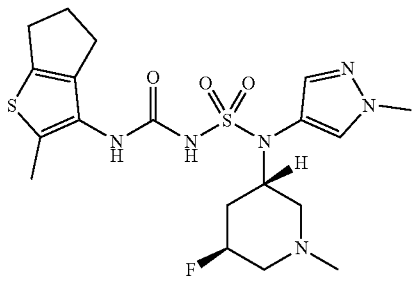 [SMILES: Cc1sc2c(c1NC(=O)NS(=O)(=O)N(c1cnn(C)c1)[C@H]1C[C@H](F)CN(C)C1)CCC2]

1-{[(3S,5S)-5-Fluoro-1-methylpiperidin-3-yl](1-methyl-1H-pyrazol-4-yl)sulfamoyl}-3-{2-methyl-4H,5H,6H-cyclopenta[b]thiophen-3-yl}urea was prepared following a procedure similar to Example 18 using Intermediate 28 and Intermediate 16, isolated as the sodium salt. $^1$H NMR (400 MHz, MeOD) δ 7.71 (s, 1H), 7.43 (s, 1H), 4.99-4.92 (m, 1H), 4.63-4.57 (m, 2H), 3.87 (s, 3H), 3.10 (t, J=12 Hz, 1H), 2.82 (t, J=7 Hz, 2H), 2.67 (t, J=7 Hz, 2H), 2.46-2.35 (m, 5H), 2.34-2.29 (m, 1H), 2.26 (s, 3H), 2.21-1.98 (m, 2H), 1.49-1.35 (m, 1H). LCMS (ESI): m/z: $[M+H]^+$=471.1.

Example 87. 1-{[(3S,5S)-5-Fluoro-1-methylpiperidin-3-yl](1-methyl-1H-pyrazol-4-yl)sulfamoyl}-3-[5-methyl-2-(propan-2-yl)thiophen-3-yl]urea [Compound 111]

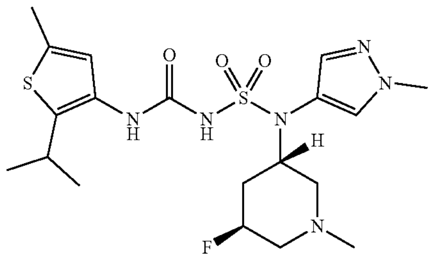 [SMILES: Cc1cc(NC(=O)NS(=O)(=O)N(c2cnn(C)c2)[C@H]2C[C@H](F)CN(C)C2)c(C(C)C)s1]

1-{[(3S,5S)-5-Fluoro-1-methylpiperidin-3-yl](1-methyl-1H-pyrazol-4-yl)sulfamoyl}-3-[5-methyl-2-(propan-2-yl)thiophen-3-yl]urea was prepared following a procedure similar to Example 1 using Intermediate 41 and Intermediate 16, isolated as the sodium salt. $^1$H NMR (400 MHz, MeOD) δ 7.71 (s, 1H), 7.42 (s, 1H), 6.85 (s, 1H), 4.98-4.95 (m, 1H), 4.63-4.56 (m, 2H), 3.85 (s, 3H), 3.16-3.01 (m, 2H), 2.38 (d, J=9 Hz, 6H), 2.32-2.26 (m, 1H), 2.21-1.96 (m, 2H), 1.51-1.29 (m, 1H), 1.23 (d, J=7 Hz, 6H). LCMS (ESI): m/z: $[M+H]^+$=473.1.

Example 88. 1-[(1-Cyclopropyl-1H-pyrazol-4-yl)(1-methylpiperidin-3-yl)sulfamoyl]-3-[5-methyl-2-(propan-2-yl)thiophen-3-yl]urea [Compound 112]

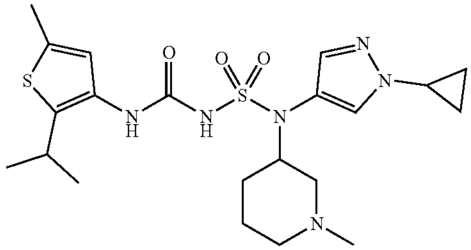 [SMILES: Cc1cc(NC(=O)NS(=O)(=O)N(c2cnn(C3CC3)c2)C2CCCN(C)C2)c(C(C)C)s1]

1-[(1-Cyclopropyl-1H-pyrazol-4-yl)(1-methylpiperidin-3-yl)sulfamoyl]-3-[5-methyl-2-(propan-2-yl)thiophen-3-yl]urea was prepared following a procedure similar to Example 18 using Intermediate 41 and Intermediate 62, isolated as the sodium salt. $^1$H NMR (400 MHz, MeOD) δ 7.70 (s, 1H), 7.41 (s, 1H), 6.84 (s, 1H), 4.40-4.28 (m, 1H), 3.64-3.50 (m, 2H), 3.15-3.05 (m, 2H), 2.64 (s, 3H), 2.49-2.33 (m, 5H), 2.07-1.99 (m, 1H), 1.95-1.71 (m, 2H), 1.25-1.13 (m, 7H), 1.08-0.96 (m, 4H). LCMS (ESI): m/z: $[M+H]^+$=481.3.

Example 89. 1-[(1-Cyclopropyl-5-fluoro-1H-pyrazol-4-yl)(1-methylpiperidin-3-yl)sulfamoyl]-3-{2-methyl-4H,5H,6H-cyclopenta[b]thiophen-3-yl}urea [Compound 113]

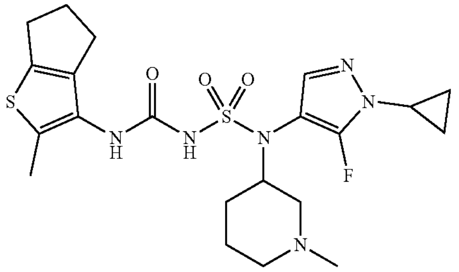 [SMILES: Cc1sc2c(c1NC(=O)NS(=O)(=O)N(c1cnn(C3CC3)c1F)C1CCCN(C)C1)CCC2]

1-[(1-Cyclopropyl-5-fluoro-1H-pyrazol-4-yl)(1-methylpiperidin-3-yl)sulfamoyl]-3-{2-methyl-4H,5H,6H-cyclopenta[b]thiophen-3-yl}urea was prepared following a procedure similar to Example 18 using Intermediate 28 and Intermediate 57, isolated as the sodium salt. $^1$H NMR (400 MHz, MeOD) δ 7.35 (d, J=3 Hz, 1H), 4.42 (t, J=11 Hz, 1H), 3.64-3.56 (m, 1H), 3.48-3.40 (m, 1H), 3.14-3.05 (m, 1H), 2.84-2.79 (m, 2H), 2.70-2.64 (m, 5H), 2.57-2.33 (m, 4H), 2.27 (s, 3H), 2.10-2.02 (m, 1H), 1.93-1.73 (m, 2H), 1.29-1.17 (m, 1H), 1.14-1.03 (m, 4H). LCMS (ESI): m/z: $[M+H]^+$=497.3.

Example 90. 1-[(1-Cyclopropyl-5-fluoro-1H-pyrazol-4-yl)(1-methylpiperidin-3-yl)sulfamoyl]-3-[5-methyl-2-(propan-2-yl)thiophen-3-yl]urea [Compound 114]

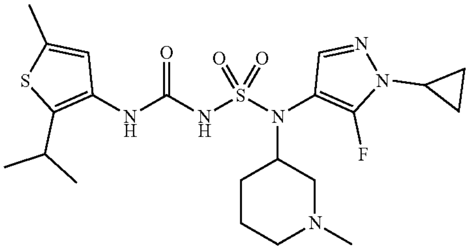 [SMILES: Cc1cc(NC(=O)NS(=O)(=O)N(c2cnn(C3CC3)c2F)C2CCCN(C)C2)c(C(C)C)s1]

1-[(1-Cyclopropyl-5-fluoro-1H-pyrazol-4-yl)(1-methylpiperidin-3-yl)sulfamoyl]-3-[5-methyl-2-(propan-2-yl)thiophen-3-yl]urea was prepared following a procedure similar to Example 18 using Intermediate 41 and Intermediate 57, isolated as the sodium salt. $^1$H NMR (400 MHz, MeOD) δ 7.34 (d, J=3 Hz, 1H), 6.82 (s, 1H), 4.43-4.38 (m, 1H), 3.58-3.56 (m, 1H), 3.46-3.41 (m, 1H), 3.16-3.12 (m, 2H), 2.68 (s, 3H), 2.56-2.42 (m, 2H), 2.38 (s, 3H), 2.12-2.03 (m, 1H), 1.95-1.88 (m, 1H), 1.86-1.75 (m, 1H), 1.24-1.21 (m, 7H), 1.10-1.05 (m, 4H). LCMS (ESI): m/z: $[M+H]^+$=499.3.

Example 91. 1-[(5-Fluoro-1-methyl-1H-pyrazol-4-yl)(1-methylpiperidin-3-yl)sulfamoyl]-3-[5-methyl-2-(propan-2-yl)thiophen-3-yl]urea [Compound 115]

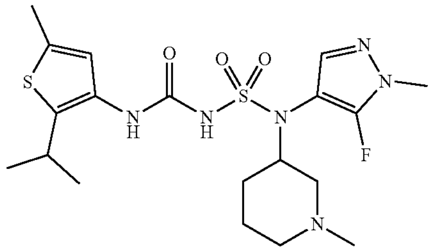 [SMILES: Cc1cc(NC(=O)NS(=O)(=O)N(c2cnn(C)c2F)C2CCCN(C)C2)c(C(C)C)s1]

1-[(5-Fluoro-1-methyl-1H-pyrazol-4-yl)(1-methylpiperidin-3-yl)sulfamoyl]-3-[5-methyl-2-(propan-2-yl)thiophen-3-yl]urea was prepared following a procedure similar to Example 18 using Intermediate 41 and Intermediate 63, isolated as the sodium salt. $^{1}$H NMR (400 MHz, MeOD) δ 7.37 (d, J=2 Hz, 1H), 6.82 (s, 1H), 4.42-4.35 (m, 1H), 3.72 (s, 3H), 3.58-3.54 (m, 1H), 3.16-3.10 (m, 2H), 2.66 (s, 3H), 2.48-2.35 (m, 5H), 2.08-2.04 (m, 1H), 1.93-1.87 (m, 1H), 1.85-1.75 (m, 1H), 1.24-1.21 (m, 7H). LCMS (ESI): m/z: $[M+H]^+$=473.2.

Example 92. 1-[(1-Methyl-1H-pyrazol-4-yl)[(3S)-1-methylpiperidin-3-yl]sulfamoyl]-3-{2-methyl-4H,5H,6H-cyclopenta[b]thiophen-3-yl}urea [Compound 116]

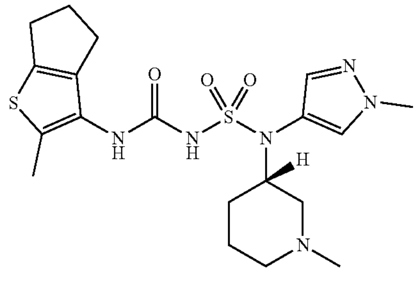 [SMILES: Cc1sc2c(c1NC(=O)NS(=O)(=O)N(c1cnn(C)c1)[C@H]1CCCN(C)C1)CCC2]

1-[(1-Methyl-1H-pyrazol-4-yl)[(3S)-1-methylpiperidin-3-yl]sulfamoyl]-3-{2-methyl-4H,5H,6H-cyclopenta[b]thiophen-3-yl}urea was prepared following a procedure similar to Example 18 using Intermediate 28 and Intermediate 33, isolated as the sodium salt. $^{1}$H NMR (400 MHz, MeOD) δ 7.64 (s, 1H), 7.41 (s, 1H), 4.35 (t, J=11 Hz, 1H), 3.86 (s, 3H), 3.58-3.48 (m, 1H), 3.14-3.05 (m, 1H), 2.81 (t, J=7 Hz, 2H), 2.67 (t, J=7 Hz, 2H), 2.61 (s, 3H), 2.43-2.34 (m, 4H), 2.26 (s, 3H), 2.04-2.00 (m, 1H), 1.92-1.84 (m, 1H), 1.83-1.70 (m, 1H), 1.26-1.14 (m, 1H). LCMS (ESI): m/z: $[M+H]^+$=453.2.

Example 93. 1-[(1-Methyl-1H-pyrazol-4-yl)(1-methylpiperidin-3-yl)sulfamoyl]-3-[2-methyl-5-(trifluoromethyl)thiophen-3-yl]urea [Compound 117]

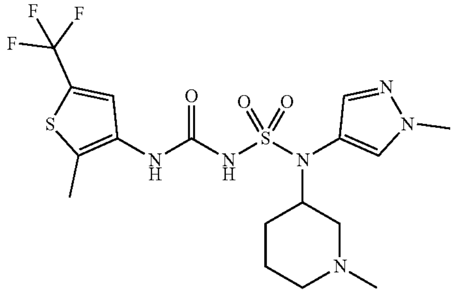 [SMILES: Cc1sc(C(F)(F)F)cc1NC(=O)NS(=O)(=O)N(c1cnn(C)c1)C1CCCN(C)C1]

1-[(1-Methyl-1H-pyrazol-4-yl)(1-methylpiperidin-3-yl)sulfamoyl]-3-[2-methyl-5-(trifluoromethyl)thiophen-3-yl]urea was prepared following a procedure similar to Example 18 using Intermediate 2 and Intermediate 64, isolated as the sodium salt. $^{1}$H NMR (400 MHz, MeOD) δ 7.68 (s, 1H), 7.63 (s, 1H), 7.41 (s, 1H), 4.39-4.33 (m, 1H), 3.84 (s, 3H), 3.70-3.60 (m, 1H), 3.25-3.15 (m, 1H), 2.73 (s, 3H), 2.72-2.52 (m, 2H), 2.31 (s, 3H), 2.06-2.03 (m, 1H), 1.98-1.90 (m, 1H), 1.86-1.73 (m, 1H), 1.29-1.24 (m, 1H). LCMS (ESI): m/z: $[M+H]^+$=481.2.

Example 94. 1-[(1-Cyclopropyl-1H-pyrazol-4-yl)(1-methylpiperidin-3-yl)sulfamoyl]-3-{2-methyl-4H,5H,6H-cyclopenta[b]thiophen-3-yl}urea [Compound 118]

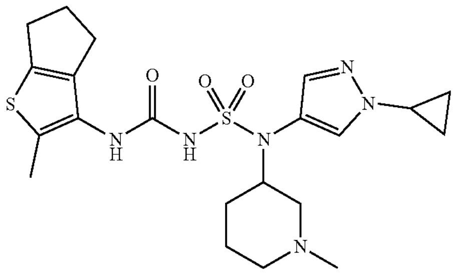 [SMILES: Cc1sc2c(c1NC(=O)NS(=O)(=O)N(c1cnn(C3CC3)c1)C1CCCN(C)C1)CCC2]

1-[(1-Cyclopropyl-1H-pyrazol-4-yl)(1-methylpiperidin-3-yl)sulfamoyl]-3-{2-methyl-4H,5H,6H-cyclopenta[b]thiophen-3-yl}urea was prepared following a procedure similar to Example 18 using Intermediate 28 and Intermediate 62, isolated as the sodium salt. $^{1}$H NMR (400 MHz, MeOD) δ 7.70 (s, 1H), 7.41 (s, 1H), 4.36-4.25 (m, 1H), 3.68-3.57 (m, 1H), 3.55-3.43 (m, 1H), 3.12-3.00 (m, 1H), 2.85-2.75 (m, 2H), 2.68-2.65 (m, 2H), 2.61 (s, 3H), 2.45-2.30 (m, 4H), 2.26 (s, 3H), 2.06-1.95 (m, 1H), 1.90-1.85 (m, 1H), 1.82-1.62 (m, 1H), 1.26-1.14 (m, 1H), 1.13-0.95 (m, 4H). LCMS (ESI): m/z: $[M+H]^+$=479.3.

Example 95. 1-[(5-Fluoro-1-methyl-1H-pyrazol-4-yl)(1-methylpiperidin-3-yl)sulfamoyl]-3-{2-methyl-4H,5H,6H-cyclopenta[b]thiophen-3-yl}urea [Compound 119]

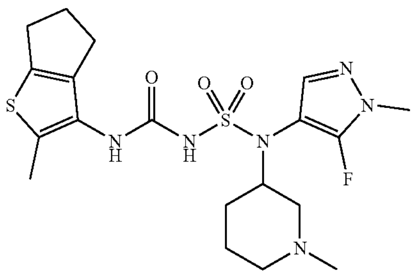 [SMILES: Cc1sc2c(c1NC(=O)NS(=O)(=O)N(c1cnn(C)c1F)C1CCCN(C)C1)CCC2]

1-[(5-Fluoro-1-methyl-1H-pyrazol-4-yl)(1-methylpiperidin-3-yl)sulfamoyl]-3-{2-methyl-4H,5H,6H-cyclopenta[b]thiophen-3-yl}urea was prepared following a procedure similar to Example 18 using Intermediate 28 and Intermediate 63, isolated as the sodium salt. $^1$H NMR (400 MHz, MeOD) δ 7.37 (s, 1H), 4.39-4.37 (m, 1H), 3.73 (s, 3H), 3.54-3.52 (m, 1H), 3.13-3.09 (m, 1H), 2.81-2.78 (m, 2H), 2.71-2.63 (m, 5H), 2.48-2.34 (m, 4H), 2.26 (s, 3H), 2.06-2.03 (m, 1H), 1.92-1.90 (m, 1H), 1.88-1.77 (m, 1H), 1.24-1.21 (m, 1H). LCMS (ESI): m/z: $[M+H]^+$=471.2.

Example 96. 1-[(5-Fluoro-1-methyl-1H-pyrazol-4-yl)(1-methylpiperidin-4-yl)sulfamoyl]-3-{2-methyl-4H,5H,6H-cyclopenta[b]thiophen-3-yl}urea [Compound 120]

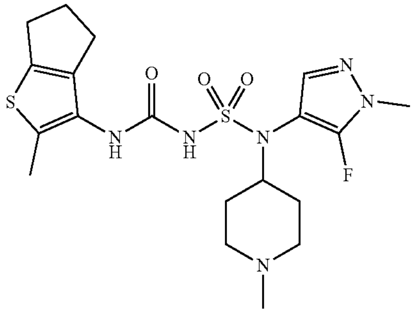 [SMILES: Cc1sc2c(c1NC(=O)NS(=O)(=O)N(c1cnn(C)c1F)C1CCN(C)CC1)CCC2]

1-[(5-Fluoro-1-methyl-1H-pyrazol-4-yl)(1-methylpiperidin-4-yl)sulfamoyl]-3-{2-methyl-4H,5H,6H-cyclopenta[b]thiophen-3-yl}urea was prepared following a procedure similar to Example 18 using Intermediate 28 and Intermediate 59, isolated as the sodium salt. $^1$H NMR (400 MHz, MeOD) δ 7.38 (d, J=2 Hz, 1H), 4.34-4.25 (m, 1H), 3.73 (s, 3H), 3.22-3.17 (m, 2H), 2.81 (t, J=7 Hz, 2H), 2.73-2.63 (m, 4H), 2.55 (s, 3H), 2.42-2.34 (m, 2H), 2.26 (s, 3H), 2.14-2.08 (m, 2H), 1.55-1.51 (m, 2H). LCMS (ESI): m/z: $[M+H]^+$=471.2.

Example 97. 1-[(1-Methyl-1H-pyrazol-4-yl)(1-methylpiperidin-3-yl)sulfamoyl]-3-[5-(propan-2-yl)-2-(trifluoromethyl)thiophen-3-yl]urea [Compound 121]

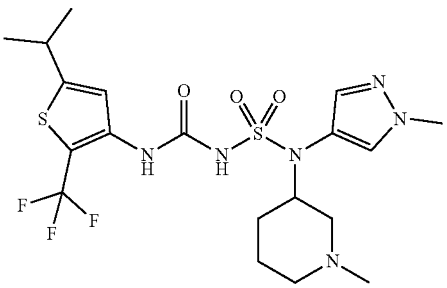 [SMILES: CC(C)c1cc(NC(=O)NS(=O)(=O)N(c2cnn(C)c2)C2CCCN(C)C2)c(C(F)(F)F)s1]

1-[(1-Methyl-1H-pyrazol-4-yl)(1-methylpiperidin-3-yl)sulfamoyl]-3-[5-(propan-2-yl)-2-(trifluoromethyl)thiophen-3-yl]urea was prepared following a procedure similar to Example 18 using Intermediate 2 and Intermediate 65, isolated as the sodium salt. $^1$H NMR (400 MHz, MeOD) δ 7.62 (s, 1H), 7.52 (s, 1H), 7.40 (s, 1H), 4.39-4.35 (m, 1H), 3.83 (s, 3H), 3.66-3.62 (m, 1H), 3.30-3.20 (m, 1H), 3.19-3.11 (m, 1H), 2.76 (s, 3H), 2.68-2.51 (m, 2H), 2.10-2.02 (m, 1H), 1.99-1.91 (m, 1H), 1.88-1.75 (m, 1H), 1.35-1.24 (m, 7H). LCMS (ESI): m/z: $[M+H]^+$=509.2.

Example 98. 3-{2-Tert-butyl-4H,5H,6H-cyclopenta[b]thiophen-3-yl}-1-[(1-methyl-1H-pyrazol-4-yl)(1-methylpiperidin-3-yl)sulfamoyl]urea [Compound 122]

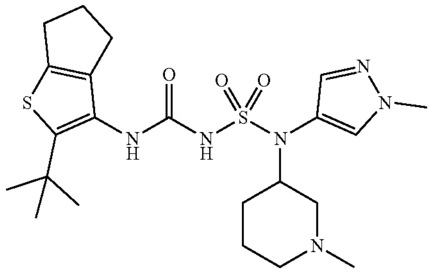 [SMILES: CN1CCCC(N(c2cnn(C)c2)S(=O)(=O)NC(=O)Nc2c(C(C)(C)C)sc3c2CCC3)C1]

3-{2-Tert-butyl-4H,5H,6H-cyclopenta[b]thiophen-3-yl}-1-[(1-methyl-1H-pyrazol-4-yl)(1-methylpiperidin-3-yl)sulfamoyl]urea was prepared following a procedure similar to Example 18 using Intermediate 2 and Intermediate 66, isolated as the sodium salt. $^1$H NMR (400 MHz, MeOD) δ 7.64 (s, 1H), 7.42 (s, 1H), 4.34-4.23 (m, 1H), 3.49-3.47 (m, 1H), 3.10-3.00 (m, 1H), 2.81 (t, J=7 Hz, 2H), 2.65 (t, J=7 Hz, 2H), 2.57 (s, 3H), 2.39-2.21 (m, 4H), 2.05-1.95 (m, 1H), 1.91-1.82 (m, 1H), 1.75-1.66 (m, 1H), 1.37 (s, 9H), 1.21-1.10 (m, 1H). LCMS (ESI): m/z: $[M+H]^+$=495.3.

Example 99. 3-[5-Chloro-2-(propan-2-yl)thiophen-3-yl]-1-[(1-methyl-1H-pyrazol-4-yl)(1-methylpiperidin-4-yl)sulfamoyl]urea [Compound 123]

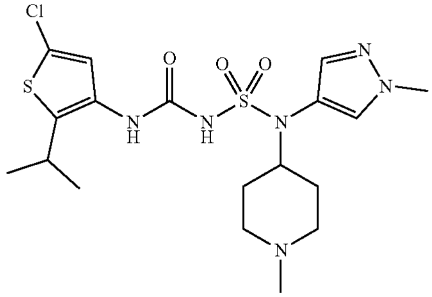 [SMILES: CC(C)c1sc(Cl)cc1NC(=O)NS(=O)(=O)N(c1cnn(C)c1)C1CCN(C)CC1]

3-[5-Chloro-2-(propan-2-yl)thiophen-3-yl]-1-[(1-methyl-1H-pyrazol-4-yl)(1-methylpiperidin-4-yl)sulfamoyl]urea was prepared following a procedure similar to Example 18 using Intermediate 37 and Intermediate 58, isolated as the sodium salt. $^1$H NMR (400 MHz, MeOD) δ 7.64 (s, 1H), 7.40 (s, 1H), 7.12 (s, 1H), 4.29-4.23 (m, 1H), 3.84 (s, 3H), 3.29-3.25 (m, 2H), 3.17-3.10 (m, 1H), 2.88-2.82 (m, 2H), 2.62 (s, 3H), 2.16-2.12 (m, 2H), 1.61-1.52 (m, 2H), 1.23 (d, J=7 Hz, 6H). LCMS (ESI): m/z: $[M+H]^+$=475.2.

Example 100. 1-[(1-Methyl-1H-pyrazol-4-yl)(1-methylpiperidin-3-yl)sulfamoyl]-3-[3-methyl-5-(propan-2-yl)-1,2-thiazol-4-yl]urea [Compound 124]

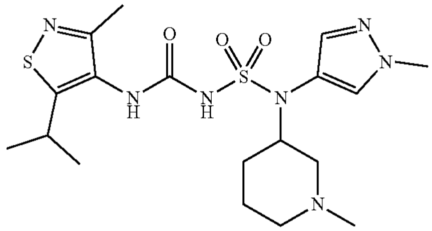 [SMILES: Cc1nsc(C(C)C)c1NC(=O)NS(=O)(=O)N(c1cnn(C)c1)C1CCCN(C)C1]

1-[(1-Methyl-1H-pyrazol-4-yl)(1-methylpiperidin-3-yl)sulfamoyl]-3-[3-methyl-5-(propan-2-yl)-1,2-thiazol-4-yl]urea was prepared following a procedure similar to Example 18 using Intermediate 2 and Intermediate 67, isolated as the sodium salt. $^1$H NMR (400 MHz, MeOD) δ 7.64 (s, 1H), 7.41 (s, 1H), 4.45-4.30 (m, 1H), 3.86 (s, 3H), 3.68-3.60 (m, 1H), 3.31-3.25 (m, 1H), 3.20-3.10 (m, 1H), 2.69 (s, 3H), 2.57-2.49 (m, 2H), 2.31 (s, 3H), 2.08-1.94 (m, 1H), 1.91-1.77 (m, 2H), 1.35-1.30 (d, J=6 Hz, 6H), 1.25-1.15 (m, 1H). LCMS (ESI): m/z: $[M+H]^+$=456.2.

Example 101. 1-[(1-Methyl-1H-pyrazol-4-yl)[(3S)-1-methylpyrrolidin-3-yl]sulfamoyl]-3-{2-methyl-4H,5H,6H-cyclopenta[b]thiophen-3-yl}urea [Compound 125]

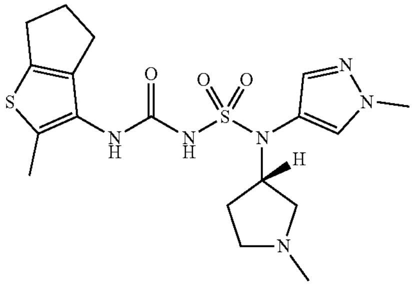 [SMILES: Cc1sc2c(c1NC(=O)NS(=O)(=O)N(c1cnn(C)c1)[C@H]1CCN(C)C1)CCC2]

1-[(1-Methyl-1H-pyrazol-4-yl)[(3S)-1-methylpyrrolidin-3-yl]sulfamoyl]-3-{2-methyl-4H,5H,6H-cyclopenta[b]thiophen-3-yl}urea was prepared following a procedure similar to Example 18 using Intermediate 28 and Intermediate 68, isolated as the sodium salt. $^1$H NMR (400 MHz, MeOD) δ 7.70 (s, 1H), 7.49 (s, 1H), 4.98-4.93 (m, 1H), 3.87 (s, 3H), 3.52-3.40 (m, 1H), 3.38-3.33 (m, 1H), 3.14-3.05 (m, 2H), 2.81 (t, J=7 Hz, 2H), 2.73 (s, 3H), 2.66 (t, J=7 Hz, 2H), 2.44-2.30 (m, 3H), 2.25 (s, 3H), 2.11-1.99 (m, 1H). $^1$H NMR (400 MHz, chloroform-d) δ 7.52 (s, 1H), 7.49 (s, 1H), 5.05-4.90 (m, 1H), 4.09-3.97 (s, 1H), 3.88 (s, 3H), 3.72-3.57 (m, 1H), 2.85-2.79 (m, 2H), 2.72-2.62 (m, 6H), 2.58-2.47 (m, 2H), 2.43-2.33 (m, 2H), 2.24 (s, 3H), 2.04-1.92 (m, 1H). LCMS (ESI): m/z: $[M+H]^+$=439.2.

Example 102. 1-[(1-Methyl-1H-pyrazol-4-yl)[(3R)-1-methylpyrrolidin-3-yl]sulfamoyl]-3-{2-methyl-4H,5H,6H-cyclopenta[b]thiophen-3-yl}urea [Compound 126]

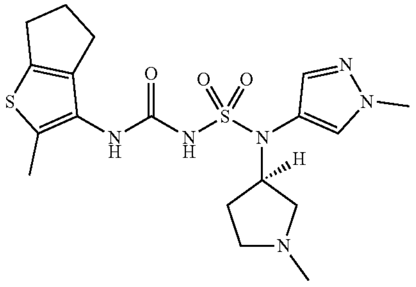 [SMILES: Cc1sc2c(c1NC(=O)NS(=O)(=O)N(c1cnn(C)c1)[C@@H]1CCN(C)C1)CCC2]

1-[(1-Methyl-1H-pyrazol-4-yl)[(3R)-1-methylpyrrolidin-3-yl]sulfamoyl]-3-{2-methyl-4H,5H,6H-cyclopenta[b]thiophen-3-yl}urea was prepared following a procedure similar to Example 18 using Intermediate 28 and Intermediate 69, isolated as the sodium salt. $^1$H NMR (400 MHz, chloroform-d) δ 7.55 (s, 1H), 7.45 (s, 1H), 7.32 (s, 1H), 4.95-4.85 (m, 1H), 3.84 (s, 3H), 3.75-3.58 (m, 1H), 3.42-3.11 (m, 1H), 2.86-2.68 (m, 3H), 2.65-2.60 (m, 2H), 2.55-2.50 (m, 4H), 2.41-2.26 (m, 3H), 2.25-2.20 (m, 3H), 1.92-1.84 (m, 1H). LCMS (ESI): m/z: $[M+H]^+$=439.1.

Example 103. 1-[(1-Methyl-1H-pyrazol-4-yl)[(3S)-1-methylpyrrolidin-3-yl]sulfamoyl]-3-[5-methyl-2-(propan-2-yl)thiophen-3-yl]urea [Compound 127]

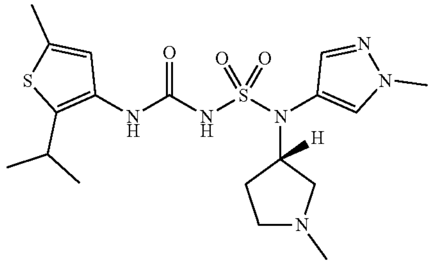 [SMILES: Cc1cc(NC(=O)NS(=O)(=O)N(c2cnn(C)c2)[C@H]2CCN(C)C2)c(C(C)C)s1]

1-[(1-Methyl-1H-pyrazol-4-yl)[(3S)-1-methylpyrrolidin-3-yl]sulfamoyl]-3-[5-methyl-2-(propan-2-yl)thiophen-3-yl]urea was prepared following a procedure similar to Example 18 using Intermediate 28 and Intermediate 69, isolated as the sodium salt. $^1$H NMR (400 MHz, MeOD) δ 7.70 (s, 1H), 7.48 (s, 1H), 6.84 (s, 1H), 4.99-4.94 (m, 1H), 3.85 (s, 3H), 3.53-3.44 (m, 1H), 3.37-3.34 (m, 1H), 3.17-3.05 (m, 3H), 2.73 (s, 3H), 2.42-2.30 (m, 4H), 2.10-1.98 (m, 1H), 1.21 (d, J=7 Hz, 6H). $^1$H NMR (400 MHz, chloroform-d) δ 7.86 (s, 1H), 7.49 (s, 1H), 7.46 (s, 1H), 6.98 (s, 1H), 5.00-4.86 (m, 1H), 4.12-3.96 (m, 1H), 3.84 (s, 3H), 3.77-3.63 (m, 1H), 3.03-2.92 (m, 1H), 2.86-2.76 (m, 1H), 2.73-2.61 (m, 4H), 2.57-2.47 (m, 1H), 2.40 (s, 3H), 2.06-1.94 (m, 1H), 1.20 (d, J=5 Hz, 6H). LCMS (ESI): m/z: $[M+H]^+$=441.2.

Example 104. 3-[5-Chloro-2-(propan-2-yl)thiophen-3-yl]-1-[(1-methyl-1H-pyrazol-4-yl)-[(3S)-1-methylpyrrolidin-3-yl]sulfamoyl]urea [Compound 128]

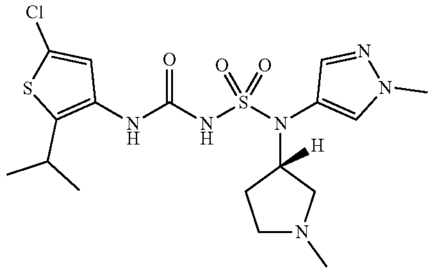 [SMILES: CC(C)c1sc(Cl)cc1NC(=O)NS(=O)(=O)N(c1cnn(C)c1)[C@H]1CCN(C)C1]

3-[5-Chloro-2-(propan-2-yl)thiophen-3-yl]-1-[(1-methyl-1H-pyrazol-4-yl)[(3S)-1-methylpyrrolidin-3-yl]sulfamoyl]urea was prepared following a procedure similar to Example 18 using Intermediate 37 and Intermediate 68, isolated as the sodium salt. $^1$H NMR (400 MHz, MeOD) δ 7.69 (s, 1H), 7.48 (s, 1H), 7.10 (s, 1H), 4.94-4.91 (m, 1H), 3.85 (s, 3H), 3.60-3.50 (m, 1H), 3.45-3.35 (m, 1H), 3.20-3.11 (m, 3H), 2.79 (s, 3H), 2.42-2.31 (m, 1H), 2.13-2.00 (m, 1H), 1.22 (d, J=7 Hz, 6H). LCMS (ESI): m/z: $[M+H]^+$=461.1.

Example 105. 3-[5-Chloro-2-(propan-2-yl)thiophen-3-yl]-1-[(1-methyl-1H-pyrazol-4-yl)-[(3R)-1-methylpyrrolidin-3-yl]sulfamoyl]urea [Compound 129]

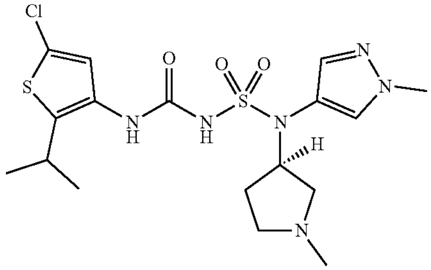 [SMILES: CC(C)c1sc(Cl)cc1NC(=O)NS(=O)(=O)N(c1cnn(C)c1)[C@@H]1CCN(C)C1]

3-[5-Chloro-2-(propan-2-yl)thiophen-3-yl]-1-[(1-methyl-1H-pyrazol-4-yl)[(3R)-1-methylpyrrolidin-3-yl]sulfamoyl]urea was prepared following a procedure similar to Example 18 using Intermediate 37 and Intermediate 69, isolated as the sodium salt. $^1$H NMR (400 MHz, chloroform-d) δ 7.93 (s, 1H), 7.50 (s, 1H), 7.46 (s, 1H), 7.21 (s, 1H), 5.00-4.86 (m, 1H), 4.15-4.11 (m, 1H), 3.90-3.71 (m, 4H), 3.01-2.82 (m, 2H), 2.80-2.68 (m, 4H), 2.60-2.48 (m, 1H), 2.07-1.97 (m, 1H), 1.23-1.12 (m, 6H). LCMS (ESI): m/z: $[M+H]^+$=461.1.

Example 106. 1-[(1-Methyl-1H-pyrazol-4-yl)[(3R)-1-methylpyrrolidin-3-yl]sulfamoyl]-3-[5-methyl-2-(propan-2-yl)thiophen-3-yl]urea [Compound 130]

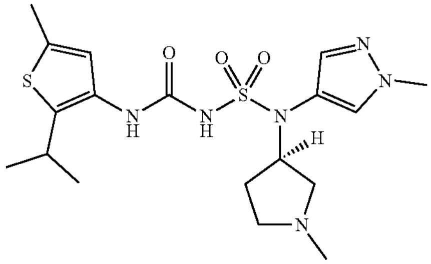 [SMILES: Cc1cc(NC(=O)NS(=O)(=O)N(c2cnn(C)c2)[C@@H]2CCN(C)C2)c(C(C)C)s1]

1-[(1-Methyl-1H-pyrazol-4-yl)[(3R)-1-methylpyrrolidin-3-yl]sulfamoyl]-3-[5-methyl-2-(propan-2-yl)thiophen-3-yl]urea was prepared following a procedure similar to Example 18 using Intermediate 41 and Intermediate 69, isolated as the sodium salt. $^1$H NMR (400 MHz, chloroform-d) δ 7.81-7.65 (br. s, 1H), 7.51 (s, 1H), 7.45 (s, 1H), 6.96 (s, 1H), 4.97-4.81 (m, 1H), 3.92-3.72 (m, 4H), 3.53-3.44 (m, 1H), 3.06-2.98 (m, 1H), 2.80-2.46 (m, 5H), 2.40-2.37 (m, 4H), 1.98-1.85 (m, 1H), 1.20 (d, J=6 Hz, 6H). LCMS (ESI): m/z: $[M+H]^+$=441.2.

Example 107. 3-[5-Cyano-2-(propan-2-yl)thiophen-3-yl]-1-[(1-methyl-1H-pyrazol-4-yl)(1-methylpiperidin-3-yl)sulfamoyl]urea [Compound 131]

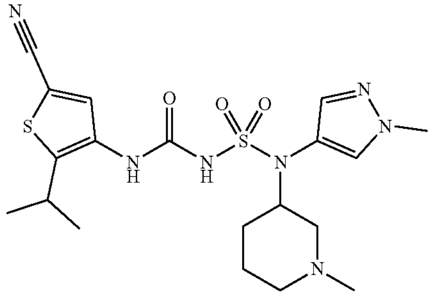 [SMILES: CC(C)c1sc(C#N)cc1NC(=O)NS(=O)(=O)N(c1cnn(C)c1)C1CCCN(C)C1]

3-[5-Cyano-2-(propan-2-yl)thiophen-3-yl]-1-[(1-methyl-1H-pyrazol-4-yl)(1-methylpiperidin-3-yl)sulfamoyl]urea was prepared following a procedure similar to Example 18 using Intermediate 2 and Intermediate 70, isolated as the sodium salt. $^1$H NMR (400 MHz, chloroform-d) δ 8.03 (s, 1H), 7.92 (s, 1H), 7.45 (s, 1H), 7.36 (s, 1H), 4.58-4.44 (m, 1H), 3.97-3.88 (m, 1H), 3.86 (s, 3H), 3.52-3.35 (m, 1H), 3.08-2.98 (m, 1H), 2.73 (s, 3H), 2.31-2.27 (m, 4H), 2.01-1.97 (m, 1H), 1.41-1.30 (m, 1H), 1.28-1.18 (m, 6H). LCMS (ESI): m/z: $[M+H]^+$=466.2.

Example 108. Biological Activity of the Compounds of the Present Disclosure

The biological activity of the compounds of the present disclosure was determined utilising the assay described herein.

PBMC $IC_{50}$ Determination Assay

The compounds of the present disclosure were tested for their inhibitory activity against IL-1β release upon NLRP3 activation in peripheral blood mononuclear cells (PBMC).

PBMC were isolated from buffy coats by density gradient centrifugation on Histopaque-1077 (Sigma, cat no. 10771). Isolated cells were seeded into the wells (280,000 cells/well) of a 96-well plate and incubated for 3 h with lipopolysaccharide (LPS, 1 μg/ml diluted 1000× from a 1 mg/ml stock solution). The compounds of the present disclosure were added (a single compound per well) and the cells were incubated for 30 min. Next, the cells were stimulated with ATP (5 mM final concentration diluted 20× from a 100 mM stock solution) for 1 h and the cell culture media from the wells were collected for further analysis.

The release of IL-1β into the media was determined by quantitative detection of IL-1β in the media using HTRF®, CisBio cat. No. 62HIL1BPEH. Briefly, cell culture supernatant were dispensed directly into the assay plate containing antibodies labelled with the HTRF® donor and acceptor. A microplate spectrophotometer (BMG) was used to detect signals at 655 nm and 620 nm. The detection range of IL-1β HTRF® was 39-6500 μg/ml.

Whole Blood (WB) Assay

The compounds of the present disclosure were tested for their inhibitory activity against IL-1β release upon NLRP3 activation in human whole blood.

Whole blood was drawn from single healthy donors and treated with sodium heparin anticoagulant. Blood was diluted with cell culture media at a 9:5 ratio, seeded in a 96-well plate and incubated for 3 h with lipopolysaccharide (LPS, 1 μg/ml final concentration diluted 1000× from a 1 mg/ml stock solution). The compounds of the present disclosure were added (a single compound concentration per well) and the blood was incubated for 30 min. Next, the blood was stimulated with ATP (5 mM final concentration diluted 20× from a 100 mM stock solution) for 1 h and the cell culture media from the wells were collected for further analysis.

The release of IL-1β into the media was determined by quantitative detection of IL-1β in the media using HTRF®, CisBio cat. No. 62HIL1BPEH. Briefly, cell culture supernatant were diluted as appropriate to bring IL-1β levels within the HTRF® detection range (36-6500 μg/ml) and subsequently dispensed into the assay plate containing antibodies labelled with the HTRF® donor and acceptor. A microplate spectrophotometer (BMG) was used to detect signals at 655 nm and 620 nm.

Determination of the $IC_{50}$ Values

The determination of the $IC_{50}$ values was preformed using the Graph Pad Prism software and the measured $IC_{50}$ values of compounds of the present disclosure are shown in Table A below. These results show that the compounds of the present disclosure are capable of inhibiting IL-1β release upon inflammasome activation.

For PBMC $IC_{50}$ values shown in Table A, "A" means $IC_{50}$<0.1 μM; "B" means $IC_{50}$ ranging between 0.1 μM and 0.5 μM; "C" means $IC_{50}$ ranging between 0.5 μM and 1 μM; "D" means $IC_{50}$ ranging between 1 μM and 5 μM; "E" means $IC_{50}$ ranging between 5 μM and 10 μM; "F" means $IC_{50}$>10 μM.

For WB $IC_{50}$ values shown in Table A, "***" means $IC_{50}$<1 μM; "" means $IC_{50}$ ranging between 1 μM and 3 μM; "*" means $IC_{50}$ ranging between 3 μM and 10 μM; "**" means $IC_{50}$ ranging between 10 μM and 20 μM; "*" means $IC_{50}$>20 μM; "ND" means not determined

TABLE A

| Compound No. | PBMC $IC_{50}$ | WB $IC_{50}$ |
|---|---|---|
| 1 | D | *** |
| 2 | C | *** |
| 3 | D | * |
| 4 | D | ** |
| 5 | E | * |
| 6 | C | * |
| 7 | D | ** |
| 8 | D | **** |
| 9 | D | *** |
| 10 | D | ** |
| 11 | A | ***** |
| 12 | C | **** |
| 13 | A | ***** |
| 14 | A | **** |
| 15 | C | * |
| 16 | B | **** |
| 17 | E | ND |
| 18 | B | **** |
| 19 | B | **** |
| 28 | B | **** |
| 29 | B | **** |
| 31 | E | ND |
| 32 | B | ***** |
| 37 | A | **** |
| 38 | A | **** |
| 43 | A | ***** |
| 50 | C | **** |
| 52 | A | **** |
| 53 | A | **** |
| 54 | A | ***** |
| 55 | A | ***** |
| 56 | A | ***** |
| 57 | B | **** |

TABLE A-continued

| Compound No. | PBMC $IC_{50}$ | WB $IC_{50}$ |
|---|---|---|
| 58 | A | ***** |
| 59 | A | **** |
| 60 | A | ***** |
| 61 | A | *** |
| 62 | C | **** |
| 63 | D | ND |
| 64 | D | ** |
| 65 | D | * |
| 66 | A | ***** |
| 67 | B | ***** |
| 68 | E | ND |
| 69 | F | * |
| 70 | B | ***** |
| 71 | B | **** |
| 72 | D | ND |
| 73 | A | ***** |
| 74 | D | ND |
| 75 | B | *** |
| 76 | B | *** |
| 77 | A | ***** |
| 78 | C | **** |
| 79 | A | ***** |
| 80 | A | ***** |
| 81 | A | ***** |
| 82 | A | **** |
| 83 | B | **** |
| 84 | A | ***** |
| 85 | A | ***** |
| 86 | B | **** |
| 87 | B | **** |
| 88 | A | ***** |
| 89 | A | **** |
| 90 | B | **** |
| 91 | A | ***** |
| 92 | A | ***** |
| 93 | B | *** |
| 94 | B | ***** |
| 95 | B | ***** |
| 96 | B | *** |
| 97 | B | ***** |
| 98 | B | **** |
| 99 | A | **** |
| 100 | B | ***** |
| 101 | A | ***** |
| 102 | B | **** |
| 103 | A | ***** |
| 104 | A | ***** |
| 105 | B | ND |
| 106 | B | **** |
| 107 | B | **** |
| 108 | A | **** |
| 109 | B | **** |
| 110 | B | **** |
| 111 | B | **** |
| 112 | A | ***** |
| 113 | A | ***** |
| 114 | A | ***** |
| 115 | A | ***** |
| 116 | A | ***** |
| 117 | B | ***** |
| 118 | A | ***** |
| 119 | A | ***** |
| 120 | A | **** |
| 121 | B | *** |
| 122 | C | ** |
| 123 | A | **** |
| 124 | F | * |
| 125 | A | ***** |
| 126 | A | ***** |
| 127 | A | ***** |
| 128 | A | ***** |
| 129 | A | ***** |
| 130 | A | ***** |
| 131 | C | *** |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound selected from:

| Compound No. | Structure |
|---|---|
| 1 | 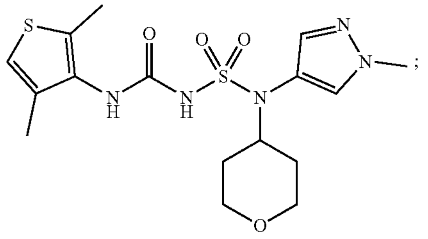 [SMILES: Cc1csc(C)c1NC(=O)NS(=O)(=O)N(c1cnn(C)c1)C1CCOCC1] |
| 2 | 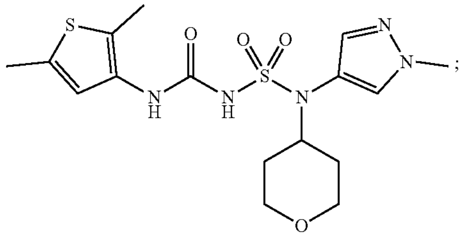 |
| 3 | 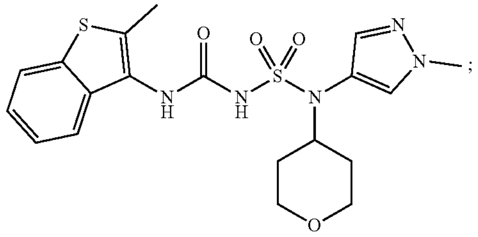 [SMILES: Cc1sc2ccccc2c1NC(=O)NS(=O)(=O)N(c1cnn(C)c1)C1CCOCC1] |

-continued
| Compound No. | Structure |
|---|---|
| 4 | 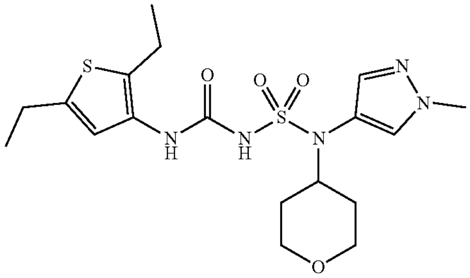 ; |
| 6 | 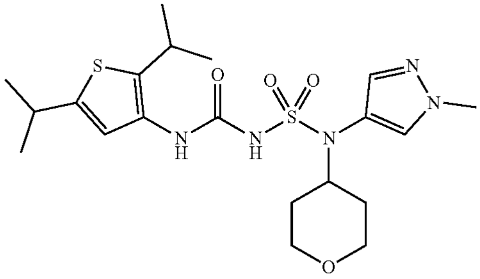 ; |
| 7 | 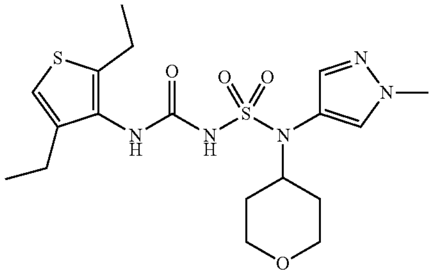 ; |
| 8 | 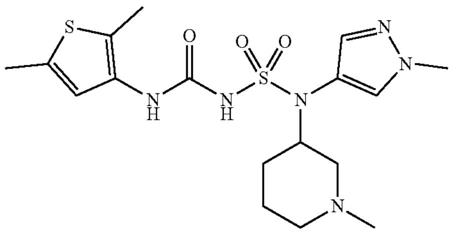 ; |
| 9 | 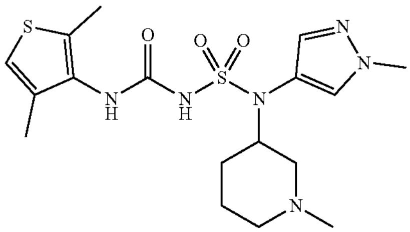 ; |
-continued
| Compound No. | Structure |
|---|---|
| 10 | 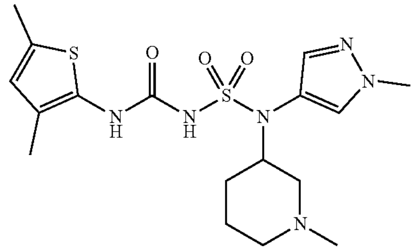 ; |
| 11 | 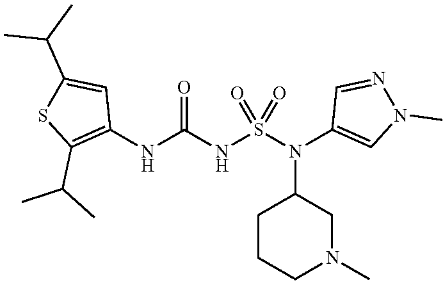 ; |
| 12 | 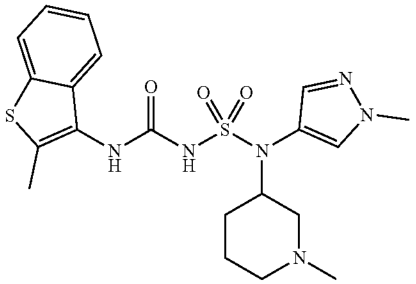 ; |
| 13 | 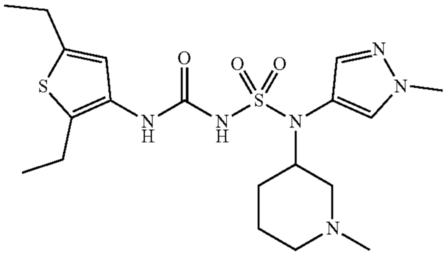 ; |
| 14 | 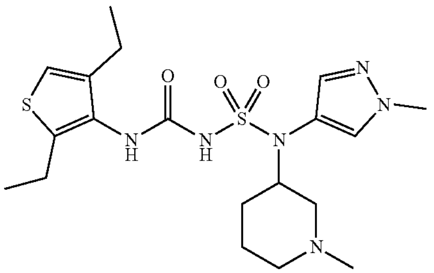 ; |

-continued
| Compound No. | Structure |
|---|---|
| 15 | 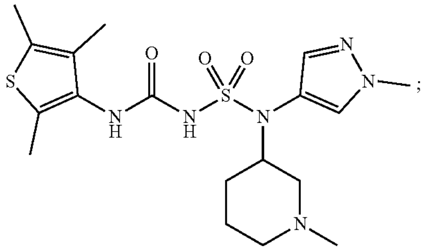 [SMILES: Cc1sc(C)c(NC(=O)NS(=O)(=O)N(c2cnn(C)c2)C2CCCN(C)C2)c1C] |
| 16 | 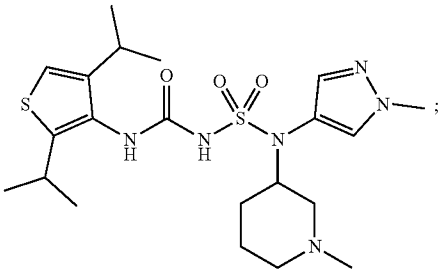 [SMILES: CC(C)c1csc(C(C)C)c1NC(=O)NS(=O)(=O)N(c1cnn(C)c1)C1CCCN(C)C1] |
| 18 | 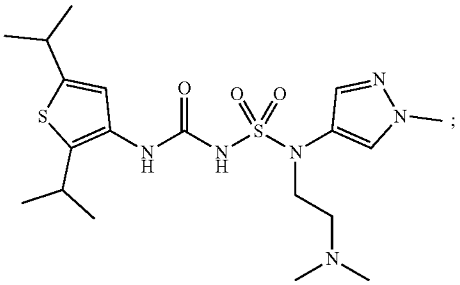 [SMILES: CC(C)c1cc(NC(=O)NS(=O)(=O)N(CCN(C)C)c2cnn(C)c2)c(C(C)C)s1] |
| 19 | 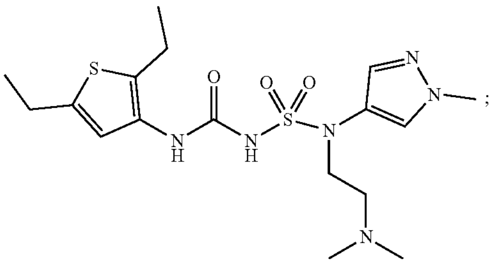 [SMILES: CCc1cc(NC(=O)NS(=O)(=O)N(CCN(C)C)c2cnn(C)c2)c(CC)s1] |
| 20 | 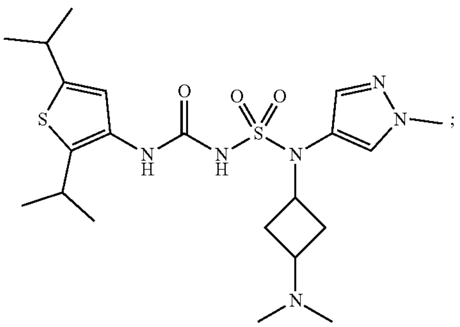 [SMILES: CC(C)c1cc(NC(=O)NS(=O)(=O)N(c2cnn(C)c2)C2CC(N(C)C)C2)c(C(C)C)s1] |
-continued
| Compound No. | Structure |
|---|---|
| 21 | 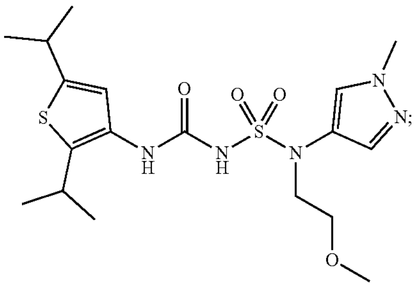 [SMILES: COCCN(c1cnn(C)c1)S(=O)(=O)NC(=O)Nc1cc(C(C)C)sc1C(C)C] |
| 22 | 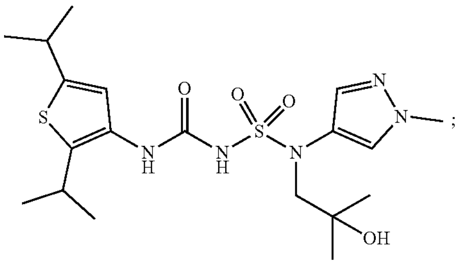 [SMILES: CC(C)c1cc(NC(=O)NS(=O)(=O)N(CC(C)(C)O)c2cnn(C)c2)c(C(C)C)s1] |
| 23 | 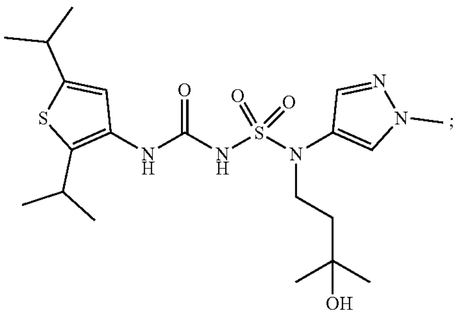 [SMILES: CC(C)c1cc(NC(=O)NS(=O)(=O)N(CCC(C)(C)O)c2cnn(C)c2)c(C(C)C)s1] |
| 24 | 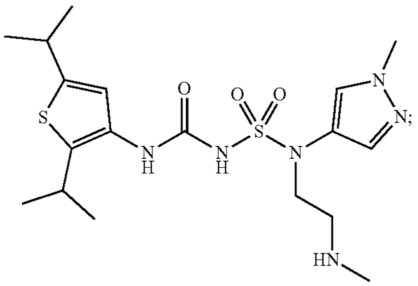 [SMILES: CNCCN(c1cnn(C)c1)S(=O)(=O)NC(=O)Nc1cc(C(C)C)sc1C(C)C] |
| 25 | 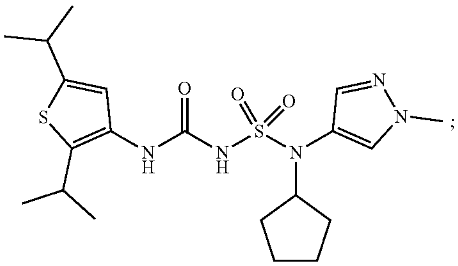 [SMILES: CC(C)c1cc(NC(=O)NS(=O)(=O)N(c2cnn(C)c2)C2CCCC2)c(C(C)C)s1] |

-continued
| Compound No. | Structure |
|---|---|
| 26 | 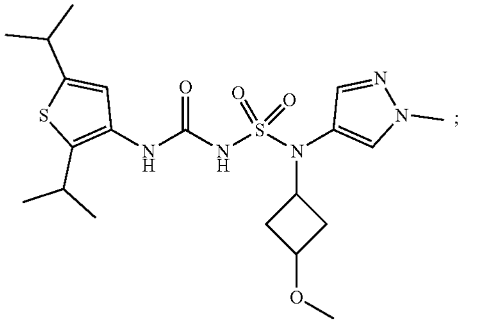 [SMILES: COC1CC(N(c2cnn(C)c2)S(=O)(=O)NC(=O)Nc2cc(C(C)C)sc2C(C)C)C1] |
| 27 | 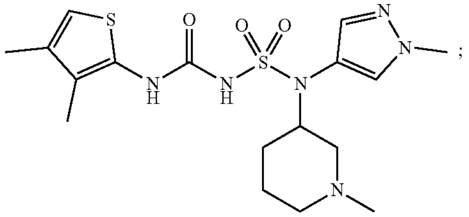 |
| 28 | 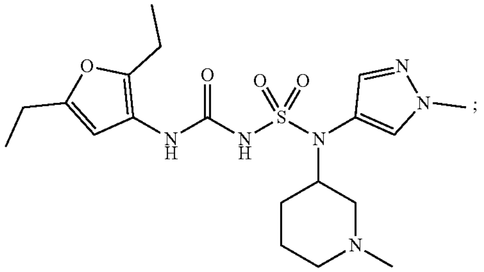 [SMILES: CCc1cc(NC(=O)NS(=O)(=O)N(c2cnn(C)c2)C2CCCN(C)C2)c(CC)o1] |
| 29 | 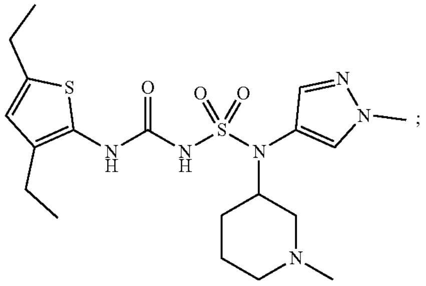 [SMILES: CCc1cc(CC)c(NC(=O)NS(=O)(=O)N(c2cnn(C)c2)C2CCCN(C)C2)s1] |
| 30 | 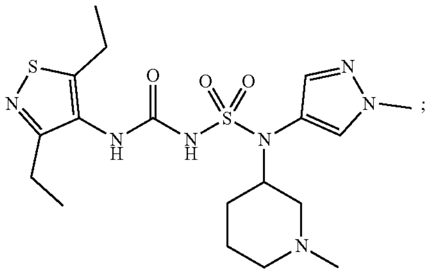 [SMILES: CCc1nsc(CC)c1NC(=O)NS(=O)(=O)N(c1cnn(C)c1)C1CCCN(C)C1] |
-continued
| Compound No. | Structure |
|---|---|
| 32 | 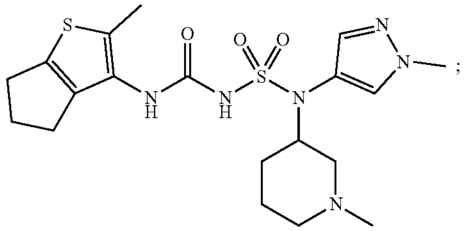 [SMILES: Cc1sc2c(c1NC(=O)NS(=O)(=O)N(c1cnn(C)c1)C1CCCN(C)C1)CCC2] |
| 33 | 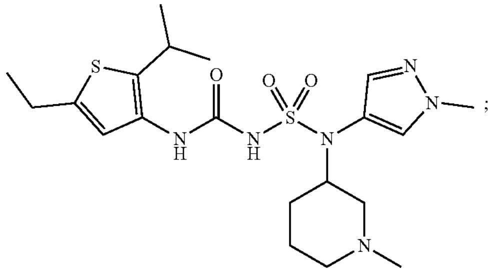 [SMILES: CCc1cc(NC(=O)NS(=O)(=O)N(c2cnn(C)c2)C2CCCN(C)C2)c(C(C)C)s1] |
| 34 | 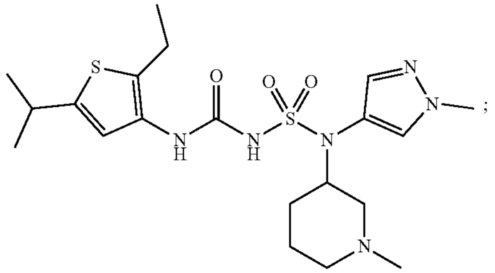 [SMILES: CCc1sc(C(C)C)cc1NC(=O)NS(=O)(=O)N(c1cnn(C)c1)C1CCCN(C)C1] |
| 35 | 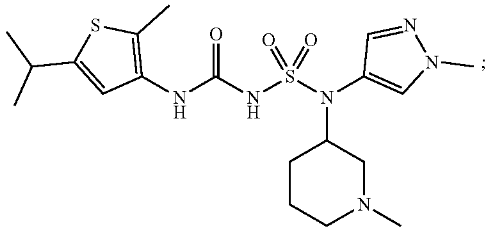 [SMILES: Cc1sc(C(C)C)cc1NC(=O)NS(=O)(=O)N(c1cnn(C)c1)C1CCCN(C)C1] |
| 36 | 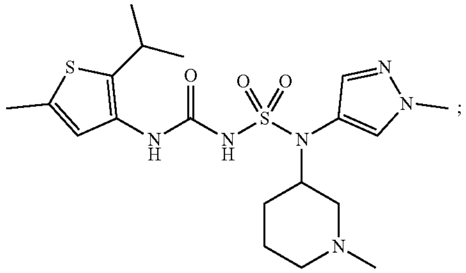 |

-continued
| Compound No. | Structure |
|---|---|
| 37 | 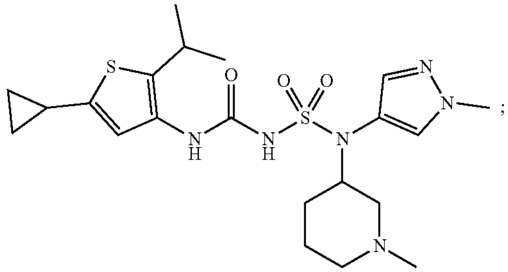 [SMILES: CC(C)c1sc(C2CC2)cc1NC(=O)NS(=O)(=O)N(c1cnn(C)c1)C1CCCN(C)C1] |
| 38 | 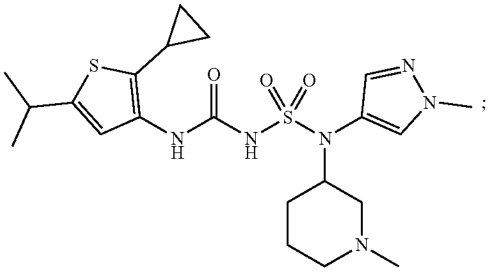 [SMILES: CC(C)c1cc(NC(=O)NS(=O)(=O)N(c2cnn(C)c2)C2CCCN(C)C2)c(C2CC2)s1] |
| 39 | 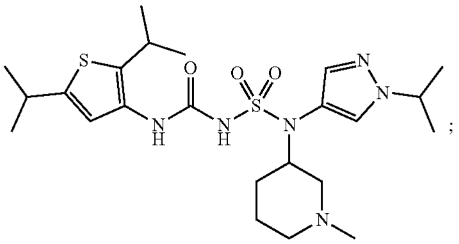 [SMILES: CC(C)c1cc(NC(=O)NS(=O)(=O)N(c2cnn(C(C)C)c2)C2CCCN(C)C2)c(C(C)C)s1] |
| 40 | 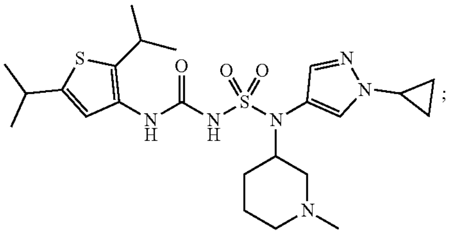 [SMILES: CC(C)c1cc(NC(=O)NS(=O)(=O)N(c2cnn(C3CC3)c2)C2CCCN(C)C2)c(C(C)C)s1] |
| 41 | 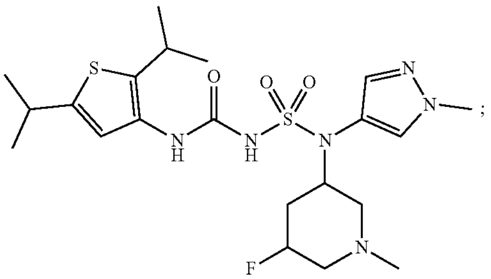 [SMILES: CC(C)c1cc(NC(=O)NS(=O)(=O)N(c2cnn(C)c2)C2CC(F)CN(C)C2)c(C(C)C)s1] |
-continued
| Compound No. | Structure |
|---|---|
| 42 | 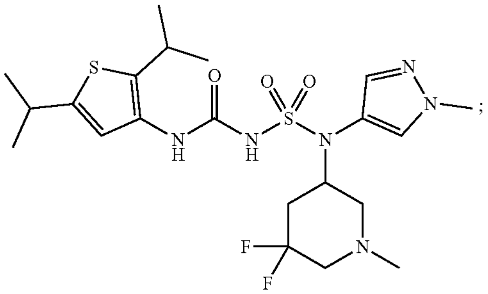 [SMILES: CC(C)c1cc(NC(=O)NS(=O)(=O)N(c2cnn(C)c2)C2CN(C)CC(F)(F)C2)c(C(C)C)s1] |
| 43 | 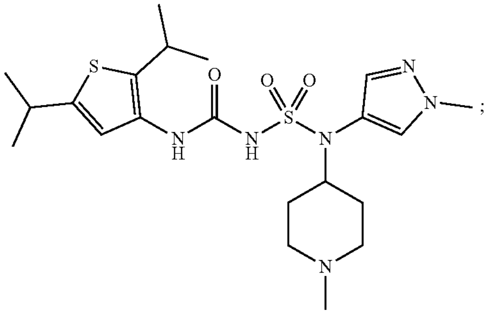 [SMILES: CC(C)c1cc(NC(=O)NS(=O)(=O)N(c2cnn(C)c2)C2CCN(C)CC2)c(C(C)C)s1] |
| 44 | 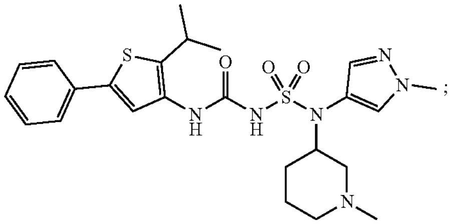 [SMILES: CC(C)c1sc(-c2ccccc2)cc1NC(=O)NS(=O)(=O)N(c1cnn(C)c1)C1CCCN(C)C1] |
| 45 | 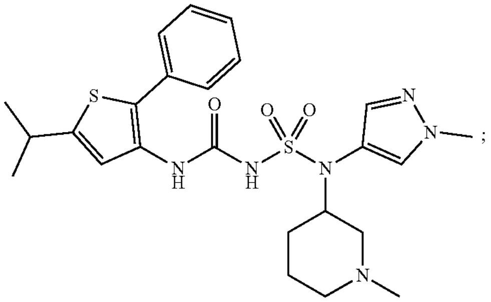 [SMILES: CC(C)c1cc(NC(=O)NS(=O)(=O)N(c2cnn(C)c2)C2CCCN(C)C2)c(-c2ccccc2)s1] |
| 46 | 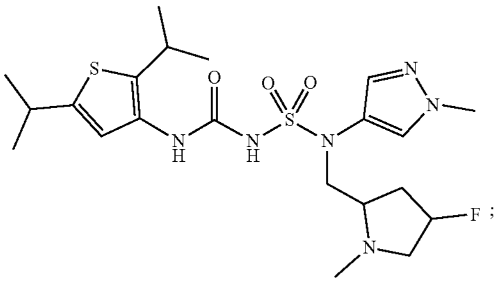 [SMILES: CC(C)c1cc(NC(=O)NS(=O)(=O)N(CC2CC(F)CN2C)c2cnn(C)c2)c(C(C)C)s1] |

-continued
| Compound No. | Structure |
| --- | --- |
| 47 | 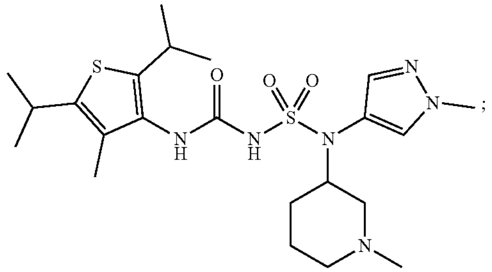 [SMILES: Cc1c(C(C)C)sc(C(C)C)c1NC(=O)NS(=O)(=O)N(c1cnn(C)c1)C1CCCN(C)C1] |
| 48 | 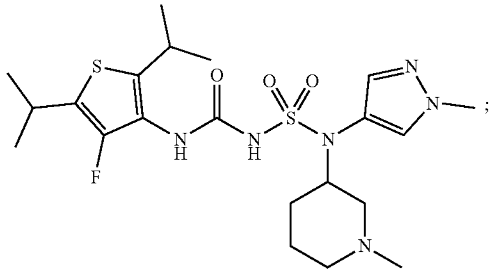 [SMILES: CC(C)c1sc(C(C)C)c(NC(=O)NS(=O)(=O)N(c2cnn(C)c2)C2CCCN(C)C2)c1F] |
| 49 | 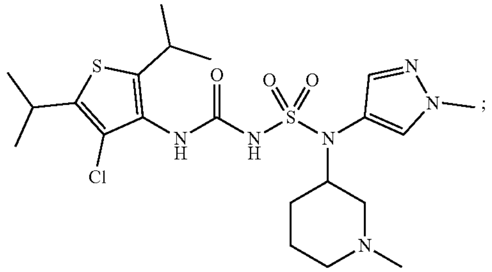 [SMILES: CC(C)c1sc(C(C)C)c(NC(=O)NS(=O)(=O)N(c2cnn(C)c2)C2CCCN(C)C2)c1Cl] |
| 50 | 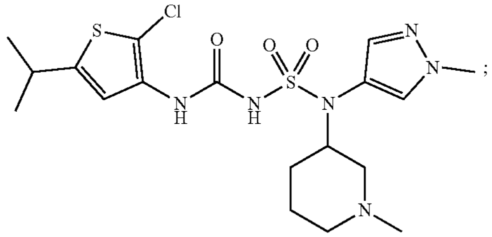 [SMILES: CC(C)c1cc(NC(=O)NS(=O)(=O)N(c2cnn(C)c2)C2CCCN(C)C2)c(Cl)s1] |
| 51 | 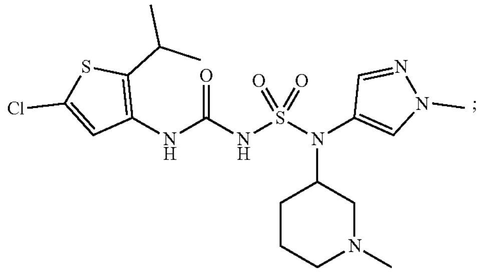 [SMILES: CC(C)c1sc(Cl)cc1NC(=O)NS(=O)(=O)N(c1cnn(C)c1)C1CCCN(C)C1] |
-continued
| Compound No. | Structure |
| --- | --- |
| 52 | 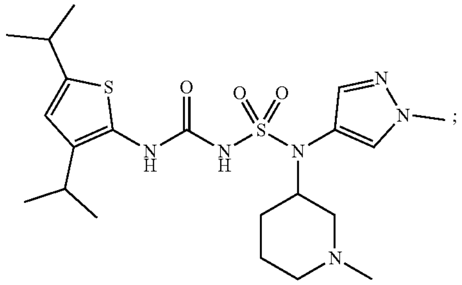 [SMILES: CC(C)c1cc(C(C)C)c(NC(=O)NS(=O)(=O)N(c2cnn(C)c2)C2CCCN(C)C2)s1] |
| 53 | 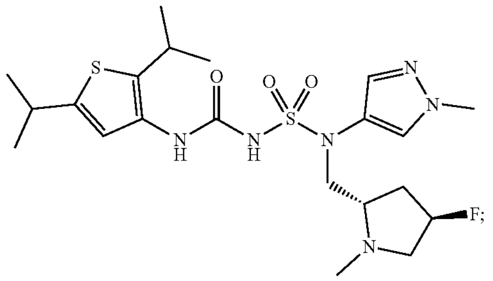 [SMILES: CC(C)c1cc(NC(=O)NS(=O)(=O)N(C[C@@H]2C[C@@H](F)CN2C)c2cnn(C)c2)c(C(C)C)s1] |
| 54 | 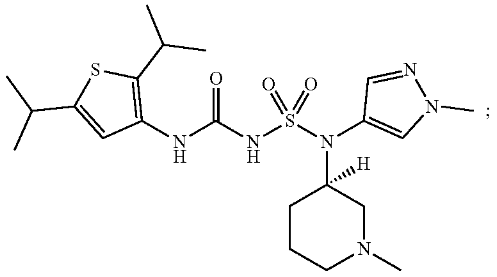 [SMILES: CC(C)c1cc(NC(=O)NS(=O)(=O)N(c2cnn(C)c2)[C@@H]2CCCN(C)C2)c(C(C)C)s1] |
| 55 | 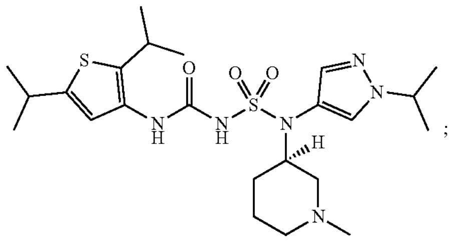 [SMILES: CC(C)c1cc(NC(=O)NS(=O)(=O)N(c2cnn(C(C)C)c2)[C@@H]2CCCN(C)C2)c(C(C)C)s1] |
| 56 | 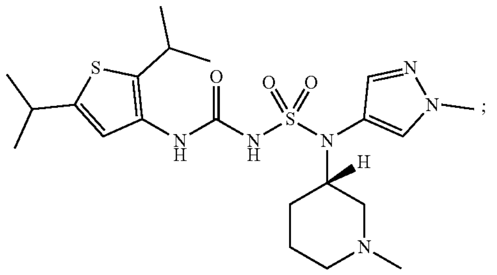 [SMILES: CC(C)c1cc(NC(=O)NS(=O)(=O)N(c2cnn(C)c2)[C@H]2CCCN(C)C2)c(C(C)C)s1] |

-continued
| Compound No. | Structure |
|---|---|
| 57 | 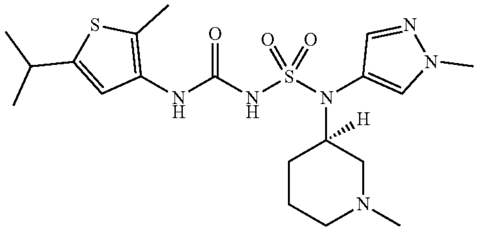 ; |
| 58 | 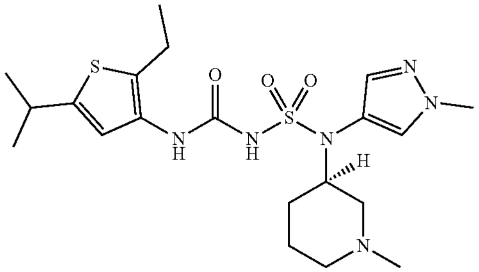 ; |
| 59 | 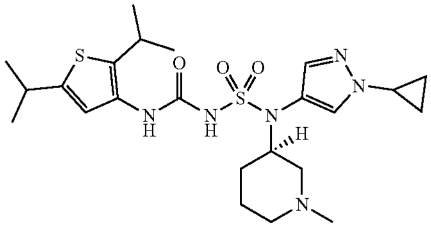 ; |
| 60 | 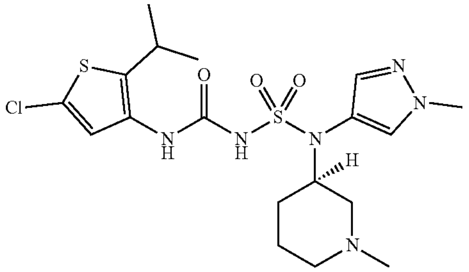 ; |
| 61 | 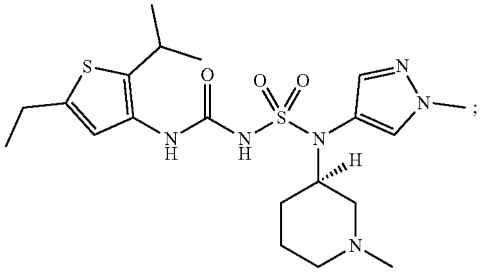 [SMILES: CCc1cc(NC(=O)NS(=O)(=O)N(c2cnn(C)c2)[C@@H]2CCCN(C)C2)c(C(C)C)s1] ; |
-continued
| Compound No. | Structure |
|---|---|
| 62 | 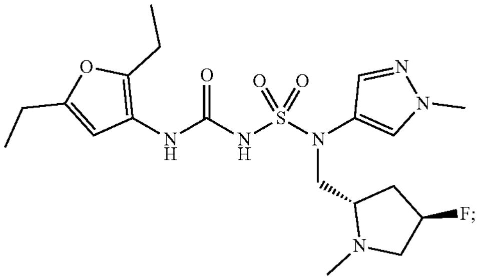 [SMILES: CCc1cc(NC(=O)NS(=O)(=O)N(C[C@@H]2C[C@@H](F)CN2C)c2cnn(C)c2)c(CC)o1] ; |
| 63 | 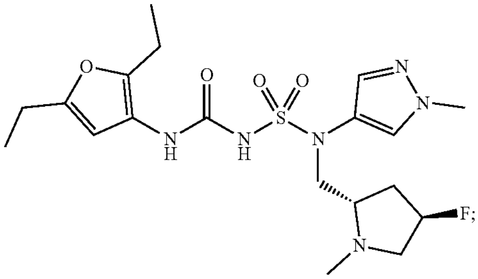 [SMILES: CCc1cc(NC(=O)NS(=O)(=O)N(C[C@@H]2C[C@@H](F)CN2C)c2cnn(C)c2)c(CC)o1] ; |
| 64 | 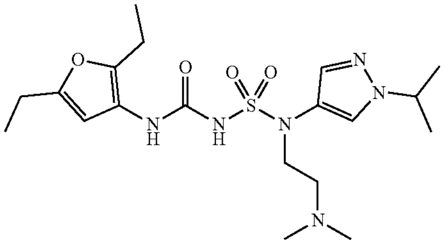 ; |
| 65 | 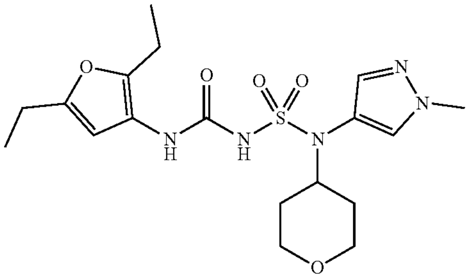 ; |
| 66 | 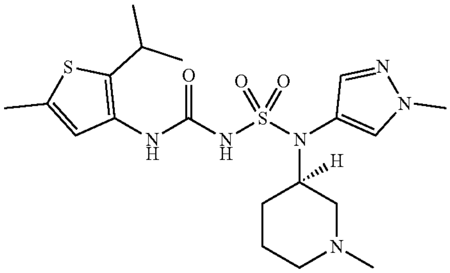 ; |

-continued
| Compound No. | Structure |
|---|---|
| 67 | 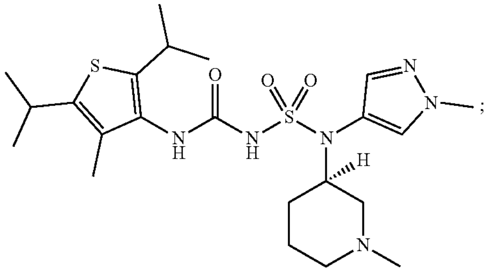 [SMILES: Cc1c(C(C)C)sc(C(C)C)c1NC(=O)NS(=O)(=O)N(c1cnn(C)c1)[C@@H]1CCCN(C)C1] |
| 70 | 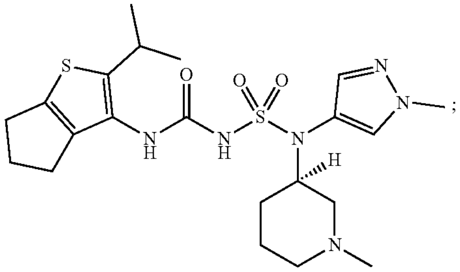 [SMILES: CC(C)c1sc2c(c1NC(=O)NS(=O)(=O)N(c1cnn(C)c1)[C@@H]1CCCN(C)C1)CCC2] |
| 71 | 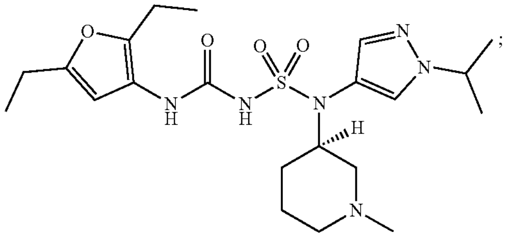 [SMILES: CCc1cc(NC(=O)NS(=O)(=O)N(c2cnn(C(C)C)c2)[C@@H]2CCCN(C)C2)c(CC)o1] |
| 72 | 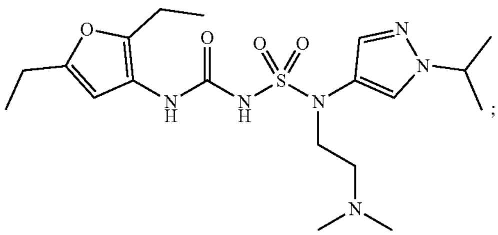 [SMILES: CCc1cc(NC(=O)NS(=O)(=O)N(CCN(C)C)c2cnn(C(C)C)c2)c(CC)o1] |
| 73 | 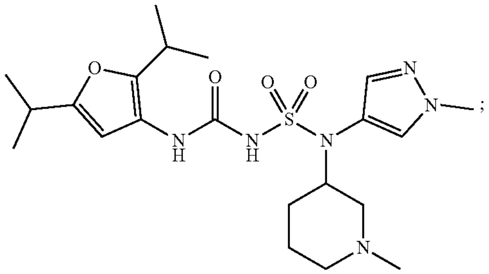 [SMILES: CC(C)c1cc(NC(=O)NS(=O)(=O)N(c2cnn(C)c2)C2CCCN(C)C2)c(C(C)C)o1] |
| 74 | 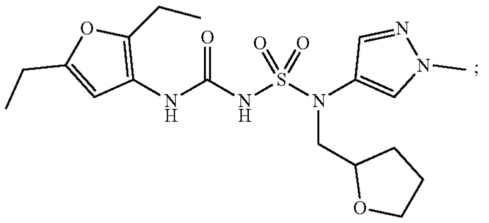 [SMILES: CCc1cc(NC(=O)NS(=O)(=O)N(CC2CCCO2)c2cnn(C)c2)c(CC)o1] |
-continued
| Compound No. | Structure |
|---|---|
| 75 | 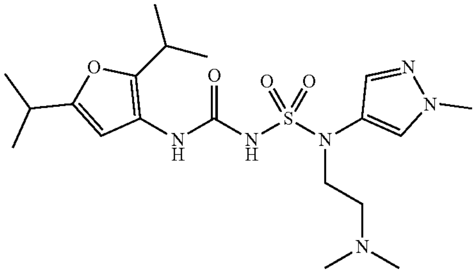 [SMILES: CC(C)c1cc(NC(=O)NS(=O)(=O)N(CCN(C)C)c2cnn(C)c2)c(C(C)C)o1] |
| 76 | 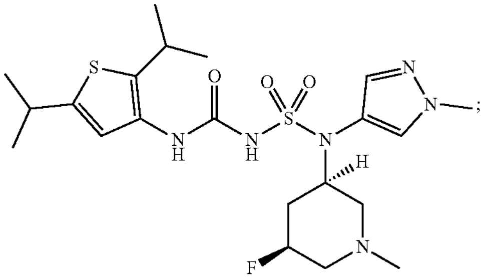 [SMILES: CC(C)c1cc(NC(=O)NS(=O)(=O)N(c2cnn(C)c2)[C@@H]2C[C@H](F)CN(C)C2)c(C(C)C)s1] |
| 77 | 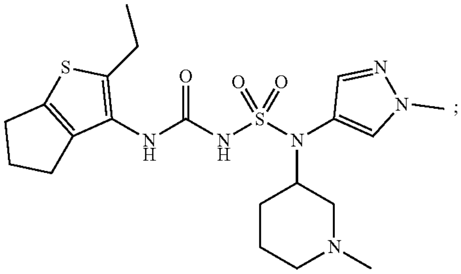 |
| 78 | 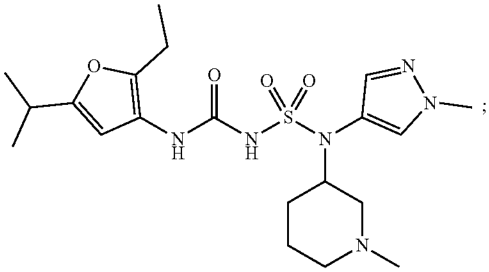 [SMILES: CCc1oc(C(C)C)cc1NC(=O)NS(=O)(=O)N(c1cnn(C)c1)C1CCCN(C)C1] |
| 79 | 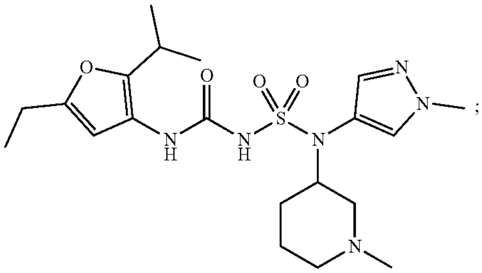 [SMILES: CCc1cc(NC(=O)NS(=O)(=O)N(c2cnn(C)c2)C2CCCN(C)C2)c(C(C)C)o1] |

-continued
| Compound No. | Structure |
|---|---|
| 80 | 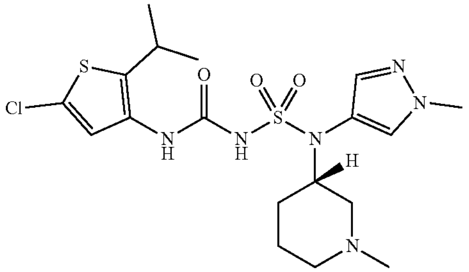 ; |
| 81 | 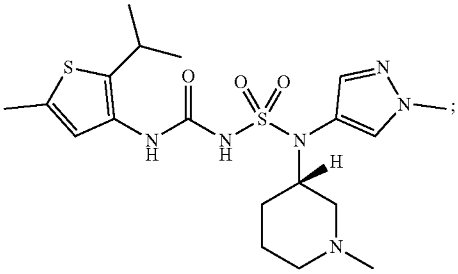 ; |
| 82 | 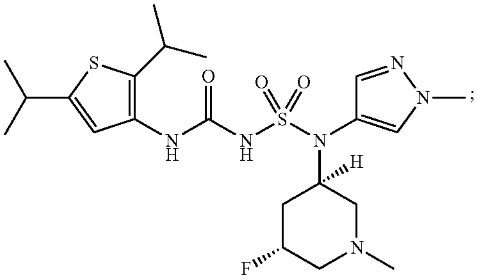 [SMILES: CC(C)c1cc(NC(=O)NS(=O)(=O)N(c2cnn(C)c2)[C@@H]2C[C@@H](F)CN(C)C2)c(C(C)C)s1] ; |
| 83 | 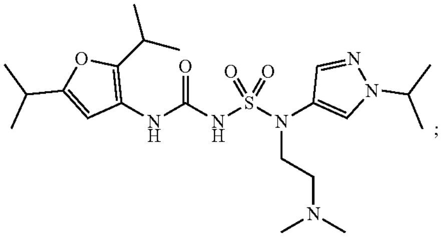 [SMILES: CC(C)c1cc(NC(=O)NS(=O)(=O)N(CCN(C)C)c2cnn(C(C)C)c2)c(C(C)C)o1] ; |
| 84 | 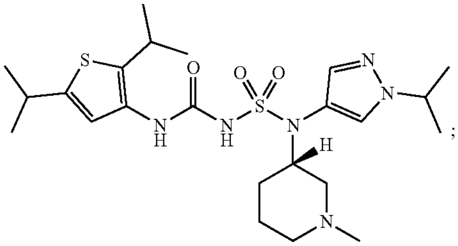 [SMILES: CC(C)c1cc(NC(=O)NS(=O)(=O)N(c2cnn(C(C)C)c2)[C@H]2CCCN(C)C2)c(C(C)C)s1] ; |
-continued
| Compound No. | Structure |
|---|---|
| 85 | 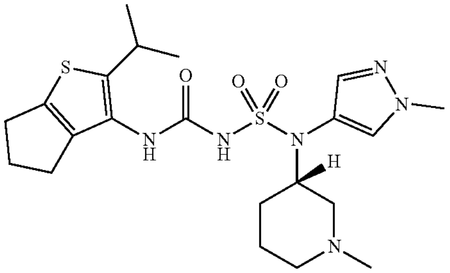 ; |
| 86 | 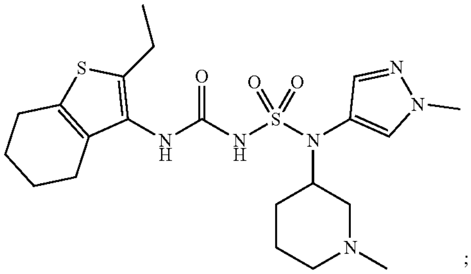 [SMILES: CCc1sc2c(c1NC(=O)NS(=O)(=O)N(c1cnn(C)c1)C1CCCN(C)C1)CCCC2] ; |
| 87 | 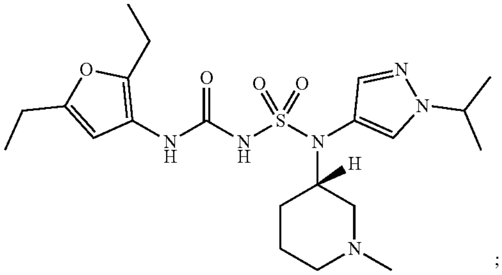 [SMILES: CCc1cc(NC(=O)NS(=O)(=O)N(c2cnn(C(C)C)c2)[C@H]2CCCN(C)C2)c(CC)o1] ; |
| 88 | 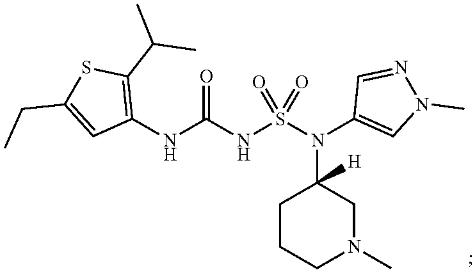 [SMILES: CCc1cc(NC(=O)NS(=O)(=O)N(c2cnn(C)c2)[C@H]2CCCN(C)C2)c(C(C)C)s1] ; |
| 89 | 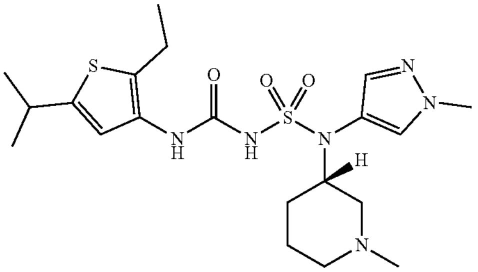 ; |

-continued
| Compound No. | Structure |
| --- | --- |
| 90 | 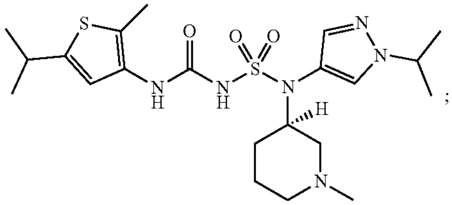 [SMILES: Cc1sc(C(C)C)cc1NC(=O)NS(=O)(=O)N(c1cnn(C(C)C)c1)[C@@H]1CCCN(C)C1] ; |
| 91 | 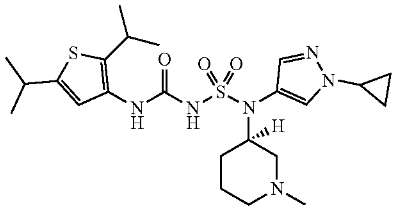 ; |
| 92 | 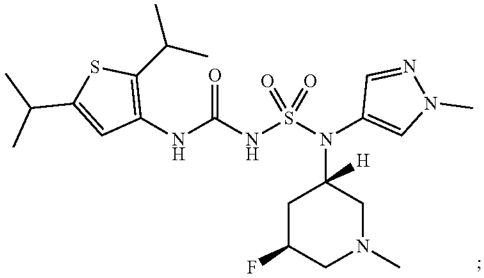 [SMILES: CC(C)c1cc(NC(=O)NS(=O)(=O)N(c2cnn(C)c2)[C@H]2C[C@H](F)CN(C)C2)c(C(C)C)s1] ; |
| 93 | 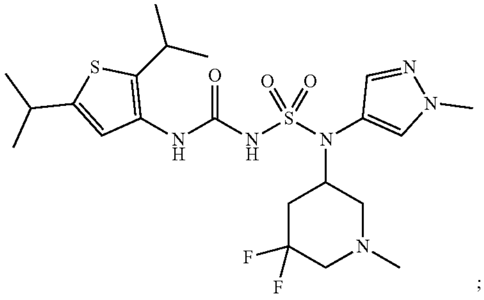 [SMILES: CC(C)c1cc(NC(=O)NS(=O)(=O)N(c2cnn(C)c2)C2CN(C)CC(F)(F)C2)c(C(C)C)s1] ; |
| 94 | 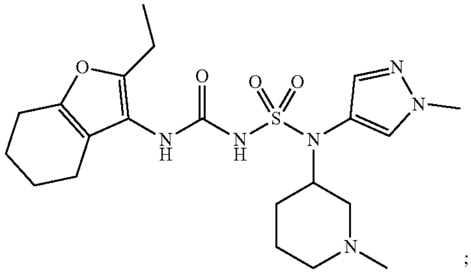 [SMILES: CCc1oc2c(c1NC(=O)NS(=O)(=O)N(c1cnn(C)c1)C1CCCN(C)C1)CCCC2] ; |
| 95 | 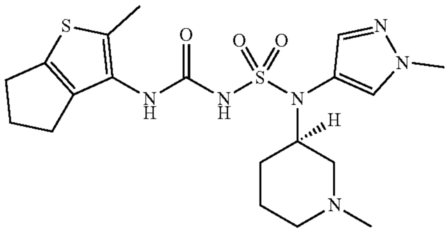 ; |
-continued
| Compound No. | Structure |
| --- | --- |
| 96 | 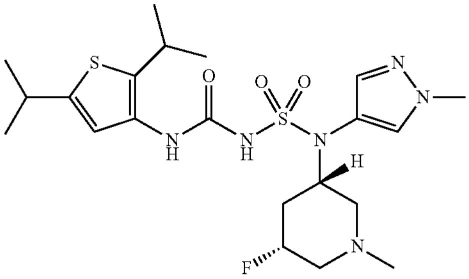 ; |
| 97 | 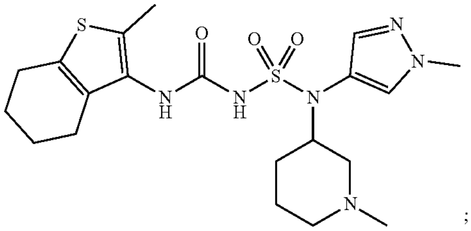 [SMILES: Cc1sc2c(c1NC(=O)NS(=O)(=O)N(c1cnn(C)c1)C1CCCN(C)C1)CCCC2] ; |
| 98 | 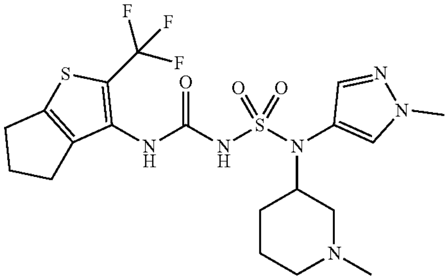 ; |
| 99 | 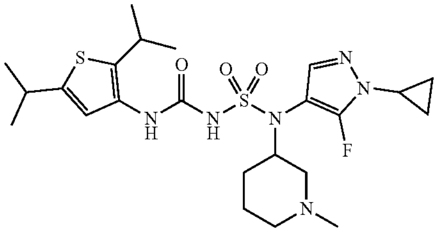 ; |
| 100 | 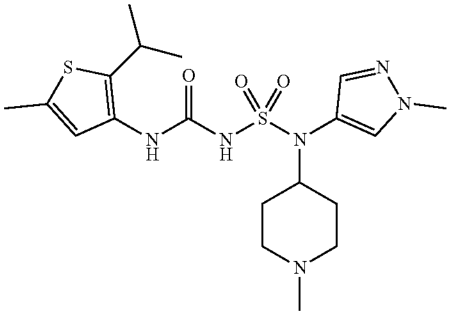 ; |

-continued
| Compound No. | Structure |
|---|---|
| 101 | 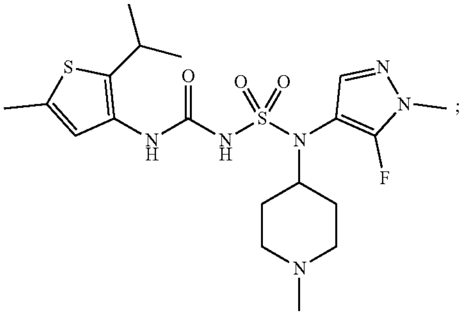 |
| 102 | 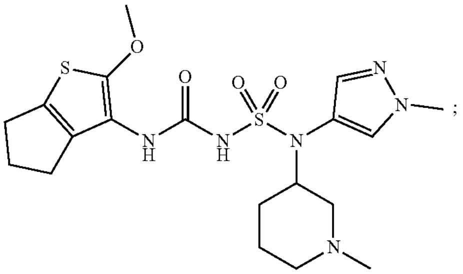 [SMILES: COc1sc2c(c1NC(=O)NS(=O)(=O)N(c1cnn(C)c1)C1CCCN(C)C1)CCC2] |
| 103 | 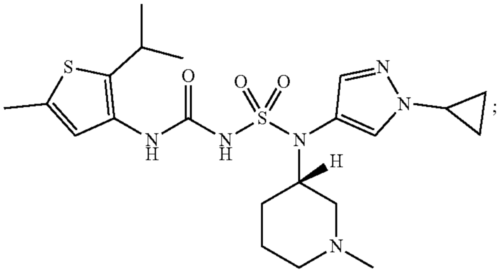 [SMILES: Cc1cc(NC(=O)NS(=O)(=O)N(c2cnn(C3CC3)c2)[C@H]2CCCN(C)C2)c(C(C)C)s1] |
| 104 | 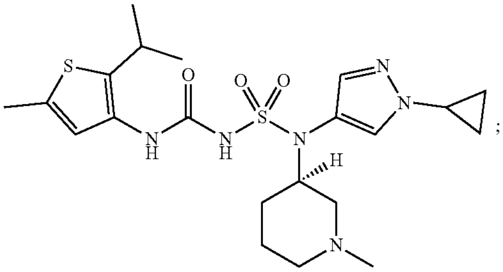 [SMILES: Cc1cc(NC(=O)NS(=O)(=O)N(c2cnn(C3CC3)c2)[C@@H]2CCCN(C)C2)c(C(C)C)s1] |
| 105 | 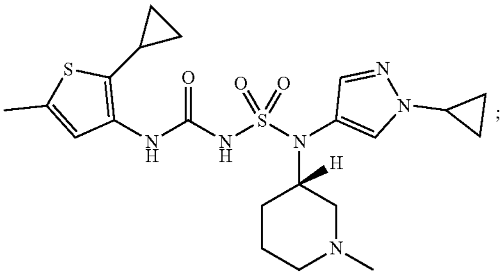 [SMILES: Cc1cc(NC(=O)NS(=O)(=O)N(c2cnn(C3CC3)c2)[C@H]2CCCN(C)C2)c(C2CC2)s1] |
-continued
| Compound No. | Structure |
|---|---|
| 106 | 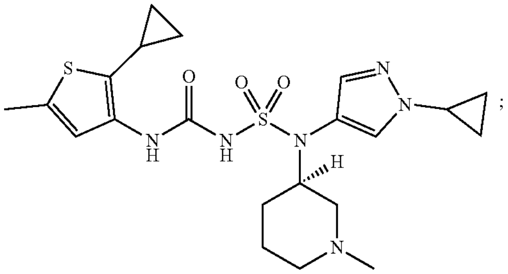 [SMILES: Cc1cc(NC(=O)NS(=O)(=O)N(c2cnn(C3CC3)c2)[C@@H]2CCCN(C)C2)c(C2CC2)s1] |
| 107 | 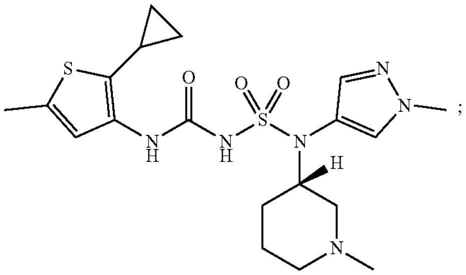 |
| 108 | 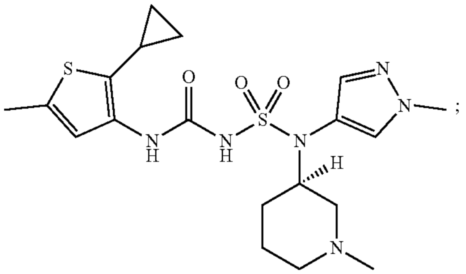 |
| 109 | 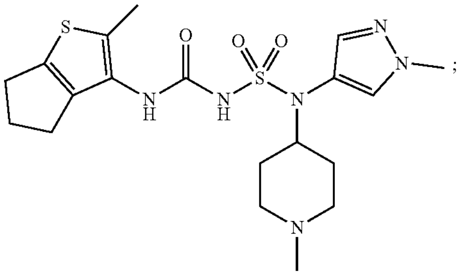 [SMILES: Cc1sc2c(c1NC(=O)NS(=O)(=O)N(c1cnn(C)c1)C1CCN(C)CC1)CCC2] |
| 110 | 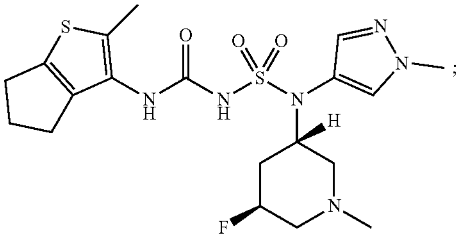 [SMILES: Cc1sc2c(c1NC(=O)NS(=O)(=O)N(c1cnn(C)c1)[C@H]1C[C@H](F)CN(C)C1)CCC2] |

-continued
| Compound No. | Structure |
|---|---|
| 111 | 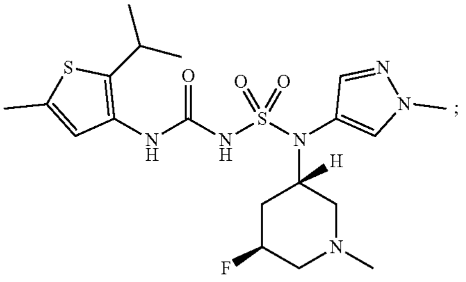 |
| 112 | 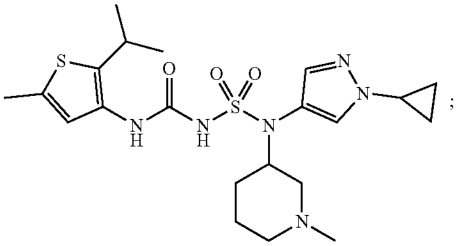 [SMILES: Cc1cc(NC(=O)NS(=O)(=O)N(c2cnn(C3CC3)c2)C2CCCN(C)C2)c(C(C)C)s1] |
| 113 | 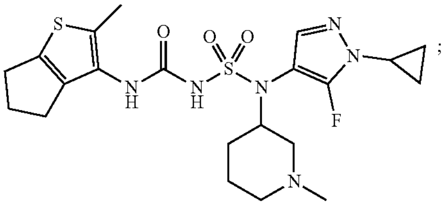 [SMILES: Cc1sc2c(c1NC(=O)NS(=O)(=O)N(c1cnn(C3CC3)c1F)C1CCCN(C)C1)CCC2] |
| 114 | 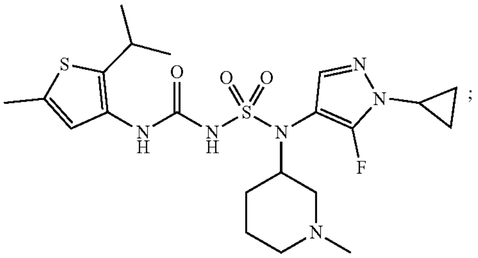 [SMILES: Cc1cc(NC(=O)NS(=O)(=O)N(c2cnn(C3CC3)c2F)C2CCCN(C)C2)c(C(C)C)s1] |
| 115 | 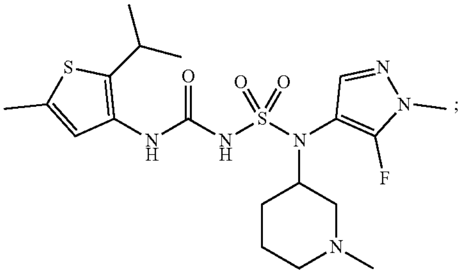 |
| 116 | 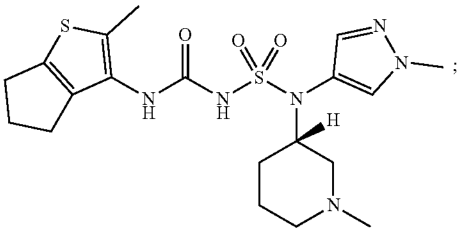 [SMILES: Cc1sc2c(c1NC(=O)NS(=O)(=O)N(c1cnn(C)c1)[C@H]1CCCN(C)C1)CCC2] |
-continued
| Compound No. | Structure |
|---|---|
| 117 | 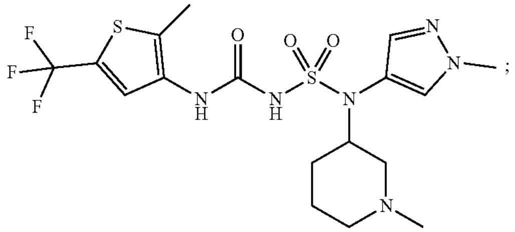 [SMILES: Cc1sc(C(F)(F)F)cc1NC(=O)NS(=O)(=O)N(c1cnn(C)c1)C1CCCN(C)C1] |
| 118 | 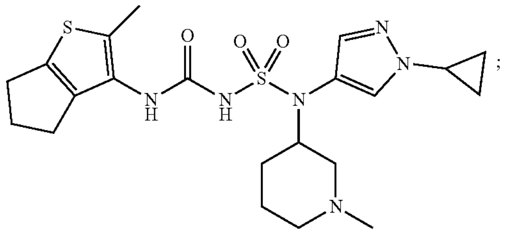 [SMILES: Cc1sc2c(c1NC(=O)NS(=O)(=O)N(c1cnn(C3CC3)c1)C1CCCN(C)C1)CCC2] |
| 119 | 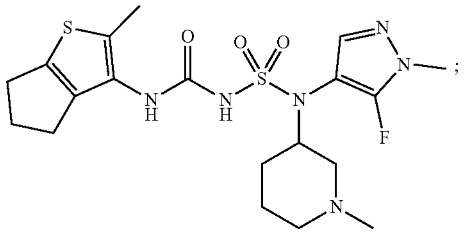 [SMILES: Cc1sc2c(c1NC(=O)NS(=O)(=O)N(c1cnn(C)c1F)C1CCCN(C)C1)CCC2] |
| 120 | 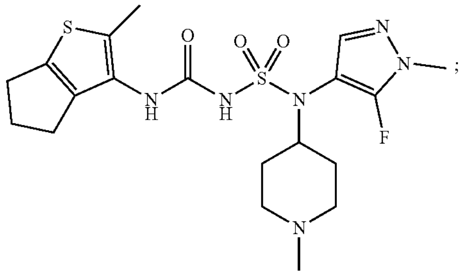 [SMILES: Cc1sc2c(c1NC(=O)NS(=O)(=O)N(c1cnn(C)c1F)C1CCN(C)CC1)CCC2] |
| 121 | 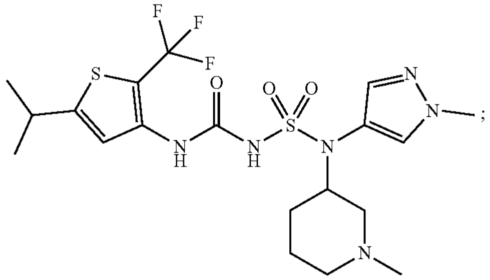 [SMILES: CC(C)c1cc(NC(=O)NS(=O)(=O)N(c2cnn(C)c2)C2CCCN(C)C2)c(C(F)(F)F)s1] |

-continued

| Compound No. | Structure |
|---|---|
| 122 | 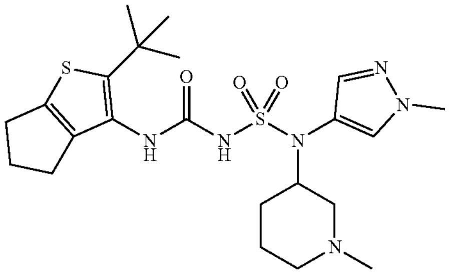 ; |
| 123 | 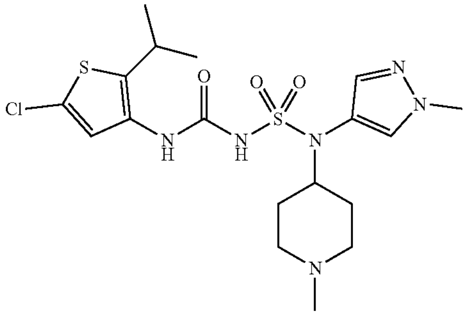 ; |
| 125 | 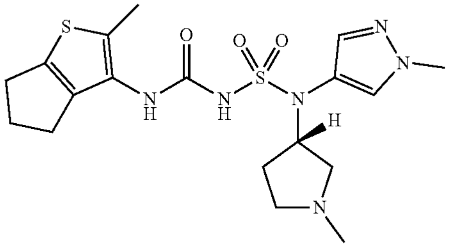 ; |
| 126 | 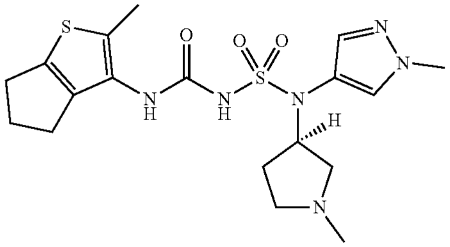 ; |
| 127 | 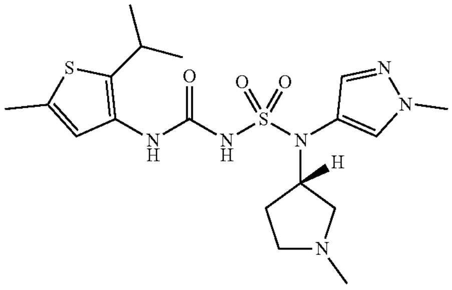 ; |

-continued

| Compound No. | Structure |
|---|---|
| 128 | 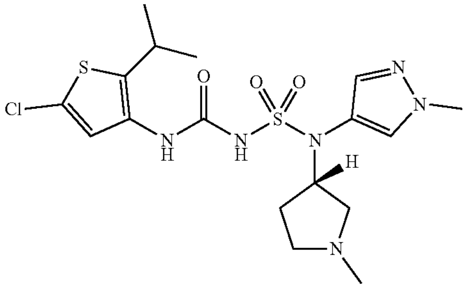 ; |
| 129 | 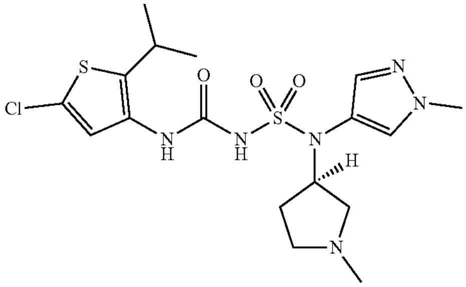 ; |
| 130 | 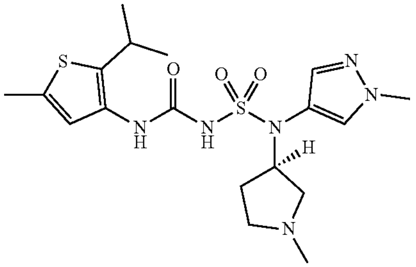 ; and |
| 131 | 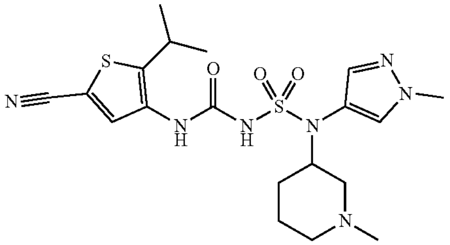 , |

or a pharmaceutically acceptable salt thereof or a deuterium labeled compound thereof.

2. A pharmaceutical composition comprising the compound of claim 1 or a pharmaceutically acceptable salt thereof, and a pharmaceutically acceptable diluent or carrier.

3. A method of inhibiting inflammasome activity, comprising contacting a cell with a compound of claim 1 or a pharmaceutically acceptable salt thereof.

4. A method of treating or preventing an autoinflammatory disorder, autoimmune disorder, neurodegenerative disease, or cancer in a subject, comprising administering to the subject a compound of claim 1 or a pharmaceutically acceptable salt thereof.

5. The method of claim 4, wherein the autoinflammatory disorder or an autoimmune disorder is selected from cryopyrin-associated auto-inflammatory syndrome (CAPS), familial Mediterranean fever (FMF), nonalcoholic fatty liver disease (NAFLD), non-alcoholic steatohepatitis (NASH), gout, rheumatoid arthritis, osteoarthritis, Crohn's disease, chronic obstructive pulmonary disease (COPD), chronic kidney disease (CKD), fibrosis, obesity, type 2 diabetes, multiple sclerosis, dermatological disease, and neuroinflammation occurring in protein misfolding diseases.

6. The method of claim 4, wherein the neurodegenerative disease is Parkinson's disease or Alzheimer's disease.

7. The method of claim 4, wherein the cancer is metastasizing cancer, brain cancer, gastrointestinal cancer, skin cancer, non-small-cell lung carcinoma, head and neck squamous cell carcinoma or colorectal adenocarcinoma.

8. The method, compound of claim 5, wherein the CAPS is familial cold autoinflammatory syndrome (FCAS), Muckle-Wells syndrome (MWS), or chronic infantile neurological cutaneous and articular (CINCA) syndrome/neonatal-onset multisystem inflammatory disease (NOMID).

9. The method of claim 5, wherein the dermatological disease is acne.

10. The method of claim 5, wherein the neuroinflammation occurring in protein misfolding diseases is a prion disease.

11. A method of treating or preventing a neurodegenerative disease in a subject, comprising administering to the subject a compound of claim 1 or a pharmaceutically acceptable salt thereof.

12. The method of claim 11, wherein the neurodegenerative disease is Parkinson's disease or Alzheimer's disease.

13. A method of treating or preventing a cancer in a subject, comprising administering to the subject a compound of claim 1 or a pharmaceutically acceptable salt thereof.

14. The method of claim 13, wherein the cancer is metastasizing cancer, brain cancer, gastrointestinal cancer, skin cancer, non-small-cell lung carcinoma, head and neck squamous cell carcinoma, or colorectal adenocarcinoma.

* * * * *